United States Patent  (10) Patent No.: US 7,723,330 B2
Blake et al.                (45) Date of Patent:    May 25, 2010

(54) HETEROBICYCLIC PYRAZOLE COMPOUNDS AND METHODS OF USE

(75) Inventors: James F. Blake, Longmont, CO (US); Steven Armen Boyd, Longmont, CO (US); Jason De Meese, Firestone, CO (US); Kin Chiu Fong, Longmont, CO (US); John J. Gaudino, Longmont, CO (US); Tomas Kaplan, Broomfield, CO (US); Allison L. Marlow, Louisville, CO (US); Jeongbeob Seo, Broomfield, CO (US); Allen A. Thomas, Louisville, CO (US); Hongqi Tian, Longmont, CO (US); Frederick Cohen, San Francisco, CA (US); Wendy B. Young, San Mateo, CA (US)

(73) Assignees: Array BioPharma Inc., Boulder, CO (US); Genentech, Inc., South San Francisco, CA (US)

( * ) Notice: Subject to any disclaimer, the term of this patent is extended or adjusted under 35 U.S.C. 154(b) by 63 days.

(21) Appl. No.: 11/714,342

(22) Filed: Mar. 6, 2007

(65) Prior Publication Data

US 2007/0238726 A1    Oct. 11, 2007

Related U.S. Application Data

(60) Provisional application No. 60/874,832, filed on Dec. 14, 2006, provisional application No. 60/779,805, filed on Mar. 7, 2006.

(51) Int. Cl.
  *A61K 31/437*    (2006.01)
  *A61K 31/5025*   (2006.01)
  *A61K 31/4985*   (2006.01)
  *A61K 31/519*    (2006.01)
  *A61K 31/55*     (2006.01)
  *A61K 31/541*    (2006.01)
  *A61K 31/5355*   (2006.01)
  *C07D 487/04*    (2006.01)
  *A61K 31/551*    (2006.01)
  *A61K 31/501*    (2006.01)
  *A61K 31/497*    (2006.01)
  *A61P 35/00*     (2006.01)

(52) U.S. Cl. ................ 514/234.2; 546/119; 546/21; 546/23; 546/120; 514/243; 514/262.1; 514/252.02; 514/252.04; 514/218; 514/217.04; 514/217.05; 514/217.06; 514/228.5; 514/303; 514/255.05; 514/252.11; 514/212.08; 514/248; 514/266.21; 514/253.04; 514/269; 544/236; 544/262; 544/232; 544/337; 544/357; 544/405; 544/115; 544/122; 544/127; 544/238; 544/114; 544/284; 544/319; 544/362; 540/524; 540/575

(58) Field of Classification Search .......... 546/119, 546/120; 514/248, 252.02, 234.2, 218, 255.05, 514/252.11, 252.04, 303, 266.21, 253.04, 514/269; 544/238, 117, 118, 357, 114, 405, 544/284, 319, 362; 540/553
See application file for complete search history.

(56) References Cited

U.S. PATENT DOCUMENTS 6,107,305 A    8/2000  Misra et al.

(Continued)

FOREIGN PATENT DOCUMENTS

EP            0251417 B1    4/1993

(Continued)

OTHER PUBLICATIONS van Niel et al., "Fluorination of 3-(3-(Piperidin-1-yl)propyl)indoles and 3-(3-(Piperazin-1-yl)propyl)indoles Gives Selective Human 5-HT1D Receptor Ligands with Improved Pharmacokinetic Profiles", J. Med. Chem, 1999, 42, 2087-2104.

(Continued)

*Primary Examiner*—Mark L Berch
*Assistant Examiner*—Cecilia M Jaisle
(74) *Attorney, Agent, or Firm*—Viksnins Harris & Padys PLLP

(57) ABSTRACT

Compounds of Formulas Ia and Ib, and stereoisomers, geometric isomers, tautomers, solvates, metabolites and pharmaceutically acceptable salts thereof, are useful for inhibiting receptor tyrosine kinases and for treating disorders mediated thereby. Methods of using compounds of Formula Ia and Ib, and stereoisomers, geometric isomers, tautomers, solvates and pharmaceutically acceptable salts thereof, for in vitro, in situ, and in vivo diagnosis, prevention or treatment of such disorders in mammalian cells, or associated pathological conditions are disclosed.

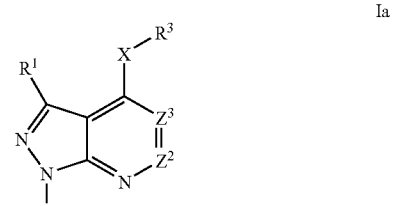

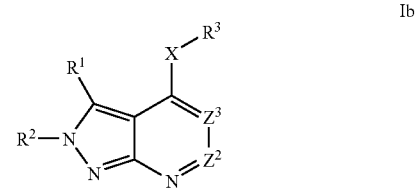

58 Claims, No Drawings

U.S. PATENT DOCUMENTS

| | | |
|---|---|---|
| 6,248,753 B1 | 6/2001 | Chen |
| 6,660,744 B1 | 12/2003 | Hirst et al. |
| 6,921,763 B2 | 7/2005 | Hirst et al. |
| 7,109,213 B2 | 9/2006 | Daines et al. |
| 7,312,212 B2 | 12/2007 | Daines et al. |
| 2004/0023992 A1 | 2/2004 | Das et al. |
| 2005/0038074 A1 | 2/2005 | Coleman et al. |
| 2005/0197340 A1 | 9/2005 | Arora et al. |
| 2005/0239820 A1 | 10/2005 | Borzilleri et al. |
| 2005/0245530 A1 | 11/2005 | Borzilleri et al. |
| 2005/0288290 A1 | 12/2005 | Borzilleri et al. |
| 2006/0041123 A1 | 2/2006 | Axten et al. |
| 2006/0058287 A1 | 3/2006 | Axten et al. |
| 2006/0089375 A1 | 4/2006 | Allen et al. |
| 2006/0211695 A1 | 9/2006 | Borzilleri et al. |
| 2006/0241104 A1 | 10/2006 | Borzilleri et al. |
| 2006/0241115 A1 | 10/2006 | Potashman et al. |
| 2006/0252777 A1 | 11/2006 | Kim et al. |
| 2006/0252790 A1 | 11/2006 | Allen et al. |
| 2007/0004675 A1 | 1/2007 | Saavedra et al. |
| 2007/0060613 A1 | 3/2007 | Kim |
| 2007/0078140 A1 | 4/2007 | Borzilleri et al. |
| 2007/0111995 A1 | 5/2007 | Allen |
| 2007/0117802 A1 | 5/2007 | Borzilleri et al. |
| 2007/0179130 A1 | 8/2007 | Bannen |
| 2008/0064718 A1 | 3/2008 | Saavedra et al. |

FOREIGN PATENT DOCUMENTS

| | | | |
|---|---|---|---|
| WO | 9534563 A1 | | 12/1995 |
| WO | 0056738 A1 | | 9/2000 |
| WO | WO/2005/085249 | * | 2/2004 |
| WO | WO/2006/014325 | * | 7/2004 |
| WO | 2006113471 A2 | | 10/2006 |
| WO | 2006116713 A1 | | 11/2006 |
| WO | 2007017577 A1 | | 2/2007 |
| WO | 2007035428 A1 | | 3/2007 |

OTHER PUBLICATIONS

Dorn et al., "Unambiguous Synthesis of 4,7-Dihydro-4-oxo-1H-pyrazolo[3,4-b]pyridine—Further Comments on the "N—C)-Rearrangement" of (2-Alkoxycarbonyl-vinyl-amino)pyrazols", Journal f.prakt. Chemie. Band 324, Heft 4, 1982, S. 557-562.

Misra et al., "1H-Pyrazolo[3,4-b]pyridine Inhibitors of Cyclin-Dependent Kinases: Highly Potent 2,6-Difluorophenacyl Analogues", Bioorganic & Medicinal Chemistry Letters 13 (2003) 2405-2408.

Misra et al., "1H-Pyrazolo[3,4-b]pyridine Inhibitors of Cyclin-Dependent Kinases", Bioorganic & Medicinal Chemistry Letters 13 (2003) 1133-1136.

* cited by examiner

HETEROBICYCLIC PYRAZOLE COMPOUNDS AND METHODS OF USE

CROSS REFERENCE TO RELATED APPLICATIONS

This application claims priority to U.S. Provisional Application Ser. Nos. 60/779,805 filed Mar. 7, 2006 and 60/874,832 filed Dec. 14, 2006, which are incorporated herein by reference in their entirety.

FIELD OF THE INVENTION

The invention relates to heterobicyclic pyrazole compounds having protein tyrosine kinase activity. The heterobicyclic pyrazole compounds may be useful in the treatment of hyperproliferative disorders, such as cancer, in mammals. The invention also relates to pharmaceutical compositions and formulations, methods of synthesis, and methods of use such as treating hyperproliferative disorders.

BACKGROUND OF THE INVENTION

Met tyrosine kinase is a high-affinity transmembrane receptor for the hepatocyte growth factor (HGF, Bottaro et al. (1991) Science 251:802-804). Met was cloned, named (Cooper et al. (1984) 311:29-33) and identified as an oncogene (Park et al. (1986) Cell 45:895-904). When deregulated by overexpression or mutations, Met receptor tyrosine kinase leads to tumor growth and invasion (Cristiani et al. (2005) Biochem. 44:14110-14119). Stimulation of Met by the ligand HGF, also known as Scatter Factor, initiates numerous physiological processes, including cell proliferation, scattering, morphogenic differentiation, angiogenesis, wound healing, tissue regeneration, and embryological development (Parr et al. (2004) Clin. Cancer Res. 10(1, Pt. 1) 202-211; Comoglio et al. (2002) J. Clin. Invest. 109:857-862; Maulik et al. (2002) Cytokine Growth Factor Reviews 13:41-59; Hecht et al. (2004) Cancer Res. 64(17):6109-6118). Receptor c-Met is rapidly internalized via clathrin-coated vesicles and traffics through an early endosomal compartment after hepatocyte growth factor stimulation. c-Met accumulates progressively in perinuclear compartments, which in part include the Golgi (Kermorgant et al. (2003) J. of Biol. Chem. 278(31):28921-28929).

The phenomena of: deregulation or dysregulation of Met and/or HGF; Met overexpression; and Met mutations are implicated in uncontrolled cell proliferation and survival, and play a key role in early-stage tumorigenesis, invasive growth of cancer cells, and metastasis (Danilkovitch-Miagkova et al. (2002) J. Clin. Invest. 109(7):863-867; Di Renzo et al. (1994) Int. J. Cancer 58:658-662; Matsumoto et al. (1994) J. Biol. Chem. 269:31807-31813; Tusolino et al. (1998) J. Cell Biol. 142:1145-1156; Jeffers et al. (1996) Mol. Cell. Biol. 16:1115-1125; Wong et al. (2004) Exper. Cell Res. 299(1): 248-256; Konda et al. (2004) J. Urology 171(6), Pt. 1:2166-2170; Heideman et al. (2004) J. Gene Med. 6(3):317-327; Ma et al. (2003) Cancer Res. 63(19):6272-6281; Maulik et al. (2002) Clin. Cancer Res. 8:620-627), making Met an important target for anticancer drug development (Cohen, P. (2002) Nat. Rev. Drug Discovery 1:309-315). Overexpression of Met and HGF is associated with poor prognosis.

Recent data demonstrating the suppression of cancer cell proliferation, survival, and invasion upon inhibition of Met binding to HGF and Met receptor dimerization (Furge et al. (2001) Proc. Natl. Acad. Sci. USA 98:10722-10727; Michieli et al. (2004) Cancer Cell 6:61-73) confirm the relevance of Met in neoplasia and provide further proof of concept for the development of small-molecule compounds for antineoplastic therapy, e.g. against multiple myeloma (Hov et al. (2004) Clin. Cancer Res. 10(19):6686-6694). Inhibition of Met results in slowing tumor growth in tumor xenograft mouse models. Antibodies specific for c-Met have been expressed to block binding of HGF to c-Met (US 2005/0037431; US 2004/0166544).

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer). Protein kinases include two classes; protein tyrosine kinases (PTK) and serine-threonine kinases (STK).

One of the prime aspects of PTK activity is their involvement with growth factor receptors which are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, (1992) Neuron 9:303-391.

Growth factor receptors with PTK activity are known as receptor tyrosine kinases (RTK, Plowman et al. (1994) DN&P, 7(6):334-339), which comprise a large family of transmembrane receptors with diverse biological activity. At present, at least nineteen (19) distinct subfamilies of RTK have been identified. An example of these is the subfamily designated the "HER" RTK, which include EGFR (epithelial growth factor receptor), HER2, HER3 and HER4. These RTK consist of an extracellular glycosylated ligand binding domain, a transmembrane domain and an intracellular cytoplasmic catalytic domain that can phosphorylate tyrosine residues on proteins. Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated alpha subunits and two beta subunits which cross the cell membrane and which contain the tyrosine kinase domain. A third RTK subfamily is referred to as the platelet derived growth factor receptor (PDGFR) group, which includes PDGFR-alpha, PDGFR-beta, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences. Another group which, because of its similarity to the PDGFR subfamily, is sometimes subsumed into the later group is the fetus liver kinase (flk) receptor subfamily. This group is believed to be made up of kinase insert domain-receptor fetal liver kinase-1 (KDR/FLK-1), flk-1R, flk-4 and fms-like tyrosine kinase 1 (flt-1). Another member of the tyrosine kinase growth factor receptor family is the fibroblast growth factor ("FGF") receptor subgroup. This group consists of four receptors, FGFR1-4, and seven ligands, FGF1-7. While not yet well defined, it appears that these receptors consist of a glycosylated extracellular domain containing a variable number of immunoglobin-like loops and an intracellular domain in which the tyrosine kinase sequence is interrupted by regions of unrelated amino acid sequences. Still another member of the tyrosine kinase growth factor receptor family is the vascular endothelial growth factor (VEGF) receptor subgroup. VEGF is a dimeric glycoprotein similar to PDGF but has different biological functions and target cell specificity in vivo. In particular, VEGF is presently thought to play an essential role is vasculogenesis and angiogenesis.

Met is still another member of the tyrosine kinase growth factor receptor family, and often referred to as c-Met or human hepatocyte growth factor receptor tyrosine kinase (hHGFR). The expression of c-Met is thought to play a role in primary tumor growth and metastasis (Kim et al. Clin. Cancer Res. (2003) 9(14):5161-5170).

Modulation of the HGF/c-Met signaling pathway may be effected by regulating binding of HGF beta chain to cMet. In particular embodiments, the zymogen-like form of HGF beta mutant was shown to bind Met with 14-fold lower affinity than the wild-type serine protease-like form, suggesting optimal interactions result from conformational changes upon cleavage of the single-chain form (US 2005/0037431). Extensive mutagenesis of the HGF beta region corresponding to the active site and activation domain of serine proteases showed that 17 of the 38 purified two-chain HGF mutants resulted in impaired cell migration or Met phosphorylation but no loss in Met binding. However, reduced biological activities were well correlated with reduced Met binding of corresponding mutants of HGF beta itself in assays eliminating dominant alpha-chain binding contributions.

Protein-tyrosine kinases (PTK) are critical components of signaling pathways that control cellular proliferation and differentiation. PTK are subdivided into two large families, receptor tyrosine kinases (RTK) and non-receptor tyrosine kinases (NRTK). RTK span the plasma membrane and contain an extra-cellular domain, which binds ligand, and an intracellular portion, which possesses catalytic activity and regulatory sequences. Most RTK, like the hepatocyte growth factor receptor c-met, possess a single polypeptide chain and are monomeric in the absence of a ligand. Ligand binding to the extracellular portion of RTK, dimerizes monomeric receptors, resulting in autophosphorylation of specific tyrosine residues in the cytoplasmic portion (for review see: Blume-Jensen, P., and Hunter, T., Nature (2001) 411:355-365; Hubbard, S. R., et al., J. Biol. Chem. 273 (1998) 11987-11990; Zwick, E., et al., Trends Mol. Med. (2002) 8:17-23). In general, tyrosine autophosphorylation either stimulates the intrinsic catalytic kinase activity of the receptor or generates recruitment sites for downstream signaling proteins containing phosphotyrosine-recognition domains, such as the Src homology 2 (SH2) domain or the phosphotyrosine-binding (PTB) domain.

PTK have become primary targets for the development of novel therapeutics designed to block cancer cell proliferation, metastasis, and angiogenesis and promote apoptosis. The strategy that has progressed farthest in clinical development is the use of monoclonal antibodies to target growth factor receptor tyrosine kinases. The use of small molecule tyrosine kinase inhibitors however could have significant theoretical advantages over monoclonal antibodies. Small molecule inhibitors could have better tissue penetration, could have activity against intracellular targets and mutated targets and could be designed to have oral bioavailability. Several lead compounds have shown promising activity against such targets as the EGFR, the vascular endothelial cell growth factor receptor and bcr-abl. The hepatocyte growth factor receptor c-Met was first identified as an activated oncogene in an N-methyl-N'-nitrosoguanidinic treated human osteogenic sarcoma cell line (MUNG-HOS) by its ability to transform NIH 3T3 mouse fibroblasts. The receptor encoded by the c-Met protooncogene (located on chromosome 7) is a two-chain protein composed of 50 kDa (alpha) chain disulfide linked to a 145 kDa (beta) chain in an alpha-beta complex of 190 kDa. The alpha-chain is exposed at the cell surface while the beta chain spans the cell membrane and possesses an intracellular tyrosine kinase domain. The presence of this intracellular tyrosine kinase domain groups c-Met as a member of the receptor tyrosine kinase (RTK) family of cell surface molecules.

Much evidence supports the role of HGF as a regulator of carcinogenesis, cancer invasion and metastasis (for review see: Herynk, M. H., and Radinsky, R. (2000) In Vivo 14:587-596; Jiang et al. (1999) Crit. Rev. Oncol. Hematol. 29:209-248; Longati (2001) Curr. Drug Targets 2:41-55; Maulik et al., (2002) Cytokine Growth Factor Rev. 13:41-59; Parr, C., and Jiang, W. G., (2001) Histol. Histopathol. 16:251-268). HGF binds to and induces tyrosine phosphorylation of the mature c-met receptor beta-chain. Such events are thought to promote binding of intracellular signaling proteins containing src homology (SH) regions such as PLC-gamma, Ras-GAP, PI-3 kinase pp$^{60}$c-src and the GRB-2 Socs complex to the activated receptor. Each SH2-containing protein may activate a different subset of signaling phosphopeptides, thus eliciting different responses within the cell. c-Met mutations have been well-described in hereditary and sporadic human papillary renal carcinomas and have been reported in ovarian cancer, childhood hepatocellular carcinoma, metastatic head and neck squamous cell carcinomas, and gastric cancer. c-Met is also over-expressed in both non-small cell lung cancer and small cell lung cancer cells, in lung, breast, colon and prostate tumors (Herynk et al. (2003) Cancer Res. 63(11): 2990-2996; Maulik et al. (2002) Clin. Cancer Res. 8:620-627). Since c-Met appears to play an important role in oncogenesis of a variety of tumors, various inhibition strategies have been employed to therapeutically target this receptor tyrosine kinase. The usefulness of inhibiting the protein-tyrosine kinase c-Met for inhibiting tumor growth and invasion has been shown in many well documented preclinical experiments (Abounader et al. (1999) J. Natl. Cancer Inst. 91:1548-1556; Laterra et al. (1997) Lab. Invest. 76:565-577; Tomioka, D. (2001) Cancer Res. 61:7518-7524; Wang et al. (2001) J. Cell Biology 153:1023-1033).

c-Met inhibitors have been reported (US 2004/0242603; US 2004/0110758; US 2005/0009845; WO 2003/000660; WO 98/007695; U.S. Pat. No. 5,792,783; U.S. Pat. No. 5,834, 504; U.S. Pat. No. 5,880,141; US 2003/0125370; U.S. Pat. No. 6,599,902; WO 2005/030140; WO 2005/070891; US 2004/0198750; U.S. Pat. No. 6,790,852; WO 2003/087026; U.S. Pat. No. 6,790,852; WO 2003/097641; U.S. Pat. No. 6,297,238; WO 2005/005378; WO 2004/076412; WO 2005/004808; WO 2005/010005; US 2005/0009840; WO 2005/121125; WO 2006/014325). PHA-665752 is a small molecule, ATP-competitive, active-site inhibitor of the catalytic activity of c-Met, as well as phenotypes such as cell growth, cell motility, invasion, and morphology of a variety of tumor cells (Ma et al. (2005) Clin. Cancer Res. 11:2312-2319; Christensen et al. (2003) Cancer Res. 63:7345-7355).

SUMMARY OF THE INVENTION

In one aspect, the invention relates to heterobicyclic pyrazole compounds that are inhibitors of receptor tyrosine kinases (RTK), including c-Met. Certain hyperproliferative disorders are characterized by the overactivation of c-Met kinase function, for example by mutations or overexpression of the protein. Accordingly, the compounds of the invention are useful in the treatment of hyperproliferative disorders such as cancer.

More specifically, one aspect of the invention provides heterobicyclic pyrazole compounds of Formulas Ia and Ib:

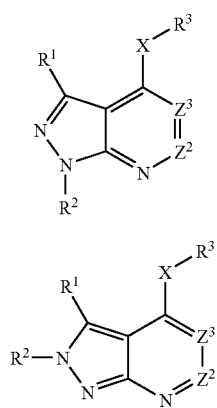

and stereoisomers, geometric isomers, tautomers, solvates, metabolites and pharmaceutically acceptable salts and prodrugs thereof, wherein $R^1$, $R^2$, $R^3$, X, $Z^2$ and $Z^3$ are as defined herein.

Another aspect of the invention provides a pharmaceutical composition comprising a heterobicyclic pyrazole compound of Formulas Ia or Ib and a pharmaceutically acceptable carrier. The pharmaceutical composition may further comprise one or more additional therapeutic agents selected from anti-proliferative agents, anti-inflammatory agents, immuno-modulatory agents, neurotropic factors, agents for treating cardiovascular disease, agents for treating liver disease, anti-viral agents, agents for treating blood disorders, agents for treating diabetes, and agents for treating immunodeficiency disorders.

Another aspect of the invention provides methods of inhibiting or modulating receptor tyrosine kinase activity, comprising contacting the kinase with an effective inhibitory amount of a compound of Formula Ia or Ib.

Another aspect of the invention provides methods of inhibiting c-Met kinase activity, comprising contacting a c-Met kinase with an effective inhibitory amount of a compound of Formula Ia or Ib, or a stereoisomer, geometric isomer, tautomer, solvate, metabolite, or pharmaceutically acceptable salt or prodrug thereof.

Another aspect of the invention provides methods of preventing or treating a disease or disorder modulated by c-Met kinases, comprising administering to a mammal in need of such treatment an effective amount of a compound of Formula Ia or Ib, or a stereoisomer, geometric isomer, tautomer, solvate, metabolite, or pharmaceutically acceptable salt or prodrug thereof. Examples of such diseases, conditions and disorders include, but are not limited to, hyperproliferative disorders (e.g., cancer, including melanoma and other cancers of the skin), neurodegeneration, cardiac hypertrophy, pain, migraine, neurotraumatic diseases, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders.

Another aspect of the invention provides methods of preventing or treating a hyperproliferative disorder, comprising administering to a mammal in need of such treatment an effective amount of a compound of Formula Ia or Ib, or a stereoisomer, geometric isomer, tautomer, solvate, metabolite, or pharmaceutically acceptable salt or prodrug thereof, alone or in combination with one or more additional compounds having anti-hyperproliferative properties.

In a further aspect the present invention provides a method of using a compound of this invention to treat a disease or condition modulated by c-Met in a mammal.

An additional aspect of the invention is the use of a compound of this invention in the preparation of a medicament for the treatment or prevention of a disease or condition modulated by c-Met in a mammal.

Another aspect of the invention includes kits comprising a compound of Formula Ia or Ib, or a stereoisomer, geometric isomer, tautomer, solvate, metabolite, or pharmaceutically acceptable salt or prodrug thereof, a container, and optionally a package insert or label indicating a treatment.

Another aspect of the invention includes methods of preparing, methods of separating, and methods of purifying compounds of Formula Ia and Ib.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkyl" includes saturated linear or branched-chain monovalent hydrocarbon radicals of one to six carbon atoms (e.g., $C_1$-$C_6$ alkyl), wherein the alkyl radical may be optionally substituted independently with one or more substituents described below.

The term "$C_1$-$C_6$ fluoroalkyl" includes an alkyl group of 1-6 carbons substituted with a fluoro group. The fluoro group can be substituted at any place on the alkyl group. Examples include, but are not limited to, CH$_2$F, CH$_2$CH$_2$F, CH$_2$CH$_2$CH$_2$F, CH$_2$CH$_2$CH$_2$CH$_2$F, CH$_2$CH$_2$CH$_2$CH$_2$CH$_2$F, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene, substituted benzenes, naphthalene, anthracene, biphenyl, indenyl, indanyl, 1,2-dihydronaphthalene, 1,2,3,4-tetrahydronaphthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The heterocyclyl may be a carbon radical or heteroatom radical. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be C-attached or N-attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Substituted alkyl", "substituted alkenyl", "substituted alkynyl", "substituted aryl", "substituted heteroaryl", "substituted heterocyclyl" and "substituted cycloalkyl" mean alkyl, alkenyl, alkynyl, aryl, heteroaryl, heterocyclyl and cycloalkyl, respectively, in which one or more hydrogen atoms are each independently replaced with a substituent. Typical substituents include, but are not limited to, F, Cl, Br, I, CN, CF$_3$, OR, R, =O, =S, =NR, =N$^+$(O)(R), =N(OR), =N$^+$(O)(OR), =N—NRR', —C(=O)R, —C(=O)OR, —C(=O)NRR', —NRR', —N$^+$RR'R", —N(R)C(=O)R', —N(R)C(=O)OR', —N(R)C(=O)NR'R", —SR, —OC(=O)R, —OC(=O)OR, —OC(=O)NRR', —OS(O)$_2$(OR), —OP(=O)(OR)(OR'), —OP(OR)(OR'), —P(=O)(OR)(OR'), —P(=O)(OR)NR'R", —S(O)R, —S(O)$_2$R, —S(O)$_2$NR, —S(O)(OR), —S(O)$_2$(OR), —SC(=O)R, —SC(=O)OR, =O and —SC(=O)NRR'; wherein each R, R' and R" is independently selected from H, C$_1$-C$_{12}$ alkyl, C$_2$-C$_8$ alkenyl, C$_2$-C$_8$ alkynyl, C$_6$-C$_{20}$ aryl and C$_2$-C$_{20}$ heterocyclyl. Substituents may also be combinations of alkyl, alkenyl, alkynyl, carbocycle, aryl, and heteroaryl radicals, such as cyclopropylmethyl, cyclohexylethyl, benzyl, and N-ethylmorpholino, and substituted forms thereof.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triazíquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); chloranbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The term "prodrug" as used in this application refers to a precursor or derivative form of a compound of the invention that is less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the cMet inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt," as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The compounds of Formulas Ia and Ib also include other salts of such compounds which are not necessarily pharmaceutically acceptable salts, and which may be useful as intermediates for preparing and/or purifying compounds of Formulas Ia or Ib and/or for separating enantiomers of compounds of Formulas Ia or Ib.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula Ia and Ib" include compounds of Formulas Ia and Ib and stereoisomers, geometric isomers, tautomers, solvates, metabolites, and pharmaceutically acceptable salts and prodrugs thereof.

The term "mammal" includes, but is not limited to, humans, dogs, cats, horses, cows, pigs, sheep, and poultry.

c-Met Inhibitor Compounds

The present invention provides heterobicyclic pyrazole compounds, and pharmaceutical formulations thereof, that are potentially useful in the treatment of diseases, conditions and/or disorders modulated by c-Met. More specifically, the present invention provides compounds of Formulas Ia and Ib

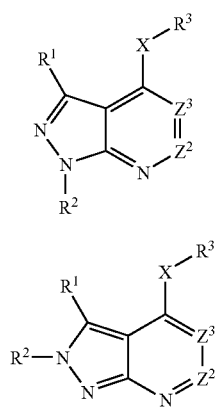

and stereoisomers, geometric isomers, tautomers, solvates, metabolites and pharmaceutically acceptable salts and prodrugs thereof, wherein:

X is O, S or $NR^{10}$;

$Z^2$ and $Z^3$ are independently selected from $CR^4$ and N, wherein zero or one of $Z^2$ and $Z^3$ is N;

$R^1$ is H, $C_1$-$C_{12}$ alkyl, $C_2$-$C_8$ alkenyl, $C_2$-$C_8$ alkynyl, —C(=O)$NR^{10}R^{11}$, or —$(CR^{14}R^{15})_r NR^{10}R^{11}$, or $R^1$ is $C_3$-$C_{12}$ carbocyclyl, $C_2$-$C_{20}$ heterocyclyl, $C_6$-$C_{20}$ aryl or $C_1$-$C_{20}$ heteroaryl, wherein said alkyl, alkenyl, alkynyl, carbocyclyl, heterocyclyl, aryl and heteroaryl are optionally substituted with one or more groups independently selected from F, Cl, Br, I, CN, $CF_3$, oxo, —$OR^{10}$, $SR^{10}$, —C(=Y)$R^{10}$, —C(=Y)$OR^{10}$, —C(=Y)$NR^{10}R^{11}$, —$(CR^{14}R^{15})_n$—$NR^{10}R^{11}$, —$NR^{10}C(=Y)R^{13}$, —$NR^{10}C(=Y)OR^{11}$, —$NR^{12}C(=Y)NR^{10}R^{11}$, —$NR^{12}SO_2R^{10}$, —OC(=Y)$R^{10}$, —OC(=Y)$OR^{10}$, —OC(=Y)$NR^{10}R^{11}$, —OS(O)$_2(OR^{10})$, —OP(=Y)($OR^{10})(OR^{11})$, —OP($OR^{10})(OR^{11})$, —S(O)$R^{10}$, —S(O)$_2R^{10}$, —S(O)$_2NR^{10}R^{11}$, —S(O)($OR^{10}$), —S(O)$_2$($OR^{10}$), —SC(=Y)$R^{10}$, —SC(=Y)$OR^{10}$, —SC(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, $C_1$-$C_{20}$ heteroaryl, —$(CR^{14}R^{15})$—$NR^{12}C(=O)(CR^{14}R^{15})_r NR^{10}R^{11}$, and $(CR^{14}R^{15})_r NR^{10}R^{11}$, or $R^1$ is $NR^xR^y$;

$R^2$ is H, $CF_3$, CN, —C(=Y)$R^{10}$, —C(=Y)$OR^{10}$, —C(=Y)$NR^{10}R^{11}$, —C(=O)$NR^{12}(CR^{14}R^{15})_r NR^{10}R^{11}$, —$SR^{10}$, —S(O)$R^{10}$, —S(O)$_2R^{10}$, S(O)$_2NR^{10}R^{11}$, —SC(=Y)$R^{10}$, —SC(=Y)$OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, $(CH_2)_n OR^{10}$, $(CH_2)_n NR^{10}R^{11}$, heteroaryl and heterocyclyl;

$R^3$ is $C_3$-$C_{12}$ carbocyclyl, $C_2$-$C_{20}$ heterocyclyl, $C_6$-$C_{20}$ aryl or $C_1$-$C_{20}$ heteroaryl, wherein said carbocyclyl, heterocyclyl, aryl and heteroaryl are optionally substituted with one or more groups independently selected from F, Cl, Br, I, CN, $CF_3$, $OR^{10}$, $SR^{10}$, —C(=Y)$R^{10}$, —C(=Y)$OR^{10}$, —C(=Y)$NR^{10}R^{11}$, —$NR^{10}R^{11}$, —$NR^{10}C(=Y)R^{13}$, —$NR^{10}C(=Y)OR^{11}$, —$NR^{12}C(=Y)NR^{10}R^{11}$, —$NR^{12}C(=O)C(=O)R^{10}R^{11}$, —$NR^{12}C(=O)C(=O)OR^a$, —$NR^{12}SO_2R^{10}$, —$NR^{12}C(=Y^1)(CR^{14}R^{15})_m C(=Y^2)NR^{10}R^{11}$, —$NR^{12}C(=Y^1)NR^{10}C(=Y^2)(CR^{14}R^{15})_n R^{11}$, —$NR^{12}C(=Y^1)(CR^{14}R^{15})_n C(=Y^2)(CR^{14}R^{15})_m R^{10}$, —OC(=Y)$R^{10}$, —OC(=Y)$OR^{10}$, —OC(=Y)$NR^{10}R^{11}$, —OS(O)$_2(OR^{10})$, —OP(=Y)($OR^{10})(OR^{11})$, —OP($OR^{10})(OR^{11})$, —S(O)$R^{10}$, —S(O)$_2R^{10}$, —S(O)$_2NR^{10}R^{11}$, —S(O)($OR^{10}$), —S(O)$_2$($OR^{10}$), —SC(=Y)$R^{10}$, —SC(=Y)$OR^{10}$, —SC(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from F, Cl, Br, I, OH, $C_1$-$C_{12}$ alkyl, $NR^{10}R^{11}$, and $(CR^{14}R^{15})_n$-aryl;

$R^4$ is H, F, Cl, Br, $CF_3$, CN, —C(=Y)$R^{10}$, —C(=Y)$OR^{10}$, —C(=Y)$NR^{10}R^{11}$, —$NR^{10}R^{11}$, $NR^{10}C(=Y)R^{11}$, $NR^{10}C(=Y)OR^{11}$, $NR^{12}C(=Y)NR^{10}R^{11}$, —$NR^{12}SO_2NR^{10}R^{11}$, —$OR^{10}$, —OC(=Y)$R^{10}$, —OC(=Y)$OR^{10}$, —OC(=Y)$NR^{10}R^{11}$, —C(=O)$NR^{12}(CR^{14}R^{15})_r NR^{10}R^{11}$, —OP(=Y)($OR^{10})(OR^{11})$, —OP($OR^{10})(OR^{11})$, —$SR^{10}$, —S(O)$R^{10}$, —S(O)$_2R^{10}$, —S(O)$_2NR^{10}R^{11}$, —SC(=Y)$R^{10}$, —SC(=Y)$OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $(CR^{14}R^{15})_n C_2$-$C_{20}$ heterocyclyl, $(CR^{14}R^{15})_n C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, $SO_2R^c$, CN, $OR^a$, $NR^aR^b$, C(=O)$NR^aR^b$, $CR^aC(=O)R^b$, $C_1$-$C_{12}$ alkyl, $C_2$-$C_8$ alkenyl, $C_2$-$C_8$ alkynyl, $C_3$-$C_{12}$ carbocyclyl, $C_6$-$C_{20}$ aryl, and $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_n OR^a$, $NR^aR^b$, $CF_3$, F, Cl, Br, I, $SO_2R^a$, C(=O)$R^a$, $NR^{10}C(=Y)R^{11}$, C(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, or $R^{10}$ and $R^{12}$ together with the atoms to which they are attached form an oxo-substituted $C_3$-$C_{20}$ heterocyclic ring optionally fused to a benzene ring;

$R^{13}$ is H, $C_1$-$C_{12}$ alkyl, $C_2$-$C_8$ alkenyl, $C_2$-$C_8$ alkynyl, $(CR^{14}R^{15})_n$-cycloalkyl, $(CR^{14}R^{15})_n$-heterocyclyl, $(CR^{14}R^{15})_n$-aryl, $(CR^{14}R^{15})_n$-heteroaryl, $(CR^{14}R^{15})_n$—O—$(CR^{14}R^{15})_m$-aryl, $(CR^{14}R^{15})_n$—$OR^{10}$, $(CR^{14}R^{15})_n$—$NR^{10}R^{11}$, $(CR^{14}R^{15})_n$—$NR^{10}C(=O)R^{11}$, or $(CR^{14}R^{15})_n$—$NR^{10}(SO_2Me)$—$R^{11}$, wherein said alkyl, alkenyl, alkynyl, cycloalkyl, heterocycloalkyl, and heteroaryl portions are optionally substituted with one or more groups independently selected from F, Cl, Br, I, oxo, $SO_2R^c$, CN, $OR^a$, $C(=O)R^a$, $C(=O)OR^a$, $NR^aR^b$, $NR^aC(=O)R^b$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, and $C_1$-$C_{20}$ heteroaryl;

each $R^{14}$ and $R^{15}$ is independently H, $C_1$-$C_{12}$ alkyl, or $(CH_2)_t$-aryl, or $R^{14}$ and $R^{15}$ together with the atoms to which they are attached form a saturated or partially unsaturated $C_3$-$C_{12}$ carbocyclic ring, or $R^{10}$ and $R^{15}$ together with the atoms to which they are attached form an oxo-substituted saturated or partially unsaturated monocyclic or bicyclic $C_1$-$C_{20}$ heterocyclic ring optionally further substituted with one or more groups independently selected from F, Cl, Br, I, $OR^a$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, or $C_1$-$C_{20}$ heteroaryl, wherein said alkyl and aryl are optionally substituted with one or more groups independently selected from F, Cl, Br, and I, or $R^{14}$ is null and $R^{10}$ and $R^{15}$ together with the atoms to which they are attached form a $C_1$-$C_{20}$ heteroaryl ring having one or more heteroatoms;

$R^a$ and $R^b$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from $C_1$-$C_6$ alkyl and halogen;

$R^c$ is $C_1$-$C_{12}$ alkyl or $C_6$-$C_{20}$ aryl, wherein said alkyl and aryl are optionally substituted with one or more groups independently selected from F, Cl, Br, I, $OR^a$ and $C(=O)NR^aR^b$;

$R^x$ is H or $C_1$-$C_6$ alkyl;

$R^y$ is (i) ($C_1$-$C_6$ alkyl)$NR^jR^k$ wherein $R^j$ and $R^k$ are independently H or $C_1$-$C_6$ alkyl; (ii) $C_5$-$C_6$ cycloalkyl optionally substituted with OH or —$OC(=O)CF_3$; or (iii) a 5-6 membered heterocyclic ring having 1 to 2 ring heteroatoms independently selected from N and O and optionally substituted with a halogen group, $C_1$-$C_6$ alkyl, ($C_1$-$C_6$ alkyl)OH, ($C_1$-$C_6$ alkyl)O($C_1$-$C_6$ alkyl), or $C_1$-$C_6$ fluoroalkyl;

Y, $Y^1$ and $Y^2$ are independently O or S;

t is 1, 2, 3, 4, 5 or 6; and n and m are independently 0, 1, 2, 3, 4, 5 or 6.

Compound of Formula Ia and Ib include compounds wherein:

X is O, S or $NR^{10}$;

$Z^2$ and $Z^3$ are independently selected from $CR^4$ and N, wherein zero or one of $Z^2$ and $Z^3$ is N;

$R^1$ is H, $C_1$-$C_{12}$ alkyl, $C_2$-$C_8$ alkenyl, $C_2$-$C_8$ alkynyl, —$C(=O)NR^{10}R^{11}$, or —$(CR^{14}R^{15})_t NR^{10}R^{11}$, or $R^1$ is $C_3$-$C_{12}$ carbocyclyl, $C_2$-$C_{20}$ heterocyclyl, $C_6$-$C_{20}$ aryl or $C_1$-$C_{20}$ heteroaryl, wherein said alkyl, alkenyl, alkynyl, carbocyclyl, heterocyclyl, aryl and heteroaryl are optionally substituted with one or more groups independently selected from F, Cl, Br, I, CN, $CF_3$, oxo, —$OR^{10}$, $SR^{10}$, —$C(=Y)R^{10}$, —$C(=Y)OR^{10}$, —$C(=Y)NR^{10}R^{11}$, —$(CR^{14}R^{15})_n NR^{10}R^{11}$, —$NR^{10}C(=Y)R^{13}$, —$NR^{10}C(=Y)OR^{11}$, —$NR^{12}C(=Y)NR^{10}R^{11}$, —$NR^{12}SO_2R^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, $C_1$-$C_{20}$ heteroaryl, —$(CR^{14}R^{15})$—$NR^{12}C(=O)(CR^{14}R^{15})NR^{10}R^{11}$, and $(CR^{14}R^{15})_t NR^{10}R^{11}$, or $R^2$ is H, $CF_3$, CN, —$C(=Y)R^{10}$, —$C(=Y)OR^{10}$, —$C(=Y)NR^{10}R^{11}$, —$C(=O)NR^{12}(CR^{14}R^{15})_t NR^{10}R^{11}$, —$SR^{10}$, —$S(O)R^{10}$, —$S(O)_2R^{10}$, $S(O)_2NR^{10}R^{11}$, —$SC(=Y)R^{10}$, —$SC(=Y)OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, $(CH_2)_n OR^{10}$, $(CH_2)_n NR^{10}R^{11}$, heteroaryl and heterocyclyl;

$R^3$ is $C_3$-$C_{12}$ carbocyclyl, $C_2$-$C_{20}$ heterocyclyl, $C_6$-$C_{20}$ aryl or $C_1$-$C_{20}$ heteroaryl, wherein said carbocyclyl, heterocyclyl, aryl and heteroaryl are optionally substituted with one or more groups independently selected from F, Cl, Br, I, CN, $CF_3$, $OR^{10}$, $SR^{10}$, —$C(=Y)R^{10}$, —$C(=Y)OR^{10}$, —$C(=Y)NR^{10}R^{11}$, —$NR^{10}R^{11}$, —$NR^{10}C(=Y)R^{13}$, —$NR^{10}C(=Y)OR^{11}$, —$NR^{12}C(=Y)NR^{10}R^{11}$, —$NR^{12}C(=O)C(=O)R^{10}R^{11}$, —$NR^{12}C(=O)C(=O)OR^a$, —$NR^{12}SO_2R^{10}$, —$NR^{12}C(=Y^1)(CR^{14}R^{15})_n C(=Y^2)NR^{10}R^{11}$, —$NR^{12}C(=Y^1)NR^{10}C(=Y^2)(CR^{14}R^{15})_n R^{11}$, —$NR^{12}C(=Y^1)(CR^{14}R^{15})_n C(=Y^2)(CR^{14}R^{15})_m R^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from F, Cl, Br, I, OH, $C_1$-$C_{12}$ alkyl, $NR^{10}R^{11}$, and $(CR^{14}R^{15})_n$-aryl;

$R^4$ is H, F, Cl, Br, $CF_3$, CN, —$C(=Y)R^{10}$, —$C(=Y)OR^{10}$, —$C(=Y)NR^{10}R^{11}$, —$NR^{10}R^{11}$, $NR^{10}C(=Y)R^{11}$, $NR^{10}C(=Y)OR^{11}$, $NR^{12}C(=Y)NR^{10}R^{11}$, —$NR^{12}SO_2NR^{10}R^{11}$, —$OR^{10}$, —$OC(=Y)R^{10}$, —$OC(=Y)OR^{10}$, —$OC(=Y)NR^{10}R^{11}$, —$C(=O)NR^{12}(CR^{14}R^{15})_t NR^{10}R^{11}$, —$OP(=Y)(OR^{10})(OR^{11})$, —$OP(OR^{10})(OR^{11})$, —$SR^{10}$, —$S(O)R^{10}$, —$S(O)_2R^{10}$, —$S(O)_2NR^{10}R^{11}$, —$SC(=Y)R^{10}$, —$SC(=Y)OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, $SO_2R^c$, CN, $OR^a$, $NR^aR^b$, $C(=O)NR^aR^b$, $CR^aC(=O)R^b$, $C_1$-$C_{12}$ alkyl, $C_2$-$C_8$ alkenyl, $C_2$-$C_8$ alkynyl, $C_3$-$C_{12}$ carbocyclyl, $C_6$-$C_{20}$ aryl, and $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_n OR^a$, $NR^aR^b$, $CF_3$, F, Cl, Br, I, $SO_2R^a$, $C(=O)R^a$, $NR^{10}C(=Y)R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, or $R^{10}$ and $R^{12}$ together with the atoms to which they are attached form an oxo-substituted $C_3$-$C_{20}$ heterocyclic ring optionally fused to a benzene ring;

$R^{13}$ is H, $C_1$-$C_{12}$ alkyl, $C_2$-$C_8$ alkenyl, $C_2$-$C_8$ alkynyl, $(CR^{14}R^{15})_n$-cycloalkyl, $(CR^{14}R^{15})_n$-heterocyclyl, $(CR^{14}R^{15})_n$-aryl, $(CR^{14}R^{15})_n$-heteroaryl, $(CR^{14}R^{15})_n$—O—$(CR^{14}R^{15})_m$-aryl, $(CR^{14}R^{15})_n$—$OR^{10}$, $(CR^{14}R^{15})_n$—$NR^{10}R^{11}$, $(CR^{14}R^{15})_n$—$NR^{10}C(=O)R^{11}$, or $(CR^{14}R^{15})_n$—$NR^{10}(SO_2Me)$—$R^{11}$, wherein said alkyl, alkenyl, alkynyl, cycloalkyl, heterocycloalkyl, and heteroaryl portions are optionally substituted with one or more groups independently selected from F, Cl, Br, I, oxo, $SO_2R^c$, CN, $OR^a$, $C(=O)R^a$, $C(=O)OR^a$, $NR^aR^b$, $NR^aC(=O)R^b$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, and $C_1$-$C_{20}$ heteroaryl;

each $R^{14}$ and $R^{15}$ is independently H, $C_1$-$C_{12}$ alkyl, or $(CH_2)_t$-aryl, or $R^{14}$ and $R^{15}$ together with the atoms to which they are attached form a saturated or partially unsaturated $C_3$-$C_{12}$ carbocyclic ring, or $R^{10}$ and $R^{15}$ together with the atoms to which they are attached form an oxo-substituted saturated or partially unsaturated $C_1$-$C_{20}$ heterocyclic ring optionally further substituted with one or more groups independently selected from F, Cl, Br, I, $OR^a$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, or $C_1$-$C_{20}$ heteroaryl, wherein said alkyl and aryl are optionally substituted with one or more groups independently selected from F, Cl, Br, and I, or $R^{14}$ is null and $R^{10}$ and $R^{15}$ together with the atoms to which they are attached form a $C_1$-$C_{20}$ heteroaryl ring having one or more heteroatoms;

$R^a$ and $R^b$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more alkyl groups;

$R^c$ is $C_1$-$C_{12}$ alkyl or $C_6$-$C_{20}$ aryl, wherein said alkyl and aryl are optionally substituted with one or more groups independently selected from F, Cl, Br, I, $OR^a$ and $C(=O)NR^aR^b$;

Y, $Y^1$ and $Y^2$ are independently O or S;

t is 1, 2, 3, 4, 5 or 6; and n and m are independently 0, 1, 2, 3, 4, 5 or 6.

Compounds of Formula Ia and Ib further include compounds of Formula Ia' and Ib':

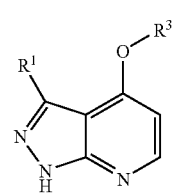

Ia'

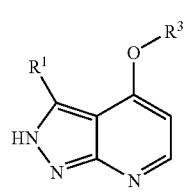

Ib' wherein $R^1$ is H, $C_1$-$C_{12}$ alkyl, $C_2$-$C_8$ alkenyl, $C_2$-$C_8$ alkynyl, —$C(=O)NR^{10}R^{11}$, or —$(CR^{14}R^{15})_t NR^{10}R^{11}$, or $R^1$ is $C_3$-$C_{12}$ carbocyclyl, $C_2$-$C_{20}$ heterocyclyl, $C_6$-$C_{20}$ aryl or $C_1$-$C_{20}$ heteroaryl, wherein said alkyl, alkenyl, alkynyl, carbocyclyl, heterocyclyl, aryl and heteroaryl are optionally substituted with one or more groups independently selected from F, Cl, Br, I, CN, $CF_3$, oxo, —$OR^{10}$, $SR^{10}$, —$C(=Y)R^{10}$, —$C(=Y)OR^{10}$, —$C(=Y)NR^{10}R^{11}$, —$(CR^{14}R^{15})_n$—$NR^{10}R^{11}$, —$NR^{10}C(=Y)R^{13}$, —$NR^{10}C(=Y)OR^{11}$, —$NR^{12}C(=Y)NR^{10}R^{11}$, —$NR^{12}SO_2R^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, $C_1$-$C_{20}$ heteroaryl, —$(CR^{14}R^{15})$—$NR^{12}C(=O)(CR^{14}R^{15})NR^{10}R^{11}$, and $(CR^{14}R^{15})_t NR^{10}R^{11}$, or $R^1$ is $NR^xR^y$; and $R^3$ is $C_3$-$C_{12}$ carbocyclyl, $C_2$-$C_{20}$ heterocyclyl, $C_6$-$C_{20}$ aryl or $C_1$-$C_{20}$ heteroaryl, wherein said carbocyclyl, heterocyclyl, aryl and heteroaryl are optionally substituted with one or more groups independently selected from F, Cl, Br, I, CN, $CF_3$, $OR^{10}$, $SR^{10}$, —$C(=Y)R^{10}$, —$C(=Y)OR^{10}$, —$C(=Y)NR^{10}R^{11}$, —$NR^{10}R^{11}$, —$NR^{10}C(=Y)R^{13}$, —$NR^{10}C(=Y)OR^{11}$, —$NR^{12}C(=Y)NR^{10}R^{11}$, —$NR^{12}C(=O)C(=O)R^{10}R^{11}$, —$NR^{12}C(=O)C(=O)OR^a$, —$NR^{12}SO_2R^{10}$, —$NR^{12}C(=Y^1)(CR^{14}R^{15})_nC(=Y^2)NR^{10}R^{11}$, —$NR^{12}C(=Y^1)NR^{10}C(=Y^2)R^{11}$, —$NR^{12}C(=Y^1)(CR^{14}R^{15})_nC(=Y^2)(CR^{14}R^{15})_mR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from F, Cl, Br, I, OH, $C_1$-$C_{12}$ alkyl, $NR^{10}R^{11}$, and $(CR^{14}R^{15})_n$-aryl.

In certain embodiments, X is O.

In certain embodiments, X is S.

In certain embodiments, X is $NR^{10}$. In certain embodiments, $R^{10}$ is $C_1$-$C_6$ alkyl. In certain embodiments, X is NH.

In certain embodiments, X is $NR^{10}$. In certain embodiments, $R^{10}$ is $(CR^{14}R^{15})_n C_2$-$C_{20}$ heterocyclyl. In certain embodiments, $R^{14}$ and $R^{15}$ are hydrogen. In certain embodiments n is 2. In certain embodiments $R^{10}$ is $(CH_2CH_2)C_4$ heterocyclyl. In certain embodiments, the heterocyclyl is a morpholinyl group.

Exemplary embodiments of X include the following structures:

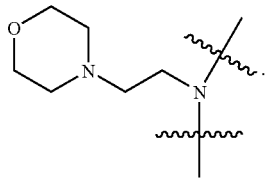

wherein the wavy lines indicate the points of attachment to the pyrazolo[3,4-b]pyridine and $R^3$.

In certain embodiments, $Z^2$ is CH, CCl, CF, or CC(=O)NH_2.

In certain embodiments, $Z^3$ is CH.

Formula Ia and Ib compounds are regioisomers, differing by the attachment of $R^2$ at the non-equivalent nitrogen atoms of the pyrazole ring. Formula Ia and Ib compounds include embodiments wherein:

(i) $Z^2$ and $Z^3$ are $CR^4$, wherein each $R^4$ is independent of the other

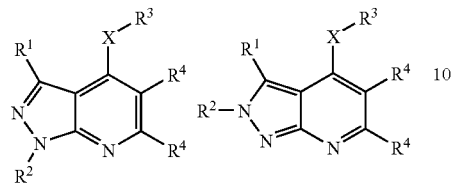

(ii) $Z^3$ is N and $Z^2$ is $CR^4$

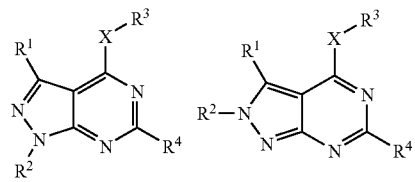

(iii) $Z^2$ is N and $Z^3$ is $CR^4$

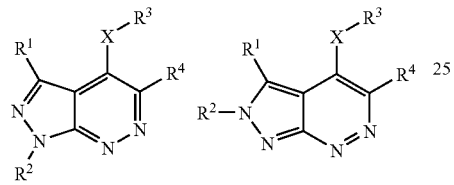

Exemplary embodiments of Formula Ia and Ib compounds include, but are not limited to, the following structures:

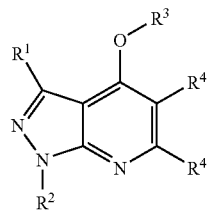 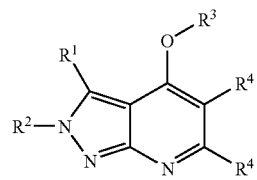

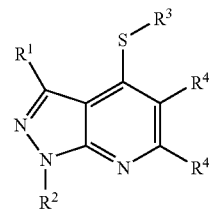 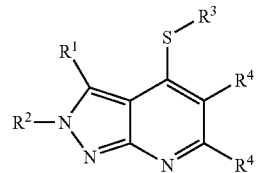

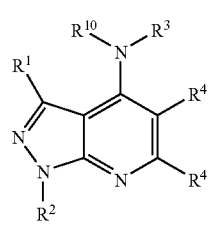 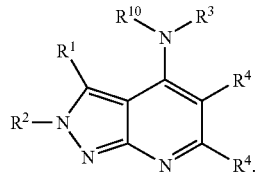

In certain embodiments, $R^2$ is H, $C_1$-$C_4$ alkyl, $CF_3$, $CHF_2$ or $CH_2F$.

In particular embodiments, $R^2$ is $C_3$-$C_6$ alkyl.

In other embodiments, $R^2$ is H.

In certain embodiments, $R^1$ is H, $C_1$-$C_4$ alkyl, $CF_3$, $CHF_2$ or $CH_2F$.

In certain embodiments, $R^1$ is optionally substituted alkynyl. For example, in certain embodiments $R^1$ is alkynyl optionally substituted by —$(CR^{14}R^{15})$—$NR^{12}C(=O)(CR^{14}R^{15})NR^{10}R^{11}$ or —$(CR^4R^5)_tNR^{10}R^{11}$, wherein t, $R^{10}$, $R^{11}$, $R^{12}$, $R^{14}$, and $R^{15}$ are as defined herein.

In certain embodiments, t is 1.

In certain embodiments, $R^{10}$ is H or $C_1$-$C_6$ alkyl.

In certain embodiments, $R^{11}$ is H or $C_1$-$C_6$ alkyl.

In other embodiments, $R^{10}$ and $R^{11}$ together with the nitrogen atom to which they are attached form a 5-6 membered heterocyclic ring optionally having a second ring heteroatom selected from N, O, SO and $SO_2$ and optionally substituted with one or two groups independently selected from $N(C_1$-$C_6$ alkyl$)_2$, OH, $CF_3$ and $C(=O)(C_1$-$C_6$ alkyl).

In certain embodiments, $R^{12}$ is H or $C_1$-$C_6$ alkyl.

In certain embodiments, $R^{14}$ and $R^{15}$ are H or Me.

Exemplary embodiments include the following structures:

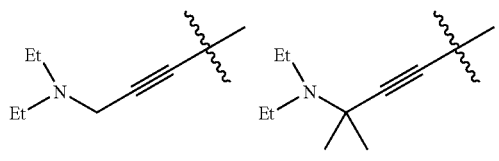

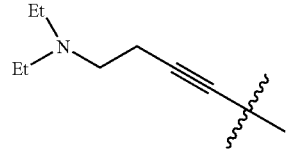

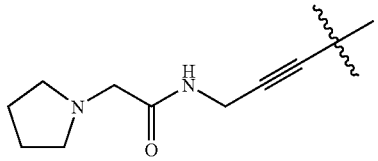

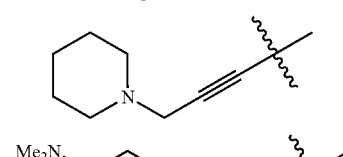

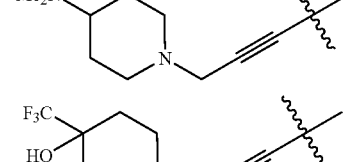

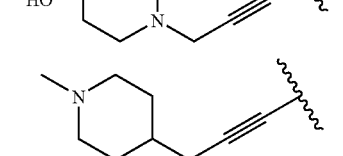

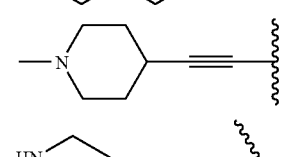

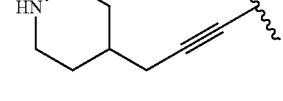

-continued

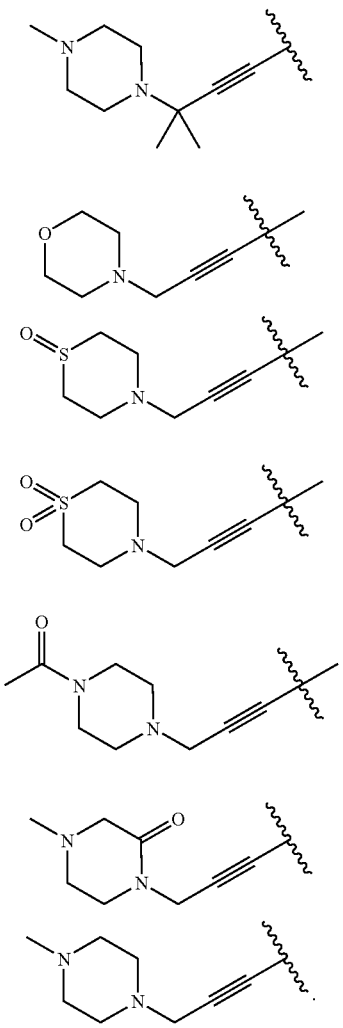

In certain embodiments, $R^1$ is an optionally substituted aryl or heteroaryl.

In certain embodiments, $R^1$ is phenyl optionally substituted with halogen (e.g., F or Cl), $C_1$-$C_6$ alkyl, $C(=O)C_1$-$C_6$ alkyl, $C(=O)(C_3$-$C_6$ cycloalkyl), $C(=O)O(C_1$-$C_6$ alkyl), $CH_2$-heteroaryl (wherein said heteroaryl is a 5 membered ring having 2-3 ring nitrogen atoms), $CH_2$-hetCyc (wherein hetCyc is a 6 membered ring having 1 to 2 ring heteroatoms independently selected from N and O and optionally substituted with $C_1$-$C_6$ alkyl), $C(=O)NH(CH_2)_2$-hetCyc wherein hetCyc is a 6 membered ring having 1 to 2 ring heteroatoms independently selected from N and O), $SO_2NH(C_1$-$C_6$ alkyl), NMeOMe, $C(=O)NR^hR^i$, or $NR^hR^i$ wherein $R^h$ and $R^i$ are independently H or $C_1$-$C_6$ alkyl.

In certain embodiments, $R^1$ is a phenyl group fused to a 6, 7, or 8 membered azacyclic ring (such as a piperidinyl ring) optionally substituted with oxo.

In certain embodiments, $R^1$ is a 5-6 membered heteroaryl having a ring heteroatom selected from N and O and optionally substituted with $C(=O)NH(C_1$-$C_6$ alkyl) or $CH_2$-hetCyc wherein hetCyc is a 6 membered azacycle (such as a piperazinyl group) optionally substituted with $C_1$-$C_6$ alkyl.

Exemplary embodiments of $R^1$ include the following structures:

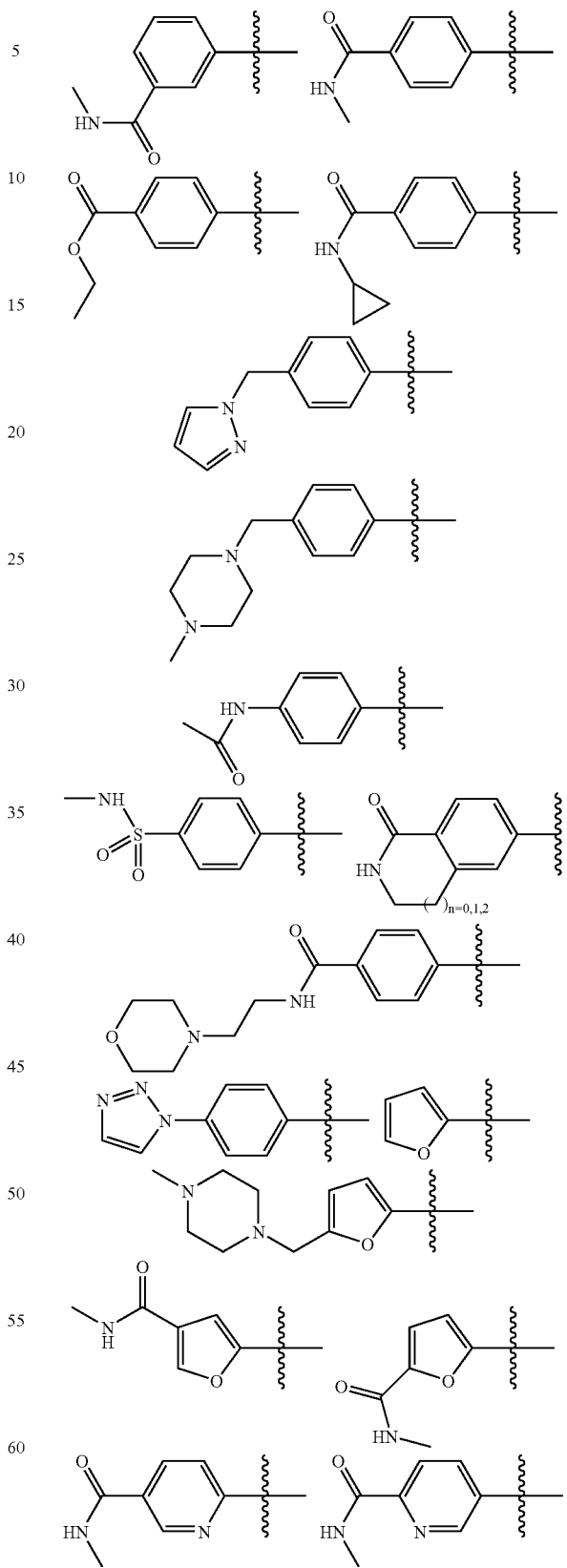

and substituted forms thereof.

Further exemplary embodiments of $R^1$ include the following structures:

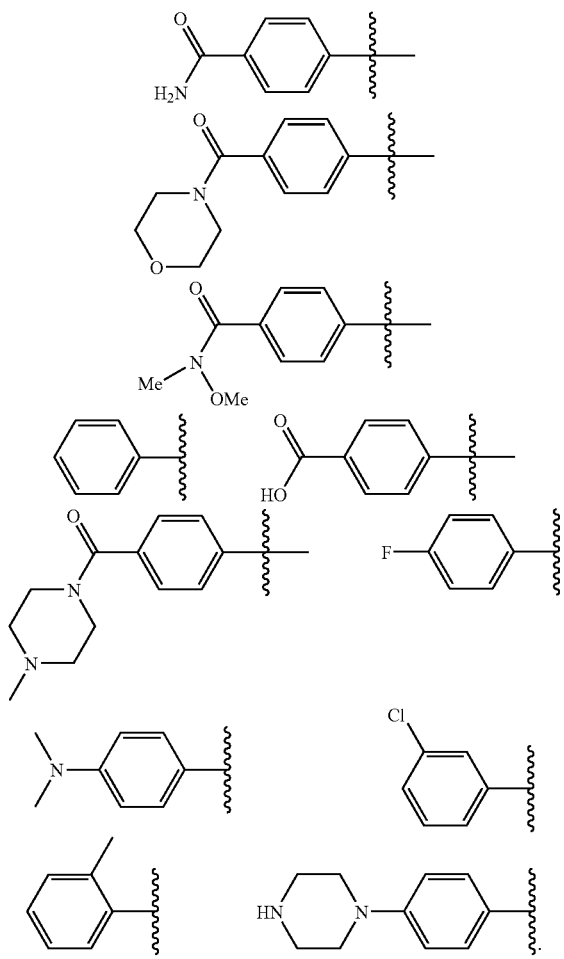

In certain embodiments, $R^1$ is a 5 membered heteroaryl having at least one N heteroatom and optionally substituted with $C_1$-$C_6$ alkyl.

Exemplary embodiments of $R^1$ include the following structures:

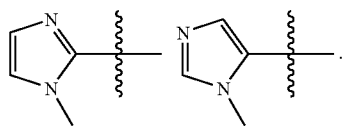

In certain embodiments, $R^1$ is —C(=O)$NR^{10}R^{11}$ or —(C$R^{14}R^{15}$)$_t$$NR^{10}R^{11}$.

In certain embodiments, $R^{14}$ and $R^{15}$ are H.

In certain embodiments, $R^{10}$ is H or $C_1$-$C_6$ alkyl.

In certain embodiments, $R^{11}$ is $C_1$-$C_6$ alkyl or ($C_1$-$C_6$ alkyl) $OR^h$ wherein $R^h$ is H or $C_1$-$C_6$ alkyl.

In certain embodiments, $R^{10}$ and $R^{11}$ together with the nitrogen atom to which they are attached form a 6 membered ring optionally having a second ring heteroatom selected from N and O optionally substituted with $C_1$-$C_6$ alkyl.

Exemplary embodiments of $R^1$ include the following structures:

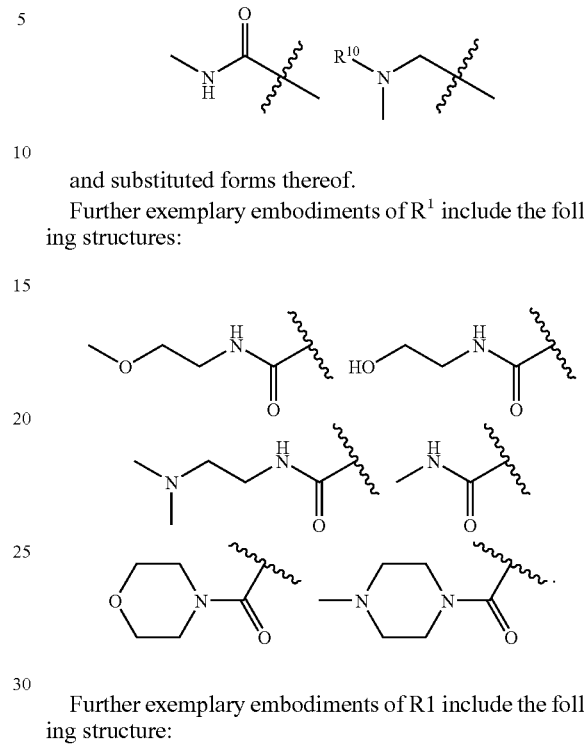

and substituted forms thereof.

Further exemplary embodiments of $R^1$ include the following structures:

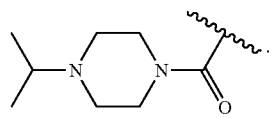

Further exemplary embodiments of R1 include the following structure:

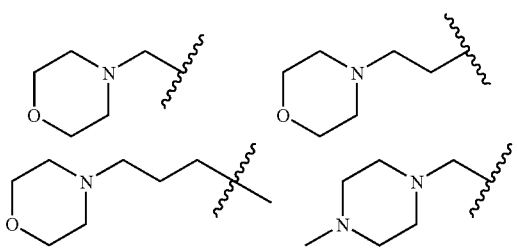

In certain embodiments of compounds of Formula Ia and Ib, $R^1$ is alkyl optionally substituted with one or more groups independently selected from $OR^{10}$, $(CH_2)_nNR^{10}R^{11}$, heterocyclyl and heteroaryl.

In certain embodiments, $R^1$ is alkyl substituted with a 6 membered heterocyclic group having a ring nitrogen atom and optionally having a second ring heteroatom selected from N and O, wherein said heterocyclic ring is optionally substituted with —O($C_1$-$C_6$ alkyl) or $C_1$-$C_6$ alkyl.

In certain embodiments, $R^1$ is alkyl substituted with a 5 membered heteroaryl group having one or two ring nitrogen heteroatoms.

Exemplary embodiments of $R^1$ include, but are not limited to, methyl, $CH_2OH$, $CH_2CH_2OH$, $CH_2CH_2CH_2OH$, $CH(OH)CH_2OH$, -continued

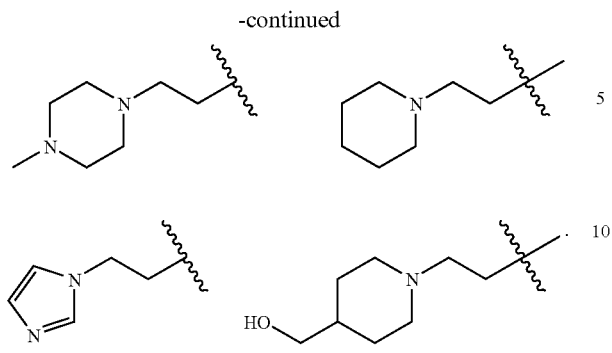

A further exemplary embodiment includes

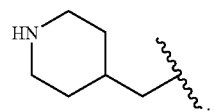

A further exemplary embodiment of $R^1$ includes the structure:

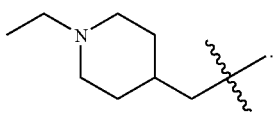

In certain embodiments of compounds of Formula Ia and Ib, $R^1$ is optionally substituted heteroaryl.

In certain embodiments, $R^1$ is a 5-6 membered heteroaryl ring having 1 to 2 ring heteroatoms independently selected from N and O and optionally substituted with one or two groups independently selected from Br, hetCyc and $CH_2$-hetCyc, wherein hetCyc is a 6 membered heterocyclic ring having a ring nitrogen atom and optionally having a second ring heteroatom selected from N and O, wherein hetCyc is optionally substituted with $C_1$-$C_6$ alkyl or ($C_1$-$C_6$ alkyl)OH.

Exemplary embodiments of $R^1$ include, but are not limited to, the following structures:

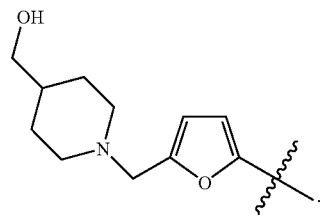

Further exemplary embodiments of $R^1$ include, but are not limited to, the following structures:

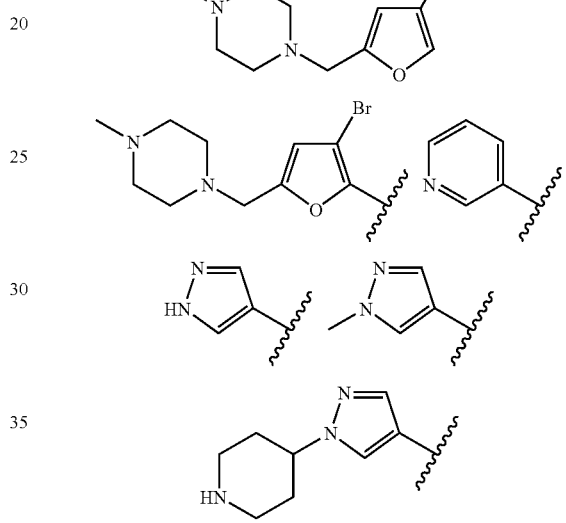

In certain embodiments of compounds of Formula Ia and Ib, $R^1$ is a saturated or partially unsaturated 5-10 membered monocyclic or bicyclic heterocyclic ring, wherein said ring has one or two ring atoms independently selected from N and O and is optionally substituted with $C_1$-$C_6$ alkyl, —($C_1$-$C_6$ alkyl)O($C_1$-$C_6$ alkyl), $NR^{10}R^{11}$ or $CH_2NR^{10}R^{11}$ wherein $R^{10}$ and $R^{11}$ are independently H, $C_1$-$C_6$ alkyl, hetCyc or $CH_2$hetCyc wherein hetCyc is a 5-6 membered ring having one or 2 ring nitrogen atoms. Exemplary embodiments of $R^1$ include, but are not limited to, the following structures:

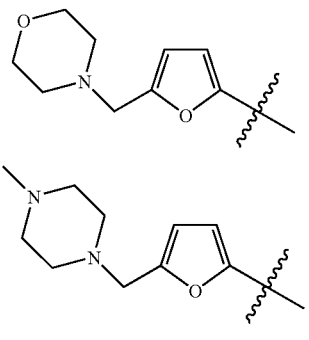

-continued

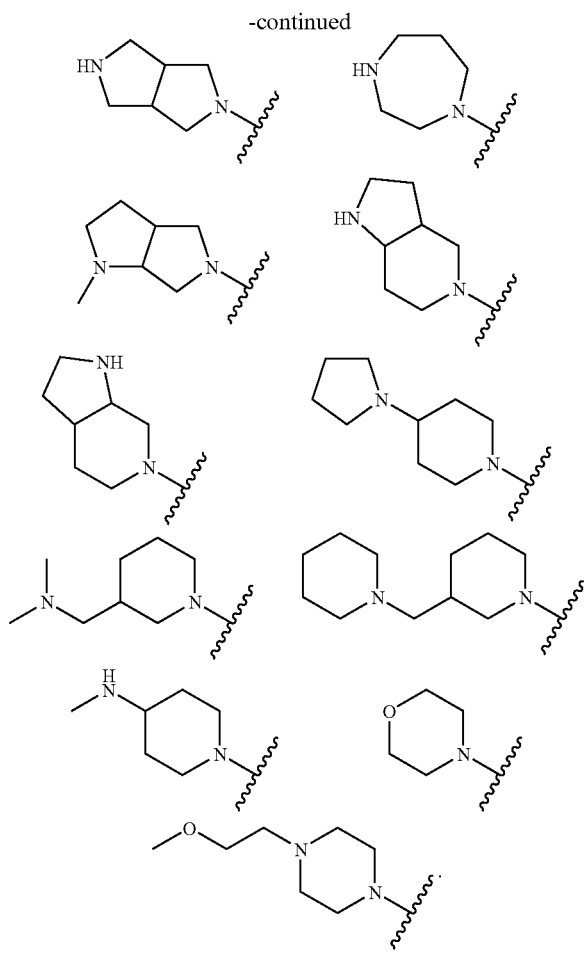

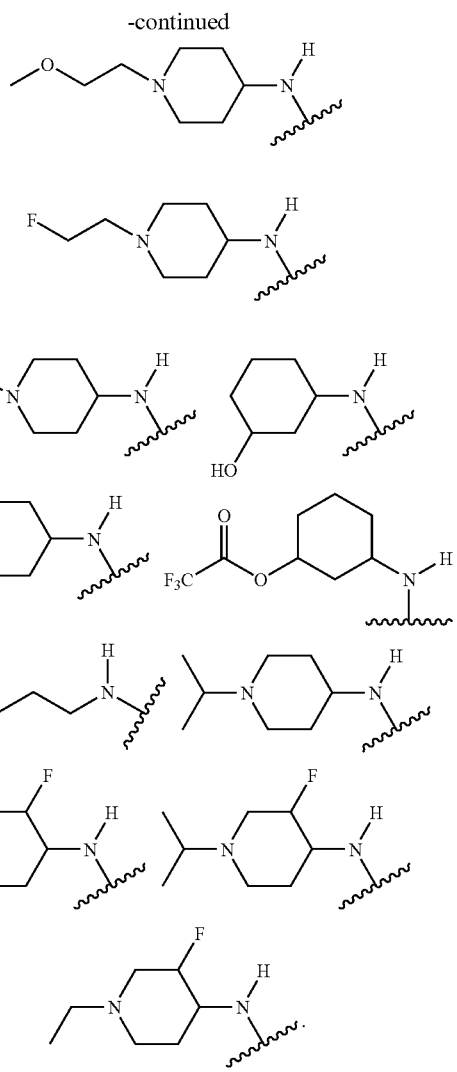

In certain embodiments of compounds of Formula Ia and Ib, $R^1$ is $NR^xR^y$.

In certain embodiments, $R^x$ is H or Me.

In certain embodiments, $R^y$ is (i) $(C_1-C_6$ alkyl)$NR^jR^k$ wherein $R^j$ and $R^k$ are independently H or $C_1-C_6$ alkyl; (ii) cyclohexyl optionally substituted with OH or $OC(=O)CF_3$; or (iii) a 5-6 membered heterocyclic ring having a ring heteroatom selected from N and O and optionally substituted with F, $(C_1-C_6$ alkyl), $(C_1-C_6$ alkyl)OH, $(C_1-C_6$ alkyl)O$(C_1-C_6$ alkyl) or $(C_1-C_6$ fluoroalkyl).

Exemplary embodiments of $R^1$ include, but are not limited to, the following structures:

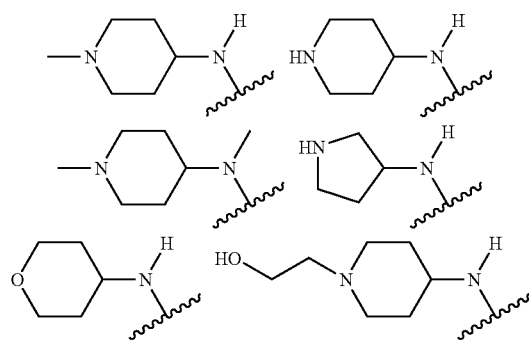

In certain embodiments of compounds of Formula Ia and Ib, $R^1$ is —$CR^{14}R^{15})_tNR^{10}R^{11}$. In certain embodiments, t is 0. In certain embodiments, $R^{10}$ is H. In certain embodiments $R^{11}$ is an 8 membered bicyclic heterocyclic ring having a N heteroatom and optionally substituted with $C_1-C_6$ alkyl.

Exemplary embodiments of R1 include the structure:

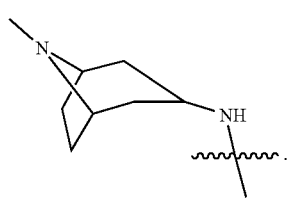

In certain embodiments of compounds of Formula Ia and Ib, $R^1$ is —$C(=Y)OR^{10}$. In certain embodiments, Y is O. In certain embodiments, $R^{10}$ is $C_1-C_6$ alkyl. A particular example is —$C(O)OCH_3$.

In certain embodiments of compounds of Formula Ia and Ib, $R^3$ has the structure:

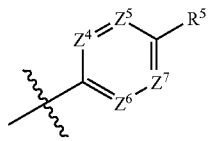

wherein the wavy line indicates the point of attachment to X;

$Z^4$, $Z^5$, $Z^6$, and $Z^7$ are independently $CR^{4a}$ or N and 0, 1, or 2 of $Z^4$, $Z^5$, $Z^6$, and $Z^7$ is N, wherein when $Z^4$ and $Z^5$ or $Z^6$ and $Z^7$ are $CR^{4a}$, then $Z^4$ and $Z^5$ or $Z^6$ and $Z^7$ optionally form a saturated, partially unsaturated or fully unsaturated carbocyclic or heterocyclic ring;

each $R^{4a}$ is independently H, F, Cl, Br, $CF_3$, CN, —C(=Y)$R^{10}$, —C(=Y)$OR^{10}$, —C(=Y)$NR^{10}R^{11}$, —$NR^{10}R^{11}$, $NR^{10}C(=Y)R^{11}$, $NR^{10}C(=Y)OR^{11}$, $NR^{12}C(=Y)NR^{10}R^{11}$, —$NR^{12}SO_2NR^{10}R^{11}$, —$OR^{10}$, —OC(=Y)$R^{10}$, —OC(=Y)$OR^{10}$, —OC(=Y)$NR^{10}R^{11}$, —C(=O)$NR^{12}(CR^{14}R^{15})_t$ $NR^{10}R^{11}$, —OP(=Y)($OR^{10}$)($OR^{11}$), —OP($OR^{10}$)($OR^{11}$), —$SR^{10}$, —S(O)$R^{10}$, —S(O)$_2R^{10}$, —S(O)$_2NR^{10}R^{11}$, —SC(=Y)$R^{10}$, —SC(=Y)$OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^5$ is F, Cl, Br, I, CN, $CF_3$, $OR^{10}$, $SR^{10}$, —C(=Y)$R^{10}$, —C(=Y)$OR^{10}$, —C(=Y)$NR^{10}R^{11}$, —$NR^{10}R^{11}$, —$NR^{10}C(=Y)R^{13}$, —$NR^{10}C(=Y)OR^{11}$, —$NR^{12}C(=Y)NR^{10}R^{11}$, —$NR^{12}C(=O)C(=O)R^{10}R^{11}$, —$NR^{12}C(=O)C(=O)OR^a$, —$NR^{12}SO_2R^{10}$, —$NR^{12}C(=Y^1)(CR^{14}R^{15})_nC(=Y^2)NR^{10}R^{11}$, —$NR^{12}C(=Y^1)NR^{10}C(=Y^2)(CR^{14}R^{15})_nR^{11}$, —$NR^{12}C(=Y^1)(CR^{14}R^{15})_nC(=Y^2)(CR^{14}R^{15})_mR^{10}$, —OC(=Y)$R^{10}$, —OC(=Y)$OR^{10}$, —OC(=Y)$NR^{10}R^{11}$, —OS(O)$_2$($OR^{10}$), —OP(=Y)($OR^{10}$)($OR^{11}$), —OP($OR^{10}$)($OR^{11}$), —S(O)$R^{10}$, —S(O)$_2R^{10}$, —S(O)$_2NR^{10}R^{11}$, —S(O)($OR^{10}$), —S(O)$_2$($OR^{10}$), —SC(=Y)$R^{10}$, —SC(=Y)$OR^{10}$, —SC(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from alkyl, $NR^{10}R^{11}$, and $(CR^{14}R^{15})_n$-aryl.

In certain embodiments of $R^3$ as defined above, $R^{4a}$ is CH or N.

For example, in certain embodiments of Formula Ia and Ib compounds, $R^3$ is selected from the structures:

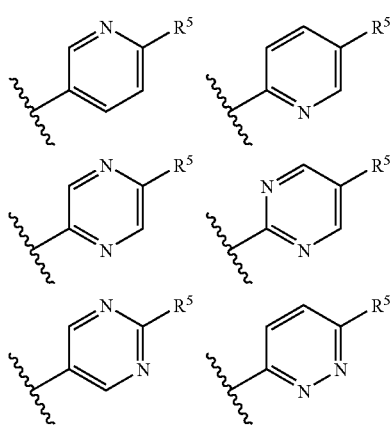

and substituted forms thereof, wherein the wavy line indicates the point of attachment to X, and $R^5$ is as defined herein. Exemplary embodiments of $R^3$ include the following structures:

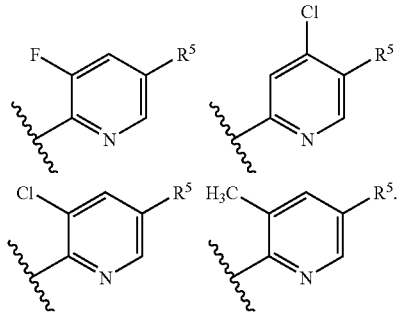

In certain embodiments of compounds of Formula Ia and Ib, $R^3$ is a bicyclic heteroaryl ring substituted with an $R^5$ group, wherein $R^5$ is as defined above. An exemplary embodiment is the structure:

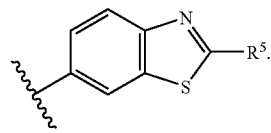

In certain embodiments of Formula Ia and Ib compounds, $R^3$ is selected from the structure:

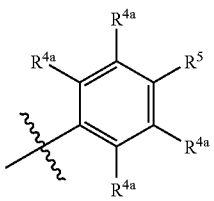

wherein the wavy line indicates the point of attachment to X, and $R^{4a}$ and $R^5$ are as defined herein.

In certain embodiments, each $R^{4a}$ is independently selected from H, F, Cl, $C_1$-$C_6$ alkyl, O—($C_1$-$C_6$ alkyl), and CN.

Exemplary embodiments of $R^3$ include the following structures:

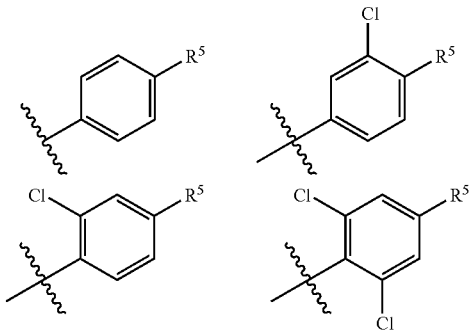

-continued

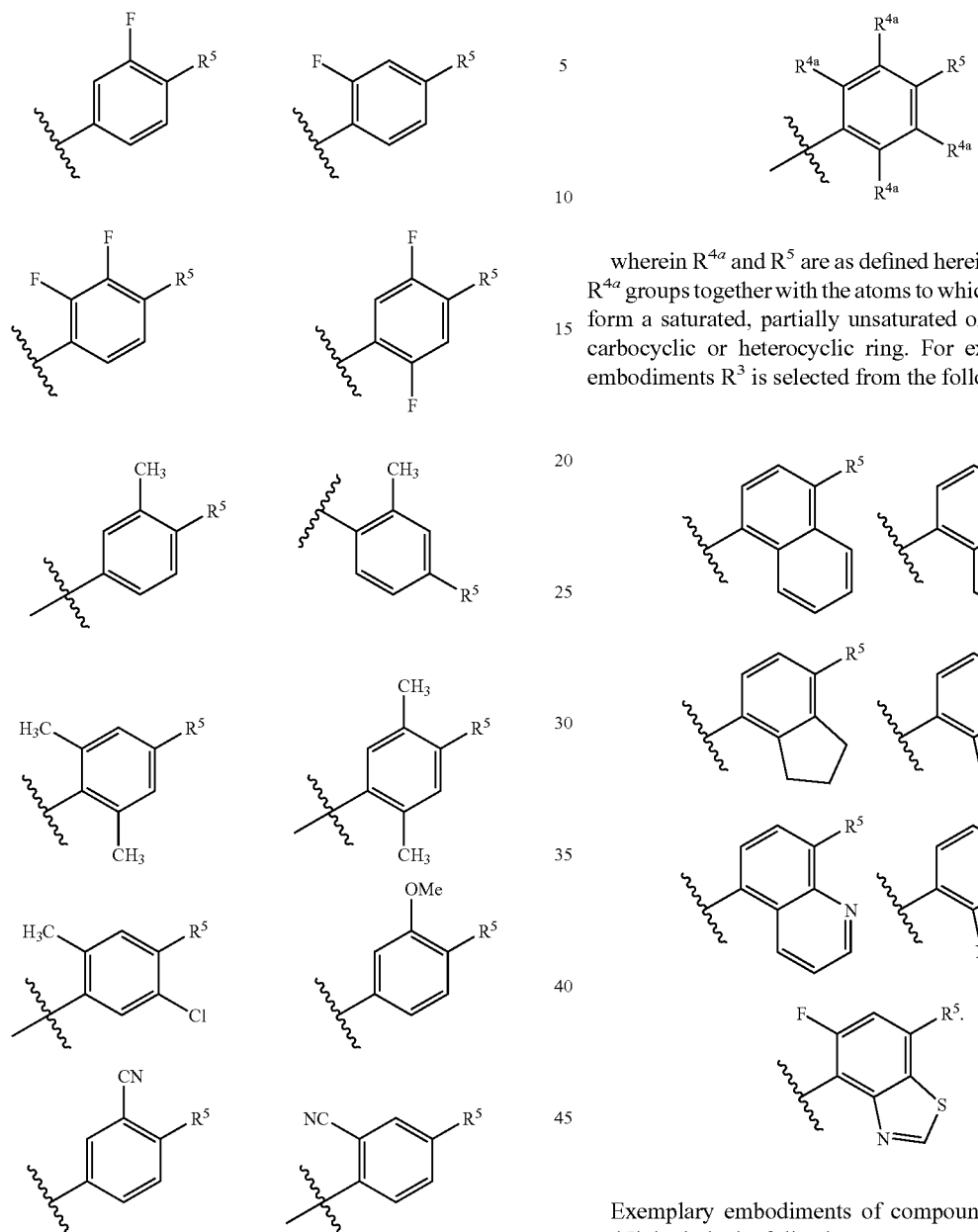

wherein the wavy line indicates the point of attachment to X, and $R^5$ is as defined herein.

Additional exemplary embodiments of $R^3$ include the structures:

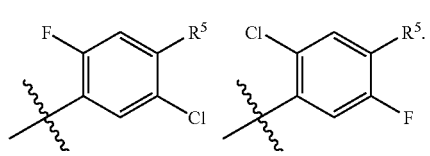

Further exemplary embodiments of Formula Ia and Ib compounds include compounds wherein $R^3$ is wherein $R^{4a}$ and $R^5$ are as defined herein and two adjacent $R^{4a}$ groups together with the atoms to which they are attached form a saturated, partially unsaturated or fully unsaturated carbocyclic or heterocyclic ring. For example, in certain embodiments $R^3$ is selected from the following structures:

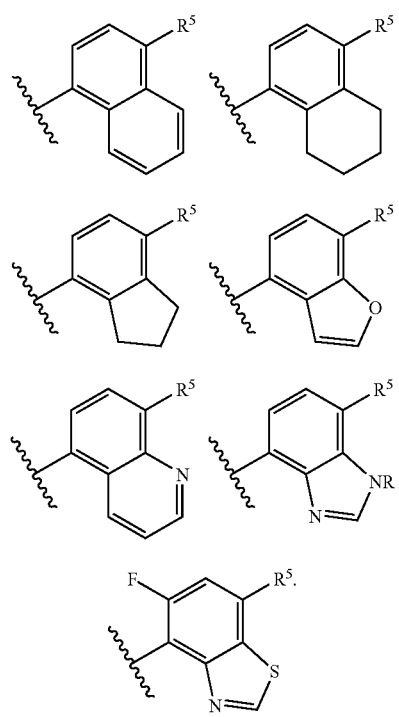

Exemplary embodiments of compounds of Formulas Ia and Ib include the following structures:

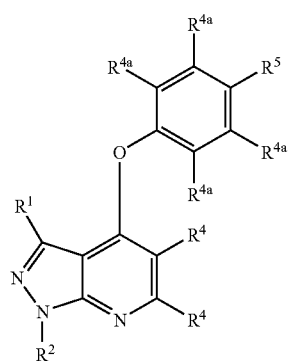

-continued

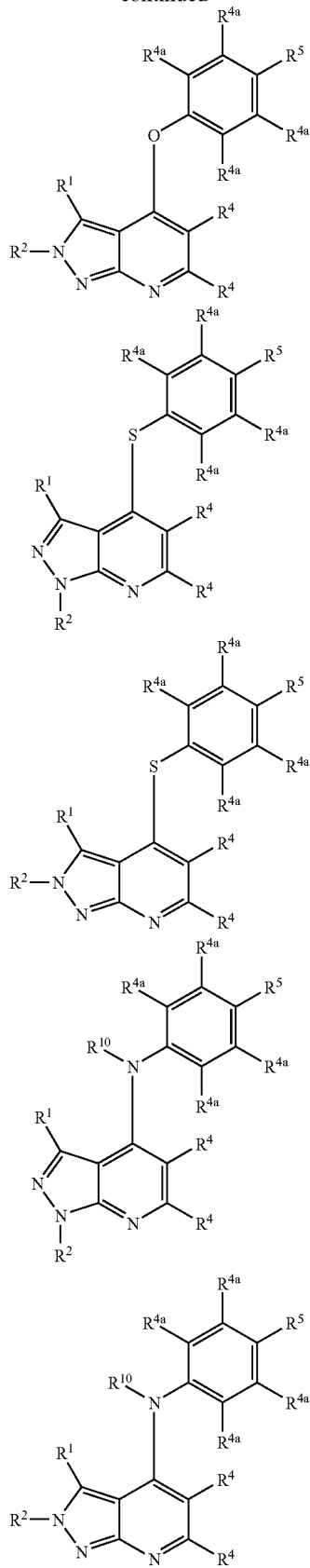

In certain embodiments of compounds of Formulas Ia and Ib, $R^5$ has the structure:

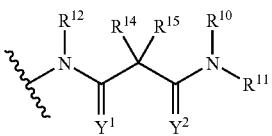

wherein $R^{10}$, $R^{11}$, $R^{12}$, $R^{14}$, $R^{15}$, $Y^1$ and $Y^2$ are as defined herein.

In certain embodiments, $Y^1$ is O.
In certain embodiments, $Y^2$ is O.
In certain embodiments, $R^{12}$ is H or $C_1$-$C_6$ alkyl.
In certain embodiments, $R^{14}$ is H.
In certain embodiments, $R^{15}$ is H.
In certain embodiments, $R^{10}$ is H.
In certain embodiments, $R^{11}$ is phenyl optionally substituted with a halogen group.

Exemplary embodiments of $R^5$ include the structure

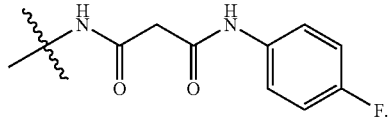

In further exemplary embodiments, $R^{14}$ and $R^{15}$ together with the atom to which they are attached form an optionally substituted carbocyclic ring. In certain embodiments, $R^{14}$ and $R^{15}$ together with the carbon atom to which they are attached form a cyclopropylidene group.

For example, in certain embodiments $R^5$ is:

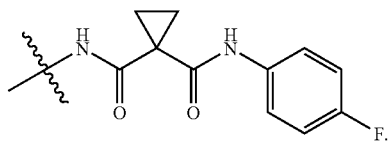

In further exemplary embodiments, $R^{15}$ and $R^{10}$ together with the atom to which they are attached form an oxo-substituted heterocyclic ring, wherein said heterocyclic ring is optionally further substituted.

In certain embodiments, $R^{10}$ and $R^{15}$ together with the atoms to which they are attached form an oxo-substituted 5, 6, or 7 membered azacyclic ring.

For example, in certain embodiments $R^5$ is selected from the structures:

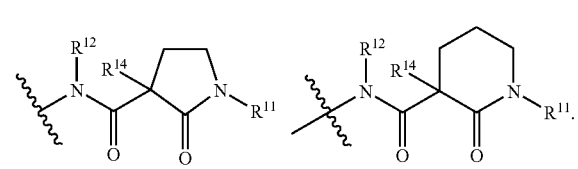

In certain embodiments, $R^{12}$ is H.
In certain embodiments, $R^{14}$ is H, methyl or benzyl.
In certain embodiments, $R^{11}$ is H, $C_1$-$C_6$ alkyl, or phenyl optionally substituted with one or two groups independently selected from F and Cl.

For example, in certain embodiments $R^5$ is selected from the structures:

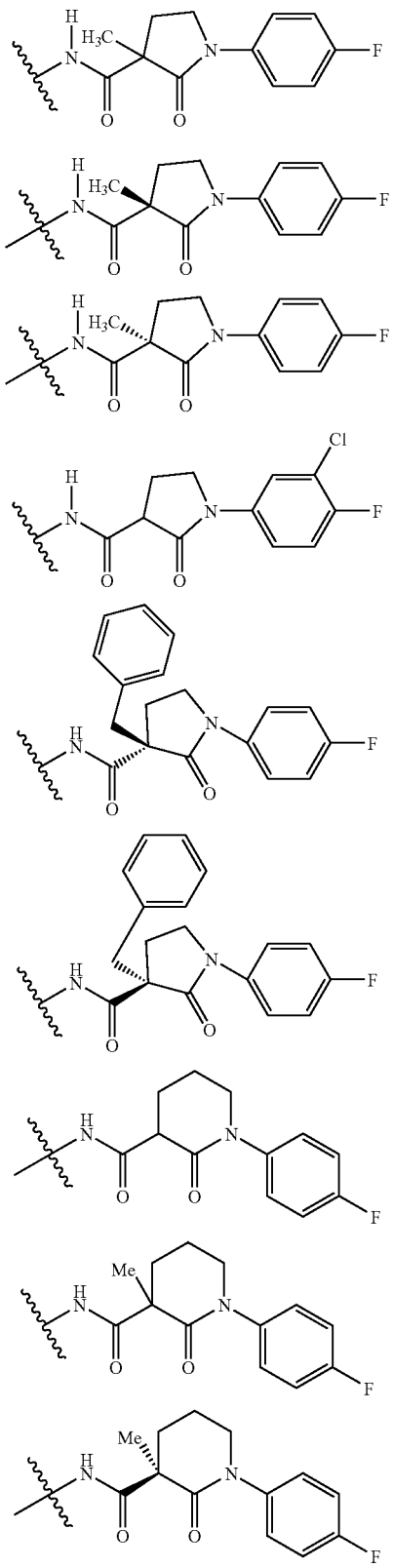

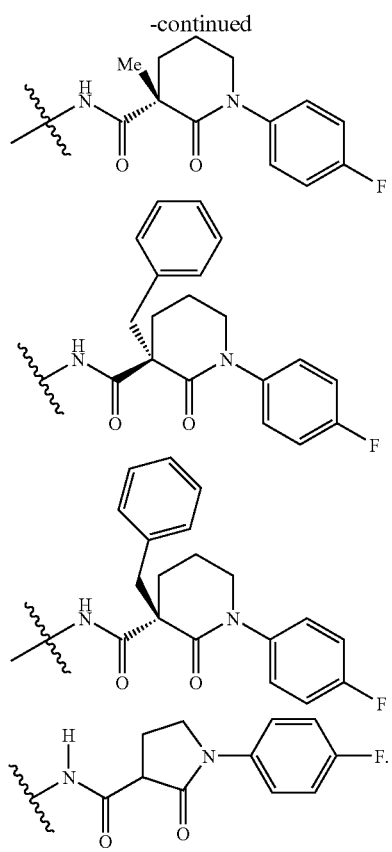

Further exemplary embodiments of $R^5$ include the structures:

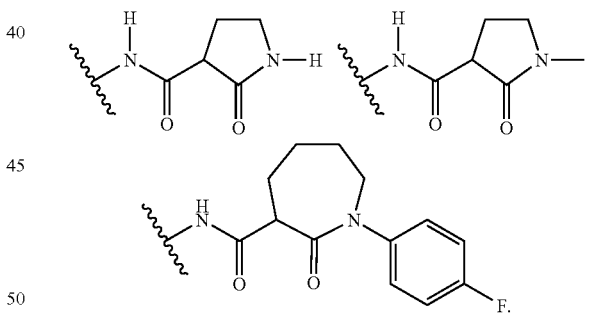

In further exemplary embodiments, $R^{15}$ and $R^{10}$ together with the atoms to which they are attached form an oxo-substituted bicyclic azacyclic ring, for example an oxo-substituted 6 membered bicyclic azacyclic ring such as an azabicyclo[3.1.0]hexane group. An exemplary embodiment of $R^5$ includes the structure:

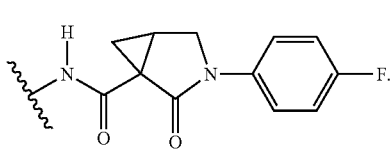

In further exemplary embodiments, $R^{14}$ is null and $R^{10}$ and $R^{15}$ together with the atoms to which they are attached form a heteroaryl ring having a ring nitrogen atom and substituted with =Y, wherein said heteroaryl ring optionally has one or more additional heteroatoms independently selected from N, O and S In certain embodiments, $R^{10}$ and $R^{15}$ together with the atoms to which they are attached form an oxo-substituted 6 membered heteroaryl ring having one or two ring nitrogen atoms.

For example, in certain embodiments $R^5$ is selected from the structures:

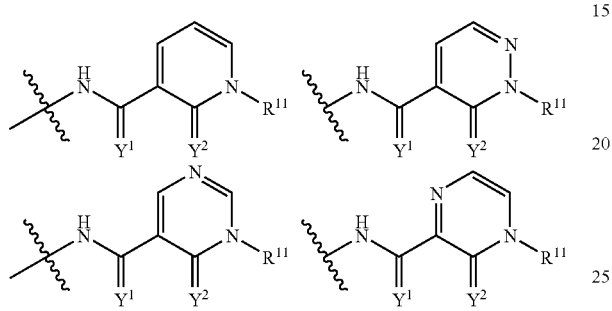

and substituted forms thereof, wherein $Y^1$, $Y^2$ and $R^{11}$ are as defined herein. In certain embodiments, $R^{11}$ is optionally substituted aryl, cycloalkyl, or alkyl.

In certain embodiments, $Y^1$ is O.
In certain embodiments, $Y^2$ is O.
In certain embodiments, $R^{11}$ is phenyl optionally substituted with F.
In certain embodiments, $R^{11}$ is benzyl.
In certain embodiments, $R^{11}$ is $C_1$-$C_6$ alkyl.

For example, in certain embodiments $R^5$ is selected from the structures:

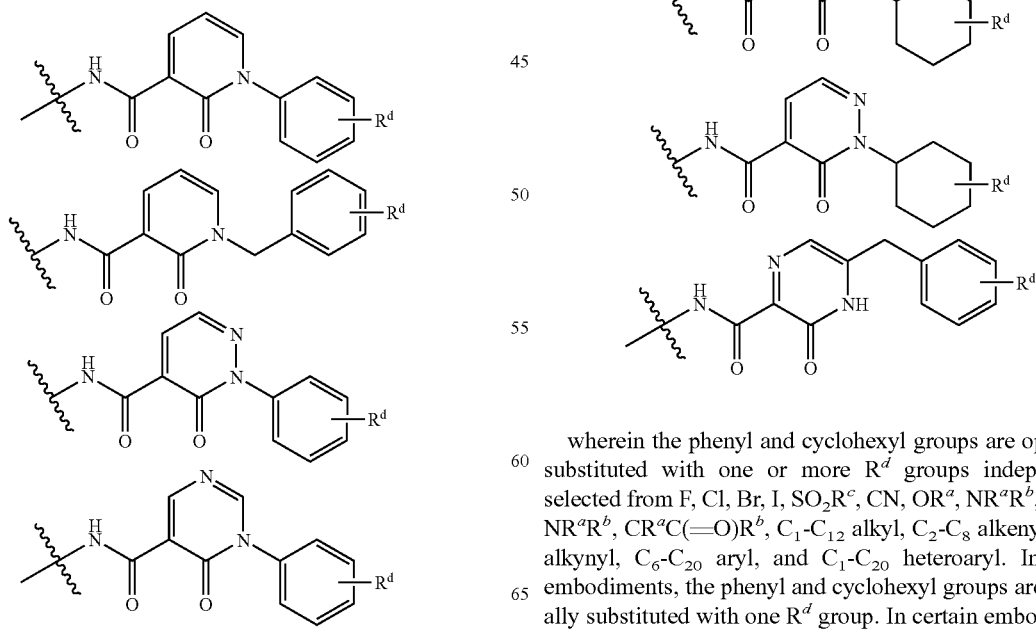

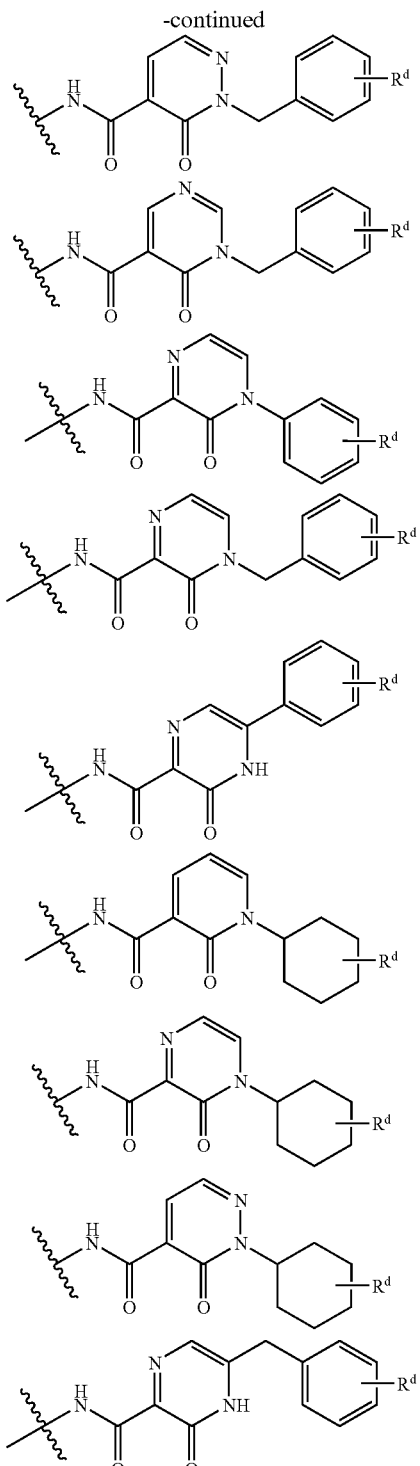

wherein the phenyl and cyclohexyl groups are optionally substituted with one or more $R^d$ groups independently selected from F, Cl, Br, I, $SO_2R^c$, CN, $OR^a$, $NR^aR^b$, C(=O)$NR^aR^b$, $CR^aC(=O)R^b$, $C_1$-$C_{12}$ alkyl, $C_2$-$C_8$ alkenyl, $C_2$-$C_8$ alkynyl, $C_6$-$C_{20}$ aryl, and $C_1$-$C_{20}$ heteroaryl. In certain embodiments, the phenyl and cyclohexyl groups are optionally substituted with one $R^d$ group. In certain embodiments, $R^d$ is F.

Exemplary embodiments of $R^5$ include the structures:

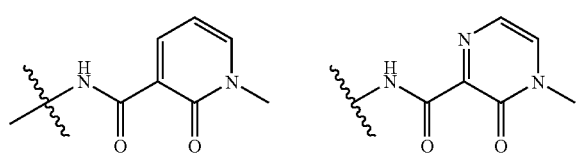

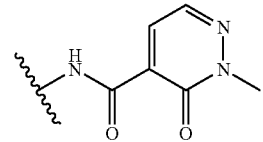

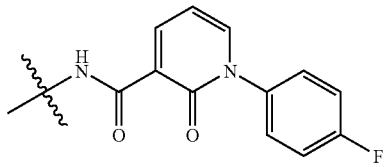

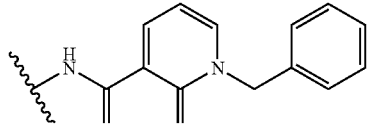

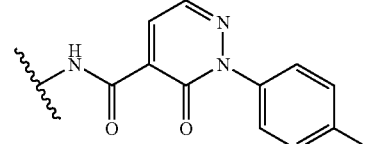

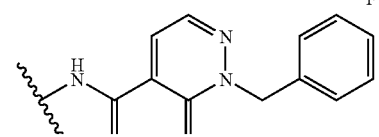

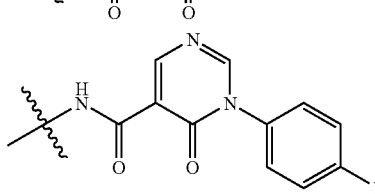

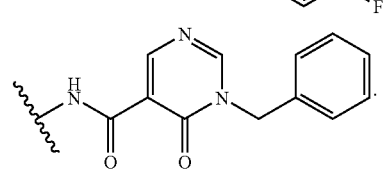

Further exemplary embodiments of R5 include the structure:

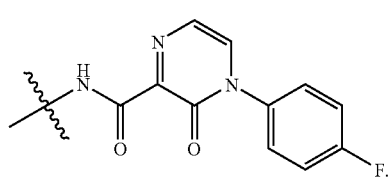

In certain embodiments, $R^{11}$ is an optionally substituted heteroaryl, such as a pyridyl group. An exemplary embodiment of $R^5$ includes the structure:

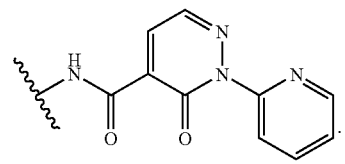

In certain embodiments of compounds of Formula Ia and Ib, $R^5$ has the structure:

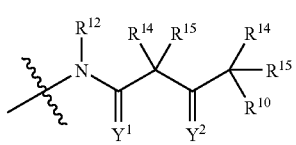

wherein $R^{10}$, $R^{12}$, $R^{14}$, $R^{15}$, $Y^1$ and $Y^2$ are as defined herein. In certain embodiments, $R^{14}$ and $R^{15}$ together with the atoms to which they are attached form an optionally substituted carbocyclic ring.

A particular example of $R^5$ is the structure:

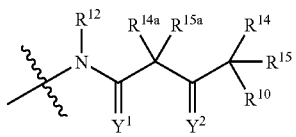

wherein $R^{10}$, $R^{12}$, $Y^1$ and $Y^2$ are as defined herein and $R^{14a}$ and $R^{15a}$ together with the carbon atom to which they are both attached form a spirocyclic carbocycle, such as a cyclopropylidene group.

In certain embodiments, $Y^1$ is O.

In certain embodiments, $Y^2$ is O.

In certain embodiments, $R^{14}$ and $R^{15}$ are H.

In certain embodiments, $R^{10}$ is phenyl optionally substituted with a halogen group. In certain embodiment, said phenyl is substituted with F.

For example, in certain embodiments $R^5$ is selected from the structures:

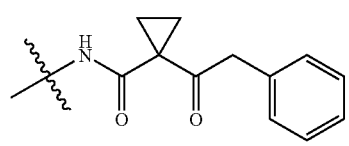

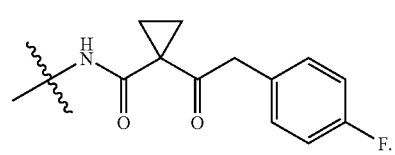

In certain embodiments of compounds of Formula Ia and Ib, $R^5$ has the structure:

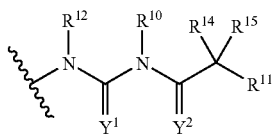

wherein $Y^1$, $Y^2$, $R^{10}$, $R^{11}$, $R^{12}$, $R^{14}$ and $R^{15}$ are as defined herein. In certain embodiments, $R^{11}$ is optionally substituted aryl.

In certain embodiments, $R^{12}$ is H or $C_1$-$C_6$ alkyl.
In certain embodiments, $R^{10}$ is H or $C_1$-$C_6$ alkyl.
In certain embodiments, $R^{14}$ is H.
In certain embodiments, $R^{15}$ is H.
In certain embodiments, $R^{11}$ is phenyl optionally substituted with halogen, for example a fluoro group.

For example, in certain embodiments $R^5$ is:

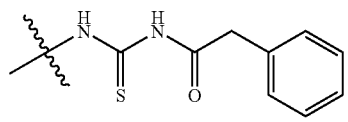

A further exemplary embodiment of $R^5$ is:

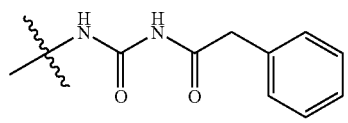

In certain embodiments of compounds of Formula Ia and Ib, $R^5$ has the following structure:

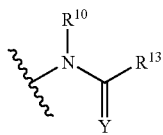

wherein Y, $R^{10}$ and $R^{13}$ are as defined herein.
In certain embodiments, Y is O.
In certain embodiments, $R^{10}$ is H.
In certain embodiments, $R^{10}$ is $CH_2Ph$.
In certain embodiments, $R^{13}$ is alkyl, $(CR^{14}R^{15})_n$—O—$(CR^{14}R^{15})_m$-aryl, $(CR^{14}R^{15})$-aryl, $(CR^{14}R^{15})$-heteroaryl, $(CR^{14}R^{15})$-heterocyclyl, $(CR^{14}R^{15})$—$N(SO_2R^a)(CR^{14}R^{15})R^{11}$, or $(CR^{14}R^{15})NR^{10}C(=O)$-aryl, wherein said alkyl, aryl, heteroaryl and heterocyclyl portions are optionally substituted.

In particular embodiments, $R^{13}$ is $CR^{14}R^{15}O(CH_2)_m$-phenyl, wherein phenyl is optionally substituted with halogen (for example Cl), $R^{14}$ and $R^{15}$ are independently H or methyl and m is 0 or 1.

In particular embodiments, $R^{13}$ is $OR^a$, wherein $R^a$ is $C_1$-$C_6$ alkyl or phenyl.

In particular embodiments, $R^{13}$ is $(C_1$-$C_3$ alkyl)-phenyl.

In particular embodiments, $R^{13}$ is $(C_1$-$C_2$ alkyl)-hetAr wherein hetAr is a 6 membered heteroaryl ring having one or two ring nitrogen atoms. A particular example of $R^{13}$ is $(C_1$-$C_2$ alkyl)-pyridyl.

In particular embodiments, $R^{13}$ is a 5-6 membered heteroaryl ring having 1 to 2 ring atoms independently selected from N, O and S and optionally substituted with one or two groups independently selected from NH-phenyl, morpholinyl, phenyl, and $C_1$-$C_6$ alkyl.

In particular embodiments, $R^{13}$ is phenyl optionally substituted with one or two groups independently selected from CN, F, phenyl, O-phenyl, $N(C_1$-$C_6$ alkyl$)_2$, and $NHC(=O)(C_1$-$C_6$ alkyl).

In particular embodiments, $R^{13}$ is $CH_2$—$N(C_1$-$C_4$ alkyl)$SO_2R^a$ or $CH_2$—$N(CH_2Ph)SO_2R^a$. In particular embodiments, $R^a$ is $C_1$-$C_6$ alkyl, phenyl or a 5 membered heteroaryl ring having one or two ring heteroatoms independently selected from N and O and optionally substituted with $C_1$-$C_6$ alkyl.

In certain embodiments, $R^{13}$ is $(CH_2)_n$-hetCyc wherein n is 0 or 1 and hetCyc is a saturated or partially saturated 6 membered heterocyclic ring having a ring nitrogen atom and optionally substituted with oxo, $C(=O)(C_1$-$C_6$ alkyl), $SO_2(C_1$-$C_6$ alkyl), $SO_2$-phenyl or $C(O)O(C_1$-$C_6$ alkyl).

In particular embodiments, $R^{13}$ is $C_1$-$C_6$ alkyl optionally substituted with $(C_3$-$C_6)$cycloalkyl or O—$(C_1$-$C_6$ alkyl).

In particular embodiments, $R^{13}$ is $CH_2N(C_1$-$C_6$ alkyl)$C(=O)$phenyl.

For example, in certain embodiments $R^5$ is selected from the structures:

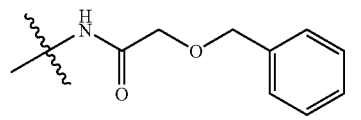

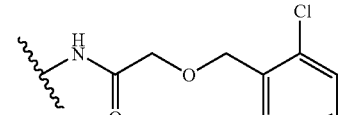

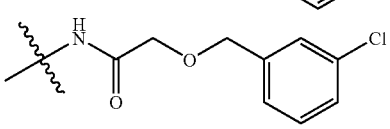

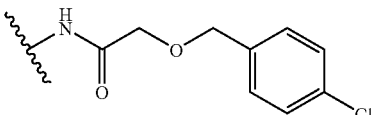

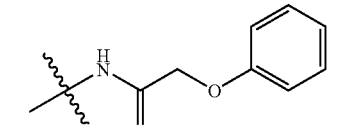

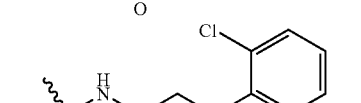

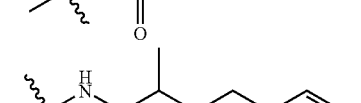

-continued
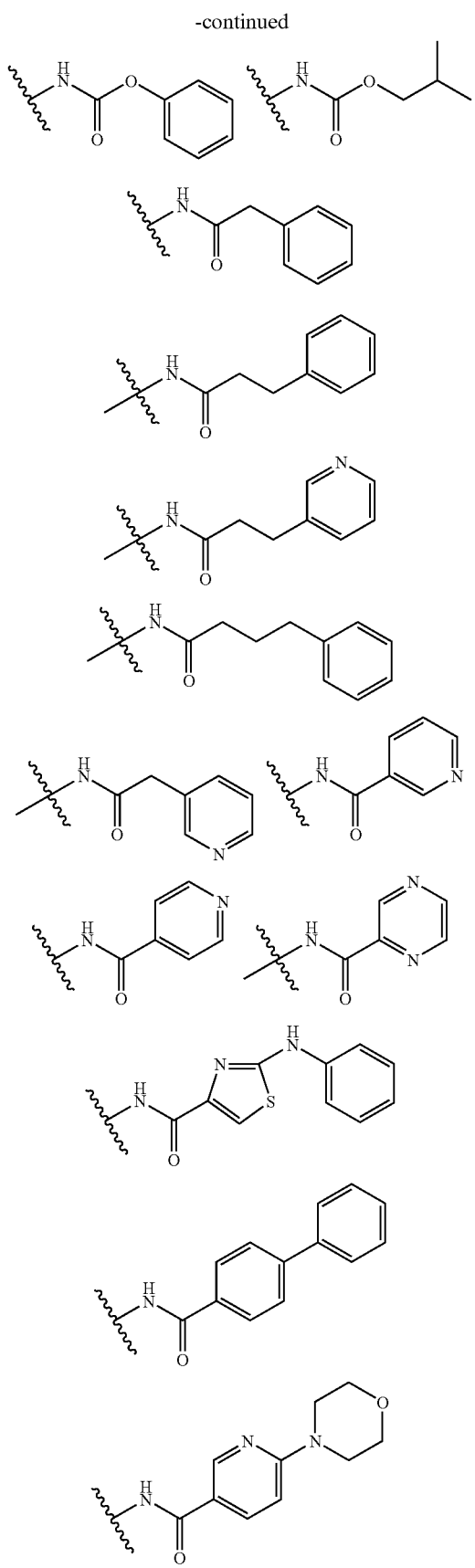
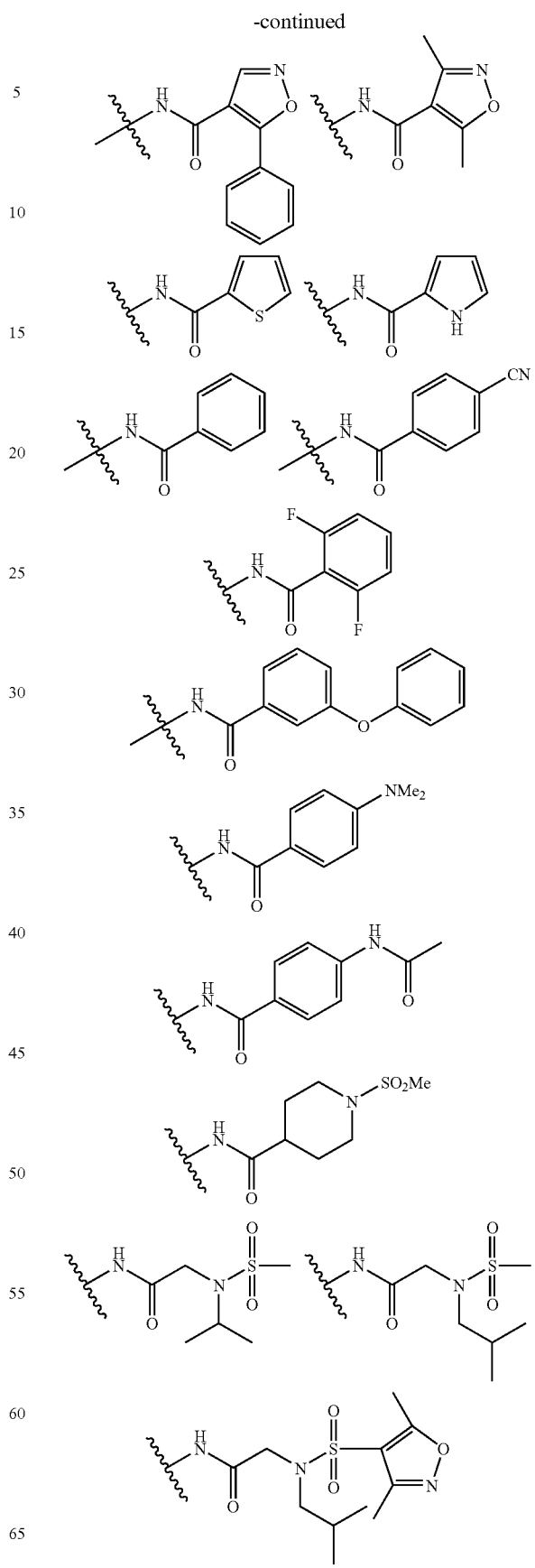

-continued

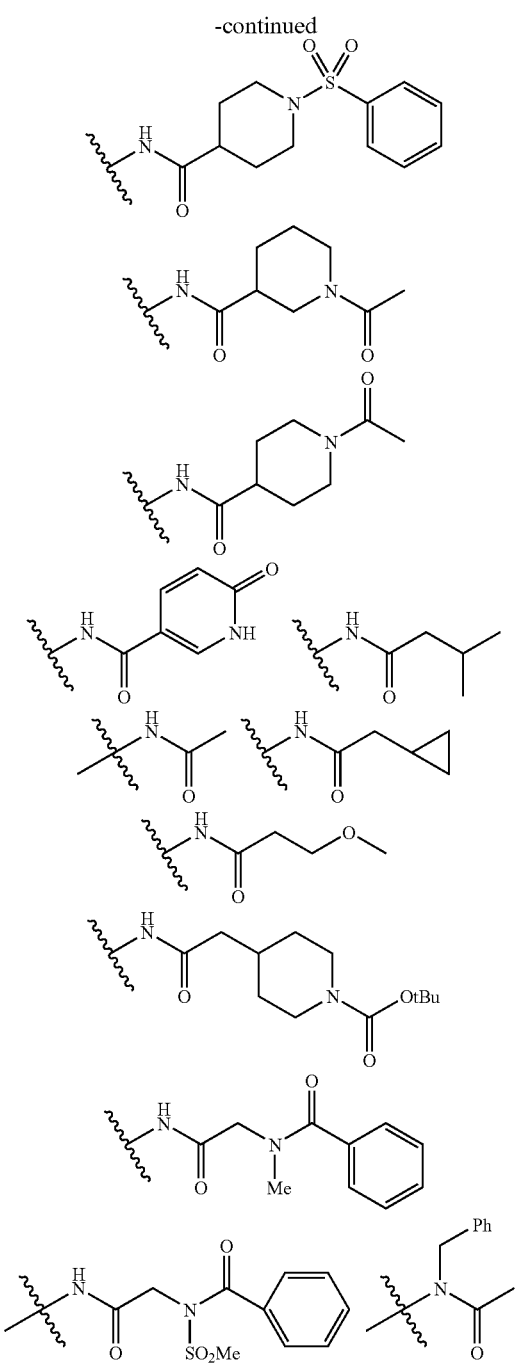

In certain embodiments of compounds of Formula Ia and Ib, $R^5$ has the following structure:

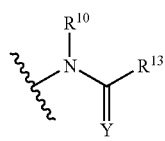

wherein Y and $R^{10}$ are as defined herein and $R^{13}$ is alkyl or $(CR^{14}R^{15})$-hetAr. In certain embodiments, $R^{14}$ and $R^{15}$ are H. In other embodiments, $R^{14}$ and $R^{15}$ together with the carbon to which they are attached from a cyclopropylidene ring. In certain embodiments, Y is O. In certain embodiments, hetAr is a 5-9 membered monocyclic or bicyclic ring having one or two ring heteroatoms independently selected from N and O. Exemplary embodiments of $R^5$ include the structures:

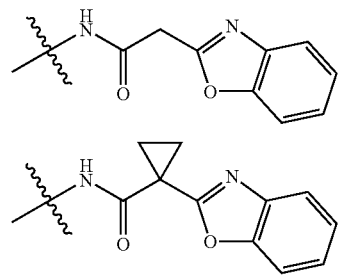

In certain embodiments of compounds of Formula Ia and Ib, $R^5$ has the structure:

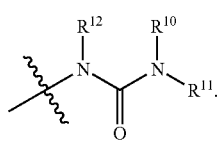

wherein $R^{10}$, $R^{11}$, and $R^{12}$ are as defined herein.

In certain embodiments, $R^{11}$ is optionally substituted aryl or heteroaryl.

In certain embodiments, $R^{11}$ is a 5-10 membered monocyclic or bicyclic heteroaryl having a ring nitrogen atom and optionally having a second heteroatom selected from N and O, wherein said heteroaryl is optionally substituted with $C_1$-$C_6$ alkyl.

In certain embodiments, $R^{12}$ is H.

In certain embodiments, $R^{10}$ is H or methyl.

For example, in certain embodiments $R^5$ is selected from the structures:

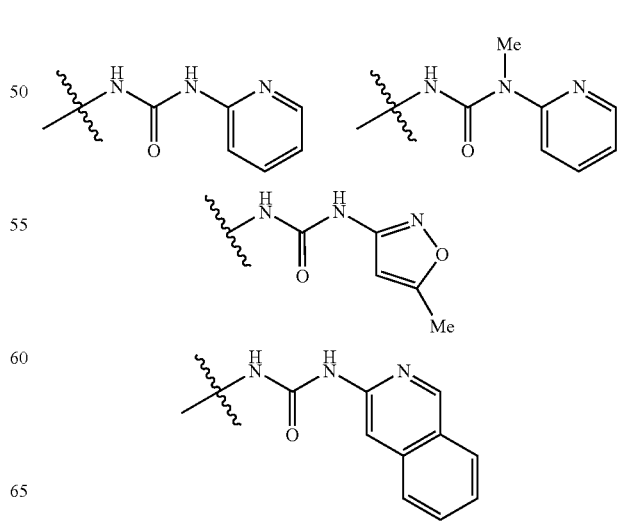

-continued

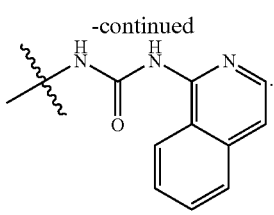

In other embodiments, $R^{10}$ and $R^{12}$ together with the atoms to which they are attached form an oxo-substituted heterocyclic ring, wherein said heterocyclic ring is optionally fused to a phenyl ring. For example, in certain embodiments $R^5$ is selected from the structures:

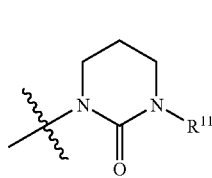 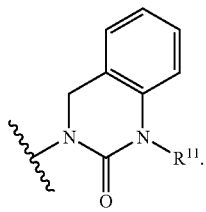

In a particular embodiment, $R^{11}$ is H.

In certain embodiments of compounds of Formula Ia and Ib, $R^5$ is $NR^{12}SO_2R^{10}$, wherein $R^{10}$ and $R^{12}$ are as defined herein.

In certain embodiments, $R^{12}$ is H.

In certain embodiments, $R^{10}$ is phenyl optionally substituted with halogen, O—($C_1$-$C_6$ alkyl), or C(=O)NH($C_1$-$C_6$ alkyl).

In certain embodiments, $R^{10}$ is an optionally substituted aryl. Exemplary embodiments of $R^5$ include the structures:

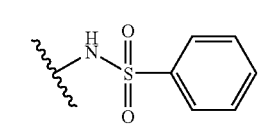 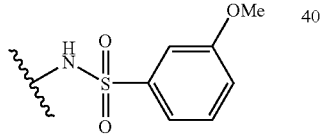
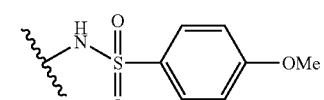 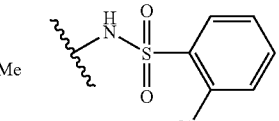
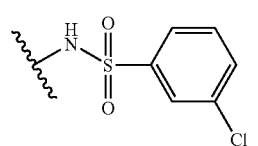 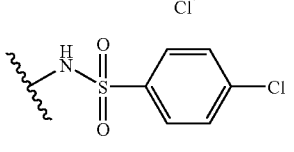
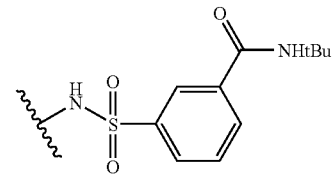
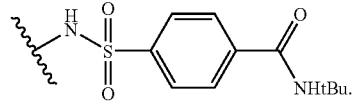

In certain embodiments of compounds of Formula Ia and Ib, $R^5$ is $NR^{12}C(=O)C(=O)NR^{10}R^{11}$, wherein $R^{10}$, $R^{11}$ and $R^{12}$ are as defined herein.

In certain embodiments, $R^{11}$ is H.

In certain embodiments, $R^{12}$ is H.

In certain embodiments, $R^{10}$ is H, $C_1$-$C_6$ alkyl, $(CH_2)_{0-2}$-phenyl optionally substituted with halogen, or a 5 membered azacyclic ring such as pyrrolidinyl.

For example, in certain embodiments $R^5$ is selected from the structures:

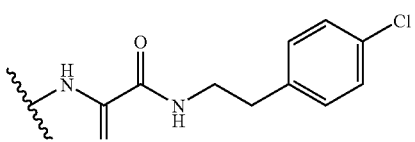
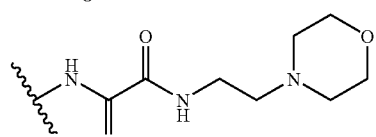
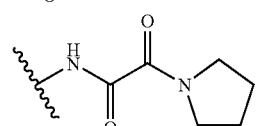
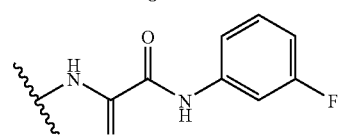
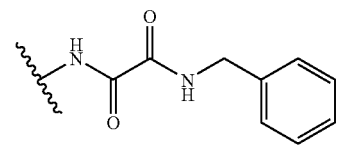
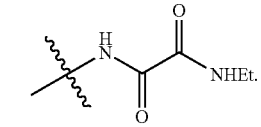

In certain embodiments of compounds of Formula Ia and Ib, $R^5$ is $NR^{12}C(=O)C(=O)OR^a$, wherein $R^{12}$ and $R^a$ are as defined herein.

In certain embodiments, $R^{12}$ is H.

In certain embodiments, $R^a$ is $C_1$-$C_6$ alkyl.

For example, in certain embodiments $R^5$ is

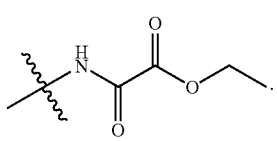

In certain embodiments of compounds of Formula Ia and Ib, $R^5$ is an optionally substituted heteroaryl. For example, in certain embodiments, $R^5$ is selected from the structures:

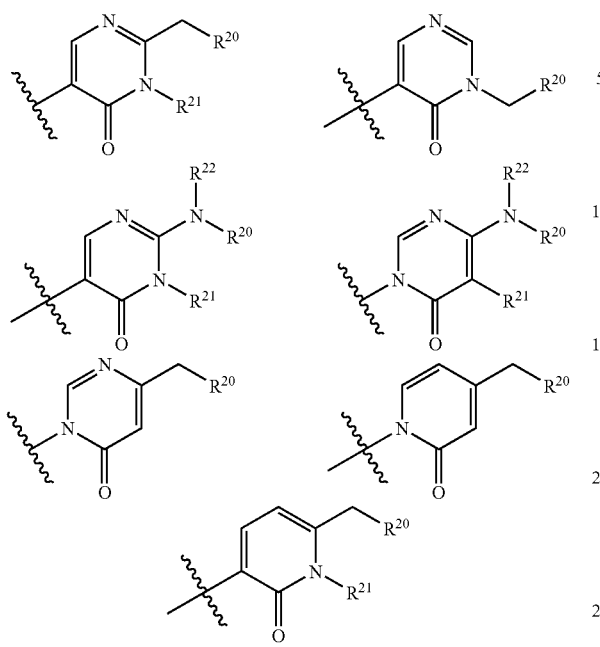

wherein $R^{20}$ is alkyl, cycloalkyl, aryl, or heteroaryl, and $R^{21}$ and $R^{22}$ are independently selected from H or alkyl, wherein said alkyl, cycloalkyl, aryl, and heteroaryl are optionally substituted with one or more groups independently selected from F, Cl, Br, I, alkyl and $C_3$-$C_6$ cycloalkyl.

Exemplary embodiments of $R^5$ include the following structures:

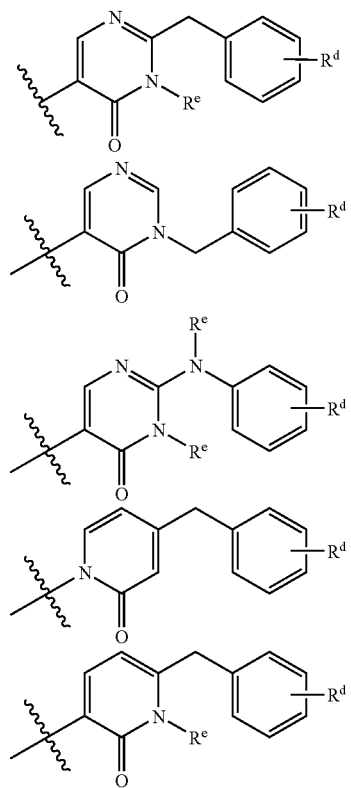

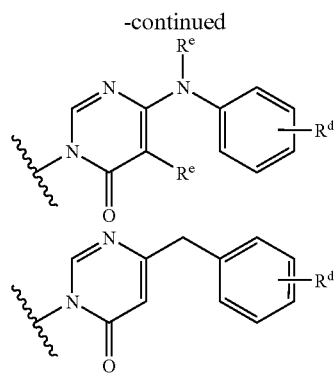

wherein $R^d$ is as defined herein and $R^e$ is H or an optionally substituted $C_1$-$C_4$ alkyl.

In certain embodiments, the phenyl group is substituted with one $R^d$ group.

In certain embodiments, $R^d$ is F, Cl, Br, I, $SO_2R^c$, CN, $OR^a$, $NR^aR^b$, $C(=O)NR^aR^b$, $CR^aC(=O)R^b$, $C_1$-$C_{12}$ alkyl, $C_2$-$C_8$ alkenyl, $C_2$-$C_8$ alkynyl, $C_6$-$C_{20}$ aryl, and $C_1$-$C_{20}$ heteroaryl.

In certain embodiments, $R^e$ is independently H or $C_1$-$C_4$ alkyl.

Further exemplary embodiments of $R^5$ include the structures:

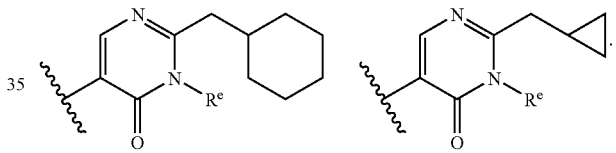

Particular embodiments of $R^5$ include the structures:

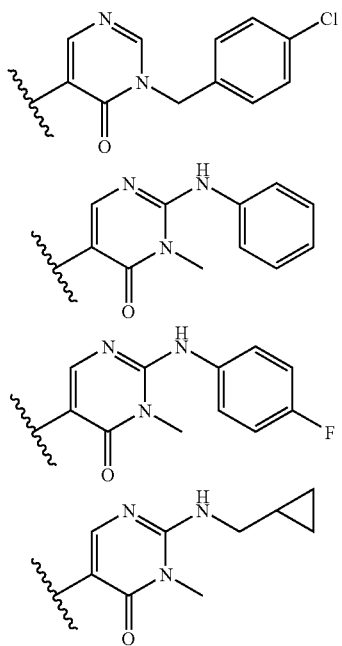

-continued

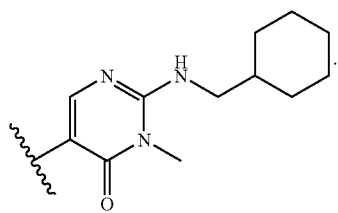

In certain embodiments of compounds of Formula Ia and Ib, $R^5$ is $NR^{10}R^{11}$. In certain embodiments, $R^{10}$ is H. In certain embodiments, $R^{11}$ is hetAr, wherein hetAr is a substituted or unsubstituted 5-6 membered heteroaryl group having at least one ring nitrogen atom and optionally having a second ring heteroatom selected from N and O. Examples of hetAr include pyridyl, isoxazolyl, and pyridazinyl groups. In certain embodiments, hetAr is substituted with one or two groups independently selected from $C_1$-$C_6$ alkyl and $C(\!=\!O)NR^aR^b$. In certain embodiments, $R^a$ is H. In certain embodiments, $R^b$ is phenyl optionally substituted with a halogen group. In certain embodiment, $R^b$ is $C_1$-$C_6$ alkyl, such as, but not limited to, methyl, ethyl or isopropyl. In certain embodiments, $R^b$ is a 6 membered heteroaryl having at least one nitrogen atom, for example pyridyl.

Exemplary embodiment of $R^5$ includes the structures:

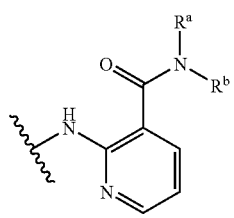 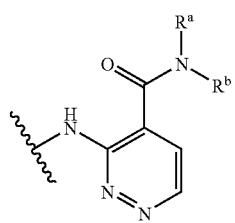

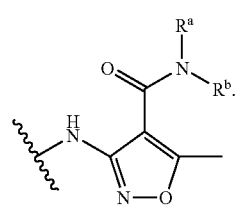

A particular embodiment of $R^5$ is the structure:

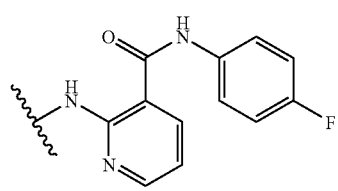

Particular embodiments of $R^3$ include the structures:

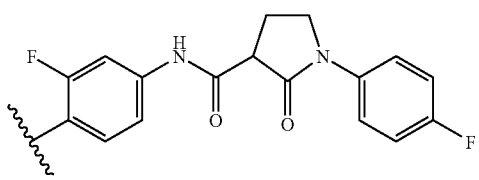

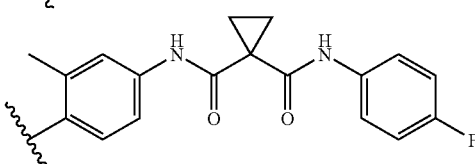

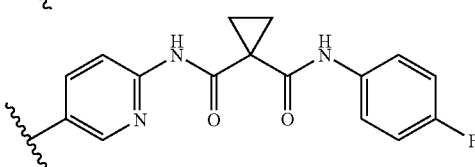

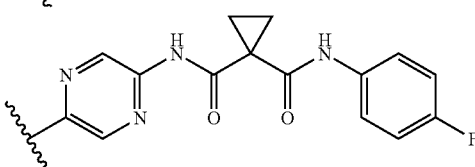

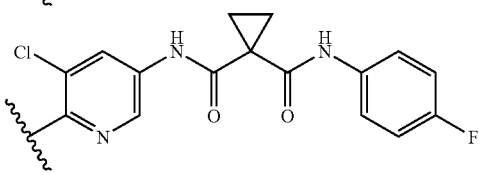

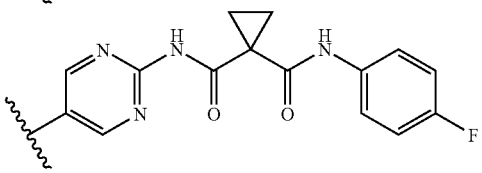

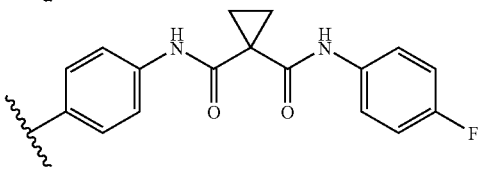

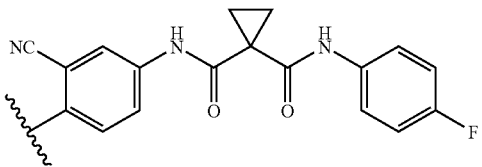

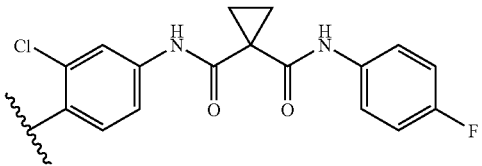

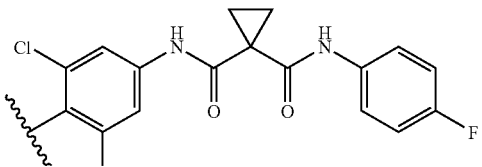

-continued
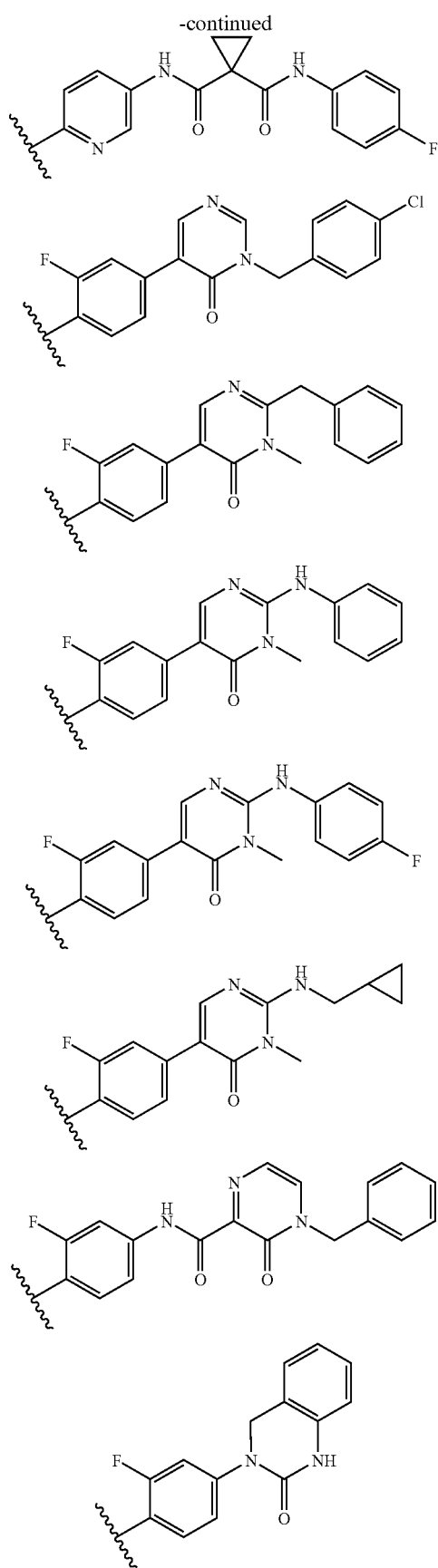
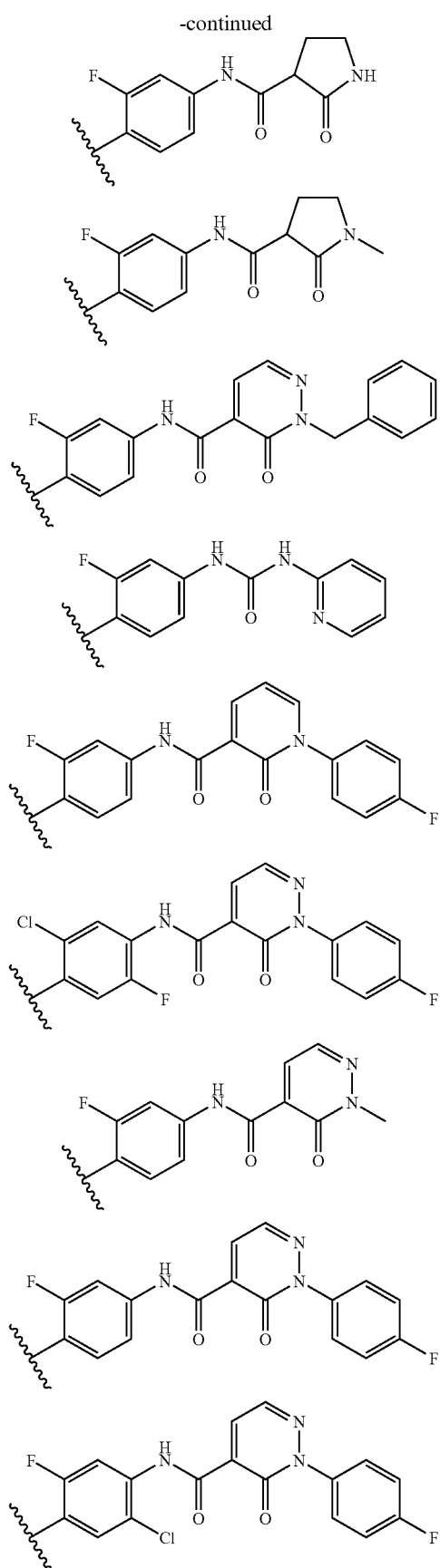

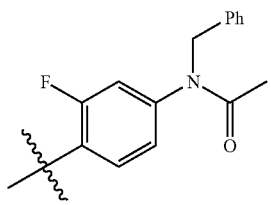
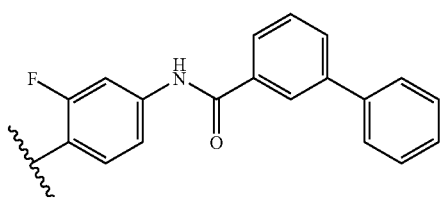
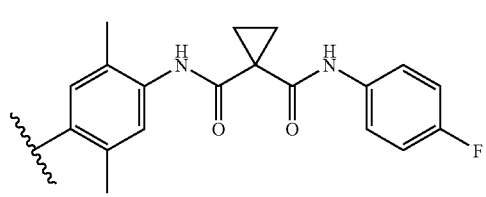
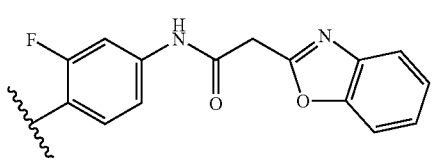
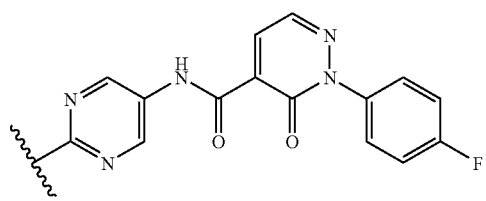
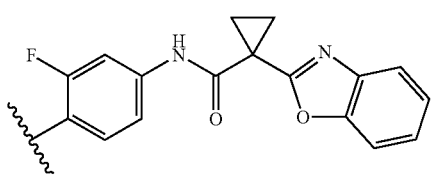
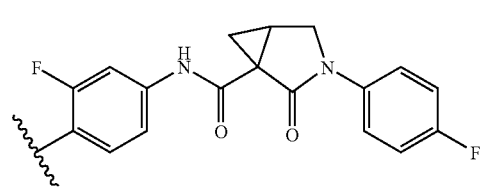
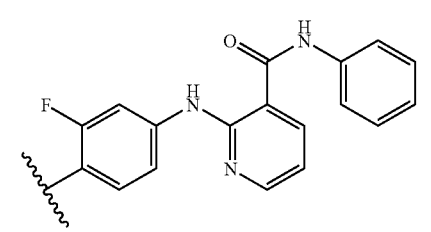
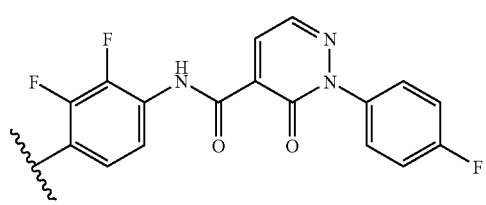
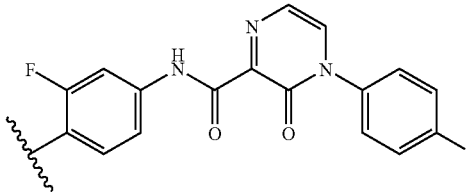
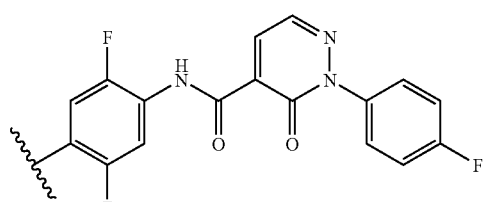
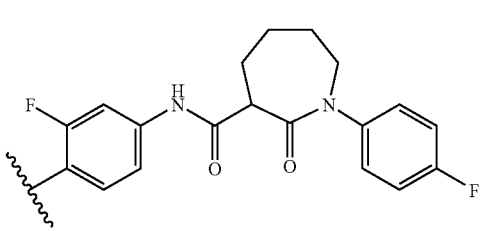

-continued

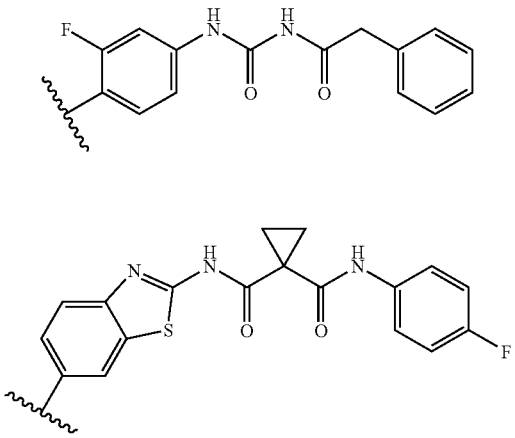

The heterobicyclic pyrazole compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a heterobicyclic pyrazole compound of the present invention incorporates a double bond or a fused ring, the cis- and trans-forms, as well as mixtures thereof, are embraced within the scope of the invention. Both the single positional isomers and mixture of positional isomers, e.g., resulting from the N-oxidation of the pyrimidine and pyrazine rings, are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^{3}$H and $^{14}$C) are useful in compound and/or substrate tissue distribution assays. Tritiated ($^{3}$H) and carbon-14 ($^{14}$C) isotopes are useful for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Synthesis of cMet Inhibitor Compounds

Heterobicyclic pyrazole compounds of Formula Ia and Ib of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

In certain embodiments, compounds of Formula Ia or Ib may be readily prepared using procedures well-known to prepare pyrazolo[3,4-b]pyridines (U.S. Pat. No. 6,531,475, WO 01/098301, WO 01/081348, and WO 99/030710); and other heterocycles, which are described in: Comprehensive Heterocyclic Chemistry, Editors Katrizky and Rees, Pergamon Press, 1984; Klemm et al. (1970) J. Hetero. Chem. 7(2):373-379; Klemm et al. (1974) J. Hetero. Chem. 11(3): 355-361; Klemm et al. (1976) J. Hetero. Chem. 13:273-275; Klemm et al. (1985) J. Hetero. Chem. 22(5):1395-1396; Bisagni et al. (1974) Bull. Soc. Chim. Fr. (3-4, Pt. 2):515-518; Frehel et al. (1984) Heterocycles 22(5):1235-1247; WO 93/13664; WO 2004/012671; WO 2005/061476; U.S. Application Publication Nos. 2003/0045540, US 2003/0105089, and 2004/0024210; and U.S. Pat. Nos. 5,252,581, 6,232,320, and 6,579,882.

Compounds of Formula Ia and Ib may be prepared singly or as compound libraries comprising at least 2, for example 5 to 1,000 compounds, or 10 to 100 compounds. Libraries of compounds of Formula Ia or Ib may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-25 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Scheme 1

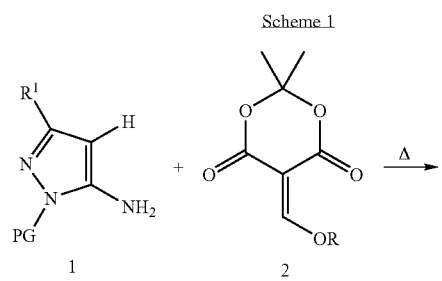

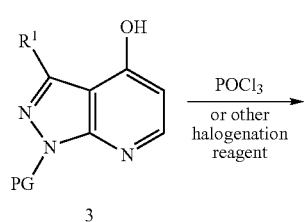

-continued

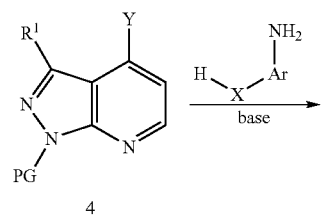

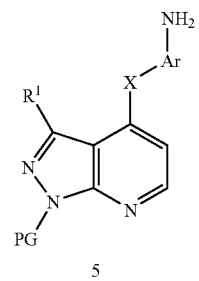

Scheme 1 shows a general scheme for the synthesis of intermediate compound 5, which is useful for the synthesis of compounds of Formula I. As shown in Scheme 1, reaction of a substituted 5-aminopyrazole 1 ($R^1$ is, for example, H, alkyl, alkenyl, alkynyl, cycloalkyl, heterocyclyl, aryl, heteroaryl, or halogen; see, Misra, R. N., et al., Bioorg. Med. Chem. Lett. 2003, 13, 1133-1136), wherein N1 is protected by an appropriate protecting group (PG may be p-methoxybenzyl, phenylsulfonyl, or the like), with a vinyl ether of Meldrum's acid 2 (R=alkyl, such as methyl or ethyl) upon heating provides a Meldrum's acid enamine of the 5-aminopyrazole (not shown). Such an enamine can be cyclized upon heating to provide phenol 3, wherein $R^1$ may be independently H, alkyl, alkenyl, alkynyl, cycloalkyl, heterocyclyl, aryl, heteroaryl, etc. Conversion of the phenol 3 to an aryl halide 4 (Y=halogen or other leaving group such as triflate, etc.) can be achieved upon reaction with an appropriate electrophilic reagent (e.g. $POCl_3$, oxalyl chloride, $NCS/PPh_3$, $POBr_3$, $NBS/PPh_3$, $CF_3SO_2Cl$/2,6-lutidine, etc.). Nucleophilic substitution of aryl halide 4 with a compound of the formula HX—Ar—$NH_2$, wherein X is O, N or S, and Ar is an aryl or heteroaryl ring as defined herein, can be conducted using an appropriate base (e.g. $Cs_2CO_3$, NaH, KOt-Bu, DMAP, or the like) to give intermediate 5.

Scheme 2

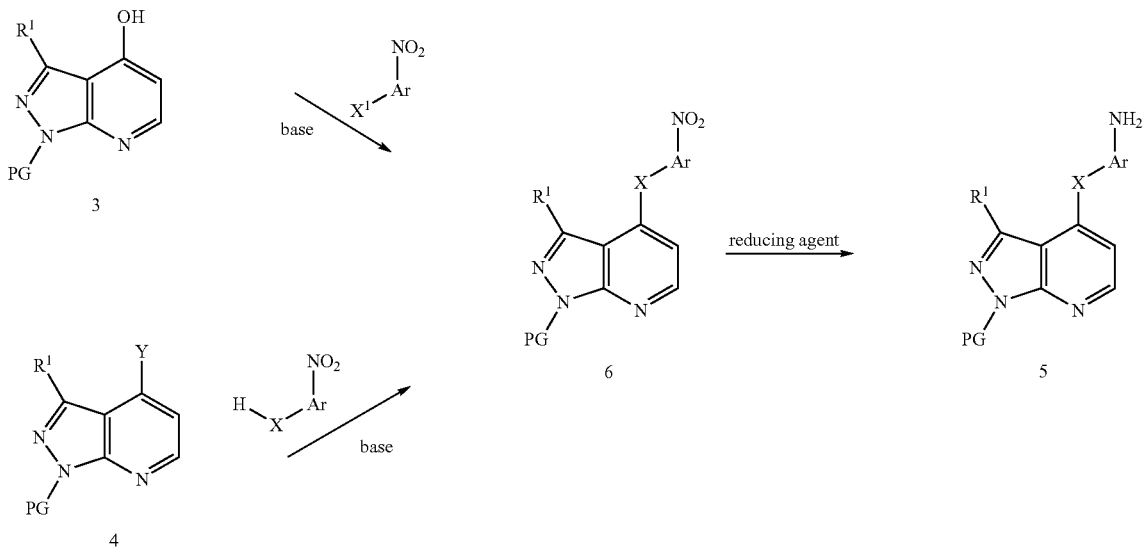

Scheme 2 shows an alternative method of preparing intermediate 5 wherein X is O, N or S. Intermediate 5 can be prepared by nucleophilic substitution of phenol 3 with a compound of the formula $X^1$—Ar—$NO_2$ (wherein $X^1$ is F, Cl, triflate or other appropriate leaving group and Ar is an aryl or heteroaryl ring as defined herein) in the presence of an appropriate base (e.g. $Cs_2CO_3$, NaH, KOt-Bu, DMAP, or the like) to give intermediate 6 (where X=O). Intermediate 6 may subsequently be reduced to give aniline 5 using an appropriate reducing agent (e.g. Zn, Fe, $H_2$/Pd, $SnCl_2$-$2H_2O$, or the like). Alternatively, intermediate 6 wherein X is O, N, or S (as determined by the choice of HX—Ar—$NO_2$) may also be prepared by nucleophilic substitution of intermediate 4 with a compound of formula HX—Ar—$NO_2$ according to the protocol described for Scheme 1.

Scheme 3

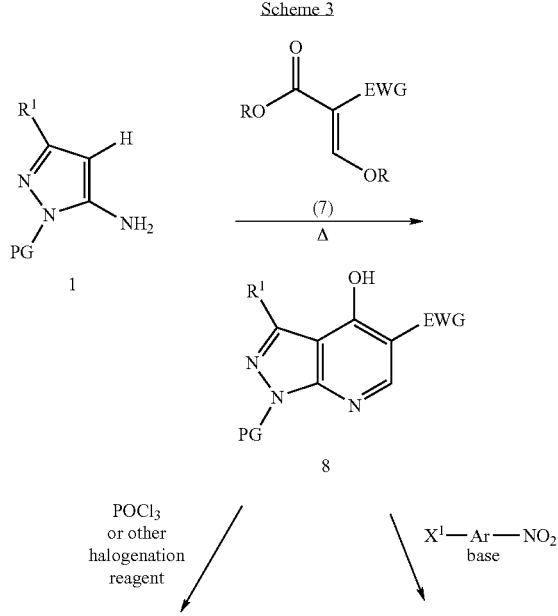

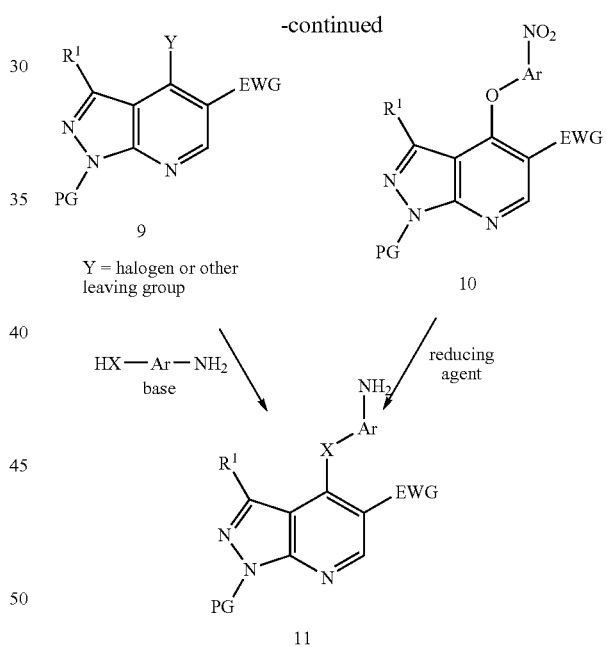

Scheme 3 shows a general scheme for the synthesis of intermediate 11 containing an electron withdrawing group (EWG), which is useful for the synthesis of compounds of Formula I. According to Scheme 3, a 5-substituted pyrazolopyridine 11 may be obtained by reacting a protected 5-aminopyrazole 1 with a vinyl ether of a malonate isostere 7 (e.g. diethyl malonate, ethyl 2-cyanoacetate, ethyl 3-oxobutanoate, or the like) containing appropriate electron-withdrawing group EWG, wherein EWG is, e.g., carboxyl, carbonyl, cyano, sulfonyl, and the like, to provide compound 8. Similar methodology has been described in WO 01/081348 and WO 99/030710. Compound 8 may be further elaborated in a similar manner as described for Schemes 1 or 2 to give intermediate 11, wherein X, Ar, and $R^1$ are as defined in Scheme 1.

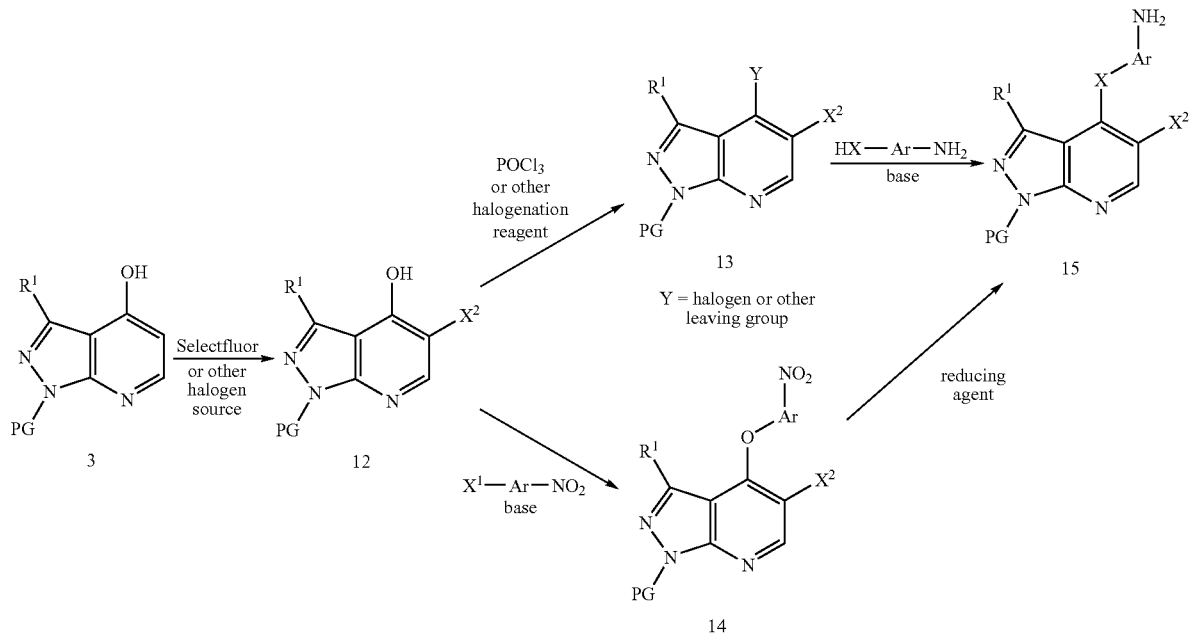

Scheme 4

Scheme 4 shows a general scheme for the synthesis of intermediate 15, which is useful for the synthesis of compounds of Formula I. As shown in Scheme 4, substitution at the 5-position of the pyrazolopyridine core may be executed by halogenation of compound 3 with an appropriate halogenation reagent (e.g., Selectfluor, bromine, sodium hypochlorite or the like) to give compound 12 wherein $X^2$ is halogen. Compound 12 may be further elaborated in a similar manner as described for Schemes 1 or 2 to give intermediate 15, wherein X, Ar, and $R^1$ are as defined in Scheme 1.

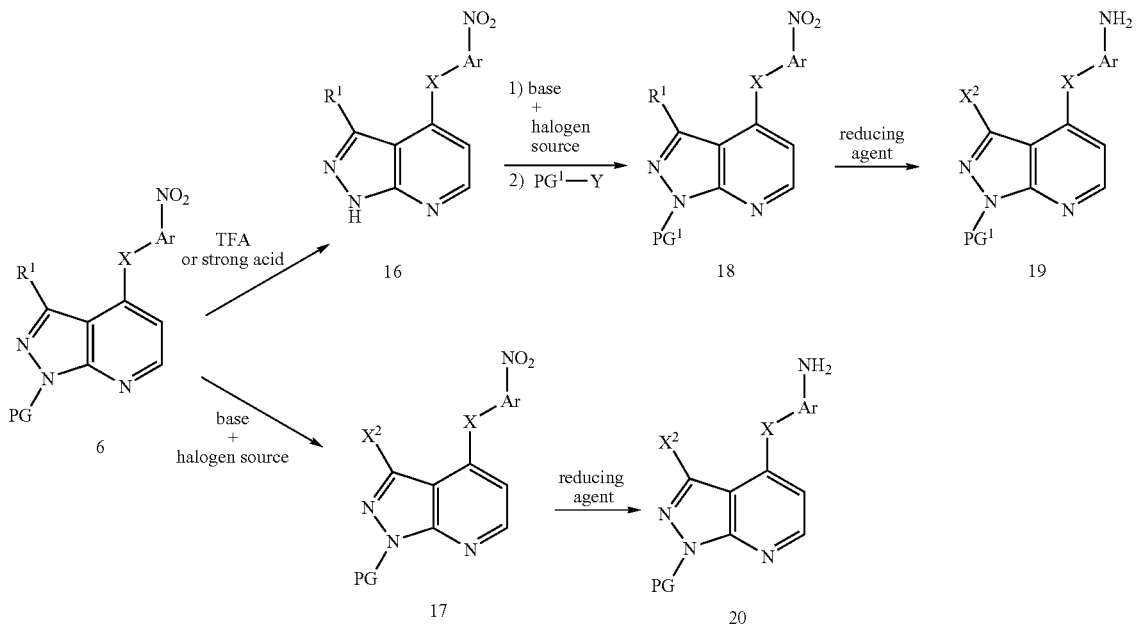

Scheme 5

Scheme 5 shows a general scheme for the synthesis of intermediates 19 and 20 ($R^1$=H; protecting groups PG and $PG^1$ may vary independently), which are useful for the synthesis of compounds of Formula I. As shown in Scheme 5, substitution at the 3-position of the pyrazolopyridine core may be achieved by halogenation (using $I_2$, $Br_2$, NIS, NBS or other halogenation reagent) of intermediate 6 (PG=phenylsulfonyl or other appropriate protecting group) which may require the presence of a base such as KOH, KOt-Bu, n-BuLi or the like, to give 17 ($X^2$=halogen, for example iodine or bromine). Alternatively, removal of protecting group PG using TFA, strong acid, or other deprotection conditions appropriate for PG removal provides intermediate 16. Intermediate 16 may be halogenated in like manner as intermediate 6 followed by introduction of a second protecting group ($PG^1$ may be p-methoxybenzyl, Boc, phenylsulfonyl, or the like; and Y may be an appropriate leaving group such as halogen) to give compound 18. Intermediates 17 and 18 may be reduced to their corresponding anilines 19 and 20, respectively, according to the protocol described for Scheme 2.

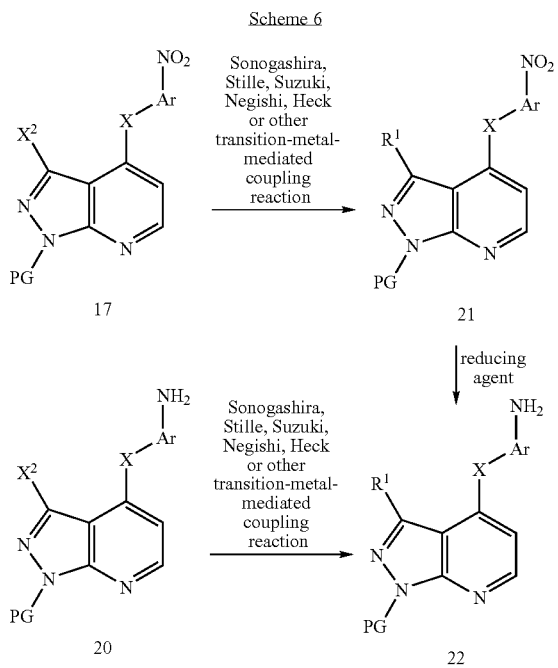

Scheme 6

Scheme 6 shows a general scheme for the synthesis of intermediates 21 and 22, which are useful for the synthesis of compounds of Formula I. Intermediate 17 ($X^2$=bromo or iodo) may be further elaborated at the 3-position by a transition-metal-mediated coupling reaction (e.g. Sonogashira, Stille, Suzuki, Negishi, Heck, or similar coupling reactions known to those skilled in the art) to give intermediate 21, wherein $R^1$ is, for example, aryl, heteroaryl, alkyl, alkenyl, alkynyl, or other functionality that can be incorporated via related transition-metal mediated coupling with intermediate 17, and X and Ar are as defined in Scheme 1. Intermediate 21 may be elaborated further as described below or converted to aniline 22 using an appropriate reducing agent as described for Scheme 2. Alternatively, aniline 20 can be elaborated in like manner as intermediate 17 by a transition-metal mediated coupling reaction to give intermediate 22. Intermediates 18 and 19, synthesized according to Scheme 5, may also be modified according to the method of Scheme 6.

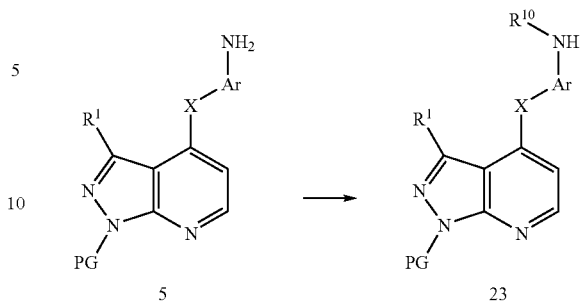

Scheme 7

Scheme 7 shows a general scheme for the synthesis of amides, sulfonamides, carbamates, and ureas 23. Compounds 23 can be prepared by reaction of an amino-containing intermediate 5 (prepared as in Schemes 1 or 2) with an activated carboxyl- or sulfonyl-containing reagent in the presence of an appropriate base (e.g. TEA, DIEA, N-methylmorpholine, pyridine, DMAP, or the like), as needed. Suitable carboxyl- or sulfonyl-containing reagents include, but are not limited to, acid chlorides, acid fluorides, sulfonyl chlorides, sulfonyl fluorides, polystyrene-2,3,5,6-tetrafluoro-4-(methylcarbamoyl)phenol (PS-TFP)-carboxylates, PS-TFP-sulfonates, carbamoyl chlorides, isocyanates, isothiocyanates, anhydrides, chloroformates, HOBt ester, carbodiimide-derived O-acylurea, and the like. For example, compounds 23 wherein $R^{10}$ is acyl, thiocarbonyl, carbamoyl, alkoxycarbonyl, or sulfonyl have been prepared by this method. Alternatively, intermediate 5 may be converted to compound 23 wherein $R^{10}$ is alkyl by reductive alkylation methods. Intermediate 5 can also be coupled with an aryl or heteroaryl halide according to the procedures of Buchwald and Hartwig to provide a substituted amine 23 wherein $R^{10}$=aryl or heteroaryl.

Intermediate compounds 11, 15, 19, 20 and 22, described in earlier schemes, can similarly be converted to the corresponding substituted amines by any of the above methods described for intermediate 5.

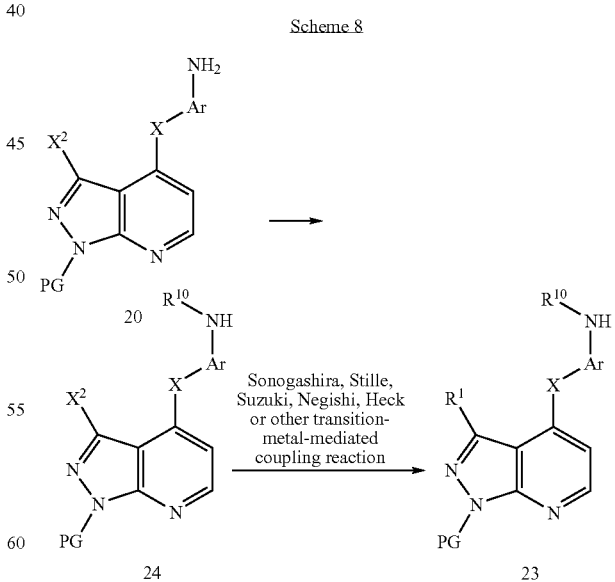

Scheme 8 shows an alternative method of preparing compound 23 from intermediate 20 ($X^2$=bromo or iodo) in a two-step process. Elaboration of the amino group of intermediate 20 using an activated carboxyl- or sulfonyl-containing reagent such as described for Scheme 7 provides intermediate 24, wherein $R^{10}$ is as described in Scheme 7. Intermediate 24can be elaborated by Pd-mediated coupling (or other transition metal-mediated coupling conditions known to those skilled in the art) using the protocol described for Scheme 6 to yield compound 23, wherein $R^1$=aryl, heteroaryl, alkyl, alkenyl, alkynyl, or other functionality that can be incorporated via related transition-metal mediated coupling with intermediate 24, and X and Ar are as defined in Scheme 1.

Scheme 9 shows a general method for the synthesis of alcohols 26a-c (wherein Z may be $NO_2$, $NH_2$, or $R^{10}NH$; $R^e$, $R^f$, and $R^g$ are independently H, alkyl, cycloalkyl, heterocyclic, aryl, or heteroaryl, or $R^f$ and $R^g$ together may form a carbocyclic or heterocyclic ring with the carbon atom to which they are attached, alternatively $R^g$ and $R^e$ together may form a carbocyclic or heterocyclic ring containing the 2 carbon atoms derived from the alkene functionality in 25a-c; $R^{10}$ is as described in Scheme 7) from alkenes 25a-c, which may be derived using synthetic methods described for Schemes 6 and 8 (e.g. Heck or Suzuki coupling and variations known to those skilled in the art, such as published by Molander, et al.). Hydroboration of 25a-c using 9-BBN or another suitable hydroboration reagent followed by an oxidative quench by addition of base NaOH or the like and oxidant $H_2O_2$ provides compounds 26a-c, wherein X, Ar, and PG are as defined in Scheme 1. Compounds 26a and 26b may be further elaborated as described for Schemes 2 and 7.

Intermediate compounds 4, 5, 6, 9, 10, 11, 13, 14, 15, 16, 21, 22, and 23 described in earlier schemes, wherein $R^1$ contains an alkenyl group can similarly be converted to the corresponding alcohols by the above method described for intermediates 25a-c.

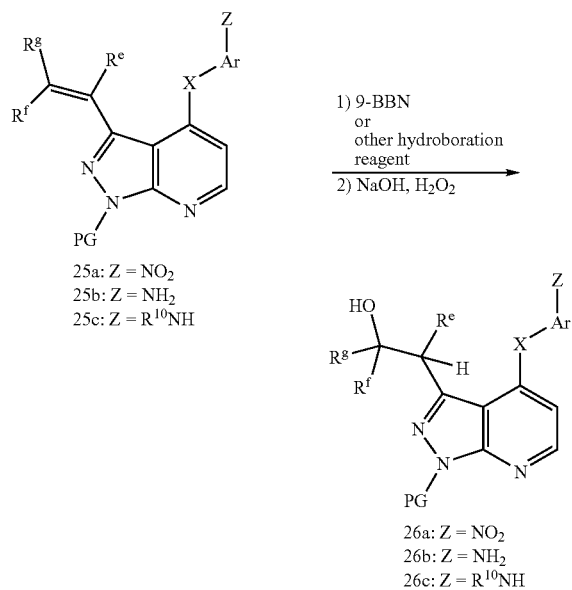

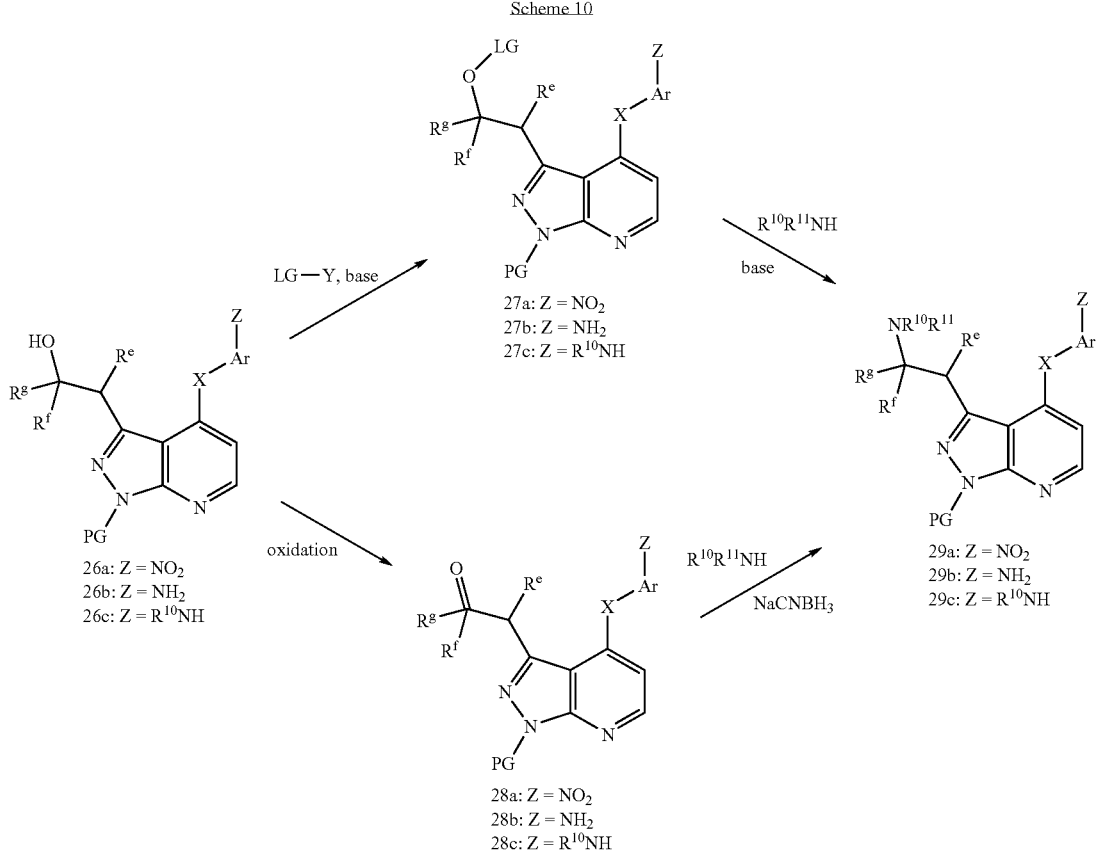

Scheme 10 shows a general method for the synthesis of amines 29a-c, wherein Z, $R^e$, $R^f$, and $R^g$ are as defined for Scheme 9, and $R^{10}$ is as described for Scheme 7. Activation of the hydroxyl group in compounds 26a-c by reaction with LG-Y (wherein LG is an appropriate leaving group, e.g. mesylate, tosylate, halogen, diazo-dicarboxylate adduct or the like; and Y is halogen or other leaving group appropriate to hydroxy-activating reagents known to those skilled in the art) provides intermediates 27a-c. Subsequent nucleophilic substitution of compounds 27a-c with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of an appropriate base as needed (DIEA, TEA, pyridine, DMAP, $Cs_2CO_3$ or the like) provides amines 29a-c. Alternatively, alcohols 26a-c can be oxidized with an appropriate oxidation reagent (Dess-Martin, Swern, or the like) to provide intermediate ketones or aldehydes 28a-c. Reductive amination of intermediates 28a-c using an amine of the formula $R^{10}R^{11}NH$ mediated by an appropriate reducing agent (e.g. sodium cyanoborohydride, sodium triacetoxyborohydride, or the like) provides amines 29a-c, wherein X, Ar, and PG are as defined in Scheme 1. Compounds 29a and 29b may be further elaborated as described for Schemes 2 and 7.

Scheme 11 shows a general method for the synthesis of alkyne 31, which can be used to prepare alkynylated derivatives 32a and 32b. Propargylic amine 31 can be prepared by reaction of propargyl bromide 30 with an amine of the formula $R^{10}R^{11}NH$ (wherein $R^{10}$ and $R^{11}$ are independently selected from H, alkyl, cycloalkyl, heterocyclic, aryl and heteroaryl, or $R^{10}$ and $R^{11}$ together with the nitrogen to which they are attached form a heterocyclic ring) in the presence of an appropriate base ($Cs_2CO_3$ or the like). For reviews of alkynyl amines and related syntheses see Booker-Milburn, K. I., Comprehensive Organic Functional Group Transformations, 1995, 2, 1039-1074; and Viehe, H. G., Angew. Chem., Int. Ed. Eng. 1967, 6(9), 767-778. Alkyne 31 can subsequently be reacted with intermediate 20 or 24 (via Sonogashira coupling), according to the descriptions provided for Schemes 6 and 8, to provide compounds 32a and 32b, respectively, wherein X, Ar, and PG are as defined in Scheme 1, and $NHR^{10}$ is as described in Scheme 7. Compound 32a may be further elaborated as described for Scheme 7.

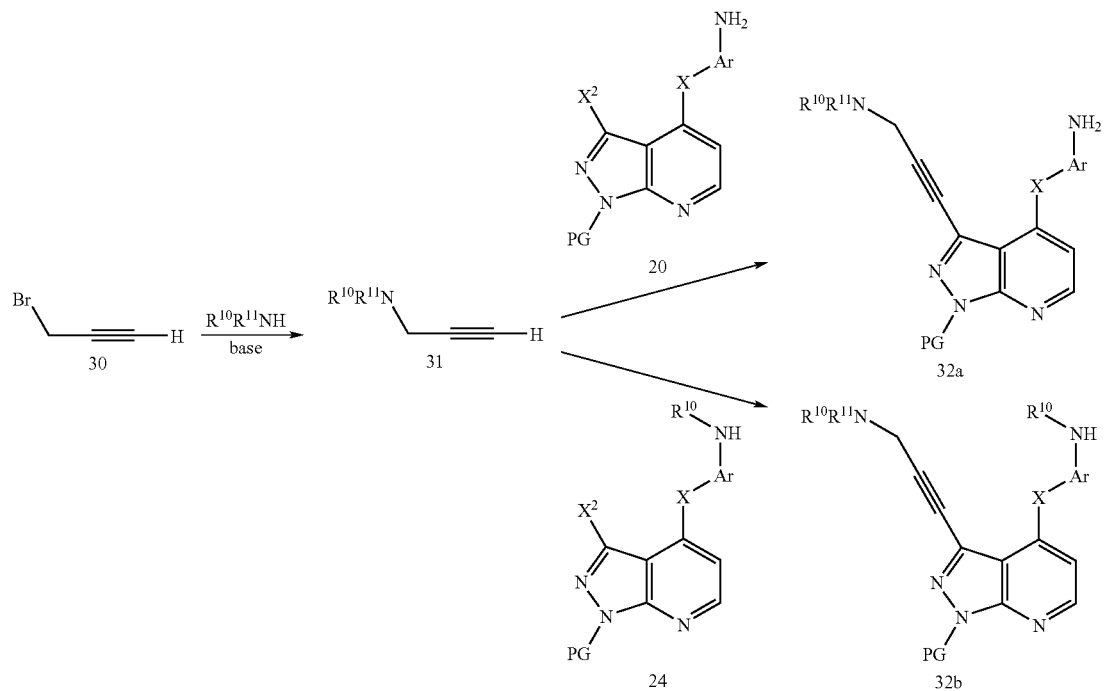

Scheme 12

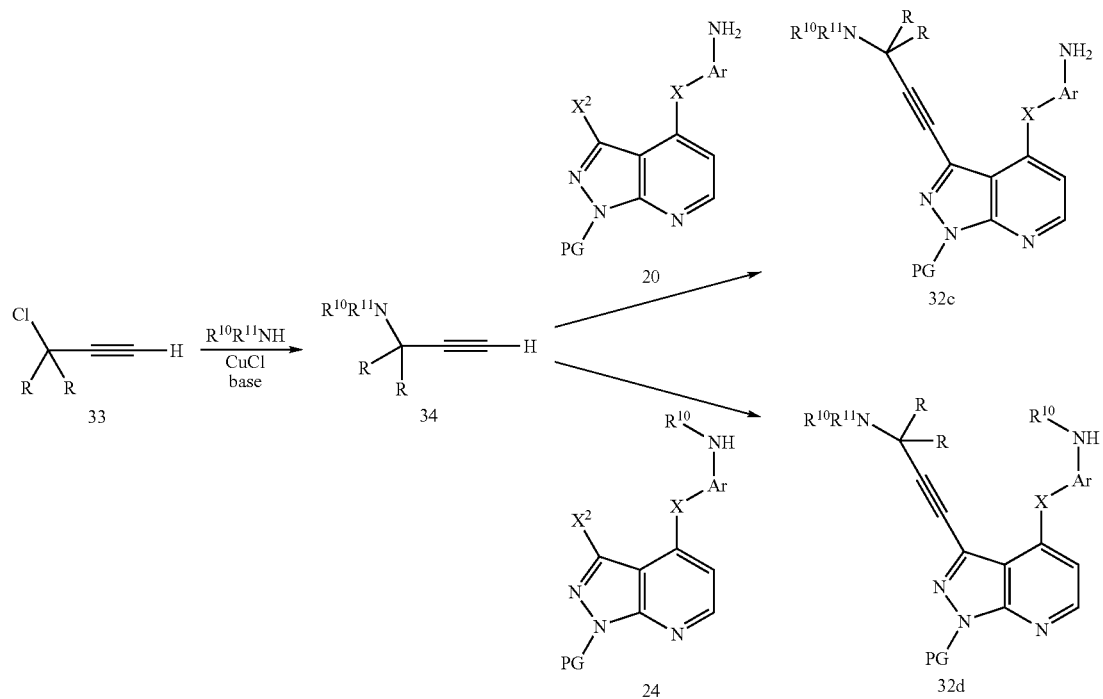

Scheme 12 shows a general method for the synthesis of alkynes 34, which can be used to prepare alkynylated derivatives 32c and 32d. Gem-dialkyl propargylic amines 34 may be prepared using methods described by Zaragoza, F., et al. J. Med. Chem. 2004, 47, 2833. According to Scheme 12, alkynyl chloride 33 (wherein each R is independently methyl, ethyl or other alkyl group, or the R groups together with the atom to which they are attached form a carbocyclic ring) can be reacted with an amine of the formula $R^{10}R^{11}NH$ (wherein $R^{10}$ and $R^{11}$ are independently H, alkyl, aryl or heteroaryl, or $R^{10}$ and $R^{11}$ together with the nitrogen to which they are attached form a heterocyclic ring) in the presence of CuCl and an appropriate base (e.g. TEA or the like) to provide the alkyne 34. Alkyne 34 can be reacted with intermediate 20 or 24 (via Sonogashira coupling), according to the descriptions provided for Schemes 6 and 8, to provide compounds 32c and 32d, respectively, wherein X, Ar, and PG are as defined in Scheme 1, and $NHR^{10}$ is as described in Scheme 7. Compound 32c may be further elaborated as described for Scheme 7.

Scheme 13

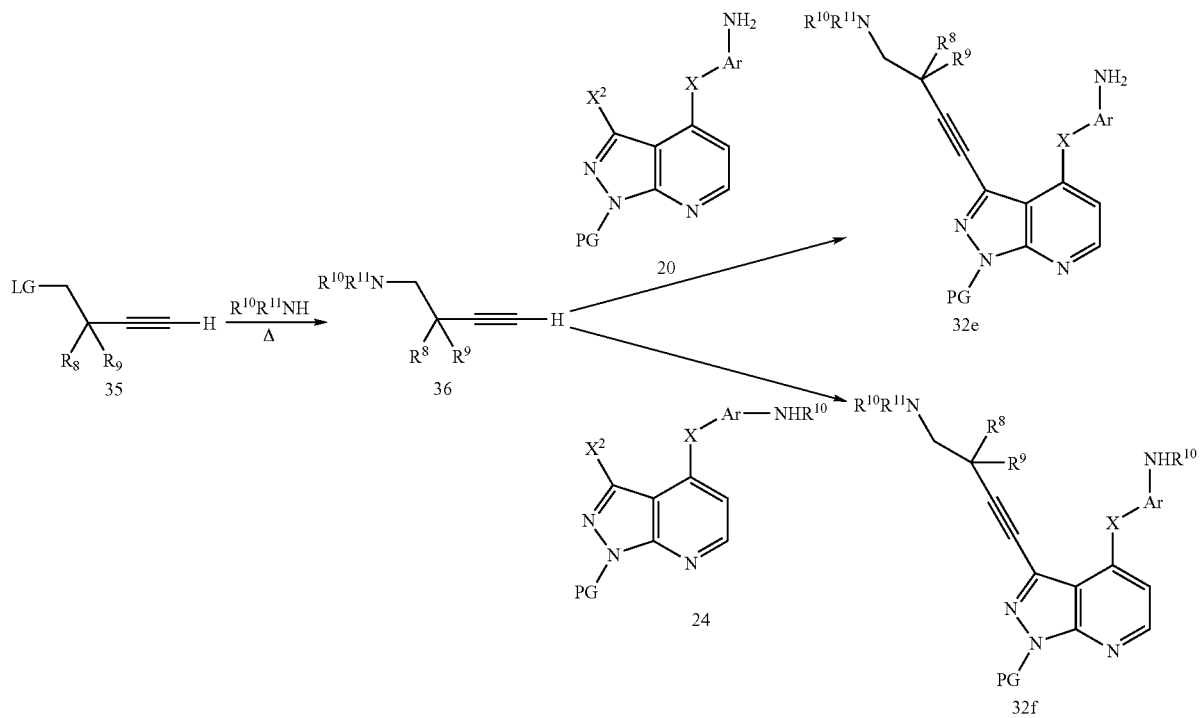

Scheme 13 shows a general scheme for the synthesis of alkynes 36, which can be used to prepare alkynylated derivatives 32e and 32f. But-3-yn-1-amine 36 (wherein $R^8$ and $R^9$ are independently H, alkyl, cycloalkyl, heterocyclyl, aryl, or heteroaryl, or $R^8$ and $R^9$ together with the carbon atom to which they are attached form a carbocyclic or heterocyclic ring) can be prepared from reaction of alkynes 35 (LG=tosylate or other leaving group) with an amine of the formula $R^{10}R^{11}NH$ (wherein $R^{10}$ and $R^{11}$ are independently SH, alkyl, cycloalkyl, heterocyclyl, aryl, or heteroaryl, or $R^{10}$ and $R^{11}$ together with the nitrogen to which they are attached form a heterocyclic ring) using the protocol described by Olomucki, M., et al., Ann. Chim. 1960, 5, 845. Alkynes 36 can subsequently be reacted with intermediates 20 or 24 (via Sonogashira coupling), according to the descriptions provided for Schemes 6 and 8 to provide compounds 32e and 32f, respectively, wherein X, Ar, and PG are as defined in Scheme 1, and $NHR^{10}$ is as described in Scheme 7. Compound 32e may be further elaborated as described in Scheme 7.

Scheme 14

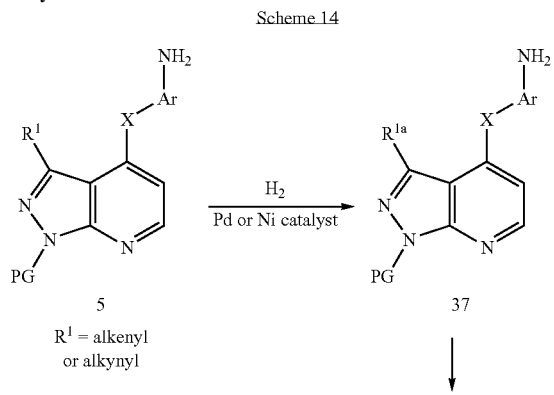

-continued

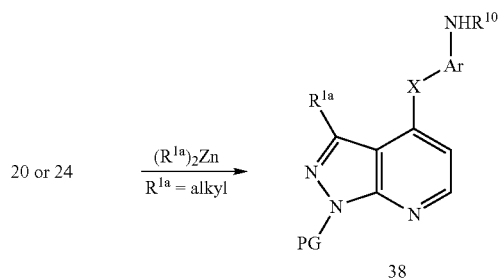

Scheme 14 shows several routes for the synthesis of 3-alkylpyrazolopyridine 37 and the corresponding amide 38. Pd or Ni-catalyzed hydrogenation of the double or triple bond of intermediate 5 ($R^1$ is an optionally substituted alkenyl or alkynyl), provides alkyl-substituted pyrazolopyridine 37 (wherein $R^{1a}$ is optionally substituted alkyl, cycloalkyl or heterocyclyl). Intermediate 37 may subsequently be elaborated into amide 38 using methods described for Scheme 7.

Alternatively, substitution at the 3-position of the pyrazolopyridine core with an alkyl group may be achieved by Negishi coupling of intermediate 20 or 24 with an appropriate alkyl zinc reagent $(R^{1a})_2Zn$ [wherein $R^{1a}$ is optionally substituted alkyl, cycloalkyl or heterocyclyl] according to the descriptions provided for Schemes 6 and 8.

Scheme 15

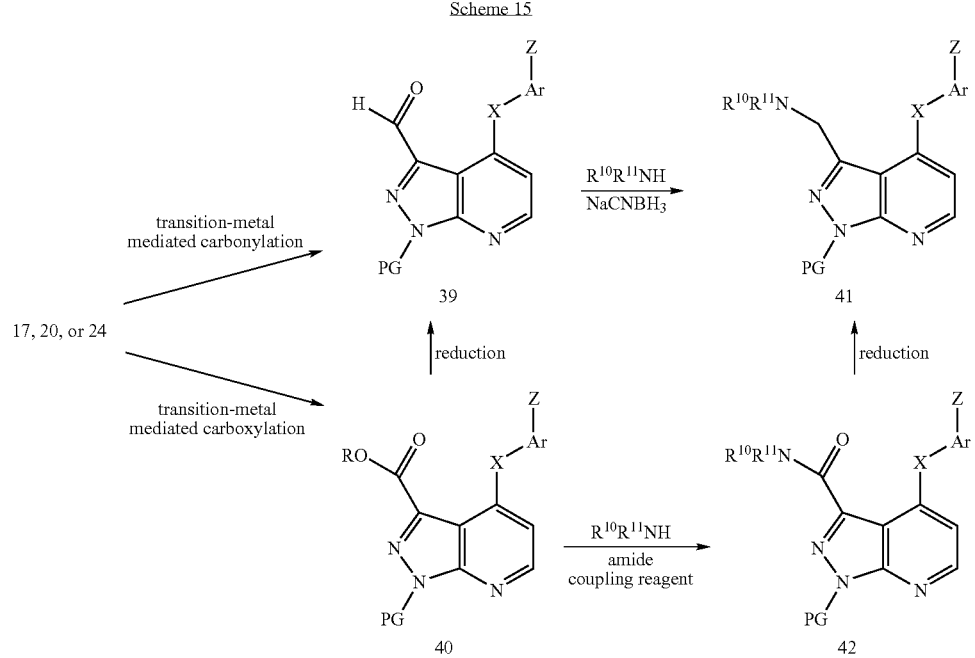

Scheme 15 shows several synthetic routes for the synthesis of amine and amide compounds 41 and 42, respectively (wherein $R^{10}$ and $R^{11}$ are independently H, alkyl, cycloalkyl, heterocyclyl, aryl or heteroaryl, or $R^{10}$ and $R^{11}$ together with the nitrogen to which they are attached form a heterocyclic ring; Z is $NO_2$, $NH_2$ or $R^2NH$ depending on the choice of 17, 20, or 24, respectively, as starting material). Transition-metal mediated (e.g. Pd, Zn, Ni, and the like) carbonylations and carboxylations using carbon monoxide or other formyl source (e.g. sodium formate) provides either aldehydes 39 or carboxylic acids or esters 40 (R is H or alkyl, respectively) under appropriate reaction conditions known to those skilled in the art. Aldehydes 39 can also be prepared by reduction of carboxylates 40 to a benzyl alcohol intermediate (not shown), followed by oxidation using Swern, Dess-Martin reagent, or like conditions. Reductive amination of aldehyde 39 with an amine of the formula $R^{10}R^{11}NH$ according to the protocol described for Scheme 10 provides amine 41, wherein X, Ar, and PG are as defined in Scheme 1. Alternatively, amine 41 can be derived by reduction (using $LiAlH_4$ or similar reducing agent) of amide 42, prepared by coupling of an amine with formula $R^{10}R^{11}NH$ to carboxylic acid 40 (wherein R is H) using amide forming conditions as described for Scheme 7.

Scheme 16

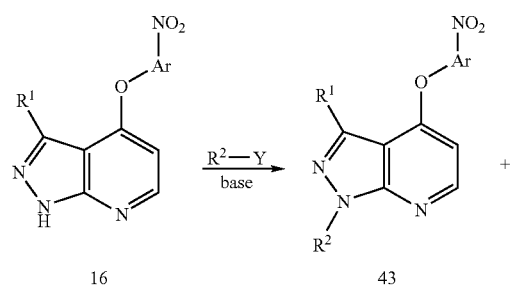

-continued

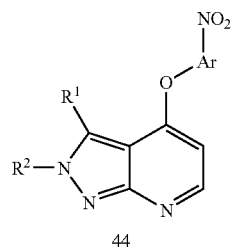

Scheme 16 shows a method for preparing N-alkylated pyrazolopyridines 43 and 44 ($R^2$ is alkyl). Reaction of intermediate 16 (wherein X is O), prepared according to the description for Scheme 5, with an alkylation agent $R^2$—Y (wherein Y is an appropriate leaving group such as halogen, tosylate, mesylate, triflate, or the like) mediated by an appropriate base (e.g. sodium alkoxides, sodium hydride, or the like) provides a mixture of isomers 43 and 44. Isomers 43 and 44 can be separated using purification techniques known to those skilled in the art (e.g. flash chromatography, reverse phase HPLC, or the like). Alternatively, compound 43 can be selectively prepared according to Schemes 1 and 2 by replacing protecting group PG with an alternative alkyl group of choice during synthesis of the starting material aminopyrazole 1 using the methodology described by Misra, R. N., et al. Bioorg. Med. Chem. Lett. 2003, 13, 1133-1136. Compounds 43 and 44 can be further elaborated as described for Schemes 2 and 5.

Scheme 17

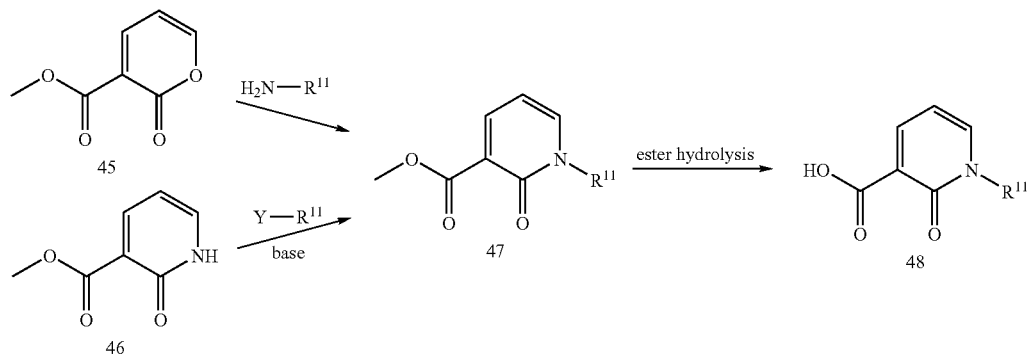

Scheme 17 shows routes for the preparation of acid intermediate 48. Acids of this type may be prepared from either reaction of the commercially available carboxypyrone ester 45 with an appropriate amine $NH_2R^{11}$ (wherein $R^{11}$ is, for example, alkyl, cycloalkyl, heterocyclyl, aryl or heteroaryl), or from the commercially available carboxy pyridone ester 46 via reaction with the appropriate activated electrophile $Y-R^{11}$ (wherein Y is an appropriate leaving group such as halogen, mesylate or tosylate; and $R^{11}$ is, for example, alkyl, cycloalkyl, or heterocyclyl) followed by hydrolysis of the resulting methyl ester 47 to the acid 48. The acid 48 may then be coupled to an appropriate aniline intermediate as in Schemes 7 or 14.

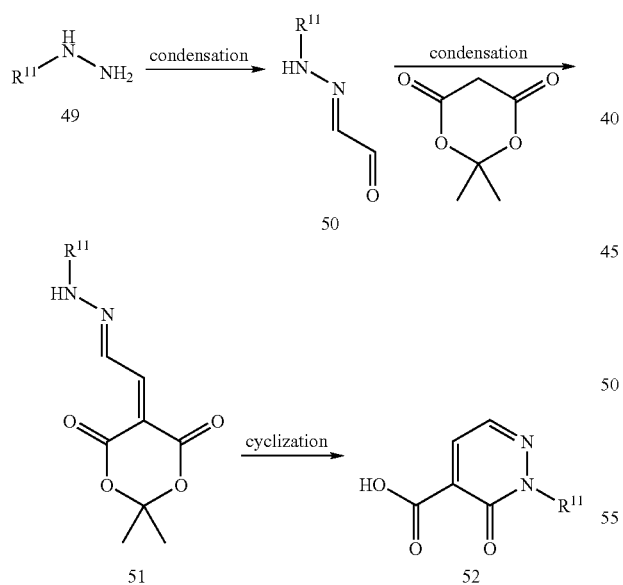

Scheme 18 shows a route for the preparation of acid intermediate 52 according to the general methods described by McNab H., et al., J. Chem. Soc. Perkin Trans. 1, 1982, 1845. Substituted hydrazine 49 (wherein $R^{11}$ is, for example, alkyl, cycloalkyl, aryl or heteroaryl) can be converted to hydrazono acetaldehyde 50 with standard dehydrating conditions such as in the presence of acetic acid at room temperature. The aldehyde/Meldrum's acid condensation product 51 is prepared in a suitable organic solvent such as toluene, benzene or dioxane at room temperature using piperidinium acetate as catalyst. Carboxylic acid pyridazinone 52 is prepared from hydrazono ethylidene 51 by cyclization under basic conditions (sodium methoxide in methanol) at 70° C. The acid can then be coupled to appropriate aniline intermediates as in Schemes 7 or 14.

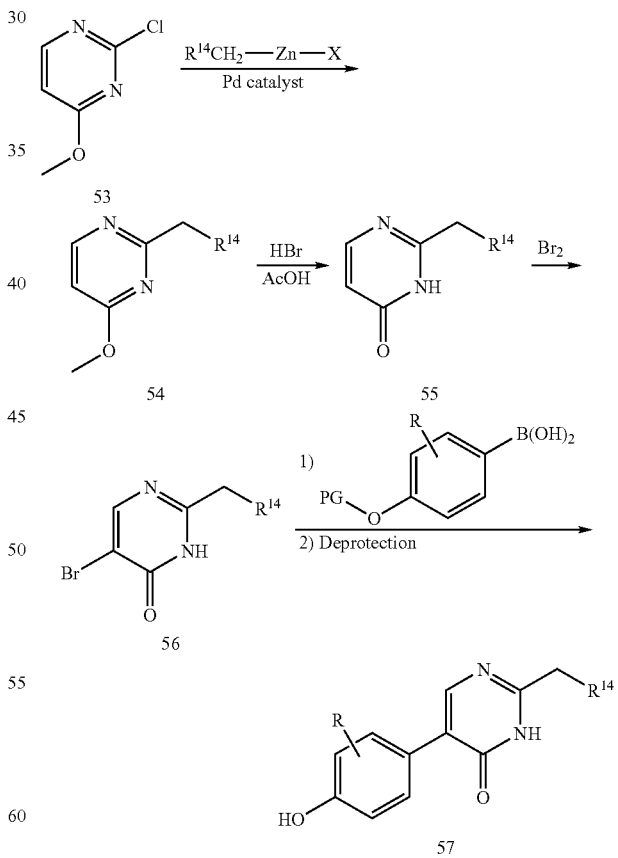

Scheme 19 shows a route for the preparation of phenol intermediate 57. Commercially available 2-chloro-4-methoxypyrimidine 53 is reacted with the appropriate zinc reagent (wherein $R^{14}$ is, for example, alkyl, cycloalkyl, heterocyclyl, heteroaryl or aryl) and palladium catalyst to give 2-substituted 4-methoxypyrimidine 54. Deprotection of the methoxypyrimidine with HBr in acetic acid provides 2-substituted pyrimidinone 55. Bromination in the 5-position gives pyrimidinone intermediate 56. Suzuki coupling of 56 to an appropriate boronic acid gives a bicyclic intermediate which after final deprotection of the phenol gives intermediate 57. Intermediate 57 can be substituted for a phenoxy aniline derivative and reacted with appropriate core intermediates as in Schemes 1, 2, 3 and 4.

is O, N or S) can be accomplished in an appropriate solvent such as n-butanol, at refluxing temperature. Deprotection of the methoxypyrimidine with HBr in acetic acid provides 2-substituted pyrimidinone 59. Alkylation of 59 to provide the 1-substituted pyrimidinone 61 can be accomplished with an alkylation agent $R^{11}$—$X^1$ (wherein $X^1$ is an appropriate leaving group such as halogen, mesylate, or tosylate) mediated by an appropriate base (e.g. sodium alkoxide, lithium or sodium hydride, or the like) providing a mixture of isomers 60 and 61. Isomers 60 and 61 can be separated using purification techniques known to those skilled in the art (e.g. flash chromatography, reverse phase HPLC, or the like). Bromination in the 5-position with a brominating agent such as $Br_2$ or NBS gives pyrimidinone intermediate 62. Suzuki coupling of 62 to an appropriate boronic acid gives a bicyclic intermediate which after final deprotection of the phenol gives intermediate 63 as described for Scheme 19. Intermediate 63 can be substituted for a phenoxy aniline derivative and reacted with appropriate core intermediates as in Schemes 1, 2, 3 and 4.

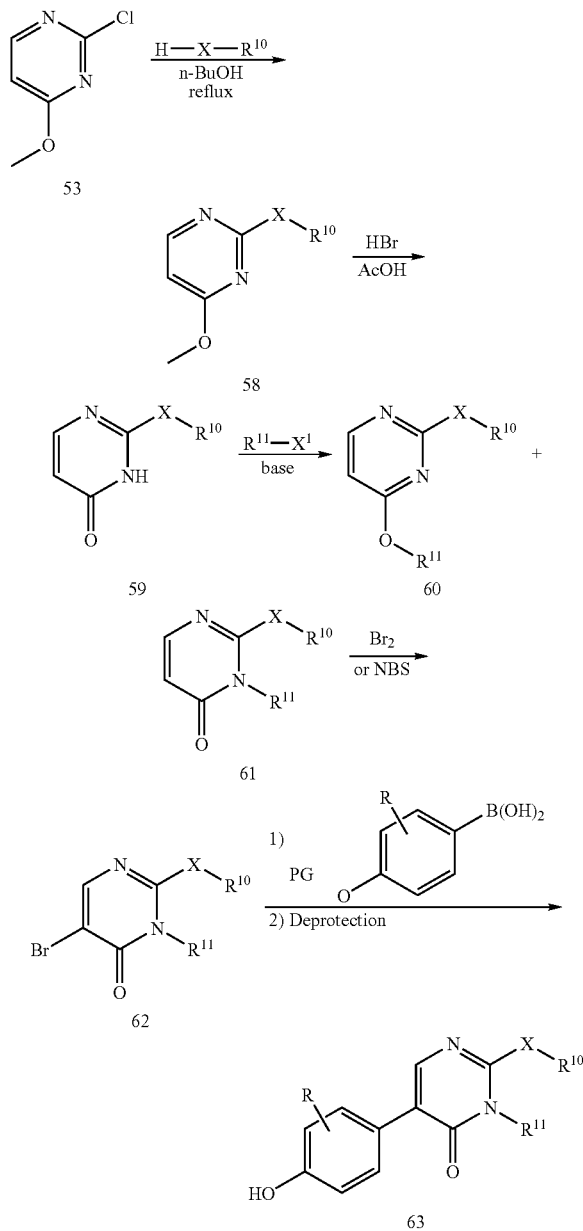

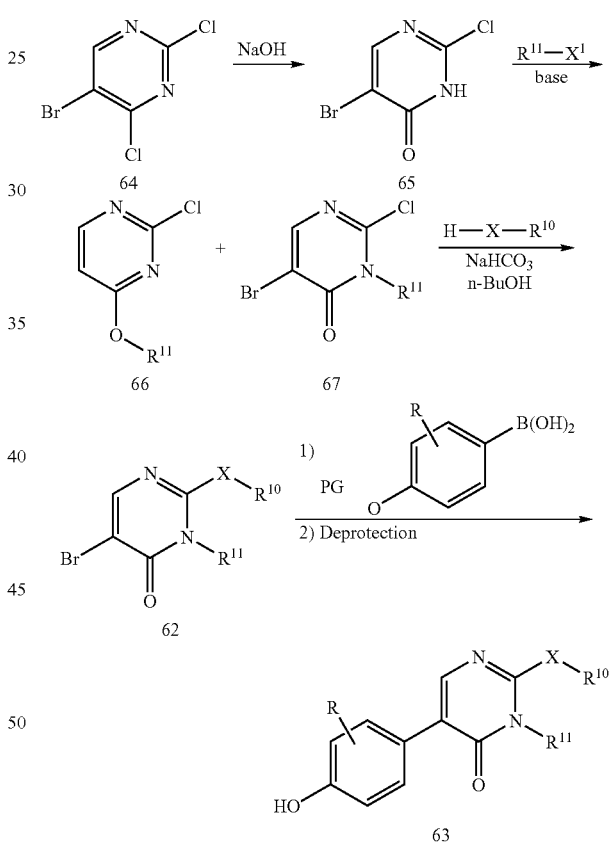

Scheme 20 shows a method for preparing phenol intermediate 63 (wherein $R^{10}$ and $R^{11}$ are independently selected from H, alkyl, cycloalkyl, heterocyclic, aryl and heteroaryl). Nucleophilic substitution of 2-chloro-4-methoxypyrimidine 53 with a compound of the formula H—X—$R^{10}$ (wherein X Alternatively, phenol intermediate 63 (wherein $R^{10}$ and $R^{11}$ are independently selected from H, alkyl, cycloalkyl, heterocyclic, aryl and heteroaryl) can be prepared as shown in Scheme 21. 5-Bromo-2,4-dichloropyrimidine 64 is hydrolyzed with NaOH to give 5-bromo-2-chloropyrimidin-4($^3$H)-one 65 as described in EP 1506967A1. Alkylation of 65 to provide the 1-substituted pyrimidinone 67 can be accomplished with an alkylation agent $R^{11}$—$X^1$ (wherein $X^1$ is an appropriate leaving group such as halogen, mesylate, or tosylate) mediated by an appropriate base (e.g. sodium alkoxide, lithium or sodium hydride, or the like) providing a mixture of isomers 66 and 67. Isomers 66 and 67 can be separated using purification techniques known to those skilled in the art (e.g. flash chromatography, reverse phase HPLC, or the like). Nucleophilic substitution of 67 with a compound of the formula H—X—R$^{10}$, (wherein X is O, N or S) can be accomplished at elevated temperature with a base such as NaHCO$_3$ in an appropriate solvent such as n-butanol. Suzuki coupling of 62 to an appropriate boronic acid gives a bicyclic intermediate which after final deprotection of the phenol gives intermediate 63. Intermediate 63 can be substituted for a phenoxy aniline derivative and reacted with appropriate core intermediates as in Schemes 1, 2, 3 and 4.

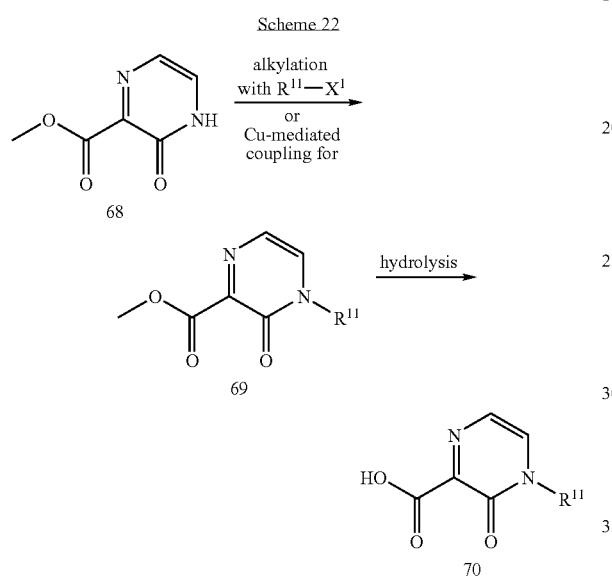

The substituted pyrazino carboxylic acid 70 can be prepared according to Scheme 22. Methyl 3-oxo-3,4-dihydropyrazine-2-carboxylate 68 can be converted to alkyl pyrazino carboxylate 69 by standard basic alkylation conditions using an appropriate alkyl halide R$^{11}$—X$^1$ (wherein R$^{11}$ may be alkyl, cycloalkyl, or heterocyclic, and X$^1$ is an appropriate leaving group such as halogen, mesylate, or tosylate). Suitable alkylation conditions include but are not limited to K$_2$CO$_3$ in a suitable solvent such as acetone or DMF at room temperature or elevated temperature, or NaH in THF at ambient or elevated temperature followed by addition of R$^{11}$—X$^1$. Preferably this alkylation is achieved with LiH in DMF at 0° C., followed by addition of alkyl chloride or alkyl bromide or alkyl iodide and warming to room temperature. When R$^{11}$=aryl or heteroaryl, the pyrazinone ester 69 can be prepared by a copper mediated cross-coupling reaction with iodobenzene, CuI catalyst, a diamine ligand and an appropriate base in a suitable organic solvent such as THF, DMF, PhMe, MeCN or dioxane at elevated temperature. For example, in certain embodiments the reaction conditions include, CuI, N,N'-dimethylethylenediamine and K$_3$PO$_4$ in dioxane at 110° C. Carboxylic acid 70 can then be obtained using standard saponification conditions such as LiOH or NaOH in mixed aqueous/organic solvent systems. The acid 70 can then be coupled to appropriate aniline intermediates as in Schemes 7 or 14.

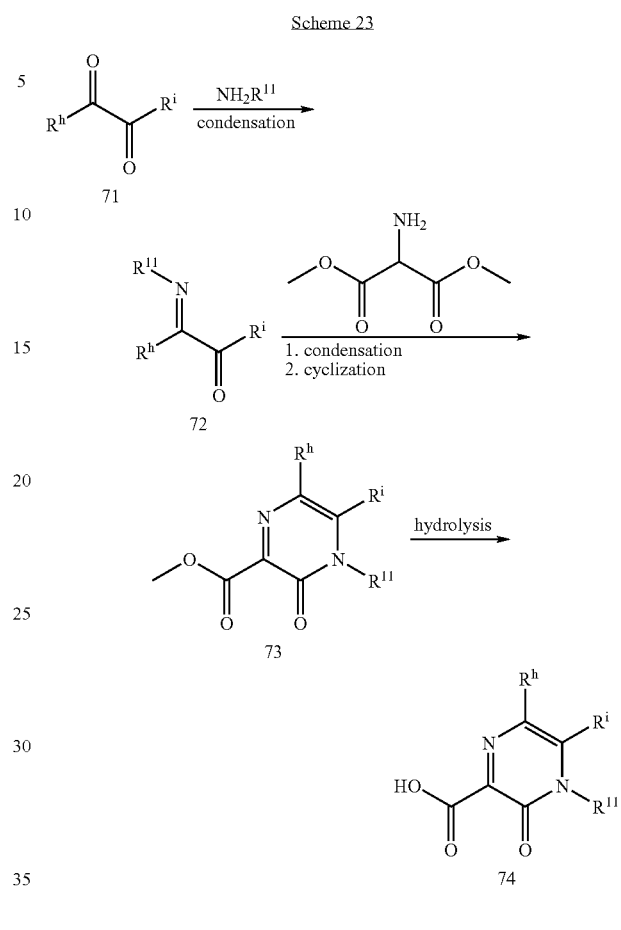

An alternative synthesis of substituted pyrazino carboxylic acid 74 (wherein R$^h$ and R$^i$ are independently H, alkyl, cycloalkyl, heterocyclic, or heteroaryl, and R$^{18}$ may be phenyl or heteroaryl) is shown in Scheme 23. Compound 71 can be converted to imino carbonyl compound 72 by standard dehydrating conditions such as in the presence of acetic acid at room temperature. The carbonyl condensation/cyclization product 73 is prepared in two steps using amino malonate followed by cyclization of the resulting intermediate (not depicted). Compound 72 can be condensed with amino malonate under standard dehydrating conditions using a Dean-Stark trap and a suitable organic solvent such as benzene or toluene at temperatures ranging from 80 to 120° C. The cyclization product 73 is then prepared under basic conditions (sodium methoxide in methanol) at 70° C. Carboxylic acid 74 can then be prepared by ester hydrolysis as described for Scheme 22. The acid 74 can then be coupled to appropriate aniline intermediates as in Schemes 7 or 14.

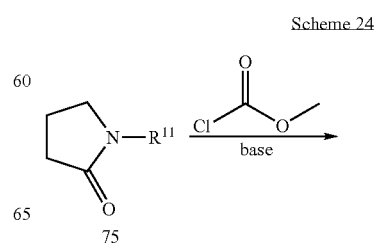

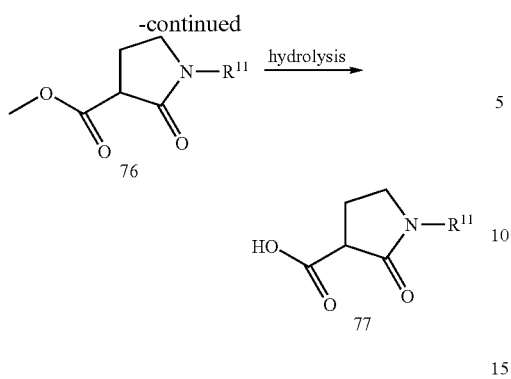

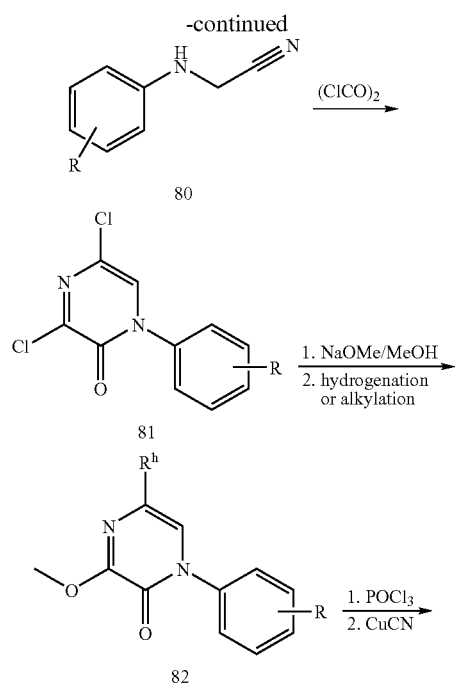

N-alkylated-2-oxopyrrolidine-3-carboxylic acid 77 (wherein $R^{11}$ may be alkyl, cycloalkyl, heterocyclic, heteroaryl, or aryl) may be synthesized according to Scheme 24. Compound 75 can be converted to ester 76 by reaction with methyl chloroformate or methyl carbono-brominate in the presence of an appropriate base (e.g. LDA, LHMDS, or the like). Carboxylic acid 77 can then be prepared from 76 by ester hydrolysis as described for Scheme 22 or using potassium trimethylsilanolate, or the like. The acid 77 can then be coupled to appropriate aniline intermediates as in Schemes 7 or 14.

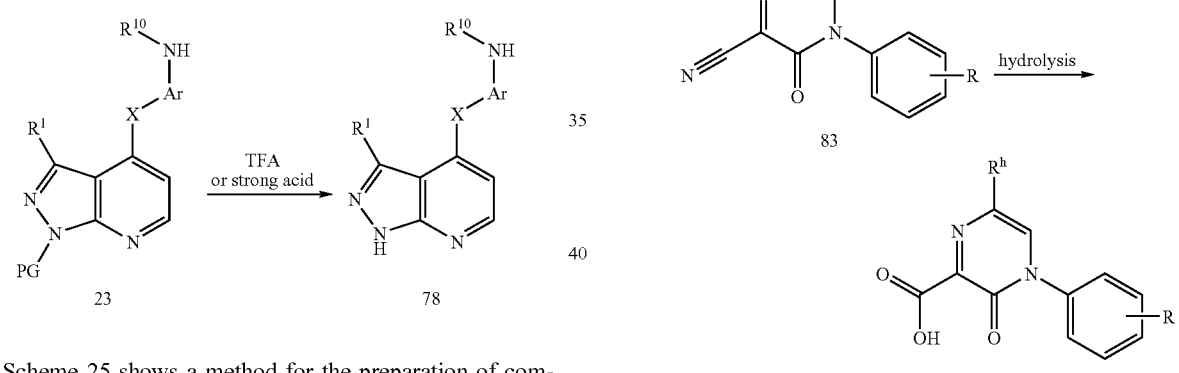

Scheme 25 shows a method for the preparation of compound 78, wherein $R^1$, X, and Ar are as described for Scheme 1, and $R^{10}$ is as described for Scheme 7. Compound 78 can be prepared from compound 23 (prepared as in Scheme 7) by removal of protecting group PG (e.g. p-methoxybenzyl, phenylsulfonyl, or the like) by heating (40-80° C.) as needed with TFA or strong acid, or using alternative deprotection conditions as necessary to remove PG (see T. W. Greene and P. G. M. Wuts, Protecting Groups in Organic Synthesis, Second Edition, Wiley, New York, 1991). Compounds 26, 29, 32, 38, 41, and 42 may be substituted for compounds 23 for removal of PG as appropriate.

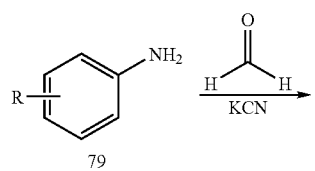

Scheme 26 shows a route for the preparation of pyrazinone acid intermediate 84 wherein $R^h$ is independently selected from H, alkyl, cycloalkyl, heterocyclic, or heteroaryl, which is useful for the synthesis of compounds of Formula I. Substituted aniline 79 can be converted to amino acetonitrile compound 80 by treating with KCN and a formaldehyde equivalent with standard dehydrating conditions, such as in the presence of acetic acid at room temperature. The cyclization product 81 is prepared by treating 80 with oxalyl dichloride in a suitable organic solvent such as dichlorobenzene at elevated temperature (100° C.). Pyrazinone 82 can be made in a two step sequence from the 3,5-dichloro pyrazinone compound 81. First, compound 81 is treated with sodium methoxide in a suitable organic solvent such as MeOH or THF or MeOH/THF mixture at temperatures ranging from 0° C. to reflux, followed by conversion of the intermediate 5-chloropyrazinone (not shown) to the 5-H pyrazinone 82. The conversion can be carried out either under reductive conditions, or, when $R^h$ is alkyl, cycloalkyl, heterocyclic, or heteroaryl, using Pd mediated cross-coupling conditions. Nitrile 83 can be synthesized from methoxy pyrazinone 82 by chlorination followed by nitrilation. The chlorination can be accomplished with POCl₃, thionyl chloride, oxalyl chloride, or PCl₅. Preferably, this transformation is achieved with POCl₃ using DMF as solvent at elevated temperature (about 90° C.). Nitrilation can be achieved by standard conditions with CuCN in a suitable organic solvent such as NMP at elevated temperature (150° C.). Carboxylic acid pyrazinone 84 can be made in a three step, one-pot reaction. First, nitrile compound 83 is treated with concentrated H₂SO₄ neat at room temperature. The resulting amide intermediate is then treated with MeOH, and this mixture is refluxed to generate methyl ester pyrazinone intermediate. Then desired carboxylic acid pyrazinone 74 can be prepared by basic hydrolysis of the methyl ester pyrazinone intermediate under standard conditions using either NaOH or LiOH in standard mixture aqueous/organic solvent systems. The acid 84 may then be coupled to an appropriate aniline intermediate as in Schemes 7 or 14 to provide compounds of Formula I.

phenoxy group into an amino linked heteroaryl amide may proceed via several pathways. Intermediate 85 bearing an appropriate leaving group X¹ may be reacted with a heteroaryl amino ester 87 typically under transition metal catalysis to provide ester 89. Ester 89 may then be converted to compound 90 using standard ester hydrolysis conditions followed by standard amide bond forming conditions. Alternatively, 85 may be reacted with a heteroaryl amino amide 91 under transition metal catalysis to give intermediate 90 directly. Alternatively, the mode of coupling may be reversed, wherein an intermediate 86 bearing an amino group may be reacted with a heteroaryl ester 88 bearing leaving group X² typically under transition metal catalyzed or thermal conditions to give intermediate 89. Intermediate 89 may then be converted to intermediate 90 using standard ester hydrolysis conditions followed by standard amide bond forming conditions. Alternatively, 86 may be reacted with a heteroaryl amide 92 bearing leaving group X², typically under transition

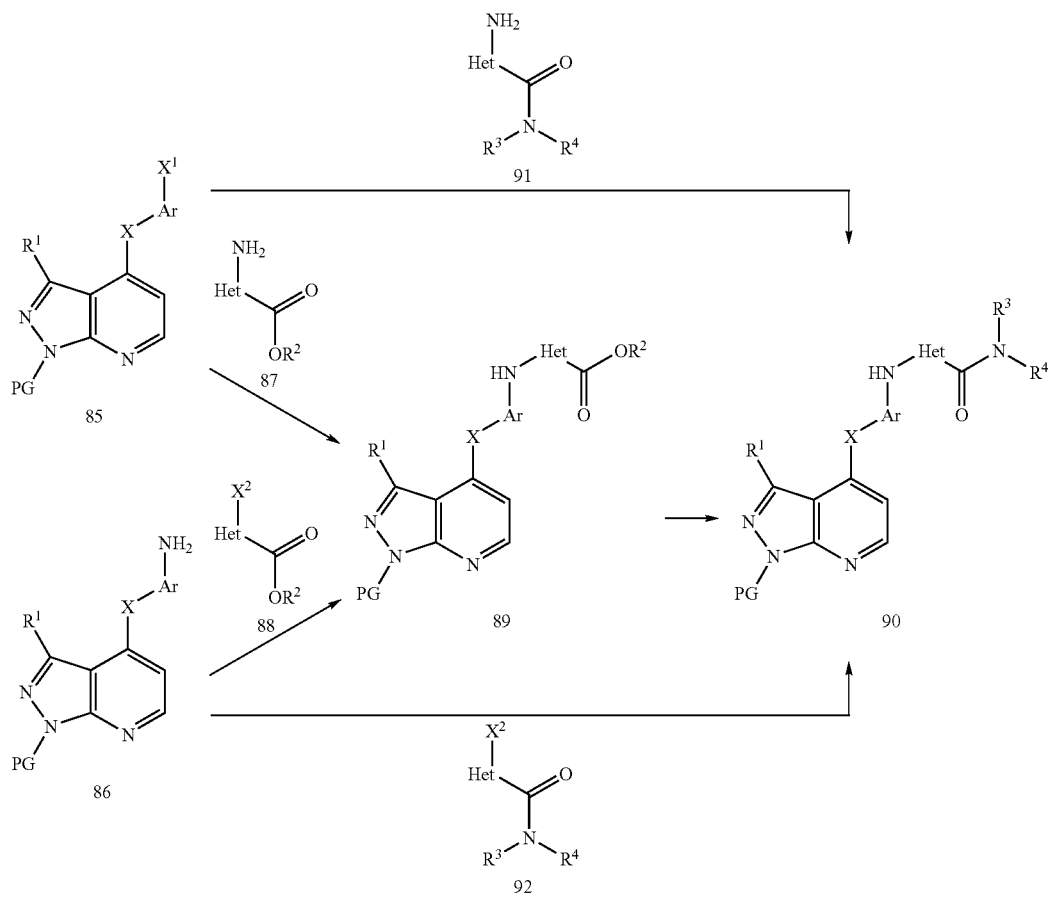

Scheme 27 shows a general scheme for the synthesis of intermediate 90, wherein Het is a substituted or unsubstituted 5-6 membered heteroaryl group having at least one ring nitrogen atom and optionally having a second ring heteroatom selected from N and O. Intermediate compounds 90 are useful for the synthesis of compounds of Formula I. As shown in Scheme 27, elaboration of the pyrazolopyridine 4-position metal catalyzed or thermal conditions to give intermediate 90 directly. When R¹ is an appropriate substituent, intermediate 90 may be deprotected to give final compounds of Formula I. If R¹ is a handle for further elaboration, intermediate 90 may be subjected to further elaboration as in Schemes 6, 8, 9, 10, 11, 12, 13 and 15 for example followed by deprotection to give compounds of Formula I.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determination of the activity of c-Met kinase activity of a compound of Formula Ia or Ib is possible by a number of direct and indirect detection methods. One example of an assay used for the determination of c-Met kinase activity is based on an enzyme linked immunosorbant assay (ELISA). The assay includes a compound of Formula Ia or Ib, c-Met (His-tagged recombinant human Met (amino acids 974-end), expressed by baculovirus), and ATP in assay buffer, as described in Example A.

In MKN45 cells, the activity of cMet inhibitors of Formulas Ia and Ib was determined by the in vitro fluorescence assay as described in Example B.

Certain exemplary compounds described herein were prepared, characterized, and assayed for their c-Met binding activity and in vitro activity against tumor cells. The range of c-Met binding activities was less than 1 nM to about 10 µM. Certain exemplary compounds of the invention had c-Met binding activity $IC_{50}$ values less than 10 nM. Certain compounds of the invention had MKN45 cell-based activity $IC_{50}$ values less than 100 nM.

Administration of Compounds of Formulas Ia and Ib

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Methods of Treatment with Compounds of Formulas Ia or Ib

Compounds of the present invention are useful for treating diseases, conditions and/or disorders including, but not limited to, those characterized by over expression of receptor tyrosine kinases (RTK), e.g. c-Met kinase. Accordingly, another aspect of this invention includes methods of treating or preventing diseases or conditions that can be treated or prevented by inhibiting receptor tyrosine kinases (RTK), including c-Met. In one embodiment, the method comprises administering to a mammal in need thereof a therapeutically effective amount of a compound of Formula Ia or Ib, or a stereoisomer, geometric isomer, tautomer, solvate, metabolite, or pharmaceutically acceptable salt or prodrug thereof.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of Formula Ia or Ib and a pharmaceutically acceptable carrier, adjuvant, or vehicle, wherein said compound of Formula Ia or Ib is present in an amount to detectably inhibit cMet kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula Ia or Ib having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formulas I may be prepared. Suitable examples of sustained-release preparations include semipermeable matrices of solid hydrophobic polymers containing a compound of Formula Ia or Ib, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula Ia or Ib suitable for oral administration may be prepared as discrete units such as pills, capsules, cachets or tablets each containing a predetermined amount of a compound of Formula Ia or Ib.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula Ia or Ib intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula Ia or Ib compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula Ia or Ib may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Also provided are compositions comprising a compound of claim 1 in an amount to detectably inhibit Met kinase activity and a pharmaceutically acceptable carrier, adjuvant, or vehicle.

Combination Therapy

The compounds of Formulas Ia and Ib may be employed alone or in combination with other therapeutic agents for the treatment of a disease or disorder described herein, such as a hyperproliferative disorder (e.g., cancer). In certain embodiments, a compound of Formula Ia or Ib is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula Ia or Ib such that they do not adversely affect each other. Such compounds are suitably present in combination, in amounts that are effective for the purpose intended. In one embodiment, a composition of this invention comprises a compound of Formula Ia or Ib, or a stereoisomer, geometric isomer, tautomer, solvate, metabolite, or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula Ia or Ib, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula Ia or Ib, or a stereoisomer, geometric isomer, tautomer, solvate, metabolite, or pharmaceutically acceptable salt or prodrug thereof, and the use of at least one other cancer treatment method. The amounts of the compound(s) of Formula Ia or Ib and the other pharmaceutically active chemotherapeutic agent(s) and the relative timings of administration will be selected in order to achieve the desired combined therapeutic effect.

Also provided are compositions comprising a compound of Formula Ia or Ib in combination with an additional therapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

Metabolites of Compounds of Formulas Ia and Ib

Also falling within the scope of this invention are the in vivo metabolic products of heterobicyclic pyrazole compounds of Formulas Ia and Ib described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formulas Ia and Ib, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Prodrugs of Compounds of Formulas Ia and Ib

In addition to compounds of Formulas Ia and Ib, the invention also includes pharmaceutically acceptable prodrugs of such compounds. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula Ia or Ib can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in Advanced Drug Delivery Reviews, (1996) 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

Free amine groups of compounds of Formulas Ia and Ib can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently $(C_1-C_{10})$alkyl, $(C_3-C_7)$cycloalkyl, or benzyl, or R-carbonyl is a natural α-aminoacyl or natural α-aminoacyl-natural α-aminoacyl, —C(OH)C(O)OY wherein Y is H, $(C_1-C_6)$alkyl or benzyl, —$C(OY_0)Y_1$ wherein $Y_0$ is $(C_1-C_4)$ alkyl and $Y_1$ is $(C_1-C_6)$ alkyl, carboxy$(C_1-C_6)$alkyl, amino$(C_1-C_4)$alkyl or mono-N— or di-N,N—$(C_1-C_6)$alkylaminoalkyl, or —$C(Y_2)Y_3$ wherein $Y_2$ is H or methyl and $Y_3$ is mono-N— or di-N,N—$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984).

Articles of Manufacture

In another embodiment of the invention, an article of manufacture, or "kit", containing materials useful for the treatment of the diseases and disorders described above is provided. In one embodiment, the kit comprises a container comprising a heterobicyclic pyrazole compound of Formula Ia or Ib, or a stereoisomer, geometric isomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula Ia or Ib or a formulation thereof which is effective for treating the condition and may have a sterile access port (for example, the container may be an intravenous solution bag or a vial having a stopper pierceable by a hypodermic injection needle). At least one active agent in the composition is a compound of Formula Ia or Ib. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula Ia or Ib can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula Ia or Ib and, if present, the second pharmaceutical formulation. For example, if the kit comprises a first composition comprising a compound of Formula Ia or Ib and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula Ia or Ib, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula Ia or Ib contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula Ia or Ib and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other c-Met inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted on a Biotage system (Manufacturer: Dyax Corporation) having a silica gel column or on a silica SEP PAK® cartridge (Waters). $^1$H NMR spectra were recorded on a Varian instrument operating at 400 MHz. $^1$H NMR spectra were obtained as $CDCl_3$, $d_6$-DMSO, $CH_3OD$ or $d_6$-acetone solutions (reported in ppm), using tetramethylsilane (0.00 ppm) or residual solvent ($CDCl_3$: 7.25 ppm; $d_6$-DMSO: 2.50 ppm; $CD_3OD$: 3.31 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Example 1

Preparation of N-(4-(1H-pyrazolo[3,4-b]pyridin-4-yloxy)-3-fluorophenylcarbamothioyl)-2-phenylacetamide

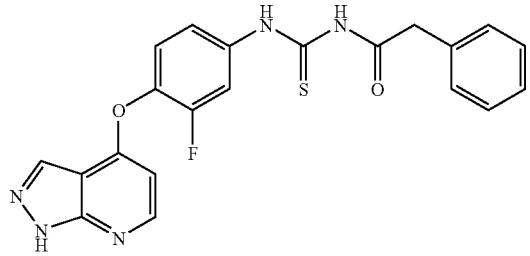

Step A: Preparation of 5-((1-(4-methoxybenzyl)-1H-pyrazol-5-ylamino)methylene)-2,2-dimethyl-1,3-dioxane-4,6-dione: A stirred mixture of triethoxymethane (339 mL, 2037 mmol), and 2,2-dimethyl-1,3-dioxane-4,6-dione (Meldrum's acid) (35.2 g, 244 mmol) was heated to 80° C. for 1 hour. A suspension of 1-(4-methoxybenzyl)-1H-pyrazol-5-amine [41.4 g, 204 mmol; prepared according to the procedure described by Misra, R. N., et al. Bioorg. Med. Chem. Lett. 2003, 13, 1133-1136, except desalting was performed as follows: 1-(4-methoxybenzyl)-1H-pyrazol-5-amine hydrochloride (44 g) was partitioned between MTBE (300 mL) and 1N aqueous NaOH (300 mL), after separating the phases, the aqueous suspension was re-extracted with MTBE (8×100 mL), followed by drying ($Na_2SO_4$) the combined organic phases, and concentration in vacuo to obtain the free-based 1-(4-methoxybenzyl)-1H-pyrazol-5-amine (30 g)] in triethoxymethane (339 mL, 2037 mmol) was added at once and heating at 80° C. was continued for 18 hours under $N_2$. After cooling to room temperature, toluene azeotrope (2×200 mL) was utilized to remove EtOH. The resulting suspension was diluted with diethyl ether (500 mL) and filtered to obtain a yellow solid (33.5 g, 46%). $^1$H NMR (400 MHz, $CDCl_3$) δ 11.13 (d, J=13 Hz, 1H), 8.26 (d, J=13 Hz, 1H), 7.50 (d, J=2 Hz, 1H), 7.25 (d, J=9 Hz, 2H), 6.88 (d, J=9 Hz, 2H), 6.21 (d, J=2 Hz, 1H), 5.28 (s, 2H), 3.78 (s, 3H), 1.74 (s, 6H).

Step B: Preparation of 1-(4-methoxybenzyl)-1H-pyrazolo[3,4-b]pyridin-4-ol: To a stirred biphenyl-diphenyl ether eutectic (also called Dowtherm) (100 mL) at 240° C. under $N_2$ was added 5-((1-(4-methoxybenzyl)-1H-pyrazol-5-ylamino)methylene)-2,2-dimethyl-1,3-dioxane-4,6-dione (33.5 g, 93.7 mmol) in portions as a solid over a 10 minute period. After addition was complete, the mixture was heated at 240° C. for 10 minutes. After cooling to room temperature, the mixture was diluted with hexanes (300 mL), and the hexanes were decanted along with the majority of the Dowtherm. The remaining residue was diluted with diethyl ether (200 mL), and the ether was decanted from the residue and discarded. Lastly the residue was suspended in DCM (100 mL). The stirred suspension was diluted with diethyl ether (300 mL) and filtered. The resulting off-white solid (22.7 g, 91%) was dried under high vacuum. $^1$H NMR (400 MHz, DMSO-d6) δ 11.7 (br s, 1H), 8.17 (br s, 1H), 8.08 (s, 1H), 7.20 (d, J=9 Hz, 2H), 6.86 (d, J=9 Hz, 2H), 6.45 (br s, 1H), 5.50 (s, 2H), 3.70 (s, 3H).

Step C: Preparation of 1-(4-methoxybenzyl)-4-(2-fluoro-4-nitrophenoxy)-1H-pyrazolo[3,4-b]pyridine: A stirred mixture of 1-(4-methoxybenzyl)-1H-pyrazolo[3,4-b]pyridin-4-ol (22.00 g, 86.18 mmol) cesium carbonate (28.08 g, 86.18 mmol), 1,2-difluoro-4-nitrobenzene (13.71 g, 86.18 mmol) and DMA (100 mL) was heated to 100° C. for 1 hour. After cooling to room temperature, the mixture was partitioned between DCM (500 mL) and water (500 mL). The phases were separated, and the organic phase washed with water (3×200 mL), dried (Na$_2$SO$_4$), filtered, and concentrated in vacuo. The resulting residue was triturated with diethyl ether (100 mL) and hexanes (200 mL) co-solvent, and the resulting beige powder was filtered. A second crop was obtained after cooling in a –10° C. freezer overnight. The two crops were combined (28 g, 82%). $^1$H NMR (400 MHz, CDCl$_3$) δ 8.45 (d, J=5.5 Hz, 1H), 8.16 (m, 2H), 7.86 (s, 1H), 7.39 (m, 1H), 7.35 (d, J=8.6 Hz, 2H), 6.84 (d, J=8.2 Hz, 2H), 6.48 (d, J=5.5 Hz, 1H), 5.65 (s, 2H), 3.76 (s, 3H). $^{19}$F NMR (376 MHz, CDCl$_3$) δ –124.2 (m).

Step D: Preparation of 4-(1-(4-methoxybenzyl)-1H-pyrazolo[3,4-b]pyridin-4-yloxy)-3-fluorobenzenamine: To a stirred solution of 1-(4-methoxybenzyl)-4-(2-fluoro-4-nitrophenoxy)-1H-pyrazolo[3,4-b]pyridine (0.560 g, 1.42 mmol) in a MeOH (20 mL) and THF (5 mL) co-solvent was added zinc (0.464 g, 7.10 mmol), followed by saturated aqueous NH$_4$Cl (5 mL). Next 6N aqueous HCl (3-4 mL) was added until all solids dissolved and the pH was 1-2. The reaction was stirred at room temperature for 18 hours. The resulting mixture was partitioned between DCM (30 mL) and saturated aqueous NH$_4$Cl (30 mL). The phases were separated, and the aqueous phase was re-extracted with DCM (20 mL). The combined organic phases were dried (Na$_2$SO$_4$), filtered, and concentrated in vacuo. The resulting waxy solid (504 mg, 72%) was used in the next step without purification. $^1$H NMR (400 MHz, CDCl$_3$) δ 8.35 (d, J=5.5 Hz, 1H), 7.72 (s, 1H), 7.32 (d, J=8.6 Hz, 2H), 7.02 (m, 1H), 6.82 (d, J=9.0 Hz, 2H), 6.40-6.55 (m, 3H), 5.61 (s, 2H), 3.82 (br s, 2H), 3.75 (s, 3H); $^{19}$F NMR (376 MHz, CDCl$_3$) δ –129.0 (m).

Step E: Preparation of 1-(4-(1-(4-methoxybenzyl)-1H-pyrazolo[3,4-b]pyridin-4-yloxy)-3-fluorophenyl)-3-(2-phenylacetyl)thiourea: To a stirred solution of 4-(1-(4-methoxybenzyl)-1H-pyrazolo[3,4-b]pyridin-4-yloxy)-3-fluorobenzenamine (0.504 g, 1.38 mmol; obtained from Example 1, Step D in THF (5 mL) was added 2-phenylethanoyl isothiocyanate (0.294 g, 1.66 mmol; prepared according to J. Org. Chem. 1964, 29, 1115-1119). The reaction was stirred at room temperature for 30 minutes. The reaction mixture was loaded directly onto a preparative TLC plate, eluting with 5% MeOH/DCM. The product was obtained as a waxy solid (630 mg, 71%). LRMS (APCI+): 93% purity, 220 nm, m/z 542 (M+1) detected; $^1$H NMR (400 MHz, CDCl$_3$) δ 12.49 (br s, 1H), 8.50 (br s, 1H), 8.38 (d, J=5.5 Hz, 1H), 7.94 (m, 1H), 7.82 (s, 1H), 7.42 (m, 4H), 7.32 (m, 4H), 7.26 (m, 1H, overlaps CHCl$_3$), 6.83 (d, J=8.6 Hz, 2H), 6.42 (d, J=5.5 Hz, 1H), 5.63 (s, 2H), 3.76 (s, 3H), 3.75 (s, 2H); $^{19}$F NMR (376 MHz, CDCl$_3$) δ –126.3 (m).

Step F: Preparation of N-(4-(1H-pyrazolo[3,4-b]pyridin-4-yloxy)-3-fluorophenylcarbamothioyl)-2-phenylacetamide: A stirred mixture of 1-(4-(1-(4-methoxybenzyl)-1H-pyrazolo[3,4-b]pyridin-4-yloxy)-3-fluorophenyl)-3-(2-phenylacetyl)thiourea (0.630 g, 1.16 mmol) and 2,2,2-trifluoroacetic acid (TFA) (1.79 mL, 23.3 mmol) was heated to 65° C. for 3 hours under N$_2$. The mixture was concentrated in vacuo using toluene (3×5 mL) to azeotrope residual TFA. The residue was partitioned between saturated aqueous NaHCO$_3$ (10 mL) and EtOAc (10 mL). The phases were separated, and the organic phase washed with brine (10 mL), dried (Na$_2$SO$_4$), filtered, and concentrated in vacuo. The residue was partially purified by preparative TLC eluting with EtOAc. The crude was then triturated with DCM (5 mL) and chilled to –10° C. to obtain the product as a white powder. The solid was suspended in abs EtOH (2×2 mL) and concentrated in vacuo to remove residual DCM. The white powder (61 mg, 12%) was then dried at 60° C. under high vacuum for 1 hour. LRMS (APCI+): 100% purity, 220 nm, m/z 422 (M+1); $^1$H NMR (400 MHz, DMSO-d6) δ 13.79 (s, 1H), 12.49 (s, 1H), 11.84 (s, 1H), 8.39 (d, J=5.5 Hz, 1H), 7.99 (d, J=12.1 Hz, 1H), 7.79 (s, 1H), 7.54 (m, 2H), 7.35 (m, 4H), 7.29 (m, 1H), 6.51 (d, J=5.5 Hz, 1H), 3.84 (s, 2H); $^{19}$F NMR (376 MHz, DMSO-d6) δ –129.2 (m).

Example 2

Preparation of N-(4-(1H-pyrazolo[3,4-b]pyridin-4-yloxy)-3-fluorophenyl)-N-(4-fluorophenyl)cyclopropane-1,1-dicarboxamide

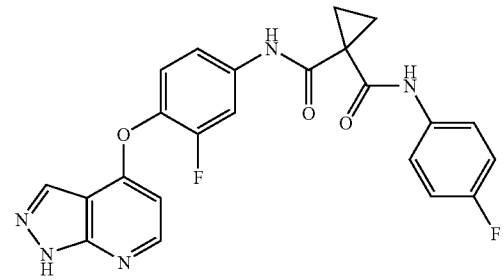

Step A: Preparation of N-(4-(1-(4-methoxybenzyl)-1H-pyrazolo[3,4-b]pyridin-4-yloxy)-3-fluorophenyl)-N-(4-fluorophenyl)cyclopropane-1,1-dicarboxamide: To a stirred mixture of 4-(1-(4-methoxybenzyl)-1H-pyrazolo[3,4-b]pyridin-4-yloxy)-3-fluorobenzenamine (73 mg, 0.20 mmol; obtained from Example 1, Step D) and ((4-fluorophenyl)carbamoyl)cyclopropanecarboxylic acid (49 mg, 0.220 mmol; prepared from cyclopropane-1,1-dicarboxylic acid and 4-fluoroaniline using the methods of WO 2005/030140 and by Shih and Rankin, Synth. Comm. 1996, 26(4), 833-836) in DMA (2 mL) was added N1-((ethylimino)methylene)-N3,N3-dimethylpropane-1,3-diamine hydrochloride (EDCI) (77 mg, 0.400 mmol). The reaction was stirred for 1 hour at room temperature. The reaction was diluted with EtOAc (10 mL) and water (10 mL). The phases were separated, and the organic phase washed with water (3×10 mL), brine (10 mL), dried (Na$_2$SO$_4$), filtered, and concentrated in vacuo. The crude was purified by preparative TLC eluting with 3% MeOH/DCM. The product was obtained as a waxy solid (42 mg, 33%). $^1$H NMR (400 MHz, CDCl$_3$) δ 9.97 (s, 1H), 8.36 (d, J=5 Hz, 1H), 8.20 (s, 1H), 7.77 (m, 2H), 7.46 (m, 2H), 7.26 (m, 4H), 7.06 (m, 2H), 6.83 (d, J=9 Hz, 2H), 6.40 (d, J=5 Hz, 1H), 5.62 (s, 2H), 3.76 (s, 3H), 1.79 (m, 2H), 1.62 (m, 2H, overlaps with water).

Step B: Preparation of N-(4-(1H-pyrazolo[3,4-b]pyridin-4-yloxy)-3-fluorophenyl)-N-(4-fluorophenyl)cyclopropane-1,1-dicarboxamide: Prepared according to the procedure for Example 1, Step F, substituting (4-(1-(4-methoxybenzyl)-1H-pyrazolo[3,4-b]pyridin-4-yloxy)-3-fluorophenyl)-N-(4-fluorophenyl)cyclopropane-1,1-dicarboxamide (0.040 g, 0.0702 mmol) for 1-(4-(1-(4-methoxybenzyl)-1H-pyrazolo[3,4-b]pyridin-4-yloxy)-3-fluorophenyl)-3-(2-phenylacetyl)thiourea. The product was obtained as a white powder (7 mg, 20%). LRMS (ESI+): 94% purity, 220 nm, m/z 450 (M+1) detected; $^1$H NMR (MeOD, 400 MHz) δ 8.34 (d, J=5 Hz, 1H), 7.85 (m, 2H), 7.56 (m, 2H), 7.42 (m, 1H), 7.35 (m, 1H), 7.06 (m, 2H), 6.49 (d, J=5 Hz, 1H), 1.64 (s, 4H).

Example 3

Preparation of N-(3-fluoro-4-(1-methyl-1H-pyrazolo[3,4-b]pyridin-4-yloxy)phenyl)-N-(4-fluorophenyl)cyclopropane-1,1-dicarboxamide

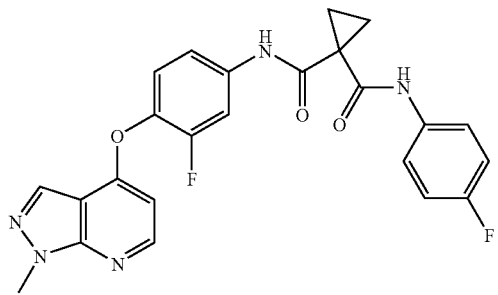

Step A: Preparation of 4-(2-fluoro-4-nitrophenoxy)-1H-pyrazolo[3,4-b]pyridine: A stirred mixture of 1-(4-methoxybenzyl)-4-(2-fluoro-4-nitrophenoxy)-1H-pyrazolo[3,4-b]pyridine (27.6 g, 70.0 mmol; obtained from Example 1, Step C) and TFA (53.9 mL, 700 mmol) was heated to reflux for 18 hours under N$_2$. The reaction was allowed to cool to room temperature, and then concentrated in vacuo using toluene (4×100 mL) to azeotrope residual TFA. The residue was diluted with EtOAc (200 mL) and carefully neutralized (pH=8-9) with saturated aqueous NaHCO$_3$ (100 mL). The biphasic suspension was stirred at room temperature for 30 minutes. The suspension was filtered. The resulting solid was dried by toluene azeotrope (2×200 mL) to obtain the product (18.7 g, 97%). $^1$H NMR (DMSO-d6, 400 MHz) δ 13.85 (br s, 1H), 8.40 (m, 2H), 8.15 (m, 1H), 7.91 (s, 1H), 7.66 (m, 1H), 6.65 (m, 1H).

Step B: Preparation of 4-(2-fluoro-4-nitrophenoxy)-1-methyl-1H-pyrazolo[3,4-b]pyridine: A similar pyrazole alkylation protocol was utilized by Lynch, B. et al. Can. J. Chem. 1988, 66, 420-428. To a stirred mixture of 4-(2-fluoro-4-nitrophenoxy)-1H-pyrazolo[3,4-b]pyridine (0.250 g, 0.912 mmol) absolute EtOH (0.5 mL), and a 1.5 M sodium ethoxide-ethanol solution (1.22 mL, 1.82 mmol; prepared from absolute EtOH and Na metal) at 0° C. under N$_2$ was added iodomethane (0.114 mL, 1.82 mmol). The suspension was allowed to warm to room temperature slowly as the ice melted, and stirring was continued for 18 hours at room temperature. The reaction was concentrated in vacuo, suspended in DCM and loaded onto a preparative TLC plate, eluting with 3% MeOH/DCM to separate the two pyrazole regioisomers. The desired 1-methyl isomer was obtained as a white solid (49 mg, 19%). $^1$H NMR (400 MHz, CDCl$_3$) δ 8.44 (d, J=5 Hz, 1H), 8.17 (m, 2H), 7.85 (s, 1H), 7.41 (m, 1H), 6.49 (d, J=5 Hz, 1H), 4.18 (s, 3H).

Step C: Preparation of 3-fluoro-4-(1-methyl-1H-pyrazolo[3,4-b]pyridin-4-yloxy)benzenamine: Prepared according to the procedure of Example 1, Step D, substituting 4-(2-fluoro-4-nitrophenoxy)-1-methyl-1H-pyrazolo[3,4-b]pyridine (49 mg, 0.17 mmol; obtained from Example 3, Step B) for 1-(4-methoxybenzyl)-4-(2-fluoro-4-nitrophenoxy)-1H-pyrazolo[3,4-b]pyridine. Yield: 22 mg, 42%. The product was used in the next step without purification. $^1$H NMR (400 MHz, CDCl$_3$) δ 8.34 (d, J=6 Hz, 1H), 7.71 (s, 1H), 7.04 (m, 1H), 6.55 (m, 1H), 6.49 (m, 1H), 6.42 (d, J=6 Hz, 1H), 4.13 (s, 3H), 3.86 (br s, 2H).

Step D: Preparation of N-(3-fluoro-4-(1-methyl-1H-pyrazolo[3,4-b]pyridin-4-yloxy)phenyl)-N-(4-fluorophenyl)cyclopropane-1,1-dicarboxamide: Prepared according to the procedure for Example 2, Step A, substituting 3-fluoro-4-(1-methyl-1H-pyrazolo[3,4-b]pyridin-4-yloxy)benzenamine (22 mg, 0.085 mmol; obtained from Example 3, Step C) for 4-(1-(4-methoxybenzyl)-1H-pyrazolo[3,4-b]pyridin-4-yloxy)-3-fluorobenzenamine. In addition, the amount of EDCI (94 mg, 0.51 mmol) and ((4-fluorophenyl)carbamoyl)cyclopropanecarboxylic acid (117 mg, 0.51 mmol) were both increased. The crude was purified by preparative TLC eluting with EtOAc. The product was obtained as a white solid (1.4 mg, 3%). LRMS (ESI+): 97% purity, 220 nm, m/z 464 (M+1) detected; $^1$H NMR (400 MHz, CDCl$_3$) δ 10.0 (br s, 1H), 8.35 (d, J=5 Hz, 1H), 8.10 (s, 1H), 7.78 (m, 1H), 7.76 (s, 1H), 7.45 (m, 2H), 7.23 (m, 1H), 7.07 (m, 2H), 6.41 (d, J=5 Hz, 1H), 4.14 (s, 3H), 1.81 (m, 2H), 1.62 (m, 2H).

Example 4

Preparation of N-(3-fluoro-4-(2-methyl-2H-pyrazolo[3,4-b]pyridin-4-yloxy)phenyl)-N-(4-fluorophenyl)cyclopropane-1,1-dicarboxamide

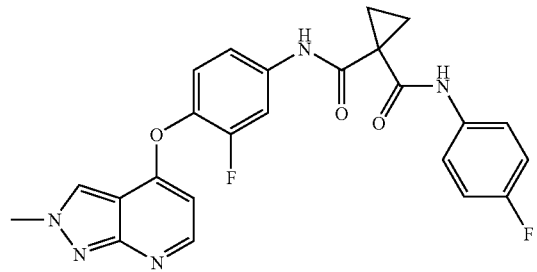

Step A: Preparation of 4-(2-fluoro-4-nitrophenoxy)-2-methyl-2H-pyrazolo[3,4-b]pyridine: Prepared from 4-(2-fluoro-4-nitrophenoxy)-1H-pyrazolo[3,4-b]pyridine (250 mg, 0.91 mmol; obtained from Example 3, Step A) according to the procedure of Example 3, Step B. The two pyrazole regioisomers were separated by preparative TLC, eluting with 3% MeOH/DCM. The desired 2-methyl isomer was obtained as a white solid (63 mg, 23%). $^1$H NMR (400 MHz, CDCl$_3$) δ 8.57 (d, J=5 Hz, 1H), 8.16 (m, 2H), 7.91 (s, 1H), 7.38 (m, 1H), 6.36 (d, J=5 Hz, 1H), 4.27 (s, 3H).

Step B: Preparation of 3-fluoro-4-(2-methyl-2H-pyrazolo[3,4-b]pyridin-4-yloxy)benzenamine: Prepared according to the procedure for Example 1, Step D, substituting 4-(2- fluoro-4-nitrophenoxy)-1-methyl-1H-pyrazolo[3,4-b]pyridine (63 mg, 0.22 mmol; obtained from Example 4, Step A) for 1-(4-methoxybenzyl)-4-(2-fluoro-4-nitrophenoxy)-1H-pyrazolo[3,4-b]pyridine. Yield: 22 mg, 30%. The product was used in the next step without purification. ¹H NMR (400 MHz, CDCl₃) δ 8.48 (d, J=5 Hz, 1H), 7.81 (s, 1H), 7.02 (m, 1H), 6.56 (m, 1H), 6.48 (m, 1H), 6.25 (d, J=5 Hz, 1H), 4.22 (s, 3H), 3.89 (br s, 2H).

Step C: Preparation of N-(3-fluoro-4-(2-methyl-2H-pyrazolo[3,4-b]pyridin-4-yloxy)phenyl)-N-(4-fluorophenyl)cyclopropane-1,1-dicarboxamide: Prepared according to the procedure of Example 3, Step D substituting 3-fluoro-4-(2-methyl-2H-pyrazolo[3,4-b]pyridin-4-yloxy)benzenamine (22 mg, 0.085 mmol; obtained from Example 4, Step B) for 3-fluoro-4-(1-methyl-1H-pyrazolo[3,4-b]pyridin-4-yloxy)benzenamine. The crude was purified by preparative TLC eluting with 10% MeOH/EtOAc. The product was obtained as a white solid (3.5 mg, 9%). LCMS (ESI+): 99% purity, 220 nm, m/z 464 (M+1) detected; ¹H NMR (400 MHz, CDCl₃) δ 10.25 (br s, 1H), 8.48 (m, 2H), 7.85 (s, 1H), 7.77 (m, 1H), 7.47 (m, 2H), 7.29 (m, 1H), 7.20 (m, 1H), 7.05 (m, 2H), 6.25 (m, 1H), 4.22 (s, 3H), 1.81 (m, 2H), 1.65 (m, 2H).

Example 5

Preparation of N-(3-fluoro-4-(3-methyl-1H-pyrazolo[3,4-b]pyridin-4-yloxy)phenylcarbamothioyl)-2-phenylacetamide

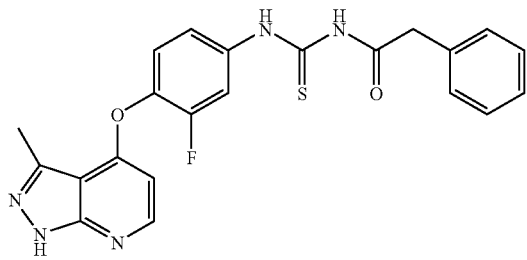

Step A: Preparation of 5-((1-(4-methoxybenzyl)-3-methyl-1H-pyrazol-5-ylamino)methylene)-2,2-dimethyl-1,3-dioxane-4,6-dione: A stirred mixture of trimethoxymethane (118 mL, 1077 mmol) and 2,2-dimethyl-1,3-dioxane-4,6-dione (Meldrum's acid) (15.5 g, 108 mmol) was heated under reflux for 1 hour. A suspension of 1-(4-methoxybenzyl)-3-methyl-1H-pyrazol-5-amine (23.4 g, 108 mmol; prepared according to the procedure described by Misra, R. N.; et al. Bioorg. Med. Chem. Lett. 2003, 13, 1133-1136) in trimethyl orthoformate (110 mL, 1075 mmol) was added at once, and the dark orange reaction was refluxed for 3 hours under N₂. After cooling to room temperature, the reaction was concentrated in vacuo, using toluene (3×100 mL) to azeotrope residual trimethyl orthoformate. The resulting deep orange residue was triturated/sonicated with diethyl ether (200 mL). The resulting peach colored solid was filtered, washing with diethyl ether (3×50 mL). Yield: 28.0 g, 70%. ¹H NMR (400 MHz, DMSO-d6) δ 11.13 (d, J=11 Hz, 1H), 8.06 (d, J=11 Hz, 1H), 7.10 (d, J=9 Hz, 2H), 6.87 (d, J=9 Hz, 2H), 6.32 (s, 1H), 5.19 (s, 2H), 3.70 (s, 3H), 2.14 (s, 3H), 1.65 (s, 6H).

Step B: Preparation of 1-(4-methoxybenzyl)-3-methyl-1H-pyrazolo[3,4-b]pyridin-4-ol: Prepared according to the procedure of Example 1, Step B substituting 5-((1-(4-methoxybenzyl)-3-methyl-1H-pyrazol-5-ylamino)-methylene)-2,2-dimethyl-1,3-dioxane-4,6-dione (9.3 g, 25 mmol) for 5-((1-(4-methoxybenzyl)-1H-pyrazol-5-ylamino)methylene)-2,2-dimethyl-1,3-dioxane-4,6-dione and performing the reaction at 220° C. rather than 240° C. The crude was purified by Biotage Flash 65, eluting with 1:1 EtOAc/hexanes, neat EtOAc, then 5% MeOH/EtOAc to elute the product. The product was obtained as a pale yellow solid (5.0 g, 74%). ¹H NMR (400 MHz, CDCl₃+ few drops DMSO-d6) δ 11.34 (br s, 1H), 7.91 (br s, 1H), 7.21 (d, J=9 Hz, 2H), 6.80 (d, J=9 Hz, 2H), 6.32 (br s, 1H), 5.44 (s, 2H), 3.74 (s, 3H), 2.63 (s, 3H).

Step C: Preparation of 1-(4-methoxybenzyl)-4-(2-fluoro-4-nitrophenoxy)-3-methyl-1H-pyrazolo[3,4-b]pyridine: Prepared according to the procedure of Example 1, Step C substituting 1-(4-methoxybenzyl)-3-methyl-1H-pyrazolo[3,4-b]pyridin-4-ol (2.69 g, 10.0 mmol) for 1-(4-methoxybenzyl)-1H-pyrazolo[3,4-b]pyridin-4-ol and substituting EtOAc for DCM during the workup. The product was obtained as a beige solid (3.90 g, 96%) and used in the next step without purification. ¹H NMR (400 MHz, CDCl₃) δ 8.36 (d, J=5 Hz, 1H), 8.16 (m, 2H), 7.37 (m, 1H), 7.34 (d, J=9 Hz, 2H), 6.83 (d, J=9 Hz, 2H), 6.27 (d, J=5 Hz, 1H), 5.58 (s, 2H), 3.76 (s, 3H), 2.65 (s, 3H).

Step D: Preparation of 4-(1-(4-methoxybenzyl)-3-methyl-1H-pyrazolo[3,4-b]pyridin-4-yloxy)-3-fluorobenzenamine: Prepared according to the procedure of Example 1, Step D, substituting 1-(4-methoxybenzyl)-4-(2-fluoro-4-nitrophenoxy)-3-methyl-1H-pyrazolo[3,4-b]pyridine (7.4 g, 18 mmol) for 1-(4-methoxybenzyl)-4-(2-fluoro-4-nitrophenoxy)-1H-pyrazolo[3,4-b]pyridine, and substituting EtOAc for DCM during the workup. The product was obtained as a gum (7.2 g, 94%) and used in the next step without purification. ¹H NMR (400 MHz, CDCl₃) δ 8.25 (d, J=5 Hz, 1H), 7.30 (d, J=9 Hz, 2H), 7.00 (m, 1H), 6.82 (d, J=9 Hz, 2H), 6.54 (m, 1H), 6.48 (m, 1H), 6.16 (d, J=5 Hz, 1H), 5.55 (s, 2H), 3.83 (br s, 2H), 3.75 (s, 3H), 2.71 (s, 3H).

Step E: Preparation of 1-(4-(1-(4-methoxybenzyl)-3-methyl-1H-pyrazolo[3,4-b]pyridin-4-yloxy)-3-fluorophenyl)-3-(2-phenylacetyl)thiourea: Prepared according to the procedure of Example 1, Step E, substituting 4-(1-(4-methoxybenzyl)-3-methyl-1H-pyrazolo[3,4-b]pyridin-4-yloxy)-3-fluorobenzenamine (378 mg, 1.00 mmol) for 4-(1-(4-methoxybenzyl)-1H-pyrazolo[3,4-b]pyridin-4-yloxy)-3-fluorobenzenamine, and using 1:1 ethanol/toluene (2 mL) as the solvent. The crude was purified by preparative TLC, eluting with 1:1 EtOAc/hexanes. The resulting solid was further purified by digestion from hot ethanol (10 mL) and trituration in hot ethanol, followed by cooling to room temperature and filtration. Yield: 260 mg, 46%. ¹H NMR (400 MHz, CDCl₃) δ 12.48 (s, 1H), 8.59 (s, 1H), 8.28 (d, J=6 Hz, 1H), 7.91 (d, J=11 Hz, 1H), 7.42 (m, 4H), 7.31 (m, 5H), 6.83 (d, J=9 Hz, 2H), 6.19 (d, J=6 Hz, 1H), 5.56 (s, 2H), 3.76 (s, 3H), 3.75 (s, 2H), 2.70 (s, 3H).

Step F: Preparation of N-(3-fluoro-4-(3-methyl-1H-pyrazolo[3,4-b]pyridin-4-yloxy)phenylcarbamothioyl)-2-phenylacetamide: Prepared according to the procedure of Example 1, Step F, substituting 1-(4-(1-(4-methoxybenzyl)-3-methyl-1H-pyrazolo[3,4-b]pyridin-4-yloxy)-3-fluorophenyl)-3-(2-phenylacetyl)thiourea (250 mg, 0.45 mmol) for 1-(4-(1-(4-methoxybenzyl)-1H-pyrazolo[3,4-b]pyridin-4-yloxy)-3-fluorophenyl)-3-(2-phenylacetyl)thiourea. The crude was purified by preparative TLC, eluting with 10% MeOH/DCM. The product was obtained as a white powder (120 mg, 61%). LRMS (APCI−): 100% purity, 220 nm, m/z 434 (M−1) detected; ¹H NMR (400 MHz, DMSO-d6) δ 13.32 (s, 1H), 12.51 (s, 1H), 11.84 (s, 1H), 8.29 (d, J=5 Hz, 1H), 8.03 (m, 1H), 7.52 (m, 2H), 7.36 (m, 5H), 6.23 (d, J=5 Hz, 1H), 3.84 (s, 2H), 2.62 (s, 3H).

Example 6

Preparation of N-(3-fluoro-4-(3-methyl-1H-pyrazolo[3,4-b]pyridin-4-yloxy)phenyl)-N-(4-fluorophenyl)cyclopropane-1,1-dicarboxamide

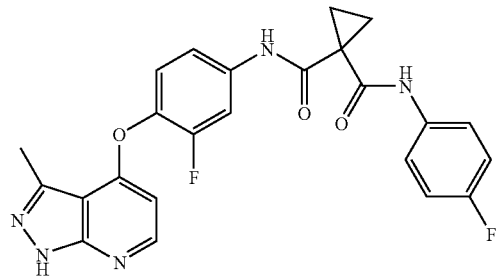

Step A: Preparation of 1-((4-fluorophenyl)carbamoyl)cyclopropanecarbonyl fluoride: Based on a procedure from Ryan, K., et. al. Tetrahedron, 2000, 56, 3309-3318. A 100 mL round-bottomed flask was charged with 2,4,6-trifluoro-1,3,5-triazine (2.66 mL, 19.7 mmol) and DCM (25 mL), and then 1-((4-fluorophenyl)carbamoyl)cyclopropanecarboxylic acid (2.20 g, 9.86 mmol) and pyridine (0.797 mL, 9.86 mmol) in DCM (20 mL) were added under nitrogen. The reaction mixture was stirred for 2 hours, and then diluted with water (50 mL). The organic layers were separated, dried over sodium sulfate, filtered, and concentrated to provide the acid fluoride as a white solid. $^1$H NMR (400 MHz, CDCl$_3$) δ 10.44 (s, 1H), 7.61 (m, 2H), 7.17 (m, 2H), 1.69 (m, 4H).

Step B: N-(4-(1-(4-methoxybenzyl)-3-methyl-1H-pyrazolo[3,4-b]pyridin-4-yloxy)-3-fluorophenyl)-N-(4-fluorophenyl)cyclopropane-1,1-dicarboxamide: A stirred mixture of 4-(1-(4-methoxybenzyl)-3-methyl-1H-pyrazolo[3,4-b]pyridin-4-yloxy)-3-fluorobenzenamine (1.89 g, 5.00 mmol; prepared as in Example 5, Step D), 1-((4-fluorophenyl)carbamoyl)cyclopropanecarbonyl fluoride (1.69 g, 7.50 mmol; obtained from Example 6, Step A), and anhydrous THF (50 mL) was heated to reflux for 22 hours under N$_2$. The reaction mixture was concentrated in vacuo, and partially purified by Biotage Flash 40M, eluting with 1:1 EtOAc/hexanes, 3:1 EtOAc/hexanes, then neat EtOAc (1 L). The product was re-chromatographed on Biotage Flash 40M, eluting with 1% MeOH/DCM, then 1.5% MeOH/DCM to elute the product. The product was obtained as a waxy solid (1.79 g, 61%). $^1$H NMR (400 MHz, CDCl$_3$) δ 10.01 (s, 1H), 8.27 (m, 2H), 7.73 (m, 1H), 7.46 (m, 2H), 7.25 (m, 4H), 7.06 (m, 2H), 6.82 (d, J=9 Hz, 2H), 6.14 (d, J=6 Hz, 1H), 5.56 (s, 2H), 3.75 (s, 3H), 2.71 (s, 3H), 1.78 (m, 2H), 1.60 (m, 2H).

Step C: Preparation of N-(3-fluoro-4-(3-methyl-1H-pyrazolo[3,4-b]pyridin-4-yloxy)phenyl)-N-(4-fluorophenyl)cyclopropane-1,1-dicarboxamide: Prepared according to the procedure of Example 1, Step F substituting N-(4-(1-(4-methoxybenzyl)-3-methyl-1H-pyrazolo[3,4-b]pyridin-4-yloxy)-3-fluorophenyl)-N-(4-fluorophenyl)cyclopropane-1,1-dicarboxamide (320 mg, 0.55 mmol) for 1-(4-(1-(4-methoxybenzyl)-1H-pyrazolo[3,4-b]pyridin-4-yloxy)-3-fluorophenyl)-3-(2-phenylacetyl)thiourea. The crude was purified by preparative TLC, eluting with 10% MeOH/DCM. Yield: 180 mg. LRMS (APCI−): 100% purity, 220 nm, m/z 462 (M−1) detected; $^1$H NMR (400 MHz, DMSO-d6) δ 13.29 (s, 1H), 10.39 (s, 1H), 10.01 (s, 1H), 8.26 (d, J=6 Hz, 1H), 7.91 (m, 1H), 7.64 (m, 2H), 7.51 (m, 1H), 7.43 (m, 1H), 7.16 (m, 2H), 6.17 (d, J=6 Hz, 1H), 2.62 (s, 3H), 1.48 (m, 4H).

Example 7

Preparation of N-(3-fluoro-4-(3-(3-(4-methylpiperazin-1-yl)prop-1-ynyl)-1H-pyrazolo[3,4-b]pyridin-4-yloxy)phenyl)-N-(4-fluorophenyl)cyclopropane-1,1-dicarboxamide

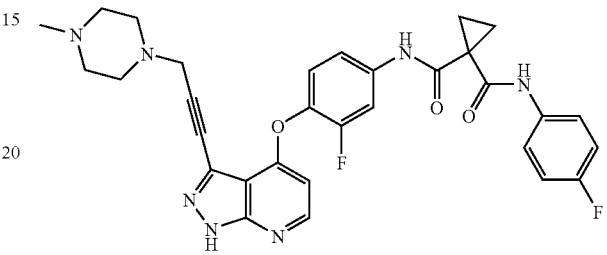

Step A: Preparation of 1-(4-methoxybenzyl)-4-(2-fluoro-4-nitrophenoxy)-3-iodo-1H-pyrazolo[3,4-b]pyridine: To a stirred solution of 4-(2-fluoro-4-nitrophenoxy)-1H-pyrazolo[3,4-b]pyridine (16.7 g, 60.9 mmol; obtained from Example 3, Step A) in DMF (250 mL) was added freshly ground potassium hydroxide (10.3 g, 183 mmol) followed by iodine (23.2 g, 91.4 mmol) under N$_2$ at room temperature. The dark reaction was stirred at room temperature for 18 hours, covered by a foil to minimize light exposure. The reaction was then heated to 50° C. for 3 hours. The reaction was allowed to cool to room temperature. The crude reaction mixture was transferred via cannula into a stirred solution of 1-(chloromethyl)-4-methoxybenzene (11.1 g, 70.7 mmol) in DMF (100 mL) which was cooled in an ice bath under N$_2$. The reaction was allowed to stir for 18 hours under N$_2$ at room temperature. The mixture was then diluted with DCM (1 L) and washed with 5% aqueous Na$_2$S$_2$O$_3$ (1 L). The aqueous phase was back-extracted with DCM (2×200 mL). The combined organic phases were washed with water (4×500 mL), dried (Na$_2$SO$_4$), filtered, and concentrated in vacuo. The resulting residue was triturated with DCM (100 mL), and the undissolved solid removed by filtration. The filtrate was purified by Biotage Flash 65, eluting with 10% EtOAc/hexanes, 20% EtOAc/hexanes, then 30% EtOAc/hexanes to elute the desired product. The product was obtained as a pale yellow solid (16.6 g, 47%). $^1$H NMR (400 MHz, CDCl$_3$) δ 8.42 (d, J=6 Hz, 1H), 8.16 (m, 2H), 7.38 (d, J=9 Hz, 2H), 7.34 (m, 1H), 6.84 (d, J=9 Hz, 2H), 6.36 (d, J=6 Hz, 1H), 5.63 (s, 2H), 3.77 (s, 3H).

Step B: Preparation of 4-(1-(4-methoxybenzyl)-3-iodo-1H-pyrazolo[3,4-b]pyridin-4-yloxy)-3-fluorobenzenamine: A stirred mixture of 1-(4-methoxybenzyl)-4-(2-fluoro-4-nitrophenoxy)-3-iodo-1H-pyrazolo[3,4-b]pyridine (10.4 g, 20.0 mmol), stannous chloride-dihydrate (22.6 g, 100.0 mmol), and absolute EtOH (200 mL) was heated to 65° C. for 1.5 hours under N$_2$. After cooling to room temperature, the reaction was concentrated in vacuo, and then diluted with DCM (100 mL) and water (100 mL). Aqueous 2N NaOH was added until the pH of the aqueous phase was in the 11-12 range. The biphasic suspension was filtered through a pad of celite, rinsing with DCM (3×100 mL). The filtered biphase was separated, and the aqueous phase was re-extracted with DCM (3×75 mL). The combined organic phases were dried (Na$_2$SO$_4$), filtered, and concentrated. Yield: 7.90 g, 78%. The product was used in the next step without purification. $^1$H NMR (400 MHz, CDCl$_3$) δ 8.30 (d, J=6 Hz, 1H), 7.35 (d, J=9 Hz, 2H), 7.03 (t, J=9 Hz, 1H), 6.83 (d, J=9 Hz, 2H), 6.53 (m, 2H), 6.24 (m, 1H), 5.61 (s, 2H), 3.81 (s, 2H), 3.76 (s, 3H).

Step C: Preparation of N-(4-(1-(4-methoxybenzyl)-3-iodo-1H-pyrazolo[3,4-b]pyridin-4-yloxy)-3-fluorophenyl)-N-(4-fluorophenyl)cyclopropane-1,1-dicarboxamide: To a stirred solution of 1-((4-fluorophenyl)carbamoyl)cyclopropanecarboxylic acid (0.341 g, 1.53 mmol; prepared from cyclopropane-1,1-dicarboxylic acid and 4-fluoroaniline using the methods of WO 2005/030140 and by Shih and Rankin, Synth. Comm., 1996, 26(4), 833-836), catalytic DMF (5 microliters), and THF (5 mL), was added oxalyl dichloride (0.194 g, 1.53 mmol) at room temperature under N$_2$. The reaction was stirred for 30 minutes at room temperature as CO$_2$ evolved. Then 4-(1-(4-methoxybenzyl)-3-iodo-1H-pyrazolo[3,4-b]pyridin-4-yloxy)-3-fluorobenzenamine (0.500 g, 1.02 mmol) was added as a solution in THF (2 mL). After stirring for 1 hour at room temperature, the reaction mixture was diluted with 5% MeOH/DCM (100 mL), saturated aqueous NaHCO$_3$ (25 mL), and water (125 mL). The cloudy phases were filtered through celite. The phases were separated, and the organic phase washed with 1N NaOH (50 mL) and then brine (50 mL). The organic phases were dried (Na$_2$SO$_4$), filtered, and concentrated in vacuo. The resulting residue was triturated with diethyl ether (50 mL) and filtered. The solid was discarded. The filtrate was concentrated, and the residue purified by preparative TLC, eluting with 10% MeOH/DCM. The product was used in the next step without further purification. Yield: 25 mg, 2.5%. LRMS (APCI+): m/z 696 (M+1) detected.

Step D: Preparation of 1-methyl-4-(prop-2-ynyl)piperazine: To a stirred, chilled suspension of 1-methylpiperazine (10.0 g, 100.0 mmol) and cesium carbonate (32.6 g, 100.0 mmol) in acetone (200 mL) was added 3-bromoprop-1-yne (11.0 mL, 100 mmol) (80% in toluene). The reaction was stirred for 18 hours at room temperature under N$_2$. The suspension was diluted with diethyl ether (200 mL) and filtered, and the filtrate was concentrated in vacuo. The resulting residue was resuspended in diethyl ether (100 mL) and refiltered. The filtrate was concentrated to an orange oil (8.2 g). The product was distilled under high vacuum. The product was distilled between 95-120° C. head temperature. The product was obtained as a colorless oil (5.46 g, 32%). $^1$H NMR (400 MHz, CDCl$_3$) δ 3.31 (m, 2H), 2.89 (m, 1H), 2.3-2.6 (m, 8H), 2.30 (m, 3H).

Step E: Preparation of N-(4-(1-(4-methoxybenzyl)-3-(3-(4-methylpiperazin-1-yl)prop-1-ynyl)-1H-pyrazolo[3,4-b]pyridin-4-yloxy)-3-fluorophenyl)-N-(4-fluorophenyl)cyclopropane-1,1-dicarboxamide: A stirred mixture of N-(4-(1-(4-methoxybenzyl)-3-iodo-1H-pyrazolo[3,4-b]pyridin-4-yloxy)-3-fluorophenyl)-N-(4-fluorophenyl)cyclopropane-1,1-dicarboxamide (25 mg, 0.036 mmol), 1-methyl-4-(prop-2-ynyl)piperazine (10 mg, 0.072 mmol; obtained from Example 7, Step D), copper(I)iodide (0.3 mg, 0.002 mmol), triethylamine (0.25 mL, 1.8 mmol), and THF (0.5 mL) was sparged with N$_2$ for 2 minutes, then tetrakis(triphenylphosphine)palladium (2 mg, 0.002 mmol) was added. The sealed reaction was heated to 50° C. for 18 hours. Additional 1-methyl-4-(prop-2-ynyl)piperazine (10 mg, 0.07 mmol), copper(I)iodide (0.3 mg, 0.002 mmol), and tetrakis(triphenylphosphine)palladium (2 mg, 0.002 mmol) were added and heating was continued at 80° C. for 5 hours. After cooling to room temperature, the entire reaction mixture was loaded directly on to a preparative TLC plate, eluting with 10% MeOH (containing 7N NH$_3$) in CHCl$_3$. The product was obtained as a waxy solid (10 mg, 37%). $^1$H NMR (400 MHz, CDCl$_3$) δ 10.06 (s, 1H), 8.30 (d, J=6 Hz, 1H), 8.25 (s, 1H), 7.77 (m, 1H), 7.45 (m, 2H), 7.34 (d, J=9 Hz, 2H), 7.24 (m, 2H), 7.06 (m, 2H), 6.82 (d, J=9 Hz, 2H), 6.25 (d, J=6 Hz, 1H), 5.60 (s, 2H), 3.76 (s, 3H), 3.55 (s, 2H), 2.68 (m, 4H), 2.39 (m, 4H), 2.23 (s, 3H), 1.81 (m, 2H), 1.62 (m, 2H).

Step F: Preparation of N-(3-fluoro-4-(3-(3-(4-methylpiperazin-1-yl)prop-1-ynyl)-1H-pyrazolo[3,4-b]pyridin-4-yloxy)phenyl)-N-(4-fluorophenyl)cyclopropane-1,1-dicarboxamide: Prepared according to the procedure of Example 1, Step F, substituting N-(4-(1-(4-methoxybenzyl)-3-(3-(4-methylpiperazin-1-yl)prop-1-ynyl)-1H-pyrazolo[3,4-b]pyridin-4-yloxy)-3-fluorophenyl)-N-(4-fluorophenyl)cyclopropane-1,1-dicarboxamide (10 mg, 0.01 mmol) for 1-(4-(1-(4-methoxybenzyl)-1H-pyrazolo[3,4-b]pyridin-4-yloxy)-3-fluorophenyl)-3-(2-phenylacetyl)thiourea. The crude was purified by preparative TLC, eluting with 10% MeOH (containing 7N NH$_3$) in CHCl$_3$. The product was obtained as a waxy solid (4 mg, 44%). LRMS (APCI+): 92% purity, 220 nm, m/z 586 (M+1) detected; $^1$H NMR (400 MHz, MeOD-d3) δ 8.24 (d, J=5 Hz, 1H), 7.81 (m, 1H), 7.51 (m, 2H), 7.36 (m, 1H), 7.28 (m, 1H), 7.03 (m, 2H), 6.29 (d, J=5 Hz, 1H), 3.60 (s, 2H), 2.69 (m, 4H), 2.36 (m, 4H), 2.16 (s, 3H), 1.60 (m, 4H).

Example 8

Preparation of N-(3-fluoro-4-(3-(2-hydroxyethyl)-1H-pyrazolo[3,4-b]pyridin-4-yloxy)phenyl)-N-(4-fluorophenyl)cyclopropane-1,1-dicarboxamide

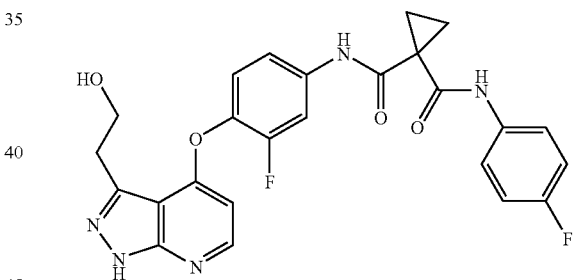

Step A: Preparation of 4-(1-(4-methoxybenzyl)-3-vinyl-1H-pyrazolo[3,4-b]pyridin-4-yloxy)-3-fluorobenzenamine: A stirred mixture of 4-(1-(4-methoxybenzyl)-3-iodo-1H-pyrazolo[3,4-b]pyridin-4-yloxy)-3-fluorobenzenamine (2.45 g, 5.00 mmol; prepared as in Example 7, Step B), potassium vinyltrifluoroborate (0.804 g, 6.00 mmol), triethylamine (0.693 mL, 5.00 mmol), and n-propanol (20 mL) was sparged with N$_2$ for 5 minutes, and then Pd(dppf)Cl$_2$ (82 mg, 0.10 mmol) was added. The sealed reaction was heated at 10° C. for 2 hours. The product and residual starting material were separated from catalyst and other by-products and re-subjected to the reaction conditions as follows. The reaction was concentrated in vacuo. The residue was partitioned between DCM (30 mL) and water (30 mL). The phases were separated, and the aqueous phase was re-extracted with DCM (2×10 mL). The combined organic phases were dried (Na$_2$SO$_4$), filtered, and concentrated in vacuo. The crude was separated from catalyst and other by-products by Biotage Flash 40, eluting with 20% EtOAc/hexanes then 1:1 EtOAc/hexanes. The product and starting material (1:1 ratio by $^1$H NMR) was resubjected to the same reaction conditions as above. After 2 hours at 100° C., all starting material had been consumed. After workup and Biotage Flash 40 purification as before, the product was obtained as an off-white solid (1.29 g, 66%). ¹H NMR (400 MHz, CDCl₃) δ 8.27 (d, J=6 Hz, 1H), 7.33 (d, J=9 Hz, 2H), 7.18 (m, 1H), 7.01 (t, J=9 Hz, 1H), 6.82 (d, J=9 Hz, 2H), 6.52 (m, 2H), 6.34 (m, 1H), 6.23 (m 1H), 5.62 (s, 2H), 5.45 (m, 1H), 3.81 (br s, 2H), 3.76 (s, 3H).

Step B: Preparation of N-(4-(1-(4-methoxybenzyl)-3-vinyl-1H-pyrazolo[3,4-b]pyridin-4-yloxy)-3-fluorophenyl)-N-(4-fluorophenyl)cyclopropane-1,1-dicarboxamide: Prepared according to the procedure for Example 7, Step C, substituting 4-(1-(4-methoxybenzyl)-3-vinyl-1H-pyrazolo[3,4-b]pyridin-4-yloxy)-3-fluorobenzenamine (0.781 g, 2.00 mmol; obtained from Example 8, Step C) for 4-(1-(4-methoxybenzyl)-3-iodo-1H-pyrazolo[3,4-b]pyridin-4-yloxy)-3-fluorobenzenamine. The crude was purified by Biotage Flash 40M, eluting with 20% EtOAc/hexanes, 1:1 EtOAc/hexanes, then neat EtOAc. The product was obtained as a waxy solid (479 mg, 39%). ¹H NMR (400 MHz, CDCl₃) δ 10.07 (s, 1H), 8.28 (d, J=5 Hz, 1H), 8.15 (s, 1H), 7.77 (m, 1H), 7.46 (m, 2H), 7.33 (d, J=9 Hz, 2H), 7.1-7.3 (m, 3H), 7.07 (t, J=9 Hz, 2H), 6.82 (d, J=9 Hz, 2H), 6.31 (d, J=18 Hz, 1H), 6.21 (d, J=5 Hz, 1H), 5.62 (s, 2H), 5.45 (d, J=13 Hz, 1H), 3.75 (s, 3H), 1.80 (m, 2H), 1.60 (m, 2H).

Step C: Preparation of N-(4-(1-(4-methoxybenzyl)-3-(2-hydroxyethyl)-1H-pyrazolo[3,4-b]pyridin-4-yloxy)-3-fluorophenyl)-N-(4-fluorophenyl)cyclopropane-1,1-dicarboxamide: To a stirred solution of N-(4-(1-(4-methoxybenzyl)-3-vinyl-1H-pyrazolo[3,4-b]pyridin-4-yloxy)-3-fluorophenyl)-N-(4-fluorophenyl)cyclopropane-1,1-dicarboxamide (0.357 g, 0.60 mmol) in THF (5 mL) was added a 0.5 M solution of 9-BBN (3.60 mL, 1.80 mmol) in THF. The reaction was stirred for 18 hours at room temperature. The reaction was cooled in an ice bath, and then was quenched by addition of 2N aqueous NaOH (3 mL). After stirring for 10 minutes in the ice bath, 30% aqueous hydrogen peroxide (0.577 mL, 6.00 mmol) was added. The reaction mixture was partitioned between water (20 mL) and EtOAc (20 mL). The phases were separated, and the aqueous phase was re-extracted with EtOAc (2×10 mL). The combined organic phases were washed with brine (20 mL), dried (Na₂SO₄), filtered, and concentrated. The crude was partially purified by Biotage Flash 40, eluting with 30% EtOAc/hexanes, 1:1 EtOAc/hexanes, 2:1 EtOAc/hexanes, then neat EtOAc. The resulting solid was further purified by preparative TLC, eluting with 5% MeOH (containing 7N NH₃) in DCM. The product was obtained as a waxy, white solid (179 mg, 48%). ¹H NMR (400 MHz, CDCl₃) δ 10.18 (s, 1H), 8.49 (s, 1H), 8.28 (d, J=6 Hz, 1H), 7.75 (m, 1H), 7.46 (m, 2H), 7.32 (d, J=9 Hz, 2H), 7.27 (m, 1H, overlaps chloroform), 7.18 (t, J=9 Hz, 1H), 7.06 (t, J=9 Hz, 2H), 6.83 (d, J=9 Hz, 2H), 6.17 (d, J=6 Hz, 1H), 5.57 (s, 2H), 4.09 (m, 2H), 3.76 (s, 3H), 3.36 (t, J=6 Hz, 2H), 2.76 (s, 1H), 1.80 (m, 2H), 1.63 (m, 2H).

Step D: Preparation of N-(3-fluoro-4-(3-(2-hydroxyethyl)-1H-pyrazolo[3,4-b]pyridin-4-yloxy)phenyl)-N-(4-fluorophenyl)cyclopropane-1,1-dicarboxamide: Prepared according to the procedure for Example 1, Step F, substituting N-(4-(1-(4-methoxybenzyl)-3-(2-hydroxyethyl)-1H-pyrazolo[3,4-b]pyridin-4-yloxy)-3-fluorophenyl)-N-(4-fluorophenyl)cyclopropane-1,1-dicarboxamide (20 mg, 0.033 mmol) for 1-(4-(1-(4-methoxybenzyl)-1H-pyrazolo[3,4-b]pyridin-4-yloxy)-3-fluorophenyl)-3-(2-phenylacetyl)thiourea, except the following modification was made. After removal of TFA in vacuo, using toluene (3×5 mL) to azeotrope, the crude was used in the next step in saponification of the resulting TFA-ester without purification. The crude was dissolved in MeOH (1 mL), and a solution of K₂CO₃ (22 mg, 0.16 mmol) in water (0.5 mL) was added. The dark mixture was vigorously stirred at room temperature for 45 minutes. The mixture was concentrated in vacuo. The residue was partitioned between EtOAc (10 mL) and a 1:1 water/saturated aqueous NaHCO₃ (10 mL) mixture. The phases were separated, and the aqueous phase was re-extracted with EtOAc (2×5 mL). The combined organic phases were dried (Na₂SO₄), filtered and concentrated. The crude was purified by preparative TLC, eluting with 10% MeOH/DCM. The product was obtained as a white powder (5 mg, 31%). LCMS (ESI+): 99% purity, 220 nm, m/z 494 (M+1) detected; ¹H NMR (400 MHz, THF-d8) δ 12.36 (br s, 0.7H), 10.83 (s, 0.3H; pyrazole tautomer), 10.29 (s, 1H), 9.52 (s, 1H), 8.16 (d, J=5 Hz, 1H), 7.91 (m, 1H), 7.61 (m, 2H), 7.40 (m, 1H), 7.29 (t, J=9 Hz, 1H), 7.04 (t, J=9 Hz, 2H), 6.14 (d, J=5 Hz, 1H), 3.93 (m, 2H), 3.63 (t, J=6 Hz, 1H), 3.25 (t, J=7 Hz, 2H), 1.58 (m, 4H).

Example 9

Preparation of N-(3-fluoro-4-(3-(2-(4-methylpiperazin-1-yl)ethyl)-1H-pyrazolo[3,4-b]pyridin-4-yloxy)phenyl)-N-(4-fluorophenyl)cyclopropane-1,1-dicarboxamide

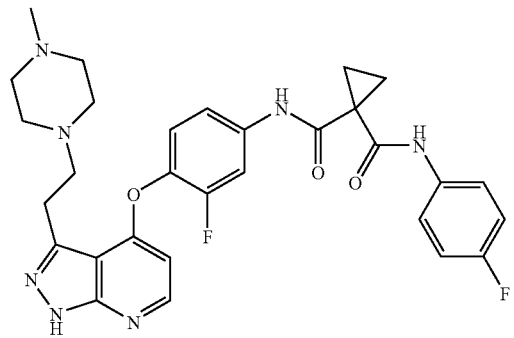

Step A: Preparation of N-(3-fluoro-4-(1-(4-methoxybenzyl)-3-(2-(4-methylpiperazin-1-yl)ethyl)-1H-pyrazolo[3,4-b]pyridin-4-yloxy)phenyl)-N-(4-fluorophenyl)cyclopropane-1,1-dicarboxamide: To a stirred mixture of N-(4-(1-(4-methoxybenzyl)-3-(2-hydroxyethyl)-1H-pyrazolo[3,4-b]pyridin-4-yloxy)-3-fluorophenyl)-N-(4-fluorophenyl)cyclopropane-1,1-dicarboxamide (100 mg, 0.16 mmol; prepared as in Example 8, Step C), DIEA (0.057 mL, 0.33 mmol), and chloroform (5 mL), cooled in an ice bath under N₂ was added methanesulfonyl chloride (0.0189 mL, 0.244 mmol). The reaction was allowed to warm to room temperature slowly as the ice melted. The solution was stirred for 30 minutes at room temperature. A portion of the reaction mixture (1.25 mL) was transferred to a second flask and concentrated in vacuo. To the residue was added 1-methylpiperazine (0.023 mL, 0.20 mmol). The neat reaction mixture was heated to 100° C. for 1 hour. The crude was partitioned between DCM (2 mL) and a 1:1 saturated aqueous NaHCO₃/water mixture (2 mL). The phases were separated, and the organic phase was dried (Na₂SO₄) and loaded directly on to a preparative TLC plate, eluting with 10% MeOH (containing 7N NH₃) in CHCl₃. Yield: 4 mg, 12%. ¹H NMR (400 MHz, CDCl₃) δ 10.02 (s, 1H), 8.36 (s, 1H), 8.28 (d, J=6 Hz, 1H), 7.76 (m, 1H), 7.47 (m, 2H), 7.30 (d, J=9 Hz, 2H), 7.26 (m, 1H, overlaps chloroform), 7.18 (t, J=9 Hz, 1H), 7.06 (t, J=9 Hz, 2H), 6.82 (d, J=9 Hz, 2H), 6.18 (d, J=6 Hz, 1H), 5.57 (s, 2H), 3.76 (s, 3H), 3.29 (m, 2H), 2.93 (m, 2H), 2.5-2.8 (m, 8H), 2.42 (s, 3H), 1.82 (m, 2H), 1.64 (m, 2H).

Step B: Preparation of N-(3-fluoro-4-(3-(2-(4-methylpiperazin-1-yl)ethyl)-1H-pyrazolo[3,4-b]pyridin-4-yloxy)phenyl)-N-(4-fluorophenyl)cyclopropane-1,1-dicarboxamide: A stirred mixture of N-(4-(1-(4-methoxybenzyl)-3-(2-(4-methylpiperazin-1-yl)ethyl)-1H-pyrazolo[3,4-b]pyridin-4-yloxy)-3-fluorophenyl)-N-(4-fluorophenyl)cyclopropane-1,1-dicarboxamide (4 mg, 0.006 mmol) and TFA (0.5 mL) was heated to 70° C. for 18 hours. The mixture was concentrated in vacuo, using toluene (2×5 mL) to azeotrope residual TFA. The residue was partitioned between EtOAc (5 mL) and a 1:1 water/saturated aqueous NaHCO$_3$ (5 mL) mixture. The phases were separated, and the aqueous phase was re-extracted with EtOAc (2×2 mL). The combined organic phases were concentrated in vacuo. The residue was loaded on to a preparative TLC plate, eluting with 10% MeOH (containing 7N NH$_3$) in CHCl$_3$. The product was further purified on a Waters SepPak silica gel column (2 g silica), eluting with DCM, 5% MeOH/DCM, then 5% MeOH (containing 7N NH$_3$) in DCM to elute the product. The product was obtained as a waxy solid (1.2 mg, 34%). LCMS (ESI+): 93% purity, 220 nm, m/z 576 (M+1) detected; $^1$H NMR (400 MHz, MeOD-d3) δ 8.27 (d, J=6 Hz, 1H), 7.84 (m, 1H), 7.55 (m, 2H), 7.43 (m, 1H), 7.37 (t, J=9 Hz, 1H), 7.07 (t, J=9 Hz, 2H), 6.29 (d, J=6 Hz, 1H), 3.65 (m, 1H, overlaps MeOD), 3.57 (m, 1H), 2.94 (m, 2H), 2.64 (m, 8H), 2.37 (s, 3H), 1.64 (m, 4H).

Example 10

Preparation of N-(3-fluoro-4-(3-(2-morpholinoethyl)-1H-pyrazolo[3,4-b]pyridin-4-yloxy)phenyl)-N-(4-fluorophenyl)cyclopropane-1,1-dicarboxamide

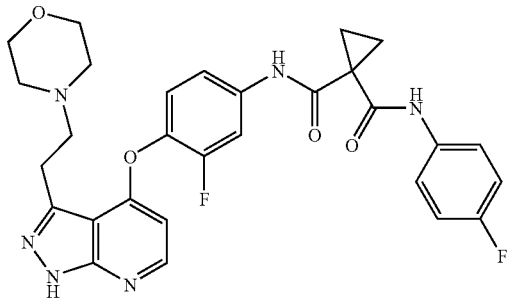

Step A: Preparation of N-(3-fluoro-4-(1-(4-methoxybenzyl)-3-(2-morpholinoethyl)-1H-pyrazolo[3,4-b]pyridin-4-yloxy)phenyl)-N-(4-fluorophenyl)cyclopropane-1,1-dicarboxamide: Prepared according to the procedure of Example 9, Step A, substituting morpholine (0.018 mL, 0.20 mmol) for 1-methylpiperazine. Yield: 4 mg, 10%. $^1$H NMR (400 MHz, CDCl$_3$) δ 10.04 (s, 1H), 8.27 (d, J=6 Hz, 1H), 8.16 (s, 1H), 7.78 (m, 1H), 7.47 (m, 2H), 7.29 (d, J=9 Hz, 2H), 7.26 (m, 1H), 7.20 (t, J=9 Hz, 1H), 7.07 (t, J=9 Hz, 2H), 6.82 (d, J=9 Hz, 2H), 6.17 (d, J=6 Hz, 1H), 5.57 (s, 2H), 3.76 (s, 3H), 3.74 (m, 4H), 3.35 (m, 2H), 2.97 (m, 2H), 2.63 (m, 4H), 1.81 (m, 2H), 1.61 (m, 2H).

Step B: Preparation of N-(3-fluoro-4-(3-(2-morpholinoethyl)-1H-pyrazolo[3,4-b]pyridin-4-yloxy)phenyl)-N-(4-fluorophenyl)cyclopropane-1,1-dicarboxamide: Prepared according to the procedure of Example 9, Step B, substituting N-(3-fluoro-4-(1-(4-methoxybenzyl)-3-(2-morpholinoethyl)-1H-pyrazolo[3,4-b]pyridin-4-yloxy)phenyl)-N-(4-fluorophenyl)cyclopropane-1,1-dicarboxamide (4 mg, 0.006 mmol; obtained from Example 10, Step A) for N-(4-(1-(4-methoxybenzyl)-3-(2-(4-methylpiperazin-1-yl)ethyl)-1H-pyrazolo[3,4-b]pyridin-4-yloxy)-3-fluorophenyl)-N-(4-fluorophenyl)cyclopropane-1,1-dicarboxamide. Yield: 0.5 mg, 13%. LCMS (ESI+): 86% purity, 220 nm, m/z 563 (M+1) detected; $^1$H NMR (400 MHz, MeOD-d3) δ 8.27 (d, J=6 Hz, 1H), 7.84 (m, 1H), 7.55 (m, 2H), 7.42 (m, 1H), 7.37 (t, J=9 Hz, 1H), 7.07 (t, J=9 Hz, 2H), 6.29 (d, J=6 Hz, 1H), 3.69 (m, 4H), 3.2-3.7 (m, 2H, overlaps MeOD), 2.94 (m, 2H), 2.62 (m, 4H), 1.64 (m, 4H).

Example 11

Preparation of N-(3-fluoro-4-(3-(2-(piperidin-1-yl)ethyl)-1H-pyrazolo[3,4-b]pyridin-4-yloxy)phenyl)-N-(4-fluorophenyl)cyclopropane-1,1-dicarboxamide

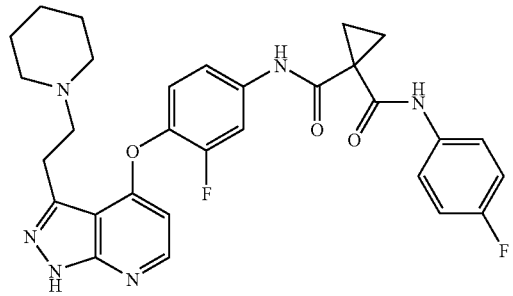

Step A: Preparation of N-(3-fluoro-4-(1-(4-methoxybenzyl)-3-(2-(piperidin-1-yl)ethyl)-1H-pyrazolo[3,4-b]pyridin-4-yloxy)phenyl)-N-(4-fluorophenyl)cyclopropane-1,1-dicarboxamide: Prepared according to the procedure of Example 9, Step A, substituting piperidine (0.020 mL, 0.20 mmol) for 1-methylpiperazine. Yield: 5 mg, 7%. $^1$H NMR (400 MHz, CDCl$_3$) δ 10.01 (s, 1H), 8.31 (s, 1H), 8.26 (d, J=6 Hz, 1H), 7.75 (m, 1H), 7.46 (m, 2H), 7.29 (d, J=9 Hz, 2H), 7.26 (m, 1H), 7.19 (t, J=9 Hz, 1H), 7.06 (m, 2H), 6.82 (d, J=9 Hz, 2H), 6.15 (d, J=6 Hz, 1H), 5.57 (s, 2H), 3.76 (s, 3H), 3.32 (m, 2H), 2.90 (m, 2H), 2.54 (m, 4H), 1.79 (m, 2H), 1.60 (m, 2H), 1.60 (m, 4H), 1.42 (m, 2H).

Step B: Preparation of N-(3-fluoro-4-(3-(2-(piperidin-1-yl)ethyl)-1H-pyrazolo[3,4-b]pyridin-4-yloxy)phenyl)-N-(4-fluorophenyl)cyclopropane-1,1-dicarboxamide: Prepared according to the procedure of Example 9, Step B, substituting N-(3-fluoro-4-(1-(4-methoxybenzyl)-3-(2-(piperidin-1-yl)ethyl)-1H-pyrazolo[3,4-b]pyridin-4-yloxy)phenyl)-N-(4-fluorophenyl)cyclopropane-1,1-dicarboxamide (5 mg, 0.007 mmol; obtained from Example 11, Step A) for N-(4-(1-(4-methoxybenzyl)-3-(2-(4-methylpiperazin-1-yl)ethyl)-1H-pyrazolo[3,4-b]pyridin-4-yloxy)-3-fluorophenyl)-N-(4-fluorophenyl)cyclopropane-1,1-dicarboxamide. Yield: 0.9 mg. LCMS (ESI+): 88% purity, 220 nm, m/z 561 (M+1) detected; $^1$H NMR (400 MHz, MeOD-d3) δ 8.28 (m, 1H), 7.88 (m, 1H), 7.58 (m, 2H), 7.43 (m, 1H), 7.37 (m, 1H), 7.07 (m, 2H), 6.30 (m, 1H), 3.2-3.7 (m, 6H, overlaps MeOD), 3.01 (m, 2H), 2.71 (m, 4H), 1.65 (m, 4H), 1.50 (m, 2H).

Example 12

Preparation of N-(3-fluoro-4-(3-(2-(4-(hydroxymethyl)piperidin-1-yl)ethyl)-1H-pyrazolo[3,4-b]pyridin-4-yloxy)phenyl)-N-(4-fluorophenyl)cyclopropane-1,1-dicarboxamide

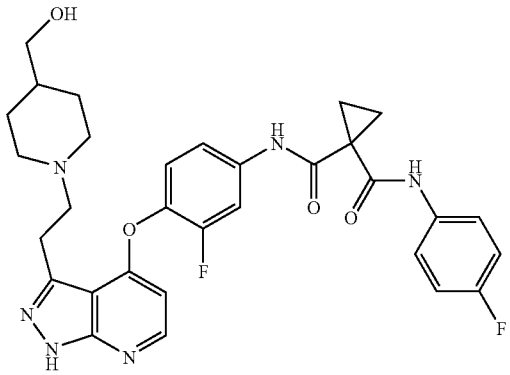

Step A: Preparation of N-(3-fluoro-4-(3-(2-(4-(hydroxymethyl)piperidin-1-yl)ethyl)-1-(4-methoxybenzyl)-1H-pyrazolo[3,4-b]pyridin-4-yloxy)phenyl)-N-(4-fluorophenyl)cyclopropane-1,1-dicarboxamide: Prepared according to the procedure of Example 9, Step A, substituting piperidin-4-ylmethanol (23 mg, 0.20 mmol) for 1-methylpiperazine. Yield: 1 mg (3%). $^1$H NMR (400 MHz, CDCl$_3$) δ 10.04 (s, 1H), 8.91 (s, 1H), 8.30 (d, J=6 Hz, 1H), 7.80 (m, 1H), 7.50 (m, 2H), 7.29 (d, J=9 Hz, 2H), 7.27 (m, 1H), 7.21 (t, J=9 Hz, 1H), 7.03 (t, J=9 Hz, 2H), 6.82 (d, J=9 Hz, 2H), 6.21 (d, J=6 Hz, 1H), 5.55 (s, 2H), 3.76 (s, 3H), 3.57 (m, 2H), 3.48 (d, J=6 Hz, 2H), 3.36 (m, 4H), 2.55 (m, 2H), 1.82 (m, 4H), 1.67 (m, 6H).

Step B: Preparation of N-(3-fluoro-4-(3-(2-(4-(hydroxymethyl)piperidin-1-yl)ethyl)-1H-pyrazolo[3,4-b]pyridin-4-yloxy)phenyl)-N-(4-fluorophenyl)cyclopropane-1,1-dicarboxamide: Prepared according to the procedure of Example 8, Step D, substituting N-(3-fluoro-4-(3-(2-(4-(hydroxymethyl)piperidin-1-yl)ethyl)-1-(4-methoxybenzyl)-1H-pyrazolo[3,4-b]pyridin-4-yloxy)phenyl)-N-(4-fluorophenyl)cyclopropane-1,1-dicarboxamide (1 mg, 0.001 mmol) for N-(4-(1-(4-methoxybenzyl)-3-(2-hydroxyethyl)-1H-pyrazolo[3,4-b]pyridin-4-yloxy)-3-fluorophenyl)-N-(4-fluorophenyl)cyclopropane-1,1-dicarboxamide. The crude was purified by preparative TLC, eluting with 10% MeOH (containing 7N NH$_3$) in DCM. The product was further purified on a Waters SepPak silica gel column (2 g silica), eluting with DCM, 5% MeOH/DCM, then 5% MeOH (containing 7N NH$_3$) in DCM to elute the product. The product was obtained as a waxy solid (0.8 mg, 85%). LRMS (ESI+): m/z 591 (M+1) detected; $^1$H NMR (400 MHz, MeOD-d3) δ 8.31 (d, J=6 Hz, 1H), 7.88 (m, 1H), 7.56 (m, 2H), 7.42 (m, 2H), 7.07 (t, J=9 Hz, 2H), 6.34 (d, J=6 Hz, 1H), 3.56 (m, 4H), 3.46 (m, 4H), 3.13 (m, 2H), 3.04 (m, 2H), 2.02 (m, 2H), 1.78 (m, 1H), 1.65 (m, 4H).

Example 13

Preparation of N-(4-fluorophenyl)-N-(4-(3-methyl-1H-pyrazolo[3,4-b]pyridin-4-yloxy)phenyl)cyclopropane-1,1-dicarboxamide

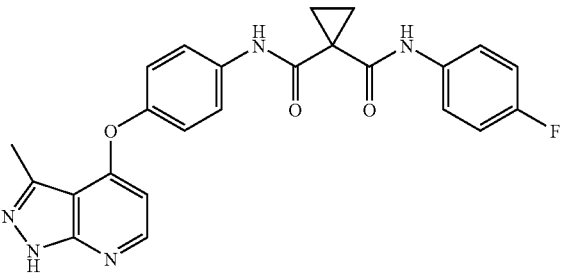

Step A: Preparation of 1-(4-methoxybenzyl)-3-methyl-4-(4-nitrophenoxy)-1H-pyrazolo[3,4-b]pyridine: A 20 mL sealable tube under nitrogen was charged with 1-(4-methoxybenzyl)-3-methyl-1H-pyrazolo[3,4-b]pyridin-4-ol (0.150 g, 0.557 mmol; prepared as in from Example 5, Step B), 1-fluoro-4-nitrobenzene (0.0786 g, 0.557 mmol), Cs$_2$CO$_3$ (0.272 g, 0.836 mmol), and DMA (4 mL). The reaction mixture was heated to 90° C. for 2 hours, then cooled to room temperature, diluted with water (10 mL) and extracted with EtOAc (15 mL). The organic layer was dried over sodium sulfate, filtered and concentrated. The crude was purified by Biotage 40S column eluting with Hexane/EtOAc 3:1, then EtOAc. Obtained the product (185 mg, 79%) as an off white solid. $^1$H NMR (CDCl$_3$, 400 MHz) δ 8.39 (d, J=5.1 Hz, 1H), 8.32 (d, J=9.4 Hz, 1H), 7.34 (d, J=8.6 Hz, 1H), 7.26 (d, J=9.4 Hz, 1H), 6.84 (d, J=8.6 Hz, 1H), 6.40 (d, J=5.5 Hz, 1H), 3.77 (s, 3H), 2.58 (s, 3H). LRMS (esi pos) m/e 391 (M+1).

Step B: Preparation of 4-(1-(4-methoxybenzyl)-3-methyl-1H-pyrazolo[3,4-b]pyridin-4-yloxy)aniline: To a 100 mL round-bottomed flask with stir bar containing 1-(4-methoxybenzyl)-3-methyl-4-(4-nitrophenoxy)-1H-pyrazolo[3,4-b]pyridine (0.185 g, 0.474 mmol) was added MeOH (10 mL) and THF (10 mL) followed by zinc (0.155 g, 2.37 mmol). Next, saturated NH$_4$Cl (0.5 mL) was added with stirring. Concentrated HCl (0.5 mL) was added until all solids dissolved (except for some zinc powder) and the pH had dropped to 2. The reaction was stirred for 18 hours at room temperature. The reaction was concentrated and partitioned between EtOAc (100 mL) and 1:1 saturated NaHCO$_3$/water (100 mL). The aqueous phase washed with EtOAc (75 mL). The combined organic phases were washed with brine (50 mL), dried (Na$_2$SO$_4$), filtered, and concentrated in vacuo. The product (160 mg, 82%) was obtained as a yellow gum. LRMS (esi pos) m/e 361 (M+1).

Step C: Preparation of N-(4-fluorophenyl)-N-(4-(1-(4-methoxybenzyl)-3-methyl-1H-pyrazolo[3,4-b]pyridin-4-yloxy)phenyl)cyclopropane-1,1-dicarboxamide: A 100 mL round-bottomed flask was charged with 1-((4-fluorophenyl)carbamoyl)cyclopropane carboxylic acid (0.3516 g, 0.9767 mmol; prepared from cyclopropane-1,1-dicarboxylic acid and 4-fluoroaniline in THF (25 mL) using the methods of WO 2005/030140 and Shih and Rankin, Synth. Comm., 1996, 26(4), 833-836). Next, catalytic DMF (10 microliters) was added. While stirring oxalyl dichloride (0.08387 mL, 0.9767 mmol) was added. The reaction mixture was stirred for 30 minutes and 4-(1-(4-methoxybenzyl)-3-methyl-1H-pyrazolo[3,4-b]pyridin-4-yloxy)benzenamine (0.160 g, 0.3907 mmol) in THF (2 mL) was added. The reaction mixture was stirred for 1 hour, the diluted with water (50 mL) and saturated NaHCO₃ (50 mL). The reaction mixture was extracted with EtOAc, washed with brine, dried organic over sodium sulfate, filtered and concentrated. The reaction mixture was purified by preparative TLC (0.5 mm) eluting with EtOAc. The product (90 mg, 28%) was obtained as a white solid. LRMS (esi pos) m/e 566 (M+1).

Step D: Preparation of N-(4-fluorophenyl)-N-(4-(3-methyl-1H-pyrazolo[3,4-b]pyridin-4-yloxy)phenyl)cyclopropane-1,1-dicarboxamide: A 40 mL vial was charged with N-(4-(1-(4-methoxybenzyl)-3-methyl-1H-pyrazolo[3,4-b]pyridin-4-yloxy)phenyl)-N-(4-fluorophenyl)cyclopropane-1,1-dicarboxamide (90 mg, 0.11 mmol) and TFA (2.0 mL). The reaction mixture was heated to 65° C. under nitrogen for 2 hours, the diluted with saturated Na₂CO₃ (15 mL) and extracted with EtOAc. The organic layer was dried over sodium sulfate, filtered and concentrated. The crude material was purified by preparative TLC (0.5 mm) eluting with EtOAc/MeOH (9:1) to provide the product as a white solid. ¹H NMR (CDCl₃, 400 MHz) δ 8.22 (d, J=5.5 Hz, 1H), 7.71 (d, J=9.0 Hz, 2H), 7.56 (m, 2H), 7.22 (d, J=9.0 Hz, 2H), 7.06 (t, J=9.0 Hz, 2H), 6.27 (d, J=5.5 Hz, 1H), 2.68 (s, 3H), 1.64 (s, 4H). LRMS (esi pos) m/e 446 (M+1).

Example 14

Preparation of N-(2-chloro-5-methyl-4-(3-methyl-1H-pyrazolo[3,4-b]pyridin-4-yloxy)phenyl)-N-(4-fluorophenyl)cyclopropane-1,1-dicarboxamide

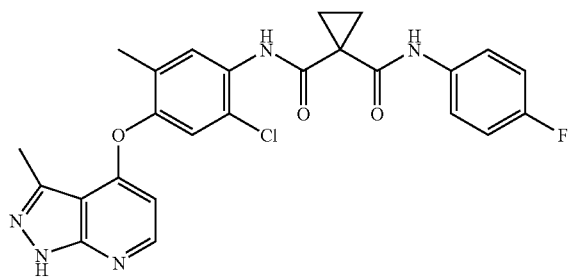

Step A: Preparation of 4-(5-chloro-2-methyl-4-nitrophenoxy)-1-(4-methoxybenzyl)-3-methyl-1H-pyrazolo[3,4-b]pyridine: Prepared from 1-(4-methoxybenzyl)-3-methyl-1H-pyrazolo[3,4-b]pyridin-4-ol (0.150 g, 0.557 mmol; prepared as in Example 5, Step B) and 1-chloro-5-fluoro-4-methyl-2-nitrobenzene (0.106 g, 0.557 mmol), according to the procedure of Example 13, Step A. Purified by Biotage 40S column eluting with 3:1 hexane/EtOAc then EtOAc to obtain the product (184 mg, 75%) as an off white solid. ¹H NMR (CDCl₃, 400 MHz) δ 8.36 (d, J=5.1 Hz, 1H), 7.95 (s, 1H), 7.35 (d, J=9.0 Hz, 1H), 7.21 (s, 1H), 6.84 (d, J=8.6 Hz, 1H), 6.23 (d, J=5.1 Hz, 1H), 5.58 (s, 1H), 3.77 (s, 3H), 2.63 (s, 3H), 2.31 (s, 3H). LRMS (APCI pos) m/e 439 (M+1).

Step B: Preparation of 2-chloro-4-(1-(4-methoxybenzyl)-3-methyl-1H-pyrazolo[3,4-b]pyridin-4-yloxy)-5-methylaniline: Prepared from 1-(4-methoxybenzyl)-4-(5-chloro-2-methyl-4-nitrophenoxy)-3-methyl-1H-pyrazolo[3,4-b]pyridine (0.184 g, 0.419 mmol) according to the procedure of Example 13, Step B. Obtain the product (170 mg, 48%) as a red gum. LRMS (esi pos) m/e 409 (M+1).

Step C: Preparation of N-(2-chloro-4-(1-(4-methoxybenzyl)-3-methyl-1H-pyrazolo[3,4-b]pyridin-4-yloxy)-5-methylphenyl)-N-(4-fluorophenyl)cyclopropane-1,1-dicarboxamide: Prepared from 1-((4-fluorophenyl)carbamoyl)cyclopropanecarboxylic acid (0.1796 g, 0.4989 mmol (prepared from cyclopropane-1,1-dicarboxylic acid and 4-fluoroaniline using the methods of WO 2005/030140 and by Shih and Rankin, Synth. Comm. 1996, 26(4), 833-836) and 4-(1-(4-methoxybenzyl)-3-methyl-1H-pyrazolo[3,4-b]pyridin-4-yloxy)-2-chloro-5-methylbenzenamine (0.170 g, 0.1996 mmol) according to the procedure of Example 13, Step C. Purified by preparative TLC (0.5 mm) eluting with EtOAc. The product (23 mg, 17%) was obtained as an orange solid. LRMS (esi pos) m/e 614 (M+1).

Step D: Preparation of N-(2-chloro-5-methyl-4-(3-methyl-1H-pyrazolo[3,4-b]pyridin-4-yloxy)phenyl)-N-(4-fluorophenyl)cyclopropane-1,1-dicarboxamide: Prepared from N-(4-(1-(4-methoxybenzyl)-3-methyl-1H-pyrazolo[3,4-b]pyridin-4-yloxy)-2-chloro-5-methylphenyl)-N-(4-fluorophenyl)cyclopropane-1,1-dicarboxamide (23 mg, 0.034 mmol) according to the procedure of Example 13, Step D. Purified by preparative TLC (0.5 mm) eluting with EtOAc/MeOH (9:1) to provide the product as a white solid (6 mg, 33%). ¹H NMR (CDCl₃, 400 MHz) δ 8.24 (d, J=5.5 Hz, 1H), 8.09 (s, 1H), 7.55 (m, 2H), 7.35 (s, 1H), 7.08 (t, J=8.8 Hz, 2H), 6.19 (d, J=5.5 Hz, 1H), 2.71 (s, 3H), 2.18 (s, 3H), 1.73 (m, 4H). LRMS (esi pos) m/e 494 (M+1).

Example 15

Preparation of N-(3-cyano-4-(3-methyl-1H-pyrazolo[3,4-b]pyridin-4-yloxy)phenyl)-N-(4-fluorophenyl)cyclopropane-1,1-dicarboxamide

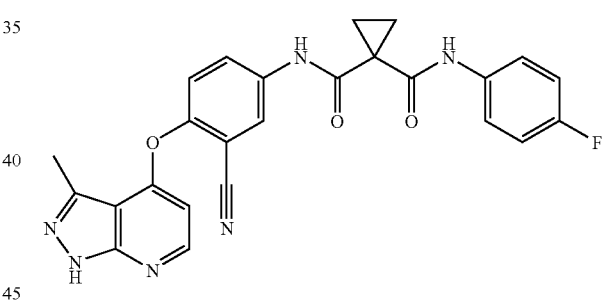

Step A: Preparation of 4-(5-chloro-2-methyl-4-nitrophenoxy)-1-(4-methoxybenzyl)-3-methyl-1H-pyrazolo[3,4-b]pyridine: Prepared from 1-(4-methoxybenzyl)-3-methyl-1H-pyrazolo[3,4-b]pyridin-4-ol (0.150 g, 0.557 mmol; prepared as in Example 5, Step B) and 2-fluoro-5-nitrobenzonitrile (0.0925 g, 0.557 mmol), according to the procedure of Example 13, Step A. The crude product was purified by Biotage 40S column eluting with 3:1 hexane/EtOAc then EtOAc to obtain the product (200 mg, 69%) as a off white solid. ¹H NMR (CDCl₃, 400 MHz) δ 8.65 (d, J=2.7 Hz, 1H), 8.51 (d, J=5.5 Hz, 1H), 8.42 (dd, J=2.7, 9.4 Hz, 1H), 7.35 (d, J=8.6 Hz, 2H), 7.17 (d, J=9.4 Hz, 1H), 6.84 (d, J=8.6 Hz, 2H), 6.60 (d, J=5.5 Hz, 1H), 5.60 (s, 2H), 3.77 (s, 3H), 2.53 (s, 3H). LRMS (esi pos) m/e 416 (M+1).

Step B: Preparation of 5-amino-2-(1-(4-methoxybenzyl)-3-methyl-1H-pyrazolo[3,4-b]pyridin-4-yloxy)benzonitrile: Prepared from 5-(1-(4-methoxybenzyl)-3-methyl-1H-pyrazolo[3,4-b]pyridin-4-yloxy)-2-nitrobenzonitrile (0.200 g, 0.481 mmol) according to the procedure of Example 13, Step B. The product (170 mg, 50%) was obtained as a yellow gum. LRMS (esi pos) m/e 386 (M+1).

Step C: Preparation of N-(3-cyano-4-(1-(4-methoxybenzyl)-3-methyl-1H-pyrazolo[3,4-b]pyridin-4-yloxy)phenyl)-N-(4-fluorophenyl)cyclopropane-1,1-dicarboxamide: Prepared from 1-((4-fluorophenyl)carbamoyl)cyclopropanecarboxylic acid (0.2183 g, 0.6065 mmol; prepared from cyclopropane-1,1-dicarboxylic acid and 4-fluoroaniline using the methods of WO 2005/030140 and by Shih and Rankin, Synth. Comm. 1996, 26(4), 833-836) and 5-(1-(4-methoxybenzyl)-3-methyl-1H-pyrazolo[3,4-b]pyridin-4-yloxy)-2-aminobenzonitrile (0.170 g, 0.2426 mmol) according to the procedure of Example 13, Step C. The crude product was purified by preparative TLC (0.5 mm) eluting with EtOAc. The product (80 mg, 29%) was obtained as a orange solid. LRMS (esi pos) m/e 591 (M+1).

Step D: Preparation of N-(3-cyano-4-(3-methyl-1H-pyrazolo[3,4-b]pyridin-4-yloxy)phenyl)-N-(4-fluorophenyl)cyclopropane-1,1-dicarboxamide: Prepared from N-(4-(1-(4-methoxybenzyl)-3-methyl-1H-pyrazolo[3,4-b]pyridin-4-yloxy)-3-cyanophenyl)-N-(4-fluorophenyl)cyclopropane-1,1-dicarboxamide (80 mg, 0.069 mmol) according to the procedure of Example 13, Step D. The crude product was purified by preparative TLC (0.5 mm) eluting with EtOAc/MeOH (9:1) and the product was obtained as a white solid (11 mg, 31%). $^1$H NMR (CDCl$_3$, 400 MHz) δ 8.31 (d, J=5.5 Hz, 1H), 8.23 (s, 1H), 7.93 (m, 1H), 7.55 (m, 2H), 7.43 (d, J=9.0 Hz, 1H), 7.06 (t, J=8.8 Hz, 2H), 6.34 (d, J=5.5 Hz, 1H), 2.70 (s, 3H), 1.65 (s, 4H). LRMS (esi pos) m/e 471 (M+1).

Example 16

Preparation of N-(3,4-dichloro-4-(3-methyl-1H-pyrazolo[3,4-b]pyridin-4-yloxy)phenyl)-N-(4-fluorophenyl)cyclopropane-1,1-dicarboxamide

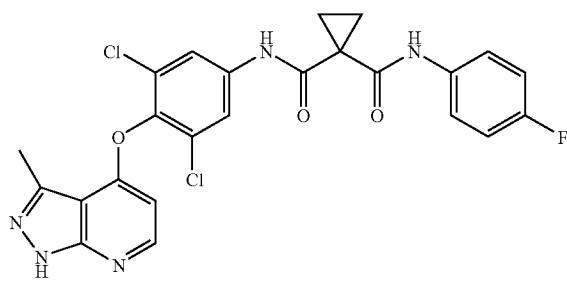

Step A: Preparation of 4-(2,6-dichloro-4-nitrophenoxy)-1-(4-methoxybenzyl)-3-methyl-1H-pyrazolo[3,4-b]pyridine: Prepared from 1-(4-methoxybenzyl)-3-methyl-1H-pyrazolo[3,4-b]pyridin-4-ol (0.150 g, 0.557 mmol; prepared as in Example 5, Step B) and 1,3-dichloro-2-fluoro-5-nitrobenzene (0.117 g, 0.557 mmol), according to the procedure of Example 13, Step A. The crude product was purified Biotage 40S column eluting with 3:1 hexane/EtOAc then EtOAc to obtain the product (195 mg, 73%) as an off white solid. $^1$H NMR (CDCl$_3$, 400 MHz) δ 8.37 (s, 1H), 8.29 (d, J=5.5 Hz, 1H), 7.37 (d, J=8.6 Hz, 2H), 6.85 (d, J=9.0 Hz, 2H), 5.93 (d, J=5.5 Hz, 1H), 5.58 (s, 2H), 3.77 (s, 3H), 2.75 (s, 3H). LRMS (esi pos) m/e 460 (M+1).

Step B: Preparation of 3,5-dichloro-4-(1-(4-methoxybenzyl)-3-methyl-1H-pyrazolo[3,4-b]pyridin-4-yloxy)aniline: Prepared from 1-(4-methoxybenzyl)-4-(2,6-dichloro-4-nitrophenoxy)-3-methyl-1H-pyrazolo[3,4-b]pyridine (0.195 g, 0.425 mmol) according to the procedure of Example 13, Step B. The product (170 mg, 35%) was obtained as a yellow gum. LRMS (esi pos) m/e 430 (M+1).

Step C: Preparation of N-(3,5-dichloro-4-(1-(4-methoxybenzyl)-3-methyl-1H-pyrazolo[3,4-b]pyridin-4-yloxy)phenyl)-N-(4-fluorophenyl)cyclopropane-1,1-dicarboxamide: Prepared from 1-((4-fluorophenyl)carbamoyl)cyclopropanecarboxylic acid (0.1354 g, 0.3762 mmol; prepared from cyclopropane-1,1-dicarboxylic acid and 4-fluoroaniline using the methods of WO 2005/030140 and by Shih and Rankin, Synth. Comm. 1996, 26(4), 833-836) and 4-(1-(4-methoxybenzyl)-3-methyl-1H-pyrazolo[3,4-b]pyridin-4-yloxy)-3,5-dichlorobenzenamine (0.170 g, 0.1505 mmol) according to the procedure of Example 13, Step C. The crude product was purified preparative TLC (0.5 mm) eluting with EtOAc. Product (12 mg, 7%) was obtained as a orange solid. LRMS (esi pos) m/e 634 (M+1).

Step D: Preparation of N-(3,5-dichloro-4-(3-methyl-1H-pyrazolo[3,4-b]pyridin-4-yloxy)phenyl)-N-(4-fluorophenyl)cyclopropane-1,1-dicarboxamide: Prepared from N-(4-(1-(4-methoxybenzyl)-3-methyl-1H-pyrazolo[3,4-b]pyridin-4-yloxy)-3,5-dichlorophenyl)-N-(4-fluorophenyl)cyclopropane-1,1-dicarboxamide (12 mg, 0.011 mmol) according to the procedure of Example 13, Step D. The crude product was purified by preparative TLC (0.5 mm) eluting with EtOAc/MeOH (9:1) to provide the product as a white solid (1.3 mg, 19%). $^1$H NMR (CDCl$_3$, 400 MHz) δ 8.24 (d, J=5.9 Hz, 1H), 7.91 (s, 2H), 7.56 (m, 2H), 7.07 (t, J=8.8 Hz, 2H), 6.13 (d, J=5.5 Hz, 1H), 2.74 (s, 3H), 1.64 (s, 4H). LRMS (esi pos) m/e 514 (M+1).

Example 17

Preparation of N-(4-fluorophenyl)-N-(3-methyl-4-(3-methyl-1H-pyrazolo[3,4-b]pyridin-4-yloxy)phenyl)cyclopropane-1,1-dicarboxamide

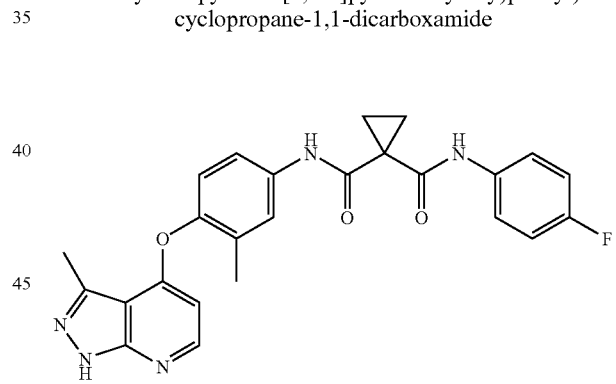

Step A: Preparation of 1-(4-methoxybenzyl)-3-methyl-4-(2-methyl-4-nitrophenoxy)-1H-pyrazolo[3,4-b]pyridine: Prepared from 1-(4-methoxybenzyl)-3-methyl-1H-pyrazolo[3,4-b]pyridin-4-ol (0.150 g, 0.557 mmol; prepared as in Example 5, Step B) and 1-fluoro-2-methyl-4-nitrobenzene (0.0864 g, 0.557 mmol) according to the procedure of Example 13, Step A. The crude product was purified by Biotage 40S column eluting with 3:1 hexane/EtOAc then EtOAc to obtain the product (107 mg, 48%) as a off white solid. $^1$H NMR (CDCl$_3$, 400 MHz) δ 8.33 (d, J=5.5 Hz, 1H), 8.25 (m, 1H), 8.15 (m, 1H), 7.35 (d, J=8.6 Hz, 2H), 7.17 (d, J=9.0 Hz, 1H), 6.84 (d, J=8.6 Hz, 2H), 6.18 (d, J=5.5 Hz, 1H), 5.57 (s, 2H), 3.77 (s, 3H), 2.64 (s, 3H), 2.36 (s, 3H). LRMS (esi pos) m/e 405 (M+1).

Step B: Preparation of 4-(1-(4-methoxybenzyl)-3-methyl-1H-pyrazolo[3,4-b]pyridin-4-yloxy)-3-methylaniline: Prepared from 1-(4-methoxybenzyl)-3-methyl-4-(2-methyl-4- nitrophenoxy)-1H-pyrazolo[3,4-b]pyridine (0.107 g, 0.265 mmol) according to the procedure of Example 13, Step B. The product (91 mg, 48%) was obtained as a yellow gum. LRMS (esi pos) m/e 375 (M+1).

Step C: Preparation of N-(4-fluorophenyl)-N-(4-(1-(4-methoxybenzyl)-3-methyl-1H-pyrazolo[3,4-b]pyridin-4-yloxy)-3-methylphenyl)cyclopropane-1,1-dicarboxamide: Prepared from 1-((4-fluorophenyl)carbamoyl)cyclopropanecarboxylic acid (0.2187 g, 0.6076 mmol; prepared from cyclopropane-1,1-dicarboxylic acid and 4-fluoroaniline using the methods of WO 2005/030140 and by Shih and Rankin, Synth. Comm. 1996, 26(4), 833-836) and 4-(1-(4-methoxybenzyl)-3-methyl-1H-pyrazolo[3,4-b]pyridin-4-yloxy)-3-methylbenzenamine (0.091 g, 0.2430 mmol) according to the procedure of Example 13, Step C. The crude product was purified by preparative TLC (0.5 mm) eluting with EtOAc. The product (18 mg, 11%) was obtained as an orange solid. LRMS (esi pos) m/e 579 (M+1).

Step D: Preparation of N-(4-fluorophenyl)-N-(3-methyl-4-(3-methyl-1H-pyrazolo[3,4-b]pyridin-4-yloxy)phenyl)cyclopropane-1,1-dicarboxamide: Prepared from N-(4-(1-(4-methoxybenzyl)-3-methyl-1H-pyrazolo[3,4-b]pyridin-4-yloxy)-3-methylphenyl)-N-(4-fluorophenyl)cyclopropane-1,1-dicarboxamide (18 mg, 0.027 mmol) according to the procedure of Example 13, Step D. The crude product was purified by preparative TLC (0.5 mm) eluting with EtOAc/MeOH (9:1) to provide the product as a white solid (3.6 mg, 29%). $^1$H NMR (CDCl$_3$, 400 MHz) δ 8.20 (d, J=5.5 Hz, 1H), 7.57 (m, 4H), 7.14 (d, J=9.0 Hz, 1H), 7.07 (t, J=9.0 Hz, 2H), 6.13 (d, J=5.5 Hz, 1H), 2.72 (s, 3H), 2.18 (s, 3H), 1.63 (s, 4H). LRMS (esi pos) m/e 460 (M+1).

Example 18

Preparation of N-(4-fluorophenyl)-N-(6-(3-methyl-1H-pyrazolo[3,4-b]pyridin-4-yloxy)pyridin-3-yl)cyclopropane-1,1-dicarboxamide

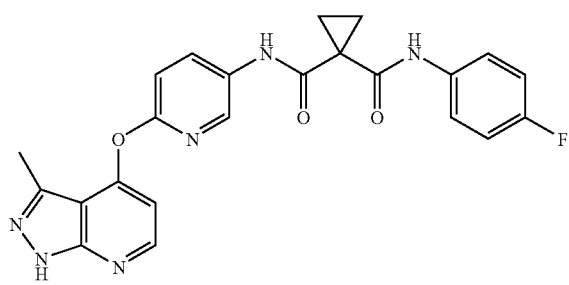

Step A: Preparation of 1-(4-methoxybenzyl)-3-methyl-4-(2-methyl-4-nitrophenoxy)-1H-pyrazolo[3,4-b]pyridine: Prepared from 1-(4-methoxybenzyl)-3-methyl-1H-pyrazolo[3,4-b]pyridin-4-ol (1.00 g, 3.71 mmol; obtained from Example 5, Step B) and 2-chloro-5-nitropyridine (0.589 g, 3.71 mmol) according to the procedure of Example 13, Step A. The crude material was purified on a Biotage 40S column, eluting with 3:1 hexane/EtOAc and then EtOAc, to obtain the product (107 mg, 48%) as a brown solid. $^1$H NMR (CDCl$_3$, 400 MHz) δ 9.06 (d, J=2.3 Hz, 1H), 8.59 (dd, J=2.3, 8.6 Hz, 1H), 8.53 (d, J=5.1 Hz, 1H), 7.35 (d, J=8.6 Hz, 2H), 7.22 (d, J=9.0 Hz, 1H), 6.88 (d, J=5.5 Hz, 1H), 6.84 (d, J=9.0 Hz, 2H), 5.59 (s, 2H), 3.77 (s, 3H), 2.40 (s, 3H). LRMS (esi pos) m/e 392 (M+1).

Step B: Preparation of 6-(1-(4-methoxybenzyl)-3-methyl-1H-pyrazolo[3,4-b]pyridin-4-yloxy)pyridin-3-amine: A 25 mL round-bottomed flask was charged with 1-(4-methoxybenzyl)-3-methyl-4-(5-nitropyridin-2-yloxy)-1H-pyrazolo[3,4-b]pyridine (1.25 g, 3.19 mmol) and EtOH (10 mL). SnCl$_2$ dihydrate (3.60 g, 16.0 mmol) was added under nitrogen and the reaction mixture was heated to 80° C. for 4 hours. The reaction mixture was cooled to room temperature, diluted with Na$_2$CO$_3$ (100 mL, 2N) and extracted with chloroform (2×100 mL). The organic layer was dried over sodium sulfate, filtered and concentrated to a dark oil. The crude material was purified on a Biotage 40S column, eluting with EtOAc, to provide the product (800 mg, 65%) as a green oil. $^1$H NMR (CDCl$_3$, 400 MHz) δ 8.31 (d, J=5.1 Hz, 1H), 7.82 (m, 1H), 7.29 (m, 2H), 7.18 (m, 1H), 6.93 (d, J=8.6 Hz, 1H), 6.82 (m, 2H), 6.40 (d, J=5.5 Hz, 1H), 5.56 (s, 2H), 3.76 (m, 5H), 2.63 (s, 3H). LRMS (APCI pos) m/e 362 (M+1).

Step C: Preparation of N-(4-fluorophenyl)-N-(6-(1-(4-methoxybenzyl)-3-methyl-1H-pyrazolo[3,4-b]pyridin-4-yloxy)pyridin-3-yl)cyclopropane-1,1-dicarboxamide: A 100 mL round-bottomed flask was charged with 6-(1-(4-methoxybenzyl)-3-methyl-1H-pyrazolo[3,4-b]pyridin-4-yloxy)pyridin-3-amine (0.500 g, 1.38 mmol), 1-((4-fluorophenyl)carbamoyl)cyclopropanecarbonyl fluoride (0.545 g, 2.42 mmol; prepared as in Example 6, Step A), and DMF (10 mL). DIEA (0.723 mL, 4.15 mmol) was added under nitrogen and the reaction mixture was heated at 50° C. for 18 hours. The reaction mixture was cooled to room temperature, diluted with water (100 mL), and extracted with EtOAc (50 mL). The organic layer was dried over sodium sulfate, filtered and concentrated to provide the crude product (1.55 g, 59%). LRMS (esi+) 567 (M+H).

Step D: Preparation of N-(4-fluorophenyl)-N-(6-(3-methyl-1H-pyrazolo[3,4-b]pyridin-4-yloxy)pyridin-3-yl)cyclopropane-1,1-dicarboxamide: Prepared from N-(6-(1-(4-methoxybenzyl)-3-methyl-1H-pyrazolo[3,4-b]pyridin-4-yloxy)pyridin-3-yl)-N-(4-fluorophenyl)cyclopropane-1,1-dicarboxamide (1.55 g, 0.821 mmol) according to the procedure of Example 13, Step D. The crude material was purified by preparative TLC (0.5 mm) eluting with EtOAc/MeOH (9:1) to provide the product as a white solid (6.0 mg, 1.6%). $^1$H NMR (CDCl$_3$, 400 MHz) δ 11.50 (br s, 1H), 10.12 (s, 1H), 8.40 (m, 2H), 8.27 (s, 1H), 8.22 (m, 1H), 7.44 (m, 2H), 7.13 (d, J=9.0 Hz, 1H), 7.08 (m, 2H), 6.64 (d, J=5.5 Hz, 1H), 2.61 (s, 3H), 1.82 (m, 2H), 1.63 (m, 2H). LRMS (esi pos) m/e 446 (M+1).

Example 19

Preparation of 2-(4-fluorophenyl)-N-(6-(3-methyl-1H-pyrazolo[3,4-b]pyridin-4-yloxy)pyridin-3-yl)-3-oxo-2,3-dihydropyridazine-4-carboxamide

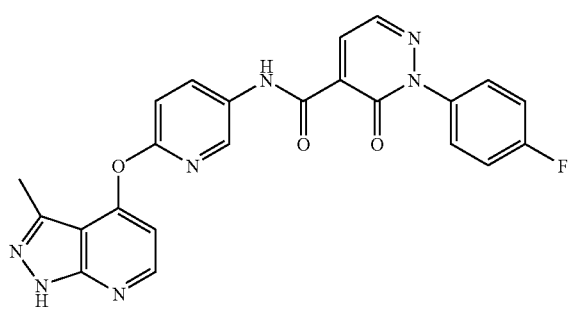

Step A: Preparation of (E)-2-(2-(4-fluorophenyl)hydrazono)acetaldehyde: A mixture of 1-(4-fluorophenyl)hydrazine hydrochloride (5.0 g, 30.75 mmol), water (20 mL), and acetic acid (20 mL) was added with stirring to a 40% aqueous solution of glyoxal (17.6 mL, 153.8 mmol) over 20 minutes. Stirring was continued for 2 hours and the mixture was then filtered. The precipitate washed with water and dried to afford 5.0 g (98%) of the desired product. $^1$H NMR (400 MHz, CDCl$_3$) δ 9.56 (d, 1H), 8.63 (br s, 1H), 7.24 (m, 1H), 7.16 (m, 2H), 7.06 (m, 2H); $^{19}$F NMR (376 MHz, CDCl$_3$) δ −120.3. LRMS (ESI pos) m/e 151.1 (M−16).

Step B: Preparation of (E)-5-(2-(2-(4-fluorophenyl)hydrazono)ethylidene)-2,2-dimethyl-1,3-dioxane-4,6-dione: A suspension of dioxan-dione (1.44 g, 10.0 mmol) and (E)-2-(2-(4-fluorophenyl)hydrazono)acetaldehyde (1.66 g, 10.0 mmol) in toluene (15 mL) was treated with acetic acid (5 drops) and piperidine (5 drops). The reaction mixture was then stirred at room temp for 17 hours. The precipitated condensation product was filtered and thoroughly washed with light petroleum to afford 2.87 g (98%) of the desired product. $^1$H NMR (400 MHz, CD$_3$OD/CDCl$_3$) δ 8.72 (d, 1H), 8.24 (d, 1H), 7.32 (m, 2H), 7.08 (t, 2H), 1.76 (s, 6H); $^{19}$F NMR (376 MHz, CDCl$_3$) δ −119.1.

Step C: Preparation of 2-(4-fluorophenyl)-3-oxo-2,3-dihydropyridazine-4-carboxylic acid: A mixture of (E)-5-(2-(2-(4-fluorophenyl)hydrazono)ethylidene)-2,2-dimethyl-1,3-dioxane-4,6-dione (0.60 g, 2.05 mmol) and NaOMe (0.133 g, 2.46 mmol) in MeOH (10 mL) was heated under reflux for 15 hours. The salt was treated with cold 1 N HCl solution, extracted with DCM, dried over MgSO$_4$, and concentrated to afford 0.42 g (87%) of the desired product. $^1$H NMR (400 MHz, CDCl$_3$) δ 13.57 (br s, 1H), 8.29 (m, 2H), 7.63 (m, 2H), 7.24 (m, 2H); $^{19}$F NMR (376 MHz, CDCl$_3$) δ −110.7. LRMS (ESI pos) m/e 235.1 (M+1).

Step D: Preparation of 2-(4-fluorophenyl)-N-(6-(1-(4-methoxybenzyl)-3-methyl-1H-pyrazolo[3,4-b]pyridin-4-yloxy)pyridin-3-yl)-3-oxo-2,3-dihydropyridazine-4-carboxamide: A 25 mL round-bottomed flask was charged with 6-(1-(4-methoxybenzyl)-3-methyl-1H-pyrazolo[3,4-b]pyridin-4-yloxy)pyridin-3-amine (15 mg, 0.0415 mmol), 2-(4-fluorophenyl)-3-oxo-2,3-dihydropyridazine-4-carboxylic acid (24.3 mg, 0.104 mmol; prepared as in Example 19, Step C) HOBT-H$_2$O (6.36 mg, 0.0415 mmol), EDCI (7.96 mg, 0.0415 mmol), N-ethyl-N-isopropylpropan-2-amine (5.36 mg, 0.0415 mmol) and DMF (3 mL). The reaction mixture was stirred at room temperature for 18 hours. Diluted with water (20 mL) and extracted with EtOAc (20 mL). The organic layer was dried over sodium sulfate, filtered and concentrated to obtain product (30 mg, 90%) as a light brown solid. LRMS (esi+) 578 (M+H).

Step E: Preparation of 2-(4-fluorophenyl)-N-(6-(3-methyl-1H-pyrazolo[3,4-b]pyridin-4-yloxy)pyridin-3-yl)-3-oxo-2,3-dihydropyridazine-4-carboxamide: Prepared from N-(6-(1-(4-methoxybenzyl)-3-methyl-1H-pyrazolo[3,4-b]pyridin-4-yloxy)pyridin-3-yl)-2-(4-fluorophenyl)-3-oxo-2,3-dihydropyridazine-4-carboxamide (30 mg, 0.037 mmol) according to the procedure of Example 13, Step D. Purified by preparative TLC (0.5 mm) eluting with EtOAc/MeOH (9:1) to provide the product as a white solid (6.0 mg, 1.6%). $^1$H NMR (CDCl$_3$, 400 MHz) δ 11.50 (br s, 1H), 10.12 (s, 1H), 8.40 (m, 2H), 8.27 (s, 1H), 8.22 (m, 1H), 7.44 (m, 2H), 7.13 (d, J=9.0 Hz, 1H), 7.08 (m, 2H), 6.64 (d, J=5.5 Hz, 1H), 2.61 (s, 3H). LRMS (esi pos) m/e 458 (M+1).

Example 20

1-(3-Fluoro-4-(3-methyl-1H-pyrazolo[3,4-b]pyridin-4-yloxy)phenyl)-3-(pyridin-2-yl)urea

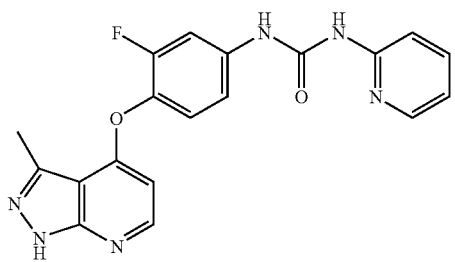

Step A: Preparation of 1-(3-fluoro-4-(1-(4-methoxybenzyl)-3-methyl-1H-pyrazolo[3,4-b]pyridin-4-yloxy)phenyl)-3-(pyridin-2-yl)urea: A 100 mL round-bottomed flask was charged with pyridine-2-carbonyl azide (39.1 mg, 0.264 mmol) and THF (10 mL). The reaction mixture was stirred at 80° C. for 4 hours. 4-(1-(4-Methoxybenzyl)-3-methyl-1H-pyrazolo[3,4-b]pyridin-4-yloxy)-3-fluorobenzenamine (20.0 mg, 0.0529 mmol; prepared as in Example 5, Step D) was added and the reaction mixture was stirred overnight. Water (10 mL) was added, and the reaction mixture was extracted with CH$_2$Cl$_2$ (3×100 mL). The combined organic layers were dried over Na$_2$SO$_4$, filtered, and concentrated, and the residue was purified by column chromatography (Silica gel, DCM/7M NH$_3$ in MeOH from 50/1 to 10/1, v/v) to afford the product (21 mg, 81%). $^1$H NMR (CDCl$_3$, 400 MHz) δ 8.20-8.30 (m, 2H), 7.81 (m, 1H), 7.70 (m, 1H), 7.36 (m, 1H), 7.32 (d, J=8.8 Hz, 2H), 7.22 (m, 1H), 7.00 (m, 1H), 6.87 (m, 1H), 6.83 (d, J=8.8 Hz, 2H), 6.19 (d, J=5.6 Hz, 1H), 5.57 (s, 2H), 3.77 (s, 3H), 2.73 (s, 3H).

Step B: Preparation of 1-(3-fluoro-4-(3-methyl-1H-pyrazolo[3,4-b]pyridin-4-yloxy)phenyl)-3-(pyridin-2-yl)urea: A 100 mL round-bottomed flask was charged with 1-(4-(1-(4-methoxybenzyl)-3-methyl-1H-pyrazolo[3,4-b]pyridin-4-yloxy)-3-fluorophenyl)-3-(pyridin-2-yl)urea (21.3 mg, 0.0427 mmol) from Example 20, Step A and 2,2,2-trifluoroacetic acid (487 mg, 4.27 mmol). The reaction mixture was stirred at 80° C. for 8 hours. The CF$_3$COOH was removed under reduced pressure and the residue was purified by column chromatography (Silica gel, DCM/7M NH$_3$ in MeOH from 50/1 to 10/1, v/v) to provide the product (14 mg, 85%). LRMS (APCI−): 100% purity, 220 nm, m/z 377 (M−1)

detected; ¹H NMR (400 MHz, CD₃OD-d4) δ 8.31 (m, 1H), 8.25 (d, J=5.6 Hz, 1H), 7.83 (m, 1H), 7.75 (m, 1H), 7.36 (m, 2H), 7.21 (d, J=8.4 Hz, 1H), 7.04 (m, 1H), 6.28 (d, J=5.6 Hz, 1H), 2.72 (s, 3H)

Example 21

N-(3-fluoro-4-(3-methyl-1H-pyrazolo[3,4-b]pyridin-4-yloxy)phenyl)-1-(4-fluorophenyl)-2-oxo-1,2-dihydropyridine-3-carboxamide

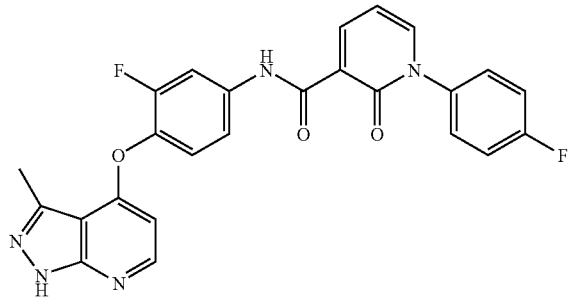

Step A: Preparation of N-(3-fluoro-4-(1-(4-methoxybenzyl)-3-methyl-1H-pyrazolo[3,4-b]pyridin-4-yloxy)phenyl)-1-(4-fluorophenyl)-2-oxo-1,2-dihydropyridine-3-carboxamide: A mixture of 1-(4-Fluorophenyl)-2-oxo-1,2-dihydropyridine-3-carboxylic acid (37 mg, 0.16 mmol), EDCI (91 mg, 0.48 mmol), and HOBt (64 mg, 0.48 mmol) in DMF (2 mL) was stirred at room temperature for 1 hour. 3-Fluoro-4-(1-(4-methoxybenzyl)-3-methyl-1H-pyrazolo[3,4-b]pyridin-4-yloxy)aniline (30 mg, 0.079 mmol; prepared as in Example 5, Step D) was added, followed by Et₃N (0.066 mL, 0.48 mmol). After stirring for 15 hours, the reaction mixture was diluted with EtOAc and washed with saturated aqueous NH₄Cl, saturated aqueous NaHCO₃, and brine. The organic layer was dried over MgSO₄ and concentrated under reduced pressure to give the crude material that was purified by silica gel flash column chromatography (2% MeOH in CH₂Cl₂) to afford 45 mg (96%) of the desired product. LRMS (ESI pos) m/e 594.2 (M+1). ¹H-NMR (400 MHz, CD₃OD/CDCl₃) δ 8.72 (dd, 1H), 8.28 (d, 1H), 7.99 (dd, 1H), 7.92 (dd, 1H), 7.51 (m, 2H), 7.41 (m, 1H), 7.32 (m, 3H), 7.24 (d, 2H), 6.84 (d, 2H), 6.75 (t, 1H), 6.28 (d, 1H), 5.54 (s, 2H), 3.76 (s, 3H), 2.71 (s, 3H); ¹⁹F NMR (376 MHz, CD₃OD/CDCl₃) δ -113.2, -128.7.

Step B: Preparation of N-(3-fluoro-4-(3-methyl-1H-pyrazolo[3,4-b]pyridin-4-yloxy)phenyl)-1-(4-fluorophenyl)-2-oxo-1,2-dihydropyridine-3-carboxamide: A mixture of N-(3-fluoro-4-(1-(4-methoxybenzyl)-3-methyl-1H-pyrazolo[3,4-b]pyridin-4-yloxy)phenyl)-1-(4-fluorophenyl)-2-oxo-1,2-dihydropyridine-3-carboxamide (0.045 g, 0.0758 mmol) and TFA (0.58 mL, 7.58 mmol) was placed in a vial and heated at 50° C. for 4 hours. The reaction mixture was concentrated under reduced pressure using toluene to azeotrope. The crude was treated with THF and Et₃N and purified by silica gel flash column chromatography (2% MeOH in CH₂Cl₂) to afford 26.5 mg (74%) of the desired product. LRMS (ESI pos) m/e 474.2 (M+1). ¹H-NMR (400 MHz, CD₃OD/CDCl₃) δ 8.72 (dd, 1H), 8.24 (d, 1H), 7.99 (dd, 1H), 7.92 (dd, 1H), 7.51 (m, 2H), 7.42 (m, 1H), 7.32 (t, 3H), 6.75 (t, 1H), 6.26 (d, 1H), 2.73 (s, 3H); ¹⁹F NMR (376 MHz, CD₃OD/CDCl₃) δ -113.2, -128.8.

Example 22

N-(3-fluoro-4-(3-methyl-1H-pyrazolo[3,4-b]pyridin-4-yloxy)phenyl)-2-(4-fluorophenyl)-3-oxo-2,3-dihydropyridazine-4-carboxamide

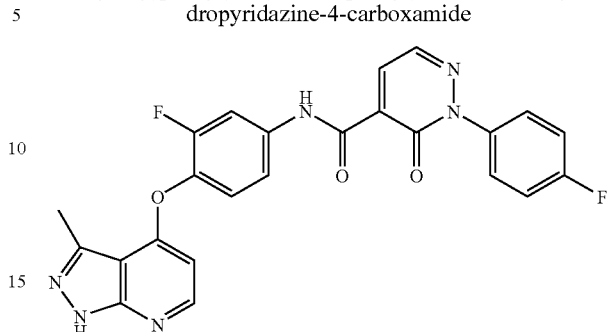

Prepared by a 2-step process from 3-fluoro-4-(1-(4-methoxybenzyl)-3-methyl-1H-pyrazolo[3,4-b]pyridin-4-yloxy) aniline (obtained from Example 5, Step D) and 2-(4-fluorophenyl)-3-oxo-2,3-dihydropyridazine-4-carboxylic acid (prepared as in Example 19, Step C) according to the method of Example 21, Steps A and B. The crude material was purified by silica gel flash column chromatography (2% MeOH in CH₂Cl₂) to afford 25 mg (68% for 2-step process) of the desired product. LRMS (ESI pos) m/e 475.2 (M+1). ¹H-NMR (400 MHz, CD₃OD/CDCl₃) δ 8.42 (d, 1H), 8.33 (d, 1H), 8.24 (d, 1H), 7.99 (dd, 1H), 7.64 (m, 2H), 7.46 (m, 1H), 7.34 (d, 1H), 7.28 (m, 2H), 6.26 (d, 1H), 2.75 (s, 3H); ¹⁹F NMR (376 MHz, CD₃OD/CDCl₃) δ -112.6, -127.6.

Example 23

N-(3-fluoro-4-(3-methyl-1H-pyrazolo[3,4-b]pyridin-4-yloxy)phenyl)-2-methyl-3-oxo-2,3-dihydropyridazine-4-carboxamide

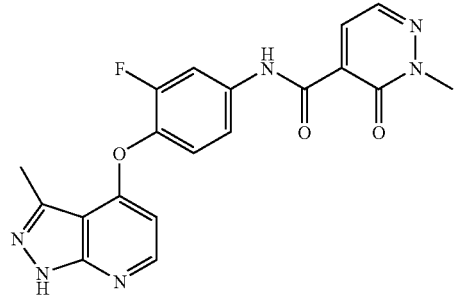

Prepared by 2-step process from 3-fluoro-4-(1-(4-methoxybenzyl)-3-methyl-1H-pyrazolo[3,4-b]pyridin-4-yloxy) aniline (prepared as in Example 5, Step D) and 2-methyl-3-oxo-2,3-dihydropyridazine-4-carboxylic acid (prepared according to the 3-step procedure of Example 19, Steps A-C, substituting methylhydrazine for 1-(4-fluorophenyl)hydrazine hydrochloride) according to the procedure of Example 21, Steps A and B. The crude material was purified by silica gel flash column chromatography (3% MeOH in CH₂Cl₂) to afford 17 mg (64% for 2-step process) of the desired product. LRMS (ESI pos) m/e 395.2 (M+1). ¹H-NMR (400 MHz, CD₃OD/CDCl₃) δ 8.30 (d, 1H), 8.25 (d, 1H), 8.17 (d, 1H), 8.02 (dd, 1H), 7.51 (m, 1H), 7.37 (t, 1H), 6.27 (d, 1H), 3.79 (s, 3H), 2.75 (s, 3H); ¹⁹F NMR (376 MHz, CD₃OD/CDCl₃) δ -128.3.

Example 24

N-(3-fluoro-4-(3-methyl-1H-pyrazolo[3,4-b]pyridin-4-yloxy)phenyl)-1-(4-fluorophenyl)-2-oxopyrrolidine-3-carboxamide

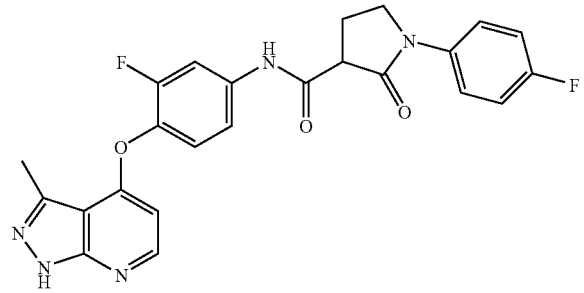

Prepared by a 2-step process from 3-fluoro-4-(1-(4-methoxybenzyl)-3-methyl-1H-pyrazolo[3,4-b]pyridin-4-yloxy)aniline (prepared as in Example 5, Step D) and 1-(4-fluorophenyl)-2-oxopyrrolidine-3-carboxylic acid according to the procedure of Example 21, Steps A and B. The crude was purified by silica gel flash column chromatography (3% MeOH in $CH_2Cl_2$) to afford 4 mg (47% for 2-step process) of the desired product. LRMS (ESI pos) m/e 464.2 (M+1). $^1$H-NMR (400 MHz, $CD_3OD/CDCl_3$) δ 8.25 (d, 1H), 7.88 (dd, 1H), 7.64 (m, 2H), 7.46 (m, 1H), 7.36 (t, 1H), 7.14 (t, 2H), 6.27 (d, 1H), 3.97 (m, 2H), 3.81 (m, 1H), 2.71 (s, 3H), 2.61 (m, 1H), 2.49 (m, 1H); $^{19}$F NMR (376 MHz, $CD_3OD/CDCl_3$) δ −119.2, −130.1.

Additional compounds which can be made according to the methods of this invention include the following structures:

| Example # | | |
|---|---|---|
| 25 | 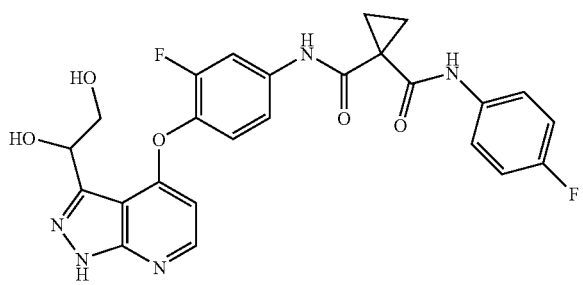 | N-(4-(3-(1,2-dihydroxyethyl)-1H-pyrazolo[3,4-b]pyridin-4-yloxy)-3-fluorophenyl)-N-(4-fluorophenyl)cyclopropane-1,1-dicarboxamide |
| 26 | 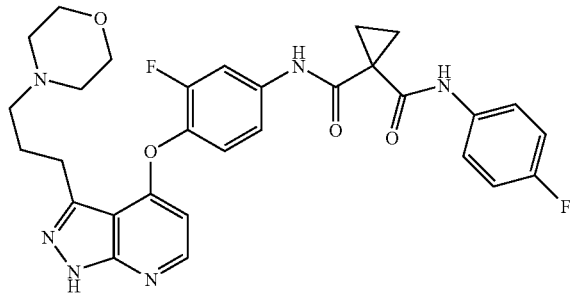 | N-(3-fluoro-4-(3-(3-morpholinopropyl)-1H-pyrazolo[3,4-b]pyridin-4-yloxy)phenyl)-N-(4-fluorophenyl)cyclopropane-1,1-dicarboxamide |
| 27 | 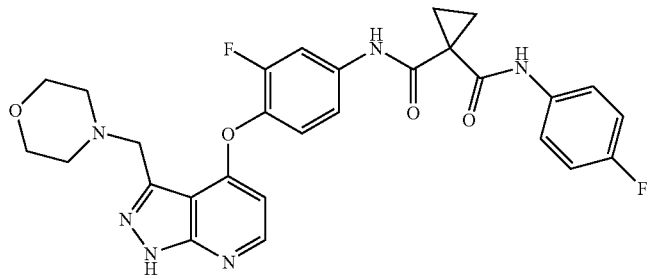 | N-(3-fluoro-4-(3-(morpholinomethyl)-1H-pyrazolo[3,4-b]pyridin-4-yloxy)phenyl)-N-(4-fluorophenyl)cyclopropane-1,1-dicarboxamide |

| Example # | | |
|---|---|---|
| 28 | 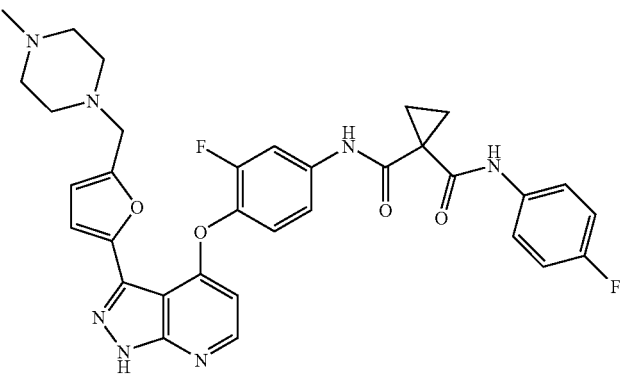 | N-(3-fluoro-4-(3-(5-((4-methyl-piperazin-1-yl)methyl)furan-2-yl)-1H-pyrazolo[3,4-b]pyridin-4-yloxy)phenyl)-N-(4-fluorophenyl)cyclopropane-1,1-dicarboxamide |
| 29 | 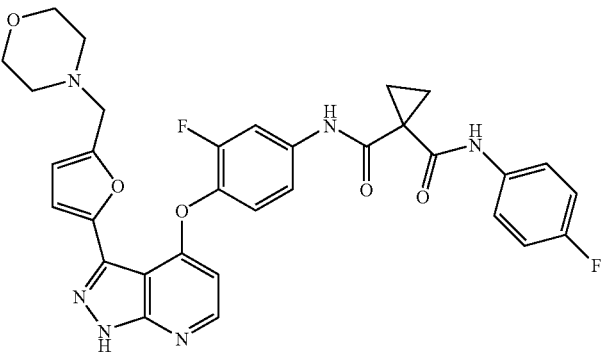 | N-(3-fluoro-4-(3-(5-(morpholinomethyl)furan-2-yl)-1H-pyrazolo[3,4-b]pyridin-4-yloxy)phenyl)-N-(4-fluorophenyl)cyclopropane-1,1-dicarboxamide |
| 30 | 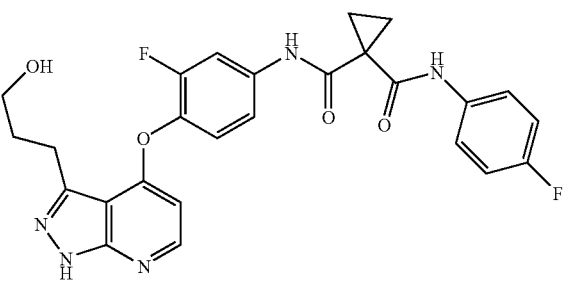 | N-(3-fluoro-4-(3-(3-hydroxypropyl)-1H-pyrazolo[3,4-b]pyridin-4-yloxy)phenyl)-N-(4-fluorophenyl)cyclopropane-1,1-dicarboxamide |
| 31 | 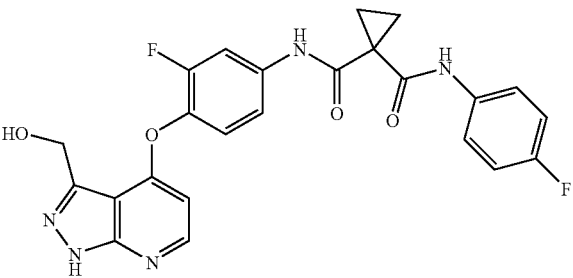 | N-(3-fluoro-4-(3-(hydroxymethyl)-1H-pyrazolo[3,4-b]pyridin-4-yloxy)phenyl)-N-(4-fluorophenyl)cyclopropane-1,1-dicarboxamide |
| 32 | 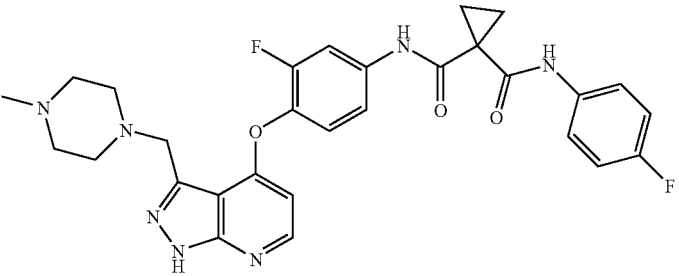 | N-(3-fluoro-4-(3-((4-methyl-piperazin-1-yl)methyl)-1H-pyrazolo[3,4-b]pyridin-4-yloxy)phenyl)-N-(4-fluorophenyl)cyclopropane-1,1-dicarboxamide |

| Example # | | |
|---|---|---|
| 33 | 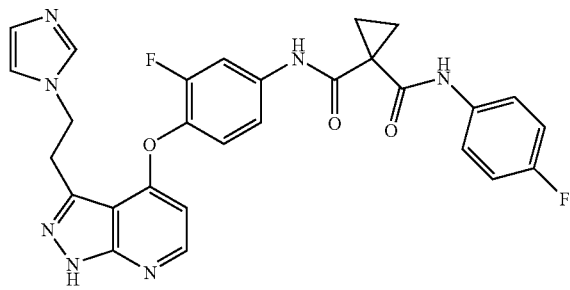 | N-(4-(3-(2-(1H-imidazol-1-yl)eth-yl)-1H-pyrazolo[3,4-b]py-ridin-4-yloxy)-3-fluoro-phenyl)-N-(4-fluoro-phenyl)cyclopropane-1,1-di-carboxamide |
| 34 | 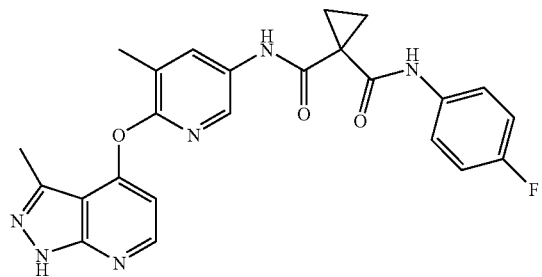 | N-(4-fluorophenyl)-N-(5-methyl-6-(3-meth-yl-1H-pyrazolo[3,4-b]pyri-din-4-yloxy)pyridin-3-yl)cyclo-propane-1,1-di-carboxamide |
| 35 | 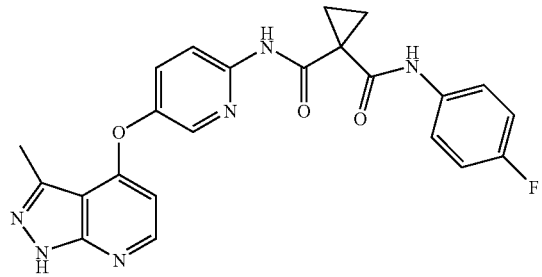 | N-(4-fluorophenyl)-N-(5-(3-meth-yl-1H-pyrazolo[3,4-b]py-ridin-4-yloxy)pyridin-2-yl)cyclo-propane-1,1-di-carboxamide |
| 36 | 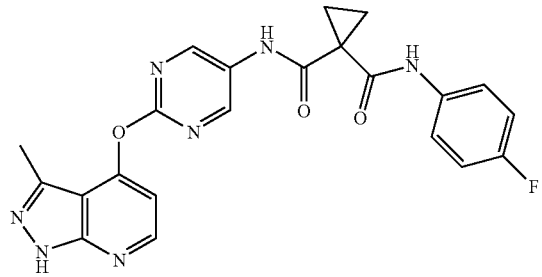 | N-(4-fluorophenyl)-N-(2-(3-meth-yl-1H-pyrazolo[3,4-b]py-ridin-4-yloxy)pyrimidin-5-yl)cyclo-propane-1,1-di-carboxamide |
| 37 | 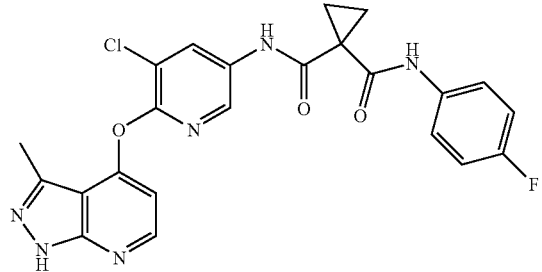 | N-(5-chloro-6-(3-methyl-1H-pyra-zolo[3,4-b]pyridin-4-yl-oxy)pyridin-3-yl)-N-(4-fluoro-phenyl)cyclopropane-1,1-di-carboxamide |

-continued

| Example # | | |
|---|---|---|
| 38 | 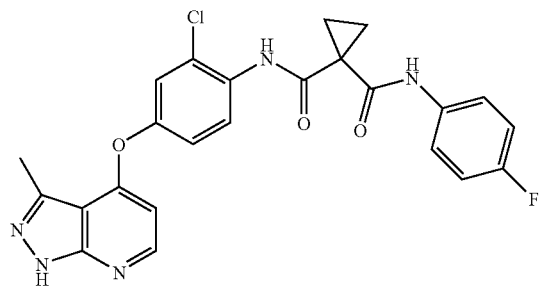 | N-(2-chloro-4-(3-methyl-1H-pyrazolo[3,4-b]pyridin-4-yloxy)phenyl)-N-(4-fluorophenyl)cyclopropane-1,1-dicarboxamide |
| 39 | 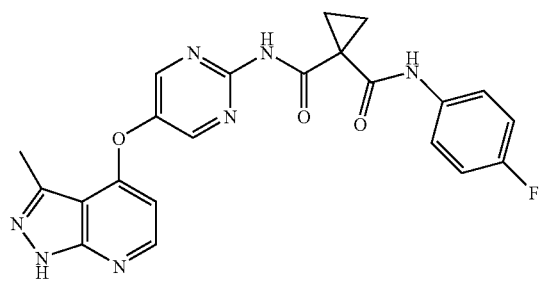 | N-(4-fluorophenyl)-N-(5-(3-methyl-1H-pyrazolo[3,4-b]pyridin-4-yloxy)pyrimidin-2-yl)cyclopropane-1,1-dicarboxamide |
| 40 | 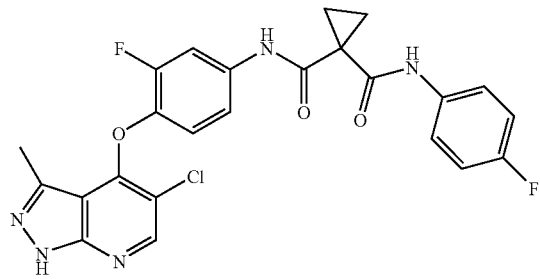 | N-(4-(5-chloro-3-methyl-1H-pyrazolo[3,4-b]pyridin-4-yloxy)-3-fluorophenyl)-N-(4-fluorophenyl)cyclopropane-1,1-dicarboxamide |
| 41 | 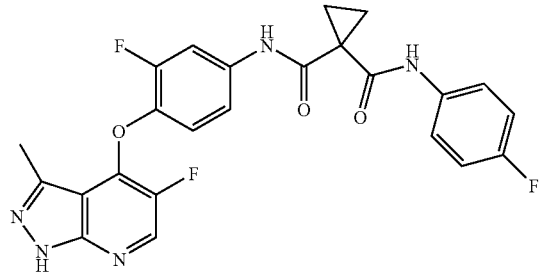 | N-(3-fluoro-4-(5-fluoro-3-methyl-1H-pyrazolo[3,4-b]pyridin-4-yloxy)phenyl)-N-(4-fluorophenyl)cyclopropane-1,1-dicarboxamide |
| 42 | 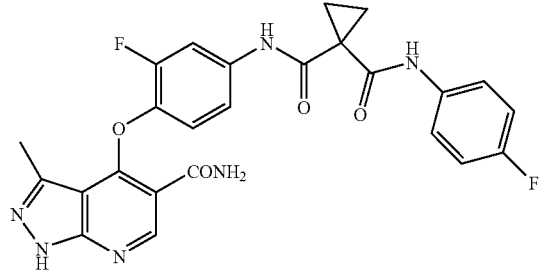 | N-(4-(5-carbamoyl-3-methyl-1H-pyrazolo[3,4-b]pyridin-4-yloxy)-3-fluorophenyl)-N-(4-fluorophenyl)cyclopropane-1,1-dicarboxamide |

Example 43

3-(4-chlorobenzyl)-5-(3-fluoro-4-(3-methyl-1H-pyrazolo[3,4-b]pyridin-4-yloxy)phenyl)pyrimidin-4(3H)-one

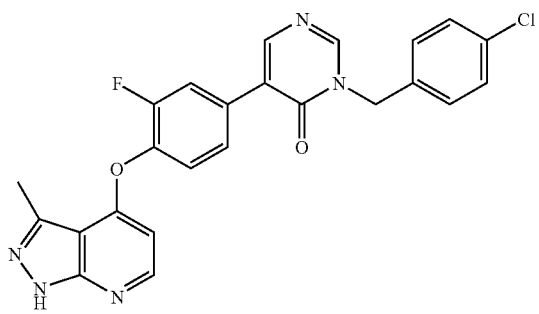

Step A: Preparation of 5-bromopyrimidin-4(3H)-one: Bromine (16.0 mL, 312 mmol) was added to a suspension of pyrimidin-4(3H)-one (30 g, 312 mmol) in chloroform (1 L) at 0° C. Methanol (10 mL) was added and the reaction mixture was stirred for 12 hours. The resulting solid was collected by filtration, washed with hexane and ether, and dried under vacuum to afford the title compound as a white solid (50 g, 91.5% yield). $^1$H NMR (400 MHz, DMSO-d$_6$) δ 11.15 (broad s, 1H), 8.42 (s, 1H), 8.40 (s, 1H).

Step B: Preparation of 3-(4-chlorobenzyl)-5-bromopyrimidin-4(3H)-one: Sodium hydride (0.343 g, 8.57 mmol) was added to a solution of 5-bromopyrimidin-4(3H)-one (1.5 g, 8.57 mmol) in THF (10 mL) and DMF (6 mL) and the reaction mixture was stirred for 10 minutes. 4-Chlorobenzyl bromide (1.76 g, 8.57 mmol) was added and the reaction mixture was stirred for an additional 1 hour. The reaction was quenched by pouring the reaction mixture into ice and diluting with ethyl acetate. The organic layer washed with brine, dried with Na$_2$SO$_4$, filtered and concentrated. The residue was purified by silica gel chromatography (Biotage 40S) to afford the title compound as white solid (0.388 g, 15.1%). LRMS (APCI pos) m/e 300.9 (M+1). $^1$H NMR (400 MHz, CDCl$_3$) δ 8.20 (s, 1H), 8.10 (s, 1H), 7.29-7.37 (m, 4H), 5.15 (s, 2H).

Step C: Preparation of 3-(4-chlorobenzyl)-5-(4-(benzyloxy)-3-fluorophenyl)pyrimidin-4(3H)-one: To a round bottom flask was added 3-(4-chlorobenzyl)-5-bromopyrimidin-4(3H)-one (0.388 g, 1.30 mmol), 4-benzyloxy-3-fluorophenylboronic acid (0.382 g, 1.55 mmol), Pd(PPh$_3$)$_4$ (0.0748 g, 0.0648 mmol), LiCl (0.275 g, 6.48 mmol), dioxane (10 mL) and 2 M aqueous sodium carbonate solution (5 mL). The reaction mixture was stirred at 10° C. for 1 hour, then quenched the reaction by pouring the mixture into water and diluting with ethyl acetate. The organic layer washed with brine, dried with Na$_2$SO$_4$, filtered and concentrated. The residue was purified by silica gel chromatography (Biotage 40S) to afford the title compound as white solid (0.17 g, 31.2% yield). LRMS (APCI pos) m/e 421.0 (M+1). $^1$H NMR (400 MHz, CDCl$_3$): δ 8.15 (s, 1H), 8.02 (s, 1H), 7.49-7.54 (m, 1H), 7.42-7.46 (m, 2H), 7.36-7.41 (m, 3H), 7.32-7.35 (m, 5H), 5.18 (s, 2H), 5.12 (s, 2H).

Step D: Preparation of 3-(4-chlorobenzyl)-5-(3-fluoro-4-hydroxyphenyl)pyrimidin-4(3H)-one: In a small round bottom flask, a solution of 3-(4-chlorobenzyl)-5-(4-(benzyloxy)-3-fluorophenyl)pyrimidin-4(3H)-one (0.17 g, 0.40 mmol) was heated in trifluoroacetic acid (5 mL) for 4 hours. The solvent was evaporated and the residue was dried under vacuum to afford the title compound as a white colored solid (0.1 g, 75%). LRMS (APCI pos) m/e 331.0 (M+1).

Step E: Preparation of 4-chloro-1-(4-methoxybenzyl)-3-methyl-1H-pyrazolo[3,4-b]pyridine: To a 500 mL round bottom flask was added phosphorous oxychloride (6.63 mL, 72.4 mmol) followed by dichloroethane (120 mL). 1-(4-Methoxybenzyl)-3-methyl-1H-pyrazolo[3,4-b]pyridin-4-ol (6.5 g, 24.1 mmol), prepared according to the procedure of Example 5, Step B, was added directly as a solid. The reaction mixture was stirred for 1 hour at refluxing temperature (115° C.) under N$_2$. The reaction mixture was cooled to room temperature and the solvent was evaporated under reduce pressure. Any remaining solvent was removed by toluene azeotrope (2×50 mL). The resulting crude material was dissolved in dichloromethane (50 mL), and saturated NaHCO$_3$ was added slowly until vigorous bubbling ceased. The biphasic mixture was diluted with additional dichloromethane and aqueous sodium bicarbonate and the organic layer washed separated, washed with brine, dried over sodium sulfate and evaporated to afford 6.6 g of off-white solid. The crude was chromatographed on Silica (Biotage 40M) loading with dichloromethane and eluting with 80/20 hexanes/ethyl acetate to obtain the product (6.0 g, 87%) as a white crystalline solid. $^1$H NMR (400 MHz, DMSO-d6) δ 8.41 (d, J=5.1 Hz, 1H), 7.24 (d, J=5.1 Hz, 1H), 7.15 (d, J=9.0 Hz, 2H), 6.80 (d, J=9.0 Hz, 2H), 5.46 (s, 2H), 3.64 (s, 3H), 2.57 (s, 3H).

Step F: Preparation of 3-(4-chlorobenzyl)-5-(3-fluoro-4-(1-(4-methoxybenzyl)-3-methyl-1H-pyrazolo[3,4-b]pyridin-4-yloxy)phenyl)pyrimidin-4(3H)-one: To a 10 mL round bottom flask was added 1-(4-methoxybenzyl)-4-chloro-3-methyl-1H-pyrazolo[3,4-b]pyridine (13.0 mg, 0.0454 mmol), prepared according to the procedure of Example 43, Step E, 3-(4-chlorobenzyl)-5-(3-fluoro-4-hydroxyphenyl)pyrimidin-4(3H)-one (10 mg, 0.0302 mmol) prepared according to the procedure of Example 43, Step D and dissolved in DMF (0.5 mL). A 1M solution of potassium t-butoxide in THF (0.0454 mL, 0.0454 mmol) and potassium carbonate (6.27 mg, 0.0454 mmol) were both added and the resulting mixture was stirred at 110° C. for 3 hours. The reaction mixture was cooled to room temperature and the crude mixture was partitioned between water (10 mL) and ethyl acetate (15 mL). The organic layer washed with brine, dried over sodium sulfate and evaporated to afford 24.1 mg of brown oil. The crude product was purified by silica gel chromatography (Biotage 12M), loading with chloroform and eluting with 1.5% MeOH in CHCl$_3$ to afford the desired product as an off-white solid (5 mg, 28%). LRMS (APCI pos) m/e 583.2 (M+1).

Step G: Preparation of 3-(4-chlorobenzyl)-5-(3-fluoro-4-(3-methyl-1H-pyrazolo[3,4-b]pyridin-4-yloxy)phenyl)pyrimidin-4(3H)-one: To a 15 mL capacity reaction tube was added 3-(4-chlorobenzyl)-5-(3-fluoro-4-(1-(4-methoxybenzyl)-3-methyl-1H-pyrazolo[3,4-b]pyridin-4-yloxy)phenyl)pyrimidin-4(3H)-one (5 mg, 0.00859 mmol) and dissolved in trifluoroacetic acid (0.5 mL). The solution was stirred at 80° C. for 30 minutes in a sealed tube under nitrogen. The reaction mixture was cooled to room temperature and the solvent was evaporated under reduced pressure. The crude residue was triturated with a 1:1 mixture of ether:hexane. The resulting solid was filtered, washed with ether, and dried to afford off-white solid as the mono-TFA salt (3.2 mg, 65%). $^1$H NMR (400 MHz, MeOD-d4) δ 8.64 (s, 1H), 8.38 (broad s, 1H), 8.25

(s, 1H), 7.80 (d, J=11.78 Hz, 1H), 7.65 (d, J=7.8 Hz, 1H), 7.50-7.37 (m, 6H), 6.42 (d, J=5.5 Hz, 1H), 5.25 (s, 2H), 2.78 (s, 3H).

Example 44

3-(3-fluoro-4-(3-methyl-1H-pyrazolo[3,4-b]pyridin-4-yloxy)phenyl)-3,4-dihydroquinazolin-2(1H)-one

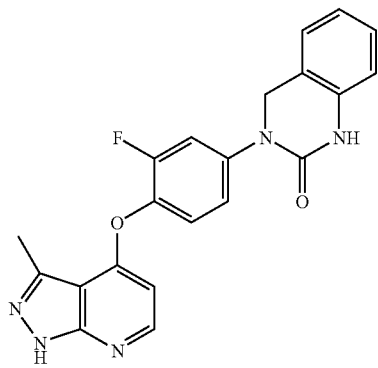

Step A: Preparation of 2-amino-N-(3-fluoro-4-methoxyphenyl)benzamide: To a stirred suspension of isatoic anhydride (1.63 g, 10 mmol) in 15 mL dioxane at room temperature under nitrogen was added powdered sodium hydroxide followed by 3-fluoro-4-methoxyaniline (1.41 g, 10 mmol). The mixture was immersed in a room temperature oil bath and slowly heated to reflux. Carbon dioxide gas evolution was evident. After stirring at reflux for 2 hours, the reaction mixture was cooled to room temperature and inorganics were filtered off with dioxane. The filtrate was concentrated to dryness to a brown solid. The crude product was dissolved in a minimum of hot 95% EtOH and crystals formed upon cooling. The crystals were filtered off and rinsed with a minimum of ice cold 95% EtOH to give a tan solid (1.0 g, 39%). $^1$H-NMR (400 MHz, CDCl$_3$) δ 7.66 (br s, 1H), 7.50 (dd, 1H), 7.44 (dd, 1H), 7.26 (m, 1H), 7.17 (m, 1H), 6.95 (m, 1H), 6.71 (m, 2H), 5.50 (br s, 2H), 3.89 (s, 3H).

Step B: Preparation of N-(2-aminobenzyl)-3-fluoro-4-methoxyaniline: To a stirred suspension of lithium aluminum hydride (121 mg, 3.2 mmol) in 2 mL dioxane at reflux under nitrogen was added 2-amino-N-(3-fluoro-4-methoxyphenyl)benzamide (260 mg, 1 mmol) as a solution in 2 mL dioxane. After refluxing overnight the reaction was cooled to room temperature and quenched by sequential treatment with H$_2$O (150 µL), 15% NaOH (150 µL) and H$_2$O (450 µL). After stirring for several minutes, the heterogeneous mixture was filtered through GF/F filter paper with dioxane and concentrated to a brown residue (246 mg, 100%). $^1$H NMR (400 MHz, CDCl$_3$) δ 7.14 (m, 2H), 6.86 (m, 1H), 6.74 (m, 2H), 6.60 (dd, 1H), 6.42 (dd, 1H), 4.15 (d, 2H), 4.12 (br s, 2H), 3.83 (s, 3H), 3.54 (br s, 1H).

Step C: Preparation of 3-(3-fluoro-4-methoxyphenyl)-3,4-dihydroquinazolin-2(1H)-one: To a stirred suspension of crude N-(2-aminobenzyl)-3-fluoro-4-methoxyaniline (246 mg, 1 mmol) in 10 mL toluene at 0° C. under a drying tube was added phosgene solution (20% in toluene, 683 µL, 1.30 mmol). The cooling bath was removed and the reaction allowed to warm to room temperature over 30 minutes. The solution was then warmed to reflux. After 1 hour, the reaction was concentrated to dryness and the residue dissolved in a minimum of hot 95% EtOH. A precipitate formed which was isolated by filtration with 95% EtOH and dried to give a tan solid (65 mg, 24%). $^1$H NMR (400 MHz, CDCl$_3$) δ 7.23 (m, 1H), 7.14 (m, 1H), 7.08 (m, 2H), 7.01 (m, 2H), 6.81 (d, 1H), 4.80 (s, 2H), 3.91 (s, 3H).

Step D: Preparation of 3-(3-fluoro-4-hydroxyphenyl)-3,4-dihydroquinazolin-2(1H)-one: To a stirred solution of 3-(3-fluoro-4-methoxyphenyl)-3,4-dihydroquinazolin-2(1H)-one (60 mg, 0.22 mmol) in 2.2 mL dichloromethane at 0° C. under a drying tube was added boron tribromide (104 µL, 1.1 mmol) neat by syringe. After 5 minutes, TLC in 1/1 EtOAc/hexanes showed complete consumption of starting material and a new slightly lower rf spot. The reaction was quenched by pouring into saturated NaHCO$_3$ (30 mL) with stirring. 9/1 Dichloromethane/methanol (30 mL) was added and the mixture stirred rapidly. The layers were separated and the organics were dried (MgSO$_4$), filtered, and concentrated to a white solid (40 mg, 70%). LRMS (APCI pos) m/e 259 (M+1). $^1$H NMR (400 MHz, CDCl$_3$) δ 7.40 (m, 1H), 7.22 (m, 1H), 7.07 (m, 2H), 6.98 (m, 2H), 6.83 (m, 1H), 4.78 (s, 2H).

Step E: Preparation of 3-(3-fluoro-4-(1-(4-methoxybenzyl)-3-methyl-1H-pyrazolo[3,4-b]pyridin-4-yloxy)phenyl)-3,4-dihydroquinazolin-2(1H)-one: To a round bottom flask were added 3-(3-fluoro-4-hydroxyphenyl)-3,4-dihydroquinazolin-2(1H)-one (19 mg, 0.074 mmol) and DMF (0.7 mL). 1-(4-Methoxybenzyl)-4-chloro-3-methyl-1H-pyrazolo [3,4-b]pyridine (25.4 mg, 0.088 mmol), prepared according to the procedure of Example 43, Step E, was added followed by potassium carbonate (12.2 mg, 0.088 mmol) and a 1 M solution of potassium t-butoxide in THF (0.088 mL, 0.088 mmol). The mixture was stirred at 110° C. for 4 hours under nitrogen. The reaction was cooled to room temperature and the reaction mixture was partitioned between water (10 mL) and ethyl acetate (20 mL). The organic layer was separated and the aqueous layer was extracted with a second portion of ethyl acetate (10 mL). The combined organic layers were washed with brine, dried over sodium sulfate and evaporated to give 29.8 mg of brown oil. The crude oil was triturated with a dichloromethane:ether mixture and the resulting solid was filtered and dried to afford the desired product as a tan solid (17.6 mg, 47%). LRMS (APCI pos): m/e 510.2 (M+1).

Step F: Preparation of 3-(3-fluoro-4-(3-methyl-1H-pyrazolo[3,4-b]pyridin-4-yloxy)phenyl)-3,4-dihydroquinazolin-2(1H)-one: To a reaction tube were added 3-(3-fluoro-4-(1-(4-methoxybenzyl)-3-methyl-1H-pyrazolo[3,4-b]pyridin-4-yloxy)phenyl)-3,4-dihydroquinazolin-2(1H)-one (17.6 mg, 0.035 mmol) and excess trifluoroacetic acid (0.5 mL). The solution was stirred at 80° C. for 30 minutes in a sealed tube under nitrogen. The reaction mixture was cooled to room temperature and the solvent was evaporated under reduced pressure. The crude residue was triturated with diethylether. The resulting solid was filtered, washed with ether, and dried to afford the desired product as an off-white solid as the mono-TFA salt (12.8 mg, 74%). LRMS (APCI pos) m/e 390.3 (M+1). $^1$H NMR (400 MHz, DMSO-d6) δ 9.77 (s, 1H), 8.30 (d, J=5.5 Hz, 1H), 7.60 (d, J=12.5 Hz, 1H), 7.50 (t, J=9.0 Hz, 1H), 7.38 (d, J=9.0 Hz, 1H), 7.20 (d, J=7.4 Hz, 2H), 6.96 (t, J=7.0 Hz, 3H), 6.90 (d, J=8.2 Hz, 2H), 6.23 (d, J=5.5 Hz, 1H), 4.89 (s, 2H), 2.64 (s, 3H).

Example 45

5-(3-fluoro-4-(3-methyl-1H-pyrazolo[3,4-b]pyridin-4-yloxy)phenyl)-3-methyl-2-(phenylamino)pyrimidin-4(3H)-one

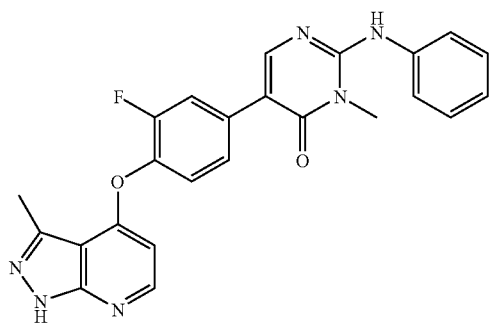

Step A: Preparation of 4-methoxy-N-phenylpyrimidin-2-amine: In a sealed tube was 2-chloro-4-methoxypyrimidine (1.00 g, 6.92 mmol) in 2-propanol (5 mL). Aniline (0.757 mL, 8.30 mmol) and DIEA (1.45 mL, 8.30 mmol) were added and the reaction mixture was stirred at 100° C. until the reaction was complete by HPLC. The reaction mixture was cooled to room temperature. The resulting thick suspension was filtered, washed with ethanol, collected and dried under vacuum to yield the desired product (0.164 g) as a white solid. The filtrate was concentrated and then partitioned between EtOAc and saturated aqueous NaCl. The phases were separated, and the aqueous phase was re-extracted with EtOAc (1×). The combined organic layers were dried ($Na_2SO_4$), filtered and concentrated to yield a yellow solid. The crude product was purified by flash column chromatography, eluting with 25:1 dichloromethane/EtOAc. The desired product (0.548 g) was obtained as a white solid, which was combined with the filtered product to yield 0.712 g (51%) total desired product. $^1$H NMR (400 MHz, DMSO-$d_6$) δ 9.51 (s, 1H), 8.20 (d, J=5.5 Hz, 1H), 7.77 (d, J=7.8 Hz, 2H), 7.27 (t, J=8.0 Hz, 2H), 6.94 (t, J=7.4 Hz, 1H), 6.28 (d, J=5.5 Hz, 1H), 3.91 (s, 3H). LRMS (ESI pos) m/e 202 (M+1).

Step B: Preparation of 2-(phenylamino)pyrimidin-4(3H)-one: To a solution of 4-methoxy-N-phenylpyrimidin-2-amine (0.632 g, 3.14 mmol) in acetic acid (20 mL) was added HBr (2.132 mL, 18.84 mmol; 48 wt % in $H_2O$). The reaction mixture was stirred at 90-95° C. for 3 hours. The reaction mixture was cooled to room temperature and diluted with $H_2O$. The pH of the reaction mixture was adjusted to 5-6 with 6 M aqueous NaOH which resulted in the formation of a solid precipitate. The solid was filtered, washed with $H_2O$, collected and dried under vacuum to yield the desired product (0.553 g, 94%) as a white solid. $^1$H NMR (400 MHz, DMSO-$d_6$) δ 10.74 (br s, 1H), 8.81 (br s, 1H), 7.76 (s, 1H), 7.60 (d, J=7.8 Hz, 2H), 7.31 (t, J=8.0 Hz, 2H), 7.02 (t, J=7.4 Hz, 1H), 5.81 (s, 1H). LRMS (ESI pos) m/e 188 (M+1).

Step C: Preparation of 3-methyl-2-(phenylamino)pyrimidin-4(3H)-one. To a solution of 2-(phenylamino)pyrimidin-4(3H)-one (0.250 g, 1.34 mmol) in DMF (10 mL) was added LiH (0.012 g, 1.47 mmol). The reaction mixture was stirred for 25 minutes and then iodomethane (0.166 mL, 2.67 mmol) was added. The reaction was stirred at room temperature for 18 hours, the quenched with $H_2O$ and partitioned between EtOAc and saturated aqueous NaCl. The phases were separated, and the aqueous phase was re-extracted with EtOAc (1×). The combined organic layers were dried ($Na_2SO_4$), filtered and concentrated to yield a crude yellow oil. The crude product was purified by flash column chromatography, eluting with 30:1 dichloromethane/methanol. The desired product (0.166 g, 62%) was obtained as a white crystalline solid. $^1$H NMR (400 MHz, CDCl$_3$) δ 7.68 (d, J=6.2 Hz, 1H), 7.46 (m, 2H), 7.39 (t, J=7.8 Hz, 2H), 7.19 (t, J=7.4 Hz, 1H), 6.48 (s, 1H), 6.01 (d, J=6.6 Hz, 1H), 3.58 (s, 3H). LRMS (ESI pos) m/e 202 (M+1).

Step D: Preparation of 5-bromo-3-methyl-2-(phenylamino)pyrimidin-4(3H)-one: To a solution of 3-methyl-2-(phenylamino)pyrimidin-4(3H)-one (0.104 g, 0.517 mmol) in CHCl$_3$ (5 mL)/MeOH (1 mL) at 0° C. was added bromine (0.027 mL, 0.517 mmol). The reaction mixture was stirred for 30 minutes at room temperature and then quenched with 10% aqueous sodium bisulfite solution. The reaction mixture was partitioned between EtOAc and $H_2O$. The phases were separated, and the aqueous phase was re-extracted with EtOAc (1×). The combined organic layers were dried ($Na_2SO_4$), filtered and concentrated to yield the desired product (0.145 g; 100%) as a white solid that was used without further purification. $^1$H NMR (400 MHz, DMSO-$d_6$) δ 8.95 (s, 1H), 7.94 (s, 1H), 7.47 (m, 2H), 7.34 (t, J=7.4 Hz, 2H), 7.14 (t, J=7.4 Hz, 1H), 3.53 (s, 3H). LRMS (ESI pos) m/e 280, 282 (M+1, Br pattern).

Step E: Preparation of 5-(4-(benzyloxy)-3-fluorophenyl)-3-methyl-2-(phenylamino)pyrimidin-4(3H)-one: A suspension of 5-bromo-3-methyl-2-(phenylamino)pyrimidin-4(3H)-one (0.145 g, 0.518 mmol), 4-(benzyloxy)-3-fluorophenylboronic acid (0.153 g, 0.621 mmol), Pd(PPh$_3$)$_4$ (0.030 g, 0.026 mmol) and lithium chloride (0.110 g, 2.59 mmol) in dioxane (1.5 mL) and 2 M aqueous Na$_2$CO$_3$ (1.5 mL) was stirred at 100° C. for 20 minutes. The reaction mixture was cooled to room temperature and then partitioned between EtOAc and $H_2O$. The phases were separated, and the aqueous phase was re-extracted with EtOAc (1×). The combined organic layers were dried ($Na_2SO_4$), filtered and concentrated to yield a crude black solid. The crude product was purified by flash column chromatography, eluting with 10:1 dichloromethane/EtOAc. The desired product (0.133 g, 64%) was obtained as an off-white waxy solid. $^1$H NMR (400 MHz, DMSO-$d_6$) δ 8.90 (br s, 1H), 7.93 (s, 1H), 7.59 (dd, J=1.95, 13.7 Hz, 1H), 7.55-7.31 (m, 10H), 7.22 (t, J=9.0 Hz, 1H), 7.14 (t, J=7.4 Hz, 1H), 5.20 (s, 2H), 3.55 (s, 3H). LRMS (ESI pos) m/e 402 (M+1).

Step F: Preparation of 5-(3-fluoro-4-hydroxyphenyl)-3-methyl-2-(phenylamino)pyrimidin-4(3H)-one: A solution of 5-(4-(benzyloxy)-3-fluorophenyl)-3-methyl-2-(phenylamino)pyrimidin-4(3H)-one (0.133 g, 0.331 mmol) in TFA (1.5 mL) was stirred at 40° C. for 3.5 hours The reaction mixture was concentrated to dryness and then purified by flash column chromatography, eluting with 20:1 dichloromethane/MeOH. The desired product (0.103 g, 100%) was obtained as a foamy white solid. $^1$H NMR (400 MHz, DMSO-$d_6$) δ 9.81 (br s, 1H), 8.96 (br s, 1H), 7.86 (s, 1H), 7.56-7.45 (m, 3H), 7.37 (t, J=7.4 Hz, 2H), 7.27 (m, 1H), 7.15 (t, J=7.2 Hz, 1H), 6.92 (t, J=9.0 Hz, 1H), 3.54 (s, 3H). LRMS (APCI pos) m/e 312 (M+1).

Step G: Preparation of 5-(3-fluoro-4-(1-(4-methoxybenzyl)-3-methyl-1H-pyrazolo[3,4-b]pyridin-4-yloxy)phenyl)-3-methyl-2-(phenylamino)pyrimidin-4(3H)-one: To a 10 mL round bottom flask was added 1-(4-methoxybenzyl)-4-chloro-3-methyl-1H-pyrazolo[3,4-b]pyridine (18.7 mg, 0.065 mmol; prepared according to the procedure of Example 43, Step E), 5-(3-fluoro-4-hydroxyphenyl)-3-methyl-2-(phenylamino)pyrimidin-4(3H)-one (13.5 mg, 0.043 mmol) and the solids were dissolved in DMF (0.5 mL). Potassium carbonate (9.0 mg, 0.065 mmol) was added followed by a 1M solution of potassium t-butoxide in THF (0.065 mL, 0.065 mmol), and the mixture was stirred at 110° C. for 18 hours. The reaction mixture was cooled to room temperature and then partitioned between water (5 mL) and ethyl acetate (10 mL). The organic layer washed with water, brine, dried over $Na_2SO_3$ and concentrated to afford 24.3 mg of crude oil. The crude product was triturated with ether to afford the desired product (16 mg, 65%) as a tan solid. LRMS (APCI pos) m/e 563.3 (M+1).

Step H: Preparation of 5-(3-fluoro-4-(3-methyl-1H-pyrazolo[3,4-b]pyridin-4-yloxy)phenyl)-3-methyl-2-(phenylamino)pyrimidin-4(3H)-one: To a 15 mL reaction tube was added 5-(3-fluoro-4-(1-(4-methoxybenzyl)-3-methyl-1H-pyrazolo[3,4-b]pyridin-4-yloxy)phenyl)-3-methyl-2-(phenylamino)pyrimidin-4(3H)-one (16 mg, 0.028 mmol) and the solids were dissolved in trifluoroacetic acid (0.5 mL, excess). The solution was stirred in a sealed tube for 1 hour at 80° C. The solvent was removed and the crude material was purified by loading onto a 0.5 mm preparative TLC plate, eluting with 8% MeOH in ethyl acetate. The product was obtained as a pale orange semi-solid (1.9 mg, 15%). LRMS (APCI pos) m/e 443.3 (M+1). $^1$H NMR (400 MHz, $CD_3OD$) δ 8.26 (d, J=5.5 Hz, 1H), 7.94 (br s, 1H), 7.73 (m, 1H), 7.54 (br d, 1H), 7.48 (br d, 1H), 7.39 (m, J=7.4 Hz, 6H), 7.23 (t, J=7.4 Hz, 1H), 6.31 (d, J=5.5 Hz, 1H), 3.66 (s, 3H), 2.72 (s, 3H).

Example 46

2-(cyclopropylmethylamino)-5-(3-fluoro-4-(3-methyl-1H-pyrazolo[3,4-b]pyridin-4-yloxy)phenyl)-3-methylpyrimidin-4(3H)-one

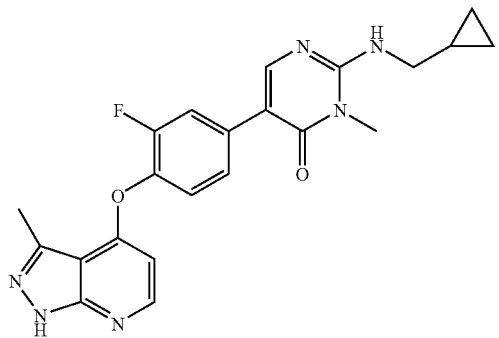

Step A: Preparation of 5-bromo-2-chloropyrimidin-4(3H)-one: 5-Bromo-2-chloropyrimidin-4(3H)-one (4.59 g, 50%) was prepared from 5-bromo-2,4-dichloropyrimidine (10.00 g, 43.88 mmol) as described in EP 1506967.

Step B: Preparation of 5-bromo-2-chloro-3-methylpyrimidin-4(3H)-one: To a solution of 5-bromo-2-chloropyrimidin-4(3H)-one (1.00 g, 4.78 mmol) in DME (12 mL)/DMF (3 mL) under $N_2$ at 0° C. was added LiH (0.044 g, 5.25 mmol), and the reaction mixture was stirred for 15 minutes at room temperature. Iodomethane (0.589 mL, 9.45 mmol) was then added and the reaction mixture was stirred at room temperature for 30 minutes and then at 60° C. for 1.5 hours. The reaction mixture was quenched with $H_2O$ and then partitioned between EtOAc and saturated aqueous NaCl. The phases were separated, and the aqueous phase was re-extracted with EtOAc (1×). The combined organic layers were dried ($Na_2SO_4$) and concentrated to yield a crude yellow oil. The crude product was purified by flash column chromatography, eluting with 25:1 dichloromethane/EtOAc. The desired product (0.764 g, 72%) was obtained as a yellow crystalline solid. $^1$H NMR (400 MHz, DMSO-$d_6$) δ 8.26 (s, 1H), 3.59 (s, 3H). LRMS (ESI pos) m/e 223, 225 (M+1, Br pattern).

Step C: Preparation of 5-bromo-2-(cyclopropylmethylamino)-3-methylpyrimidin-4(3H)-one: A mixture of 5-bromo-2-chloro-3-methylpyrimidin-4(3H)-one (0.100 g, 0.45 mmol), cyclopropylmethanamine (0.051 mL, 0.58 mmol) and $NaHCO_3$ (0.150 g, 1.79 mmol) in n-BuOH (3 mL) was stirred at 60° C. for 1 hour. The reaction mixture was cooled to room temperature and then diluted with EtOAc. The EtOAc layer washed with $H_2O$ and saturated aqueous NaCl. The aqueous phase was re-extracted with EtOAc (1×). The combined EtOAc layers were dried ($Na_2SO_4$), filtered and concentrated to yield the desired product (0.114 g, 98%) as a pale yellow solid that was used without further purification. $^1$H NMR (400 MHz, DMSO-$d_6$) δ 7.93 (s, 1H), 7.46 (t, J=5.5 Hz, 1H), 3.33 (s, 3H), 3.19 (t, J=6.2 Hz, 2H), 1.12 (m, 1H), 0.43 (m, 2H), 0.24 (m, 2H). LRMS (ESI pos) m/e 258, 260 (M+1, Br pattern).

Step D: Preparation of 5-(4-(benzyloxy)-3-fluorophenyl)-2-(cyclopropylmethylamino)-3-methylpyrimidin-4(3H)-one: A suspension of 5-bromo-2-(cyclopropylmethylamino)-3-methylpyrimidin-4(3H)-one (0.112 g, 0.434 mmol), 4-(benzyloxy)-3-fluorophenylboronic acid (0.128 g, 0.521 mmol), $Pd(PPh_3)_4$ (0.025 g, 0.022 mmol) and lithium chloride (0.092 g, 2.17 mmol) in dioxane (1.5 mL) and 2M aqueous $Na_2CO_3$ (1.5 mL) was stirred at 100° C. for 30 minutes. The reaction mixture was cooled to room temperature and then partitioned between EtOAc and $H_2O$. The phases were separated, and the aqueous phase was re-extracted with EtOAc (1×). The combined organic layers were dried ($Na_2SO_4$), filtered and concentrated to yield a crude black solid. The crude product was purified by flash column chromatography, eluting with 10:1 dichloromethane/EtOAc. The desired product (0.128 g, 78%) was obtained as a foamy off-white solid. $^1$H NMR (400 MHz, DMSO-$d_6$) δ 7.93 (s, 1H), 7.57 (dd, J=2.0, 13.7 Hz, 1H), 7.49-7.31 (m, 7H), 7.19 (t, J=9.0 Hz, 1H), 5.19 (s, 2H), 3.35 (s, 3H), 3.24 (t, J=6.1 Hz, 2H), 1.16 (m, 1H), 0.44 (m, 2H), 0.25 (m, 1H). LRMS (APCI pos) m/e 380 (M+1).

Step E: Preparation of 2-(cyclopropylmethylamino)-5-(3-fluoro-4-hydroxyphenyl)-3-methylpyrimidin-4(3H)-one: A solution of 5-(4-(benzyloxy)-3-fluorophenyl)-2-(cyclopropylmethylamino)-3-methylpyrimidin-4(3H)-one (0.128 g, 0.337 mmol) in TFA (2 mL) was stirred at 40° C. for 2 hours and 45 minutes. The reaction mixture was concentrated to dryness and then purified by flash column chromatography, eluting with 20:1 dichloromethane/MeOH. The desired product (0.080 g, 82%) was obtained as a colorless glassy solid. $^1$H NMR (400 MHz, DMSO-$d_6$) δ 9.71 (s, 1H), 7.87 (s, 1H), 7.46 (dd, J=2.3, 13.7 Hz, 1H), 7.35 (t, J=5.3 Hz, 1H), 7.24 (dd, J=2.3, 8.4 Hz, 1H), 6.90 (dd, J=8.4, 9.6 Hz, 1H), 3.34 (s, 3H), 3.24 (t, J=6.2 Hz, 2H), 1.16 (m, 1H), 0.44 (m, 2H), 0.26 (m, 2H). LRMS (ESI pos) m/e 290 (M+1).

Step F: Preparation of 2-(cyclopropylmethylamino)-5-(3-fluoro-4-(1-(4-methoxybenzyl)-3-methyl-1H-pyrazolo[3,4-b]pyridin-4-yloxy)phenyl)-3-methylpyrimidin-4(3H)-one: To a 15 mL capacity reaction tube were added 1-(4-methoxybenzyl)-4-chloro-3-methyl-1H-pyrazolo[3,4-b]pyridine (20 mg, 0.07 mmol; prepared according to the procedure of Example 43, Step E) and 2-(cyclopropylmethylamino)-5-(3-fluoro-4-hydroxyphenyl)-3-methylpyrimidin-4(3H)-one (22.1 mg, 0.077 mmol) and the solids were dissolved in DMF (1 mL) under nitrogen. Potassium carbonate (10.6 mg, 0.0765 mmol) was added, followed by KOtBu (0.077 mL, 0.077 mmol, 1M solution in THF). The reaction tube was sealed and the reaction mixture was stirred at 110° C. for 1 hour. The reaction mixture was partitioned between water (5 mL) and ethyl acetate (10 mL). The organic layer was separated and the aqueous layer was extracted with a second portion of ethyl acetate. The combined organic layers were washed with saturated aqueous NaCl, dried over sodium sulfate and evaporated to afford 37.5 mg of a red semi-solid. The crude product was purified by silica gel chromatography (Biotage 12M) eluting with 2% MeOH/DCM to afford a red colored glass (23.8 mg, 63%). LRMS (APCI pos) m/e 541.3 (M+1).

Step G: Preparation of 2-(cyclopropylmethylamino)-5-(3-fluoro-4-(3-methyl-1H-pyrazolo[3,4-b]pyridin-4-yloxy)phenyl)-3-methylpyrimidin-4(3H)-one: To a 15 mL capacity reaction tube was added 2-(cyclopropylmethylamino)-5-(3-fluoro-4-(1-(4-methoxybenzyl)-3-methyl-1H-pyrazolo[3,4-b]pyridin-4-yloxy)phenyl)-3-methylpyrimidin-4(3H)-one (23.8 mg, 0.044 mmol) and the solids were dissolved in TFA (0.5 mL, excess). The reaction mixture was stirred at 80° C. for 1 hour in a sealed tube. The excess solvent was evaporated and the crude residue was purified by silica gel chromatography (Biotage 12M) loading with EtOAc and eluting with 3% MeOH/EtOAc to give the title compound as pink solid (8.5 mg, 46%). LRMS (APCI pos) m/e 421.3 (M+1). $^1$H NMR (400 MHz, DMSO-$d_6$) δ 13.29 (s, 1H), 8.27 (d, J=5.5 Hz, 1H), 8.10 (s, 1H), 7.85 (br d, 1H), 7.65 (d, J=8.6 Hz, 1H), 7.53 (t, J=5.5 Hz, 1H), 7.43 (t, J=8.6 Hz, 1H), 6.23 (d, J=5.5 Hz, 1H), 3.38 (s, 3H), 3.28 (t, J=6.2 Hz, 2H), 2.63 (s, 3H), 1.17 (t, J=7.2 Hz, 1H), 0.46 (q, J=6.8 Hz, 2H), 0.28 (q, J=4.9 Hz, 2H).

Example 47

4-benzyl-N-(3-fluoro-4-(3-methyl-1H-pyrazolo[3,4-b]pyridin-4-yloxy)phenyl)-3-oxo-3,4-dihydropyrazine-2-carboxamide

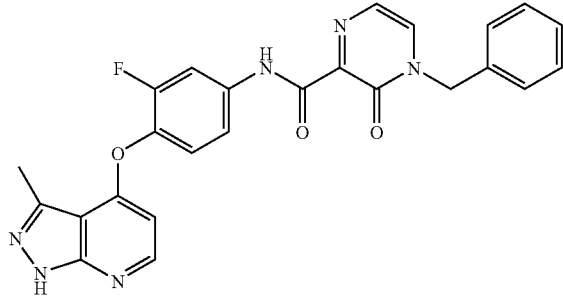

Step A: Preparation of methyl 4-benzyl-3-oxo-3,4-dihydropyrazine-2-carboxylate: LiH was added to the solution of methyl 3-oxo-3,4-dihydropyrazine-2-carboxylate (0.10 g, 0.65 mmol) in DMF (3 mL) at 0° C. After stirring for 30 minutes, benzyl chloride (0.15 mL, 1.30 mmol) was added to the reaction mixture at the temperature, and the reaction was warmed to room temperature. After stirring for 3 days, the reaction mixture was diluted with EtOAc, quenched with ice water, extracted with EtOAc, dried over MgSO$_4$, and concentrated to give the desired product, which was purified by silica gel flash column chromatography (2% MeOH in CH$_2$Cl$_2$, 0.102 g, 64%). $^1$H NMR (400 MHz, CDCl$_3$) δ 7.35-7.40 (m, 6H), 7.29 (d, 1H), 5.14 (s, 2H), 3.99 (s, 3H).

Step B: Preparation of 4-benzyl-3-oxo-3,4-dihydropyrazine-2-carboxylic acid: LiOH (0.82 mL, 0.82 mmol, 1.0 M) was added to a solution of methyl 4-benzyl-3-oxo-3,4-dihydropyrazine-2-carboxylate (0.10 g, 0.41 mmol) in a mixture of THF-MeOH (3:1 ratio, 6 mL) at room temperature. After stirring for 4 hours, 1 N HCl (0.9 mL) was added. The reaction mixture was extracted with EtOAc, dried over MgSO$_4$, and concentrated to give the desired product (0.077 g, 82%). $^1$H NMR (400 MHz, CD$_3$OD) δ 8.0 (d, 1H), 7.68 (d, 1H), 7.36-7.42 (m, 5H), 5.29 (s, 2H).

Step C: Preparation of 4-benzyl-N-(3-fluoro-4-(3-methyl-1H-pyrazolo[3,4-b]pyridin-4-yloxy)phenyl)-3-oxo-3,4-dihydropyrazine-2-carboxamide: Prepared by a 2-step process from 3-fluoro-4-(1-(4-methoxybenzyl)-3-methyl-1H-pyrazolo[3,4-b]pyridin-4-yloxy)aniline (prepared according to Example 5, Step D) and 4-benzyl-3-oxo-3,4-dihydropyrazine-2-carboxylic acid according to the procedure described for Example 21 (Steps A and B). The crude was purified by silica gel flash column chromatography (5% MeOH in CH$_2$Cl$_2$) to afford 18 mg with TFA salt (49% for 2-step process) of the desired product. LRMS (APCI pos) m/e 471.3 (M+1). $^1$H NMR (400 MHz, CD$_3$OD/CDCl$_3$) δ 8.25 (d, 1H), 8.06 (dd, 1H), 7.99 (d, 1H), 7.75 (d, 1H), 7.55 (m, 1H), 7.35-7.46 (m, 6H), 6.28 (d, 1H), 5.33 (s, 2H), 2.73 (s, 3H); $^{19}$F NMR (376 MHz, CD$_3$OD/CDCl$_3$) δ −129.0.

Example 48

N-(3-fluoro-4-(3-methyl-1H-pyrazolo[3,4-b]pyridin-4-yloxy)phenyl)-2-oxopyrrolidine-3-carboxamide

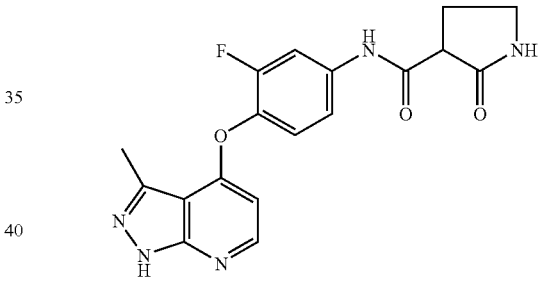

Step A: Preparation of N-(4-(1-(4-methoxybenzyl)-3-methyl-1H-pyrazolo[3,4-b]pyridin-4-yloxy)-3-fluorophenyl)-2-oxopyrrolidine-3-carboxamide: A 100 mL round-bottomed flask was charged with 4-(1-(4-methoxybenzyl)-3-methyl-1H-pyrazolo[3,4-b]pyridin-4-yloxy)-3-fluorobenzenamine (20.0 mg, 0.053 mmol; obtained from Example 5, Step D), 2-oxopyrrolidine-3-carboxylic acid (34.1 mg, 0.26 mmol), N1-((ethylimino)methylene)-N3,N3-dimethylpropane-1,3-diamine hydrochloride (50.7 mg, 0.26 mmol), 1H-benzo[d][1,2,3]triazol-1-ol (35.7 mg, 0.26 mmol), N-ethyl-N-isopropylpropan-2-amine (34.2 mg, 0.26 mmol), and THF (10 mL). The reaction mixture was stirred at room temperature until LC-MS showed that the starting material had been consumed (2 days). Water (10 mL) was added and extracted with CH$_2$Cl$_2$ (3×50 mL). The organic layers were combined, dried over Na$_2$SO$_4$ and concentrated. The residue purified by silica gel chromatography (DCM/7 M NH$_3$ in MeOH from 50/1 to 10/1, v/v) to afford the desired product (22.3 mg, 86.2%). LRMS (APCI neg) m/e 488 (M−1).

Step B: Preparation of N-(3-fluoro-4-(3-methyl-1H-pyrazolo[3,4-b]pyridin-4-yloxy)phenyl)-2-oxopyrrolidine-3-carboxamide: A 100 mL round-bottomed flask was charged with N-(4-(1-(4-methoxybenzyl)-3-methyl-1H-pyrazolo[3,4-b]pyridin-4-yloxy)-3-fluorophenyl)-2-oxopyrrolidine-3-carboxamide (22.3 mg, 0.046 mmol) and 2,2,2-trifluoroacetic acid (259.7 mg, 2.28 mmol). The reaction mixture was stirred at 60° C. until LC-MS showed that the starting material was consumed (8 hour). The CF$_3$COOH was removed under reduced pressure and the residue purified by column (Silica gel, DCM/7 M NH$_3$ in MeOH from 50/1 to 10/1, v/v) to give the desired product (14.9 mg, 88.6%). HPLC: >99% purity, 1.91 min (254 nm); LRMS (APCI neg) m/e 368 (M−1). $^1$H NMR (400 MHz, CD$_3$OD) δ 8.25 (d, J=5.6 Hz, 1H), 7.85 (dd, J=12.4, 2.4 Hz, 1H), 7.43 (m, 1H), 7.37 (t, J=8.8 Hz, 1H), 6.25 (dd, J=5.6, 0.8 Hz, 1H), 3.52-3.38 (m, 2H), 3.31 (m, 1H), 2.71 (s, 3H), 2.52-2.59 (m, 1H), 2.38-2.44 (m, 1H).

Example 49

N-(3-fluoro-4-(3-methyl-1H-pyrazolo[3,4-b]pyridin-4-yloxy)phenyl)-1-methyl-2-oxopyrrolidine-3-carboxamide

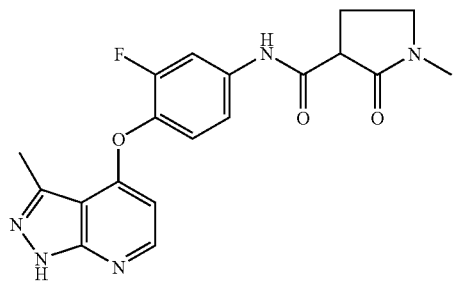

Step A: Preparation of methyl 1-methyl-2-oxopyrrolidine-3-carboxylate: A 250 mL round-bottomed flask was charged with 1-methylpyrrolidin-2-one (5.05 mL, 52.5 mmol), LDA (43.8 mL, 78.8 mmol, 1.8 M), and THF (125 mL). The reaction mixture stirred at −78° C. for 1 hour. Methyl chloroformate (6.06 mL, 78.8 mmol), was added, and the reaction mixture was stirred at room temperature until LC-MS showed that the starting material had been consumed (4 hours). Water (125 mL) was added, and the aqueous layer was extracted with EtOAc (3×250 mL). The combined organic layers were dried over Na$_2$SO$_4$ and concentrated to afford the crude product 7.35 g (89%), which was used in the next step without further purification. $^1$H NMR (400 MHz, CDCl$_3$) δ 3.37 (s, 3H), 3.28-3.25 (m, 2H), 2.85 (s, 3H), 2.62-2.67 (m, 1H), 2.13-2.22 (m, 1H), 1.99-2.06 (m, 1H).

Step B: Preparation of 1-methyl-2-oxopyrrolidine-3-carboxylic acid: A 250 mL round-bottomed flask was charged with methyl 1-methyl-2-oxopyrrolidine-3-carboxylate (1.89 g, 12.0 mmol), potassium trimethylsilanolate (4.64 g, 36.1 mmol), and THF (100 mL). The reaction mixture was stirred at room temperature overnight, then HCl (50 mL, 2.0 M in Et$_2$O) was added and the reaction mixture was stirred for 5 minutes. The solid was removed by filtration and the filtrate concentrated to give the crude product 1.28 g (74.2%), which was used in the next step without further purification. $^1$H NMR (400 MHz, CDCl$_3$) δ 3.40-3.49 (m, 3H), 2.94 (s, 3H), 2.37-2.47 (m, 2H).

Step C: Preparation of N-(4-(1-(4-methoxybenzyl)-3-methyl-1H-pyrazolo[3,4-b]pyridin-4-yloxy)-3-fluorophenyl)-1-methyl-2-oxopyrrolidine-3-carboxamide: A 100 mL round-bottomed flask was charged with 4-(1-(4-methoxybenzyl)-3-methyl-1H-pyrazolo[3,4-b]pyridin-4-yloxy)-3-fluorobenzenamine (15.0 mg, 0.040 mmol; obtained from Example 5, Step D), 1-methyl-2-oxopyrrolidine-3-carboxylic acid (28.4 mg, 0.20 mmol), N1-((ethylimino)methylene)-N3,N3-dimethylpropane-1,3-diamine hydrochloride (38.0 mg, 0.20 mmol), 1H-benzo[d][1,2,3]triazol-1-ol (26.8 mg, 0.20 mmol), N-ethyl-N-isopropylpropan-2-amine (0.035 mL, 0.20 mmol) and CH$_2$Cl$_2$ (10 mL). The reaction mixture was stirred at room temperature until LC-MS showed that the starting material was consumed. Water (10 mL) was added, and the aqueous layer was extracted with CH$_2$Cl$_2$ (3×50 mL). The combined organic layers were dried (Na$_2$SO$_4$) and concentrated, and the resulting residue was purified by silica gel chromatography (DCM/7 M NH$_3$ in MeOH from 50/1 to 10/1, v/v) to afford the desired product (14.8 mg, 74.1%). LRMS (APCI neg) m/e 502 (M−1). $^1$H NMR (400 MHz, CDCl$_3$) δ 10.03 (s, 1H), 8.25 (d, J=5.2 Hz, 1H), 7.78 (dd, J=12.4, 2.4 Hz, 1H), 7.31 (d, J=8.8 Hz, 2H), 7.25-7.34 (m, 1H), 7.18 (m, 1H), 6.82 (d, J=8.8 Hz, 2H), 6.14 (m, 1H), 5.56 (s, 2H), 3.78 (s, 3H), 3.38-3.49 (m, 3H), 2.88 (s, 3H), 2.71 (s, 3H), 2.36-2.48 (m, 1H), 2.22-2.31 (m, 1H).

Step D: Preparation of N-(3-fluoro-4-(3-methyl-1H-pyrazolo[3,4-b]pyridin-4-yloxy)phenyl)-1-methyl-2-oxopyrrolidine-3-carboxamide: A 100 mL round-bottomed flask was charged with N-(4-(1-(4-methoxybenzyl)-3-methyl-1H-pyrazolo[3,4-b]pyridin-4-yloxy)-3-fluorophenyl)-1-methyl-2-oxopyrrolidine-3-carboxamide (14.8 mg, 0.0294 mmol) and 2,2,2-trifluoroacetic acid (335 mg, 2.94 mmol). The reaction mixture was stirred at 60° C. until LC-MS showed that the starting material was consumed. The CF$_3$COOH was removed under reduced pressure and purified the resulting residue was purified by silica gel chromatography (DCM/7 M NH$_3$ in MeOH from 50/1 to 10/1, v/v) to give the desired product (10.2 mg, 90.5%). LRMS (APCI neg) m/e 382 (M−1). $^1$H NMR (400 MHz, CD$_3$OD) δ 8.25 (d, J=6.0 Hz, 1H), 7.85 (dd, J=12.8, 2.4 Hz, 1H), 7.42 (m, 1H), 7.37 (m, 1H), 6.25 (m, 1H), 3.44-3.59 (m, 2H), 3.31 (m, 1H), 2.90 (s, 3H), 2.71 (s, 3H), 2.44-2.49 (m, 1H), 2.30-2.37 (m, 1H).

Example 50

N-(3-fluoro-4-(3-methyl-1H-pyrazolo[3,4-b]pyridin-4-yloxy)phenyl)-1-methyl-2-oxo-1,2-dihydropyridine-3-carboxamide

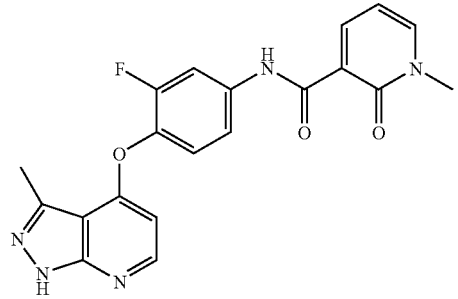

Step A: Preparation of methyl 1-methyl-2-oxo-1,2-dihydropyridine-3-carboxylate: LiH (10 mg, 1.3 mmol) was added to the solution of methyl 2-oxo-1,2-dihydropyridine-3-carboxylate (0.10 g, 0.65 mmol) in DMF (3 mL) at 0° C. After stirring for 30 minutes, iodomethane (0.08 mL, 1.30 mmol) was added to the reaction mixture at the temperature, and the reaction was warmed to room temperature. After stirring for 3 days, the reaction mixture was diluted with EtOAc, quenched with ice water, extracted with EtOAc, dried over MgSO$_4$, and concentrated to give the desired product.

Step B: Preparation of 1-methyl-2-oxo-1,2-dihydropyridine-3-carboxylic acid: LiOH (1.3 mL, 1.3 mmol, 1.0 M) was added to a solution of methyl 1-methyl-2-oxo-1,2-dihydropyridine-3-carboxylate (0.11 g, 0.65 mmol) in a mixture of THF-MeOH (3:1 ratio, 8 mL) at room temperature. After stirring for 2 hours, 1 N HCl (1.3 mL) was added. The reaction mixture was extracted with EtOAc, dried over MgSO$_4$, and concentrated to give the desired product (0.044 g, 44% for 2 step process).

Step C: Preparation of N-(3-fluoro-4-(3-methyl-1H-pyrazolo[3,4-b]pyridin-4-yloxy)phenyl)-1-methyl-2-oxo-1,2-dihydropyridine-3-carboxamide: Prepared by a 2-step process from 3-fluoro-4-(1-(4-methoxybenzyl)-3-methyl-1H-pyrazolo[3,4-b]pyridin-4-yloxy)aniline (prepared according to Example 5, Step D) and 1-methyl-2-oxo-1,2-dihydropyridine-3-carboxylic acid according to the procedure described for Example 21 (Steps A and B). The crude was purified by silica gel flash column chromatography (3% MeOH in CH$_2$Cl$_2$) to afford 16 mg (99%) of the desired product. LRMS (ESI pos) m/e 394.2 (M+1). $^1$H NMR (400 MHz, CD$_3$OD) δ 8.56 (dd, 1H), 8.26 (d, 1H), 8.02 (m, 2H), 7.47 (m, 1H), 7.39 (t, 1H), 6.62 (t, 1H), 6.29 (d, 1H), 3.72 (s, 3H), 2.72 (s, 3H); $^{19}$F-NMR (376 MHz, CD$_3$OD) δ −130.0.

Example 51

5-(3-fluoro-4-(3-methyl-1H-pyrazolo[3,4-b]pyridin-4-yloxy)phenyl)-2-(4-fluorophenylamino)-3-methylpyrimidin-4(3H)-one

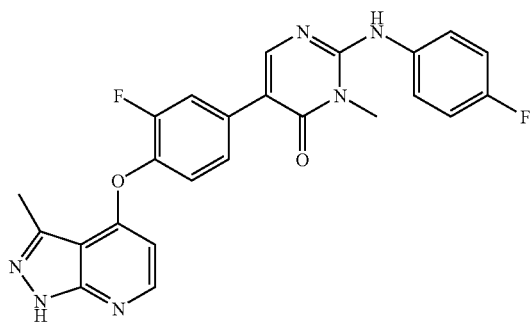

Step A: Preparation of 5-bromo-2-(4-fluorophenylamino)-3-methylpyrimidin-4(3H)-one: A mixture of 5-bromo-2-chloro-3-methylpyrimidin-4(3H)-one (0.100 g, 0.448 mmol; prepared according to the procedure of Example 46, Step B), 4-fluorobenzenamine (0.056 ml, 0.582 mmol) and NaHCO$_3$ (0.150 g, 1.79 mmol) in n-BuOH (3 mL) was stirred at 60° C. overnight. The reaction mixture was cooled to room temperature and then diluted with EtOAc. The EtOAc layer washed with H$_2$O and saturated aqueous NaCl. The aqueous phase was re-extracted with EtOAc. The combined EtOAc layers were dried (Na$_2$SO$_4$), filtered and concentrated to yield the desired product (0.132 g, 99%) as a pale yellow solid that was used without further purification.

Step B: Preparation of 5-(4-(benzyloxy)-3-fluorophenyl)-2-(4-fluorophenylamino)-3-methylpyrimidin-4(3H)-one: A suspension of 5-bromo-2-(4-fluorophenylamino)-3-methylpyrimidin-4(3H)-one (0.130 g, 0.436 mmol), 4-(benzyloxy)-3-fluorophenylboronic acid (0.129 g, 0.523 mmol), Pd(PPh$_3$)$_4$ (0.025 g, 0.022 mmol) and lithium chloride (0.092 g, 2.18 mmol) in dioxane (1.5 mL) and 2 M aqueous Na$_2$CO$_3$ (1.5 mL) was stirred at 100° C. for 30 minutes. The reaction mixture was cooled to room temperature and then partitioned between EtOAc and H$_2$O. The phases were separated, and the aqueous phase was re-extracted with EtOAc (1×). The combined organic layers were dried (Na$_2$SO$_4$), filtered and concentrated to yield a crude black solid. The crude product was purified by flash column chromatography, eluting with 10:1 dichloromethane/EtOAc. The desired product (0.139 g, 76%) was obtained as a grey-white solid.

Step C: Preparation of 5-(3-fluoro-4-hydroxyphenyl)-2-(4-fluorophenylamino)-3-methylpyrimidin-4(3H)-one: A solution of 5-(4-(benzyloxy)-3-fluorophenyl)-2-(4-fluorophenylamino)-3-methylpyrimidin-4(3H)-one (0.139 g, 0.331 mmol) in TFA (1.5 mL) was stirred at 40° C. for 3 hours. The reaction mixture was concentrated to dryness and then purified by flash column chromatography, eluting with 20:1 dichloromethane/MeOH. The desired product (0.089 g, 82%) was obtained as a white solid.

Step D: Preparation of 5-(3-fluoro-4-(1-(4-methoxybenzyl)-3-methyl-1H-pyrazolo[3,4-b]pyridin-4-yloxy)phenyl)-2-(4-fluorophenylamino)-3-methylpyrimidin-4(3H)-one: To a mixture of 5-(3-fluoro-4-hydroxyphenyl)-2-(4-fluorophenylamino)-3-methylpyrimidin-4(3H)-one (25.2 mg, 0.077 mmol) and 1-(4-methoxybenzyl)-4-chloro-3-methyl-1H-pyrazolo[3,4-b]pyridine (20 mg, 0.070 mmol) dissolved in DMF (0.5 mL), added KOtBu (0.077 ml, 0.077 mmol) 1M solution in THF, and potassium carbonate (10.6 mg, 0.077 mmol). The mixture was stirred at 110° C. overnight. Cooled to room temperature and partitioned between EtOAc (15 mL) and water (20 mL). The organic layer was dried with brine, Na$_2$SO$_4$, and evaporated to afford 27 mg of crude product. Purified by silica gel column chromatography (Biotage 12M) eluting with 5% MeOH/EtOAc to afford desired product as white solid (4.6 mg, 11%). LRMS (APCI pos) m/e 581.2 (M+1).

Step E: Preparation of 5-(3-fluoro-4-(3-methyl-1H-pyrazolo[3,4-b]pyridin-4-yloxy)phenyl)-2-(4-fluorophenylamino)-3-methylpyrimidin-4(3H)-one: A stirred mixture of 5-(3-fluoro-4-(1-(4-methoxybenzyl)-3-methyl-1H-pyrazolo[3,4-b]pyridin-4-yloxy)phenyl)-2-(4-fluorophenylamino)-3-methylpyrimidin-4(3H)-one (4.6 mg, 0.008 mmol) and TFA (0.5 mL) was heated to 50° C. for 1 hour. The mixture was concentrated in vacuo, using toluene (2×5 mL) to azeotrope residual TFA. Purified by trituration with 1:1 ether:hexanes and the resulting white solid was removed by filtration and dried to afford desired product as the TFA salt (3.9 mg, 86%). $^1$H NMR (400 MHz, DMSO-d6) δ 9.09 (broad s, 1H), 8.28 (d, 1H), 8.07 (s, 1H), 7.86 (d, 2H), 7.67 (d, 2H), 7.53 (broad s, 1H), 7.46 (t, 1H), 7.22 (t, 2H), 6.25 (d, 1H), 3.57 (s, 3H), 2.63 (s, 3H). LRMS (APCI pos) m/e 461.4 (M+H).

Example 52

N-(3-fluoro-4-(3-(2-hydroxyethyl)-1H-pyrazolo[3,4-b]pyridin-4-yloxy)phenyl)-2-(4-fluorophenyl)-3-oxo-2,3-dihydropyridazine-4-carboxamide

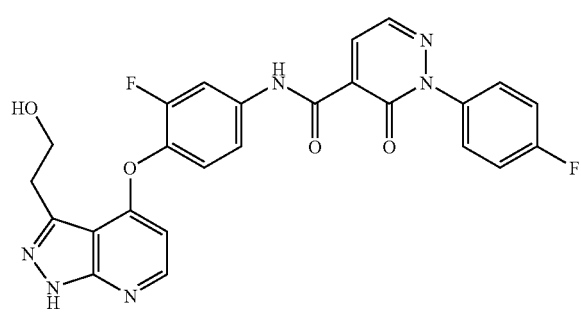

Step A: Preparation of 4-(1-(4-methoxybenzyl)-3-vinyl-1H-pyrazolo[3,4-b]pyridin-4-yloxy)-3-fluorobenzenamine: A mixture of 4-(1-(4-methoxybenzyl)-3-iodo-1H-pyrazolo[3,4-b]pyridin-4-yloxy)-3-fluorobenzenamine (3.68 g, 7.50 mmol, prepared according to the procedure for Example 7, Step B), potassium vinyltrifluoroborate (2.01 g, 15.0 mmol), triethylamine (2.08 ml, 15.0 mmol) and n-propanol (20 mL) was sparged with $N_2$ for 5 min, and then Pd(dppf)Cl$_2$ (0.306 g, 0.375 mmol) was added. The reaction was heated at 100° C. for 3 hours in a sealed vessel. After cooling to ambient temperature, the reaction was concentrated in vacuo. The residue was partitioned between DCM (30 mL) and water (30 mL). The phases were separated, and the aqueous phase was re-extracted with DCM (2×10 mL). The combined organic phases were dried (Na$_2$SO$_4$), filtered, and concentrated in vacuo. The crude was purified by Biotage Flash 65 chromatography system, eluting with 20% EtOAc/hexanes (1 L), 1:1 EtOAc/hexanes (1 L), then 2:1 EtOAc/hexanes (2 L). The product was obtained as a reddish colored solid (2.00 g, 64%).

Step B: Preparation of 2-(1-(4-methoxybenzyl)-4-(4-amino-2-fluorophenoxy)-1H-pyrazolo[3,4-b]pyridin-3-yl)ethanol: To a stirred solution of 4-(1-(4-methoxybenzyl)-3-vinyl-1H-pyrazolo[3,4-b]pyridin-4-yloxy)-3-fluorobenzenamine (1.17 g, 3.00 mmol) in THF (5 mL) was added 9-BBN (24.0 ml, 12.0 mmol, 0.5 M in THF). The reaction was stirred for 18 hours at room temperature. The reaction was chilled (submerged in an ice bath) and then quenched by addition of 5N aqueous sodium hydroxide (6.00 mL, 30.0 mmol). After stirring for 30 minutes in the ice bath, 30% aqueous hydrogen peroxide (2.88 mL, 30.0 mmol) was added. After stirring for 5 minutes at 0° C., the reaction was allowed to stir for 30 minutes at room temperature. The reaction mixture was partitioned between water (20 mL) and EtOAc (20 mL). The phases were separated, and the aqueous phase was re-extracted with EtOAc (2×10 mL). The combined organic phases were washed with brine (20 mL), dried (Na$_2$SO$_4$), filtered, and concentrated. The crude was purified by Biotage Flash 40M, eluting with 2% MeOH in DCM (2 L). The product was obtained as a waxy solid (1.0 g, 78%).

Step C: Preparation of N-(3-fluoro-4-(3-methyl-1H-pyrazolo[3,4-b]pyridin-4-yloxy)phenyl)-1-methyl-2-oxo-1,2-dihydropyridine-3-carboxamide: Prepared by a 2-step process from 2-(4-(4-amino-2-fluorophenoxy)-1H-pyrazolo[3,4-b]pyridin-3-yl)ethanol and 2-(4-fluorophenyl)-3-oxo-2,3-dihydropyridazine-4-carboxylic acid (prepared as in Example 19, Step C) according to the procedure described for Example 21, Steps A and B, except that the crude was treated with aqueous NaHCO$_3$ solution. The crude was purified by silica gel flash column chromatography (4% MeOH in CH$_2$Cl$_2$) to afford 6.6 mg (64%) of the desired product. LRMS (ESI pos) m/e 505.2 (M+1). $^1$H NMR (400 MHz, CDCl$_3$/CD$_3$OD) δ 8.41 (d, 1H), 8.32 (d, 1H), 8.25 (d, 1H), 8.0 (dd, 1H), 7.64 (m, 2H), 7.46 (m, 1H), 7.33 (t, 1H), 7.28 (m, 2H), 6.26 (d, 1H), 4.06 (t, 2H), 3.38 (t, 2H); $^{19}$F NMR (376 MHz, CDCl$_3$/CD$_3$OD) δ −112.4, −127.5.

Example 53

N-(3-fluoro-4-(3-(3-(methylcarbamoyl)phenyl)-1H-pyrazolo[3,4-b]pyridin-4-yloxy)phenyl)-N-(4-fluorophenyl)cyclopropane-1,1-dicarboxamide

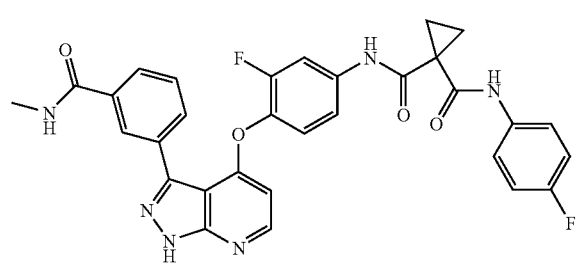

Step A: Preparation of N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide: A stirred mixture of N-(3-fluoro-4-(3-iodo-1-(4-methoxybenzyl)-1H-pyrazolo[3,4-b]pyridin-4-yloxy)phenyl)-N-(4-fluorophenyl)cyclopropane-1,1-dicarboxamide (100 mg, 0.144 mmol; prepared as in Example 7, Step C), 3-(N-methylaminocarbonyl)phenyl boronic acid (51.47 mg, 0.288 mmol), Pd(PPh$_3$)$_4$ (8.31 mg, 0.0072 mmol) dissolved in 3:1 DME:aqueous 2N Na$_2$CO$_3$ (8 mL) was heated at 70° C. Reaction was monitored by TLC (90/10 CHCl$_3$/MeOH). After stirring for 6 hours, the reaction mixture was partitioned between ethyl acetate (25 mL) and water (50 mL). The organic layer washed with brine, dried over sodium sulfate, filtered and evaporated to afford crude product. The crude was purified by silica gel column chromatography (Biotage 12M) eluting with 2% MeOH/DCM to give the product as pale orange glass (36 mg, 35%). LRMS (APCI pos) m/e 703.2 (M+H).

Step B: Preparation of N-(3-fluoro-4-(3-(3-(methylcarbamoyl)phenyl)-1H-pyrazolo[3,4-b]pyridin-4-yloxy)phenyl)-N-(4-fluorophenyl)cyclopropane-1,1-dicarboxamide: A stirred mixture of N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide (35 mg, 0.050 mmol) and TFA (0.5 mL) was heated to 70° C. for 3 hours, or until reaction was complete as determined by LC/MS. The mixture was concentrated in vacuo, using toluene (2×5 mL) to azeotrope residual TFA. The crude was purified by silica gel column chromatography (Biotage 12M) eluting with 1-10% MeOH/CHCl$_3$ to give the desired product as off-white solid (19 mg, 55%). $^1$H NMR (400 MHz, DMSO-d6) δ 14.03 (s, 1H), 10.39 (s, 1H), 10.00 (s, 1H), 8.49 (s, 2H), 8.38 (d, 1H), 8.12 (d, 1H), 7.87 (m, 2H), 7.64 (m, 2H), 7.55 (t, 1H), 7.47 (m, 2H), 7.15 (t, 2H), 6.32 (d, 1H), 2.78 (d, 3H), 1.47 (d, 4H). LRMS (APCI pos) m/e 583.1 (M+H).

Example 54

N-(4-(3-(4-carbamoylphenyl)-1H-pyrazolo[3,4-b]pyridin-4-yloxy)-3-fluorophenyl)-N-(4-fluorophenyl)cyclopropane-1,1-dicarboxamide

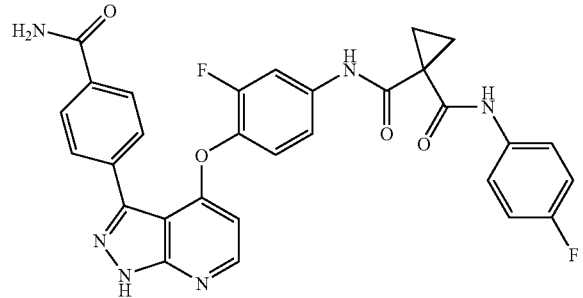

Step A: Preparation of N-(4-(3-(4-carbamoylphenyl)-1-(4-methoxybenzyl)-1H-pyrazolo[3,4-b]pyridin-4-yloxy)-3-fluorophenyl)-N-(4-fluorophenyl)cyclopropane-1,1-dicarboxamide: Prepared according to the procedure of Example 53, Step A, substituting benzamide-4-boronic acid (47.4 mg, 0.288 mmol) for 3-(N-methylaminocarbonyl)phenyl boronic acid. Yield: 12 mg, 12%. LRMS (APCI pos) m/e 689.1 (M+H).

Step B: Preparation of N-(4-(3-(4-carbamoylphenyl)-1H-pyrazolo[3,4-b]pyridin-4-yloxy)-3-fluorophenyl)-N-(4-fluorophenyl)cyclopropane-1,1-dicarboxamide: Prepared according to the procedure of Example 53, Step B, substituting N-(4-(3-(4-carbamoylphenyl)-1-(4-methoxybenzyl)-1H-pyrazolo[3,4-b]pyridin-4-yloxy)-3-fluorophenyl)-N-(4-fluorophenyl)cyclopropane-1,1-dicarboxamide (12 mg, 0.017 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. Yield: 5.2 mg, 53%. LRMS (APCI pos) m/e 569.1 (M+H).

Example 55

N-(3-fluoro-4-(3-(4-(morpholine-4-carbonyl)phenyl)-1H-pyrazolo[3,4-b]pyridin-4-yloxy)phenyl)-N-(4-fluorophenyl)cyclopropane-1,1-dicarboxamide

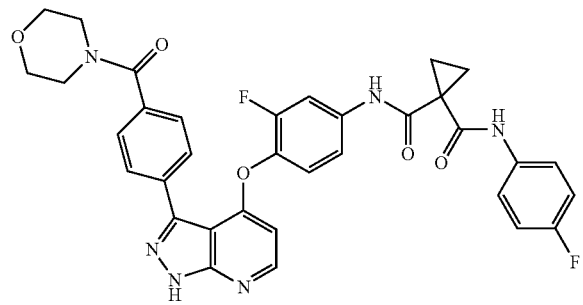

Step A: Preparation of N-(3-fluoro-4-(1-(4-methoxybenzyl)-3-(4-(morpholine-4-carbonyl)phenyl)-1H-pyrazolo[3,4-b]pyridin-4-yloxy)phenyl)-N-(4-fluorophenyl)cyclopropane-1,1-dicarboxamide: Prepared according to the procedure of Example 53, Step A, substituting 4-(morpholine-4-carbonyl)phenyl boronic acid (67.6 mg, 0.288 mmol) for 3-(N-methylaminocarbonyl)phenyl boronic acid. Yield: 62 mg at 75% purity, 43%. The crude material used as directly in the next step without further purification. LRMS (APCI pos) m/e 759.1 (M+H).

Step B: Preparation of N-(3-fluoro-4-(3-(4-(morpholine-4-carbonyl)phenyl)-1H-pyrazolo[3,4-b]pyridin-4-yloxy)phenyl)-N-(4-fluorophenyl)cyclopropane-1,1-dicarboxamide: Prepared according to the procedure of Example 53, Step B, substituting N-(3-fluoro-4-(1-(4-methoxybenzyl)-3-(4-(morpholine-4-carbonyl)phenyl)-1H-pyrazolo[3,4-b]pyridin-4-yloxy)phenyl)-N-(4-fluorophenyl)cyclopropane-1,1-dicarboxamide (62 mg, 0.0817 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. Yield: 31 mg, 50%. $^1$H NMR (400 MHz, DMSO-d6) δ 14.05 (s, 1H), 10.39 (s, 1H), 10.0 (s, 1H), 8.38 (d, 1H), 8.07 (d, 2H), 7.89 (broad d, 1H), 7.64 (q, 2H), 7.51 (d, 2H), 7.47 (m, 2H), 7.15 (t, 2H), 6.34 (d, 1H), 3.61 (broad d, 8H), 1.47 (d, 4H). LRMS (APCI pos) m/e 639.1 (M+H).

Example 56

N-(3-fluoro-4-(3-(4-(methoxy(methyl)carbamoyl)phenyl)-1H-pyrazolo[3,4-b]pyridin-4-yloxy)phenyl)-N-(4-fluorophenyl)cyclopropane-1,1-dicarboxaide

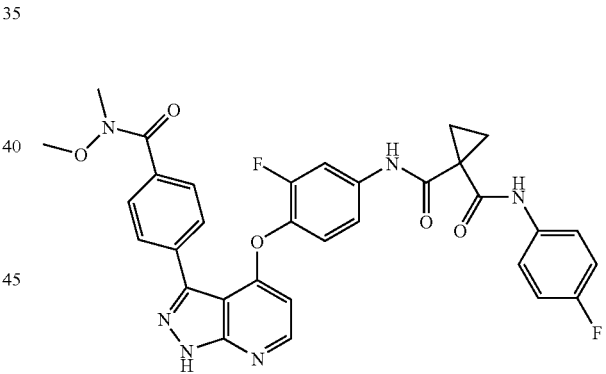

Step A: Preparation of N-(3-fluoro-4-(3-(4-(methoxy(methyl)carbamoyl)phenyl)-1-(4-methoxybenzyl)-1H-pyrazolo[3,4-b]pyridin-4-yloxy)phenyl)-N-(4-fluorophenyl)cyclopropane-1,1-dicarboxamide: Prepared according to the procedure of Example 53, Step A, substituting 4-(N,O-dimethylhydroxylaminocarbonyl)phenyl boronic acid (60.1 mg, 0.288 mmol) for 3-(N-methylaminocarbonyl)phenyl boronic acid. Yield: 59 mg, 56%. LRMS (APCI pos) m/e 733.0 (M+H).

Step B: Preparation of N-(3-fluoro-4-(3-(4-(methoxy(methyl)carbamoyl)phenyl)-1H-pyrazolo[3,4-b]pyridin-4-yloxy)phenyl)-N-(4-fluorophenyl)cyclopropane-1,1-dicarboxamide: Prepared according to the procedure of Example 53, Step B, substituting N-(3-fluoro-4-(3-(4-(methoxy(methyl)carbamoyl)phenyl)-1-(4-methoxybenzyl)-1H-pyrazolo

[3,4-b]pyridine-4-yloxy)phenyl)-N-(4-fluorophenyl)cyclopropane-1,1-dicarboxamide (59 mg, 0.0805 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. Yield: 15.2 mg, 26%. ¹H NMR (400 MHz, DMSO-d6) δ 14.05 (s, 1H), 10.39 (s, 1H), 10 (s, 1H), 8.38 (d, 1H), 8.07 (d, 2H), 7.90 (broad d, 1H), 7.69 (d, 2H), 7.64 (q, 2H), 7.50 (m, 2H), 7.15 (t, 2H), 6.34 (d, 1H), 3.58 (s, 3H), 3.27 (s, 3H), 1.47 (d, 4H). LRMS (APCI pos) m/e 613.1 (M+H).

Example 57

N-(4-(3-(4-((1H-pyrazol-1-yl)methyl)phenyl)-1H-pyrazolo[3,4-b]pyridin-4-yloxy)-3-fluorophenyl)-N-(4-fluorophenyl)cyclopropane-1,1-dicarboxamide

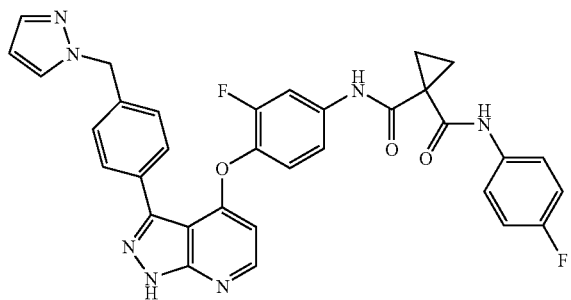

Step A: Preparation of N-(4-(3-(4-((1H-pyrazol-1-yl)methyl)phenyl)-1-(4-methoxybenzyl)-1H-pyrazolo[3,4-b]pyridin-4-yloxy)-3-fluorophenyl)-N-(4-fluorophenyl)cyclopropane-1,1-dicarboxamide: Prepared according to the procedure of Example 53, Step A, substituting 1H-pyrazole-1-benzyl-4-boronic acid (58.1 mg, 0.288 mmol) for 3-(N-methylaminocarbonyl)phenyl boronic acid. Yield: 52 mg, 47%. LRMS (APCI pos) m/e 726.2 (M+H).

Step B: Preparation of N-(4-(3-(4-((1H-pyrazol-1-yl)methyl)phenyl)-1H-pyrazolo[3,4-b]pyridin-4-yloxy)-3-fluorophenyl)-N-(4-fluorophenyl)cyclopropane-1,1-dicarboxamide: Prepared according to the procedure of Example 53, Step B, substituting N-(4-(3-(4-((1H-pyrazol-1-yl)methyl)phenyl)-1-(4-methoxybenzyl)-1H-pyrazolo[3,4-b]pyridin-4-yloxy)-3-fluorophenyl)-N-(4-fluorophenyl)cyclopropane-1,1-dicarboxamide (51.7 mg, 0.0712 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. Yield: 12 mg, 23%. ¹H NMR (400 MHz, CDCl₃) δ 8.37 (d, 1H), 8.21 (s, 1H), 8.12 (s, 1H), 7.86 (m, 1H), 7.56 (m, 2H), 7.44 (m, 1H), 7.33 (t, 1H), 7.07 (t, 2H), 6.40 (s, 1H), 5.38 (s, 2H), 1.65 (d, 4H). LRMS (APCI pos) m/e 606.2 (M+H).

Example 58

N-(4-fluorophenyl)-N-(6-(3-methyl-1H-pyrazolo[3,4-b]pyridin-4-yloxy)benzo[d]thiazol-2-yl)cyclopropane-1,1-dicarboxamide

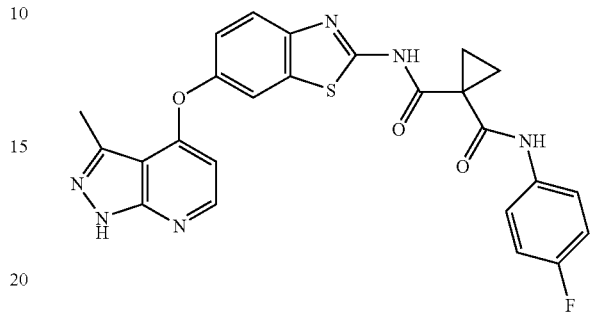

Step A: Preparation of 6-(3-methyl-1H-pyrazolo[3,4-b]pyridin-4-yloxy)benzo[d]thiazol-2-amine: A 20 mL sealable tube was charged with 1-(4-methoxybenzyl)-4-chloro-3-methyl-1H-pyrazolo[3,4-b]pyridine (0.500 g, 1.74 mmol; prepared according to the procedure of Example 43, Step E), 2-aminobenzo[d]thiazol-6-ol (0.433 g, 2.61 mmol), N,N-dimethylpyridin-4-amine (0.0425 g, 0.348 mmol), and bromobenzene (4 mL). The reaction mixture was heated under nitrogen to 150° C. for 12 hours, then cooled to room temperature and concentrated under reduced pressure. The crude material was used directly in next step. LRMS (APCI pos) m/e 418.2 (M+1).

Step B: Preparation of N-(4-fluorophenyl)-N-(6-(3-methyl-1H-pyrazolo[3,4-b]pyridin-4-yloxy)benzo[d]thiazol-2-yl)cyclopropane-1,1-dicarboxamide: Prepared by 2-step process (Example 6, Steps B and C) from 6-(1-(4-methoxybenzyl)-3-methyl-1H-pyrazolo[3,4-b]pyridin-4-yloxy)benzo[d]thiazol-2-amine (0.700 g, 1.68 mmol), and 1-((4-fluorophenyl)carbamoyl)cyclopropanecarbonyl fluoride (0.415 g, 1.84 mmol; obtained from Example 6, Step A). The crude material was purified by preparative TLC (0.5 mm thickness, EtOAc) to afford 2 mg (1% for 2-step process) of the desired product. LRMS (ESI pos) m/e 503.2 (M+1).

Example 59

N-(2,5-dimethyl-4-(3-methyl-1H-pyrazolo[3,4-b]pyridin-4-yloxy)phenyl)-N-(4-fluorophenyl)cyclopropane-1,1-dicarboxamide

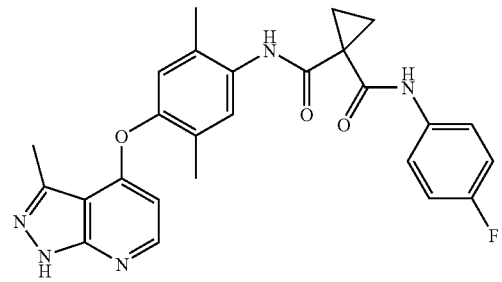

Step A: Preparation of 2,5-dimethyl-4-(3-methyl-1H-pyrazolo[3,4-b]pyridin-4-yloxy)aniline: Prepared according to the procedure for Example 58 step A, substituting, 4-amino-2,5-dimethylphenol (0.358 g, 2.61 mmol), for 2-aminobenzo[d]thiazol-6-ol. The crude material was used directly in next step. LRMS (APCI pos) m/e 389.2 (M+1).

Step B: Preparation of N-(2,5-dimethyl-4-(3-methyl-1H-pyrazolo[3,4-b]pyridin-4-yloxy)phenyl)-N-(4-fluorophenyl)cyclopropane-1,1-dicarboxamide: Prepared by 2-step process (Example 6, Steps B and C) from 4-(1-(4-methoxybenzyl)-3-methyl-1H-pyrazolo[3,4-b]pyridin-4-yloxy)-2,5-dimethylbenzenamine (0.675 g, 1.74 mmol) and 1-((4-fluorophenyl)carbamoyl)cyclopropanecarbonyl fluoride (0.391 g, 1.74 mmol; obtained from Example 6, Step A). The crude material was purified by preparative TLC (2.0 mm thickness, EtOAc/Hexane 4:1) to afford 5.3 mg (1% for 2-step process) of the desired product. LRMS M+1 (474.3) observed. $^1$H NMR (400 MHz, DMSO-d6) δ 8.10 (d, J=5 Hz, 1H), 7.49 (m, 3H), 6.98 (m, 3H), 6.07 (d, J=5 Hz, 1H), 2.63 (s, 3H), 2.19 (s, 3H), 2.05 (s, 3H), 1.60 (m, 4H).

Example 60

N-(4-fluorophenyl)-N-(2-methyl-4-(3-methyl-1H-pyrazolo[3,4-b]pyridin-4-yloxy)phenyl)cyclopropane-1,1-dicarboxamide

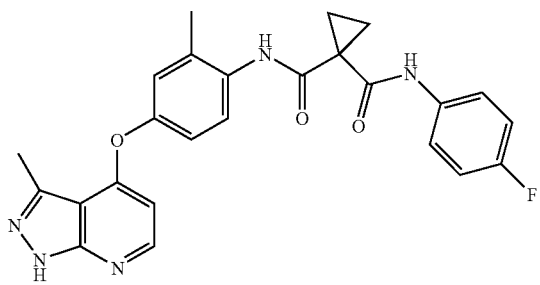

Step A: Preparation of 2-methyl-4-(3-methyl-1H-pyrazolo[3,4-b]pyridin-4-yloxy)aniline: Prepared according to the procedure for Example 58 step A, substituting, 4-amino-3-methylphenol (0.321 g, 2.61 mmol) for 2-aminobenzo[d]thiazol-6-ol. The crude material was used directly in next step. LRMS (APCI pos) m/e 375.2 (M+1).

Step B: Preparation of N-(4-fluorophenyl)-N-(2-methyl-4-(3-methyl-1H-pyrazolo[3,4-b]pyridin-4-yloxy)phenyl)cyclopropane-1,1-dicarboxamide: Prepared by 2-step process (Example 6, Steps B and C) from 4-(1-(4-methoxybenzyl)-3-methyl-1H-pyrazolo[3,4-b]pyridin-4-yloxy)-2-methylbenzenamine (0.650 g, 1.74 mmol), and 1-((4-fluorophenyl)carbamoyl)cyclopropanecarbonyl fluoride (0.391 g, 1.74 mmol; obtained from Example 6, Step A). The crude material was purified by preparative TLC (2.0 mm thickness, EtOAc/Hexane 4:1) to afford 11.1 mg (1% for 2-step process) of the desired product. LRMS M+1 (460.3) observed. $^1$H NMR (400 MHz, DMSO-d6) δ 8.11 (d, J=5.5 Hz, 1H), 7.59 (d, J=8.6 Hz, 1H), 7.44 (m, 2H), 7.03 (m, 1H), 6.96 (m, 3H), 6.19 (d, J=5.5 Hz, 1H), 2.58 (s, 3H), 2.23 (s, 3H), 1.62 (m, 4H).

Example 61

N-(4-(3-(4-(cyclopropylcarbamoyl)phenyl)-1H-pyrazolo[3,4-b]pyridin-4-yloxy)-3-fluorophenyl)-N-(4-fluorophenyl)cyclopropane-1,1-dicarboxamide

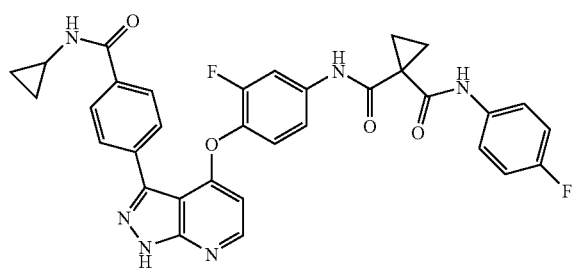

Step A: Preparation of N-(4-(3-(4-(cyclopropylcarbamoyl)phenyl)-1-(4-methoxybenzyl)-1H-pyrazolo[3,4-b]pyridin-4-yloxy)-3-fluorophenyl)-N-(4-fluorophenyl)cyclopropane-1,1-dicarboxamide: Prepared according to the procedure of Example 53, Step A, substituting 4-cyclopropylaminocarbonylphenylboronic acid (59.0 mg, 0.288 mmol) for 3-(N-methylaminocarbonyl)phenyl boronic acid. Yield: 37.6 mg at 80% purity, 29%. LRMS (APCI pos) m/e 729.0 (M+H).

Step B: Preparation of N-(4-(3-(4-(cyclopropylcarbamoyl)phenyl)-1H-pyrazolo[3,4-b]pyridin-4-yloxy)-3-fluorophenyl)-N-(4-fluorophenyl)cyclopropane-1,1-dicarboxamide: Prepared according to the procedure of Example 53, Step B, substituting N-(4-(3-(4-(cyclopropylcarbamoyl)phenyl)-1-(4-methoxybenzyl)-1H-pyrazolo[3,4-b]pyridin-4-yloxy)-3-fluorophenyl)-N-(4-fluorophenyl)cyclopropane-1,1-dicarboxamide (37 mg, 0.0508 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. Yield: 11 mg, 30%. $^1$H NMR (400 MHz, DMSO-d6) δ 10.46 (s, 1H), 9.97 (s, 1H), 8.56 (d, 1H), 8.35 (d, 2H), 8.08 (d, 2H), 7.87 (d, 1H), 7.83 (m, 1H), 7.55 (m, 2H), 7.40 (broad d, 1H), 7.30 (t, 1H), 7.06 (t, 2H), 6.39 (d, 1H), 1.63 (s, 4H), 0.80 (m, 2H), 0.64 (m, 2H). LRMS (APCI pos) m/e 609.1 (M+H).

Example 62

N-(2-fluoro-4-(3-methyl-1H-pyrazolo[3,4-b]pyridin-4-yloxy)phenyl)-N-(4-fluorophenyl)cyclopropane-1,1-dicarboxamide

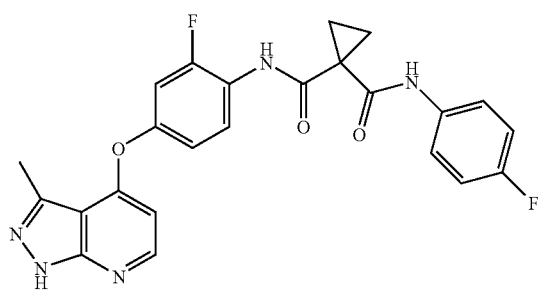

Step A: Preparation of 2-fluoro-4-(3-methyl-1H-pyrazolo[3,4-b]pyridin-4-yloxy)aniline: Prepared according to the procedure for Example 58 step A, substituting 4-amino-3-fluorophenol (0.331 g, 2.61 mmol) for 2-aminobenzo[d]thiazol-6-ol. The crude material was used directly in next step. LRMS (APCI pos) m/e 379.1 (M+1).

Step B: Preparation of N-(2-fluoro-4-(3-methyl-1H-pyrazolo[3,4-b]pyridin-4-yloxy)phenyl)-N-(4-fluorophenyl)cyclopropane-1,1-dicarboxamide: Prepared by 2-step process (Example 6, Steps B and C) from 4-(1-(4-methoxybenzyl)-3-methyl-1H-pyrazolo[3,4-b]pyridin-4-yloxy)-2-fluorobenzenamine (0.250 g, 0.661 mmol) and 1-((4-fluorophenyl)carbamoyl)cyclopropanecarbonyl fluoride (0.164 g, 0.727 mmol; obtained from Example 6, Step A). The crude material was purified by preparative TLC (1.0 mm thickness, EtOAc/Hexane 4:1) to afford 1.7 mg (0.5% for 2-step process) of the desired product. LRMS M+1 (464.2) observed. $^1$H NMR (400 MHz, CDCl$_3$) δ 10.13 (s, 1H), 8.45 (t, J=9 Hz, 1H), 8.19 (d, J=6 Hz, 2H), 7.47 (m, 2H), 7.07 (t, J=8 Hz, 3H), 6.47 (d, J=6 Hz, 1H), 5.20 (br s, 2H), 2.90 (s, 3H), 1.83 (m, 2H), 1.68 (m, 2H). $^{19}$F NMR (376 MHz, CDCl$_3$) δ −76.5 (3F), −116.8 (1F), −123.8 (1F).

Example 63

N-(3-fluoro-4-(3-(4-(morpholine-4-carbonyl)phenyl)-1H-pyrazolo[3,4-b]pyridin-4-yloxy)phenyl)-2-(4-fluorophenyl)-3-oxo-2,3-dihydropyridazine-4-carboxamide

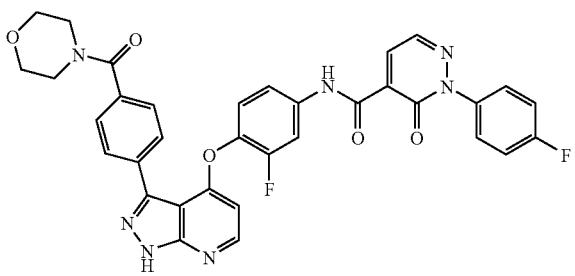

Step A: Preparation of N-(3-fluoro-4-(3-iodo-1-(4-methoxybenzyl)-1H-pyrazolo[3,4-b]pyridin-4-yloxy)phenyl)-2-(4-fluorophenyl)-3-oxo-2,3-dihydropyridazine-4-carboxamide: To a mixture of 4-(1-(4-methoxybenzyl)-3-iodo-1H-pyrazolo[3,4-b]pyridin-4-yloxy)-3-fluorobenzenamine (1.50 g, 3.06 mmol; prepared as in Example 7, Step B), 2-(4-fluorophenyl)-3-oxo-2,3-dihydropyridazine-4-carboxylic acid (1.43 g, 6.12 mmol; prepared as in Example 19, Step C), and HOBT-H$_2$O (2.81 g, 18.4 mmol) dissolved in dry DMF (30 mL) was added EDCI (3.52 g, 18.4 mmol). The mixture was stirred at room temperature for 3 hours. The reaction mixture was then partitioned between ethyl acetate (60 mL) and aqueous NH$_4$Cl (100 mL). The organic layer was separated, washed with saturated NaHCO$_3$, dried over NaSO$_4$, and evaporated to dryness. The crude material was triturated with MeOH and the solid removed by filtration, dried to afford the title compound as yellow solid. Yield: 1.93 g, 89%. LRMS (APCI pos) m/e 707.0 (M+H).

Step B: Preparation of N-(3-fluoro-4-(1-(4-methoxybenzyl)-3-(4-(morpholine-4-carbonyl)phenyl)-1H-pyrazolo[3,4-b]pyridin-4-yloxy)phenyl)-2-(4-fluorophenyl)-3-oxo-2,3-dihydropyridazine-4-carboxamide: To a small round bottom flask was added N-(3-fluoro-4-(3-iodo-1-(4-methoxybenzyl)-1H-pyrazolo[3,4-b]pyridin-4-yloxy)phenyl)-2-(4-fluorophenyl)-3-oxo-2,3-dihydropyridazine-4-carboxamide (30 mg, 0.0425 mmol), 4-(morpholine-4-carbonyl)phenylboronic acid (20.0 mg, 0.0849 mmol), and Pd(PPh$_3$)$_4$ (2.45 mg, 0.00212 mmol) and the mixture was dissolved in 3:1 DME: aqueous 2N Na$_2$CO$_3$ (2 mL). The mixture was stirred at 70° C. until the reaction was determined to be complete by LC/MS (1-18 hours). The reaction mixture was then partitioned between ethyl acetate (15 mL) and water (30 mL). The organic layer washed with brine, dried over Na$_2$SO$_4$ and evaporated to afford crude product. Purified by silica gel column chromatography (Biotage 12M) eluting with 1-5% MeOH/CHCl$_3$ to give the desired product. Yield: 40.2 mg, 81%. LRMS (APCI pos) m/e 770.1 (M+H).

Step C: Preparation of N-(3-fluoro-4-(3-(4-(morpholine-4-carbonyl)phenyl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting N-(3-fluoro-4-(1-(4-methoxybenzyl)-3-(4-(morpholine-4-carbonyl)phenyl)-1H-pyrazolo[3,4-b]pyridin-4-yloxy)phenyl)-2-(4-fluorophenyl)-3-oxo-2,3-dihydropyridazine-4-carboxamide (40 mg, 0.0520 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. Purified by silica gel column chromatography (Biotage 12M) eluting with 1-2% MeOH/CHCl$_3$ to give the desired product as yellow solid (16.2 mg, 48%). $^1$H NMR (400 MHz, DMSO-d6) δ 11.71 (s, 1H), 8.39 (t, 2H), 8.27 (d, 1H), 8.07 (d, 2H), 8.03 (s, 1H), 7.69 (m, 2H), 7.58 (m, 2H), 7.53 (t, 2H), 7.41 (t, 2H), 6.40 (d, 1H), 3.61 (broad s, 8H). LRMS (APCI pos) m/e 650.1 (M+H).

Example 64

N-(3-fluoro-4-(3-phenyl-1H-pyrazolo[3,4-b]pyridin-4-yloxy)phenyl)-N-(4-fluorophenyl)cyclopropane-1,1-dicarboxamide

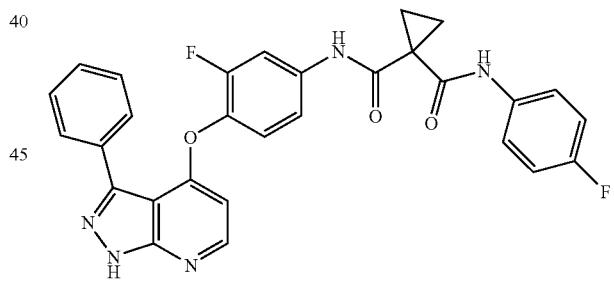

Step A: Preparation of N-(3-fluoro-4-(1-(4-methoxybenzyl)-3-phenyl-1H-pyrazolo[3,4-b]pyridin-4-yloxy)phenyl)-N-(4-fluorophenyl)cyclopropane-1,1-dicarboxamide: Prepared according to the procedure of Example 53, Step A, substituting phenylboronic acid (35 mg, 0.28 mmol) for 3-(N-methylaminocarbonyl)phenyl boronic acid. Purified by silica gel column chromatography (Biotage 12M) eluting with 50:50 hexanes:ethyl acetate. Yield: 32 mg, 35%. LRMS (APCI pos) m/e 646.2 (M+H).

Step B: Preparation of N-(3-fluoro-4-(3-phenyl-1H-pyrazolo[3,4-b]pyridin-4-yloxy)phenyl)-N-(4-fluorophenyl)cyclopropane-1,1-dicarboxamide: Prepared according to the procedure of Example 53, Step B, substituting N-(3-fluoro-4-(1-(4-methoxybenzyl)-3-phenyl-1H-pyrazolo[3,4-b]pyridin-4-yloxy)phenyl)-N-(4-fluorophenyl)cyclopropane-1,1-dicarboxamide (32 mg, 0.049 mmol) for N-(3-fluoro-4-(1-(4- methoxybenzyl)-3-(3-(methylcarbamoyl)phenyl)-1H-pyrazolo[3,4-b]pyridin-4-yloxy)phenyl)-N-(4-fluorophenyl) cyclopropane-1,1-dicarboxamide. Purified by trituration of crude with 1:1 ether:hexanes to afford the desired product as the TFA salt. Yield: 19 mg, 61%. ¹H NMR (400 MHz, DMSO-d6) δ 13.96 (s, 1H), 10.39 (s, 1H), 10 (s, 1H), 8.36 (d, 1H), 7.98 (d, 2H), 7.89 (d, 2H), 7.64 (d, 1H), 7.48 (m, 2H), 7.39 (t, 2H), 7.15 (t, 2H), 6.31 (d, 1H), 5.75 (s, 1H) 1.47 (d, 4H). LRMS (APCI pos) m/e 526.2 (M+H).

Example 65

4-(4-(2-fluoro-4-(1-(4-fluorophenylcarbamoyl)cyclopropanecarboxamido)phenoxy)-1H-pyrazolo[3,4-b]pyridin-3-yl)benzoic acid

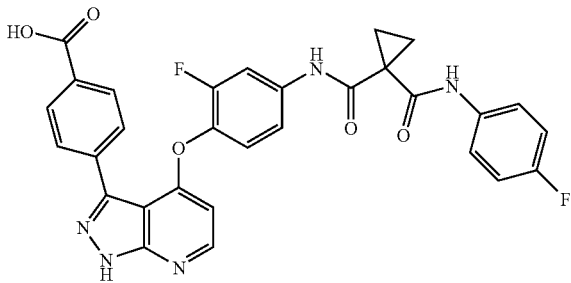

Step A: Preparation of methyl 4-(4-(2-fluoro-4-(1-(4-fluorophenyl carbamoyl)cyclopropanecarboxamido)phenoxy)-1-(4-methoxybenzyl)-1H-pyrazolo[3,4-b]pyridin-3-yl)benzoate: Prepared according to the procedure of Example 53, Step A, substituting 4-methoxycarbonylphenylboronic acid (207 mg, 1.15 mmol) for 3-(N-methylaminocarbonyl)phenyl boronic acid. The crude material was purified by silica gel column chromatography (Biotage 12M) eluting with 50:50 hexanes:ethyl acetate. Yield: 223 mg at 92% purity, 50%. LRMS (APCI pos) m/e 704.1 (M+H).

Step B: Preparation of 4-(4-(2-fluoro-4-(1-(4-fluorophenylcarbamoyl)cyclopropanecarboxamido)phenoxy)-1-(4-methoxybenzyl)-1H-pyrazolo[3,4-b]pyridin-3-yl)benzoic acid: Dissolved methyl 4-(4-(2-fluoro-4-(1-(4-fluorophenyl carbamoyl)cyclopropanecarboxamido)phenoxy)-1-(4-methoxybenzyl)-1H-pyrazolo[3,4-b]pyridin-3-yl)benzoate (230 mg, 0.327 mmol) in MeOH (5 mL) and added 10% aqueous solution of NaOH (0.65 ml, 1.63 mmol). The mixture was stirred at room temperature for 4 hours. The solvent was evaporated to a minimal volume and the crude was partitioned between ethyl acetate (50 mL) and water (50 mL). The organic layer washed with brine, dried over Na₂SO₄ and evaporated to afford the desired product as white solid (191 mg at 90% purity, 76%) LRMS (APCI pos) m/e 690.2 (M+H).

Step C: Preparation of 4-(4-(2-fluoro-4-(1-(4-fluorophenylcarbamoyl)cyclopropanecarboxamido)phenoxy)-1H-pyrazolo[3,4-b]pyridin-3-yl)benzoic acid: Prepared according to the procedure of Example 53, Step B, substituting 4-(4-(2-fluoro-4-(1-(4-fluorophenylcarbamoyl)cyclopropanecarboxamido)phenoxy)-1-(4-methoxybenzyl)-1H-pyrazolo[3,4-b]pyridin-3-yl)benzoic acid (20 mg, 0.029 mmol) for N-(3-fluoro-4-(1-(4-methoxybenzyl)-1H-pyrazolo[3,4-b]pyridin-4-yloxy)phenyl)-N-(4-fluorophenyl)cyclopropane-1,1-dicarboxamide. The crude material was purified by trituration of crude with 1:1 ether:hexanes to afford desired product as TFA salt. Yield: 9.2 mg, 46%. ¹H NMR (400 MHz, DMSO-d6) δ 10.39 (s, 1H), 10.01 (s, 1H), 8.39 (d, 1H), 8.12 (d, 2H), 8.02 (d, 2H), 7.92 (s, 1H), 7.64 (m, 2H), 7.50 (m, 2H), 7.15 (t, 2H), 6.35 (d, 1H), 1.47 (d, 4H). LRMS (APCI pos) m/e 570.2 (M+H).

Example 66

N-(3-fluoro-4-(3-(5-((4-methylpiperazin-1-yl)methyl)furan-3-yl)-1H-pyrazolo[3,4-b]pyridin-4-yloxy)phenyl)-N-(4-fluorophenyl)cyclopropane-1,1-dicarboxamide Step A: Preparation of 1-((4-bromofuran-2-yl)methyl)-4-methylpiperazine: To a stirred mixture of 4-bromofuran-2-carbaldehyde (2.10 g, 12.0 mmol) and THF (10 mL) that was cooled in an ice bath was added 1-methylpiperazine (1.60 ml, 14.4 mmol) dropwise, followed by sodium triacetoxyborohydride (3.81 g, 18.0 mmol) in 3 portions as solid. Acetic acid (0.343 ml, 6.00 mmol) was added, and the reaction was stirred for 18 hours at ambient temperature. The dark mixture was diluted with water (10 mL) and basified to pH>12 by addition of 5N NaOH. The mixture was extracted with diethyl ether (3×50 mL). The combined organic phases were dried (Na₂SO₄), filtered, and concentrated in vacuo. The resulting black oil (2.10 g, 66%) was carried forward without purification.

Step B: Preparation of 1-methyl-4-((4-(tributylstannyl)furan-2-yl)methyl)piperazine: A stirred mixture of 1-((4-bromofuran-2-yl)methyl)-4-methylpiperazine (2.10 g, 8.10 mmol) and THF (50 mL) was cooled to −78° C. in a dry ice/acetone bath. tert-Butyllithium (7.60 mL, 12.2 mmol; 1.6 M in pentane) was added and the reaction mixture was stirred for 30 minutes. Next, tributylchlorostannane (2.09 ml, 7.70 mmol) was added and the reaction mixture was stirred for 30 minutes. The reaction was quenched by addition of pH 7 phosphate buffer (20 mL) and warming to room temperature. The mixture was extracted with diethyl ether, dried over sodium sulfate, filtered and concentrated. The crude material was purified on a Biotage 40S column, eluting with 1:1 EtOAc/hexanes (500 mL), 2:1 EtOAc/hexanes (500 mL), then EtOAc (1 L) to provide a product mixture as a light yellow oil (0.77 g, 86:14 ratio of 1-((4-bromo-5-(tributylstannyl)furan-2-yl)methyl)-4-methylpiperazine to 1-methyl-4-((4-(tributylstannyl)furan-2-yl)methyl)piperazine by ¹H-NMR). The mixture was carried forward without separation at this step.

Step C: Preparation of N-(4-(1-(4-methoxybenzyl)-3-iodo-1H-pyrazolo[3,4-b]pyridin-4-yloxy)-3-fluorophenyl)-N-(4-fluorophenyl)cyclopropane-1,1-dicarboxamide: 4-(1-(4-Methoxybenzyl)-3-iodo-1H-pyrazolo[3,4-b]pyridin-4-yloxy)-3-fluorobenzenamine (0.490 g, 1.0 mmol, prepared according to Example 7, Step B) and acetonitrile (5 mL) were heated with 1-((4-(fluorophenyl)carbamoyl)-cyclopropanecarbonyl fluoride (0.450 g, 2.00 mmol, prepared according to Example 6, Step A) at 100° C. in a sealed vessel for 4 hours. The suspension was allowed to cool to ambient temperature,

163 and then in an ice bath for 15 minutes. The solid was filtered to provide pure desired product (0.52 g, 75%) by LRMS (APCI−): 100% purity, 220 nm, m/z 694 (M−1) detected.

Step D: Preparation of N-(4-(1-(4-methoxybenzyl)-3-(5-((4-methylpiperazin-1-yl)methyl)furan-3-yl)-1H-pyrazolo [3,4-b]pyridin-4-yloxy)-3-fluorophenyl)-N-(4-fluorophenyl)cyclopropane-1,1-dicarboxamide: A stirred mixture of N-(4-(1-(4-methoxybenzyl)-3-iodo-1H-pyrazolo[3,4-b]pyridin-4-yloxy)-3-fluorophenyl)-N-(4-fluorophenyl)cyclopropane-1,1-dicarboxamide (35 mg, 0.0503 mmol) and a 14:86 mixture of 1-methyl-4-((4-(tributylstannyl)furan-2-yl)methyl)piperazine and 1-((4-bromo-5-(tributylstannyl)furan-2-yl)methyl)-4-methylpiperazine (26.0 mg, 0.0554 mmol, prepared in Example 66, Step B) in dioxane (0.5 mL) was sparged with $N_2$ for 2 minutes. $PdCl_2(PPh_3)_2$ (2 mg, 0.003 mmol) was added, and the reaction was heated to 90° C. for 18 hours in a sealed vessel. After cooling to ambient temperature, the crude reaction mixture was loaded directly on to a preparative TLC plate (0.5 mm thickness, Rf=0.60) eluting with 90:10 $CHCl_3$/MeOH (containing 7N $NH_3$). Isolated product as an off-white solid (27 mg, 83:17 mixture of N-(4-(1-(4-methoxybenzyl)-3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)cyclopropane-1,1-dicarboxamide and N-(4-(1-(4-methoxybenzyl)-3-(5-((4-methylpiperazin-1-yl)methyl)furan-3-yl)-1H-pyrazolo[3,4-b]pyridin-4-yloxy)-3-fluorophenyl)-N-(4-fluorophenyl) cyclopropane-1,1-dicarboxamide by $^1$H-NMR). The mixture of products were carried forward without further purification.

Step E: Preparation of N-(3-fluoro-4-(3-(5-((4-methylpiperazin-1-yl)methyl)furan-3-yl)-1H-pyrazolo[3,4-b]pyridin-4-yloxy)phenyl)-N-(4-fluorophenyl)cyclopropane-1,1-dicarboxamide: A 17:83 mixture of N-(4-(1-(4-methoxybenzyl)-3-(5-((4-methylpiperazin-1-yl)methyl)furan-3-yl)-1H-pyrazolo[3,4-b]pyridin-4-yloxy)-3-fluorophenyl)-N-(4-fluorophenyl)cyclopropane-1,1-dicarboxamide and N-(4-(1-(4-methoxybenzyl)-3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)-cyclopropane-1,1-dicarboxamide (26 mg, 0.035 mmol) were heated with TFA (0.5 mL) at 80° C. for 2 hours in a sealed vessel. After cooling to ambient temperature, the mixture was concentrated in vacuo, using toluene to azeotrope. The resulting solid was portioned between EtOAc (5 mL) and 1:1 saturated aqueous $NaHCO_3$/water (5 mL). The phases were separated, and the aqueous phase was re-extracted with EtOAc. The combined organic phases were washed with brine (5 mL), dried (Na2SO4), filtered, and concentrated. The crude products were separated by preparative TLC (0.5 mm thickness; N-(4-(3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl) cyclopropane-1,1-dicarboxamide: Rf=0.33; N-(3-fluoro-4-(3-(5-((4-methylpiperazin-1-yl)methyl)furan-3-yl)-1H-pyrazolo[3,4-b]pyridin-4-yloxy)phenyl)-N-(4-fluorophenyl) cyclopropane-1,1-dicarboxamide: Rf=0.25), eluting with 10% MeOH (containing 7N NH3) in $CHCl_3$. The product, N-(3-fluoro-4-(3-(5-((4-methylpiperazin-1-yl)methyl)furan-3-yl)-1H-pyrazolo[3,4-b]pyridin-4-yloxy)phenyl)-N-(4-fluorophenyl)cyclopropane-1,1-dicarboxamide, was obtained as a white powder (1 mg, 5%). HPLC: 98% purity (254 nm); LRMS (ESI+): 100% purity, 220 nm, 628 m/z (M+1) detected; $^1$H NMR (400 MHz, $CDCl_3$) δ 10.06 (s, 1H), 8.32 (d, J=5 Hz, 1H), 8.18 (m, 2H), 7.77 (m, 1H), 7.45 (m, 2H), 7.24 (m, 1H), 7.07 (t, J=9 Hz, 2H), 6.92 (s, 1H), 6.32 (d, J=5 Hz, 1H), 3.62 (s, 2H), 2.64 (br s, 8H), 2.37 (s, 3H), 1.83 (m, 2H), 1.63 (m, 2H).

164

Example 67

N-(4-(3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)cyclopropane-1,1-dicarboxamide

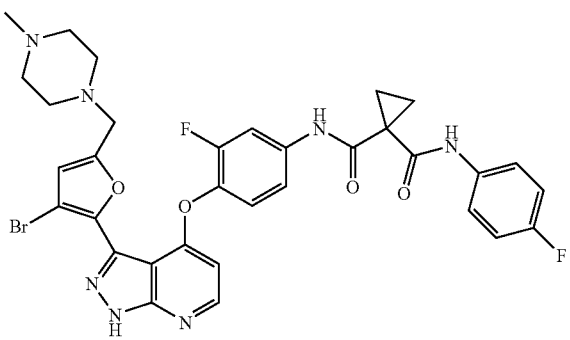

Step A: Preparation of N-(4-(1-(4-methoxybenzyl)-3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)cyclopropane-1,1-dicarboxamide: A stirred mixture of N-(4-(1-(4-methoxybenzyl)-3-iodo-1H-pyrazolo [3,4-b]pyridin-4-yloxy)-3-fluorophenyl)-N-(4-fluorophenyl)cyclopropane-1,1-dicarboxamide (35 mg, 0.0503 mmol, prepared according to Example 66, Step C) and a 14:86 mixture of 1-methyl-4-((4-(tributylstannyl)furan-2-yl)methyl)piperazine and 1-((4-bromo-5-(tributylstannyl)furan-2-yl)methyl)-4-methylpiperazine (26.0 mg, 0.0554 mmol, prepared according to Example 66, Step B) in dioxane (0.5 mL) was sparged with $N_2$ for 2 minutes, and then $PdCl_2(PPh_3)_2$ (2 mg, 0.003 mmol) was added. The reaction was heated at 90° C. for 18 hours in a sealed vessel. After cooling to ambient temperature, the crude reaction mixture was loaded directly on to a preparative TLC plate (0.5 mm thickness, Rf=0.60) eluting with 90:10 $CHCl_3$/MeOH (containing 7N $NH_3$). The product was isolated as an off-white solid (27 mg, 83:17 mixture of N-(4-(1-(4-methoxybenzyl)-3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)cyclopropane-1,1-dicarboxamide and N-(4-(1-(4-methoxybenzyl)-3-(5-((4-methylpiperazin-1-yl)methyl)furan-3-yl)-1H-pyrazolo[3,4-b]pyridin-4-yloxy)-3-fluorophenyl)-N-(4-fluorophenyl)cyclopropane-1,1-dicarboxamide). $^1$H-NMR (400 MHz, $CDCl_3$) δ 9.95 (s, 1H), 8.32 (d, J=6 Hz, 1H), 8.18 (s, 1H), 7.71 (m, 1H), 7.42 (m, 4H), 7.21 (m, 2H), 7.06 (t, J=9 Hz, 2H), 6.84 (d, J=9 Hz, 2H), 6.41 (s, 1H), 6.26 (d, J=6 Hz, 1H), 5.70 (s, 2H), 3.76 (s, 3H), 3.54 (m, 2H), 2.25-2.63 (m, 8H), 2.19 (s, 3H), 1.79 (m, 2H), 1.61 (m, 2H). The mixture of products was used directly in the next step.

Step B: Preparation of N-(4-(3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)cyclopropane-1,1-dicarboxamide: A 17:83 mixture of N-(4-(1-(4-methoxybenzyl)-3-(5-((4-methylpiperazin-1-yl)methyl)furan-3-yl)-1H-pyrazolo[3,4-b]pyridin-4-yloxy)-3-fluorophenyl)-N-(4-fluorophenyl)cyclopropane-1,1-dicarboxamide and N-(4-(1-(4-methoxybenzyl)-3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)-cyclopropane-1,1-dicarboxamide (26 mg, 0.035 mmol) were heated with TFA (0.5 mL) at 80° C. for 2 hours in a sealed vessel. After cooling to ambient temperature, the mixture was concentrated in vacuo, using toluene to azeotrope. The resulting solid was partitioned between EtOAc (5 mL) and 1:1 saturated aqueous NaHCO$_3$/water (5 mL). The phases were separated, and the aqueous phase was re-extracted with EtOAc. The combined organic phases were washed with brine, dried (Na$_2$SO$_4$), filtered, and concentrated. The crude products were separated by preparative TLC (0.5 mm thickness; N-(4-(3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)cyclopropane-1,1-dicarboxamide: Rf=0.33; N-(3-fluoro-4-(3-(5-((4-methylpiperazin-1-yl)methyl)furan-3-yl)-1H-pyrazolo[3,4-b]pyridin-4-yloxy)phenyl)-N-(4-fluorophenyl) cyclopropane-1,1-dicarboxamide: Rf=0.25), eluting with 10% MeOH (containing 7N NH$_3$) in CHCl$_3$. The product, N-(4-(3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)cyclopropane-1,1-dicarboxamide, was obtained as a white powder (8 mg, 32%). HPLC: 98% purity (254 nm); LRMS (ESI+): 100% purity, 220 nm, 708, 606 (loss of piperazine) m/z (M+1) detected; $^1$H NMR (400 MHz, CDCl$_3$+few drops CD$_3$OD) δ 8.31 (d, J=5 Hz, 1H), 7.73 (m, 1H), 7.48 (m, 2H), 7.32 (m, 1H), 7.21 (t, J=9 Hz, 1H), 7.04 (t, J=9 Hz, 2H), 6.48 (s, 1H), 6.33 (d, J=5 Hz, 1H), 3.55 (s, 2H), 2.48 (m, 8H), 2.21 (s, 3H), 1.69 (m, 4H). $^1$H NMR/$^{13}$C-NMR correlation spectroscopy was consistent with the depicted bromo-furan regioisomer.

Example 68

N-(3-fluoro-4-(3-(4-(4-methylpiperazine-1-carbonyl)phenyl)-1H-pyrazolo[3,4-b]pyridin-4-yloxy)phenyl)-N-(4-fluorophenyl)cyclopropane-1,1-dicarboxamide

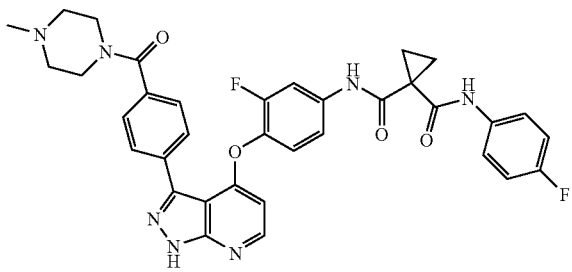

Step A: Preparation of N-(3-fluoro-4-(1-(4-methoxybenzyl)-3-(4-(4-methylpiperazine-1-carbonyl)phenyl)-1H-pyrazolo[3,4-b]pyridin-4-yloxy)phenyl)-N-(4-fluorophenyl)cyclopropane-1,1-dicarboxamide: To a mixture of 4-(4-(2-fluoro-4-(1-(4-fluorophenylcarbamoyl)cyclopropanecarboxamido)phenoxy)-1-(4-methoxybenzyl)-1H-pyrazolo[3,4-b]pyridin-3-yl)benzoic acid (20.7 mg, 0.0300 mmol; prepared in Example 66, Step B) and HOBt-H$_2$O (4.59 mg, 0.0300 mmol) in DMF (2 mL) was added EDCI (5.74 mg, 0.030 mmol) and the reaction mixture was stirred at room temperature for 30 minutes. 1-Methylpiperazine (0.0028 ml, 0.025 mmol) was added followed by TEA (0.0042 ml, 0.0300 mmol) and the mixture was stirred at room temperature under nitrogen atmosphere until all starting material was consumed as determined by LC/MS. The crude reaction mixture was partitioned between aqueous NH$_4$Cl (10 mL) and ethyl acetate (15 mL). The organic layer washed with saturated NaHCO$_3$, dried over Na$_2$SO$_4$, and evaporated to afford crude product as colorless oil. Purified by silica gel column chromatography (Biotage 12M) eluting with 4% MeOH/CHCl$_3$ to give the desired product as colorless glass (10 mg at 95% purity, 49%). LRMS (APCI pos) m/e 772.2 (M+H).

Step B: Preparation of N-(3-fluoro-4-(3-(4-(4-methylpiperazine-1-carbonyl)phenyl)-1H-pyrazolo[3,4-b]pyridin-4-yloxy)phenyl)-N-(4-fluorophenyl)cyclopropane-1,1-dicarboxamide: Prepared according to the procedure of Example 53, Step B, substituting N-(3-fluoro-4-(1-(4-methoxybenzyl)-3-(4-(4-methylpiperazine-1-carbonyl)phenyl)-1H-pyrazolo[3,4-b]pyridin-4-yloxy)phenyl)-N-(4-fluorophenyl)cyclopropane-1,1-dicarboxamide (10 mg, 0.013 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by trituration with 5% MeOH in ether to afford desired product as the di-TFA salt (7.82 mg, 68%). $^1$H NMR (400 MHz, DMSO-d6) δ 10.42 (s, 1H), 9.98 (s, 1H), 8.39 (d, 1H), 8.11 (d, 2H), 7.90 (d, 1H), 7.64 (d, 2H), 7.57 (d, 2H), 7.50 (m, 2H), 7.16 (t, 2H), 6.35 (d, 1H), 1.48 (d, 4H). LRMS (APCI pos) m/e 652.2 (M+H).

Example 69

N-(3-fluoro-4-(3-(4-(2-methoxyethylcarbamoyl)phenyl)-1H-pyrazolo[3,4-b]pyridin-4-yloxy)phenyl)-N-(4-fluorophenyl)cyclopropane-1,1-dicarboxamide

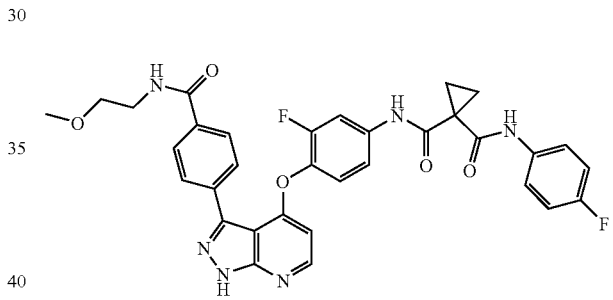

Step A: Preparation of N-(3-fluoro-4-(1-(4-methoxybenzyl)-3-(4-(2-methoxyethylcarbamoyl)phenyl)-1H-pyrazolo[3,4-b]pyridin-4-yloxy)phenyl)-N-(4-fluorophenyl)cyclopropane-1,1-dicarboxamide: Prepared according to the procedure of Example 68, Step A, substituting 2-methoxyethanamine (0.0031 ml, 0.036 mmol) for 1-methylpiperazine. The crude material was purified by silica gel column chromatography (Biotage 12M) eluting with 3% MeOH/CHCl$_3$ to afford desired product as colorless glass (21.7 mg at 90% purity, 73%). LRMS (APCI pos) m/e 747.1 (M+H).

Step B: Preparation of N-(3-fluoro-4-(3-(4-(2-methoxyethylcarbamoyl)phenyl)-1H-pyrazolo[3,4-b]pyridin-4-yloxy)phenyl)-N-(4-fluorophenyl)cyclopropane-1,1-dicarboxamide: Prepared according to the procedure of Example 53, Step B, substituting N-(3-fluoro-4-(1-(4-methoxybenzyl)-3-(4-(2-methoxyethylcarbamoyl)phenyl)-1H-pyrazolo[3,4-b]pyridin-4-yloxy)phenyl)-N-(4-fluorophenyl)cyclopropane-1,1-dicarboxamide (21.7 mg, 0.029 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 5% MeOH/CHCl$_3$ to give the desired product as white solid (9.7 mg at 95% purity, 50%). $^1$H NMR (400 MHz, DMSO-d6) δ 10.4 (s, 1H), 10 (s, 1H), 8.54 (t, 1H), 8.38 (d, 1H), 8.07 (d, 2H), 7.93 (d, 2H), 7.88 (s, 1H), 7.64 (m, 2H), 7.50 (m, 2H), 7.15 (t, 2H), 6.34 (d, 1H), 3.45 (m, 4H), 3.26 (s, 3H), 1.47 (d, 4H). LRMS (APCI pos) m/e 627.2 (M+H).

Example 70

N-(3-fluoro-4-(3-(4-(2-hydroxyethylcarbamoyl)phenyl)-1H-pyrazolo[3,4-b]pyridin-4-yloxy)phenyl)-N-(4-fluorophenyl)cyclopropane-1,1-dicarboxamide

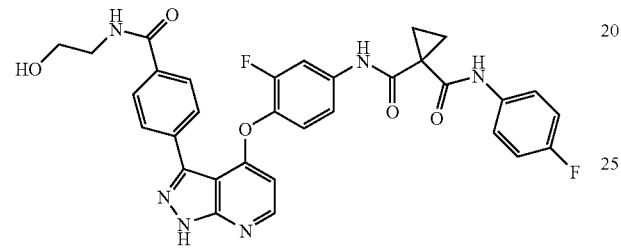

Step A: Preparation of N-(3-fluoro-4-(3-(4-(2-hydroxyethylcarbamoyl)phenyl)-1-(4-methoxybenzyl)-1H-pyrazolo[3,4-b]pyridin-4-yloxy)phenyl)-N-(4-fluorophenyl)cyclopropane-1,1-dicarboxamide: Prepared according to the procedure of Example 68, Step A, substituting 2-aminoethanol (0.0027 ml, 0.044 mmol) for 1-methylpiperazine. The crude material was purified by recrystallization from DCM/ether to afford the desired product as white solid (17.2 mg at 95% purity, 50%). LRMS (APCI pos) m/e 733.1 (M+H).

Step B: Preparation of N-(3-fluoro-4-(3-(4-(2-hydroxyethylcarbamoyl)phenyl)-1H-pyrazolo[3,4-b]pyridin-4-yloxy)phenyl)-N-(4-fluorophenyl)cyclopropane-1,1-dicarboxamide: Prepared according to the procedure of Example 53, Step B, substituting N-(3-fluoro-4-(3-(4-(2-hydroxyethylcarbamoyl)phenyl)-1-(4-methoxybenzyl)-1H-pyrazolo[3,4-b]pyridin-4-yloxy)phenyl)-N-(4-fluorophenyl)cyclopropane-1,1-dicarboxamide (17.2 mg, 0.0235 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude was dissolved in MeOH (2 mL) and added aqueous sodium bicarbonate (~1 mL). The reaction mixture was stirred for 2 hours and monitored by LC/MS. The methanol was evaporated and the remaining aqueous was partitioned between ethyl acetate and 10% $Na_2CO_3$ solution. The organic was separated, dried over $Na_2SO_4$ and evaporated to afford the title compound as white solid (12.1 mg, 84%) $^1$H NMR (400 MHz, DMSO-d6) δ 10.4 (s, 1H), 10 (s, 1H), 8.45 (t, 1H), 8.38 (d, 1H), 8.07 (d, 2H), 7.94 (d, 2H), 7.88 (s, 1H), 7.66 (s, 1H), 7.62 (m, 2H), 7.50 (m, 2H), 7.15 (t, 2H), 6.34 (d, 1H), 3.50 (m, 2H), 3.34 (m, 2H), 1.47 (d, 4H). LRMS (APCI pos) m/e 613.1 (M+H).

Example 71

N-(4-(3-(4-(2-(dimethylamino)ethylcarbamoyl)phenyl)-1H-pyrazolo[3,4-b]pyridin-4-yloxy)-3-fluorophenyl)-N-(4-fluorophenyl)cyclopropane-1,1-dicarboxamide Step A: Preparation of N-(4-(3-(4-(2-(dimethylamino)ethylcarbamoyl)phenyl)-1-(4-methoxybenzyl)-1H-pyrazolo[3,4-b]pyridin-4-yloxy)-3-fluorophenyl)-N-(4-fluorophenyl)cyclopropane-1,1-dicarboxamide: Prepared according to the procedure of Example 68, Step A, substituting N,N-dimethylethane-1,2-diamine (0.0035 ml, 0.032 mmol) for 1-methylpiperazine. The crude material was purified by silica gel column chromatography (Biotage 12M) eluting with 10% MeOH/CHCl₃ to afford the desired product as opaque semi-solid. Yield 18 mg, 75%. LRMS (APCI pos) m/e 760.2 (M+H).

Step B: Preparation of N-(4-(3-(4-(2-(dimethylamino)ethylcarbamoyl)phenyl)-1H-pyrazolo[3,4-b]pyridin-4-yloxy)-3-fluorophenyl)-N-(4-fluorophenyl)cyclopropane-1,1-dicarboxamide: Prepared according to the procedure of Example 53, Step B, substituting N-(4-(3-(4-(2-(dimethylamino)ethylcarbamoyl)phenyl)-1-(4-methoxybenzyl)-1H-pyrazolo[3,4-b]pyridin-4-yloxy)-3-fluorophenyl)-N-(4-fluorophenyl)cyclopropane-1,1-dicarboxamide (18 mg, 0.0237 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was used purified by trituration of crude with ether:hexanes to afford desired product as the di-TFA salt (14 mg, 71%). $^1$H NMR (400 MHz, DMSO-d6) δ 10.42 (s, 1H), 9.97 (s, 1H), 8.69 (t, 1H), 8.39 (d, 1H), 8.11 (d, 2H), 7.96 (d, 2H), 7.90 (d, 1H), 7.63 (m, 2H), 7.50 (m, 2H), 7.16 (t, 2H), 6.35 (d, 1H), 3.62 (m, 2H), 3.27 (m, 2H), 2.85 (s, 6H) 1.48 (d, 4H). LRMS (APCI pos) m/e 640.2 (M+H).

Example 72

N-(3-fluoro-4-(3-(4-(methylcarbamoyl)phenyl)-1H-pyrazolo[3,4-b]pyridin-4-yloxy)phenyl)-1-methyl-2-oxopyrrolidine-3-carboxamide

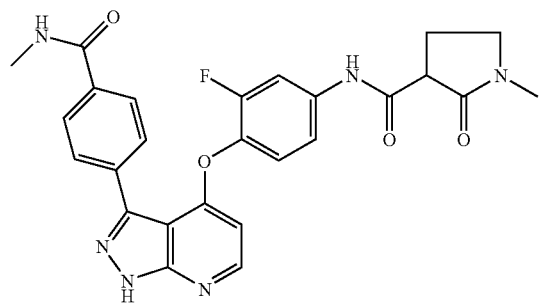

Step A: Preparation of N-(3-fluoro-4-(3-iodo-1-(4-methoxybenzyl)-1H-pyrazolo[3,4-b]pyridin-4-yloxy)phenyl)-1-methyl-2-oxopyrrolidine-3-carboxamide: A 100 mL round-bottomed flask was charged with 4-(1-(4-methoxybenzyl)-3-iodo-1H-pyrazolo[3,4-b]pyridin-4-yloxy)-3-fluorobenzenamine (300.0 mg, 0.6119 mmol), 1-methyl-2-oxopyrrolidine-3-carboxylic acid (87.59 mg, 0.6119 mmol), N1-((ethylimino)methylene)-N³,N³-dimethylpropane-1,3-diamine hydrochloride (351.9 mg, 1.836 mmol), 1H-benzo[d][1,2,3]triazol-1-ol (248.0 mg, 1.836 mmol), N-ethyl-N-isopropylpropan-2-amine (395.4 mg, 3.060 mmol) and THF (50 mL). The reaction mixture was stirred at ambient temperature overnight, and then partitioned between EtOAc and H₂O. The phases were separated, and the aqueous phase was re-extracted with EtOAc. The combined organic layers were dried (Na₂SO₄), filtered and concentrated to yield a crude product. The crude product was purified by silica gel chromatography (DCM/7 M NH₃ in MeOH from 100/1 to 10/1, v/v) to afford product (0.360 g, 95.6%). LRMS (APCI pos): m/e 616 (M+1). ¹H NMR (400 MHz, CDCl₃) δ 10.04 (s, 1H), 8.31 (d, 1H), 7.79 (dd, 1H), 7.36 (d, 2H), 7.29 (m, 1H), 7.20 (t, 1H), 6.83 (m, 2H), 6.20 (d, 1H), 5.61 (s, 2H), 3.78 (s, 3H), 3.42-3.50 (m, 3H), 2.94 (s, 3H), 2.50-2.61 (m, 1H), 2.35-2.48 (m, 1H).

Step B: Preparation of N-(3-fluoro-4-(1-(4-methoxybenzyl)-3-(4-(methylcarbamoyl)phenyl)-1H-pyrazolo[3,4-b]pyridin-4-yloxy)phenyl)-1-methyl-2-oxopyrrolidine-3-carboxamide: A 50 mL round-bottomed flask was charged with N-(4-(1-(4-methoxybenzyl)-3-iodo-1H-pyrazolo[3,4-b]pyridin-4-yloxy)-3-fluorophenyl)-1-methyl-2-oxopyrrolidine-3-carboxamide (20.0 mg, 0.0325 mmol), 4-(methylcarbamoyl)phenylboronic acid (17.5 mg, 0.0975 mmol), tetrakis(triphenylphosphine) palladium (7.51 mg, 0.00650 mmol), Na₂CO₃ (0.0812 ml, 0.162 mmol) and DME (10 mL). The reaction mixture was stirred at 60° C. for 4 hours, and then partitioned between EtOAc and H₂O. The phases were separated, and the aqueous phase was re-extracted with EtOAc. The combined organic layers were dried (Na₂SO₄), filtered and concentrated to yield a crude product. The crude product was purified by silica gel chromatography (DCM/7 M NH₃ in MeOH from 100/1 to 10/1, v/v) to afford product (10.8 mg, 53.4%). LRMS (APCI pos) m/e 623 (M+1).

Step C: Preparation of N-(3-fluoro-4-(3-(4-(methylcarbamoyl)phenyl)-1H-pyrazolo[3,4-b]pyridin-4-yloxy)phenyl)-1-methyl-2-oxopyrrolidine-3-carboxamide: A 50 mL round-bottomed flask was charged with N-(4-(1-(4-methoxybenzyl)-3-(4-(methylcarbamoyl)phenyl)-1H-pyrazolo[3,4-b]pyridin-4-yloxy)-3-fluorophenyl)-1-methyl-2-oxopyrrolidine-3-carboxamide (10.8 mg, 0.0173 mmol) and CF₃COOH (2 mL). The reaction mixture was stirred at 80° C. for 4 hours. Then the CF₃COOH was removed under reduced pressure. The residue was purified by silica gel chromatography (DCM/7 M NH₃ in MeOH from 50/1 to 10/1, v/v) to afford product (3.9 mg, 44.7%). LRMS (APCI pos): >99% purity, 254 nm, m/e 503 (M+1). ¹H NMR (400 MHz, CD₃OD) δ 8.35 (d, 1H), 8.10 (d, 2H), 7.83-7.90 (m, 3H), 7.40 (d, 1H), 7.32 (t, 1H), 6.40 (d, 1H), 3.44-3.60 (m, 3H), 2.92 (s, 3H), 2.90 (s, 3H), 2.28-2.51 (m, 2H).

Example 73

N-(3-fluoro-4-(3-(4-fluorophenyl)-1H-pyrazolo[3,4-b]pyridin-4-yloxy)phenyl)-2-(4-fluorophenyl)-3-oxo-2,3-dihydropyridazine-4-carboxamide

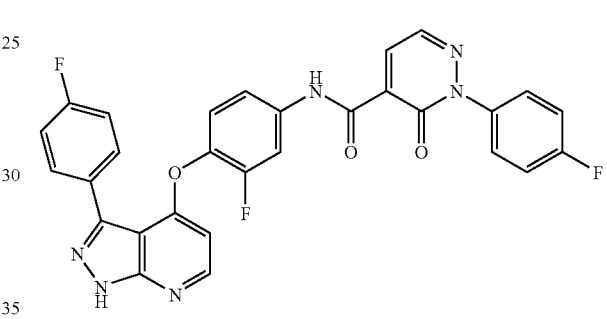

Step A: Preparation of N-(3-fluoro-4-(3-(4-fluorophenyl)-1-(4-methoxybenzyl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 63, Step B, substituting 4-fluorophenylboronic acid (11.9 mg, 0.0849 mmol) for 4-(morpholine-4-carbonyl)phenylboronic acid. The crude material was purified by silica gel column chromatography (Biotage 12M) eluting with 1.5% MeOH/CHCl₃ to afford the desired product. Yield: 34 mg at 65% purity, 77%. LRMS (APCI pos) m/e 675.3 (M+H).

Step B: Preparation of N-(3-fluoro-4-(3-(4-fluorophenyl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting N-(3-fluoro-4-(3-(4-fluorophenyl)-1-(4-methoxybenzyl)-1H-pyrazolo[3,4-b]pyridin-4-yloxy)phenyl)-2-(4-fluorophenyl)-3-oxo-2,3-dihydropyridazine-4-carboxamide (34 mg, 0.033 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 3% MeOH/CHCl₃ to afford the desired product. Yield: 10 mg, 55%. ¹H NMR (400 MHz, DMSO-d6) δ 13.97 (s, 1H), 11.71 (s, 1H), 8.38 (t, 2H), 8.27 (d, 1H), 8.06 (m, 3H), 7.70 (q, 2H), 7.67 (m, 2H), 7.42 (t, 2H), 7.31 (t, 2H), 6.36 (d, 1H). LRMS (APCI pos) m/e 555.3 (M+H).

Example 74

N-(2-chloro-5-methyl-4-(3-(4-(morpholine-4-carbonyl)phenyl)-1H-pyrazolo[3,4-b]pyridin-4-yloxy)phenyl)-2-(4-fluorophenyl)-3-oxo-2,3-dihydropyridazine-4-carboxamide

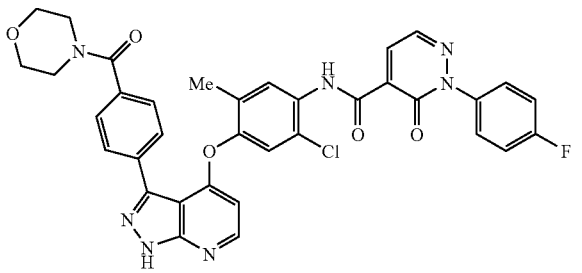

Step A: Preparation of 1-(4-methoxybenzyl)-4-(5-chloro-2-methyl-4-nitrophenoxy)-1H-pyrazolo[3,4-b]pyridine: A stirred mixture of 1-(4-methoxybenzyl)-1H-pyrazolo[3,4-b]pyridin-4-ol (255 g, 999 mmol, prepared using the procedure described in Example 1, Step B), 1-chloro-5-fluoro-4-methyl-2-nitrobenzene (94.7 g, 499 mmol), cesium carbonate (325 g, 1.0 mol) and DMF (2 L) was heated to 95° C. for 6 hours. The reaction was cooled to ambient temperature and partitioned between EtOAc and water. The phases were filtered and then separated. The aqueous phase was re-extracted with EtOAc. The combined organic phases were washed with water, brine, dried (Na$_2$SO$_4$), filtered, and concentrated in vacuo. The crude was purified by Biotage Flash 75 L chromatographic system, eluting with 5% EtOAc/hexanes (12 L), 10% EtOAc/hexanes (6 L), 20% EtOAc/hexanes (6 L), then 30% EtOAc/hexanes (6 L). The product was obtained as a viscous oil (42 g, 9%).

Step B: Preparation of 4-(5-chloro-2-methyl-4-nitrophenoxy)-1H-pyrazolo[3,4-b]pyridine: 1-(4-Methoxybenzyl)-4-(5-chloro-2-methyl-4-nitrophenoxy)-1H-pyrazolo[3,4-b]pyridine (42 g, 98.9 mmol) and 2,2,2-trifluoroacetic acid (76.2 ml, 989 mmol) were stirred at reflux for 4 h. The reaction was concentrated in vacuo, using toluene to azeotrope. The residue was diluted with EtOAc and saturated NaHCO$_3$ was added to neutralize the acid, and the resulting suspension was stirred for 20 minutes. The precipitate was filtered and washed with water to remove residual NaHCO$_3$. The solid was further dried by toluene azeotrope. The tan solid was left under high vacuum for 18 hours. The product (22 g, 70%) was carried forward without further purification.

Step C: Preparation of 4-(5-chloro-2-methyl-4-nitrophenoxy)-3-iodo-1H-pyrazolo[3,4-b]pyridine: To a stirred solution of 4-(5-chloro-2-methyl-4-nitrophenoxy)-1H-pyrazolo[3,4-b]pyridine (21.0 g, 68.9 mmol) in DMF (100 mL) was added freshly ground (mortar/pestle) potassium hydroxide (11.6 g, 207 mmol) flakes followed immediately by iodine (26.2 g, 103 mmol) under N$_2$ at 25° C. The dark reaction was heated to 50° C. for 6 hours. The mixture was quenched by addition of aqueous 10% NaHSO$_3$ (75 mL). The suspension was further diluted by addition of water (100 mL) and filtered. The resulting precipitate washed with water, dried by toluene azeotrope, and then left under high vacuum for 2 days. The beige powder (26.5 g, 69%) was carried forward without further purification.

Step D: Preparation of 1-(4-methoxybenzyl)-4-(5-chloro-2-methyl-4-nitrophenoxy)-3-iodo-1H-pyrazolo[3,4-b]pyridine: 4-(5-Chloro-2-methyl-4-nitrophenoxy)-3-iodo-1H-pyrazolo[3,4-b]pyridine (26.5 g, 61.5 mmol) was dissolved in stirring DMF (100 mL). K$_2$CO$_3$ (17.0 g, 123 mmol) and 1-(chloromethyl)-4-methoxybenzene (10.1 ml, 73.9 mmol) were added and the reaction mixture was stirred at ambient temperature under N$_2$ for 18 hours. The mixture was diluted with water, and then the water was decanted. The gum washed a second time with water, and the water decanted. The residue was partitioned between EtOAc (250 mL) and brine (100 mL). The phases were separated, and the organic phase was dried (Na$_2$SO$_4$), filtered, and concentrated. The resulting solid was triturated with diethyl ether (100 mL), and the yellow powder (27.3 g, 80%) filtered. The product was a 9:1 mixture of pyrazole regioisomers as determined by $^1$H NMR: (400 MHz, CDCl$_3$, major regioisomer reported) δ 8.43 (d, J=5 Hz, 1H), 7.95 (s, 1H), 7.38 (d, J=9 Hz, 2H), 7.19 (s, 1H), 6.84 (d, J=9 Hz, 2H), 6.35 (d, J=5 Hz, 1H), 5.64 (s, 2H), 3.77 (s, 3H), 2.36 (s, 3H).

Step E: Preparation of 2-chloro-4-(3-iodo-1-(4-methoxybenzyl)-1H-pyrazolo[3,4-b]pyridin-4-yloxy)-5-methylaniline: To a 100 mL round bottom flask added 1-(4-methoxybenzyl)-4-(5-chloro-2-methyl-4-nitrophenoxy)-3-iodo-1H-pyrazolo[3,4-b]pyridine (544 mg, 0.99 mmol) and suspended in absolute ethanol (10 mL). Added tin(II)chloride dihydrate (1.1 g, 4.94 mmol) and stirred at 25° C. under N$_2$(g) for 18 hours, during which a white precipitate formed. The reaction mixture was cooled to 0° C. and the solid was removed by filtration and washed with cold ethanol. The solid was air-dried to afford the desired product as white solid. Yield: 417 mg, 81%. LRMS (APCI pos) m/e 521.1 (M+H).

Step F: Preparation of N-(2-chloro-4-(3-iodo-1-(4-methoxybenzyl)-1H-pyrazolo[3,4-b]pyridin-4-yloxy)-5-methylphenyl)-2-(4-fluorophenyl)-3-oxo-2,3-dihydropyridazine-4-carboxamide: Prepared according to the procedure of Example 82, Step B, substituting 2-chloro-4-(3-iodo-1-(4-methoxybenzyl)-1H-pyrazolo[3,4-b]pyridin-4-yloxy)-5-methylaniline (70 mg, 0.13 mmol) for tert-butyl 4-(4-(4-amino-2-fluorophenoxy)-1-(4-methoxybenzyl)-1H-pyrazolo[3,4-b]pyridin-3-yl)piperazine-1-carboxylate. The crude material was purified by silica gel column chromatography (Biotage 25M) eluting with 70/30 hexanes/EtOAc to afford the desired product. Yield: 62 mg, 63%. LRMS (APCI pos) m/e 737.1 (M+H).

Step G: Preparation of N-(2-chloro-4-(1-(4-methoxybenzyl)-3-(4-(morpholine-4-carbonyl)phenyl)-1H-pyrazolo[3,4-b]pyridin-4-yloxy)-5-methylphenyl)-2-(4-fluorophenyl)-3-oxo-2,3-dihydropyridazine-4-carboxamide: Prepared according to the procedure of Example 63, Step B, substituting N-(2-chloro-4-(3-iodo-1-(4-methoxybenzyl)-1H-pyrazolo[3,4-b]pyridin-4-yloxy)-5-methylphenyl)-2-(4-fluorophenyl)-3-oxo-2,3-dihydropyridazine-4-carboxamide (22 mg, 0.030 mmol) for N-(3-fluoro-4-(3-iodo-1-(4-methoxybenzyl)-1H-pyrazolo[3,4-b]pyridin-4-yloxy)phenyl)-2-(4-fluorophenyl)-3-oxo-2,3-dihydropyridazine-4-carboxamide. The crude material was purified by silica gel column chromatography (Biotage 12M) eluting with 2% MeOH/CHCl$_3$ to afford the desired product. Yield: 23 mg, 96%. LRMS (APCI pos) m/e 800.2 (M+H).

Step H: Preparation of N-(2-chloro-5-methyl-4-(3-(4-(morpholine-4-carbonyl)phenyl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting N-(2-chloro-4-(1-(4-methoxybenzyl)-3-(4-(morpholine-4-carbonyl)phenyl)-1H-pyrazolo[3,4-b]pyridin-4-yloxy)-5-methylphenyl)-2-(4-fluorophenyl)-3-oxo-2,3-dihydropyridazine-4-carboxamide (23 mg, 0.0287 mmol) for N-(3-fluoro-4-(1-(4- methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 2% MeOH/CHCl₃ to afford the desired product. Yield: 9.7 mg, 50%. ¹H NMR (400 MHz, DMSO-d6) δ 14.02 (s, 1H), 12.08 (s, 1H), 8.59 (s, 1H), 8.41 (d, 1H), 8.36 (t, 2H), 8.09 (d, 2H), 7.68 (m, 2H), 7.61 (s, 1H), 7.52 (d, 2H), 7.42 (t, 2H), 6.30 (d, 1H), 3.60 (broad s, 8H), 3.29 (s, 3H). LRMS (APCI pos) m/e 680.2 (M+H).

Example 75

N-(3-fluoro-4-(3-(pyridin-3-yl)-1H-pyrazolo[3,4-b]pyridin-4-yloxy)phenyl)-2-(4-fluorophenyl)-3-oxo-2,3-dihydropyridazine-4-carboxamide

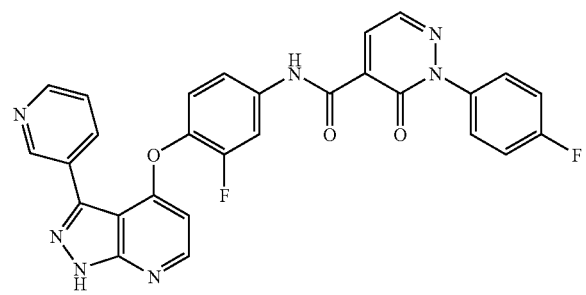

Step A: Preparation of N-(3-fluoro-4-(1-(4-methoxybenzyl)-3-(pyridin-3-yl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 63, Step B, substituting pyridine-3-boronic acid (10.4 mg, 0.085 mmol) for 4-(morpholine-4-carbonyl)phenylboronic acid. The crude material was purified by silica gel column chromatography (Biotage 12M) eluting with 2% MeOH/CHCl₃ to afford the desired product. Yield: 18 mg at 85% purity, 55%. LRMS (APCI pos) m/e 658.3 (M+H).

Step B: Preparation of N-(3-fluoro-4-(3-(pyridin-3-yl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting N-(3-fluoro-4-(1-(4-methoxybenzyl)-3-(pyridin-3-yl)-1H-pyrazolo[3,4-b]pyridin-4-yloxy)phenyl)-2-(4-fluorophenyl)-3-oxo-2,3-dihydropyridazine-4-carboxamide (18 mg, 0.0274 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 3% MeOH/CHCl₃ to afford the desired product. Yield: 7 mg, 47%. LRMS (APCI pos) m/e 538.3 (M+H).

Example 76

N-(3-fluoro-4-(1-methyl-3-phenyl-1H-pyrazolo[3,4-b]pyridin-4-yloxy)phenyl)-2-(4-fluorophenyl)-3-oxo-2,3-dihydropyridazine-4-carboxamide

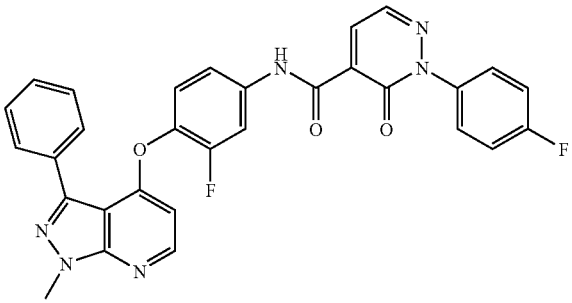

Step A: Preparation of 4-(2-fluoro-4-nitrophenoxy)-3-iodo-1-methyl-1H-pyrazolo[3,4-b]pyridine: To a stirred solution of 4-(2-fluoro-4-nitrophenoxy)-1H-pyrazolo[3,4-b]pyridine (12.0 g, 43.8 mmol, prepared using the procedure described in Example 3, Step A) in DMF (100 mL) was added freshly ground (mortar/pestle) potassium hydroxide (7.37 g, 131 mmol) followed immediately by iodine (16.7 g, 65.6 mmol) under N₂(g) at 25° C. The dark reaction was heated to 50° C. for 3 hours. One third of the reaction mixture volume was poured into a stirred solution of iodomethane (3.09 g, 21.7 mmol) in DMF (25 mL) at 0° C. under N₂. The reaction was allowed to warm to 25° C. and stirred for 18 hours under N₂. The mixture was diluted with CH₂Cl₂ (50 mL) and washed with a co-solvent of saturated aqueous Na₂S₂O₃ (10 mL) and water (40 mL). The aqueous phase was extracted with 10% MeOH in CH₂Cl₂ (30 mL). The combined organic phases were washed with the Na₂S₂O₃/water mixture followed by water, dried (Na₂SO₄), filtered, and concentrated in vacuo. The resulting residue was triturated with diethyl ether, and the solid filtered to afford the desired product (4.01 g, 62%).

Step B: Preparation of 3-fluoro-4-(3-iodo-1-methyl-1H-pyrazolo[3,4-b]pyridin-4-yloxy)benzenamine: Prepared from 4-(2-fluoro-4-nitrophenoxy)-3-iodo-1-methyl-1H-pyrazolo[3,4-b]pyridine (2.07 g, 5.0 mmol) and SnCl₂-dihydrate (5.64 g, 25.0 mmol) according to the procedure of Example 18, Step B. The product (1.30 g, 68%) was used directly in the next step without purification.

Step C: Preparation of N-(3-fluoro-4-(3-iodo-1-methyl-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 63, Step A, substituting 3-fluoro-4-(3-iodo-1-methyl-1H-pyrazolo[3,4-b]pyridin-4-yloxy)aniline (100 mg, 0.260 mmol) for 4-(1-(4-methoxybenzyl)-3-iodo-1H-pyrazolo[3,4-b]pyridin-4-yloxy)-3-fluorobenzenamine. The crude material was purified by silica gel column chromatography (Biotage 25M)

eluting with 2% MeOH/CHCl₃ to afford the desired product as yellow solid. Yield: 125 mg, 80%. LRMS (APCI pos) m/e 601.2 (M+H).

Step D: Preparation of N-(3-fluoro-4-(1-methyl-3-phenyl-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 63, Step B, substituting phenylboronic acid (12 mg, 0.100 mmol) for 4-(morpholine-4-carbonyl)phenylboronic acid. The crude material was purified by silica gel column chromatography (Biotage 12M) eluting with 2% MeOH/CHCl₃ to afford the desired product. Yield: 15 mg at 92% purity, 50%. ¹H NMR (400 MHz, DMSO-d6) δ 11.7 (s, 1H), 8.42 (d, 1H), 8.38 (d, 1H), 8.27 (d, 1H), 8.05 (dd, 1H), 7.97 (d, 1H), 7.69 (q, 2H), 7.58 (m, ³H), 7.47 (t, 2H), 7.41 (t, 3H), 6.41 (d, 1H), 4.13 (s, 3H). LRMS (APCI pos) m/e 551.3 (M+H).

Example 77

N-(3-fluoro-4-(3-(4-fluorophenyl)-1-methyl-1H-pyrazolo[3,4-b]pyridin-4-yloxy)phenyl)-2-(4-fluorophenyl)-3-oxo-2,3-dihydropyridazine-4-carboxamide

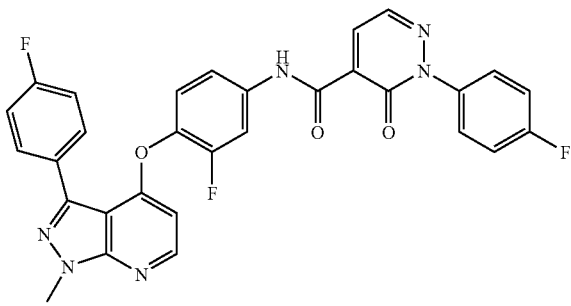

Step A: Preparation of N-(3-fluoro-4-(3-(4-fluorophenyl)-1-methyl-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 63, Step B, substituting 4-fluorophenylboronic acid (14.0 mg, 0.10 mmol) for 4-(morpholine-4-carbonyl)phenylboronic acid and using N-(3-fluoro-4-(3-iodo-1-methyl-1H-pyrazolo[3,4-b]pyridin-4-yloxy)phenyl)-2-(4-fluorophenyl)-3-oxo-2,3-dihydropyridazine-4-carboxamide as prepared in Example 76, Step B. The crude material was purified by silica gel column chromatography (Biotage 12M) eluting with 2% MeOH/CHCl₃ to afford the desired product. Yield: 19.8 mg at 93% purity, 65%. ¹H NMR (400 MHz, DMSO-d6) δ 11.71 (s, 1H), 8.40 (dd, 2H), 8.27 (d, 1H), 8.03 (m, 3H), 7.69 (t, 2H), 7.58 (m, 2H), 7.41 (t, 2H), 7.32 (t, 2H), 6.41 (d, 1H), 4.12 (s, 3H). LRMS (APCI pos) m/e 569.3 (M+H).

Example 78

N-(3-Fluoro-4-(3-(1,2,3,6-tetrahydropyridin-4-yl)-1H-pyrazolo[3,4-b]pyridin-4-yloxy)phenyl)-2-(4-fluorophenyl)-3-oxo-2,3-dihydropyridazine-4-carboxamide

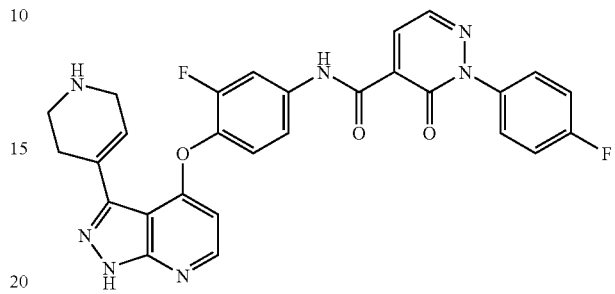

Step A: Preparation of tert-butyl 4-(4-(4-amino-2-fluorophenoxy)-1-(4-methoxybenzyl)-1H-pyrazolo[3,4-b]pyridin-3-yl)-5,6-dihydropyridine-1(2H)-carboxylate: A 100 mL round-bottomed flask was charged with 4-(1-(4-methoxybenzyl)-3-iodo-1H-pyrazolo[3,4-b]pyridin-4-yloxy)-3-fluorobenzenamine (250.0 mg, 0.5099 mmol, prepared in Example 7, step B), tert-butyl 4-(4,4,5,5-tetramethyl-1,3,2-dioxaborolan-2-yl)-5,6-dihydropyridine-1(2H)-carboxylate (315.3 mg, 1.020 mmol), tetrakis(triphenylphosphine) palladium (117.8 mg, 0.1020 mmol), Na₂CO₃ (1.275 ml, 2.550 mmol) and DME (25 mL). The reaction mixture was stirred at 100° C. overnight, then partitioned between EtOAc (100 mL) and H₂O (100 mL). The phases were separated and the aqueous phase was re-extracted with EtOAc. The combined organic layers were dried (Na₂SO₄), filtered and concentrated to yield a crude product. The crude product was purified by silica gel chromatography (DCM/7 M NH₃ in MeOH from 100/1 to 10/1, v/v) to afford product (273.3 mg, 98%). LRMS (APCI pos) m/e 546 (M+1).

Step B: Preparation of tert-butyl 4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)-5,6-dihydropyridine-1(2H)-carboxylate: A 50 mL round-bottomed flask was charged with tert-butyl 4-(1-(4-methoxybenzyl)-4-(4-amino-2-fluorophenoxy)-1H-pyrazolo[3,4-b]pyridin-3-yl)-5,6-dihydropyridine-1(2H)-carboxylate (50.0 mg, 0.0916 mmol), 2-(4-fluorophenyl)-3-oxo-2,3-dihydropyridazine-4-carboxylic acid (42.9 mg, 0.183 mmol), N1-((ethylimino)methylene)-N³,N³-dimethylpropane-1,3-diamine hydrochloride (52.7 mg, 0.275 mmol), 1H-benzo[d][1,2,3]triazol-1-ol (37.1 mg, 0.275 mmol), N-ethyl-N-isopropylpropan-2-amine (0.0818 ml, 0.458 mmol) and DMF (5 mL). The reaction mixture was stirred at room temperature until LC-MS showed that the starting material had been consumed (2 days). The reaction was partitioned between EtOAc and H₂O. The phases were separated and the aqueous phase was re-extracted with EtOAc. The combined organic layers were dried (Na₂SO₄), filtered and concentrated to yield a crude product. The crude material was purified by silica gel chromatography (DCM/7 M NH₃ in MeOH from 100/1 to 10/1, v/v) to afford product (38.3 mg, 54.9%). LRMS (APCI pos) m/e 662 (M−99).

Step C: Preparation of N-(3-fluoro-4-(3-(1,2,3,6-tetrahydropyridin-4-yl)-1H-pyrazolo[3,4-b]pyridin-4-yloxy)phenyl)-2-(4-fluorophenyl)-3-oxo-2,3-dihydropyridazine-4- carboxamide: A 50 mL round-bottomed flask was charged with tert-butyl 4-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)-5,6-dihydropyridine-1(2H)-carboxylate (38.3 mg, 0.0503 mmol) and CF$_3$COOH (5 mL). The reaction mixture was stirred at 60° C. for 4 hours. Then the solvent was removed and the residue was purified by silica gel chromatography (DCM/7 M NH$_3$ in MeOH from 50/1 to 10/1, v/v) to give product 21.8 mg, the yield is 80.1%. LRMS (APCI pos): >99% purity, 254 nm, m/e 542 (M+1). $^1$H NMR (400 MHz, DMSO-d$_6$) δ 11.71 (s, 1H), 8.38 (d, 1H), 8.30 (d, 1H), 8.27 (d, 1H), 8.04 (dd, 1H), 6.82 (m, 2H), 7.59 (d, 1H), 7.49 (m, 1H), 7.42 (m, 2H), 6.69 (s, 1H), 6.31 (d, 1H), 3.39 (m, 2H), 2.94 (m, 2H), 2.58 (m, 2H).

Example 79

N-(4-(3-(4-(dimethylamino)phenyl)-1H-pyrazolo[3,4-b]pyridin-4-yloxy)-3-fluorophenyl)-2-(4-fluorophenyl)-3-oxo-2,3-dihydropyridazine-4-carboxamide

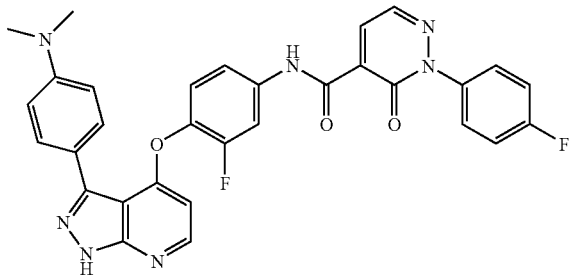

Step A: Preparation of N-(4-(3-(4-(dimethylamino)phenyl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide: Prepared according to the procedure of Example 63, Step B, substituting 4-(dimethylamino)phenylboronic acid (23 mg, 0.14 mmol) for 4-(morpholine-4-carbonyl)phenylboronic acid. The crude material was purified by silica gel column chromatography (Biotage 12M) eluting with 1% MeOH/CHCl$_3$ to afford the desired product. Yield: 39 mg, 79%. LRMS (APCI pos) m/e 700.3 (M+H).

Step B: Preparation of N-(4-(3-(4-(dimethylamino)phenyl)-1H-pyrazolo[3,4-b]pyridin-4-yloxy)-3-fluorophenyl)-2-(4-fluorophenyl)-3-oxo-2,3-dihydropyridazine-4-carboxamide: Prepared according to the procedure of Example 53, Step B, substituting N-(4-(3-(4-(dimethylamino)phenyl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide (39 mg, 0.0557 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 2% MeOH/CHCl$_3$ to afford the desired product. Yield: 18 mg at 90% purity, 50%. $^1$H NMR (400 MHz, DMSO-d6) δ 13.68 (s, 1H), 11.7 (s, 1H), 8.38 (d, 1H), 8.32 (d, 1H), 8.27 (d, 1H), 8.04 (d, 1H), 7.83 (d, 2H), 7.69 (q, 2H), 7.55 (m, 3H), 7.41 (t, 2H), 6.80 (d, 1H), 6.29 (d, 1H), 2.93 (s, 6H). LRMS (APCI pos) m/e 580.4 (M+H).

Example 80

N-(4-(3-(3-chlorophenyl)-1H-pyrazolo[3,4-b]pyridin-4-yloxy)-3-fluorophenyl)-2-(4-fluorophenyl)-3-oxo-2,3-dihydropyridazine-4-carboxamide

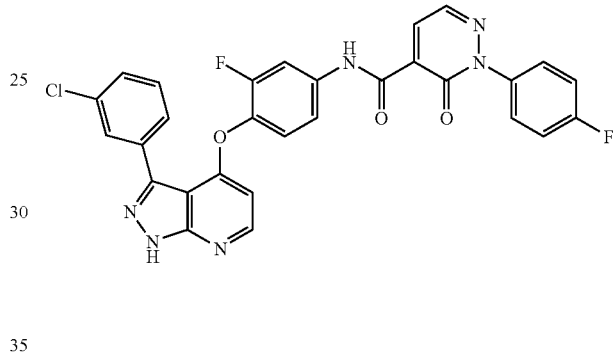

Step A: Preparation of N-(4-(3-(3-chlorophenyl)-1-(4-methoxybenzyl)-1H-carboxamide: Prepared according to the procedure of Example 63, Step B, substituting 3-chlorophenylboronic acid (17.7 mg, 0.113 mmol) for 4-(morpholine-4-carbonyl)phenylboronic acid. The crude material was purified by trituration with 60/40 hexanes/EtOAc to afford the desired product as yellow solid. Yield: 32 mg, 82%. LRMS (APCI pos) m/e 691.2 (M+H).

Step B: Preparation of N-(4-(3-(3-chlorophenyl)-1H-pyrazolo[3,4-b]pyridin-4-yloxy)-3-fluorophenyl)-2-(4-fluorophenyl)-3-oxo-2,3-dihydropyridazine-4-carboxamide: Prepared according to the procedure of Example 53, Step B, substituting N-(4-(3-(3-chlorophenyl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide (32 mg, 0.0463 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by trituration with 20% MeOH/ether to afford the desired product as pale yellow solid. Yield: 24 mg, 90%. $^1$H NMR (400 MHz, DMSO-d6) δ 11.71 (s, 1H), 8.39 (t, 2H), 8.37 (d, 1H), 8.27 (dd, 2H), 7.97 (d, 2H), 7.69 (q, 2H), 7.59-7.44 (m, 3H), 7.43-7.39 (m, 2H), 6.41 (d, 1H). LRMS (APCI pos) m/e 571.3 (M+H).

Example 81

N-(4-(3-(1H-pyrazol-4-yl)-1H-pyrazolo[3,4-b]pyridin-4-yloxy)-3-fluorophenyl)-2-(4-fluorophenyl)-3-oxo-2,3-dihydropyridazine-4-carboxamide

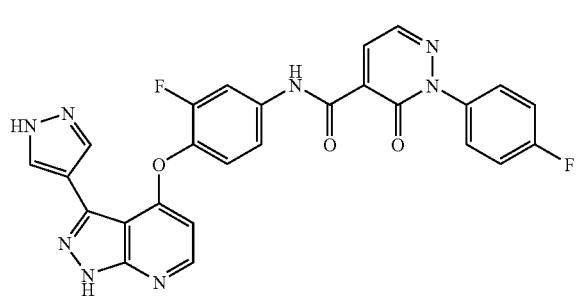

Step A: Preparation of tert-butyl 4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)-1H-pyrazole-1-carboxylate: A 50 mL round-bottomed flask was charged with N-(4-(1-(4-methoxybenzyl)-3-iodo-1H-pyrazolo[3,4-b]pyridin-4-yloxy)-3-fluorophenyl)-2-(4-fluorophenyl)-3-oxo-2,3-dihydropyridazine-4-carboxamide (40.0 mg, 0.0566 mmol, prepared in Example 63, step A), tert-butyl 4-(4,4,5,5-tetramethyl-1,3,2-dioxaborolan-2-yl)-1H-pyrazole-1-carboxylate (50.0 mg, 0.170 mmol), Pd(OAc)$_2$ (2.54 mg, 0.0113 mmol), tricyclohexylphosphine (4.76 mg, 0.0170 mmol), cesium fluoride (77.4 mg, 0.510 mmol) and CH$_3$CN (10 mL). The reaction mixture was stirred at 100° C. for 1 hour. The reaction was cooled to room temperature and then the reaction was partitioned between EtOAc and H$_2$O. The phases were separated and the aqueous phase was re-extracted with EtOAc. The combined organic layers were dried (Na$_2$SO$_4$), filtered and concentrated to yield a crude product. The crude material was purified by silica gel chromatography (DCM/7 M NH$_3$ in MeOH from 100/1 to 10/1, v/v) to afford product (29.7 mg, 70.2%). LRMS (APCI neg): >96% purity, 254 nm, m/e 745 (M−1).

Step B: Preparation of N-(4-(3-(1H-pyrazol-4-yl)-1H-pyrazolo[3,4-b]pyridin-4-yloxy)-3-fluorophenyl)-2-(4-fluorophenyl)-3-oxo-2,3-dihydropyridazine-4-carboxamide: A 50 mL round-bottomed flask was charged with tert-butyl 4-(1-(4-methoxybenzyl)-4-(2-fluoro-4-(1-(4-fluorophenyl)-6-oxo-1,6-dihydropyridazine-5-carboxamido) phenoxy)-1H-pyrazolo[3,4-b]pyridin-3-yl)-1H-pyrazole-1-carboxylate (29.7 mg, 0.0398 mmol) and CF$_3$COOH (5 mL). The reaction mixture was stirred at 60° C. for 4 hours. Then the solvent was removed and the residue was purified by silica gel chromatography (DCM/7 M NH$_3$ in MeOH from 50/1 to 10/1, v/v) to give product (17.8 mg, 85.0%). LRMS (APCI pos): >99% purity, 254 nm, m/e 527 (M+1). $^1$H NMR (400 MHz, DMSO-d$_6$) δ 13.65 (s, 1H), 13.0 (s, 1H), 11.74 (s, 1H), 8.38 (d, 1H), 8.32 (d, 1H), 8.27 (d, 1H), 8.22 (s, 1H), 8.01-8.12 (m, 2H), 7.69 (m, 2H), 7.61 (m, 2H), 7.42 (m, 2H), 6.32 (d, 1H).

Example 82

N-(3-Fluoro-4-(3-(piperazin-1-yl)-1H-pyrazolo[3,4-b]pyridin-4-yloxy)phenyl)-2-(4-fluorophenyl)-3-oxo-2,3-dihydropyridazine-4-carboxamide

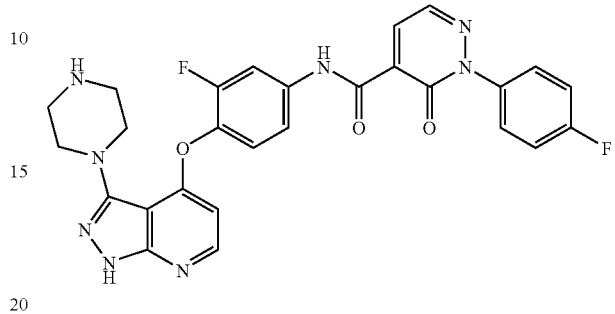

Step A: Preparation of tert-butyl 4-(4-(4-amino-2-fluorophenoxy)-1-(4-methoxybenzyl)-1H-pyrazolo[3,4-b]pyridin-3-yl)piperazine-1-carboxylate: A 100 mL round-bottomed flask was charged with 4-(1-(4-methoxybenzyl)-3-iodo-1H-pyrazolo[3,4-b]pyridin-4-yloxy)-3-fluorobenzenamine (100.0 mg, 0.2040 mmol, prepared in Example 7, step B), tert-butyl piperazine-1-carboxylate (114.0 mg, 0.6119 mmol), copper(I)iodide (7.769 mg, 0.04079 mmol), (S)-pyrrolidine-2-carboxylic acid (9.393 mg, 0.08159 mmol), K$_2$CO$_3$ (140.9 mg, 1.020 mmol) and DMSO (10 mL). The reaction mixture was stirred at 100° C. for 4 hours. The reaction was cooled to room temperature and partitioned between EtOAc and H$_2$O. The phases were separated and the aqueous phase was re-extracted with EtOAc. The combined organic layers were dried (Na$_2$SO$_4$), filtered and concentrated to yield a crude product. The crude material was purified by silica gel chromatography (DCM/7 M NH$_3$ in MeOH from 50/1 to 10/1, v/v) to afford product (63.5 mg, 56.75%). LRMS (APCI pos) m/e 549 (M+1).

Step B: Preparation of tert-butyl 4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)piperazine-1-carboxylate: A 50 mL round-bottomed flask was charged with tert-butyl 4-(1-(4-methoxybenzyl)-4-(4-amino-2-fluorophenoxy)-1H-pyrazolo[3,4-b]pyridin-3-yl)piperazine-1-carboxylate (63.5 mg, 0.1157 mmol), 2-(4-fluorophenyl)-3-oxo-2,3-dihydropyridazine-4-carboxylic acid (54.21 mg, 0.2315 mmol), N1-((ethylimino)methylene)-N3,N3-dimethylpropane-1,3-diamine hydrochloride (110.9 mg, 0.5787 mmol), 1H-benzo[d][1,2,3]triazol-1-ol (78.20 mg, 0.5787 mmol), N-ethyl-N-isopropylpropan-2-amine (0.2066 ml, 1.157 mmol) and DMF (10 mL). The reaction mixture was stirred at ambient temperature overnight. The reaction was partitioned between EtOAc and H$_2$O. The phases were separated and the aqueous phase was re-extracted with EtOAc. The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (56.8 mg, 64.17%). LRMS (APCI pos) m/e 765 (M+1).

Step C: Preparation of N-(3-fluoro-4-(3-(piperazin-1-yl)-1H-pyrazolo[3,4-b]pyridin-4-yloxy)phenyl)-2-(4-fluorophenyl)-3-oxo-2,3-dihydropyridazine-4-carboxamide: A 50 mL round-bottomed flask was charged with tert-butyl 4-(1-(4-methoxybenzyl)-4-(2-fluoro-4-(1-(4-fluorophenyl)-

6-oxo-1,6-dihydropyridazine-5-carboxamido)phenoxy)-1H-pyrazolo[3,4-b]pyridin-3-yl)piperazine-1-carboxylate (56.8 mg, 0.0743 mmol) and CF₃COOH (5 mL). The reaction mixture was stirred at 60° C. overnight. The solvent was removed and the residue was purified by silica gel chromatography (DCM/7 M NH₃ in MeOH from 50/1 to 10/1, v/v) to afford product (35.3 mg, 87.3%). LRMS (APCI pos): >99% purity, 254 nm, m/e 545 (M+1). ¹H NMR (400 MHz, CDCl₃) δ 11.83 (s, 1H), 8.41 (d, 1H), 8.24 (m, 2H), 7.90 (dd, 1H), 7.60 (m, 2H), 7.41 (d, 1H), 7.24 (m, 3H), 6.21 (d, 1H), 3.46 (m, 4H), 3.04 (m, 4H).

Example 83

N-(3-fluoro-4-(3-(1-methyl-1H-pyrazol-4-yl)-1H-pyrazolo[3,4-b]pyridin-4-yloxy)phenyl)-2-(4-fluorophenyl)-3-oxo-2,3-dihydropyridazine-4-carboxamide

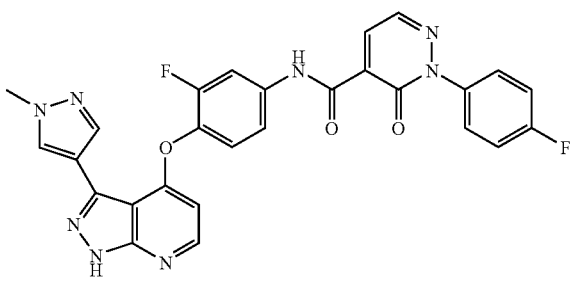

Step A: Preparation of N-(3-fluoro-4-(1-(4-methoxybenzyl)-3-(1-methyl-1H-pyrazol-4-yl)-1H-pyrazolo[3,4-b]pyridin-4-yloxy)phenyl)-2-(4-fluorophenyl)-3-oxo-2,3-dihydropyridazine-4-carboxamide: A 100 mL round-bottomed flask was charged with N-(4-(1-(4-methoxybenzyl)-3-iodo-1H-pyrazolo[3,4-b]pyridin-4-yloxy)-3-fluorophenyl)-2-(4-fluorophenyl)-3-oxo-2,3-dihydropyridazine-4-carboxamide (50.0 mg, 0.0708 mmol, prepared in Example 63, step A), 1-methyl-4-(4,4,5,5-tetramethyl-1,3,2-dioxaborolan-2-yl)-1H-pyrazole (44.2 mg, 0.212 mmol), Pd(OAc)₂ (3.18 mg, 0.0142 mmol), tricyclohexylphosphine (5.95 mg, 0.0212 mmol), cesium fluoride (96.8 mg, 0.637 mmol) and CH₃CN (10 mL). The reaction mixture was stirred at 100° C. 1 hour. The reaction was cooled to room temperature and partitioned between EtOAc and H₂O. The phases were separated and the aqueous phase was re-extracted with EtOAc. The combined organic layers were dried (Na₂SO₄), filtered and concentrated to yield a crude product. The crude material was purified by silica gel chromatography (DCM/7 M NH₃ in MeOH from 100/1 to 10/1, v/v) to afford product (23.8 mg, 50.9%). LRMS (APCI pos): >95% purity, 254 nm, m/e 661 (M+1).

Step B: Preparation of N-(3-fluoro-4-(3-(1-methyl-1H-pyrazol-4-yl)-1H-pyrazolo[3,4-b]pyridin-4-yloxy)phenyl)-2-(4-fluorophenyl)-3-oxo-2,3-dihydropyridazine-4-carboxamide: A 50 mL round-bottomed flask was charged N-(4-(1-(4-methoxybenzyl)-3-(1-methyl-1H-pyrazol-4-yl)-1H-pyrazolo[3,4-b]pyridin-4-yloxy)-3-fluorophenyl)-2-(4-fluorophenyl)-3-oxo-2,3-dihydropyridazine-4-carboxamide (23.8 mg, 0.0360 mmol) and CF₃COOH (5 mL). The reaction mixture was stirred at 60° C. until LC-MS showed that the starting material had been consumed (overnight). The solvent was removed under reduced pressure and the residue was purified by silica gel chromatography (DCM/7 M NH₃ in MeOH from 50/1 to 10/1, v/v) to give product (11.3 mg, 58%). LRMS (APCI pos): >99% purity, 254 nm, m/e 541 (M+1). ¹H NMR (400 MHz, DMSO-d₆) δ 13.66 (s, 1H), 11.72 (s, 1H), 8.38 (d, 1H), 8.31 (d, 1H), 8.27 (d, 1H), 8.18 (s, 1H), 8.06 (dd, 1H), 7.96 (s, 1H), 7.69 (m, 2H), 7.60 (m, 2H), 7.42 (m, 2H), 6.31 (d, 1H), 3.89 (s, 3H).

Example 84

5-(3-fluoro-4-(3-(4-(morpholine-4-carbonyl)phenyl)-1H-pyrazolo[3,4-b]pyridin-4-yloxy)phenyl)-3-methyl-2-(phenylamino)pyrimidin-4(3H)-one

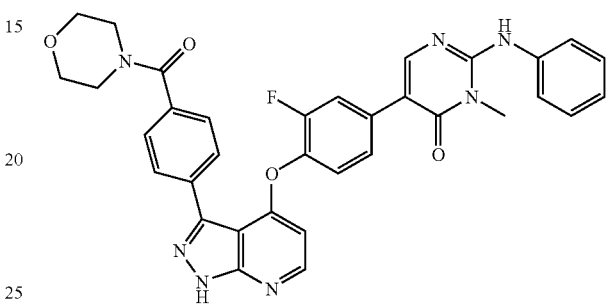

Step A: Preparation of 4-chloro-1H-(4-methoxybenzyl)-1H-pyrazolo[3,4-b]pyridine: To a solution of phosphoryl trichloride (3.227 ml, 35.26 mmol) in dichloroethane (60 mL) was added 1-(4-methoxybenzyl)-1H-pyrazolo[3,4-b]pyridin-4-ol (3.00 g, 11.75 mmol; prepared according to the procedure of Example 1, Step B) as a solid in one portion. The reaction was stirred under N₂ at reflux for 4 hours. The reaction mixture was cooled to ambient temperature and then poured slowly onto ice water. Saturated NaHCO₃ was slowly added until the reaction mixture was neutral by pH paper and then extracted with CH₂Cl₂ (added a small amount of methanol to help resolve layers). The aqueous phase was re-extracted with CH₂Cl₂. The combined organic layers were washed with brine, dried over Na₂SO₄, filtered and concentrated to yield the crude product as a black oil. The crude material was purified by flash column chromatography, eluting with 10:1 hexanes/EtOAc. The desired product (1.056 g, 47%) was obtained as a white crystalline solid. LRMS (APCI pos) m/e 274, 276 (M+, Cl pattern).

Step B: Preparation of 4-chloro-1H-pyrazolo[3,4-b]pyridine: 4-chloro-1-(4-methoxybenzyl)-1H-pyrazolo[3,4-b]pyridine (1.506 g, 5.502 mmol) was dissolved in neat TFA (8.478 ml, 110.0 mmol) and the reaction mixture was stirred at 75° C. for 2 hours. The reaction mixture was concentrated to a dark yellow oil and MeOH was added to give a thick white precipitate that was filtered and washed with MeOH. The filtrate, which contained the desired product, was concentrated to a yellow oil that was dried in vacuo overnight to yield a yellow waxy solid. The crude solid was partitioned between EtOAc and saturated NaHCO₃. The phases were separated, and the aqueous layer was re-extracted with EtOAc (1×). The combined organic phases were dried over Na₂SO₄, filtered and concentrated to yield the desired product (0.845 g, 100%) as a yellow solid. LRMS (APCI pos) m/e 154, 156 (M+, Cl pattern).

Step C: Preparation of 4-chloro-3-iodo-1H-pyrazolo[3,4-b]pyridine: To a solution of 4-chloro-1H-pyrazolo[3,4-b]pyridine (0.849 g, 5.53 mmol) in DMF (25 mL) was added potassium hydroxide flakes (0.931 g, 16.6 mmol) followed by I₂ (2.53 g, 9.95 mmol). The reaction mixture was stirred at 50° C. for 1.5 hours. The reaction mixture was cooled to room temperature and then quenched with 10% aqueous sodium bisulfite solution during which a precipitate formed. The resulting suspension was diluted with H$_2$O, filtered and washed with H$_2$O to yield a pale yellow solid. The solid was dissolved with CH$_2$Cl$_2$/MeOH, concentrated, and dried in vacuo overnight to yield the desired product (1.41 g, 91%) as a yellow solid. LRMS (APCI pos) m/e 280, 282 (M+, Cl pattern).

Step D: Preparation of 4-chloro-3-iodo-1-(4-methoxybenzyl)-1H-pyrazolo[3,4-b]pyridine: To a solution of 4-chloro-3-iodo-1H-pyrazolo[3,4-b]pyridine (1.31 g, 4.688 mmol) in DMF (40 mL) was added K$_2$CO$_3$ (1.30 g, 9.38 mmol) and 1-(chloromethyl)-4-methoxybenzene (0.766 ml, 5.63 mmol). The reaction mixture was stirred at room temperature overnight to yield two regioisomeric products is a 5.5:1 ratio by LC-MS. The mixture was partitioned between EtOAc and H$_2$O. The phases were separated and the organic layer washed with brine, dried over Na$_2$SO$_4$, filtered and concentrated to afford a dark yellow solid. The crude product was purified by flash column chromatography, eluting with 3:1 hexanes/EtOAc and loaded with 10:1:1 CH$_2$Cl$_2$/MeOH/THF due to poor solubility. The desired N1-regioisomeric product (1.256 g, 67%) was obtained as a white crystalline solid. LRMS (APCI pos) m/e 400, 402 (M+, Cl pattern). The undesired N2-regioisomer, 4-chloro-3-iodo-2-(4-methoxybenzyl)-2H-pyrazolo[3,4-b]pyridine, was not isolated.

Step E: Preparation of 5-(3-fluoro-4-(3-iodo-1-(4-methoxybenzyl)-1H-pyrazolo[3,4-b]pyridin-4-yloxy)phenyl)-3-methyl-2-(phenylamino)pyrimidin-4(3H)-one: A mixture of 5-(3-fluoro-4-hydroxyphenyl)-3-methyl-2-(phenylamino) pyrimidin-4(3H)-one (0.009 g, 0.03 mmol, prepared in Example 45, step F), 4-chloro-3-iodo-1-(4-methoxybenzyl)-1H-pyrazolo[3,4-b]pyridine (0.010 g, 0.0250 mmol) and DMAP (0.006 g, 0.05 mmol) in bromobenzene (0.300 mL) under N$_2$ was stirred at 150° C. for 3 days. The reaction was concentrated in vacuo to remove as much bromobenzene as possible and then purified directly by flash column chromatography, eluting with 10:1 CH$_2$Cl$_2$/MeOH. The desired product (0.013 g, 76%) was obtained as a yellow solid. LRMS (APCI pos) m/e 675 (M+1).

Step F: Preparation of 5-(3-fluoro-4-(1-(4-methoxybenzyl)-3-(4-(morpholine-4-carbonyl)phenyl)-1H-pyrazolo[3,4-b]pyridin-4-yloxy)phenyl)-3-methyl-2-(phenylamino)pyrimidin-4(3H)-one: A suspension of 5-(3-fluoro-4-(3-iodo-1-(4-methoxybenzyl)-1H-pyrazolo[3,4-b]pyridin-4-yloxy) phenyl)-3-methyl-2-(phenylamino)pyrimidin-4(3H)-one (0.013 g, 0.019 mmol), 4-(morpholine-4-carbonyl)phenylboronic acid (0.005 g, 0.02 mmol), Pd(PPh$_3$)$_4$ (0.001 g, 0.0009 mmol) and lithium chloride (0.003 g, 0.08 mmol) in dioxane (0.5 mL) and 2 M aqueous Na$_2$CO$_3$ (0.5 mL) was stirred at 100° C. for 1 hour. The reaction mixture was cooled to room temperature and then partitioned between EtOAc and H$_2$O. The layers were separated and the aqueous layer was re-extracted with EtOAc. The combined organic layers were dried over Na$_2$SO$_4$, filtered and concentrated to yield 0.014 g crude product as a yellow gum. The crude material was used without further purification in the following step. LRMS (APCI pos) m/e 738 (M+1).

Step G: Preparation of 5-(3-fluoro-4-(3-(4-(morpholine-4-carbonyl)phenyl)-1H-pyrazolo[3,4-b]pyridin-4-yloxy)phenyl)-3-methyl-2-(phenylamino)pyrimidin-4(3H)-one: A solution of 5-(3-fluoro-4-(1-(4-methoxybenzyl)-3-(4-(morpholine-4-carbonyl)phenyl)-1H-pyrazolo[3,4-b]pyridin-4-yloxy)phenyl)-3-methyl-2-(phenylamino)pyrimidin-4(3H)-one (0.014 g, 0.0190 mmol) in TFA (1 mL) was stirred at 60° C. for 3.5 hours. The reaction mixture was concentrated in vacuo to yield a crude yellow gum. The crude product was purified by flash column chromatography, eluting with 10:1 CH$_2$Cl$_2$/MeOH. The isolated product was then partitioned between EtOAc and saturated NaHCO$_3$. The layers were separated and the aqueous layer was re-extracted with EtOAc. The combined EtOAc layers were dried over Na$_2$SO$_4$, filtered and concentrated to yield the desired product (6.9 mg; 59%) as a yellow solid. $^1$H NMR (400 MHz, DMSO-d$_6$) δ 9.03 (br s, 1H), 8.40 (d, 1H), 8.09 (s, 1H), 8.08 (m, 2H), 7.86 (dd, 1H), 7.66 (m, 1H), 7.57-7.48 (m, 5H), 7.38 (m, 2H), 7.16 (m, 1H), 6.41 (d, 1H), 3.60 (m, 8H), 3.58 (s, 3H). LRMS (APCI pos) m/e 618 (M+1).

Example 85

N-(3-fluoro-4-(3-o-tolyl-1H-pyrazolo[3,4-b]pyridin-4-yloxy)phenyl)-2-(4-fluorophenyl)-3-oxo-2,3-dihydropyridazine-4-carboxamide

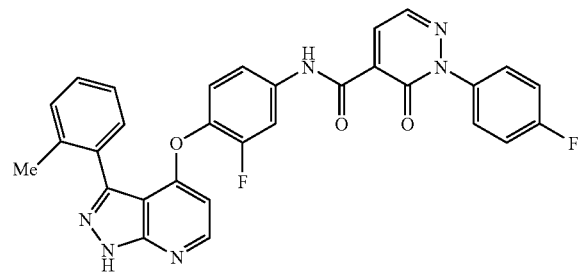

Step A: Preparation of N-(3-fluoro-4-(1-(4-methoxybenzyl)-3-o-tolyl-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 63, Step B, substituting o-tolylboronic acid (15.4 mg, 0.113 mmol) for 4-(morpholine-4-carbonyl)phenylboronic acid. The desired product isolated as yellow oil and was not purified further. Yield: 42 mg at 70% purity, 77%. LRMS (APCI pos) m/e 671.2 (M+H).

Step B: Preparation of N-(3-fluoro-4-(3-o-tolyl-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting N-(3-fluoro-4-(1-(4-methoxybenzyl)-3-o-tolyl-1H-pyrazolo[3,4-b]pyridin-4-yloxy)phenyl)-2-(4-fluorophenyl)-3-oxo-2,3-dihydropyridazine-4-carboxamide (42 mg, 0.0438 mmol) for N-(3-fluoro-4-(1-(4-methoxybenzyl)-3-(3-(methylcarbamoyl)phenyl)-1H-pyrazolo[3,4-b]pyridin-4-yloxy) phenyl)-N-(4-fluorophenyl)cyclopropane-1,1-dicarboxamide. The crude material was purified by silica gel column chromatography (Biotage 12M) eluting with 2% MeOH/CHCl$_3$ to afford the desired product as yellow solid. Yield: 12.5 mg, 52%. $^1$H NMR (400 MHz, DMSO-d6) δ 13.87 (s, 1H), 11.66 (s, 1H), 8.37 (d, 1H), 8.25 (d, 1H), 7.96 (dd, 2H), 7.68 (q, 2H), 7.57 (d, 1H), 7.47 (d, 1H), 7.43-7.33 (m, 4H), 7.30 (d, 2H), 6.32 (d, 1H), 2.32 (s, 3H). LRMS (APCI pos) m/e 551.3 (M+H).

Example 86

N-(3-Fluoro-4-(3-(4-methylpiperazin-1-yl)-1H-pyrazolo[3,4-b]pyridin-4-yloxy)phenyl)-2-(4-fluorophenyl)-3-oxo-2,3-dihydropyridazine-4-carboxamide

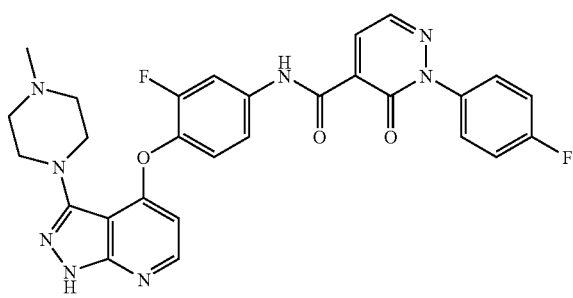

Step A: Preparation of 3-fluoro-4-(1-(4-methoxybenzyl)-3-(4-methylpiperazin-1-yl)-1H-pyrazolo[3,4-b]pyridin-4-yloxy)aniline: A 100 mL round-bottomed flask was charged with 4-(1-(4-methoxybenzyl)-3-iodo-1H-pyrazolo[3,4-b]pyridin-4-yloxy)-3-fluorobenzenamine (100.0 mg, 0.2040 mmol, prepared in Example 7, step B), 1-methylpiperazine (61.29 mg, 0.6119 mmol), copper(I)iodide (11.65 mg, 0.06119 mmol), (S)-pyrrolidine-2-carboxylic acid (7.045 mg, 0.06119 mmol), $K_2CO_3$ (140.9 mg, 1.020 mmol) and DMSO (10 mL). The reaction mixture, was stirred at 100° C. for 8 hours. The reaction was cooled to room temperature and partitioned between EtOAc and $H_2O$. The phases were separated and the aqueous phase was re-extracted with EtOAc. The combined organic layers were dried ($Na_2SO_4$), filtered and concentrated to yield a crude product. The crude product was purified by silica gel chromatography (DCM/7 M $NH_3$ in MeOH from 100/1 to 10/1, v/v) to afford product (36.8 mg, 39.01%). LRMS (APCI pos): >99% purity, 254 nm, m/e 463 (M+1).

Step B: Preparation of N-(3-fluoro-4-(1-(4-methoxybenzyl)-3-(4-methylpiperazin-1-yl)-3-oxo-2,3-dihydropyridazine-4-carboxamide: A 100 mL round-bottomed flask was charged with 4-(1-(4-methoxybenzyl)-3-(4-methylpiperazin-1-yl)-1H-pyrazolo[3,4-b]pyridin-4-yloxy)-3-fluorobenzenamine (36.8 mg, 0.07956 mmol), 2-(4-fluorophenyl)-3-oxo-2,3-dihydropyridazine-4-carboxylic acid (27.95 mg, 0.1193 mmol), N1-((ethylimino)methylene)-N3,N3-dimethylpropane-1,3-diamine hydrochloride (45.76 mg, 0.2387 mmol), 1H-benzo[d][1,2,3]triazol-1-ol (32.25 mg, 0.2387 mmol), N-ethyl-N-isopropylpropan-2-amine (0.07102 ml, 0.3978 mmol) and DMF (10 mL). The reaction mixture was stirred at room temperature until LC-MS showed that the starting material had been consumed (overnight). Then the reaction was partitioned between EtOAc and $H_2O$. The phases were separated and the aqueous phase was re-extracted with EtOAc. The combined organic layers were dried ($Na_2SO_4$), filtered and concentrated. The crude material was purified by silica gel chromatography (DCM/7 M $NH_3$ in MeOH from 100/1 to 10/1, v/v) to afford product (33.2 mg, 61.48%). LRMS (APCI neg): >95% purity, 254 nm, m/e 677 (M–1).

Step C: Preparation of N-(3-fluoro-4-(3-(4-methylpiperazin-1-yl)-1H-pyrazolo[3,4-b]pyridin-4-yloxy)phenyl)-2-(4-fluorophenyl)-3-oxo-2,3-dihydropyridazine-4-carboxamide: A 50 mL round-bottomed flask was charged with N-(4-(1-(4-methoxybenzyl)-3-(4-methylpiperazin-1-yl)-1H-pyrazolo[3,4-b]pyridin-4-yloxy)-3-fluorophenyl)-2-(4-fluorophenyl)-3-oxo-2,3-dihydropyridazine-4-carboxamide (33.2 mg, 0.0489 mmol) and $CF_3COOH$ (5 mL). The reaction mixture was stirred at 60° C. until LC-MS showed that the starting material had been consumed (overnight). Then the solvent was removed and the residue was purified by silica gel chromatography (DCM/7 M $NH_3$ in MeOH from 50/1 to 10/1, v/v) to afford product (24.6 mg, 90%). LRMS (APCI pos): >99% purity, 254 nm, m/e 559 (M+1). $^1$H NMR (400 MHz, $CDCl_3$) δ 11.85 (s, 1H), 10.33 (s, 1H), 8.42 (d, 1H), 8.25 (m, 2H), 7.97 (dd, 1H), 7.61 (m, 2H), 7.41 (d, 1H), 7.23-7.30 (m, 3H), 6.20 (d, 1H), 3.56 (m, 4H), 2.69 (m, 4H), 2.40 (s, 3H).

Example 87

4-benzyl-N-(3-fluoro-4-(3-(4-(morpholine-4-carbonyl)phenyl)-1H-pyrazolo[3,4-b]pyridin-4-yloxy)phenyl)-3-oxo-3,4-dihydropyrazine-2-carboxamide

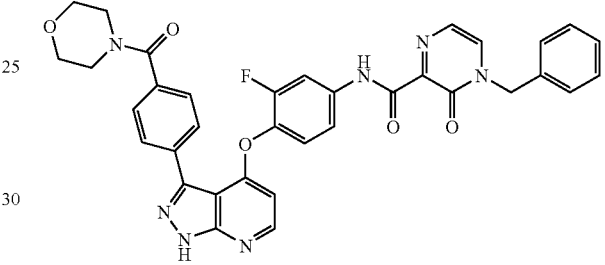

Step A: Preparation of methyl 4-benzyl-3-oxo-3,4-dihydropyrazine-2-carboxylate: LiH (7.8 mg, 0.980 mmol) was added to the solution of methyl 3-oxo-3,4-dihydropyrazine-2-carboxylate (100 mg, 0.65 mmol) in DMF (3 mL) at 0° C. After 30 minutes stirring, (chloromethyl)benzene (0.15 mL, 1.30 mmol) was added to the reaction mixture at 0° C., and then the reaction was warmed to room temperature. After stirring for 4 hours, the reaction mixture was quenched with ice water, extracted with EtOAc, washed with brine, dried over $MgSO_4$, and concentrated to give the crude material that was purified by silica gel flash column chromatography (2% MeOH in $CH_2Cl_2$) to afford 0.102 g (64%) of the desired product.

Step B: Preparation of 4-benzyl-3-oxo-3,4-dihydropyrazine-2-carboxylic acid: LiOH (0.82 mL, 0.82 mmol, 1.0 M in $H_2O$) was added to a solution of methyl 4-benzyl-3-oxo-3,4-dihydropyrazine-2-carboxylate (100 mg, 0.41 mmol) in a mixture of THF (4.5 mL) and MeOH (1.5 mL) at ambient temperature for 4 hours. The reaction mixture was acidified to pH 1 with aqueous 1 N HCl solution and treated with water (5 mL), extracted with EtOAc, washed with brine, dried over $MgSO_4$, and concentrated to afford 77 mg (82%) of the desired product.

Step C: Preparation of (4-(4-(4-amino-2-fluorophenoxy)-1-(4-methoxybenzyl)-1H-pyrazolo[3,4-b]pyridin-3-yl)phenyl)(morpholino)methanone: A mixture of 4-(1-(4-methoxybenzyl)-3-iodo-1H-pyrazolo[3,4-b]pyridin-4-yloxy)-3-fluorobenzenamine (0.30 g, 0.612 mmol; prepared as in Example 7, Step B), $Cs_2CO_3$ (0.299 g, 0.918 mmol), and 4-(morpholine-4-carbonyl)phenylboronic acid (0.151 g, 0.643 mmol) in DME (3 mL) was degassed under nitrogen for 10 minutes and tetrakistriphenylphosphinepalladium (0.035 g, 0.03 mmol) was added. The reaction mixture was heated at 85° C. for 15 hours. The precipitate was removed by filtration with a mixture of EtOAc and MeOH. The filtrate was concentrated and the crude material was purified by silica gel flash column chromatography (1% MeOH in CH$_2$Cl$_2$) to afford 39 mg (12%) of the desired product. LRMS (APCI pos) m/e 554.1 (M+1).

Step D: Preparation of 4-benzyl-N-(3-fluoro-4-(3-(4-(morpholine-4-carbonyl)phenyl)-1H-pyrazolo[3,4-b]pyridin-4-yloxy)phenyl)-3-oxo-3,4-dihydropyrazine-2-carboxamide: Prepared by a 2-step process from (4-(4-(4-amino-2-fluorophenoxy)-1-(4-methoxybenzyl)-1H-pyrazolo[3,4-b]pyridin-3-yl)phenyl)(morpholino)methanone and 4-benzyl-3-oxo-3,4-dihydropyrazine-2-carboxylic acid according to the procedure described for Example 21 (Steps A and B). The crude was rinsed with Et$_2$O to afford 11 mg (45% for 2-step process) of the desired product as the TFA salt. LRMS (ESI pos) m/e 646.4 (M+1). $^1$H-NMR (400 MHz, CD$_3$OD) δ 8.35 (d, 1H), 8.12 (d, 2H), 8.03 (m, 2H), 7.76 (m, 1H), 7.53 (d, 2H), 7.33-7.45 (m, 7H), 6.42 (d, 1H), 5.34 (s, 2H), 3.60-3.80 (m, 8H); $^{19}$F-NMR (376 MHz, CD$_3$OD) δ −129.8.

Example 88

N-(3-fluoro-4-(3-(4-(morpholine-4-carbonyl)phenyl)-1H-pyrazolo[3,4-b]pyridin-4-yloxy)phenyl)-4-methyl-3-oxo-3,4-dihydropyrazine-2-carboxamide

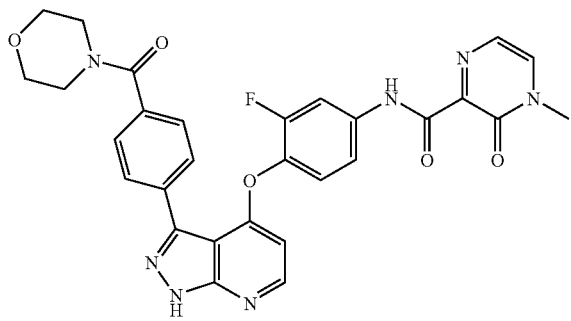

Prepared by 2-step process from (4-(4-(4-amino-2-fluorophenoxy)-1-(4-methoxybenzyl)-1H-pyrazolo[3,4-b]pyridin-3-yl)phenyl)(morpholino)methanone (prepared as in Example 87, Step C) and 4-methyl-3-oxo-3,4-dihydropyrazine-2-carboxylic acid (prepared from methyl 3-oxo-3,4-dihydropyrazine-2-carboxylate with iodomethane, followed by hydrolysis using the methods described in Example 87, steps A and B) according to the procedure of Example 21, Steps A and B. The crude was rinsed with Et$_2$O to afford 7 mg (35% for 2-step process) of the desired product as the TFA salt. LRMS (ESI pos) m/e 570.3 (M+1). $^1$H-NMR (400 MHz, CD$_3$OD) δ 8.37 (d, 1H), 8.12 (d, 2H), 8.05 (m, 2H), 7.76 (d, 1H), 7.54 (m, 3H), 7.38 (t, 1H), 6.44 (d, 1H), 3.75 (s, 3H), 3.60-3.80 (m, 8H); $^{19}$F-NMR (376 MHz, CD$_3$OD) δ −129.8.

Example 89

N-(3-fluoro-4-(3-(4-(piperazin-1-yl)phenyl)-1H-pyrazolo[3,4-b]pyridin-4-yloxy)phenyl)-2-(4-fluorophenyl)-3-oxo-2,3-dihydropyridazine-4-carboxamide

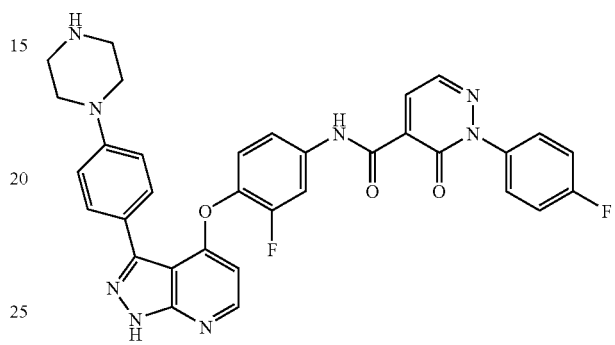

Step A: Preparation of tert-butyl 4-(4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)phenyl)piperazine-1-carboxylate: Prepared according to the procedure of Example 63, Step B, substituting 4-(4-(tert-butoxycarbonyl)piperazin-1-yl)phenylboronic acid (34.67 mg, 0.1132 mmol) for 4-(morpholine-4-carbonyl)phenylboronic acid. The crude material was purified by silica gel column chromatography (Biotage 12M) eluting with 2% MeOH/CHCl$_3$ to afford the desired product. Yield: 50 mg at 85% purity, 89%. LRMS (APCI pos) m/e 785.2 (M-Boc tert-butyl).

Step B: Preparation of N-(3-fluoro-4-(3-(4-(piperazin-1-yl)phenyl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting tert-butyl 4-(4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)phenyl)piperazine-1-carboxylate (50 mg, 0.0595 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by trituration of crude with DCM:ether to afford desired product as the di-TFA salt. Yield: 29 mg (54%) at 95% purity. $^1$H NMR (400 MHz, DMSO-d6) δ 13.8 (s, 1H), 11.71 (s, 1H), 8.68 (broad s, 1H), 8.39 (d, 1H), 8.34 (d, 1H), 8.27 (d, 1H), 8.05 (dd, 1H), 7.90 (d, 2H), 7.69 (q, 2H), 7.60-7.52 (m, 2H), 7.42 (t, 2H), 7.09 (d, 2H), 6.33 (d, 1H), 3.61-3.39 (broad m, 8H). LRMS (APCI pos) m/e 621.4 (M+H).

Example 90

5-(3-fluoro-4-(3-(4-fluorophenyl)-1H-pyrazolo[3,4-b]pyridin-4-yloxy)phenyl)-3-methyl-2-(phenylamino)pyrimidin-4(3H)-one

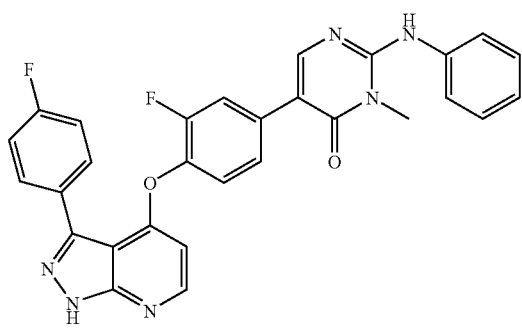

Step A: Preparation of 5-(3-fluoro-4-(3-(4-fluorophenyl)-1-(4-methoxybenzyl)-1H-pyrazolo[3,4-b]pyridin-4-yloxy)phenyl)-3-methyl-2-(phenylamino)pyrimidin-4(3H)-one: A suspension of 5-(3-fluoro-4-(3-iodo-1-(4-methoxybenzyl)-1H-pyrazolo[3,4-b]pyridin-4-yloxy)phenyl)-3-methyl-2-(phenylamino)pyrimidin-4(3H)-one (0.025 g, 0.0371 mmol; prepared according to the procedure of Example 86, Step E), 4-fluorophenylboronic acid (0.006 g, 0.04 mmol), Pd(PPh$_3$)$_4$ (0.002 g, 0.002 mmol) and lithium chloride (0.006 g, 0.15 mmol) in dioxane (1 mL) and 2 M aqueous Na$_2$CO$_3$ (1 mL) was stirred at 110° C. for 35 minutes and then at ambient temperature overnight. The reaction mixture was partitioned between EtOAc and H$_2$O. The layers were separated and the aqueous layer was re-extracted with EtOAc. The combined organic layers were dried over Na$_2$SO$_4$, filtered and concentrated to yield 0.031 g crude product as a yellow gum. The crude material was used without further purification in the following step. LRMS (APCI pos) m/e 643 (M+1).

Step B: Preparation of 5-(3-fluoro-4-(3-(4-fluorophenyl)-1H-pyrazolo[3,4-b]pyridin-4-yloxy)phenyl)-3-methyl-2-(phenylamino)pyrimidin-4(3H)-one. 5-(3-fluoro-4-(3-(4-fluorophenyl)-1-(4-methoxybenzyl)-1H-pyrazolo[3,4-b]pyridin-4-yloxy)phenyl)-3-methyl-2-(phenylamino)pyrimidin-4(3H)-one (0.024 g, 0.037 mmol) was dissolved in TFA (1 mL) and the reaction mixture was stirred at 60° C. for 3 hours and then at room temperature overnight. The reaction mixture was concentrated in vacuo and the residue was partitioned between EtOAc and saturated NaHCO$_3$. The layers were separated and the aqueous layer was re-extracted with EtOAc (1×). The combined EtOAc layers were dried over Na$_2$SO$_4$, filtered and concentrated. The crude product was purified by flash column chromatography, eluting with 10:1 CH$_2$Cl$_2$/MeOH. The product was obtained (15.2 mg; 78%) as a yellow solid. $^1$H NMR (400 MHz, DMSO-d$_6$) δ 13.97 (br s, 1H), 9.02 (br s, 1H), 8.38 (d, 1H), 8.09 (s, 1H), 8.03 (m, 2H), 7.85 (dd, 1H), 7.69-7.48 (m, 4H), 7.38 (t, 2H), 7.32 (t, 2H), 7.17 (t, 1H), 6.38 (d, 1H), 3.58 (s, 3H). LRMS (APCI pos) m/e 523 (M+1).

Example 91

2-(cyclohexylmethyl)-5-(3-fluoro-4-(3-(4-(morpholine-4-carbonyl)phenyl)-1H-pyrazolo[3,4-b]pyridin-4-yloxy)phenyl)-3-methylpyrimidin-4(3H)-one

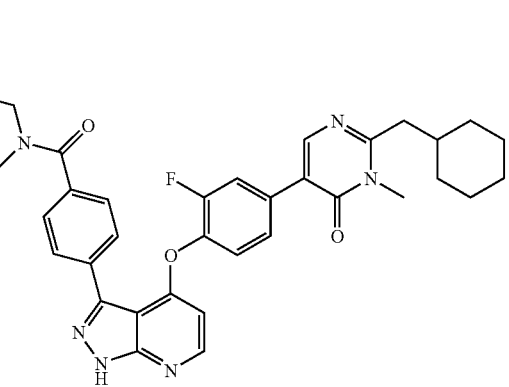

Step A: Preparation of 5-bromo-2-(cyclohexylmethyl)-3-methylpyrimidin-4(3H)-one: A solution of 5-bromo-2-chloro-3-methylpyrimidin-4(3H)-one (0.100 g, 0.448 mmol; prepared according to the procedure of Example 46, Step B) and PdCl$_2$(PPh$_3$)$_2$ (0.016 g, 0.022 mmol) in THF (2.5 mL) was sparged with N$_2$, and then (cyclohexylmethyl)zinc(II) bromide (0.904 ml, 0.452 mmol; 0.5 M solution in THF) was added. The reaction mixture was stirred at 100° C. for 1.5 hours. The reaction mixture was cooled to room temperature and then partitioned between EtOAc and H$_2$O. The aqueous layer was re-extracted with EtOAc (1×). The combined organic layers were dried over Na$_2$SO$_4$, filtered and concentrated. The crude material was purified by flash column chromatography, eluting with 10:1 CH$_2$Cl$_2$/EtOAc to afford 0.047 g (37%) of the product as a waxy yellow solid. LRMS (APCI pos) m/e 285, 287 (M+, Br pattern).

Step B: Preparation of 5-(4-(benzyloxy)-3-fluorophenyl)-2-(cyclohexylmethyl)-3-methylpyrimidin-4(3H)-one: A suspension of 5-bromo-2-(cyclohexylmethyl)-3-methylpyrimidin-4(3H)-one (0.047 g, 0.165 mmol), 4-(benzyloxy)-3-fluorophenylboronic acid (0.049 g, 0.198 mmol), Pd(PPh$_3$)$_4$ (0.009 g, 0.008 mmol) and lithium chloride (0.028 g, 0.659 mmol) in dioxane (1 mL) and 2 M aqueous Na$_2$CO$_3$ (1 mL) was stirred at 100° C. for 1 hour. The reaction mixture was cooled to room temperature and then partitioned between EtOAc and H$_2$O. The layers were separated and the aqueous layer was re-extracted with EtOAc (1×). The combined organic layers were dried over Na$_2$SO$_4$, filtered and concentrated. The crude product was purified by flash column chromatography, eluting with 10:1 CH$_2$Cl$_2$/EtOAc. The product was obtained (0.048 g; 72%) as an off-white solid. LRMS (APCI pos) m/e 407 (M+1).

Step C: Preparation of 2-(cyclohexylmethyl)-5-(3-fluoro-4-hydroxyphenyl)-3-methylpyrimidin-4(3H)-one: A solution of 5-(4-(benzyloxy)-3-fluorophenyl)-2-(cyclohexylmethyl)-3-methylpyrimidin-4(3H)-one (0.046 g, 0.11 mmol) in TFA (2 mL) was stirred at 40° C. for 2.5 hours. The reaction mixture was cooled to room temperature and concentrated to dryness. The crude product was purified by flash column chromatography, eluting with 20:1 CH$_2$Cl$_2$/MeOH. The product was obtained (0.026 g; 73%) as a white foamy solid. LRMS (APCI pos) m/e 317 (M+1).

Step D: Preparation of 2-(cyclohexylmethyl)-5-(3-fluoro-4-(3-iodo-1-(4-methoxybenzyl)-1H-pyrazolo[3,4-b]pyridin-4-yloxy)phenyl)-3-methylpyrimidin-4(3H)-one: A mixture of 2-(cyclohexylmethyl)-5-(3-fluoro-4-hydroxyphenyl)-3-methylpyrimidin-4(3H)-one (0.026 g, 0.082 mmol), 4-chloro-3-iodo-1-(4-methoxybenzyl)-1H-pyrazolo[3,4-b]pyridine (0.033 g, 0.083 mmol; prepared according to the procedure of Example 84, Step D), and DMAP (0.020 g, 0.165 mmol) in bromobenzene (1 mL) under N$_2$ was stirred at 150° C. for 4 days. The reaction was concentrated in vacuo to remove as much bromobenzene as possible and then purified directly by flash column chromatography, eluting with 20:1 CH$_2$Cl$_2$/MeOH. The desired product (0.048 g, 86%) was obtained as a pale yellow solid. LRMS (APCI pos) m/e 680 (M+1).

Step E: Preparation of 2-(cyclohexylmethyl)-5-(3-fluoro-4-(1-(4-methoxybenzyl)-3-(4-(morpholine-4-carbonyl)phenyl)-1H-pyrazolo[3,4-b]pyridin-4-yloxy)phenyl)-3-methylpyrimidin-4(3H)-one: A suspension of 2-(cyclohexylmethyl)-5-(3-fluoro-4-(3-iodo-1-(4-methoxybenzyl)-1H-pyrazolo[3,4-b]pyridin-4-yloxy)phenyl)-3-methylpyrimidin-4(3H)-one (0.025 g, 0.037 mmol), 4-(morpholine-4-carbonyl)phenylboronic acid (0.010 g, 0.044 mmol), Pd(PPh$_3$)$_4$ (0.002 g, 0.002 mmol) and lithium chloride (0.006 g, 0.147 mmol) in dioxane (1 mL) and 2 M aqueous Na$_2$CO$_3$ (1 mL) was stirred at 100° C. for 35 minutes and then at room temperature overnight. The reaction mixture was partitioned between EtOAc and H$_2$O. The layers were separated and the aqueous layer was re-extracted with EtOAc (1×). The combined organic layers were dried over Na$_2$SO$_4$, filtered and concentrated to yield 0.027 g crude product as a yellow gum. The crude material was used without further purification in the following step. LRMS (APCI pos) m/e 743 (M+1).

Step F: Preparation of 2-(cyclohexylmethyl)-5-(3-fluoro-4-(3-(4-(morpholine-4-carbonyl)phenyl)-1H-pyrazolo[3,4-b]pyridin-4-yloxy)phenyl)-3-methylpyrimidin-4(3H)-one: A solution of 2-(cyclohexylmethyl)-5-(3-fluoro-4-(1-(4-methoxybenzyl)-3-(4-(morpholine-4-carbonyl)phenyl)-1H-pyrazolo[3,4-b]pyridin-4-yloxy)phenyl)-3-methylpyrimidin-4 (3H)-one (0.027 g, 0.0363 mmol) in TFA (1 mL) was stirred at 60° C. for 3 minutes and then at ambient temperature overnight. The reaction mixture was concentrated in vacuo and the residue was partitioned between EtOAc and saturated NaHCO$_3$. The layers were separated and the aqueous layer was re-extracted with EtOAc (1×). The combined EtOAc layers were dried over Na$_2$SO$_4$, filtered and concentrated. The crude product was purified by flash column chromatography, eluting with 10:1 CH$_2$Cl$_2$/MeOH. The product was obtained (17.3 mg; 76%) as a yellow solid. $^1$H NMR (400 MHz, DMSO-d$_6$) δ 8.41 (d, 1H), 8.27 (s, 1H), 8.08 (d, 2H), 7.89 (m, 1H), 7.71 (m, 1H), 7.59-7.49 (m, 4H), 6.43 (d, 1H), 3.60 (m, 8H), 3.53 (s, 3H), 2.73 (d, 2H), 1.96 (m, 1H), 1.82-1.59 (m, 5H), 1.34-0.99 (m, 5H). LRMS (APCI pos) m/e 623 (M+1).

Example 92

2-(4-fluorophenyl)-N-(2-(3-methyl-1H-pyrazolo[3,4-b]pyridin-4-yloxy)pyrimidin-5-yl)-3-oxo-2,3-dihydropyridazine-4-carboxamide

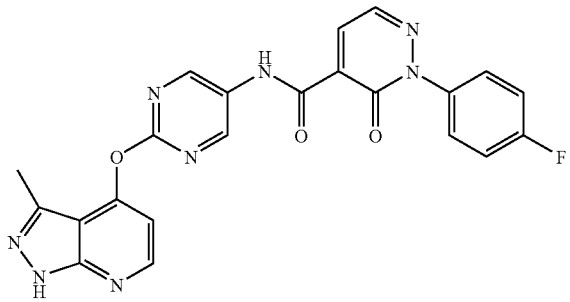

Step A: 1-(4-methoxybenzyl)-3-methyl-4-(5-nitropyrimidin-2-yloxy)-1H-pyrazolo[3,4-b]pyridine: A 100 mL flask was charged with 1-(4-methoxybenzyl)-3-methyl-1H-pyrazolo[3,4-b]pyridin-4-ol (1.00 g, 3.71 mmol obtained from Example 5, step B), 2-chloro-5-nitropyrimidine (0.592 g, 3.71 mmol), cesium carbonate (1.21 g, 3.71 mmol) and DMF (20 mL). The solution was allowed to stir overnight at room temperature for 16.5 hours. The crude product was isolated by filtration and flash chromatography (EtOAc/Hexane 1:2) to afford 0.44 g (29%) of the desired product. LRMS M+1 (393.0) observed.

Step B: 2-(1-(4-methoxybenzyl)-3-methyl-1H-pyrazolo[3,4-b]pyridin-4-yloxy)pyrimidin-5-amine: A 250 mL round-bottomed flask was charged with 1-(4-methoxybenzyl)-3-methyl-4-(5-nitropyrimidin-2-yloxy)-1H-pyrazolo[3,4-b]pyridine (0.420 g, 1.07 mmol), SnCl$_2$ dihydrate (1.45 g, 6.42 mmol), and EtOH (100 mL). The reaction mixture was heated to 70° C. under nitrogen for 2 hours, then concentrated in vacuo. The residue was diluted with EtOAc, water, and brine. Aqueous saturated Na$_2$CO$_3$ was added until the pH was in the 9-10 range. The combined organic phases were dried (Na$_2$SO$_4$). The product was isolated by filtration and flash chromatography (EtOAc/MeOH 95:5) to afford 0.10 g (25%). LRMS M+1 (363.0) observed.

Step C: 2-(4-fluorophenyl)-N-(2-(3-methyl-1H-pyrazolo[3,4-b]pyridin-4-yloxy)pyrimidin-5-yl)-3-oxo-2,3-dihydropyridazine-4-carboxamide: Prepared by 2-step process (Example 19, Step D and Example 13 Step D) from 2-(4-fluorophenyl)-3-oxo-2,3-dihydropyridazine-4-carboxylic acid (0.103 g, 0.442 mmol obtained from Example 19, step C), and 2-(1-(4-methoxybenzyl)-3-methyl-1H-pyrazolo[3,4-b]pyridin-4-yloxy)pyrimidin-5-amine (0.04 g, 0.110 mmol). The crude material was purified by preparative TLC (1.0 mm thickness, EtOAc) to afford 2.3 mg (9%) of the desired product. LRMS M+1 (459.0) observed. $^1$H NMR (400 MHz, CDCl$_3$) δ 11.88 (s, 1H), 9.04 (s, 2H), 8.51 (br s, 1H), 8.40 (m, 1H), 8.27 (m, 1H), 7.59 (m, 2H), 7.23 (m, 2H), 6.94 (m, 1H), 2.50 (s, 3H).

Example 93

N-(4-(3-(4-(Dimethylamino)piperidin-1-yl)-1H-pyrazolo[3,4-b]pyridin-4-yloxy)-3-fluorophenyl)-2-(4-fluorophenyl)-3-oxo-2,3-dihydropyridazine-4-carboxamide

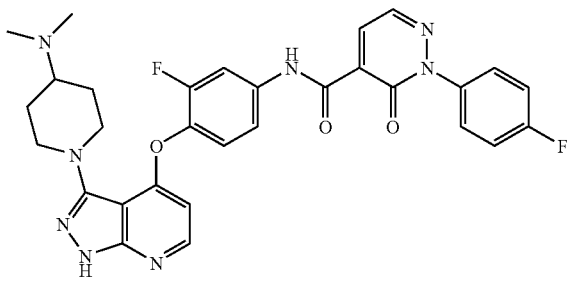

Step A: Preparation of 1-(4-(4-amino-2-fluorophenoxy)-1-(4-methoxybenzyl)-1H-pyrazolo[3,4-b]pyridin-3-yl)-N,N-dimethylpiperidin-4-amine: A 100 mL round-bottomed flask was charged with 4-(1-(4-methoxybenzyl)-3-iodo-1H-pyrazolo[3,4-b]pyridin-4-yloxy)-3-fluorobenzenamine (50.0 mg, 0.102 mmol, prepared in Example 7, step B), N,N-dimethylpiperidin-4-amine (39.2 mg, 0.306 mmol), copper(I)iodide (3.88 mg, 0.0204 mmol), (S)-pyrrolidine-2-carboxylic acid (4.70 mg, 0.0408 mmol), $K_2CO_3$ (70.5 mg, 0.510 mmol) and DMF (10 mL). The reaction mixture was stirred at 100° C. overnight. Then the reaction was cooled to room temperature and partitioned between EtOAc and $H_2O$. The phases were separated and the aqueous phase was re-extracted with EtOAc. The combined organic layers were dried ($Na_2SO_4$), filtered and concentrated to yield a crude product. The crude product was purified by silica gel chromatography (DCM/7 M $NH_3$ in MeOH from 50/1 to 10/1, v/v) to afford product (35.8 mg, 71.6%). LRMS (APCI pos): >98% purity, 254 nm, m/e 491 (M+1).

Step B: Preparation of N-(4-(3-(4-(dimethylamino)piperidin-1-yl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide: A 100 mL round-bottomed flask was charged with 1-(1-(4-methoxybenzyl)-4-(4-amino-2-fluorophenoxy)-1H-pyrazolo[3,4-b]pyridin-3-yl)-N,N-dimethylpiperidin-4-amine (35.8 mg, 0.07298 mmol), 2-(4-fluorophenyl)-3-oxo-2,3-dihydropyridazine-4-carboxylic acid (25.63 mg, 0.1095 mmol), N1-((ethylimino)methylene)-$N^3,N^3$-dimethylpropane-1,3-diamine hydrochloride (69.95 mg, 0.3649 mmol), 1H-benzo[d][1,2,3]triazol-1-ol (49.30 mg, 0.3649 mmol), N-ethyl-N-isopropylpropan-2-amine (47.16 mg, 0.3649 mmol) and DMF (5 mL). The reaction mixture was stirred at room temperature overnight. Then the reaction was partitioned between EtOAc and $H_2O$. The phases were separated and the aqueous phase was re-extracted with EtOAc. The combined organic layers were dried ($Na_2SO_4$), filtered and concentrated to yield a crude product. The crude product was purified by silica gel chromatography (DCM/7 M $NH_3$ in MeOH from 100/1 to 10/1, v/v) to afford product (33.1 mg, 64.18%). LRMS (APCI pos): m/e 707 (M+1).

Step C: Preparation of N-(4-(3-(4-(dimethylamino)piperidin-1-yl)-1H-pyrazolo[3,4-b]pyridin-4-yloxy)-3-fluorophenyl)-2-(4-fluorophenyl)-3-oxo-2,3-dihydropyridazine-4-carboxamide: A 50 mL round-bottomed flask was charged with N-(4-(1-(4-methoxybenzyl)-3-(4-(dimethylamino)piperidin-1-yl)-1H-pyrazolo[3,4-b]pyridin-4-yloxy)-3-fluorophenyl)-2-(4-fluorophenyl)-3-oxo-2,3-dihydropyridazine-4-carboxamide (33.1 mg, 0.0468 mmol) and $CF_3COOH$ (5 mL). The reaction mixture was stirred at 80° C. overnight. Then the solvent was removed and the residue was purified by silica gel chromatography (DCM/7 M $NH_3$ in MeOH from 50/1 to 10/1, v/v) to afford the product (18.3 mg, 66.6%). LRMS (APCI pos): >99% purity, 254 nm, m/e 587 (M+1). $^1$H NMR (400 MHz, $CDCl_3$) δ 11.83 (s, 1H), 10.80 (s, 1H), 8.42 (d, 1H), 8.28 (d, 1H), 8.24 (m, 1H), 7.98 (dd, 1H), 7.60 (m, 2H), 7.41 (d, 1H), 7.21-7.33 (m, 3H), 6.20 (d, 1H), 4.12 (m, 2H), 2.91 (m, 2H), 2.63 (m, 1H), 2.47 (s, 6H), 2.01 (m, 2H), 1.80 (m, 2H).

Example 94

N-(3-fluoro-4-(3-(piperidin-4-yl)-1H-pyrazolo[3,4-b]pyridin-4-yloxy)phenyl)-2-(4-fluorophenyl)-3-oxo-2,3-dihydropyridazine-4-carboxamide

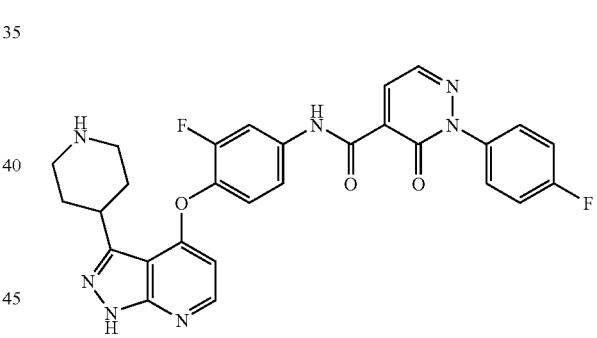

A 50 mL round-bottomed flask was charged with tert-butyl 4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)piperidine-1-carboxylate (30.0 mg, 0.0393 mmol) (Example 105, step D) and $CF_3COOH$ (5 mL). The reaction mixture was stirred at 80° C. overnight. Then the solvent was removed and the residue was purified by silica gel chromatography (DCM/7 M $NH_3$ in MeOH from 50/1 to 10/1, v/v) to afford product (19.5 mg, 91.3%). LRMS (APCI pos): >99% purity, 254 nm, m/e 544 (M+1). $^1$H NMR (400 MHz, $CDCl_3$+$CD_3OD$, 50/50, v/v) δ 11.94 (s, 1H), 8.42 (m, 1H), 8.28 (m, 2H), 8.00 (m, 1H), 7.62 (m, 2H), 7.46 (m, 1H), 7.35 (m, 1H), 7.24-7.32 (m, 2H), 6.16 (d, 1H), 3.64 (m, 1H), 3.50 (m, 2H), 3.14 (m, 2H), 2.38 (m, 2H), 2.25 (m, 2H).

Example 95

N-benzyl-N-(3-fluoro-4-(3-methyl-1H-pyrazolo[3,4-b]pyridin-4-yloxy)phenyl)acetamide

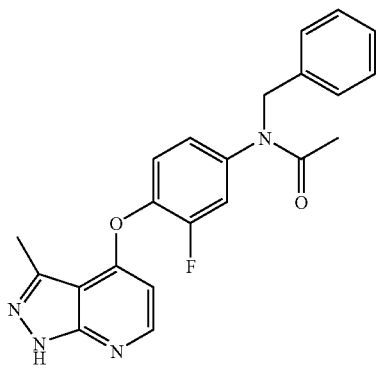

Step A: Preparation of (E)-4-(benzylideneamino)-2-fluorophenol: To a stirred solution of 4-amino-2-fluorophenol (1.27 g, 10 mmol) in 30 mL of toluene at room temperature under nitrogen in a Dean Stark apparatus was added benzaldehyde (1.01 ml, 10 mmol) followed by p-toluenesulfonic acid monohydrate (38 mg, 0.2 mmol). The mixture was heated to reflux for 4 hours. The reaction was cooled to room temperature and a solid crystallized out of the reaction mixture. The mixture was cooled to 0° C. and then filtered and the solids rinsed with toluene. The isolated tan crystals were dried under high vacuum (1.5 gm, 70% yield).

Step B: Preparation of N-benzyl-N-(3-fluoro-4-hydroxyphenyl)acetamide: To a stirred solution of (E)-4-(benzylideneamino)-2-fluorophenol (430 mg, 2 mmol) in 1 mL glacial acetic acid at 0° C. under nitrogen was added a solution of trimethylamine/borane complex (160 mg, 2.2 mmol) in 1 mL glacial acetic acid dropwise by syringe. After complete addition, the reaction was allowed to warm to room temperature and was then heated to reflux overnight. 6N NaOH was then added until pH was neutral. The aqueous solution was extracted with ether, and the combined ether extracts were dried (MgSO$_4$), filtered and concentrated. The material was loaded onto a Biotage 40S column with dichloromethane and eluted with 4/1 hexanes/EtOAc to afford the product as a white solid (200 mg, 39% yield).

Step C: Preparation of N-benzyl-N-(3-fluoro-4-(1-(4-methoxybenzyl)-3-methyl-1H-pyrazolo[3,4-b]pyridin-4-yloxy)phenyl)acetamide: To a stirred solution of N-benzyl-N-(3-fluoro-4-hydroxyphenyl)acetamide (34 mg, 0.13 mmol) and 1-(4-methoxybenzyl)-4-chloro-3-methyl-1H-pyrazolo[3,4-b]pyridine (29 mg, 0.1 mmol) (prepared in Example 43, step E) in 400 µL bromobenzene in a capped reaction vial was added DMAP (25 mg, 0.20 mmol). The solution was heated to 150° C. overnight. The reaction was cooled to ambient temperature and loaded onto a Biotage 12S column with dichloromethane and eluted with ethyl acetate to provide the desired product as a tan solid (38 mg, 74% yield).

Step D: Preparation of N-benzyl-N-(3-fluoro-4-(3-methyl-1H-pyrazolo[3,4-b]pyridin-4-yloxy)phenyl)acetamide: To a flask containing N-benzyl-N-(3-fluoro-4-(1-(4-methoxybenzyl)-3-methyl-1H-pyrazolo[3,4-b]pyridin-4-yloxy)phenyl) acetamide (38 mg, 0.074 mmol) at ambient temperature under a drying tube was added TFA (2 mL). The mixture was heated to 50° C. and stirred for 4 hours. The reaction was cooled to ambient temperature and concentrated. The residue was treated with 5 mL 10% sodium carbonate and then 5 mL dichloromethane. The mixture was rapidly stirred and the layers separated. The aqueous phase was extracted with dichloromethane and the combined organic layers were dried (MgSO$_4$), filtered, and concentrated. The crude material was loaded onto a Biotage 12S column with dichloromethane and eluted with 7/3 EtOAc/hexanes to provide the desired product as a white foam (17 mg, 59% yield). $^1$H NMR (400 MHz, CDCl$_3$) δ 11.68 (br s, 1H), 8.35 (m, 1H), 7.31 (m, 3H), 7.23 (m, 3H), 6.93 (m, 2H), 6.16 (d, 1H), 4.93 (s, 2H), 2.73 (s, 3H), 2.00 (br s, 3H). LCMS (APCI+): m/z 391 (M+1) detected.

Example 96

N-(2,5-difluoro-4-(3-methyl-1H-pyrazolo[3,4-b]pyridin-4-yloxy)phenyl)-2-(4-fluorophenyl)-3-oxo-2,3-dihydropyridazine-4-carboxamide

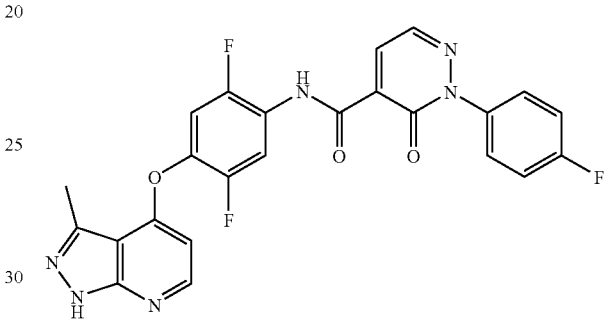

Step A: 4-(2,5-difluoro-4-nitrophenoxy)-1-(4-methoxybenzyl)-3-methyl-1H-pyrazolo[3,4-b]pyridine: A 100 mL flask was charged with 1-(4-methoxybenzyl)-3-methyl-1H-pyrazolo[3,4-b]pyridin-4-ol (1.00 g, 3.71 mmol obtained from Example 5, step B), 1,2,4-trifluoro-5-nitrobenzene (1.32 g, 7.43 mmol), potassium carbonate (1.03 g, 7.43 mmol), and DMF (25 mL). The solution was allowed to stir overnight at room temperature for 3 days. The crude material was isolated by filtration and flash chromatography (EtOAc/Hexane 1:3) to afford 2.50 g (55%) of the desired product. LRMS M+1 (426.9) observed.

Step B: 2,5-difluoro-4-(1-(4-methoxybenzyl)-3-methyl-1H-pyrazolo[3,4-b]pyridin-4-yloxy)aniline: Prepared by process from Example 92 Step B using 1-(4-methoxybenzyl)-4-(2,5-difluoro-4-nitrophenoxy)-3-methyl-1H-pyrazolo[3,4-b]pyridine (2.50 g, 5.86 mmol). The crude material was purified by silica gel chromotography (EtOAc/Hexane 1:2) to afford 0.75 g (35%) of the desired product. LRMS M+1 (397.1) observed.

Step C: N-(2,5-difluoro-4-(3-methyl-1H-pyrazolo[3,4-b]pyridin-4-yloxy)phenyl)-2-(4-fluorophenyl)-3-oxo-2,3-dihydropyridazine-4-carboxamide: Charge a 100 mL round-bottomed flask with 2-(4-fluorophenyl)-3-oxo-2,3-dihydropyridazine-4-carboxylic acid (0.103 g, 0.442 mmol obtained from Example 19, step C), and CH$_2$Cl$_2$ (10 mL). Oxalyl chloride in DCM (2M) (2.84 ml, 5.68 mmol) and DMF (3 drops) were added. The reaction mixture was stirred for 1 hour and concentrated. The crude material was resuspend in DCM and 4-(1-(4-methoxybenzyl)-3-methyl-1H-pyrazolo[3,4-b]pyridin-4-yloxy)-2,5-difluorobenzenamine (0.750 g, 1.89 mmol), N,N-dimethylpyridin-4-amine (0.0231 g, 0.189 mmol) and triethylamine (0.287 g, 2.84 mmol) were added. The reaction mixture was stirred at r ambient temperature for 16 hours, then diluted with water and DCM. The organic layer washed with brine, dried over sodium sulfate, filtered and concentrated. The crude material was purified by chromatography, eluting with EtOAc and concentrated. To the crude material in a 25 mL RBF was add TFA (3 mL). The mixture was heated to 70° C. for 2 hours, then cooled to ambient temperature and concentrated. The residue was triturated with DCM/MeOH 1:1 (5 mL) to afford 461 mg (46%) of the desired product. LRMS M+1 (493.1) observed. $^1$H NMR (400 MHz, DMSOd6) δ12.14 (s, 1H), 8.54 (s, 1H), 8.43 (m, 1H), 8.36 (m, 1H), 8.30 (m, 1H), 7.77 (m, 1H), 7.68 (m, 2H), 7.42 (t, J=8 Hz, 2H), 6.35 (d, J=5 Hz, 1H), 2.62 (s, 3H).

Example 97

N-(2,3-difluoro-4-(3-methyl-1H-pyrazolo[34-b]pyridin-4-yloxy)phenyl)-2-(4-fluorophenyl)-3-oxo-2,3-dihydropyridazine-4-carboxamide

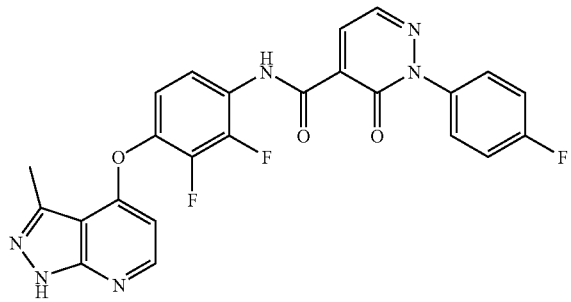

Step A: 1-(4-methoxybenzyl)-4-(2,3-difluoro-4-nitrophenoxy)-3-methyl-1H-pyrazolo[3,4-b]pyridine: Prepared according to the procedure of Example 96, substituting 1,2,3-trifluoro-4-nitrobenzene (1.51 g, 8.54 mmol) for 1,2,4-trifluoro-5-nitrobenzene to provide 2.24 g (67%) of the desired product. LRMS M+1 (426.9) observed.

Step B: 4-(1-(4-methoxybenzyl)-3-methyl-1H-pyrazolo[3,4-b]pyridin-4-yloxy)-2,3-difluorobenzenamine: Prepared by process of Example 92 Step B, substituting 1-(4-methoxybenzyl)-4-(2,3-difluoro-4-nitrophenoxy)-3-methyl-1H-pyrazolo[3,4-b]pyridine (2.24 g, 5.25 mmol). The crude material was purified by chromatography (EtOAc/Hexane 1:2) to afford 1.00 g (45%) as a mixture of the desired product and the ortho SnAr product. The crude material was in the next step without purification. LRMS M+1 (397.1) observed.

Step C: N-(2,3-difluoro-4-(3-methyl-1H-pyrazolo[3,4-b]pyridin-4-yloxy)phenyl)-2-(4-fluorophenyl)-3-oxo-2,3-dihydropyridazine-4-carboxamide: Prepared by process of Example 9 Step C, substituting 4-(1-(4-methoxybenzyl)-3-methyl-1H-pyrazolo[3,4-b]pyridin-4-yloxy)-2,3-difluorobenzenamine (15 mg, 0.0378 mmol). The crude material was purified by preparative TLC (1.0 mm thickness, EtOAc/Hexane 3:1) to afford 4.3 mg (20%) of the desired product. LRMS M+1 (493.3) observed. $^1$H NMR (400 MHz, DMSO-d6) δ 12.14 (s, 1H), 8.54 (s, 1H), 8.43 (m, 1H), 8.36 (m, 1H), 8.30 (m, 1H), 7.68 (m, 2H), 7.42 (t, J=8 Hz, 2H), 7.15 (m, 1H), 6.35 (d, J=5 Hz, 1H), 2.62 (s, 3H).

Example 98

N-(4-(3-(4-(dimethylamino)piperidin-1-yl)-1H-pyrazolo[3,4-b]pyridin-4-yloxy)-3-fluorophenyl)-3-(4-fluorophenyl)-2-oxo-3-azabicyclo[3.1.0]hexane-1-carboxamide

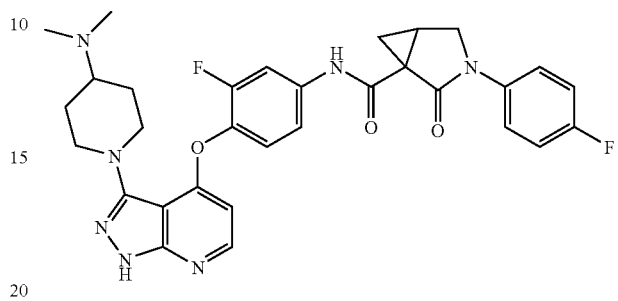

Step A: Preparation of N-allyl-4-fluorobenzenamine: A suspension of 4-fluorobenzenamine (25 g, 225 mmol), 3-bromoprop-1-ene (19.0 ml, 225 mmol) and K$_2$CO$_3$ (31.1 g, 225 mmol) was stirred in THF (1 L) for 2 days. Water (20 mL) and EtOAc (1 L) were added into the reaction mixture. The organic layer was separated and washed with brine, dried with Na$_2$SO$_4$, filtered and concentrated. The residue was purified by flash column chromatography (20% EtOAc in hexane) to afford the product (16 g, 47.0% yield) as an orange oil.

Step B: Preparation of methyl 3-(allyl(4-fluorophenyl)amino)-3-oxopropanoate: Methyl 3-chloro-3-oxopropanoate (9.4 ml, 87 mmol) was added into a solution of N-allyl-4-fluorobenzenamine (12 g, 79 mmol), DIEA (15 ml, 87 mmol) and DMAP (0.97 mg, 7.9 mmol) in CH$_2$Cl$_2$ (200 mL) at 0° C. under nitrogen. The reaction was stirred at 0° C. for 1 hour. The reaction mixture was poured into ice and water, extracted with CH$_2$Cl$_2$, washed with saturated aqueous NaHCO$_3$ and brine. The organic layer was dried with Na$_2$SO$_4$, filtered and concentrated. The residue was purified by flash column chromatography (50% EtOAc in hexane) to afford the product (18.3 g, 92% yield) as brown oil.

Step C: Preparation of methyl 3-(4-fluorophenyl)-2-oxo-3-aza-bicyclo[3.1.0]hexane-1-carboxylate: A solution of methyl 3-(allyl(4-fluorophenyl)amino)-3-oxopropanoate (10 g, 39.7 mmol) in acetic acid (50 mL) was added into a suspension of manganese(III)acetate dihydrate (21 g, 79.7 mmol) and copper (II) acetate monohydrate (7.9 g, 39.7 mmol) in acetic acid (200 mL). The reaction was stirred for 3 days, then quenched with 10% aqueous sodium bisulfite solution (100 mL). The reaction mixture was diluted with EtOAc, washed with saturated aqueous NaHCO$_3$, brine, dried with Na$_2$SO$_4$, filtered and concentrated. The residue was purified by flash column chromatography (50% EtOAc in hexane) to afford the product (1.2 g, 12% yield) as a brown powder. LRMS (APCI pos) m/e 250.1 (M+1).

Step D: Preparation of 3-(4-fluorophenyl)-2-oxo-3-aza-bicyclo[3.1.0]hexane-1-carboxylic acid: LiOH (0.2 g, 8.4 mmol) was added into a suspension of methyl 3-(4-fluorophenyl)-2-oxo-3-aza-bicyclo[3.1.0]hexane-1-carboxylate (1.2 g, 4.8 mmol) in THF (20 mL) and water (1 mL). The reaction was stirred for 1 hour. The reaction mixture was poured into water and the solution brought to pH 4 with 1M HCl. The mixture was extracted with EtOAc, washed with brine, dry with Na$_2$SO$_4$, filtered and concentrated to afford the title compound (1 g, 79% yield) as a light brown solid. LRMS (APCI pos) m/e 235.9 (M+1).

Step E: Preparation of N-(4-(3-(4-(dimethylamino)piperidin-1-yl)-1-(4-methoxybenzyl)-1H-pyrazolo[3,4-b]pyridin-4-yloxy)-3-fluorophenyl)-3-(4-fluorophenyl)-2-oxo-3-azabicyclo[3.1.0]hexane-1-carboxamide: A solution of 1-(1-(4-methoxybenzyl)-4-(4-amino-2-fluorophenoxy)-1H-pyrazolo[3,4-b]pyridin-3-yl)-N,N-dimethylpiperidin-4-amine (39 mg, 0.079 mmol, obtained from Example 93, Step A), 3-(4-fluorophenyl)-2-oxo-3-aza-bicyclo[3.1.0]hexane-1-carboxylic acid (37 mg, 0.16 mmol), EDCI (91 mg, 0.48 mmol) and HOBT (64 mg, 0.48 mmol) was stirred in DMF (10 mL) for 12 hours. The reaction mixture was poured into saturated aqueous NH$_4$Cl and extracted with EtOAc. The organic layer washed with NaHCO$_3$, 10% aqueous LiCl, dry with Na$_2$SO$_4$, filtered and concentrated. The residue was purified with flash silica gel chromatography (5% MeOH in CH$_2$Cl$_2$) to afford the product (30 mg, 53%) as a white solid. LRMS (APCI pos) m/e 708.3 (M+1).

Step F: Preparation of N-(4-(3-(4-(dimethylamino)piperidin-1-yl)-1H-pyrazolo[3,4-b]pyridin-4-yloxy)-3-fluorophenyl)-3-(4-fluorophenyl)-2-oxo-3-aza-bicyclo[3.1.0]hexane-1-carboxamide: A solution of N-(4-(1-(4-methoxybenzyl)-3-(4-(dimethylamino)piperidin-1-yl)-1H-pyrazolo[3,4-b]pyridin-4-yloxy)-3-fluorophenyl)-3-(4-fluorophenyl)-2-oxo-3-aza-bicyclo[3.1.0]hexane-1-carboxamide (30 mg, 0.042 mmol) was heated in TFA (2 mL) for 4 hours. Excess TFA was evaporated and the residue was purified on a SCX column (7N ammonia in MeOH) to afford the product (17 mg, 68% yield) as a yellow solid. LRMS (APCI pos) m/e 588.2 (M+1). $^1$H NMR (400 MHz, CDCl$_3$) δ 10.50 (s, 1H), 9.80 (s, 1H), 8.30 (s, 1H), 7.78-7.90 (m, 1H), 7.40-7.60 (m, 2H), 7.00-7.40 (m, 4H), 6.10-6.20 (m, 1H), 4.00-4.20 (m, 4H), 3.70-3.80 (m, 1H), 2.80-3.00 (m, 4H), 2.40 (s, 6H), 1.20-2.10 (m, 5H).

Example 99

N-(3-fluoro-4-(3-(piperazin-1-yl)-1H-pyrazolo[3,4-b]pyridin-4-yloxy)phenyl)-3-(4-fluorophenyl)-2-oxo-3-azabicyclo[3.1.0]hexane-1-carboxamide

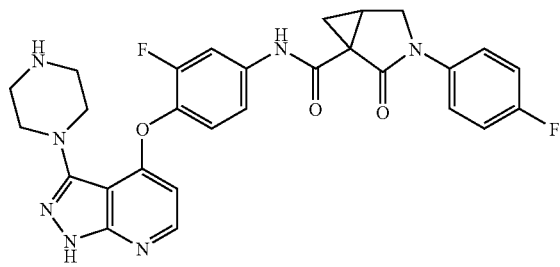

Step A: Preparation of tert-butyl 4-(1-(4-methoxybenzyl)-4-(2-fluoro-4-(3-(4-fluorophenyl)-2-oxo-3-aza-bicyclo[3.1.0]hexane-1-carboxamido)phenoxy)-1H-pyrazolo[3,4-b]pyridin-3-yl)piperazine-1-carboxylate: A solution of tert-butyl 4-(1-(4-methoxybenzyl)-4-(4-amino-2-fluorophenoxy)-1H-pyrazolo[3,4-b]pyridin-3-yl)piperazine-1-carboxylate (100 mg, 0.182 mmol, obtained from Example 82 Step A), 3-(4-fluorophenyl)-2-oxo-3-aza-bicyclo[3.1.0]hexane-1-carboxylic acid (85.7 mg, 0.365 mmol, obtained from Example 98 Step D), EDCI (210 mg, 1.09 mmol) and HOBT (148 mg, 1.09 mmol) was stirred in DMF (6 mL) for 12 hours. The reaction mixture was poured into saturated aqueous NH$_4$Cl and extracted with EtOAc. The organic layer was washed with saturated aqueous NaHCO$_3$, 10% aqueous LiCl, dry with Na$_2$SO$_4$, filtered and concentrated. The residue was purified by flash silica gel chromatography (5% MeOH in CH$_2$Cl$_2$) to afford the product (100 mg, 71.6% yield) as a white solid. LRMS (APCI pos) m/e 766.2 (M+1).

Step B: Preparation of N-(3-fluoro-4-(3-(piperazin-1-yl)-1H-pyrazolo[3,4-b]pyridin-4-yloxy)phenyl)-3-(4-fluorophenyl)-2-oxo-3-aza-bicyclo[3.1.0]hexane-1-carboxamide: A solution of tert-butyl 4-(1-(4-methoxybenzyl)-4-(2-fluoro-4-(3-(4-fluorophenyl)-2-oxo-3-aza-bicyclo[3.1.0]hexane-1-carboxamido)phenoxy)-1H-pyrazolo[3,4-b]pyridin-3-yl)piperazine-1-carboxylate (100 mg, 0.131 mmol) was heated in TFA (4 mL) for 12 hours. Excess TFA was removed and the residue was purified by flash column chromatography (20% MeOH in CH$_2$Cl$_2$) to afford the product N-(3-fluoro-4-(3-(piperazin-1-yl)-1H-pyrazolo[3,4-b]pyridin-4-yloxy)phenyl)-3-(4-fluorophenyl)-2-oxo-3-aza-bicyclo[3.1.0]hexane-1-carboxamide (32 mg, 44.9% yield) as a yellow solid. LRMS (APCI pos) m/e 546.3 (M+1). $^1$H NMR (DMSO-d$_6$, 400 MHz) δ 12.90 (s, 1H), 10.48 (s, 1H), 8.88 (s, br, 1H), 8.25 (d, 1H), 7.92 (d, 1H), 7.60-7.69 (m, 2H), 7.47-7.53 (m, 2H), 7.22-7.30 (m, 2H), 6.16-6.22 (d, 1H), 4.09-4.17 (m, 1H), 3.77-3.80 (m, 1H), 3.50-3.60 (m, 1H), 3.35-3.40 (m, 1H), 3.22-3.33 (m, 4H), 3.16-3.21 (m, 1H), 2.66-2.74 (m, 1H), 1.80-1.84 (m, 1H), 1.46-1.52 (m, 1H), 1.06-1.12 (m, 1H).

Example 100

N-(2-chloro-5-fluoro-4-(3-methyl-1H-pyrazolo[3,4-b]pyridin-4-yloxy)phenyl)-2-(4-fluorophenyl)-3-oxo-2,3-dihydropyridazine-4-carboxamide

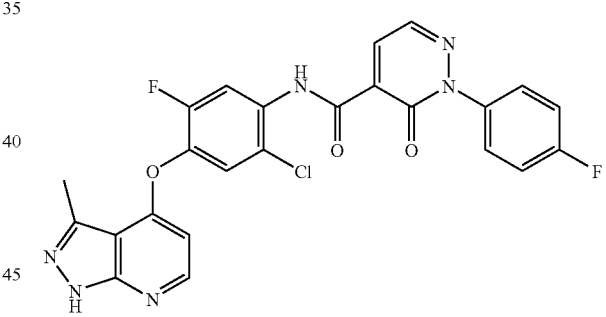

Step A: 1-(4-methoxybenzyl)-4-(5-chloro-2-fluoro-4-nitrophenoxy)-3-methyl-1H-pyrazolo[3,4-b]pyridine: Made according to the procedure of Example 96, Step A substituting 1-chloro-4,5-difluoro-2-nitrobenzene (0.791 g, 4.08 mmol made from US20040082784) for 1,2,4-trifluoro-5-nitrobenzene to provide the desired product (1.59; 96%). LRMS M+1 (443.0) observed.

Step B: 4-(1-(4-methoxybenzyl)-3-methyl-1H-pyrazolo[3,4-b]pyridin-4-yloxy)-2-chloro-5-fluorobenzenamine: Prepared by process from Example 92, Step B, substituting 1-(4-methoxybenzyl)-4-(5-chloro-2-fluoro-4-nitrophenoxy)-3-methyl-1H-pyrazolo[3,4-b]pyridine (1.59 g, 3.59 mmol). The reaction mixture was diluted with EtOAc (250 mL) and saturated Na$_2$CO$_3$ (50 mL) was added. The solids were filtered through a celite plug and the organic layer was dried over sodium sulfate and concentrated to provide the desired product (1.25 g, 85%). The crude material was used in the next step without purification. LRMS M+1 (413.0) observed.

Step C: N-(2,3-difluoro-4-(3-methyl-1H-pyrazolo[3,4-b]pyridin-4-yloxy)phenyl)-2-(4-fluorophenyl)-3-oxo-2,3-dihydropyridazine-4-carboxamide: Prepared by process from Example 9, Step C, substituting 4-(1-(4-methoxybenzyl)-3-methyl-1H-pyrazolo[3,4-b]pyridin-4-yloxy)-2-chloro-5-fluorobenzenamine (0.500 g, 1.21 mmol). The crude material was purified by reverse phase HPLC to afford 17.7 mg (3%). LRMS M+1 (508.9) observed. $^1$H NMR (400 MHz, CDCl$_3$) δ 12.31 (s, 1H), 8.69 (d, J=12 Hz, 1H), 8.41 (m, 2H), 8.28 (d, J=5 Hz, 1H), 7.92 (d, J=8 Hz, 1H), 7.69 (m, 3H), 7.43 (t, J=8 Hz, 2H), 6.34 (d, J=5 Hz, 1H), 2.62 (s, 3H)

Example 101

N-(3-fluoro-4-(3-(1-methylpiperidin-4-ylamino)-1H-pyrazolo[3,4-b]pyridin-4-yloxy)phenyl)-2-(4-fluorophenyl)-3-oxo-2,3-dihydropyridazine-4-carboxamide

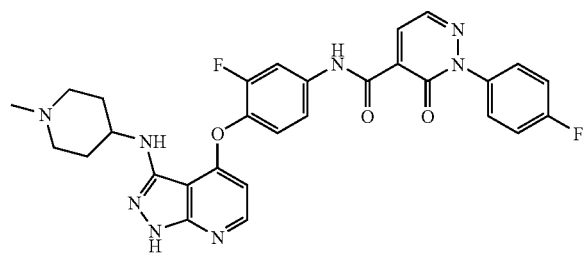

Step A: Preparation of 4-(4-amino-2-fluorophenoxy)-1-(4-methoxybenzyl)-N-(1-methylpiperidin-4-yl)-1H-pyrazolo[3,4-b]pyridin-3-amine: A mixture of 4-(1-(4-methoxybenzyl)-3-iodo-1H-pyrazolo[3,4-b]pyridin-4-yloxy)-3-fluorobenzenamine (0.10 g, 0.20 mmol; prepared as in Example 7, Step B), 1-methylpiperidin-4-amine (0.070 g, 0.61 mmol), (S)-pyrrolidine-2-carboxylic acid (9.4 mg, 0.82 mmol), CuI (7.8 mg, 0.041 mmol), and K$_2$CO$_3$ (0.14 g, 1.0 mmol) was heated in DMSO (4 mL) with sealed tube at 100° C. for 17 hours. The reaction mixture was cooled to ambient temperature and treated with CH$_2$Cl$_2$, washed with water, dried over MgSO$_4$, and concentrated to give crude material which was purified by silica gel flash column chromatography (10% MeOH in CH$_2$Cl$_2$) to afford 49 mg (50%) of the desired product. LRMS (ESI pos) m/e 477.1 (M+1).

Step B: Preparation of N-(3-fluoro-4-(3-(1-methylpiperidin-4-ylamino)-1H-pyrazolo[3,4-b]pyridin-4-yloxy)phenyl)-2-(4-fluorophenyl)-3-oxo-2,3-dihydropyridazine-4-carboxamide: Prepared by a 2-step process from 4-(4-amino-2-fluorophenoxy)-1-(4-methoxybenzyl)-N-(1-methylpiperidin-4-yl)-1H-pyrazolo[3,4-b]pyridin-3-amine and 2-(4-fluorophenyl)-3-oxo-2,3-dihydropyridazine-4-carboxylic acid (prepared as in Example 19, Step C) according to the procedure described for Example 21, Steps A and B, except that the crude was treated with aqueous NaHCO$_3$). The crude was rinsed with Et$_2$O to afford 34 mg (96%) of the desired product. LRMS (ESI pos) m/e 573.0 (M+1). $^1$H-NMR (400 MHz, CDCl$_3$/CD$_3$OD) δ 8.39 (d, 1H), 8.32 (d, 1H), 8.14 (d, 1H), 8.03 (dd, 1H), 7.66 (m, 2H), 7.48 (m, 1H), 7.39 (t, 1H), 7.28 (t, 2H), 6.12 (d, 1H), 3.76 (m, 1H), 3.25 (m, 2H), 2.51 (m, 2H), 2.46 (s, 3H), 2.25 (m, 2H), 1.73 (m, 2H); $^{19}$F-NMR (376 MHz, CDCl3/CD3OD) δ −113.8, −128.4.

Example 102

2-(benzo[d]oxazol-2-yl)-N-(4-(3-(4-(dimethylamino)piperidin-1-yl)-1H-pyrazolo[3,4-b]pyridin-4-yloxy)-3-fluorophenyl)acetamide

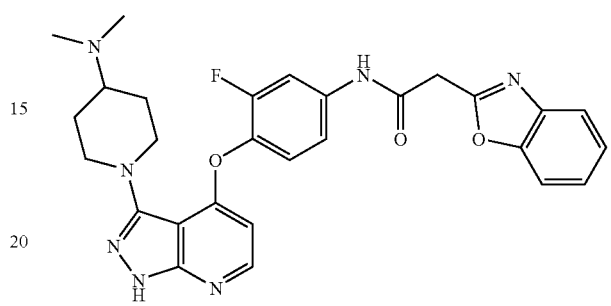

Prepared by a 2-step process from 1-(4-(4-amino-2-fluorophenoxy)-1-(4-methoxybenzyl)-1H-pyrazolo[3,4-b]pyridin-3-yl)-N,N-dimethylpiperidin-4-amine (prepared as in Example 93, Step A) and 2-(benzo[d]oxazol-2-yl)acetic acid according to the procedure of Example 21, Steps A and B, except that the crude was treated with aqueous NaHCO$_3$ solution to remove TFA. The crude was rinsed with Et$_2$O to afford 13 mg (80%) of the desired product. LRMS (ESI pos) m/e 530.1 (M+1). $^1$H-NMR (400 MHz, CD$_3$OD/CDCl$_3$) δ 8.20 (d, 1H), 7.86 (dd, 1H), 7.72 (m, 1H), 7.60 (m, 1H), 7.41 (m, 3H), 7.30 (t, 1H), 6.22 (d, 1H), 4.15 (m, 2H), 2.95 (t, 3H), 2.64 (s, 6H), 2.09 (m, 2H), 1.84 (m, 2H); $^{19}$F-NMR (376 MHz, CD$_3$OD/CDCl$_3$) δ −128.7.

Example 103

(S)—N-(4-(3-(3-(dimethylamino)pyrrolidin-1-yl)-1H-pyrazolo[3,4-b]pyridin-4-yloxy)-3-fluorophenyl)-2-(4-fluorophenyl)-3-oxo-2,3-dihydropyridazine-4-carboxamide

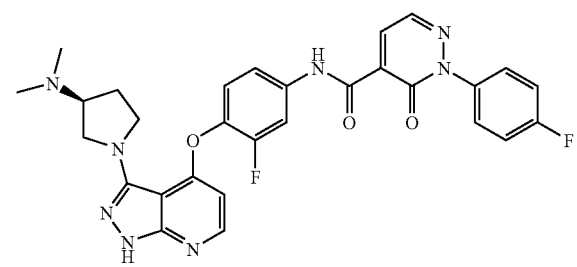

Step A: Preparation of (S)-1-(4-(4-amino-2-fluorophenoxy)-1-(4-methoxybenzyl)-1H-pyrazolo[3,4-b]pyridin-3- yl)-N,N-dimethylpyrrolidin-3-amine: To a stirred solution of 4-(1-(4-methoxybenzyl)-3-iodo-1H-pyrazolo[3,4-b]pyridin-4-yloxy)-3-fluorobenzenamine (49 mg, 0.1 mmol) (prepared in Example 7, step B) in 300 μL DMSO at ambient temperature in a capped reaction vial was added (S)—N,N-dimethylpyrrolidin-3-amine (19 uL, 0.15 mmol) followed by K₂CO₃ (27 mg, 0.2 mmol), Cu(I)I (19 mg, 0.01 mmol) and L-proline (2.3 mg, 0.02 mmol). The mixture was heated 90° C. overnight, then the mixture was cooled to room temperature, diluted to 30 mL with dichloromethane and washed with H₂O. The organic layer was dried (MgSO₄), filtered and concentrated. The crude product was loaded onto a Biotage 12S column with dichloromethane and eluted with 5/95 MeOH/dichloromethane to provide the product as a tan oil (9.5 mg, 20% yield).

Step B: Preparation of (S)—N-(4-(3-(3-(dimethylamino)pyrrolidin-1-yl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide: To a stirred suspension of 2-(4-fluorophenyl)-3-oxo-2,3-dihydropyridazine-4-carboxylic acid (prepared in Example 19, step C) (7 mg, 0.03 mmol) in 300 μL dichloromethane at room temperature under nitrogen was added DIEA (10 μL, 0.06 mmol) followed by EDCI (5.7 mg, 0.03 mmol) and HOBT-H₂O (4.6 mg, 0.03 mmol). After stirring for 10 minutes, a solution of (S)-1-(1-(4-methoxybenzyl)-4-(4-amino-2-fluorophenoxy)-1H-pyrazolo[3,4-b]pyridin-3-yl)-N,N-dimethylpyrrolidin-3-amine (9.5 mg, 0.02 mmol) in 300 μL dichloromethane was added. After stirring overnight, the reaction was diluted to 30 mL with CH₂Cl₂ and washed with 10% sodium carbonate solution. The organic layers were dried (MgSO₄), filtered and concentrated. The crude product was loaded onto a Biotage 12S column with dichloromethane and eluted with a step gradient of dichloromethane (150 mL), 2.5/97.5 MeOH/dichloromethane (150 mL) and 5/95 MeOH/dichloromethane (200 mL) to afford the desired product as a tan oil (14 mg, 100%).

Step C: Preparation of (S)—N-(4-(3-(3-(dimethylamino)pyrrolidin-1-yl)-1H-pyrazolo[3,4-b]pyridin-4-yloxy)-3-fluorophenyl)-2-(4-fluorophenyl)-3-oxo-2,3-dihydropyridazine-4-carboxamide: To a flask containing (S)—N-(4-(1-(4-methoxybenzyl)-3-(3-(dimethylamino)pyrrolidin-1-yl)-1H-pyrazolo[3,4-b]pyridin-4-yloxy)-3-fluorophenyl)-2-(4-fluorophenyl)-3-oxo-2,3-dihydropyridazine-4-carboxamide (14 mg, 0.02 mmol) at ambient temperature under a drying tube was added TFA (1 mL), and the reaction mixture was heated at 50° C. overnight. After cooling, the reaction was concentrated to dryness and then redissolved in 5 mL dichloromethane, to which 5 mL of 10% sodium carbonate was added. After stirring for a few minutes, the layers were separated and the organics were washed with 10% sodium carbonate. The organics were dried (MgSO₄), filtered and concentrated to a crude oil. Biotage 12S with step gradient of dichloromethane (100 mL), 5/95 MeOH/dichloromethane (100 mL), and 9/1 dichloromethane/MeOH (200 mL) eluted the product. The product containing fractions were pooled and concentrated to a yellow solid (4.2 mg, 36%). ¹H NMR (400 MHz, CDCl₃) δ 11.83 (br s, 1H), 8.41 (d, 1H), 8.23 (m, 1H), 7.96 (m, 1H), 7.60 (m, 2H), 7.40 (m, 1H), 7.24 (m, 2H), 6.16 (d, 1H), 3.82 (m, 1H), 3.72 (m, 2H), 3.56 (m, 1H), 2.87 (m, 1H), 2.30 (s, 6H), 2.20 (m, 1H), 1.94 (m, 1H). LCMS (APCI+): m/z 573 (M+1) detected.

Example 104

(R)—N-(4-(3-(3-(dimethylamino)pyrrolidin-1-yl)-1H-pyrazolo[3,4-b]pyridin-4-yloxy)-3-fluorophenyl)-2-(4-fluorophenyl)-3-oxo-2,3-dihydropyridazine-4-carboxamide

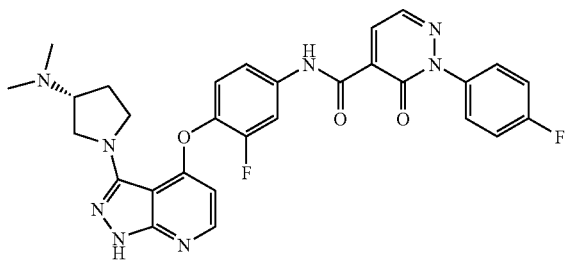

Step A: Preparation of (R)-1-(4-(4-amino-2-fluorophenoxy)-1-(4-methoxybenzyl)-1H-pyrazolo[3,4-b]pyridin-3-yl)-N,N-dimethylpyrrolidin-3-amine: To a stirred suspension of 4-(1-(4-methoxybenzyl)-3-iodo-1H-pyrazolo[3,4-b]pyridin-4-yloxy)-3-fluorobenzenamine (49 mg, 0.1 mmol) (prepared according to Example 7, step B) and (R)—N,N-dimethylpyrrolidin-3-amine (23 mg, 0.2 mmol) in 300 μL THF at ambient temperature in a capped reaction vial was added racemic Binap (9 mg, 0.015 mmol) followed by NaOtBu (14 mg, 0.15 mmol) and 18-crown-6 (40 mg, 0.1499 mmol). The reaction purged with nitrogen gas and then held under a balloon of nitrogen. Pd(dba)₂ (6 mg, 0.01 mmol) was then added and the reaction was sealed and heated to 40° C. After stirring for 72 hours, the reaction was cooled to ambient temperature, diluted to 30 mL with dichloromethane and washed with 10% sodium carbonate solution. The organics were dried (MgSO₄), filtered and concentrated. The brown residue was dissolved in a minimum of dichloromethane and loaded onto a Biotage 12S column. The column was eluted with 95/5 dichloromethane/MeOH to provide the product as a tan foam (40 mg, 84%).

Step B: Preparation of (R)—N-(4-(3-(3-(dimethylamino)pyrrolidin-1-yl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide: Carried out according to the procedure of Example 103, Step B, substituting (R)-1-(1-(4-methoxybenzyl)-4-(4-amino-2-fluorophenoxy)-1H-pyrazolo[3,4-b]pyridin-3-yl)-N,N-dimethylpyrrolidin-3-amine for (S)-1-(1-(4-methoxybenzyl)-4-(4-amino-2-fluorophenoxy)-1H-pyrazolo[3,4-b]pyridin-3-yl)-N,N-dimethylpyrrolidin-3-amine. The product was isolated as a tan oil (36 mg, 99%).

Step C: Preparation of (R)—N-(4-(3-(3-(dimethylamino)pyrrolidin-1-yl)-1H-pyrazolo[3,4-b]pyridin-4-yloxy)-3-fluorophenyl)-2-(4-fluorophenyl)-3-oxo-2,3-dihydropyridazine-4-carboxamide: Carried out according to the procedure of Example 103, Step C, substituting (R)—N-(4-(3-(3-(dimethylamino)pyrrolidin-1-yl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide for (S)—N-(4-(3-(3-(dimethylamino)pyrrolidin-1-yl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide. The crude material was purified to provide the product as a yellow solid (11 mg, 37%). ¹H NMR (400 MHz, CDCl₃) δ 11.83 (br s, 1H), 10.25 (br s, 1H), 8.43 (d, 1H), 8.24 (d, 1H), 8.22 (br s, 1H), 7.96 (m, 1H), 7.61 (m, 2H), 7.40 (d, 1H), 7.25 (m, 3H), 6.15 (d, 1H), 3.83 (m, 1H), 3.73 (m, 2H), 3.57 (m, 1H), 2.88 (m, 1H), 2.30 (s, 6H), 2.20 (m, 1H), 1.95 (m, 1H). LCMS (APCI+): m/z 573 (M+1) detected.

Example 105

N-(3-Fluoro-4-(3-(1-methylpiperidin-4-yl)-1H-pyrazolo[3,4-b]pyridin-4-yloxy)phenyl)-2-(4-fluorophenyl)-3-oxo-2,3-dihydropyridazine-4-carboxamide

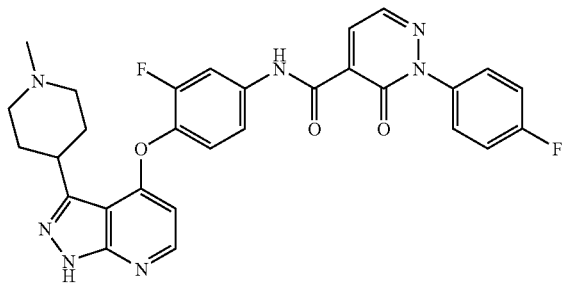

Step A: Preparation of tert-butyl 4-(4-(4-amino-2-fluorophenoxy)-1-(4-methoxybenzyl)-1H-pyrazolo[3,4-b]pyridin-3-yl)-5,6-dihydropyridine-1(2H)-carboxylate: A 100 mL round-bottomed flask was charged with 4-(1-(4-methoxybenzyl)-3-iodo-1H-pyrazolo[3,4-b]pyridin-4-yloxy)-3-fluorobenzenamine (250.0 mg, 0.5099 mmol, prepared in Example 7, step B), tert-butyl 4-(4,4,5,5-tetramethyl-1,3,2-dioxaborolan-2-yl)-5,6-dihydropyridine-1(2H)-carboxylate (315.3 mg, 1.020 mmol), tetrakis(triphenylphosphine)palladium (117.8 mg, 0.1020 mmol), 1M Na$_2$CO$_3$ (1.275 ml, 2.550 mmol) and DME (25 mL). The reaction mixture was stirred at 100° C. overnight. The reaction was cooled to room temperature and partitioned between EtOAc and H$_2$O. The phases were separated and the aqueous phase was re-extracted with EtOAc. The combined organic layers were dried (Na$_2$SO$_4$), filtered and concentrated to yield a crude product. The crude material was purified by silica gel chromatography (DCM/7 M NH$_3$ in MeOH from 100/1 to 10/1, v/v) to afford product (273.3 mg, 98%). LRMS (APCI pos): >99% purity, 254 nm, m/e 546 (M+1).

Step B: Preparation of tert-butyl 4-(4-(4-amino-2-fluorophenoxy)-1-(4-methoxybenzyl)-1H-pyrazolo[3,4-b]pyridin-3-yl)piperidine-1-carboxylate: A 100 mL round-bottomed flask was charged with tert-butyl 4-(1-(4-methoxybenzyl)-4-(4-amino-2-fluorophenoxy)-1H-pyrazolo[3,4-b]pyridin-3-yl)-5,6-dihydropyridine-1(2H)-carboxylate (0.248 g, 0.455 mmol), 4-methylbenzenesulfonohydrazide (0.0846 g, 0.455 mmol) and toluene (10 mL). The reaction mixture was stirred at 100° C. for 4 days. The reaction was cooled to ambient temperature and partitioned between EtOAc and H$_2$O. The phases were separated and the aqueous phase was re-extracted with EtOAc. The combined organic layers were dried (Na$_2$SO$_4$), filtered and concentrated. The crude material was purified by silica gel chromatography (DCM/7 M NH$_3$ in MeOH from 100/1 to 10/1, v/v) to afford the product (84.3 mg, 33.9%). LRMS (APCI pos): >96% purity, 254 nm, m/e 548 (M+1).

Step C: Preparation of tert-butyl 4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)piperidine-1-carboxylate: A round-bottomed flask was charged with tert-butyl 4-(1-(4-methoxybenzyl)-4-(4-amino-2-fluorophenoxy)-1H-pyrazolo[3,4-b]pyridin-3-yl)piperidine-1-carboxylate (84.3 mg, 0.1539 mmol), 2-(4-fluorophenyl)-3-oxo-2,3-dihydropyridazine-4-carboxylic acid (108.1 mg, 0.4618 mmol, prepared according to Example 19, step C), N1-((ethylimino)methylene)-N3,N3-dimethylpropane-1,3-diamine hydrochloride (147.6 mg, 0.7697 mmol), 1H-benzo[d][1,2,3]triazol-1-ol (104.0 mg, 0.7697 mmol), N-ethyl-N-isopropylpropan-2-amine (199.0 mg, 1.539 mmol) and DMF (10 mL). The reaction mixture was stirred at room temperature overnight. The reaction was partitioned between EtOAc and H$_2$O. The phases were separated and the aqueous phase was re-extracted with EtOAc. The combined organic layers were dried (Na$_2$SO$_4$), filtered and concentrated to yield a crude product. The crude product was purified by silica gel chromatography (DCM/7 M NH$_3$ in MeOH from 50/1 to 10/1, v/v) to afford the desired product (108.3 mg, 92.11%). LRMS (APCI pos): m/e 664 (M−99).

Step D: Preparation of N-(3-fluoro-4-(1-(4-methoxybenzyl)-3-(piperidin-4-yl)-1H-pyrazolo[3,4-b]pyridin-4-yloxy)phenyl)-2-(4-fluorophenyl)-3-oxo-2,3-dihydropyridazine-4-carboxamide: A round-bottomed flask was charged with tert-butyl 4-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)piperidine-1-carboxylate (74.3 mg, 0.0973 mmol), 2,2,2-trifluoroacetic acid (111 mg, 0.973 mmol) and CH$_2$Cl$_2$ (10 mL). The reaction mixture was stirred at ambient temperature 1 hour. The solvent was removed and the residue was purified by silica gel chromatography (DCM/7 M NH$_3$ in MeOH from 50/1 to 10/1, v/v) to afford product (58.8 mg, 91.1%). LRMS (APCI pos): >99% purity, 254 nm, m/e 664 (M+1).

Step E: Preparation of N-(3-fluoro-4-(1-(4-methoxybenzyl)-3-(1-methylpiperidin-4-yl)-1H-pyrazolo[3,4-b]pyridin-4-yloxy)phenyl)-2-(4-fluorophenyl)-3-oxo-2,3-dihydropyridazine-4-carboxamide: A round-bottomed flask was charged with N-(4-(1-(4-methoxybenzyl)-3-(piperidin-4-yl)-1H-pyrazolo[3,4-b]pyridin-4-yloxy)-3-fluorophenyl)-2-(4-fluorophenyl)-3-oxo-2,3-dihydropyridazine-4-carboxamide (20.0 mg, 0.0301 mmol), formaldehyde (0.905 mg, 0.0301 mmol), sodium triacetoxyborohydride (6.39 mg, 0.0301 mmol) and CH$_2$Cl$_2$ (10 mL). The reaction mixture was stirred at ambient temperature for 2 days. Then the reaction was partitioned between EtOAc and H$_2$O. The phases were separated and the aqueous phase was re-extracted with EtOAc. The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (16.3 mg, 79.8%). LRMS (APCI pos): >99% purity, 254 nm, m/e 678 (M+1).

Step F: Preparation of N-(3-fluoro-4-(3-(1-methylpiperidin-4-yl)-1H-pyrazolo[3,4-b]pyridin-4-yloxy)phenyl)-2-(4-fluorophenyl)-3-oxo-2,3-dihydropyridazine-4-carboxamide: A 50 mL round-bottomed flask was charged with N-(4-(1-(4-methoxybenzyl)-3-(1-methylpiperidin-4-yl)-1H-pyrazolo[3,4-b]pyridin-4-yloxy)-3-fluorophenyl)-2-(4-fluorophenyl)-3-oxo-2,3-dihydropyridazine-4-carboxamide (16.3 mg, 0.0241 mmol) and CF$_3$COOH (5 mL). The reaction mixture was stirred at 80° C. overnight. The solvent was removed and the residue was purified by silica gel chromatography (DCM/7 M NH$_3$ in MeOH from 50/1 to 10/1, v/v) to afford product, which was further purified by preparative HPLC to afford the desired product (3.2 mg, 16.9%). LRMS (APCI pos): >99% purity, 254 nm, m/e 558 (M+1). $^1$H NMR (400 MHz, CD$_3$OD) δ 11.94 (s, 1H), 8.24-8.36 (m, 3H), 8.03 (dd, 1H), 7.65 (m, 2H), 7.49 (m, 1H), 7.41 (m, 1H), 7.22-7.30 (m, 2H), 6.31 (d, 1H), 3.62 (m, 2H), 3.45 (m, 1H), 3.14-3.26 (m, 2H), 2.87 (s, 3H), 2.39-2.58 (m, 2H), 2.14-2.32 (m, 2H).

Example 106

N-(3-Fluoro-4-(3-(hexahydropyrrolo[34-c]pyrrol-2(1H)-yl)-1H-pyrazolo[3,4-b]pyridin-4-yloxy)phenyl)-2-(4-fluorophenyl)-3-oxo-2,3-dihydropyridazine-4-carboxamide

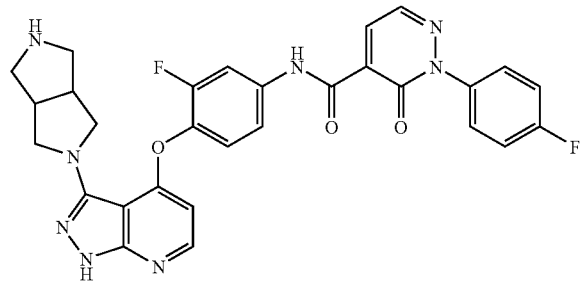

Step A: Preparation of tert-butyl 5-(4-(4-amino-2-fluorophenoxy)-1-(4-methoxybenzyl)-1H-pyrazolo[3,4-b]pyridin-3-yl)hexahydropyrrolo[3,4-c]pyrrole-2(1H)-carboxylate: A 100 mL round-bottomed flask was charged with 4-(1-(4-methoxybenzyl)-3-iodo-1H-pyrazolo[3,4-b]pyridin-4-yloxy)-3-fluorobenzenamine (100 mg, 0.204 mmol, prepared in Example 7, step B), tert-butyl hexahydropyrrolo[3,4-c]pyrrole-2(1H)-carboxylate (217 mg, 1.02 mmol), copper(I) iodide (15.5 mg, 0.0816 mmol), (S)-pyrrolidine-2-carboxylic acid (18.8 mg, 0.163 mmol), K₂CO₃ (141 mg, 1.02 mmol) and DMSO (10 mL). The reaction mixture was stirred at 100° C. overnight. The reaction was cooled to ambient temperature and partitioned between EtOAc and H₂O. The phases were separated and the aqueous phase was re-extracted with EtOAc. The combined organic layers were dried (Na₂SO₄), filtered and concentrated. The crude product was purified by silica gel chromatography (DCM/7 M NH₃ in MeOH from 50/1 to 10/1, v/v) to afford the desired product (44.8 mg, 38.2%). LRMS (APCI pos): m/e 575 (M+1).

Step B: Preparation of tert-butyl 5-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)hexahydropyrrolo[3,4-c]pyrrole-2(1H)-carboxylate: A round-bottomed flask was charged with tert-butyl 5-(1-(4-methoxybenzyl)-4-(4-amino-2-fluorophenoxy)-1H-pyrazolo[3,4-b]pyridin-3-yl)-hexahydropyrrolo[3,4-c]pyrrole-2(1H)-carboxylate (44.8 mg, 0.0780 mmol), 2-(4-fluorophenyl)-3-oxo-2,3-dihydropyridazine-4-carboxylic acid (54.8 mg, 0.234 mmol), N1-((ethylimino)methylene)-N³,N³-dimethylpropane-1,3-diamine hydrochloride (74.7 mg, 0.390 mmol), 1H-benzo[d][1,2,3]triazol-1-ol (52.7 mg, 0.390 mmol), N-ethyl-N-isopropylpropan-2-amine (101 mg, 0.780 mmol) and DMF (10 mL). The reaction mixture was stirred at ambient temperature overnight. The reaction was partitioned between EtOAc and H₂O. The phases were separated and the aqueous phase was re-extracted with EtOAc. The combined organic layers were dried (Na₂SO₄), filtered and concentrated. The crude material was purified by silica gel chromatography (DCM/7 M NH₃ in MeOH from 50/1 to 10/1, v/v) to afford product (42.5 mg, 68.9%). LRMS (APCI pos): m/e 691 (M−99).

Step C: Preparation of N-(3-fluoro-4-(3-(hexahydropyrrolo[3,4-c]pyrrol-2(1H)-yl)-1-(4-methoxybenzyl)-1H-pyrazolo[3,4-b]pyridin-4-yloxy)phenyl)-2-(4-fluorophenyl)-3-oxo-2,3-dihydropyridazine-4-carboxamide: A round-bottomed flask was charged with tert-butyl 5-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)-hexahydropyrrolo[3,4-c]pyrrole-2(1H)-carboxylate (42.5 mg, 0.0537 mmol), 2,2,2-trifluoroacetic acid (123 mg, 1.07 mmol) and CH₂Cl₂ (10 mL). The reaction mixture was stirred at ambient temperature for 4 hours. The solvent was removed and the residue was purified by silica gel chromatography (DCM/7 M NH₃ in MeOH from 50/1 to 10/1, v/v) to give product (13.8 mg, 37.2%). LRMS (APCI neg): m/e 690 (M).

Step D: Preparation of N-(3-fluoro-4-(3-(hexahydropyrrolo[3,4-c]pyrrol-2(1H)-yl)-1H-pyrazolo[3,4-b]pyridin-4-yloxy)phenyl)-2-(4-fluorophenyl)-3-oxo-2,3-dihydropyridazine-4-carboxamide: A round-bottomed flask was charged with N-(4-(1-(4-methoxybenzyl)-3-(hexahydropyrrolo[3,4-c]pyrrol-2(1H)-yl)-1H-pyrazolo[3,4-b]pyridin-4-yloxy)-3-fluorophenyl)-2-(4-fluorophenyl)-3-oxo-2,3-dihydropyridazine-4-carboxamide (13.8 mg, 0.0200 mmol) and CF₃COOH (5 mL). The reaction mixture was stirred at 80° C. overnight. The solvent was removed and the residue was purified by silica gel chromatography (DCM/7 M NH₃ in MeOH from 50/1 to 10/1, v/v) to give product, which was further purified by preparative HPLC to afford the desired product (2.1 mg, 13.2%). LRMS (APCI pos): >99% purity, 254 nm, m/e 571 (M+1). ¹H NMR (400 MHz, CD₃OD) δ 11.92 (s, 1H), 8.34 (d, 1H), 8.29 (d, 1H), 8.21 (d, 1H), 8.03 (d, 1H), 7.65 (m, 2H), 7.48 (d, 1H), 7.41 (m, 1H), 7.26 (m, 2H), 6.26 (d, 1H), 3.74 (d, 2H), 3.57 (m, 2H), 3.08-3.38 (m, 6H).

Example 107

N-(4-(3-(1,4-Diazepan-1-yl)-1H-pyrazolo[3,4-b]pyridin-4-yloxy)-3-fluorophenyl)-2-(4-fluorophenyl)-3-oxo-2,3-dihydropyridazine-4-carboxamide

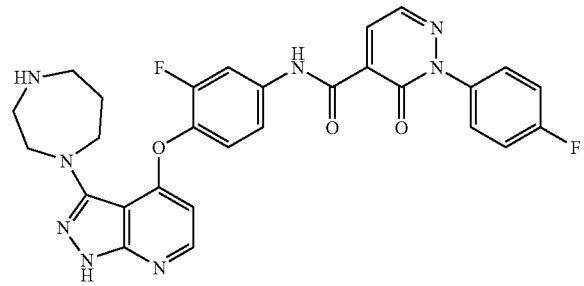

Step A: Preparation of tert-butyl 4-(4-(4-amino-2-fluorophenoxy)-1-(4-methoxybenzyl)-1H-pyrazolo[3,4-b]pyridin-3-yl)-1,4-diazepane-1-carboxylate: A round-bottomed flask was charged with 4-(1-(4-methoxybenzyl)-3-iodo-1H-pyrazolo[3,4-b]pyridin-4-yloxy)-3-fluorobenzenamine (100.0 mg, 0.2040 mmol, prepared according to Example 7, step B), tert-butyl 1,4-diazepane-1-carboxylate (204.3 mg, 1.020 mmol), copper(I)iodide (15.54 mg, 0.08159 mmol), (S)-pyrrolidine-2-carboxylic acid (18.79 mg, 0.1632 mmol), K₂CO₃ (140.9 mg, 1.020 mmol) and DMSO (10 mL). The reaction mixture was stirred at 100° C. overnight. The reaction was partitioned between EtOAc and H₂O. The phases were separated and the aqueous phase was re-extracted with EtOAc. The combined organic layers were dried (Na₂SO₄), filtered and concentrated to yield a crude product. The crude product was purified by silica gel chromatography (DCM/7 M NH₃ in MeOH from 50/1 to 10/1, v/v) to afford product (110.4 mg, 96.2%). LRMS (APCI pos): m/e 563 (M+1).

Step B: Preparation of tert-butyl 4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)-1,4-diazepane-1-carboxylate: A 100 mL round-bottomed flask was charged with tert-butyl 4-(1-(4-methoxybenzyl)-4-(4-amino-2-fluorophenoxy)-1H-pyrazolo[3,4-b]pyridin-3-yl)-1,4-diazepane-1-carboxylate (110.4 mg, 0.1962 mmol), 2-(4-fluorophenyl)-3-oxo-2,3-dihydropyridazine-4-carboxylic acid (137.9 mg, 0.5887 mmol, prepared according to Example 19, step C), N1-((ethylimino)methylene)-N³,N³-dimethylpropane-1,3-diamine hydrochloride (188.1 mg, 0.9811 mmol), 1H-benzo[d][1,2,3]triazol-1-ol (132.6 mg, 0.9811 mmol), N-ethyl-N-isopropylpropan-2-amine (253.6 mg, 1.962 mmol) and DMSO (25 mL). The reaction mixture was stirred at room temperature overnight. The reaction was partitioned between EtOAc and H₂O. The phases were separated and the aqueous phase was re-extracted with EtOAc. The combined organic layers were dried (Na₂SO₄), filtered and concentrated. The crude material was purified by silica gel chromatography (DCM/7 M NH₃ in MeOH from 100/1 to 10/1, v/v) to afford product (118.3 mg, 77.4%). LRMS (APCI pos): m/e 679 (M−99).

Step C: Preparation of N-(4-(3-(1,4-diazepan-1-yl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide: A round-bottomed flask was charged with tert-butyl 4-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)-1,4-diazepane-1-carboxylate (118.3 mg, 0.1519 mmol), 2,2,2-trifluoroacetic acid (346.4 mg, 3.038 mmol) and CH₂Cl₂ (10 mL). The reaction mixture was stirred at room temperature for one hour. The solvent was removed and the residue was purified by silica gel chromatography (DCM/7 M NH₃ in MeOH from 50/1 to 10/1, v/v) to give product (60.7 mg, 58.88%). LRMS (APCI pos): m/e 679 (M+1).

Step D: Preparation of N-(4-(3-(1,4-diazepan-1-yl)-1H-pyrazolo[3,4-b]pyridin-4-yloxy)-3-fluorophenyl)-2-(4-fluorophenyl)-3-oxo-2,3-dihydropyridazine-4-carboxamide: A 100 mL round-bottomed flask was charged with N-(4-(1-(4-methoxybenzyl)-3-(1,4-diazepan-1-yl)-1H-pyrazolo[3,4-b]pyridin-4-yloxy)-3-fluorophenyl)-2-(4-fluorophenyl)-3-oxo-2,3-dihydropyridazine-4-carboxamide (60.7 mg, 0.0894 mmol) and CF₃COOH (5 mL). The reaction mixture was stirred at 80° C. overnight. The solvent was removed and the residue was purified by silica gel chromatography (DCM/7 M NH₃ in MeOH from 50/1 to 10/1, v/v) to afford product, which was further purified by preparative HPLC to afford the product (0.9 mg, 1.28%). LRMS (APCI pos): >99% purity, 254 nm, m/e 559 (M+1). ¹H NMR (400 MHz, CD₃OD) δ 8.34 (m, 2H), 8.22 (d, 1H), 8.07 (d, 1H), 7.67 (m, 2H), 7.52 (d, 1H), 7.43 (t, 1H), 7.30 (m, 2H), 6.27 (d, 1H), 3.91 (m, 2H), 3.75 (m, 2H), 3.48 (m, 2H), 3.39 (m, 2H), 2.23 (m, 2H).

Example 108

N-(4-(3-(3-(dimethylamino)propylamino)-1H-pyrazolo[3,4-b]pyridin-4-yloxy)-3-fluorophenyl)-2-(4-fluorophenyl)-3-oxo-2,3-dihydropyridazine-4-carboxamide

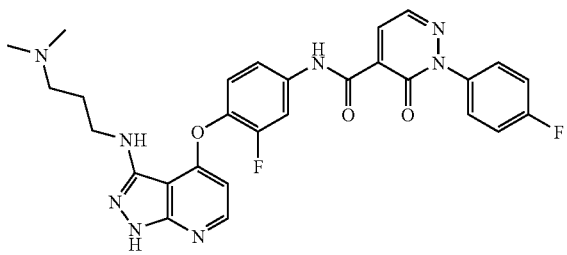

Step A: Preparation of N1-(4-(4-amino-2-fluorophenoxy)-1-(4-methoxybenzyl)-1H-pyrazolo[3,4-b]pyridin-3-yl)-N3,N3-dimethylpropane-1,3-diamine: Prepared according to the procedure of Example 82, Step A, substituting N,N-dimethyl-1,3-propanediamine (0.13 ml, 1.02 mmol) for tert-butyl piperazine-1-carboxylate. Purified by silica gel column chromatography (Biotage 25S) eluting with 5-10% MeOH/CHCl₃ to afford the desired product as opaque oil. Yield: 62 mg, 65%. LRMS (APCI pos) m/e 465.2 (M+H).

Step B: Preparation of N-(4-(3-(3-(dimethylamino)propylamino)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide: Prepared according to the procedure of Example 82, Step B, substituting N1-(4-(4-amino-2-fluorophenoxy)-1-(4-methoxybenzyl)-1H-pyrazolo[3,4-b]pyridin-3-yl)-N3,N3-dimethylpropane-1,3-diamine (60 mg, 0.129 mmol) for tert-butyl 4-(4-(4-amino-2-fluorophenoxy)-1-(4-methoxybenzyl)-1H-pyrazolo[3,4-b]pyridin-3-yl)piperazine-1-carboxylate. The crude material was purified by silica gel column chromatography (Biotage 25S) eluting with 5-7% MeOH/CH₂Cl₂ to afford the desired product as yellow oil. Yield: 55 mg at 90% purity, 56%. LRMS (APCI pos) m/e 681.2 (M+H).

Step C: Preparation of N-(4-(3-(3-(dimethylamino)propylamino)-1H-pyrazolo[3,4-b]pyridin-4-yloxy)-3-fluorophenyl)-2-(4-fluorophenyl)-3-oxo-2,3-dihydropyridazine-4-carboxamide: Prepared according to the procedure of Example 53, Step B, substituting N-(4-(3-(3-(dimethylamino)propylamino)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide (55 mg, 0.0808 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 5-10% MeOH/CH₂Cl₂ to afford desired product as the di-TFA salt. Yield 17.5 mg, 27%. ¹H NMR (400 MHz, DMSO-d6) δ 12.23 (s, 1H), 11.7 (s, 1H), 9.35 (broad s, 1H), 8.39 (d, 1H), 8.26 (d, 1H), 8.15 (d, 1H), 8.04 (d, 1H), 7.68 (q, 2H), 7.61 (d, 1H), 7.49 (t, 1H), 7.42 (t, 2H), 6.04 (d, 1H), 5.87 (broad s, 2H), 3.14 (broad m, 2H), 2.79 (s, 6H), 2.01 (m, 2H). LRMS (APCI pos) m/e 561.2 (M+H).

Example 109

N-(3-fluoro-4-(3-(1-methylhexahydropyrrolo[3,4-b]pyrrol-5(1H)-yl)-1H-pyrazolo[3,4-b]pyridin-4-yloxy)phenyl)-2-(4-fluorophenyl)-3-oxo-2,3-dihydropyridazine-4-carboxamide

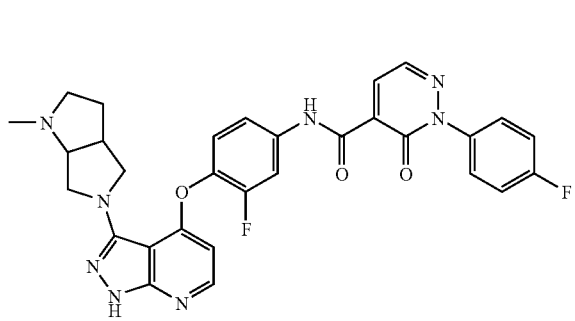

Step A: Preparation of 3-fluoro-4-(1-(4-methoxybenzyl)-3-(1-methylhexahydropyrrolo[3,4-b]pyrrol-5(1H)-yl)-1H-pyrazolo[3,4-b]pyridin-4-yloxy)aniline: Prepared according to the procedure of Example 82, Step A, substituting 1-methyl-octahydropyrrolo[3,4-b]pyrrole (129 mg, 1.02 mmol) for tert-butyl piperazine-1-carboxylate. The crude material was purified by silica gel column chromatography (Biotage 25S) eluting with 5-10% MeOH/CHCl$_3$ to afford the desired product as opaque oil. Yield: 35 mg, 35%. LRMS (APCI pos) m/e 489.2 (M+H).

Step B: Preparation of N-(3-fluoro-4-(1-(4-methoxybenzyl)-3-(1-methylhexahydropyrrolo[3,4-b]pyrrol-5(1H)-yl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 82, Step B, substituting 3-fluoro-4-(1-(4-methoxybenzyl)-3-(1-methylhexahydropyrrolo[3,4-b]pyrrol-5(1H)-yl)-1H-pyrazolo[3,4-b]pyridin-4-yloxy)aniline (35 mg, 0.072 mmol) for tert-butyl 4-(4-(4-amino-2-fluorophenoxy)-1-(4-methoxybenzyl)-1H-pyrazolo[3,4-b]pyridin-3-yl)piperazine-1-carboxylate. The crude material was purified by silica gel column chromatography (Biotage 25S) eluting with 5-7% MeOH/CH$_2$Cl$_2$ to afford the desired product. Yield: 22 mg, 44%. LRMS (APCI pos) m/e 705.3 (M+H).

Step C: Preparation of N-(3-fluoro-4-(3-(1-methylhexahydropyrrolo[3,4-b]pyrrol-5(1H)-yl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting N-(3-fluoro-4-(1-(4-methoxybenzyl)-3-(1-methylhexahydropyrrolo[3,4-b]pyrrol-5(1H)-yl)-1H-[3,4-b]pyridin-4-yloxy)phenyl)-2-(4-fluorophenyl)-3-oxo-2,3-dihydropyridazine-4-carboxamide (22 mg, 0.0312 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 2% MeOH/CH$_2$Cl$_2$ to afford desired product as 2TFA salt. Yield 14 mg, 55%. LRMS (APCI pos) m/e 585.3 (M+H).

Example 110

N-(3-fluoro-4-(3-(piperidin-4-ylamino)-1H-pyrazolo[3,4-b]pyridin-4-yloxy)phenyl)-2-(4-fluorophenyl)-3-oxo-2,3-dihydropyridazine-4-carboxamide

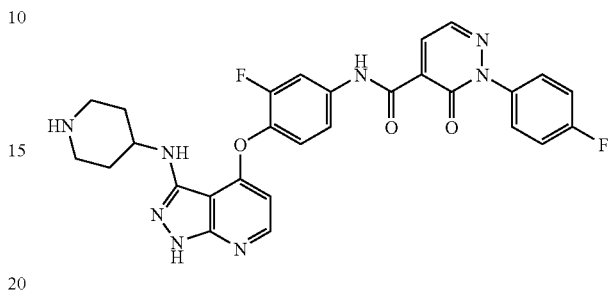

Prepared by a 2-step process from tert-butyl 4-(4-(4-amino-2-fluorophenoxy)-1-(4-methoxybenzyl)-1H-pyrazolo[3,4-b]pyridin-3-ylamino)piperidine-1-carboxylate (prepared as described in Example 101, Step A, using tert-butyl 4-aminopiperidine-1-carboxylate) and 2-(4-fluorophenyl)-3-oxo-2,3-dihydropyridazine-4-carboxylic acid according to the procedure of Example 101, Step B. The crude material was purified by silica gel flash column chromatography (60% MeOH in CH$_2$Cl$_2$) to afford 19 mg (34%) of the desired product. LRMS (ESI pos) m/e 559.1 (M+1). $^1$H-NMR (400 MHz, CD$_3$OD/CDCl$_3$) δ 8.41 (d, 1H), 8.33 (d, 1H), 8.14 (d, 1H), 8.02 (dd, 1H), 7.65 (m, 2H), 7.47 (d, 1H), 7.37 (t, 1H), 7.28 (t, 2H), 6.12 (d, 1H), 3.80 (m, 1H), 3.16 (d, 2H), 2.79 (t, 2H), 2.24 (d, 2H), 1.53 (m, 2H); $^{19}$F NMR (376 MHz, CD$_3$OD/CDCl$_3$) δ −113.1, −127.7.

Example 111

Preparation of ±N-(3-fluoro-4-(3-((3R*,7S*)-hexahydro-1H-pyrrolo[3,2-c]pyridin-5(6H)-yl)-1H-pyrazolo[3,4-b]pyridin-4-yloxy)phenyl)-2-(4-fluorophenyl)-3-oxo-2,3-dihydropyridazine-4-carboxamide

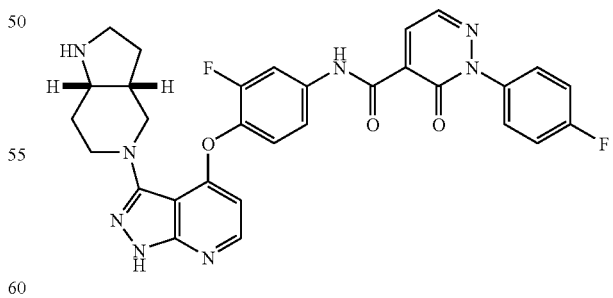

Step A: Preparation of tert-butyl 1H-pyrrolo[3,2-c]pyridine-1-carboxylate: To a stirred mixture of 1H-pyrrolo[3,2-c]pyridine (2.3 g, 20 mmol) and N,N-dimethylpyridin-4-amine (2.4 g, 20 mmol) in CH$_3$CN (20 mL) was added Boc-anhydride (3.9 g, 18 mmol). The mixture was stirred for 18 hours at ambient temperature. The reaction was concentrated in vacuo, and then purified by Biotage Flash 40S, eluting with 1:1 EtOAc/hexanes. The product was obtained as a colorless oil (4.0 g, 101%).

Step B: Preparation of ±(3R*,7S*)-tert-butyl octahydropyrrolo[3,2-c]pyridine-1-carboxylate: A mixture of tert-butyl 1H-pyrrolo[3,2-c]pyridine-1-carboxylate (0.22 g, 1.0 mmol), EtOH (10 mL), and acetic acid (5 mL) was purged with $N_2$, and then Adam's catalyst $PtO_2$ (69 mg, 0.30 mmol) was added. The reaction was shaken in a Parr apparatus under 50 psi $H_2$ for 3 days at ambient temperature. The mixture was filtered through a pad of celite, washing with DCM. The filtrate was concentrated in vacuo, then resuspended in DCM (10 mL) and basified with saturated aqueous $Na_2CO_3$ (10 mL). The phases were separated, and the aqueous phase was re-extracted with DCM. The combined organic phases were dried ($Na_2SO_4$), filtered, and concentrated. The crude was purified by preparative TLC (2 mm thickness, Rf=0.31), eluting with 10% MeOH (containing 7N $NH_3$) in DCM. Yield: 95 mg (42%).

Step C: Preparation of ±(3R*,7S*)-tert-butyl 5-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)-octahydropyrrolo[3,2-c]pyridine-1-carboxylate: A mixture of N-(4-(1-(4-methoxybenzyl)-3-iodo-1H-pyrazolo[3,4-b]pyridin-4-yloxy)-3-fluorophenyl)-2-(4-fluorophenyl)-3-oxo-2,3-dihydropyridazine-4-carboxamide (0.0706 g, 0.10 mmol, prepared according to Example 63, Step A), ±(3R*,7S*)-tert-butyl octahydropyrrolo[3,2-c]pyridine-1-carboxylate (0.0951 g, 0.420 mmol), copper(I)iodide (0.00381 g, 0.0200 mmol), (S)-pyrrolidine-2-carboxylic acid (0.00461 g, 0.0400 mmol), $K_2CO_3$ (0.0691 g, 0.500 mmol), and DMSO (10 mL) was stirred at 100° C. for 18 hours in a sealed vessel. The reaction was cooled to ambient temperature, water (25 mL) was added, and the aqueous phase was extracted with EtOAc. The combined organic layers were dried over ($Na_2SO_4$), concentrated and purified by preparative TLC (Rf=0.28, 1 mm thickness), eluting with 1:1 EtOAc/hexanes. The product was obtained as a waxy solid (8 mg, 9%).

Step D: Preparation of ±N-(3-fluoro-4-(3-((3R*,7S*)-hexahydro-1H-pyrrolo[3,2-c]pyridin-5(6H)-yl)-1H-pyrazolo[3,4-b]pyridin-4-yloxy)phenyl)-2-(4-fluorophenyl)-3-oxo-2,3-dihydropyridazine-4-carboxamide: A mixture of ±(3R*,7S*)-tert-butyl 5-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)-octahydropyrrolo[3,2-c]pyridine-1-carboxylate (8 mg, 0.00994 mmol), and 2,2,2-trifluoroacetic acid (0.498 ml, 6.46 mmol) was heated to 80° C. in a sealed vessel for 6 hours. After cooling to ambient temperature, the reaction was concentrated in vacuo, using toluene to azeotrope residual TFA (2×5 mL). The resulting residue was dissolved in DCM, and purified by preparative TLC (0.5 mm thickness, Rf=0.03), eluting with 10% MeOH (containing 7N $NH_3$) in $CHCl_3$. The product was obtained as a pale yellow powder (4.5 mg, 73%). HPLC: 94% purity (220 nm); LRMS (ESI+): 100% purity, 220 nm, m/z 585 (M+1) detected; $^1$H NMR (400 MHz, $CD_3OD$) δ 8.35 (d, J=4 Hz, 1H), 8.30 (d, J=4 Hz, 1H), 8.22 (d, J=5 Hz, 1H), 8.06 (m, 1H), 7.68 (m, 2H), 7.51 (m, 1H), 7.41 (t, J=9 Hz, 1H), 7.29 (t, J=9 Hz, 2H), 6.27 (d, J=5 Hz, 1H), 3.78 (m, 3H), 3.48 (m, 1H), 3.36 (m, 2H), 3.17 (m, 1H), 2.60 (m, 1H), 2.37 (m, 1H), 2.01 (m, 3H).

Example 112

±N-(3-fluoro-4-(3-((3 S*,7S*)-octahydropyrrolo[2,3-c]pyridin-6-yl)-1H-pyrazolo[3,4-b]pyridin-4-yloxy) phenyl)-2-(4-fluorophenyl)-3-oxo-2,3-dihydropyridazine-4-carboxamide

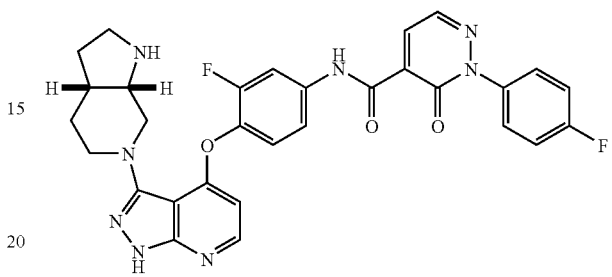

Step A: Preparation of tert-butyl 1H-pyrrolo[2,3-c]pyridine-1-carboxylate: Prepared from 1H-pyrrolo[2,3-c]pyridine (2.3 g, 20 mmol) using the same procedure described for Example 111, Step A. The product was obtained as a colorless oil (4.0 g, 101%).

Step B: Preparation of ±(3R*,7S*)-tert-butyl octahydropyrrolo[2,3-c]pyridine-1-carboxylate: Prepared from tert-butyl 1H-pyrrolo[2,3-c]pyridine-1-carboxylate (0.218 g, 1.0 mmol) using the same procedure as described for Example 111, Step B. Yield: 91 mg (40%).

Step C: Preparation of ±(3R*,7S*)-tert-butyl 6-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)-octahydropyrrolo[2,3-c]pyridine-1-carboxylate: Prepared from N-(4-(1-(4-methoxybenzyl)-3-iodo-1H-pyrazolo[3,4-b]pyridin-4-yloxy)-3-fluorophenyl)-2-(4-fluorophenyl)-3-oxo-2,3-dihydropyridazine-4-carboxamide (0.0706 g, 0.10 mmol) and ±(3R*,7S*)-tert-butyl octahydropyrrolo[2,3-c]pyridine-1-carboxylate (0.0905 g, 0.400 mmol) according to the procedure described for Example 111, Step C. The product was obtained as a waxy solid (14 mg, 17%).

Step D: Preparation of ±N-(3-fluoro-4-(3-((3S*,7S*)-octahydropyrrolo[2,3-c]pyridin-6-yl)-1H-pyrazolo[3,4-b]pyridin-4-yloxy)phenyl)-2-(4-fluorophenyl)-3-oxo-2,3-dihydropyridazine-4-carboxamide: Prepared ±(3R*,7S*)-tert-butyl 6-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)-octahydropyrrolo[2,3-c]pyridine-1-carboxylate (14 mg, 0.0174 mmol) according to the procedure described for Example 111, Step D. The product was obtained as a pale yellow powder (4.5 mg, 42%). HPLC: 95% purity (220 nm); LRMS (ESI+): 100% purity, 220 nm, m/z 585 (M+1) detected; $^1$H NMR (400 MHz, MeOD-$d_3$) δ 8.31 (d, J=4 Hz, 1H), 8.26 (d, J=4 Hz, 1H), 8.18 (d, J=6 Hz, 1H), 8.02 (m, 1H), 7.64 (m, 2H), 7.45 (m, 1H), 7.37 (t, J=9 Hz, 1H), 7.25 (t, J=9 Hz, 2H), 6.22 (d, J=6 Hz, 1H), 3.96 (m, 1H), 3.85 (m, 1H), 3.48 (m, 1H), 3.34 (m, 2H), 3.14 (m, 1H), 2.99 (m, 1H), 2.34 (m, 1H), 2.05 (m, 1H), 1.81 (m, 2H), 1.59 (m, 1H).

Example 113

1-(benzo[d]oxazol-2-yl)-N-(4-(3-(4-(dimethylamino)piperidin-1-yl)-1H-pyrazolo[3,4-b]pyridin-4-yloxy)-3-fluorophenyl)cyclopropanecarboxamide

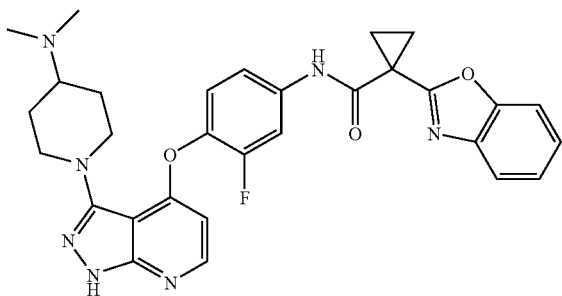

Step A: Preparation of methyl 1-(2-hydroxyphenylcarbamoyl)cyclopropane carboxylate: To a stirred suspension of potassium 1-(methoxycarbonyl)cyclopropanecarboxylate (182 mg, 1 mmol) in 3 mL THF at room temperature under nitrogen was added 15 µL of DMF. Oxalyl chloride (87 µL, 1 mmol) was then added neat dropwise by syringe. After stirring at ambient temperature for 2 hours, the reaction was cooled to 0° C. and treated with DIEA (0.497 ml, 2.85 mmol) followed by 2-aminophenol (104 mg, 0.951 mmol) neat as a solid. The cooling bath was allowed to melt and the reaction was then stirred at ambient temperature overnight. The reaction was diluted to 30 mL with ethyl acetate and washed with 2N HCl, water, saturated sodium bicarbonate and brine. The organics were dried (MgSO$_4$), filtered and concentrated to a yellow solid (147 mg, 68% yield).

Step B: Preparation of methyl 1-(benzo[d]oxazol-2-yl)cyclopropanecarboxylate: To a stirred suspension of methyl 1-((2-hydroxyphenyl)carbamoyl)cyclopropanecarboxylate (0.147 g, 0.62 mmol) in 2.5 mL THF at room temperature under nitrogen was added triphenylphosphine (0.361 g, 1.375 mmol) followed by DIAD (0.2663 ml, 1.375 mmol). After 2 hours, the reaction mixture was loaded directly onto a Biotage 40S column in THF and was eluted with 9/1 hexanes/EtOAc to provide the desired product as a yellow oil (132 mg, 97%).

Step C: Preparation of 1-(benzo[d]oxazol-2-yl)cyclopropanecarboxylic acid: To a stirred solution of methyl 1-(benzo[d]oxazol-2-yl)cyclopropanecarboxylate (0.132 g, 0.6077 mmol) in 3 mL 3:2 THF:H$_2$O at room temperature under nitrogen was added LiOH (0.02911 g, 1.215 mmol). After stirring at ambient temperature overnight the reaction was diluted to 30 mL with ethyl acetate and washed with 2N HCl, water and brine. The organics were dried (MgSO$_4$), filtered and concentrated to a white solid (100 mg, 81% yield).

Step D: Preparation of 1-(benzo[d]oxazol-2-yl)-N-(4-(3-(4-(dimethylamino)piperidin-1-yl)-1-(4-methoxybenzyl)-1H-pyrazolo[3,4-b]pyridin-4-yloxy)-3-fluorophenyl)cyclopropanecarboxamide: To a stirred solution of 1-(benzo[d]oxazol-2-yl)cyclopropanecarboxylic acid (3.8 mg, 0.019 mmol) in 150 µL dichloromethane at room temperature under nitrogen was added DIEA (8 µL, 0.047 mmol) followed by EDCI (4.5 mg, 0.024 mmol) and HOBT-H$_2$O (3.6 mg, 0.024 mmol). After 15 minutes, a solution of 1-(1-(4-methoxybenzyl)-4-(4-amino-2-fluorophenoxy)-1H-pyrazolo[3,4-b]pyridin-3-yl)-N,N-dimethylpiperidin-4-amine (7.7 mg, 0.016 mmol) (prepared in Example 93, Step A) in 150 µL dichloromethane was added. After stirring for 48 hours, the reaction was diluted to 30 mL with dichloromethane and washed with 10% sodium carbonate solution. The organics were dried (MgSO$_4$), filtered and concentrated. The crude product was loaded onto a Biotage 12S column with dichloromethane and eluted with a step gradient of dichloromethane (100 mL), 2.5/97.5 MeOH/dichloromethane (100 mL) and 5/95 MeOH/dichloromethane to provide the desired product as a white foam (6.6 mg, 62% yield).

Step E: Preparation of 1-(benzo[d]oxazol-2-yl)-N-(4-(3-(4-(dimethylamino)piperidin-1-yl)-1H-pyrazolo[3,4-b]pyridin-4-yloxy)-3-fluorophenyl)cyclopropanecarboxamide: To a flask containing N-(4-(1-(4-methoxybenzyl)-3-(4-(dimethylamino)piperidin-1-yl)-1H-pyrazolo[3,4-b]pyridin-4-yloxy)-3-fluorophenyl)-1-(benzo[d]oxazol-2-yl)cyclopropanecarboxamide (6.6 mg, 0.01 mmol) at room temperature under a drying tube was added TFA (2 mL). The reaction was warmed to 50° C. overnight. The reaction was cooled to room temperature and was concentrated. The residue was dissolved in 10 mL dichloromethane and stirred rapidly with 10 mL 10% sodium carbonate solution. The layers were separated and the organics dried (MgSO$_4$). The crude product was concentrated and the crude material was loaded onto a Biotage 12S column with dichloromethane. The column was eluted with a step gradient of dichloromethane (150 mL) and 94.5/5/0.5 dichloromethane/MeOH, concentrated ammonium hydroxide to provide the desires product as a yellow glass (2.7 mg, 50% yield). $^1$H NMR (400 MHz, CDCl$_3$) δ 12.17 (br s, 1H), 9.92 (br s, 1H), 8.24 (d, 1H), 7.90 (m, 1H), 7.73 (m, 1H), 7.48 (m, 2H), 7.38 (m, 2H), 7.30 (m, 1H), 6.21 (d, 1H), 4.11 (m, 2H), 2.91 (m, 2H), 2.40 (m, 1H), 2.34 (s, 6H), 2.08 (m, 2H), 1.96 (br m, 2H), 1.90 (m, 2H), 1.74 (br m, 2H). LCMS (APCI+): m/z 556 (M+1) detected.

Example 114

N-(3-fluoro-4-(3-(4-(pyrrolidin-1-yl)piperidin-1-yl)-1H-pyrazolo[3,4-b]pyridin-4-yloxy)phenyl)-2-(4-fluorophenyl)-3-oxo-2,3-dihydropyridazine-4-carboxamide

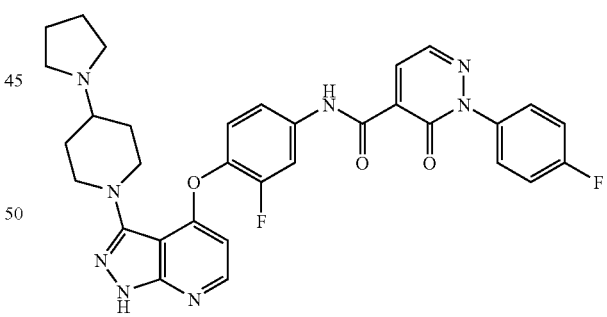

Step A: Preparation of 3-fluoro-4-(1-(4-methoxybenzyl)-3-(4-(pyrrolidin-1-yl)piperidin-1-yl)-1H-pyrazolo[3,4-b]pyridin-4-yloxy)aniline: Prepared according to the procedure of Example 82, Step A, substituting 4-(1-pyrrolidinyl)piperidine (315 mg, 2.04 mmol) for tert-butyl piperazine-1-carboxylate. The crude material was purified by silica gel column chromatography (Biotage 25S) eluting with 7% MeOH/CHCl$_3$ to afford the desired product as orange semi-solid. Yield: 43 mg, 20%. LRMS (APCI pos) m/e 517.2 (M+H).

Step B: Preparation of N-(3-fluoro-4-(1-(4-methoxybenzyl)-3-(4-(pyrrolidin-1-yl)piperidin-1-yl)-1H-pyrazolo[3,4-b]pyridin-4-yloxy)phenyl)-2-(4-fluorophenyl)-3-oxo-2,3- dihydropyridazine-4-carboxamide: Prepared according to the procedure of Example 82, Step B, substituting 3-fluoro-4-(1-(4-methoxybenzyl)-3-(4-(pyrrolidin-1-yl)piperidin-1-yl)-1H-pyrazolo[3,4-b]pyridin-4-yloxy)aniline (43 mg, 0.0832 mmol) for tert-butyl 4-(4-(4-amino-2-fluorophenoxy)-1-(4-methoxybenzyl)-1H-pyrazolo[3,4-b]pyridin-3-yl)piperazine-1-carboxylate. The crude material was purified by silica gel column chromatography (Biotage 25S) eluting with 5-10% MeOH/CH$_2$Cl$_2$ to afford the desired product as yellow solid. Yield: 28.6 mg, 47%. LRMS (APCI pos) m/e 733.3 (M+H).

Step C: Preparation of N-(3-fluoro-4-(3-(4-(pyrrolidin-1-yl)piperidin-1-yl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting N-(3-fluoro-4-(1-(4-methoxybenzyl)-3-(4-(pyrrolidin-1-yl)piperidin-1-yl)-1H-pyrazolo[3,4-b]pyridin-4-yloxy)phenyl)-2-(4-fluorophenyl)-3-oxo-2,3-dihydropyridazine-4-carboxamide (28 mg, 0.0382 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 5/95/0.1 MeOH/DCM/NH$_4$OH to afford desired product as pale yellow solid. Yield 10.4 mg, 44%. LRMS (APCI pos) m/e 613.2 (M+H).

Example 115

N-(4-(3-(2-((dimethylamino)methyl)piperidin-1-yl)-1H-pyrazolo[3,4-b]pyridin-4-yloxy)-3-fluorophenyl)-2-(4-fluorophenyl)-3-oxo-2,3-dihydropyridazine-4-carboxamide

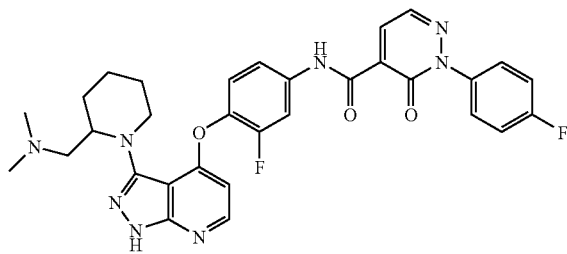

Step A: Preparation of 4-(3-(2-((dimethylamino)methyl)piperidin-1-yl)-1-(4-methoxybenzyl)-1H-pyrazolo[3,4-b]pyridin-4-yloxy)-3-fluoroaniline: Prepared according to the procedure of Example 82, Step A, substituting N-(2-piperidylmethyl)-dimethylamine (145 mg, 1.02 mmol) for tert-butyl piperazine-1-carboxylate. The crude material was purified by silica gel column chromatography (Biotage 25S) eluting with 10% MeOH/CH$_2$Cl$_2$ to afford the desired product as yellow semi-solid. Yield: 9.6 mg, 9.3%. LRMS (APCI pos) m/e 505.2 (M+H).

Step B: Preparation of N-(4-(3-(2-((dimethylamino)methyl)piperidin-1-yl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide: Prepared according to the procedure of Example 82, Step B, substituting 4-(3-(2-((dimethylamino)methyl)piperidin-1-yl)-1-(4-methoxybenzyl)-1H-pyrazolo[3,4-b]pyridin-4-yloxy)-3-fluoroaniline (10 mg, 0.0198 mmol) for tert-butyl 4-(4-(4-amino-2-fluorophenoxy)-1-(4-methoxybenzyl)-1H-pyrazolo[3,4-b]pyridin-3-yl)piperazine-1-carboxylate. The crude material was purified by silica gel column chromatography (Biotage 12S) eluting with 5% MeOH/CH$_2$Cl$_2$ to afford the desired product as yellow solid. Yield: 7.2 mg, 50%. LRMS (APCI pos) m/e 721.3 (M+H).

Step C: Preparation of N-(4-(3-(2-((dimethylamino)methyl)piperidin-1-yl)-1H-pyrazolo[3,4-b]pyridin-4-yloxy)-3-fluorophenyl)-2-(4-fluorophenyl)-3-oxo-2,3-dihydropyridazine-4-carboxamide: Prepared according to the procedure of Example 53, Step B, substituting N-(4-(3-(2-((dimethylamino)methyl)piperidin-1-yl)-1-(4-methoxybenzyl)-1H-pyrazolo[3,4-b]pyridin-4-yloxy)-3-fluorophenyl)-2-(4-fluorophenyl)-3-oxo-2,3-dihydropyridazine-4-carboxamide (7.2 mg, 0.010 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 5/95/0.1 MeOH/DCM/NH$_4$OH to afford desired product as pale yellow solid. Yield 4.7 mg, 78%. LRMS (APCI pos) m/e 601.2 (M+H).

Example 116

N-(5-chloro-2-fluoro-4-(3-methyl-1H-pyrazolo[3,4-b]pyridin-4-yloxy)phenyl)-2-(4-fluorophenyl)-3-oxo-2,3-dihydropyridazine-4-carboxamide

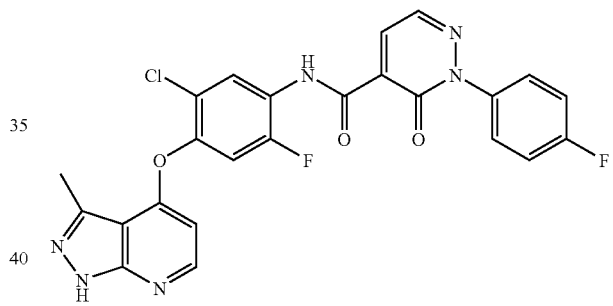

Step A: 1-(4-methoxybenzyl)-4-(2-chloro-5-fluoro-4-nitrophenoxy)-3-methyl-1H-pyrazolo[3,4-b]pyridine: Made according to the procedure for Example 96, Step A, substituting 1-chloro-2,4-difluoro-5-nitrobenzene (0.826 g, 4.27 mmol made from US20040082784 substituting 1-chloro-2,4-difluorobenzene for 1-chloro-4,5-difluoro-benzene) for 1,2,4-trifluoro-5-nitrobenzene. Obtained 1.01 g (52%) of the desired product. LRMS M+1 (442.9) observed.

Step B: 4-(1-(4-methoxybenzyl)-3-methyl-1H-pyrazolo[3,4-b]pyridin-4-yloxy)-5-chloro-2-fluorobenzenamine: Prepared by process from Example 92, Step B, substituting 1-(4-methoxybenzyl)-4-(2-chloro-5-fluoro-4-nitrophenoxy)-3-methyl-1H-pyrazolo[3,4-b]pyridine (0.850 g, 1.92 mmol). The reaction mixture was dilute with EtOAc (250 mL) and saturated Na$_2$CO$_3$ (50 mL) was added. The solution was filtered through celite and the filtrate was dried over sodium sulfate and concentrated to provide the product (0.325 g, 35%). The crude material was used in the next step without purification.

Step C: N-(5-chloro-2-fluoro-4-(3-methyl-1H-pyrazolo[3,4-b]pyridin-4-yloxy)phenyl)-2-(4-fluorophenyl)-3-oxo-2,3-dihydropyridazine-4-carboxamide: Prepared by process from Example 9, Step C, substituting 4-(1-(4-methoxybenzyl)-3-methyl-1H-pyrazolo[3,4-b]pyridin-4-yloxy)-5- chloro-2-fluorobenzenamine (0.325 g, 0.787 mmol). The crude material was purified by reverse phase HPLC to afford 1 mg (1%) of the desired product. LRMS M+1 (508.9) observed. 1H NMR (400 MHz, CDCl₃) δ 12.31 (s, 1H), 8.69 (m, 1H), 8.41 (m, 2H), 8.28 (m, 1H), 7.69 (m, 4H), 7.43 (m, 2H), 6.20 (m, 1H), 2.62 (s, 3H)

Example 117

(R)—N-(3-fluoro-4-(3-(2-(pyrrolidin-1-ylmethyl) pyrrolidin-1-yl)-1H-pyrazolo[3,4-b]pyridin-4-yloxy) phenyl)-2-(4-fluorophenyl)-3-oxo-2,3-dihydropyridazine-4-carboxamide

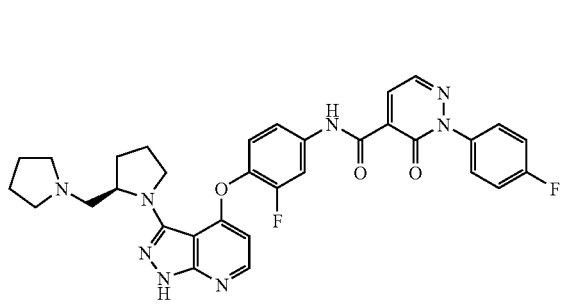

Step A: Preparation of (R)-3-fluoro-4-(1-(4-methoxybenzyl)-3-(2-(pyrrolidin-1-ylmethyl)pyrrolidin-1-yl)-1H-pyrazolo[3,4-b]pyridin-4-yloxy)aniline: Prepared according to the procedure of Example 82, Step A, substituting (S)-(+)-(2-pyrrolidinylmethyl)pyrrolidine (0.33 ml, 2.04 mmol) for tert-butyl piperazine-1-carboxylate. The crude material was purified by silica gel column chromatography (Biotage 25S) eluting with 7% MeOH/CH₂Cl₂ to afford the desired product as yellow semi-solid. Yield: 29.5 mg at 82% purity, 11.5% yield. LRMS (APCI pos) m/e 517.2 (M+H).

Step B: Preparation of (R)—N-(3-fluoro-4-(1-(4-methoxybenzyl)-3-(2-(pyrrolidin-1-ylmethyl)pyrrolidin-1-yl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 82, Step B, substituting (R)-3-fluoro-4-(1-(4-methoxybenzyl)-3-(2-(pyrrolidin-1-ylmethyl)pyrrolidin-1-yl)-1H-pyrazolo[3,4-b]pyridin-4-yloxy)aniline (25 mg, 0.048 mmol) for tert-butyl 4-(4-(4-amino-2-fluorophenoxy)-1-(4-methoxybenzyl)-1H-pyrazolo[3,4-b]pyridin-3-yl)piperazine-1-carboxylate. The crude material was purified by silica gel column chromatography (Biotage 12M) eluting with 5% MeOH/CH₂Cl₂ to afford the desired product. Yield: 6 mg, 17%. LRMS (APCI pos) m/e 733.3 (M+H).

Step C: Preparation of (R)—N-(3-fluoro-4-(3-(2-(pyrrolidin-1-ylmethyl)pyrrolidin-1-yl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting (R)—N-(3-fluoro-4-(1-(4-methoxybenzyl)-3-(2-(pyrrolidin-1-ylmethyl)pyrrolidin-1-yl)-1H-pyrazolo[3,4-b]pyridin-4-yloxy)phenyl)-2-(4-fluorophenyl)-3-oxo-2,3-dihydropyridazine-4-carboxamide (6 mg, 0.0082 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by silica gel column chromatography (Biotage 12M) eluting with 5/95/0.1 MeOH/DCM/NH₄OH to afford desired product as yellow semi-solid. Yield 1.9 mg at 90% purity, 34% yield. ¹H NMR (400 MHz, CDCl₃) δ 11.84 (s, 1H), 8.41 (d, 1H), 8.24 (d, 1H), 8.21 (d, 1H), 7.96 (d, 1H), 7.60 (q, 2H), 7.40 (d, 1H), 7.27-7.21 (m, 2H) 6.14 (d, 1H), 4.37 (broad m, 2H), 3.95 (q, 2H), 3.51 (m, 2H), 3.04-2.74 (broad m, 6H), 2.33 (m, 2H), 2.01 (m, 2H). LRMS (APCI pos) m/e 613.2 (M+H).

Example 118

N-(3-fluoro-4-(3-(1-methylpiperidin-4-ylamino)-1H-pyrazolo[3,4-b]pyridin-4-yloxy)phenyl)-1-(4-fluorophenyl)-2-oxo-1,2-dihydropyridine-3-carboxamide

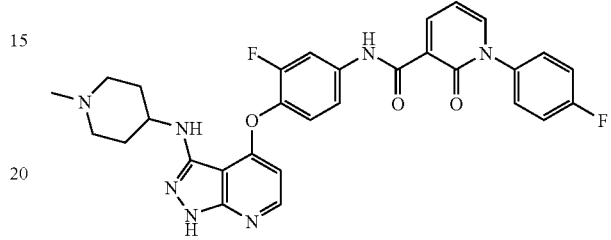

Prepared by a 2-step process from 4-(4-amino-2-fluorophenoxy)-1-(4-methoxybenzyl)-N-(1-methylpiperidin-4-yl)-1H-pyrazolo[3,4-b]pyridin-3-amine (prepared in Example 101, step A) and 1-(4-fluorophenyl)-2-oxo-1,2-dihydropyridine-3-carboxylic acid (prepared from methyl 2-oxo-2H-pyran-3-carboxylate with 4-fluoroaniline and followed by hydrolysis using the methods described in US Publication No. 2005/0239820) according to the procedure of Example 101. The crude was rinsed with Et₂O to afford 14 mg (73%) of the desired product. LRMS (ESI pos) m/e 572.0 (M+1). ¹H-NMR (400 MHz, CD₃OD/CDCl₃) δ 8.72 (d, 1H), 8.24 (d, 1H), 8.02 (dd, 1H), 8.02 (dd, 1H), 7.87 (d, 1H), 7.47 (m, 2H), 7.41 (m, 1H), 7.38 (m, 3H), 6.72 (m, 1H), 6.12 (d, 1H), 3.70 (m, 1H), 2.88 (d, 2H), 2.35 (s, 3H), 2.24 (m, 1H), 2.21 (m, 2H), 1.62 (m, 2H); ¹⁹F NMR (376 MHz, CD₃OD/CDCl₃) δ −112.6, −128.0.

Example 119

N-(3-fluoro-4-(3-(methyl(1-methylpiperidin-4-yl)amino)-1H-pyrazolo[3,4-b]pyridin-4-yloxy)phenyl)-2-(4-fluorophenyl)-3-oxo-2,3-dihydropyridazine-4-carboxamide

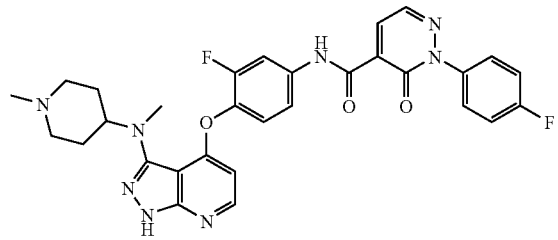

Prepared by a 2-step process from 4-(4-amino-2-fluorophenoxy)-1-(4-methoxybenzyl)-N-methyl-N-(1-methylpiperidin-4-yl)-1H-pyrazolo[3,4-b]pyridin-3-amine (prepared as described in Example 101, Step A, using N,1-dimethylpiperidin-4-amine) and 2-(4-fluorophenyl)-3-oxo-2,3-dihydropyridazine-4-carboxylic acid according to the procedure of Example 101, Step B. The crude was rinsed with Et₂O to afford 5.9 mg (55%) of the desired product. LRMS (ESI pos) m/e 587.0 (M+1). ¹H-NMR (400 MHz, CD₃OD/CDCl₃) δ 8.42 (d, 1H), 8.37 (d, 1H), 8.20 (d, 1H), 8.02 (dd, 1H), 7.64 (m, 2H), 7.46 (d, 1H), 7.26 (m, 3H), 6.20 (d, 1H), 3.70 (m, 1H), 2.98 (m, 2H), 2.90 (s, 3H), 2.28 (s, 3H), 2.08 (m, 2H), 1.93 (m, 2H), 1.81 (m, 2H); ¹⁹F NMR (376 MHz, CD₃OD/CDCl₃) δ −112.1, −127.3.

Example 120

N-(3-fluoro-4-(3-(4-(methylamino)piperidin-1-yl)-1H-pyrazolo[3,4-b]pyridin-4-yloxy)phenyl)-2-(4-fluorophenyl)-3-oxo-2,3-dihydropyridazine-4-carboxamide

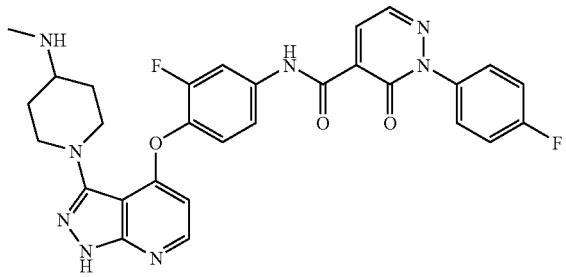

Step A: Preparation of tert-butyl 1-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)piperidin-4-yl(methyl)carbamate: A round-bottomed flask was charged with N-(4-(1-(4-methoxybenzyl)-3-iodo-1H-pyrazolo[3,4-b]pyridin-4-yloxy)-3-fluorophenyl)-2-(4-fluorophenyl)-3-oxo-2,3-dihydropyridazine-4-carboxamide (100 mg, 0.142 mmol, prepared in Example 63, step A), tert-butyl methyl(piperidin-4-yl)carbamate (152 mg, 0.708 mmol), copper(I)iodide (5.39 mg, 0.0283 mmol), (S)-pyrrolidine-2-carboxylic acid (6.52 mg, 0.0566 mmol), K₂CO₃ (97.8 mg, 0.708 mmol) and DMSO (10 mL). The reaction mixture was stirred at 100° C. overnight. The reaction was cooled to ambient temperature and partitioned between EtOAc and H₂O. The phases were separated and the aqueous phase was re-extracted with EtOAc. The combined organic layers were dried (Na₂SO₄), filtered and concentrated to yield a crude product. The crude product was purified by silica gel chromatography (DCM/7 M NH₃ in MeOH from 100/1 to 10/1, v/v) to afford product (98.5 mg, 87.8%). LRMS (APCI pos): m/e 693 (M−99).

Step B: Preparation of N-(3-fluoro-4-(3-(4-(methylamino)piperidin-1-yl)-1H-pyrazolo[3,4-b]pyridin-4-yloxy)phenyl)-2-(4-fluorophenyl)-3-oxo-2,3-dihydropyridazine-4-carboxamide: A round-bottomed flask was charged with tert-butyl 1-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-yl)piperidin-4-yl(methyl)carbamate (98.5 mg, 0.124 mmol) and CF₃COOH (5 mL). The reaction mixture was stirred at 80° C. overnight. The solvent was removed and the residue was purified by silica gel chromatography (DCM/7 M NH₃ in MeOH from 50/1 to 10/1, v/v) to give the product, which was not pure enough. The impure product was further purified by preparative HPLC to afford product (17.3 mg, 24.3%). LRMS (APCI pos) m/e 573 (M+1). ¹H NMR (400 MHz, CD₃OD) δ 11.97 (s, 1H), 8.38 (d, 1H), 8.33 (d, 1H), 8.25 (d, 1H), 8.08 (m, 1H), 7.65 (m, 2H), 7.48 (d, 1H), 7.40 (m, 1H), 7.28 (m, 2H), 6.28 (d, 1H), 4.10 (m, 2H), 3.32 (m, 1H), 3.01 (m, 2H), 2.72 (s, 3H), 2.18 (m, 2H), 2.81 (m, 2H).

Example 121

N-(3-Fluoro-4-(3-(pyrrolidin-3-ylamino)-1H-pyrazolo[3,4-b]pyridin-4-yloxy)phenyl)-2-(4-fluorophenyl)-3-oxo-2,3-dihydropyridazine-4-carboxamide

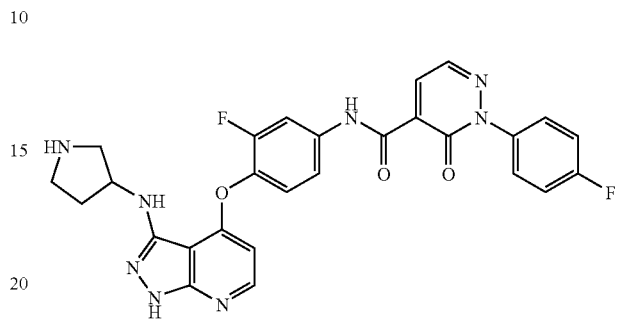

Step A: Preparation of tert-butyl 3-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-ylamino)pyrrolidine-1-carboxylate: A round-bottomed flask was charged with N-(4-(1-(4-methoxybenzyl)-3-iodo-1H-pyrazolo[3,4-b]pyridin-4-yloxy)-3-fluorophenyl)-2-(4-fluorophenyl)-3-oxo-2,3-dihydropyridazine-4-carboxamide (100 mg, 0.142 mmol, prepared in Example 63, step A), tert-butyl 3-aminopyrrolidine-1-carboxylate (132 mg, 0.708 mmol), copper(I)iodide (5.39 mg, 0.0283 mmol), (S)-pyrrolidine-2-carboxylic acid (6.52 mg, 0.0566 mmol), K₂CO₃ (97.8 mg, 0.708 mmol) and DMSO (10 mL). The reaction mixture was stirred at 80° C. overnight. The reaction was cooled to ambient temperature and partitioned between EtOAc and H₂O. The phases were separated and the aqueous phase was re-extracted with EtOAc. The combined organic layers were dried (Na₂SO₄), filtered and concentrated to yield a crude product. The crude product was purified by silica gel chromatography (DCM/7 M NH₃ in MeOH from 100/1 to 10/1, v/v) to afford product (61.3 mg, 56.6%). LRMS (APCI pos): m/e 765 (M+1).

Step B: Preparation of N-(3-fluoro-4-(1-(4-methoxybenzyl)-3-(pyrrolidin-3-ylamino)-1H-pyrazolo[3,4-b]pyridin-4-yloxy)phenyl)-2-(4-fluorophenyl)-3-oxo-2,3-dihydropyridazine-4-carboxamide: A round-bottomed flask was charged with tert-butyl 3-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-ylamino)pyrrolidine-1-carboxylate (61.3 mg, 0.08015 mmol), 2,2,2-trifluoroacetic acid (182.8 mg, 1.603 mmol) and CH₂Cl₂ (5 mL). The reaction mixture was stirred at room temperature for 4 hours. The solvent was removed and the residue was purified by silica gel chromatography (DCM/7 M NH₃ in MeOH from 50/1 to 10/1, v/v) to give product (40.8 mg, 76.58%). LRMS (APCI pos) m/e 665 (M+1).

Step C: Preparation of N-(3-fluoro-4-(3-(pyrrolidin-3-ylamino)-1H-pyrazolo[3,4-b]pyridin-4-yloxy)phenyl)-2-(4-fluorophenyl)-3-oxo-2,3-dihydropyridazine-4-carboxamide: A 100 mL round-bottomed flask was charged with N-(4-(1-(4-methoxybenzyl)-3-(pyrrolidin-3-ylamino)-1H-pyrazolo[3,4-b]pyridin-4-yloxy)-3-fluorophenyl)-2-(4-fluorophenyl)-3-oxo-2,3-dihydropyridazine-4-carboxamide (40.8 mg, 0.0614 mmol) and CF₃COOH (5 mL). The reaction mixture was stirred at 80° C. overnight. The solvent was removed and the residue was purified by silica gel chromatography (DCM/7 M NH$_3$ in MeOH from 50/1 to 10/1, v/v) to give product, which was further purified by preparative HPLC to afford product (1.9 mg, 5.68%). LRMS (APCI pos): m/e 545 (M+1). $^1$H NMR (400 MHz, CD$_3$OD) δ 11.96 (s, 1H), 8.36 (d, 1H), 8.31 (d, 1H), 8.19 (d, 1H), 8.04 (dd, 1H), 7.68 (m, 2H), 7.51 (d, 1H), 7.40 (t, 1H), 7.29 (m, 2H), 6.16 (d, 1H), 4.48 (m, 1H), 3.56 (m, 3H), 3.39 (m, 1H), 2.42 (m, 1H), 2.32 (m, 1H).

Example 122

N-(3-fluoro-4-(3-(tetrahydro-2H-pyran-4-ylamino)-1H-pyrazolo[3,4-b]pyridin-4-yloxy)phenyl)-2-(4-fluorophenyl)-3-oxo-2,3-dihydropyridazine-4-carboxamide

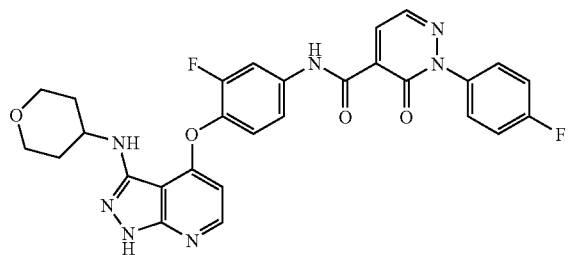

Prepared by a 2-step process from 4-(4-amino-2-fluorophenoxy)-1-(4-methoxybenzyl)-N-(tetrahydro-2H-pyran-4-yl)-1H-pyrazolo[3,4-b]pyridin-3-amine (prepared as described in Example 101, Step A except using tetrahydro-2H-pyran-4-amine) and 2-(4-fluorophenyl)-3-oxo-2,3-dihydropyridazine-4-carboxylic acid according to the procedure of Example 101, Step B. The crude was purified by silica gel flash column chromatography (2% MeOH in CH$_2$Cl$_2$) to afford 82 mg (77%) of the desired product. LRMS (ESI pos) m/e 560.0 (M+1). $^1$H NMR (400 MHz, CD$_3$OD/CDCl$_3$) δ 8.41 (d, 1H), 8.33 (d, 1H), 8.14 (d, 1H), 8.02 (dd, 1H), 7.66 (m, 2H), 7.47 (d, 1H), 7.37 (t, 1H), 7.28 (t, 2H), 6.12 (d, 1H), 4.02 (m, 2H), 3.89 (m, 1H), 3.59 (m, 2H), 2.18 (m, 2H), 1.64 (m, 2H); $^{19}$F NMR (376 MHz, CD$_3$OD/CDCl$_3$) δ −113.2, −127.8.

Example 123

N-(3-fluoro-4-(3-(1-methylpiperidin-4-ylamino)-1H-pyrazolo[3,4-b]pyridin-4-yloxy)phenyl)biphenyl-3-carboxamide

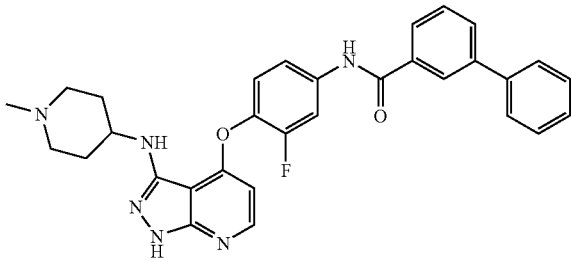

Step A: Preparation of N-(3-fluoro-4-(1-(4-methoxybenzyl)-3-(1-methylpiperidin-4-ylamino)-1H-pyrazolo[3,4-b]pyridin-4-yloxy)phenyl)biphenyl-3-carboxamide: To a stirred solution of 1-(4-methoxybenzyl)-4-(4-amino-2-fluorophenoxy)-N-(1-methylpiperidin-4-yl)-1H-pyrazolo[3,4-b]pyridin-3-amine (12 mg, 0.026 mmol) (prepared in Example 101, step A) in 260 μL dichloromethane at 0° C. under nitrogen was added DIEA (14 μL, 0.078 mmol) followed by biphenyl-3-carbonyl chloride (7 mg, 0.031 mmol). The reaction was allowed to warm to room temperature overnight. The reaction was diluted to 10 mL with dichloromethane and stirred rapidly with 10% sodium carbonate solution for 5 minutes. The organics were isolated and dried (MgSO$_4$). The organics were filtered and concentrated to a residue that was loaded onto a Biotage 12S column with dichloromethane and eluted with 4/1 EtOAc/hexanes. The product containing fractions were pooled and concentrated to a yellow oil (10 mg, 59% yield).

Step B: Preparation of N-(3-fluoro-4-(3-(1-methylpiperidin-4-ylamino)-1H-pyrazolo[3,4-b]pyridin-4-yloxy)phenyl)biphenyl-3-carboxamide: To a flask containing N-(3-fluoro-4-(1-(4-methoxybenzyl)-3-(1-methylpiperidin-4-ylamino)-1H-pyrazolo[3,4-b]pyridin-4-yloxy)phenyl)biphenyl-3-carboxamide (10 mg, 0.015 mmol) at room temperature under a drying tube was added TFA (1 mL). The solution was warmed to 50° C. for 3 hours. After cooling to ambient temperature, the solution was concentrated, and the residue was redissolved in 5 mL dichloromethane and stirred rapidly with 5 mL 10% sodium carbonate solution to provide the free base. The organic layer was isolated, dried (MgSO$_4$), filtered and concentrated. The crude product was passed through a small gravity silica cartridge with 95/5 dichloromethane/MeOH to provide the desired product as a clear oil (2.2 mg, 27% yield). $^1$H NMR (400 MHz, CDCl$_3$) δ 9.40 (br s, 1H), 8.20 (d, 1H), 8.11 (m, 1H), 8.01 (m, 1H), 7.92 (m, 1H), 7.85 (m, 1H), 7.82 (m, 1H), 7.65 (m, 2H), 7.60 (m, 1H), 7.50 (m, 2H), 7.41 (m, 2H), 7.30 (m, 1H), 6.10 (d, 1H), 4.54 (m, 1H), 3.73 (br m, 1H), 2.89 (br m, 2H), 2.34 (s, 3H), 2.24 (br m, 3H), 1.68 (br m, 2H). LCMS (APCI+): m/z 537 (M+1) detected.

Example 124

N-(3-fluoro-4-(3-morpholino-1H-pyrazolo[3,4-b]pyridin-4-yloxy)phenyl)-2-(4-fluorophenyl)-3-oxo-2,3-dihydropyridazine-4-carboxamide

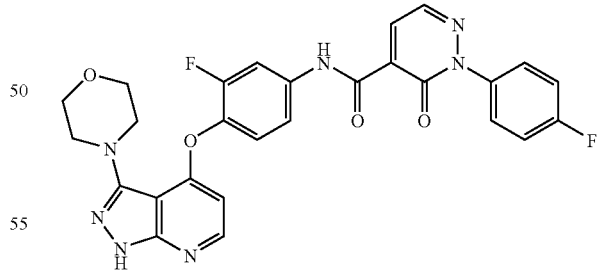

Prepared by a 2-step process from 3-fluoro-4-(1-(4-methoxybenzyl)-3-morpholino-1H-pyrazolo[3,4-b]pyridin-4-yloxy)aniline (prepared as described in Example 101, Step A, except using morpholine) and 2-(4-fluorophenyl)-3-oxo-2,3-dihydropyridazine-4-carboxylic acid according to the procedure of Example 101, Step B. The crude was purified by silica gel flash column chromatography (2% MeOH in CH$_2$Cl$_2$) to afford 7.6 mg (37%) of the desired product. LRMS (ESI pos) m/e 546.0 (M+1). $^1$H-NMR (400 MHz, CD$_3$OD/CDCl$_3$) δ

8.41 (d, 1H), 8.33 (d, 1H), 8.21 (d, 1H), 8.02 (dd, 1H), 7.65 (m, 2H), 7.46 (d, 1H), 7.34 (t, 1H), 7.28 (t, 2H), 6.25 (d, 1H), 3.89 (m, 4H), 3.47 (m, 4H); $^{19}$F-NMR (376 MHz, CD$_3$OD/CDCl$_3$) δ −113.1, −128.2.

Example 125

N-(3-fluoro-4-(3-(1-methylpiperidin-4-ylamino)-1H-pyrazolo[3,4-b]pyridin-4-yloxy)phenyl)-4-(4-fluorophenyl)-3-oxo-3,4-dihydropyrazine-2-carboxamide

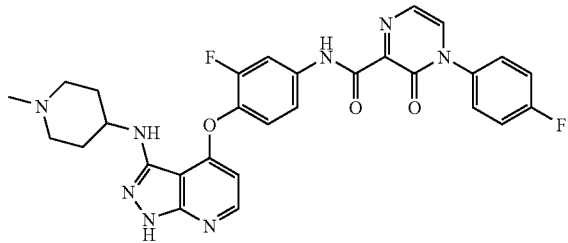

Step A: Preparation of 5-chloro-1-(4-fluorophenyl)-3-methoxypyrazin-2(1H)-one: 3,5-dichloro-1-(4-fluorophenyl)pyrazin-2(1H)-one (13.0 g, 50.2 mmol; prepared by according to the general methods described by M. Tutonda, et al., *Tetrahedron*, 1990, 46, 5715) dissolved in absolute methanol (100 mL) was treated with NaOMe (6.78 g, 125 mmol). The reaction mixture was stirred at room temperature for 1 hour, neutralized with 2 N HCl (Et$_2$O solution), and evaporated the solvent under reduced pressure. The residue was treated with EtOAc, washed with 0.5 N HCl, dried over MgSO$_4$, and concentrated under reduced pressure to give the desired product (12.8 g, 100%). LRMS (ESI pos) m/e 254.9, 256.9 (M+1, Cl pattern).

Step B: Preparation of 1-(4-fluorophenyl)-3-methoxypyrazin-2(1H)-one: K$_2$CO$_3$ (1.09 g, 7.85 mmol) and 10% Pd/C (0.42 g, 0.39 mmol) were added to 5-chloro-1-(4-fluorophenyl)-3-methoxypyrazin-2(1H)-one (2.0 g, 7.85 mmol) in MeOH (100 mL) at room temperature under a H$_2$ atmosphere and the reaction was stirred for 6 hours. The reaction mixture was filtered with MeOH and concentrated under reduced pressure. The crude was treated with CH$_2$Cl$_2$, washed with water, dried over MgSO$_4$, and concentrated to give the desired product (1.55 g, 90%). LRMS (ESI pos) m/e 221.0 (M+1).

Step C: Preparation of 3-chloro-1-(4-fluorophenyl) pyrazin-2(1H)-one: POCl$_3$ (5.6 mL, 61.3 mmol) was added dropwise to a solution of 1-(4-fluorophenyl)-3-methoxypyrazin-2(1H)-one in DMF (30 mL) with stirring at 0° C. followed by heating at 90° C. for 1.5 hours. The residue was cooled to 0° C., quenched by adding saturated sodium acetate solution, extracted with CH$_2$Cl$_2$, washed with water, dried over MgSO$_4$, and concentrated. The crude was purified by silica gel flash column chromatography (0.7% MeOH in CH$_2$Cl$_2$) to afford 3.52 g (64%) of the desired product. LRMS (ESI pos) m/e 224.9, 227.0 (M+1, Cl pattern).

Step D: Preparation of 4-(4-fluorophenyl)-3-oxo-3,4-dihydropyrazine-2-carbonitrile: A mixture of 3-chloro-1-(4-fluorophenyl)pyrazin-2(1H)-one (3.52 g, 15.7 mmol), CuCN (2.81 g, 31.3 mmol) and N-methylpyrrolidone (30 mL) was heated for 5.5 hours at 150° C. while being stirred. The residue was triturated with hot CHCl$_3$ and filtered over charcoal. The filtrate was evaporated and concentrated under reduced pressure. The residue was triturated with CH$_2$Cl$_2$ and the solution was concentrated. The crude was purified by silica gel flash column chromatography (3:1=CH$_2$Cl$_2$:Hexane then CH$_2$Cl$_2$) to afford 0.78 g (23%) of the desired product. LRMS (ESI pos) m/e 215.9 (M+1).

Step E: Preparation of 4-(4-fluorophenyl)-3-oxo-3,4-dihydropyrazine-2-carboxylic acid: A mixture of 4-(4-fluorophenyl)-3-oxo-3,4-dihydropyrazine-2-carbonitrile (0.42 g, 1.95 mmol) and H$_2$SO$_4$ (4.16 mL, 78.1 mmol) was stirred at ambient temperature for 17 hours. Then the reaction mixture (amide intermediate) was added to MeOH (50 mL), and then the reaction was heated at 70° C. for 2.5 hours. The reaction mixture was quenched with ice-water and treated with aqueous 2N NaOH solution at 0° C. The mixture was acidified with aqueous 1N HCl, extracted with EtOAc, dried over MgSO$_4$, and concentrated to afford 0.315 g of the desired product (69% for 3-step process in one pot reaction), which was rinsed with Et$_2$O.

Step F: Preparation of N-(3-fluoro-4-(3-(1-methylpiperidin-4-ylamino)-1H-pyrazolo[3,4-b]pyridin-4-yloxy)phenyl)-4-(4-fluorophenyl)-3-oxo-3,4-dihydropyrazine-2-carboxamide: Prepared by a 2-step process from 4-(4-amino-2-fluorophenoxy)-1-(4-methoxybenzyl)-N-(1-methylpiperidin-4-yl)-1H-pyrazolo[3,4-b]pyridin-3-amine and 4-(4-fluorophenyl)-3-oxo-3,4-dihydropyrazine-2-carboxylic acid according to the procedure of Example 101, Step B. The crude was rinsed with Et$_2$O to afford 8.8 mg (53%) of the desired product. LRMS (ESI pos) m/e 573.0 (M+1). $^1$H NMR (400 MHz, CD$_3$OD/CDCl$_3$) δ 8.14 (d, 1H), 8.05 (dd, 1H), 7.86 (m, 2H), 7.57 (m, 2H), 7.51 (d, 1H), 7.34 (m, 3H), 6.12 (d, 1H), 3.71 (m, 1H), 2.92 (m, 2H), 2.35 (s, 3H), 2.29 (m, 2H), 2.22 (m, 2H), 1.65 (m, 2H); $^{19}$F NMR (376 MHz, CD$_3$OD/CDCl$_3$) δ −112.1, −129.4.

Example 126

N-(3-fluoro-4-(3-(1-(2-hydroxyethyl)piperidin-4-ylamino)-1H-pyrazolo[3,4-b]pyridin-4-yloxy)phenyl)-2-(4-fluorophenyl)-3-oxo-2,3-dihydropyridazine-4-carboxamide

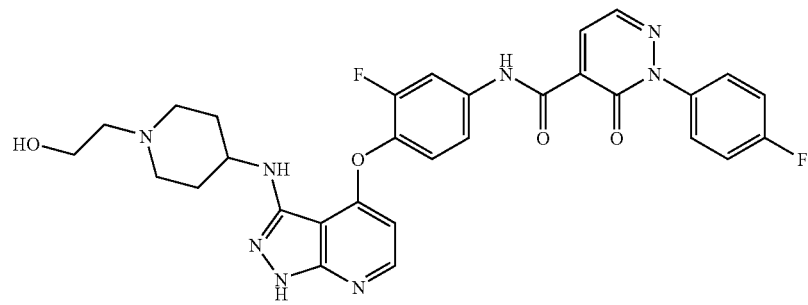

Prepared by a 2-step process from 2-(4-(4-(4-amino-2-fluorophenoxy)-1-(4-methoxybenzyl)-1H-pyrazolo[3,4-b]pyridin-3-ylamino)piperidin-1-yl)ethanol (prepared as described in Example 101, Step A except using 2-(4-aminopiperidin-1-yl)ethanol) and 2-(4-fluorophenyl)-3-oxo-2,3-dihydropyridazine-4-carboxylic acid according to the procedure of Example 101, Step B. The crude material was rinsed with Et$_2$O to afford 11 mg (55%) of the desired product. LRMS (ESI pos) m/e 603.1 (M+1). $^1$H-NMR (400 MHz, CD$_3$OD/CDCl$_3$) δ 8.42 (d, 1H), 8.31 (d, 1H), 8.13 (d, 1H), 8.0 (dd, 1H), 7.63 (m, 2H), 7.45 (d, 1H), 7.33 (t, 1H), 7.28 (t, 2H), 6.10 (d, 1H), 3.72 (m, 3H), 3.03 (m, 2H), 2.65 (m, 2H), 2.40 (m, 2H), 2.25 (m, 2H), 1.67 (m, 2H); $^{19}$F NMR (376 MHz, CD$_3$OD/CDCl$_3$) δ −112.1, −126.9.

Example 127

N-(3-fluoro-4-(3-(1-methylpiperidin-4-ylamino)-1H-pyrazolo[3,4-b]pyridin-4-yloxy)phenyl)-1-(4-fluorophenyl)-2-oxoazepane-3-carboxamide

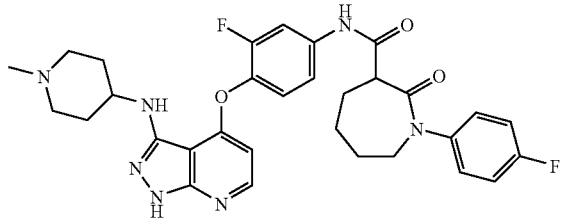

Step A: Preparation of 1-(4-fluorophenyl)azepan-2-one: A suspension of ε-caprolactam (10 g, 90 mmol), 1-fluoro-4-iodobenzene (10 ml, 90 mmol), L-proline (4.1 g, 36 mmol), K$_2$CO$_3$ (37 g, 270 mmol), and Cu(I)I (3.4 g, 18 mmol) was stirred in DMSO (50 mL) and heated to 100° C. for 12 hours. Water (50 mL) was added and the reaction mixture was extracted with EtOAc. The organic layer washed with water) and brine, dried with Na$_2$SO$_4$, filtered and concentrated. The residue was purified by silica gel chromatography (50% EtOAc in hexane) to afford the product (1.2 g, 6.4% yield) as brown oil. LRMS (APCI pos) m/e 208.0 (M+1).

Step B: Preparation of benzyl 1-(4-fluorophenyl)-2-oxoazepane-3-carboxylate: A solution of 1-(4-fluorophenyl)azepan-2-one (1.1 g, 5.3 mmol) was dissolved in THF (5 mL) and was added into LDA (11 mmol) at −78° C. and stirred for 5 minutes. Benzyl chloroformate (1.6 ml, 11 mmol) was added at −78° C. and the reaction warmed to ambient temperature. The solution was poured into ice and diluted with EtOAc (100 mL). The organic layer washed with brine, dried with Na$_2$SO$_4$, filtered and concentrated. The residue was purified by column chromatography (50% EtOAc in hexane) to afford the product (1 g, 55% yield) as brown oil.

Step C: Preparation of 1-(4-fluorophenyl)-2-oxoazepane-3-carboxylic acid: A mixture of benzyl 1-(4-fluorophenyl)-2-oxoazepane-3-carboxylate (1 g, 3 mmol) and Pd/C (0.1 g, 10% wet) was stirred in MeOH (5 mL) under a H$_2$ atmosphere. After 4 hours, the catalyst was removed by filtration through a pad of silica gel with MeOH. Solvent was evaporated to afford the product (0.3 g, 41% yield) as a white solid. LRMS (APCI pos) m/e 251.8 (M+1).

Step D: Preparation of N-(4-(1-(4-methoxybenzyl)-3-(1-methylpiperidin-4-ylamino)-1H-pyrazolo[3,4-b]pyridin-4-yloxy)-3-fluorophenyl)-1-(4-fluorophenyl)-2-oxoazepane-3-carboxamide: EDCI (48 mg, 0.25 mmol) was added to a mixture of the 1-(4-fluorophenyl)-2-oxoazepane-3-carboxylic acid (21 mg, 0.084 mmol) and HOBT (34 mg, 0.25 mmol) in DMF (0.5 mL) at ambient temperature, and the reaction mixture was stirred for 10 minutes at ambient temperature. 1-(4-methoxybenzyl)-4-(4-amino-2-fluorophenoxy)-N-(1-methylpiperidin-4-yl)-1H-pyrazolo[3,4-b]pyridin-3-amine (20 mg, 0.042 mmol, obtained from Example 101, Step A) and triethylamine (0.035 ml, 0.25 mmol) were added. The resulting mixture was stirred for 12 hours at ambient temperature. The reaction mixture was diluted with EtOAc. The organic layer washed with 10% aqueous LiCl, dried over Na$_2$SO$_4$, and concentrated. The residue was purified by flash column chromatography (5% MeOH in CH$_2$Cl$_2$) to afford the product (20 mg, 67% yield) as a white solid. LRMS (APCI pos) m/e 710.3 (M+1).

Step E: Preparation of N-(3-fluoro-4-(3-(1-methylpiperidin-4-ylamino)-1H-pyrazolo[3,4-b]pyridin-4-yloxy)phenyl)-1-(4-fluorophenyl)-2-oxoazepane-3-carboxamide: A solution of N-(4-(1-(4-methoxybenzyl)-3-(1-methylpiperidin-4-ylamino)-1H-pyrazolo[3,4-b]pyridin-4-yloxy)-3-fluorophenyl)-1-(4-fluorophenyl)-2-oxoazepane-3-carboxamide (20 mg, 0.028 mmol) was heated in TFA (1 mL) at 55° C. for 3 hours. TFA was evaporated and EtOAc was added to dilute the mixture. The mixture washed with saturated aqueous NaHCO$_3$, brine, dry with Na$_2$SO$_4$, filtered and concentrated. The residue was purified by flash column chromatography (20% MeOH in CH$_2$Cl$_2$) to afford the product (5 mg, 30% yield) as a white solid. LRMS (APCI pos) m/e 590.1 (M+1). $^1$H NMR (400 MHz, DMSO-d$_6$): δ 12.15 (s, 1H), 10.20 (s, 1H), 8.10 (s, 1H), 7.82 (d, 1H), 7.18-7.50 (m, 7H), 5.98-6.00 (m, 1H), 5.10-5.20 (m, 1H), 3.90-4.02 (m, 2H), 3.40-3.62 (m, 2H), 2.62-2.80 (m, 1H), 2.15 (s, 3H), 1.90-2.02 (m, 5H), 1.50-1.88 (m, 6H).

Example 128

N-(2-chloro-5-fluoro-4-(3-(1-methylpiperidin-4-ylamino)-1H-pyrazolo[3,4-b]pyridin-4-yloxy)phenyl)-2-(4-fluorophenyl)-3-oxo-2,3-dihydropyridazine-4-carboxamide

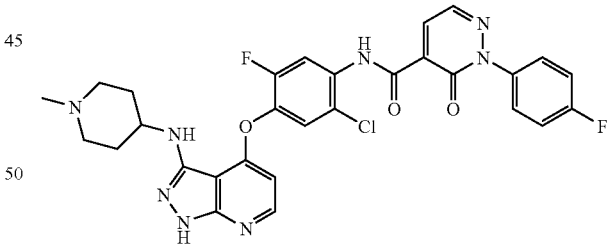

Step A: Preparation of 1-chloro-4,5-difluoro-2-nitrobenzene: To 4-chloro-1,2-difluorobenzene (25.0 g, 168.3 mmol) cooled to 0° C. was added fuming nitric acid (50.0 ml, 168.3 mmol) dropwise over 30 minutes. The solution was warmed to room temperature and stirred for 2 hours. The solution was poured slowly over ice and the resultant mixture extracted with diethyl ether. The diethyl ether layers were washed with brine, dried with Na$_2$SO$_4$, filtered and concentrated to afford the product (28 g, 81% yield) as orange oil. $^1$H NMR (CDCl$_3$, 400 MHz) δ 7.89 (s, 1H), 7.46 (s, 1H).

Step B: Preparation of 1-(4-methoxybenzyl)-3-iodo-1H-pyrazolo[3,4-b]pyridin-4-ol: A mixture of 1-(4-methoxybenzyl)-4-chloro-3-iodo-1H-pyrazolo[3,4-b]pyridine (7.00 g, 17.52 mmol, obtained from Example 84, Step D), cesium acetate (33.62 g, 175.2 mmol) and DMF (175 mL) was heated to 100° C. for 12 hours. The reaction was cooled to room temperature, diluted with water (50 mL), extracted with EtOAc (100 mL), dried over sodium sulfate, filtered and concentrated. The residue was purified by flash column chromatography (5% MeOH in $CH_2Cl_2$) to afford the product (2.23 g, 79% yield) as a light orange solid. LRMS (APCI pos) m/e 381.9 (M+H).

Step C: Preparation of 1-(4-methoxybenzyl)-4-(5-chloro-2-fluoro-4-nitrophenoxy)-3-iodo-1H-pyrazolo[3,4-b]pyridine: A mixture of 1-chloro-4,5-difluoro-2-nitrobenzene (2.23 g, 11.5 mmol), 1-(4-methoxybenzyl)-3-iodo-1H-pyrazolo[3,4-b]pyridin-4-ol (4.00 g, 10.5 mmol), $K_2CO_3$ (1.60 g, 11.5 mmol) and DMF (100 mL) was heated to 50° C. for 18 hours. The reaction was cooled to ambient temperature, diluted with water (500 mL), extracted with EtOAc, dry over sodium sulfate, filter and concentrate. The residue was purified by flash column chromatography (5% MeOH in $CH_2Cl_2$) to provide a light pink solid. The solid was triturated with hot MeOH to afford the product (2.35 g, 40% yield) as a white solid. LRMS (APCI pos) m/e 554.8 (M+H).

Step D: Preparation of 4-(1-(4-methoxybenzyl)-3-iodo-1H-pyrazolo[3,4-b]pyridin-4-yloxy)-2-chloro-5-fluorobenzenamine: A mixture of 1-(4-methoxybenzyl)-4-(5-chloro-2-fluoro-4-nitrophenoxy)-3-iodo-1H-pyrazolo[3,4-b]pyridine (2.85 g, 5.14 mmol), $SnCl_2$ dihydrate (4.64 g, 20.6 mmol) and EtOH (70 mL) was heated to 70° C. for 8 hours. The reaction mixture was cooled to room temperature, diluted with EtOAc, washed with saturated aqueous $Na_2CO_3$, dried over sodium sulfate and concentrated. The residue was purified by flash column chromatography (5% MeOH in $CH_2Cl_2$) to afford the product (2.02 g, 64% yield) as a light yellow solid. LRMS (APCI pos) m/e 524.9 (M+H).

Step E: Preparation of 1-(4-methoxybenzyl)-4-(4-amino-5-chloro-2-fluorophenoxy)-N-(1-methylpiperidin-4-yl)-1H-pyrazolo[3,4-b]pyridin-3-amine: 4-(1-(4-methoxybenzyl)-3-iodo-1H-pyrazolo[3,4-b]pyridin-4-yloxy)-2-chloro-5-fluorobenzenamine (200 mg, 0.38 mmol) was added into a suspension of 4-amino-1-methylpiperidine (131 mg, 1.14 mmol), Cu(I)I (14.5 mg, 0.0762 mmol), $K_2CO_3$ (263 mg, 1.91 mmol) and L-proline (17.6 mg, 0.152 mmol) in DMSO (6 mL) and the reaction mixture was heated at 100° C. for 12 hours. The reaction with diluted with $CH_2Cl_2$ and water (10 mL) was added. The organic layer was then washed with water (10 mL), brine, dried over $Na_2SO_4$, filtered and concentrated. The residue was purified by flash column chromatography (5% MeOH in $CH_2Cl_2$) to afford the product (130 mg, 66.7% yield) as a brown oil. LRMS (APCI pos) m/e 511.1 (M+H).

Step F: Preparation of N-(4-(1-(4-methoxybenzyl)-3-(1-methylpiperidin-4-ylamino)-1H-pyrazolo[3,4-b]pyridin-4-yloxy)-2-chloro-5-fluorophenyl)-2-(4-fluorophenyl)-3-oxo-2,3-dihydropyridazine-4-carboxamide: A solution of 1-(4-methoxybenzyl)-4-(4-amino-5-chloro-2-fluorophenoxy)-N-(1-methylpiperidin-4-yl)-1H-pyrazolo[3,4-b]pyridin-3-amine (130 mg, 0.254 mmol) in $CH_2Cl_2$ (1 mL) was added into a solution of 2-(4-fluorophenyl)-3-oxo-2,3-dihydropyridazine-4-carboxylic acid (119 mg, 0.509 mmol, obtained from Example 19 Step C), triethylamine (0.213 ml, 1.53 mmol), EDCI (293 mg, 1.53 mmol) and HOBT (206 mg, 1.53 mmol) in $CH_2Cl_2$ (2 mL). The reaction mixture was stirred for 12 hours at ambient temperature. The reaction was diluted with $CH_2Cl_2$ and washed with saturated aqueous $NaHCO_3$ and brine. The organic layer obtained was dried with $Na_2SO_4$, filtered and concentrated. The residue was purified by flash column chromatography (5% MeOH in $CH_2Cl_2$) to afford the product (100 mg, 54.1% yield) as a yellow solid. LRMS (APCI pos) m/e 727.2 (M+H).

Step G: Preparation of N-(2-chloro-5-fluoro-4-(3-(1-methylpiperidin-4-ylamino)-1H-pyrazolo[3,4-b]pyridin-4-yloxy)phenyl)-2-(4-fluorophenyl)-3-oxo-2,3-dihydropyridazine-4-carboxamide: A solution of N-(4-(1-(4-methoxybenzyl)-3-(1-methylpiperidin-4-ylamino)-1H-pyrazolo[3,4-b]pyridin-4-yloxy)-2-chloro-5-fluorophenyl)-2-(4-fluorophenyl)-3-oxo-2,3-dihydropyridazine-4-carboxamide (100 mg, 0.138 mmol) was dissolved in TFA (2 mL) and the solution was heated to 50° C. for 1 hour. Excess TFA was evaporated and the crude material was dissolved in EtOAc. The organic layer washed with saturated aqueous $NaHCO_3$, brine, dried with $Na_2SO_4$, filtered and concentrated to afford a yellow solid. The solid washed with diethyl ether to afford the product (35 mg, 41.9% yield) as a yellow solid. LRMS (APCI pos) m/e 607.0 (M+H). $^1$H NMR (DMSO-$d_6$, 400 MHz) δ 12.32 (s, 1H), 12.22 (s, 1H), 8.70 (d, 1H), 8.42 (dd, 12H), 8.17 (d, 1H), 7.91 (d, 1H), 7.74-7.67 (m, 2H), 7.49-7.41 (m, 2H), 6.17-6.13 (m, 1H), 5.23-5.18 (m, 1H), 3.60-3.42 (m, 1H), 2.85-2.73 (m, 2H), 2.20 (s, 3H), 2.10-1.96 (m, 4H), 1.65-1.53 (m, 2H).

Example 129

N-(3-fluoro-4-(3-(1-(piperidin-4-yl)-1H-pyrazol-4-yl)-1H-pyrazolo[3,4-b]pyridin-4-yloxy)phenyl)-2-(4-fluorophenyl)-3-oxo-2,3-dihydropyridazine-4-carboxamide

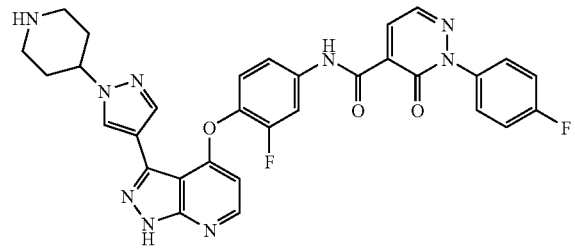

Step A: Preparation of tert-butyl 4-(4-(4,4,5,5-tetramethyl-1,3,2-dioxaborolan-2-yl)-1H-pyrazol-1-yl)piperidine-1-carboxylate: A 1 L, 1-neck flask was charged with 4-(4,4,5,5-tetramethyl-1,3,2-dioxaborolan-2-yl)-1H-pyrazole (20.0 g, 103 mmol), and DMF (250 mL). The reaction mixture was cooled to 0° C. and NaH (2.73 g, 108 mmol) (95%) was added. The reaction mixture was stirred at 0° C. for 1 hour. tert-Butyl 4-(methylsulfonyloxy)piperidine-1-carboxylate (30.2 g, 108 mmol; prepared as in WO 06/021881) was added and the reaction mixture was heated at 100° C. overnight. The reaction mixture was cooled to ambient temperature and diluted with water. The reaction mixture was extracted with EtOAc, and the organic layer washed with brine, dried over sodium sulfate, filtered and concentrated. The crude material was purified on a Biotage 40S column eluting with EtOAc/Hexane 10% to 25% EtOAc. The product was isolated as a white solid (11.3 g, 29%).

Step B: tert-butyl 4-(4-(4-(4-amino-2-fluorophenoxy)-1-(4-methoxybenzyl)-1H-pyrazolo[3,4-b]pyridin-3-yl)-1H-pyrazol-1-yl)piperidine-1-carboxylate: A 100 mL round-bottomed flask was charged with tert-butyl 4-(4-(4,4,5,5-tetramethyl-1,3,2-dioxaborolan-2-yl)-1H-pyrazol-1-yl)piperidine-1-carboxylate (0.289 g, 0.765 mmol), 4-(1-(4-methoxybenzyl)-3-iodo-1H-pyrazolo[3,4-b]pyridin-4- yloxy)-3-fluorobenzenamine (0.250 g, 0.510 mmol from Example 63, Step A), potassium carbonate (0.106 g, 0.765 mmol), Pd(PPh₃)₄ (0.0295 g, 0.0255 mmol), degassed DMF (2 mL) and water (0.5 mL). The reaction mixture was heated at 100° C. using a CEM microwave for 2 hours. The reaction mixture was cooled to ambient temperature and extracted with EtOAc/water. The organic layer was dried over sodium sulfate, filtered and concentrated. The crude material was purified by preparative TLC (2.0 mm eluting with EtOAc). Isolated 0.113 g (32%) of the desired product. LRMS M+1 (614.1) observed.

Step C: tert-butyl 4-(4-(4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)-1H-pyrazol-1-yl)piperidine-1-carboxylate: A 25 mL round-bottomed flask was charged with 2-(4-fluorophenyl)-3-oxo-2,3-dihydropyridazine-4-carboxylic acid (0.0840 g, 0.358 mmol obtained from Example 19, step C), EDCI (0.0687 g, 0.358 mmol), HOBT (0.0549 g, 0.358 mmol), and DMF (5 mL). The reaction mixture was stirred for 30 minute and tert-butyl 4-(4-(1-(4-methoxybenzyl)-4-(4-amino-2-fluorophenoxy)-1H-pyrazolo[3,4-b]pyridin-3-yl)-1H-pyrazol-1-yl)piperidine-1-carboxylate (0.110 g, 0.179 mmol) and Hunig's base (0.0463 g, 0.358 mmol) were added. The reaction mixture was stirred for 18 hours, then diluted with water and extracted with EtOAc. The organic layer was dried over sodium sulfate, filtered and concentrated. The crude material was purified by preparative TLC (0.5 mm thickness) eluting with CHCl₃/MeOH(NH₃ 7N) 4:1. To the isolated product was added TFA (2 mL) and the solution was heated to 70° C. for 1 hour. The solution was concentrated and triturated with DCM/MeOH 1:1. The solids were collected by filtration to provide 5.1 mg (5%) of the desired product. LRMS M+1 (610.0) observed Example 130

2-(3-fluoro-4-(3-(1-methylpiperidin-4-ylamino)-1H-pyrazolo[3,4-b]pyridin-4-yloxy)phenylamino)-N-(4-fluorophenyl)nicotinamide

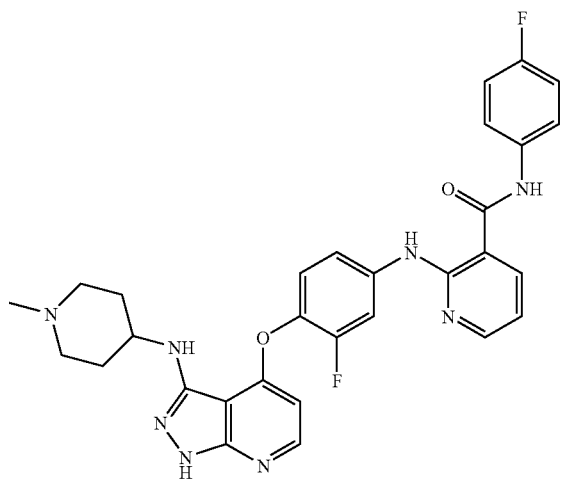

Step A: 2-amino-N-(4-fluorophenyl)nicotinamide: A 1 L round-bottomed flask was charged with HOBT-H₂O (20.37 g, 133.0 mmol), EDCI (25.50 g, 133.0 mmol), 2-aminonicotinic acid (12.25 g, 88.69 mmol), and DMF (750 mL). The reaction mixture was stirred for 30 minutes, then Hunig's base (30.90 ml, 177.4 mmol) and 4-fluorobenzenamine (10.65 ml, 110.9 mmol) were added. The reaction mixture was stirred for 18 hours, then diluted with water. After 30 minutes the resulting precipitate was collected by filtration and dried to provide the product. LRMS M+1 (231.9) observed.

Step B: 2-(3-fluoro-4-methoxyphenylamino)-N-(4-fluorophenyl)nicotinamide: A 1 L round-bottomed flask was charged with cesium carbonate (11.1 g, 34.1 mmol), 4-bromo-2-fluoro-1-methoxybenzene (5.00 g, 24.4 mmol), 2-amino-N-(4-fluorophenyl)nicotinamide (7.61 g, 32.9 mmol), and dioxane (250 mL). The reaction mixture was degassed with nitrogen for 10 minutes, and Xanphos (0.564 g, 0.975 mmol) and Pd₂dba₃ (0.670 g, 0.732 mmol) were added. The reaction mixture was heated at 90° C. for 48 hours. The reaction mixture was cooled to ambient temperature and diluted with water. The reaction mixture was extracted with EtOAc, dried over sodium sulfate, filtered and concentrated. The crude material was purified by silica gel chromatography (biotage 65) eluting with DCM/MeOH (3%). Isolated 8.50 g (93%) of the product. LRMS M+1 (365.0) observed.

Step C: 2-(3-fluoro-4-hydroxyphenylamino)-N-(4-fluorophenyl)nicotinamide: A 250 mL round-bottomed flask was charged with 2-(3-fluoro-4-methoxyphenylamino)-N-(4-fluorophenyl)nicotinamide (8.00 g, 22.5 mmol) and DCM (75 mL). The reaction mixture was cooled to 0° C. and BBr₃ (10.9 ml, 115 mmol) was added dropwise over 5 minutes. The reaction mixture was stirred for 2 hours, then slowly quenched by pipetting the reaction into a flask (500 mL) containing saturated NaHCO₃ (20 mL), water (150 mL). This solution was extracted with EtOAc. The organic layer was dried and concentrated to provide the product 6.25 g (73%). LRMS M-1 (339.9) observed.

Step D: 2-(4-(1-(4-methoxybenzyl)-3-iodo-1H-pyrazolo[3,4-b]pyridin-4-yloxy)-3-fluorophenylamino)-N-(4-fluorophenyl)nicotinamide: A 100 mL sealable tube was charged with 1-(4-methoxybenzyl)-4-chloro-3-iodo-1H-pyrazolo[3,4-b]pyridine (0.250 g, 0.626 mmol Example 84, Step D), 2-(3-fluoro-4-hydroxyphenylamino)-N-(4-fluorophenyl)nicotinamide (0.427 g, 1.25 mmol), cesium carbonate (0.408 g, 1.25 mmol), and 1-bromobenzene (6.26 ml, 0.626 mmol). The reaction mixture was heated to 160° C. for 18 hours. The reaction mixture was cooled to ambient temperature and concentrated. The residue was dissolved in EtOAc and washed with brine. The crude material was purified by silica gel (Biotage 40S) eluting with 4:1 Hexane/EtOAc to provide the product (0.35 g, 71%). LRMS M-1 (704.9) observed.

Step E: 2-(4-(1-(4-methoxybenzyl)-3-(1-methylpiperidin-4-ylamino)-1H-pyrazolo[3,4-b]pyridin-4-yloxy)-3-fluorophenylamino)-N-(4-fluorophenyl)nicotinamide: A 25 mL round-bottomed flask was charged with Cu(I)I (0.0108 g, 0.0568 mmol), 1-methylpiperidin-4-amine (0.0973 g, 0.852 mmol), K₂CO₃ (0.196 g, 1.42 mmol), L-Proline (0.0131 g, 0.114 mmol) and DMSO (2.5 mL). The reaction mixture was stirred for 5 minutes and 2-(4-(1-(4-methoxybenzyl)-3-iodo-1H-pyrazolo[3,4-b]pyridin-4-yloxy)-3-fluorophenylamino)-N-(4-fluorophenyl)nicotinamide (0.200 g, 0.284 mmol) in DMSO (2.5 mL) was added. The reaction mixture was heated to 100° C. for 18 hours. The reaction mixture was cooled to ambient temperature and DCM and water (10 mL) were added. The organic layer washed with brine, dried over sodium sulfate, filtered and concentrated. The crude material was purified by silica gel chromatography, eluting with EtOAc to provide the product (23 mg, 11%). LRMS M-1 (691.2) observed.

Step F: 2-(3-fluoro-4-(3-(1-methylpiperidin-4-ylamino)-1H-pyrazolo[3,4-b]pyridin-4-yloxy)phenylamino)-N-(4-fluorophenyl)nicotinamide: A 25 mL round-bottomed flask was charged with 2-(4-(1-(4-methoxybenzyl)-3-(1-methylpiperidin-4-ylamino)-1H-pyrazolo[3,4-b]pyridin-4-yloxy)-3-fluorophenylamino)-N-(4-fluorophenyl)nicotinamide (0.023 g, 0.0333 mmol) and TFA (3 mL). The reaction mixture was heated to 70° C. for 1 hour. The reaction was concentrated and the residue was purified by preparative TLC [0.5 mm thickness eluting with 15% MeOH(NH$_3$)/CHCl$_3$] to provide the product (9 mg, 46%). LRMS M−1 (571.1) observed. $^1$H NMR (400 MHz, CDCl$_3$) δ 10.56 (s, 1H), 10.12 (br s, 1H), 8.43 (m, 1H), 8.18 (m, 1H), 8.06 (m, 2H), 7.91 (m, 1H), 7.53 (m, 2H), 7.31 (m, 1H), 7.13 (m, 3H), 6.86 (m, 1H), 6.11 (m, 1H), 4.58 (d, J=7 Hz, 1H), 3.74 (br s, 1H), 2.92 (br s, 2H), 2.37 (s, 3H), 2.27 (br s, 2H), 1.72 (br s, 2H), 1.59 (br s, 1H). $^{19}$F NMR (376 MHz, CDCl$_3$) δ −76.0 (3F), −117.0 (1F), −127.6 (1F).

Example 131

3-(4-(2-fluoro-4-(2-(4-fluorophenyl)-3-oxo-2,3-dihydropyridazine-4-carboxamido)phenoxy)-1H-pyrazolo[3,4-b]pyridin-3-ylamino)cyclohexyl 2,2,2-trifluoroacetate Step C: Preparation of 3-(4-(2-fluoro-4-(1-(4-fluorophenyl)-6-oxo-1,6-dihydropyridazine-5-carboxamido)phenoxy)-1H-pyrazolo[3,4-b]pyridin-3-ylamino)cyclohexyl 2,2,2-trifluoroacetate: A solution of N-(4-(1-(4-methoxybenzyl)-3-(3-hydroxycyclohexylamino)-1H-pyrazolo[3,4-b]pyridin-4-yloxy)-3-fluorophenyl)-2-(4-fluorophenyl)-3-oxo-2,3-dihydropyridazine-4-carboxamide (40 mg, 0.058 mmol) in TFA (1 mL) was heated to 50° C. for 1 hour. Excess TFA was evaporated and the residue was dissolved in EtOAc. The organic layer was then washed with saturated aqueous NaHCO$_3$, brine, dried with Na$_2$SO$_4$, filtered and concentrated to afford the product (30 mg, 78% yield) as a yellow solid. LRMS (APCI pos) m/e 670.2 (M+H). $^1$H NMR (DMSO-d$_6$, 400 MHz): δ 12.20 (d, 1H), 11.70 (s, 1H), 8.38 (d, 1H), 8.26 (d, 1H), 8.12 (dd, 1H), 8.02 (dd, 1H), 7.66-7.70 (m, 2H), 7.56-7.62 (m, 1H), 7.46-7.52 (m, 1H), 7.38-7.44 (m, 2H),

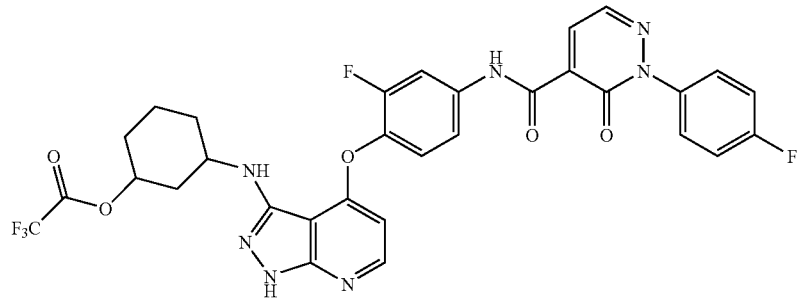

Step A: Preparation of 3-(1-(4-methoxybenzyl)-4-(4-amino-2-fluorophenoxy)-1H-pyrazolo[3,4-b]pyridin-3-ylamino)cyclohexanol: A suspension of 4-(1-(4-methoxybenzyl)-3-iodo-1H-pyrazolo[3,4-b]pyridin-4-yloxy)-3-fluorobenzenamine (100 mg, 0.204 mmol, obtained from Example 7, Step B), 3-aminocyclohexanol (70.5 mg, 0.612 mmol), Cu(I)I (7.77 mg, 0.0408 mmol), K$_2$CO$_3$ (141 mg, 1.02 mmol) and L-proline (9.39 mg, 0.082 mmol) was stirred in DMSO (5 mL) and heated to 100° C. for 12 hours. Water (5 mL) was added and the reaction mixture was extracted with CH$_2$Cl$_2$. The organic layer washed with water and brine, dried with Na$_2$SO$_4$, filtered and concentrated. The residue was purified by flash column chromatography (5% MeOH in CH$_2$Cl$_2$) to afford the product (47 mg, 48.3% yield) as a brown oil. LRMS (APCI pos) m/e 694.2 (M+H).

Step B: Preparation of N-(4-(1 (4-methoxybenzyl)-3-(3-hydroxycyclohexylamino)-dihydropyridazine-4-carboxamide: A solution of 3-(1-(4-methoxybenzyl)-4-(4-amino-2-fluorophenoxy)-1H-pyrazolo[3,4-b]pyridin-3-ylamino) cyclohexanol (50 mg, 0.10 mmol), 2-(4-fluorophenyl)-3-oxo-2,3-dihydropyridazine-4-carboxylic acid (74 mg, 0.31 mmol, obtained from Example 19 Step C), EDCI (120 mg, 0.63 mmol), Et$_3$N (0.1 mL) and HOBT-H$_2$O (96 mg, 0.63 mmol) was stirred in DMF (1 mL) for 10 hours. The reaction mixture was poured into water and extracted with CH$_2$Cl$_2$. The organic layer washed with saturated aqueous NaHCO$_3$, 10% aqueous LiCl, dried with Na$_2$SO$_4$, filtered and concentrated. The residue was purified with flash silica gel chromatography (5% MeOH in CH$_2$Cl$_2$) to afford the product (35 mg, 48% yield) as a brown solid. LRMS (APCI pos) m/e 694.2 (M+H).

6.02 (d, 2H), 5.20-5.40 (m, 1H), 3.60-3.80 (m, 1H), 2.20-2.30 (m, 1H), 2.00-2.10 (m, 2H), 1.80-1.90 (m, 2H), 1.60-1.80 (m, 2H), 1.30-1.45 (m, 1H).

Example 132

N-(3-fluoro-4-(3-(3-hydroxycyclohexylamino)-1H-pyrazolo[3,4-b]pyridin-4-yloxy)phenyl)-2-(4-fluorophenyl)-3-oxo-2,3-dihydropyridazine-4-carboxamide

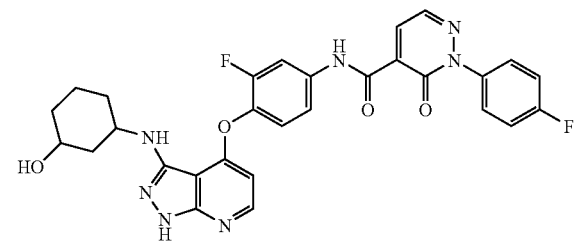

LiOH (2M solution, 2 drops) was added into a solution of 3-(4-(2-fluoro-4-(1-(4-fluorophenyl)-6-oxo-1,6-dihydropyridazine-5-carboxamido)phenoxy)-1H-pyrazolo[3,4-b]pyridin-3-ylamino)cyclohexyl 2,2,2-trifluoroacetate (10 mg, 0.015 mmol, obtained from Example 131, Step C) in THF (0.5 mL) and MeOH (0.1 mL). HCl (5M, 0.1 mL). EtOAc was added to dilute the reaction mixture. The organic layer was separated, washed with brine, dried with Na$_2$SO$_4$, filtered and concentrated to afford the product (2.5 mg, 29% yield) as a yellow solid. LRMS (APCI pos) m/e 574.2 (M+H). $^1$H NMR (DMSO-d$_6$, 400 MHz): δ 8.38 (d, 1H), 8.26 (d, 1H), 8.12 (d, 1H), 8.05 (dd, 1H), 7.66-7.70 (m, 2H), 7.56-7.62 (m, 1H), 7.48-7.54 (m, 1H), 7.38-7.44 (m, 2H), 6.80-7.00 (m, 1H), 6.00-6.05 (m, 1H), 3.80-4.00 (m, 2H), 3.50-3.80 (m, 1H), 1.80-2.00 (m, 1H), 1.60-1.80 (m, 2H), 1.40-1.60 (m, 1H), 1.10-1.30 (m, 2H), 0.80-0.90 (m, 2H).

Example 133

Methyl 4-(2-fluoro-4-(2-(4-fluorophenyl)-3-oxo-2,3-dihydropyridazine-4-carboxamido)phenoxy)-1H-pyrazolo[3,4-b]pyridine-3-carboxylate

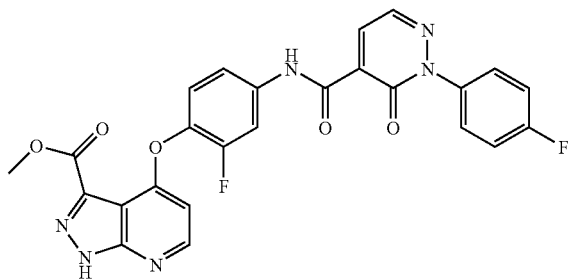

Step A: Preparation of methyl 4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridine-3-carboxylate: To a suspension of N-(4-(1-(4-methoxybenzyl)-3-iodo-1H-pyrazolo[3,4-b]pyridin-4-yloxy)-3-fluorophenyl)-2-(4-fluorophenyl)-3-oxo-2,3-dihydropyridazine-4-carboxamide (1.0 g, 1.42 mmol; prepared as in Example 7, Step B) in 1:2 DMF:MeOH (60 mL) was added triethylamine (0.434 ml, 3.11 mmol) and 1,1-bis(diphenylphosphino)ferrocenedichloropalladium(II) (0.116 g, 0.142 mmol). The mixture was purged with N$_2$(g) and CO(g) and then held under balloon pressure CO(g). The mixture was heated at 70° C. and stirred overnight (18 hours). The heat was removed and the excess solvent was evaporated. Diethyl ether (100 mL) was added and the resulting solid removed by filtration to afford the desired product as white solid. Yield (735 mg, 81%). LRMS (APCI pos) m/e 639.1 (M+H).

Step B: Preparation of methyl 4-(2-fluoro-4-(2-(4-fluorophenyl)-3-oxo-2,3-dihydropyridazine-4-carboxamido)phenoxy)-1H-pyrazolo[3,4-b]pyridine-3-carboxylate: Prepared according to the procedure of Example 53, Step B, substituting methyl 4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridine-3-carboxylate (735 mg, 1.04 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. Purified by trituration with 10% MeOH/ether to afford desired product as pale green solid. Yield 504 mg, 94%. $^1$H NMR (400 MHz, DMSO-d6) δ 11.69 (s, 1H), 8.41 (d, 1H), 8.38 (d, 1H), 8.26 (d, 1H), 8.04 (dd, 1H), 7.69 (q, 2H), 7.57 (d, 1H), 7.41 (m, 3H), 6.51 (d, 1H), 3.85 (s, 3H). LRMS (APCI pos) m/e 519.1 (M+H).

Example 134

N-(3-fluoro-4-(3-(4-methylpiperazin-1-yl)-1H-pyrazolo[3,4-b]pyridin-4-yloxy)phenyl)-3-oxo-2-(pyridin-2-yl)-2,3-dihydropyridazine-4-carboxamide

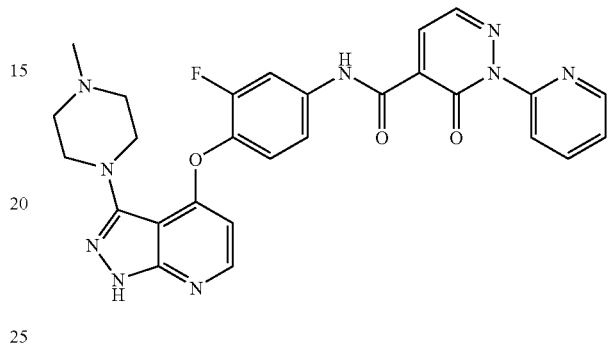

Step A: Preparation of N-(4-(1-(4-methoxybenzyl)-3-(4-methylpiperazin-1-yl)-1H-pyrazolo[3,4-b]pyridin-4-yloxy)-3-fluorophenyl)-3-oxo-2-(pyridin-2-yl)-2,3-dihydropyridazine-4-carboxamide: 3-Oxo-2-(pyridin-2-yl)-2,3-dihydropyridazine-4-carboxylic acid (0.0282 g, 0.130 mmol; prepared as in Example 141, Steps A-C) was dissolved in 5 mL of CH$_2$Cl$_2$ and cooled to 0° C. HOBt (0.0351 g, 0.259 mmol), EDCI (0.0497 g, 0.259 mmol), and NMM (0.0333 ml, 0.303 mmol) were added and the reaction mixture was stirred under N$_2$(g) for 15 minutes. 4-(1-(4-Methoxybenzyl)-3-(4-methylpiperazin-1-yl)-1H-pyrazolo[3,4-b]pyridin-4-yloxy)-3-fluorobenzenamine (0.020 g, 0.0432 mmol; prepared according to Example 86, Step A) in 2 mL of 1:1 CH$_2$Cl$_2$/DMF was added and the reaction was stirred at ambient temperature for 5 hours. The mixture was partitioned between EtOAc and aqueous NaHCO$_3$. The organic layer washed with brine, dried over Na$_2$SO$_4$, filtered and concentrated. The residue was purified by silica gel column chromatography (Flash 5 g) eluting with 3% MeOH/CH$_2$Cl$_2$ to afford the desired product as yellow semi-solid. Yield: 25.8 mg, 86%. LRMS (APCI pos) m/e 662 (M+H).

Step B: Preparation of N-(3-fluoro-4-(3-(4-methylpiperazin-1-yl)-1H-pyrazolo[3,4-b]pyridin-4-yloxy)phenyl)-3-oxo-2-(pyridin-2-yl)-2,3-dihydropyridazine-4-carboxamide: Prepared according to the procedure of Example 53, Step B, substituting N-(4-(1-(4-methoxybenzyl)-3-(4-methylpiperazin-1-yl)-1H-pyrazolo[3,4-b]pyridin-4-yloxy)-3-fluorophenyl)-3-oxo-2-(pyridin-2-yl)-2,3-dihydropyridazine-4-carboxamide (25.8 mg, 0.039 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The residue was purified by trituration with diethyl ether to afford desired product as yellow solid. Yield 14.7 mg, 69%. $^1$H NMR (400 MHz, DMSO-d6) δ 12.78 (s, 1H), 11.6 (s, 1H), 8.67 (d, 1H), 8.39 (d, 1H), 8.30 (d, 1H), 8.22 (d, 1H), 8.12 (m, 1H), 8.03 (dd, 1H), 7.73 (d, 1H), 7.64-7.57 (m, 2H), 7.51 (t, 1H), 6.18 (d, 1H). LRMS (APCI pos) m/e 542.3 (M+H).

Example 135

N-(3-fluoro-4-(3-((1,4-trans)-4-hydroxycyclohexy-lamino)-1H-pyrazolo[3,4-b]pyridin-4-yloxy)phenyl)-2-(4-fluorophenyl)-3-oxo-2,3-dihydropyridazine-4-carboxamide

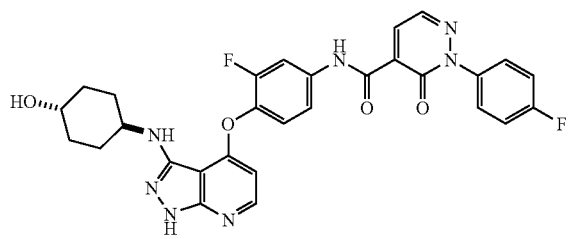

Prepared by a 2-step process from (1,4-trans)-4-(4-(4-amino-2-fluorophenoxy)-1-(4-methoxybenzyl)-1H-pyrazolo[3,4-b]pyridin-3-ylamino)cyclohexanol (prepared as described in Example 101, Step A except using (1,4-trans)-4-aminocyclohexanol) and 2-(4-fluorophenyl)-3-oxo-2,3-dihydropyridazine-4-carboxylic acid according to the procedure of Example 101, Step B. The crude was rinsed with $Et_2O$ to afford 28 mg (79%) of the desired product. LRMS (APCI pos) m/e 574.3 (M+1). $^1$H-NMR (400 MHz, $CD_3OD/CDCl_3$) δ 8.41 (d, 1H), 8.33 (d, 1H), 8.14 (m, 1H), 8.0 (dd, 1H), 7.65 (m, 2H), 7.46 (d, 1H), 7.36 (t, 1H), 7.28 (t, 2H), 6.10 (d, 1H), 3.63 (m, 2H), 2.27 (m, 2H), 2.02 (m, 2H), 1.47 (q, 2H), 1.37 (q, 2H); $^{19}$F NMR (376 MHz, $CD_3OD/CDCl_3$) δ −113.0, −127.6.

Example 136

N-(3-fluoro-4-(3-((1,4-trans)-4-hydroxycyclohexy-lamino)-1H-pyrazolo[3,4-b]pyridin-4-yloxy)phenyl)-4-(4-fluorophenyl)-3-oxo-3,4-dihydropyrazine-2-carboxamide

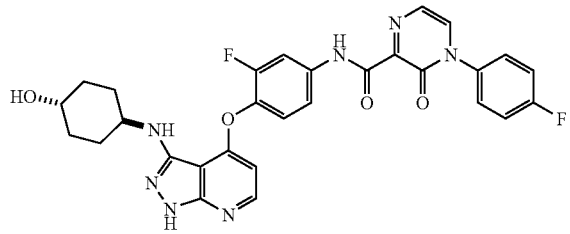

Prepared by a 2-step process from (1,4-trans)-4-(4-(4-amino-2-fluorophenoxy)-1-(4-methoxybenzyl)-1H-pyrazolo[3,4-b]pyridin-3-ylamino)cyclohexanol (prepared as described in Example 101, Step A except using (1,4-trans)-4-aminocyclohexanol) and 4-(4-fluorophenyl)-3-oxo-3,4-dihydropyrazine-2-carboxylic acid according to the procedure of Example 101, Step B. The crude was rinsed with $Et_2O$ to afford 24 mg (81%) of the desired product. LRMS (ESIpos) m/e 574.1 (M+1). $^1$H-NMR (400 MHz, $CD_3OD$) δ 8.14 (d, 1H), 8.04 (dd, 1H), 7.92 (d, 1H), 7.79 (d, 1H), 7.61 (m, 2H), 7.53 (d, 1H), 7.51 (t, 1H), 7.40 (t, 2H), 6.11 (d, 1H), 3.60 (m, 2H), 2.21 (m, 2H), 1.99 (m, 2H), 1.40 (m, 4H); $^{19}$F NMR (376 MHz, $CD_3OD/CDCl_3$) δ −113.5, −129.3.

Example 137

N-(3-fluoro-4-(3-(piperidin-4-ylmethyl)-1H-pyrazolo[3,4-b]pyridin-4-yloxy)phenyl)-2-(4-fluorophenyl)-3-oxo-2,3-dihydropyridazine-4-carboxamide

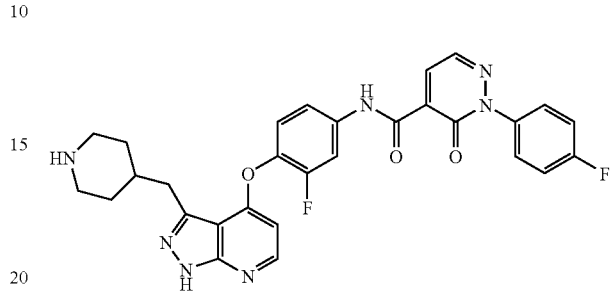

Step A: Preparation of tert-butyl 4-((4-(4-amino-2-fluorophenoxy)-1-(4-methoxybenzyl)-1H-pyrazolo[3,4-b]pyridin-3-yl)methyl)piperidine-1-carboxylate: To a 10 mL reaction flask was added tert-butyl 4-methylenepiperidine-1-carboxylate (81 mg, 0.411 mmol) and was purged with $N_2$(g) three times. 9-BBN (0.821 ml, 0.411 mmol) was added and the clear solution refluxed (72° C.) for 1 hour. The reaction was cooled to ambient temperature and then added directly to a mixture of 4-(1-(4-methoxybenzyl)-3-iodo-1H-pyrazolo[3,4-b]pyridin-4-yloxy)-3-fluorobenzenamine (181 mg, 0.370 mmol; prepared as in Example 7, Step B), 1,1'-bis(diphenylphosphino)ferrocenedichloropalladium(II) (10.1 mg, 0.0123 mmol) and potassium carbonate (68.1 mg, 0.493 mmol) in $DMF:H_2O$ (1 mL:0.1 mL). The dark orange mixture was stirred at 60° C. for 6 hours, then cooled to ambient temperature and poured into water. The pH was adjusted to 11 with 1N NaOH, and the aqueous layer was extracted with ethyl acetate. The organic layer was washed with brine, dried over $Na_2SO_4$, and evaporated. The residue was purified by silica gel column chromatography (Biotage 25M) eluting with 3% $MeOH/CH_2Cl_2$ to afford the desired product. Yield: 25 mg, 11%. LRMS (APCI pos) m/e 562.1 (M+H).

Step B: Preparation of tert-butyl 4-((4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)methyl)piperidine-1-carboxylate: Prepared according to the procedure of Example 82, Step B, substituting tert-butyl 4-((4-(4-amino-2-fluorophenoxy)-1-(4-methoxybenzyl)-1H-pyrazolo[3,4-b]pyridin-3-yl)methyl)piperidine-1-carboxylate (25 mg, 0.045 mmol) for tert-butyl 4-(4-(4-amino-2-fluorophenoxy)-1-(4-methoxybenzyl)-1H-pyrazolo[3,4-b]pyridin-3-yl)piperazine-1-carboxylate. The crude material was purified by silica gel column chromatography (Isolute 10 g) eluting with 1% $MeOH/CH_2Cl_2$ to afford the desired product as pale yellow semi-solid. Yield: 12 mg, 35%. LRMS (APCI pos) m/e 778.4 (M+H).

Step C: Preparation of N-(3-fluoro-4-(3-(piperidin-4-ylmethyl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 53, Step B, substituting tert-butyl 4-((4-(2-fluoro-4-(2-(4-fluorophenyl)-3-oxo-2,3-dihydropyridazine-4-carboxamido)phenoxy)-1-(4-methoxybenzyl)-1H-pyrazolo[3,4-b]pyridin-3-yl)methyl)piperidine-1-carboxylate (12 mg, 0.0154 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The crude material was purified by trituration with 10% MeOH/ether to afford desired product as yellow solid. Yield: 7.5 mg, 87%. $^1$H NMR (400 MHz). LRMS (APCI pos) m/e 558.3 (M+H).

Example 138

N-(3-fluoro-4-(3-(1-(2-methoxyethyl)piperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride

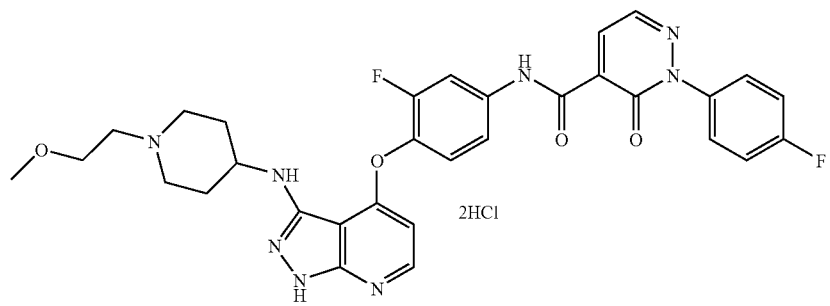

Step A: Preparation of tert-butyl 1-(2-methoxyethyl)piperidin-4-ylcarbamate: A stirred mixture of tert-butyl piperidin-4-ylcarbamate (1.1 g, 5.5 mmol), 1-bromo-2-methoxyethane (0.69 g, 5.0 mmol), potassium iodide (0.83 g, 5.0 mmol), K$_2$CO$_3$ (0.69 g, 5.0 mmol) and CH$_3$CN (10 mL) was heated to 80° C. in a sealed vessel for 18 hours. After cooling to ambient temperature, the mixture was diluted with EtOAc (15 mL) and water (15 mL). The phases were separated, and the organic phase washed with water, brine, dried (Na$_2$SO$_4$), filtered, and concentrated. The product was obtained as a waxy solid (1.0 g, 77%).

Step B: Preparation of 1-(2-methoxyethyl)piperidin-4-amine: A mixture of tert-butyl 1-(2-methoxyethyl)piperidin-4-ylcarbamate (0.842 g, 3.26 mmol) and 2,2,2-trifluoroacetic acid (2.51 ml, 32.6 mmol) was stirred for 15 minutes at ambient temperature. The mixture was concentrated in vacuo, using toluene (2×10 mL) to azeotrope residual TFA. The crude TFA salt of the product was converted to the free base using Biotage Flash 40M flash chromatography, eluting with 10% MeOH (containing 7N NH$_3$) in DCM (500 mL), followed by 20% MeOH (containing 7N NH$_3$) in DCM (500 mL). The product was obtained as an oil (195 mg, 37%).

Step C: Preparation of 1-(4-methoxybenzyl)-4-(4-amino-2-fluorophenoxy)-N-(1-(2-methoxyethyl)piperidin-4-yl)-1H-pyrazolo[3,4-b]pyridin-3-amine: A mixture of 4-(1-(4-methoxybenzyl)-3-iodo-1H-pyrazolo[3,4-b]pyridin-4-yloxy)-3-fluorobenzenamine (0.123 g, 0.25 mmol, prepared according to Example 7, Step B), 1-(2-methoxyethyl)piperidin-4-amine (0.119 g, 0.750 mmol), copper(I)iodide (0.00952 g, 0.0500 mmol), (S)-pyrrolidine-2-carboxylic acid (0.0115 g, 0.100 mmol), K$_2$CO$_3$ (0.173 g, 1.25 mmol), and DMSO (0.5 mL) was stirred at 100° C. for 3 days in a sealed vessel. The reaction was partitioned between EtOAc and water. The phases were separated and the aqueous phase was re-extracted with EtOAc. The combined organic phases were washed with water, dried (Na$_2$SO$_4$), filtered, and concentrated. The crude was purified by preparative TLC (1 mm thickness) eluting with 10% MeOH/CHCl$_3$. Yield: 42 mg (32%). LRMS (APCI+): 100% purity, 220 nm, m/z 521 (M+1) detected.

Step D: Preparation of N-(4-(1-(4-methoxybenzyl)-3-(1-(2-methoxyethyl)piperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide: EDCI (47 mg, 0.24 mmol) was added to a stirred mixture of 2-(4-fluorophenyl)-3-oxo-2,3-dihydropyridazine-4-carboxylic acid (57 mg, 0.24 mmol, prepared according to the procedure for Example 19, Step C), HOBt-hydrate (38 mg, 0.24 mmol), and DIEA (0.070 mL, 0.404 mmol) in DCM (1 mL) at ambient temperature, and the reaction was stirred for 15 minutes at ambient temperature. 1-(4-Methoxybenzyl)-4-(4-amino-2-fluorophenoxy)-N-(1-(2-methoxyethyl)piperidin-4-yl)-1H-pyrazolo[3,4-b]pyridin-3-amine (42 mg, 0.0807 mmol) was added, and the resulting solution was stirred for 2 days at ambient temperature. The crude reaction mixture was loaded directly on to a preparative TLC plate (2 mm thickness) and eluted with 10% MeOH/DCM. The product was obtained as a waxy solid (45 mg, 76%). LRMS (APCI+): 100% purity, 220 nm, m/z 737 (M+1) detected.

Step E: Preparation of N-(3-fluoro-4-(3-(1-(2-methoxyethyl)piperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride: A stirred mixture of N-(4-(1-(4-methoxybenzyl)-3-(1-(2-methoxyethyl)piperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide (45 mg, 0.0611 mmol) and 2,2,2-trifluoroacetic acid (0.471 ml, 6.11 mmol) were heated to 60° C. in a sealed vessel for 18 hours. After cooling to ambient temperature, the reaction was concentrated in vacuo, using toluene to azeotrope residual TFA (2×5 mL). The crude was partitioned between DCM and saturated aqueous NaHCO$_3$. The phases were separated, and the aqueous phase was re-extracted with DCM. The combined organic phases were dried (Na$_2$SO$_4$), filtered, and concentrated in vacuo. The resulting crude was re-dissolved in DCM, and purified by Biotage Flash 40S, eluting with 5% MeOH/DCM (500 mL), 10% MeOH/DCM (500 mL), and then 15% MeOH/DCM (500 mL). The resulting free base (21 mg) was dissolved in DCM (1 mL) and MeOH (0.2 mL) and 2N HCl in ether (0.5 mL) was added. The mixture was concentrated in vacuo, using absolute EtOH (3×5 mL) to azeotropically remove residual solvents. The product was obtained as a pale yellow powder (23 mg, 54%). HPLC: 98% purity (220 nm); LRMS (APCI+): 100% purity, 220 nm, m/z 617 (M+1) detected; $^1$H NMR (400 MHz, MeOD-d3) δ 12.0 (s, 1H), 8.36 (m, 3H), 8.12 (m, 1H), 7.68 (m, 2H), 7.55 (m, 2H), 7.29 (m, 2H), 6.38

(m, 1H), 3.94 (m, 1H), 3.75 (m, 3H), 3.42 (m, 6H), 3.22 (m, 1H), 2.42 (m, 2H), 2.26 (m, 1H), 2.07 (m, 2H).

Example 139

N-(3-fluoro-4-(3-(1-(2-fluoroethyl)piperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride

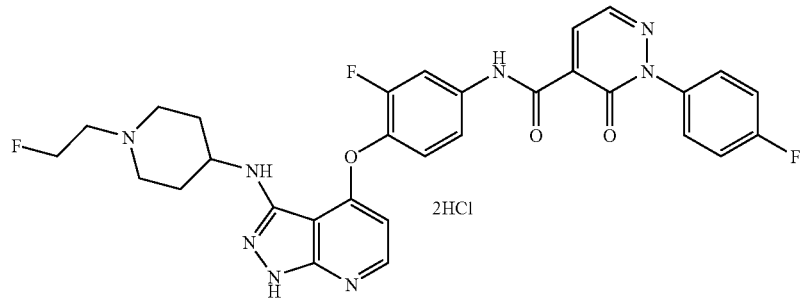

Step A: Preparation of tert-butyl 1-(2-fluoroethyl)piperidin-4-ylcarbamate: To a stirred mixture of tert-butyl piperidin-4-ylcarbamate (1.00 g, 5.0 mmol) and 1-bromo-2-fluoroethane (0.952 g, 7.50 mmol) in DMF (10 mL) was added NaH (0.180 g, 7.50 mmol) at ambient temperature. The mixture was heated to 50° C. for 18 hours under $N_2$. After cooling to ambient temperature, the mixture was diluted with EtOAc and water. The phases were separated, and the organic phase was washed with water, brine, dried ($Na_2SO_4$), filtered, and concentrated. The product was obtained as a waxy solid (1.05 g, 84%).

Step B: Preparation of 1-(2-fluoroethyl)piperidin-4-amine: Prepared from tert-butyl 1-(2-fluoroethyl)piperidin-4-ylcarbamate (1.05 g, 4.26 mmol) according to the procedure described for Example 138, Step B. The product was obtained as an oil (444 mg, 70%).

Step C: Preparation of 1-(4-methoxybenzyl)-4-(4-amino-2-fluorophenoxy)-N-(1-(2-fluoroethyl)piperidin-4-yl)-1H-pyrazolo[3,4-b]pyridin-3-amine: Prepared from 4-(1-(4-methoxybenzyl)-3-iodo-1H-pyrazolo[3,4-b]pyridin-4-yloxy)-3-fluorobenzenamine (245 mg, 0.500 mmol, prepared according to Example 7, Step B) and 1-(2-fluoroethyl)piperidin-4-amine (219 mg, 1.50 mmol) according to the procedure described for Example 138, Step C. Yield: 128 mg (50%). LRMS (APCI+): 100% purity, 220 nm, m/z 509 (M+1) detected.

Step D: Preparation of N-(4-(1-(4-methoxybenzyl)-3-(1-(2-fluoroethyl)piperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide: Prepared from 2-(4-fluorophenyl)-3-oxo-2,3-dihydropyridazine-4-carboxylic acid (177 mg, 0.755 mmol, prepared according to the procedure for Example 19, Step C) and 1-(4-methoxybenzyl)-4-(4-amino-2-fluorophenoxy)-N-(1-(2-fluoroethyl)piperidin-4-yl)-1H-pyrazolo[3,4-b]pyridin-3-amine (128 mg, 0.252 mmol) according to the procedure for Example 138, Step D. The product was obtained as a waxy solid (145 mg, 80%). LRMS (APCI+): 100% purity, 220 nm, m/z 725 (M+1) detected.

Step E: Preparation of N-(3-fluoro-4-(3-(1-(2-fluoroethyl)piperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride: Prepared from N-(4-(1-(4-methoxybenzyl)-3-(1-(2-fluoroethyl)piperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide (145 mg, 0.200 mmol) according to the procedure for Example 138, Step E. The product was obtained as a pale yellow powder (83 mg, 60%). HPLC: 98% purity (220 nm); LRMS (APCI+): 100% purity, 220 nm, m/z 605 (M+1) detected; $^1$H NMR (400 MHz, MeOD-d3) δ 11.98 (s, 1H), 8.32 (m, 4H), 8.10 (d, J=12 Hz, 1H), 7.67 (m, 2H), 7.54 (m, 2H), 7.29 (m, 2H), 6.38 (d, J=6 Hz, 1H), 4.95 (m, 2H), 3.97 (m, 1H), 3.76 (m, 2H), 3.61 (m, 4H), 2.42 (m, 3H), 2.13 (m, 2H).

Example 140

N-(3-fluoro-4-(3-(4-(2-methoxyethyl)piperazin-1-yl)-1H-pyrazolo[3,4-b]pyridin-4-yloxy)phenyl)-2-(4-fluorophenyl)-3-oxo-2,3-dihydropyridazine-4-carboxamide

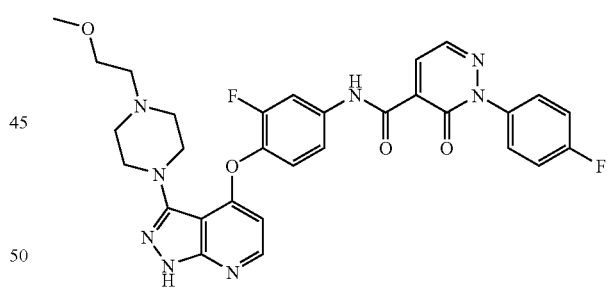

Step A: Preparation of tert-butyl 4-(2-methoxyethyl)piperazine-1-carboxylate: Prepared from tert-butyl piperazine-1-carboxylate (1.02 g, 5.50 mmol) and 1-bromo-2-methoxyethane (0.695 g, 5.0 mmol) according to the procedure described for Example 138, Step A. The product was obtained as a waxy solid (11.10 g, 89%).

Step B: Preparation of 1-(2-methoxyethyl)piperazine: Prepared from tert-butyl 4-(2-methoxyethyl)piperazine-1-carboxylate (1.10 g, 4.50 mmol) according to the procedure for Example 138, Step B. The product was obtained as an oil (246 mg, 38%).

Step C: Preparation of 4-(1-(4-methoxybenzyl)-3-(4-(2-methoxyethyl)piperazin-1-yl)-1H-pyrazolo[3,4-b]pyridin-4-yloxy)-3-fluorobenzenamine: Prepared from 4-(1-(4-methoxybenzyl)-3-iodo-1H-pyrazolo[3,4-b]pyridin-4-yloxy)-3-fluorobenzenamine (20 mg, 0.0408 mmol, prepared according to Example 7, Step B) and 1-(2-methoxyethyl)-piperazine (17.6 mg, 0.122 mmol) according to the procedure described for Example 138, Step C. Yield: 12 mg (51%).

Step D: Preparation of N-(4-(1-(4-methoxybenzyl)-3-(4-(2-methoxyethyl)piperazin-1-yl)-1H-pyrazolo[3,4-b]pyridin-4-yloxy)-3-fluorophenyl)-2-(4-fluorophenyl)-3-oxo-2,3-dihydropyridazine-4-carboxamide: EDCI (27 mg, 0.14 mmol) was added to a stirred mixture of 2-(4-fluorophenyl)-3-oxo-2,3-dihydropyridazine-4-carboxylic acid (11 mg, 0.047 mmol, prepared according to the procedure described for Example 19, Step C) and HOBt-hydrate (22 mg, 0.14 mmol) in DMF (0.3 mL) at ambient temperature, and the reaction mixture was stirred for 15 minutes at ambient temperature. 4-(1-(4-Methoxybenzyl)-3-(4-(2-methoxyethyl)piperazin-1-yl)-1H-pyrazolo[3,4-b]pyridin-4-yloxy)-3-fluorobenzenamine (12 mg, 0.024 mmol) and triethylamine (0.020 ml, 0.14 mmol) were then added, and the resulting mixture was stirred for 18 hours at ambient temperature. The reaction mixture was diluted with EtOAc and washed with water. The aqueous phase was re-extracted with EtOAc. The combined organic phases were washed with water, dried ($Na_2SO_4$), filtered, and concentrated in vacuo. The crude material was purified by preparative TLC (0.5 mm) and eluted with 15% MeOH/DCM (Rf=0.74). The product was obtained as a waxy solid (2 mg, 10%).

Step E: Preparation of N-(3-fluoro-4-(3-(4-(2-methoxyethyl)piperazin-1-yl)-1H-pyrazolo[3,4-b]pyridin-4-yloxy)phenyl)-2-(4-fluorophenyl)-3-oxo-2,3-dihydropyridazine-4-carboxamide: A stirred mixture of N-(4-(1-(4-methoxybenzyl)-3-(4-(2-methoxyethyl)piperazin-1-yl)-1H-pyrazolo[3,4-b]pyridin-4-yloxy)-3-fluorophenyl)-2-(4-fluorophenyl)-3-oxo-2,3-dihydropyridazine-4-carboxamide (2 mg, 0.002767 mmol), and 2,2,2-trifluoroacetic acid (0.2132 ml, 2.767 mmol) was heated to 60° C. in a sealed vessel for 18 hours. After cooling to ambient temperature, the reaction was concentrated in vacuo, using toluene to azeotrope residual TFA. The resulting residue was dissolved in DCM, and purified by preparative TLC (0.5 mm thickness, Rf=0.50), eluting with 10% MeOH (containing 7N $NH_3$) in DCM. The product was obtained as a pale yellow powder (1 mg, 48%). HPLC: 89% purity (220 nm); LRMS (APCI+): 100% purity, 220 nm, m/z 603 (M+1) detected; $^1$H NMR (400 MHz, $CDCl_3$) δ 11.87 (s, 1H), 9.81 (s, 1H), 8.44 (m, 1H), 8.26 (m, 2H), 7.98 (m, 1H), 7.63 (m, 2H), 7.42 (m, 1H), 7.28 (m, 3H), 6.22 (m, 1H), 3.75 (m, 1H), 3.61 (m, 3H), 3.39 (s, 3H), 2.73 (m, 4H), 1.5-2.2 (m, 4H).

Example 141

N-(3-fluoro-4-(3-(1-methylpiperidin-4-ylamino)-1H-pyrazolo[3,4-b]pyridin-4-yloxy)phenyl)-3-oxo-2-(pyridin-2-yl)-2,3-dihydropyridazine-4-carboxamide

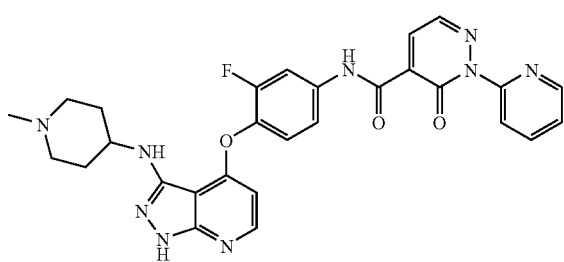

Step A: Preparation of (E)-2-(2-(pyridin-2-yl)hydrazono)acetaldehyde: A mixture of the 1-(pyridin-2-yl)hydrazine (2.00 g, 18.33 mmol), water (13 mL), and acetic acid (10.49 ml, 183.3 mmol) was added with stirring into a 40% aqueous solution of glyoxal (10.51 ml, 91.63 mmol) over 20 minutes. Stirring was continued for 18 hours and then the aqueous was extracted with EtOAc. The diluted aqueous layer was slowly basified with sodium hydrogen carbonate (15.40 g, 183.3 mmol). The resulting solids were collected by filtration and washed with water to afford 1.65 g (85%) of the desired product and dimer. LRMS (apci pos): 150 (M+H).

Step B: Preparation of (E)-2,2-dimethyl-5-(2-(2-(pyridin-2-yl)hydrazono)ethylidene)-1,3-dioxane-4,6-dione: A suspension of dioxan-dione (0.676 g, 4.69 mmol) and (E)-2-(2-(pyridin-2-yl)hydrazono)acetaldehyde (0.700 g, 4.69 mmol) in toluene (20 mL) was treated with acetic acid (10 drops) and piperidine (10 drops). The reaction mixture was then stirred at room temp for 17 hours. The precipitate was filtered and thoroughly washed with light petroleum to afford 174.6 mg (12%) of the desired product. LRMS (apci pos): 276 (M+H).

Step C: Preparation of 3-oxo-2-(pyridin-2-yl)-2,3-dihydropyridazine-4-carboxylic acid: A mixture of (E)-2,2-dimethyl-5-(2-(2-(pyridin-2-yl)hydrazono)ethylidene)-1,3-dioxane-4,6-dione (0.050 g, 0.182 mmol) and NaOMe (0.0118 g, 0.218 mmol) in MeOH (6 mL) was heated under reflux for 15 hours. The salt was treated with cold 1 N HCl solution, extracted with DCM, dried over $MgSO_4$, and concentrated to afford 17.6 mg (45%) of the desired product. LRMS (apci pos): 218 (M+H).

Step D: Preparation of N-(4-(1-(4-methoxybenzyl)-3-(1-methylpiperidin-4-ylamino)-1H-pyrazolo[3,4-b]pyridin-4-yloxy)-3-fluorophenyl)-3-oxo-2-(pyridin-2-yl)-2,3-dihydropyridazine-4-carboxamide: To a 50 mL round bottom flask charged with 3-oxo-2-(pyridin-2-yl)-2,3-dihydropyridazine-4-carboxylic acid (0.0273 g, 0.126 mmol) in 2 mL of DCM was added HOBt (0.0340 g, 0.252 mmol), EDCI (0.0483 g, 0.252 mmol), and NMM (0.0323 ml, 0.294 mmol) at 0° C. The reaction mixture was stirred under $N_2$ for 15 minutes, and then 1-(4-methoxybenzyl)-4-(4-amino-2-fluorophenoxy)-N-(1-methylpiperidin-4-yl)-1H-pyrazolo[3,4-b]pyridin-3-amine (0.020 g, 0.0420 mmol, prepared according to procedure of Example 101, Step A) in 1 mL DCM was added. The reaction was stirred for 18 hours, then diluted with DCM and washed with $NaHCO_3$ and brine. The organic layer was dried over $Na_2SO_4$, filtered and concentrated. The crude material was purified by flash silica gel chromatography, eluting with 1-3% MeOH/DCM up to 90:9:1 DCM:MeOH:$NH_4OH$ to afford 43 mg of a yellow residue, which was further purified on a Horizon 12M eluting with 20-60% ACN/$H_2O$ to afford 10 mg (35%) of desired product. LRMS (apci pos) 676 (M+H).

Step E: Preparation of N-(3-fluoro-4-(3-(1-methylpiperidin-4-ylamino)-1H-pyrazolo[3,4-b]pyridin-4-yloxy)phenyl)-3-oxo-2-(pyridin-2-yl)-2,3-dihydropyridazine-4-carboxamide: A stirred mixture of N-(4-(1-(4-methoxybenzyl)-3-(1-methylpiperidin-4-ylamino)-1H-pyrazolo[3,4-b]pyridin-4-yloxy)-3-fluorophenyl)-3-oxo-2-(pyridin-2-yl)-2,3-dihydropyridazine-4-carboxamide (0.014 g, 0.02072 mmol) and 2,2,2-trifluoroacetic acid (TFA) (0.1596 ml, 2.072 mmol) was heated to 60° C. for 18 hours under $N_2$. The mixture was concentrated in vacuo using toluene (3×5 mL) to azeotrope residual TFA. The residue was partitioned between saturated aqueous NaHCO₃ and EtOAc. The phases were separated, and the organic phase washed with brine, dried (Na₂SO₄), filtered, and concentrated in vacuo. The residue was triturated with ether and decanted to obtain the product as a brown powder (10 mg, 86%). LRMS (apci pos): >99% purity, 220 nm, m/z 556 (M+H); ¹H NMR (400 MHz, CDCl₃) δ 11.77 (s, 1H), 8.74 (m, 1H), 7.44 (d, 1H), 8.28 (d, 1H), 8.02 (m, 2H), 7.66 (d, 1H), 7.53 (t, 1H), 7.42 (m, 1H), 7.24 (m, 1H), 6.10 (br s, 1H), 4.55 (bd, 1H), 3.80 (br s, 1H), 3.16 (br s, 2H), 2.44 (m, 10H); ¹⁹F NMR (376 MHz, CDCl₃) δ −125.2 (m).

Example 142

N-(4-(3-(1-ethylpiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide

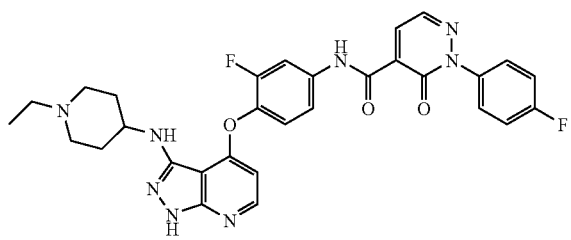

Prepared by a 2-step process from 4-(4-amino-2-fluorophenoxy)-N-(1-ethylpiperidin-4-yl)-1-(4-methoxybenzyl)-1H-pyrazolo[3,4-b]pyridin-3-amine (prepared as described in Example 101, Step A except using 1-ethylpiperidin-4-amine) and 2-(4-fluorophenyl)-3-oxo-2,3-dihydropyridazine-4-carboxylic acid according to the procedure of Example 101, Step B. The crude was rinsed with Et₂O to afford 16 mg with HCl salt (76%) of the desired product. LRMS (APCI pos) m/e 587.2 (M+1). ¹H NMR (400 MHz, CD₃OD/CDCl₃) δ 8.40 (d, 1H), 8.34 (d, 1H), 8.30 (m, 1H), 8.10 (d, 1H), 7.66 (m, 2H), 7.53 (m, 1H), 7.48 (m, 1H), 7.29 (t, 2H), 6.35 (d, 1H), 4.0 (m, 1H), 3.68 (m, 2H), 3.23 (m, 2H), 3.14 (m, 2H), 2.43 (m, 2H), 2.10 (m, 2H), 1.41 (m, 3H); ¹⁹F NMR (376 MHz, CD₃OD/CDCl₃) δ −113.7, −128.1.

Example 143

N-(3-fluoro-4-(3-(1-isopropylpiperidin-4-ylamino)-1H-pyrazolo[3,4-b]pyridin-4-yloxy)phenyl)-2-(4-fluorophenyl)-3-oxo-2,3-dihydropyridazine-4-carboxamide

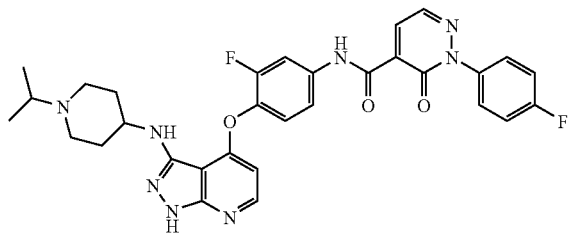

Prepared by a 2-step process from 4-(4-amino-2-fluorophenoxy)-N-(1-isopropyl piperidin-4-yl)-1-(4-methoxybenzyl)-1H-pyrazolo[3,4-b]pyridin-3-amine (prepared as described in Example 101, Step A except using 1-isopropylpiperidin-4-amine) and 2-(4-fluorophenyl)-3-oxo-2,3-dihydropyridazine-4-carboxylic acid according to the procedure of Example 101, Step B. The crude was rinsed with Et₂O to afford 14 mg with HCl salt (76%) of the desired product. LRMS (APCI pos) m/e 601.3 (M+1). ¹H NMR (400 MHz, CD₃OD/CDCl₃) δ 8.41 (d, 1H), 8.33 (d, 1H), 8.15 (m, 1H), 8.01 (dd, 1H), 7.64 (m, 2H), 7.47 (m, 1H), 7.36 (t, 1H), 7.28 (t, 2H), 6.12 (d, 1H), 3.83 (m, 1H), 3.23 (m, 3H), 2.82 (m, 2H), 2.34 (m, 2H), 1.83 (m, 2H), 1.27 (m, 6H); ¹⁹F NMR (376 MHz, CD₃OD/CDCl₃) δ −112.8, −127.6.

Example 144

N-(3-fluoro-4-(3-(4-methylpiperazine-1-carbonyl)-1H-pyrazolo[3,4-b]pyridin-4-yloxy)phenyl)-2-(4-fluorophenyl)-3-oxo-2,3-dihydropyridazine-4-carboxamide

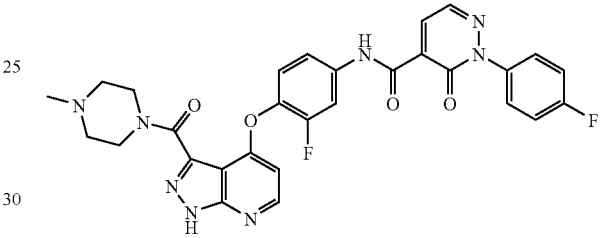

Step A: Preparation of 3-fluoro-4-(3-iodo-1H-pyrazolo[3,4-b]pyridin-4-yloxy)aniline: Dissolved 4-(1-(4-methoxybenzyl)-3-iodo-1H-pyrazolo[3,4-b]pyridin-4-yloxy)-3-fluorobenzenamine (50 mg, 0.102 mmol; prepared as in Example 7, Step B) in excess TFA (1 mL). The dark solution was stirred at 50° C. for (20 hours. The mixture was concentrated in vacuo, using toluene (2×5 mL) to azeotrope residual TFA. The crude was partitioned between CH₂Cl₂ and NaHCO₃. The cloudy organic layer was evaporated and the resulting semi-solid triturated with diethyl ether to afford the desired product. Yield: 33 mg, 87%. LRMS (APCI pos) m/e 371.1 (M+H).

Step B: Preparation of (4-(4-amino-2-fluorophenoxy)-1H-pyrazolo[3,4-b]pyridin-3-yl)(4-methylpiperazin-1-yl)methanone: 3-Fluoro-4-(3-iodo-1H-pyrazolo[3,4-b]pyridin-4-yloxy)aniline (30 mg, 0.0811 mmol) was dissolved in DMF (1 mL), and 1-methylpiperazine (0.045 ml, 0.405 mmol) and 1,1'-bis(diphenylphosphino) ferrocenedichloropalladium(II) (6.67 mg, 0.0081 mmol) were added. The reaction mixture was purged with N₂(g) followed by CO(g) and then held under balloon pressure of CO(g). The mixture was stirred at 70° C. for 18 hours. The crude mixture was partitioned between ethyl acetate and water. The organic layer washed with brine, dried over Na₂SO₄ and evaporated to afford crude product. The residue was purified by silica gel column chromatography (Biotage 12M) eluting with 5% MeOH/CHCl₃ to afford the desired product. Yield: 14 mg at 80% purity, 37%. LRMS (APCI pos) m/e 371.1 (M+H).

Step C: Preparation of N-(3-fluoro-4-(3-(4-methylpiperazine-1-carbonyl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 82, Step B, substituting (4-(4-amino-2-fluorophenoxy)-1H-pyrazolo[3,4-b]pyridin-3-yl)(4-methylpiperazin- 1-yl)methanone (14 mg, 0.0302 mmol) for tert-butyl 4-(4-(4-amino-2-fluorophenoxy)-1-(4-methoxybenzyl)-1H-pyrazolo[3,4-b]pyridin-3-yl)piperazine-1-carboxylate. The crude material was purified by preparative TLC (1 mm thickness) eluting with 5% MeOH/CH$_2$Cl$_2$. The di-HCl salt was prepared with 2N HCl/ether to afford the desired product as white solid. Yield: 4.3 mg, 22%. $^1$H NMR (400 MHz, DMSO-d6) δ 11.71 (s, 1H), 8.38 (d, 1H), 8.36 (d, 1H), 8.26 (d, 1H), 8.05 (dd, 1H), 7.69 (q, 2H), 7.62 (d, 1H), 7.50 (t, 1H), 7.41 (t, 2H), 6.34 (d, 1H), 3.89 (broad s, 8H). LRMS (APCI pos) m/e 587.1 (M+H).

Example 145

±N-(3-fluoro-4-(3-((3R*,4S*)-3-fluoropiperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride

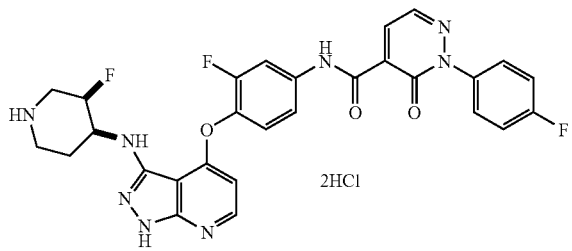

Step A: Preparation of ±(3R*,4S*)-tert-butyl 4-(1-(4-methoxybenzyl)-4-(4-amino-2-fluorophenoxy)-1H-pyrazolo[3,4-b]pyridin-3-ylamino)-3-fluoropiperidine-1-carboxylate: A mixture of 4-(1-(4-methoxybenzyl)-3-iodo-1H-pyrazolo[3,4-b]pyridin-4-yloxy)-3-fluorobenzenamine (0.123 g, 0.25 mmol, prepared according to Example 7, Step B), ±(3S*,4R*)-tert-butyl 4-amino-3-fluoropiperidine-1-carboxylate (0.164 g, 0.750 mmol, prepared according to WO 2006/087543), copper(I)iodide (0.00952 g, 0.0500 mmol), (S)-pyrrolidine-2-carboxylic acid (0.0115 g, 0.100 mmol), K$_2$CO$_3$ (0.173 g, 1.25 mmol), and DMSO (1 mL) was stirred at 100° C. for 3 days. The reaction was partitioned between EtOAc and water. The phases were separated and the aqueous phase was re-extracted with EtOAc (5 mL). The combined organic phases were washed with water, dried (Na$_2$SO$_4$), filtered, and concentrated. The crude was purified by preparative TLC (1 mm thickness, Rf=0.56) eluting with 10% MeOH/CHCl$_3$. LRMS (APCI+): m/z 581 (M+1) detected.

Step B: Preparation of ±(3R*,4S*)-tert-butyl 4-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-ylamino)-3-fluoropiperidine-1-carboxylate: EDCI (43.6 mg, 0.227 mmol) was added to a stirred mixture of 2-(4-fluorophenyl)-3-oxo-2,3-dihydropyridazine-4-carboxylic acid (53.2 mg, 0.227 mmol, prepared according to the procedure for Example 19, Step C), HOBt-hydrate (34.8 mg, 0.227 mmol) and DIEA (0.0792 ml, 0.455 mmol) in DCM (1 mL) at ambient temperature, and the reaction mixture was stirred for 15 minutes at ambient temperature. ±(3R*,4S*)-tert-Butyl 4-(1-(4-methoxybenzyl)-4-(4-amino-2-fluorophenoxy)-1H-pyrazolo[3,4-b]pyridin-3-ylamino)-3-fluoropiperidine-1-carboxylate (66 mg, 0.114 mmol) was then added. The resulting solution was stirred for 18 hours at ambient temperature. To a separate 1 dram vial was added an additional equivalent of the 2-(4-fluorophenyl)-3-oxo-2,3-dihydropyridazine-4-carboxylic acid, HOBt, DIEA, and EDCI in DCM (0.5 mL). This mixture was stirred for 15 minutes, then added to the original reaction mixture, which was stirred for an additional day at ambient temperature. The crude reaction mixture was loaded directly on to a preparative TLC plate (2 mm thickness) and eluted with 10% MeOH/DCM (Rf=0.70). A second preparative TLC plate (1 mm thickness, Rf=0.17) eluting with 1:1 EtOAc/hexanes was utilized to obtain pure product (35 mg, 39%)

Step C: Preparation of ±N-(3-fluoro-4-(3-((3R*,4S*)-3-fluoropiperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride: A stirred mixture of ±(3R*,4S*)-tert-butyl 4-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-ylamino)-3-fluoropiperidine-1-carboxylate (35 mg, 0.0439 mmol), and 2,2,2-trifluoroacetic acid (0.338 ml, 4.39 mmol) was heated to 80° C. in a sealed vessel for 2 hours. The reaction was concentrated in vacuo, using toluene (2×5 mL) to azeotrope residual TFA. The resulting residue was dissolved in DCM, and purified by preparative TLC (0.5 mm thickness, Rf=0.13), eluting with 20% MeOH/DCM. The purified product was re-dissolved in DCM (1 mL) and acidified with 2N HCl in diethyl ether (0.5 mL). The solvent and excess HCl was removed in vacuo, using EtOH to azeotrope (3×5 mL). The product was obtained as a pale yellow powder (12 mg, 40%). HPLC: 96% purity (220 nm); LRMS (ESI+): 100% purity, 220 nm, m/z 577 (M+1) detected; $^1$H NMR (400 MHz, MeOD-d$_3$) δ 11.99 (s, 1H), 8.32 (m, 3H), 8.10 (d, J=12 Hz, 1H), 7.68 (m, 2H), 7.54 (m, 2H), 7.30 (m, 2H), 6.42 (d, J=6 Hz, 1H), 5.26 (m, 1H), 4.26 (m, 1H), 3.78 (m, 1H), 3.54 (m, 3H), 2.27 (m, 2H).

Example 146

±N-(3-fluoro-4-(3-((3S*,4S*)-3-fluoropiperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride

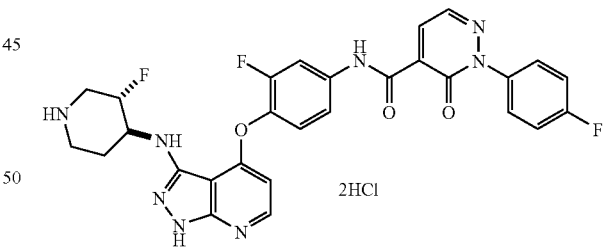

Step A: Preparation of ±(3S*,4S*)-tert-butyl 4-(1-(4-methoxybenzyl)-4-(4-amino-2-fluorophenoxy)-1H-pyrazolo[3,4-b]pyridin-3-ylamino)-3-fluoropiperidine-1-carboxylate: Prepared from 4-(1-(4-methoxybenzyl)-3-iodo-1H-pyrazolo[3,4-b]pyridin-4-yloxy)-3-fluorobenzenamine (0.123 g, 0.25 mmol, prepared according to Example 7, Step B), and ±(3S*,4S*)-tert-butyl 4-amino-3-fluoropiperidine-1-carboxylate (0.164 g, 0.750 mmol, prepared according to the procedure described in WO 2006/087543) according to the procedure described for Example 143, Step A. LRMS (APCI+): m/z 581 (M+1) detected.

Step B: Preparation of ±(3S*,4S*)-tert-butyl 4-(1-(4-methoxybenzyl)-4-(2-fluoro-4-(1-(4-fluorophenyl)-6-oxo-1, 6-dihydropyridazine-5-carboxamido)phenoxy)-1H-pyrazolo[3,4-b]pyridin-3-ylamino)-3-fluoropiperidine-1-carboxylate: Prepared from 2-(4-fluorophenyl)-3-oxo-2,3-dihydropyridazine-4-carboxylic acid (50.8 mg, 0.217 mmol, prepared according to the procedure for Example 19, Step C) and ±(3S*,4S*)-tert-butyl 4-(1-(4-methoxybenzyl)-4-(4-amino-2-fluorophenoxy)-1H-pyrazolo[3,4-b]pyridin-3-ylamino)-3-fluoropiperidine-1-carboxylate (63 mg, 0.109 mmol) according to the procedure described for Example 143, Step B. Yield: 17 mg (20%).

Step C: Preparation of ±N-(3-fluoro-4-(3-((3S*,4S*)-3-fluoropiperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride: Prepared from ±(3S*,4S*)-tert-butyl 4-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-ylamino)-3-fluoropiperidine-1-carboxylate (17 mg, 0.0213 mmol) and 2,2,2-trifluoroacetic acid (0.164 ml, 2.13 mmol) according to the procedure described for Example 143, Step C. The product was obtained as a pale yellow powder (9 mg, 63%). HPLC: 97% purity (220 nm); LRMS (ESI+):100% purity, 220 nm, m/z 577 (M+1) detected; $^1$H NMR (400 MHz, MeOD-d3) δ 11.99 (s, 1H), 8.36 (d, J=4 Hz, 1H), 8.32 (m, 2H), 8.11 (d, J=12 Hz, 1H), 7.68 (m, 2H), 7.54 (m, 2H), 7.29 (t, J=9 Hz, 2H), 6.41 (d, J=6 Hz, 1H), 5.27 (m, 1H), 5.15 (m, 1H), 4.23 (m, 1H), 3.70 (m, 1H), 3.47 (m, 1H), 3.41 (m, 1H), 3.25 (m, 1H), 2.46 (m, 1H), 2.18 (m, 1H).

Example 147

N-(3-fluoro-4-(3-(1-methyl-1H-imidazol-2-yl)-1H-pyrazolo[3,4-b]pyridin-4-yloxy)phenyl)-2-(4-fluorophenyl)-3-oxo-2,3-dihydropyridazine-4-carboxamide

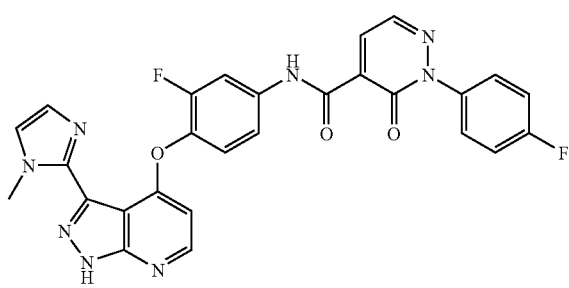

Step A: Preparation of 3-Fluoro-4-(1-(4-methoxybenzyl)-3-(1-methyl-1H-imidazol-2-yl)-1H-pyrazolo[3,4-b]pyridin-4-yloxy)aniline: 4-(1-(4-Methoxybenzyl)-3-iodo-1H-pyrazolo[3,4-b]pyridin-4-yloxy)-3-fluorobenzenamine (200 mg, 0.408 mmol, prepared in Example 7, step B), 1-methyl-2-(tributylstannyl)-1H-imidazole (908.4 mg, 2.45 mmol), tetrakis (triphenylphosphine) palladium (94.28 mg, 0.0816 mmol) and toluene (4 mL) were charged in a 25 mL, single-neck, round-bottomed flask. The reaction mixture was stirred at 60° C. until the starting material had been consumed (4 hours). Then the reaction mixture was cooled to room temperature and partitioned between EtOAc (100 mL) and H$_2$O (50 mL). The phases were separated, and the aqueous phase was re-extracted with EtOAc (3×50 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (0.143 g, 79%). LRMS (APCI pos): >99% purity, 254 nm, m/e 445 (M+1). $^1$H NMR (400 MHz, CDCl$_3$) δ 8.31 (m, 1H), 7.71 (m, 1H), 7.50 (m, 1H), 7.35 (m, 2H), 6.94 (m, 1H), 6.84 (m, 2H), 6.50 (m, 1H), 6.43 (m, 1H), 6.28 (d, 1H), 5.64 (s, 2H), 3.90 (s, 3H), 3.75 (s, 3H), 3.67 (s, 2H, NH$_2$).

Step B: Preparation of N-(3-fluoro-4-(1-(4-methoxybenzyl)-3-(1-methyl-1H-imidazol-2-yl)-1H-pyrazolo[3,4-b]pyridin-4-yloxy)phenyl)-2-(4-fluorophenyl)-3-oxo-2,3-dihydropyridazine-4-carboxamide: 4-(1-(4-Methoxybenzyl)-3-(1-methyl-1H-imidazol-2-yl)-1H-pyrazolo[3,4-b]pyridin-4-yloxy)-3-fluorobenzenamine (143.2 mg, 0.322 mmol), 2-(4-fluorophenyl)-3-oxo-2,3-dihydropyridazine-4-carboxylic acid (377.3 mg, 1.61 mmol, prepared in Example 19, step C), N1-((ethylimino)methylene)-N3,N3-dimethylpropane-1,3-diamine hydrochloride (308.8 mg, 1.61 mmol), 1H-benzo[d][1,2,3]triazol-1-ol (217.7 mg, 1.61 mmol), N-ethyl-N-isopropylpropan-2-amine (208.2 mg, 1.61 mmol) and CH$_2$Cl$_2$ (5 mL) were charged in a 25 mL, single-neck, round-bottomed flask. The reaction mixture was stirred at room temperature until the starting material had been consumed (overnight). Then the reaction mixture was partitioned between EtOAc (50 mL) and H$_2$O (50 mL). The phases were separated and the aqueous phase was re-extracted with EtOAc (3×50 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (127 mg, 59.67%). LRMS (APCI pos): >99% purity, 254 nm, m/e 661 (M+1).

Step C: Preparation of N-(3-fluoro-4-(3-(1-methyl-1H-imidazol-2-yl)-1H-pyrazolo[3,4-b]pyridin-4-yloxy)phenyl)-2-(4-fluorophenyl)-3-oxo-2,3-dihydropyridazine-4-carboxamide: N-(4-(1-(4-Methoxybenzyl)-3-(1-methyl-1H-imidazol-2-yl)-1H-pyrazolo[3,4-b]pyridin-4-yloxy)-3-fluorophenyl)-2-(4-fluorophenyl)-3-oxo-2,3-dihydropyridazine-4-carboxamide (127 mg, 0.192 mmol) and TFA (2 mL) were charged in a 50 mL single-neck, round-bottomed flask. The reaction mixture was stirred at 60° C. until the starting material had been consumed (overnight). Then the reaction was cooled to room temperature and the CF$_3$COOH was removed under reduced pressure. The residue was partitioned between DCM (50 mL) and saturated NaHCO$_3$ (50 mL). The phases were separated and the aqueous phase was extracted with DCM (3×50 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (62.5 mg, 60.2%). LRMS (APCI pos): >99% purity, 254 nm, m/e 541 (M+1). $^1$H NMR (400 MHz, DMSO-d$_6$) δ 14.01 (s, 1H), 11.71 (s, 1H), 8.37 (m, 2H), 8.27 (d, 1H), 8.06 (m, 1H), 7.76 (d, 1H), 7.68 (m, 2H), 7.52-7.63 (m, 2H), 7.47 (d, 1H), 7.41 (m, 2H), 6.36 (d, 1H), 3.31 (s, 3H).

Example 148

±N-(4-(3-((3R*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide dihydrochloride

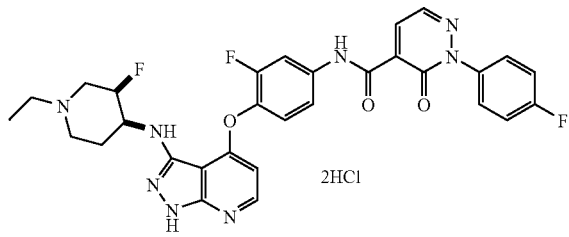

2HCl

Step A: Preparation of ±N-(4-(1-(4-methoxybenzyl)-3-((3R*,4S*)-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide bis-trifluoroacetic acid salt: A mixture of ±(3R*,4S*)-tert-butyl 4-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-ylamino)-3-fluoropiperidine-1-carboxylate (58 mg, 0.0728 mmol) prepared according to Example 145, Step B and 2,2,2-trifluoroacetic acid (0.280 ml, 3.64 mmol) was stirred for 5 minutes at room temperature under $N_2$. The mixture was concentrated in vacuo, using toluene to azeotrope (3×5 mL) residual TFA. The crude product was carried forward as a TFA salt without purification at this step. LRMS (APCI+): m/z 697 (M+1) detected.

Step B: Preparation of ±N-(4-(1-(4-methoxybenzyl)-3-((3R*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide: A mixture of ±N-(4-(1-(4-methoxybenzyl)-3-((3R*,4S*)-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide bis-trifluoroacetic acid salt (72 mg, 0.0779 mmol), acetaldehyde (5 mg, 0.1 mmol), sodium triacetoxyborohydride (25 mg, 0.12 mmol), and DCM (0.5 mL) was stirred at room temperature for 18 hours. Water (5 mL) was added, and the aqueous layer was extracted with DCM (3×5 mL). The organic layers were combined and dried ($Na_2SO_4$). Concentrated and purified by preparative TLC, eluting with 5% MeOH (containing 7N $NH_3$) in $CHCl_3$. Yield: 8 mg (14%). LRMS (APCI+): m/z 725 (M+1) detected.

Step C: Preparation of ±N-(4-(3-((3R*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide: Prepared from ±N-(4-(1-(4-methoxybenzyl)-3-((3R*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide (8 mg, 0.01 mmol) and 2,2,2-trifluoroacetic acid (0.43 mL, 5.5 mmol) according to the procedure described for Example 145, Step C. The product was obtained as a pale yellow powder (4 mg, 51%). HPLC: 95% purity (220 nm); LRMS (ESI+): 97% purity, 220 nm, m/z 605 (M+1) detected; $^1$H NMR (400 MHz, MeOD-d3) δ 11.98 (s, 1H), 8.35 (m, 3H), 8.09 (d, J=13 Hz, 1H), 7.67 (m, 2H), 7.53 (m, 2H), 7.29 (t, J=9 Hz, 2H), 6.42 (d, J=5 Hz, 1H), 5.37 (d, J=47 Hz, 1H), 4.26 (m, 1H), 3.97 (m, 1H), 3.66 (m, 1H), 3.52 (m, 1H), 3.28 (m, 2H), 2.34 (m, 2H), 1.39 (t, J=7 Hz, 3H).

Example 149

±N-(4-(3-((3S*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide dihydrochloride

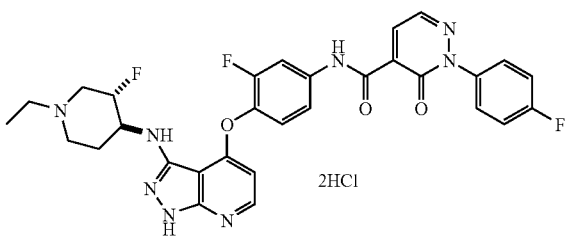

2HCl

Step A: Preparation of ±N-(4-(1-(4-methoxybenzyl)-3-((3S*,4S*)-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide bis-trifluoroacetic acid salt: Prepared from ±(3S*,4S*)-tert-butyl 4-(1-(4-methoxybenzyl)-4-(2-fluoro-4-(1-(4-fluorophenyl)-6-oxo-1,6-dihydropyridazine-5-carboxamido)phenoxy)-1H-pyrazolo[3,4-b]pyridin-3-ylamino)-3-fluoropiperidine-1-carboxylate (13 mg, 0.016 mmol, obtained from Example 146, Step B) according to the procedure for Example 148, Step A. The crude product was carried forward as a TFA salt without purification at this step. LRMS (APCI+): m/z 697 (M+1) detected.

Step B: Preparation of ±N-(4-(1-(4-methoxybenzyl)-3-((3S*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide: Prepared from ±N-(4-(1-(4-methoxybenzyl)-3-((3S*,4S*)-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide bis-trifluoroacetic acid salt (18 mg, 0.020 mmol) according to the procedure described for Example 148, Step B. Yield: 5 mg (35%). LRMS (APCI+): m/z 725 (M+1) detected.

Step C: Preparation of ±N-(4-(3-((3S*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide dihydrochloride: Prepared from ±N-(4-(1-(4-methoxybenzyl)-3-((3S*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide (5 mg, 0.007 mmol) and 2,2,2-trifluoroacetic acid (0.27 mL, 3.5 mmol) according to the procedure for Example 145, Step C. The product was obtained as a pale yellow powder (3 mg, 58%). HPLC: 91% purity (220 nm); LRMS (ESI+): 93% purity, 220 nm, m/z 605 (M+1) detected; $^1$H NMR (400 MHz, MeOD-d3) δ 11.97 (s, 1H), 8.36 (m, 2H), 8.28 (m, 1H), 8.06 (m, 1H), 7.67 (m, 2H), 7.52 (m, 2H), 7.29 (t, J=9 Hz, 2H), 6.34 (d, J=6 Hz, 1H), 5.47

(d, J=47 Hz, 1H), 4.26 (m, 1H), 3.86 (m, 1H), 3.47 (m, 2H), 3.26 (m, 2H), 2.47 (m, 2H), 1.37 (t, J=7 Hz, 3H).

Example 150

N-(3-fluoro-4-(3-(1-isopropylpiperidin-4-ylamino)-1H-pyrazolo[3,4-b]pyridin-4-yloxy)phenyl)-4-(4-fluorophenyl)-3-oxo-3,4-dihydropyrazine-2-carboxamide

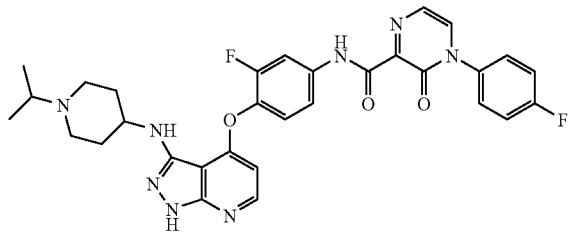

Prepared by a 2-step process from 4-(4-amino-2-fluorophenoxy) N-(1-isopropylpiperidin-4-yl)-1-(4-methoxybenzyl)-1H-pyrazolo[3,4-b]pyridin-3-amine (prepared as described in Example 101, Step A except using 1-isopropylpiperidin-4-amine) and 4-(4-fluorophenyl)-3-oxo-3,4-dihydropyrazine-2-carboxylic acid (Example 125, Step E) according to the procedure of Example 101, Step B. The crude was rinsed with Et$_2$O to afford 4.6 mg (64%) of the desired product. The desired product was treated with 2N HCl (Et$_2$O solution) in a solution of MeOH and EtOAc to afford HCl salt compound. LRMS (APClpos) m/e 601.3 (M+1). $^1$H-NMR (400 MHz, CD$_3$OD/CDCl$_3$) δ 8.17 (d, 1H), 8.06 (dd, 1H), 7.91 (d, 1H), 7.84 (d, 1H), 7.55 (m, 2H), 7.49 (d, 1H), 7.34 (t, 3H), 6.14 (d, 1H), 3.93 (m, 1H), 3.52 (m, 2H), 3.17 (m, 2H), 2.47 (m, 2H), 1.96 (m, 2H), 1.40 (d, 6H); $^{19}$F NMR (376 MHz, CD$_3$OD/CDCl$_3$) δ −111.0, −127.6.

Example 151

N-(3-fluoro-4-(3-(1-methyl-1H-imidazol-5-yl)-1H-pyrazolo[3,4-b]pyridin-4-yloxy)phenyl)-2-(4-fluorophenyl)-3-oxo-2,3-dihydropyridazine-4-carboxamide

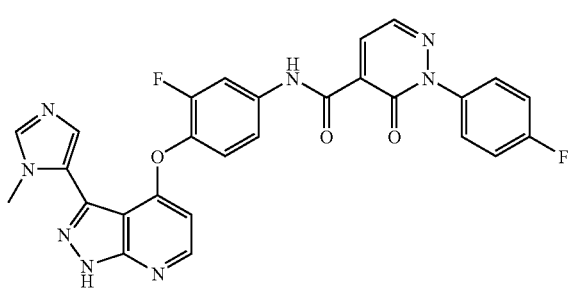

Step A: Preparation of 3-fluoro-4-(1-(4-methoxybenzyl)-3-(1-methyl-1H-imidazol-5-yl)-1H-pyrazolo[3,4-b]pyridin-4-yloxy)aniline: 4-(1-(4-Methoxybenzyl)-3-iodo-1H-pyrazolo[3,4-b]pyridin-4-yloxy)-3-fluorobenzenamine (300 mg, 0.612 mmol, prepared in Example 7, step B), 1-methyl-5-(tributylstannyl)-1H-imidazole (681 mg, 1.84 mmol) (Org. Proc. Res. & Dev., 2003, 7(5), 676-683), tetrakis (triphenylphosphine) palladium (0) (141 mg, 0.122 mmol) and toluene (5 mL) were charged in a 25 mL, single-neck, round-bottomed flask. The reaction mixture was stirred at 100° C. until the starting material had been consumed (2 days). Then the reaction was cooled to room temperature and then partitioned between EtOAc (50 mL) and water (50 mL). The phases were separated and the aqueous phase was extracted with EtOAc (3×50 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (213 mg, 78.3%). LRMS (APCI pos): >95% purity, 254 nm, m/e 445 (M+1). $^1$H NMR (400 MHz, CDCl$_3$) δ 8.32 (d, 1H), 7.71 (m, 1H), 7.50 (m, 1H), 7.36 (m, 2H), 6.96 (m, 1H), 6.83 (m, 2H), 6.52 (m, 1H), 6.46 (m, 1H), 6.28 (d, 1H), 5.65 (s, 2H), 3.92 (s, 3H), 3.77 (s, 3H), 3.67 (s, 2H, NH$_2$), Step B: Preparation of N-(3-fluoro-4-(1-(4-methoxybenzyl)-3-(1-methyl-1H-imidazol-5-yl)-1H-pyrazolo[3,4-b]pyridin-4-yloxy)phenyl)-2-(4-fluorophenyl)-3-oxo-2,3-dihydropyridazine-4-carboxamide: 4-(1-(4-Methoxybenzyl)-3-(1-methyl-1H-imidazol-5-yl)-1H-pyrazolo[3,4-b]pyridin-4-yloxy)-3-fluorobenzenamine (0.213 g, 0.479 mmol), 2-(4-fluorophenyl)-3-oxo-2,3-dihydropyridazine-4-carboxylic acid (0.561 g, 2.40 mmol, prepared in Example 19, step C), N1-((ethylimino)methylene)-N3,N3-dimethylpropane-1,3-diamine hydrochloride (0.459 g, 2.40 mmol), 1H-benzo[d][1,2,3]triazol-1-ol hydrate (0.367 g, 2.40 mmol), N-ethyl-N-isopropylpropan-2-amine (0.310 g, 2.40 mmol) and CH$_2$Cl$_2$ (5 mL) were charged in a 50 mL single-neck, round-bottomed flask. The reaction mixture was stirred at room temperature until LC-MS shows that the starting material had been consumed (overnight). Then the reaction was partitioned between EtOAc (50 mL) and water (50 mL). The phases were separated and the aqueous phase was extracted with EtOAc (3×50 mL). The combined organic layers were dried (Na$_2$SO$_4$), filtered and concentrated to yield a crude product. The crude product was purified by silica gel chromatography (CH$_2$Cl$_2$/MeOH from 100/1 to 50/1, v/v) to afford product (0.201 g, 63.5%). LRMS (APCI pos): >95% purity, 254 nm, m/e 661 (M+1). $^1$H NMR (400 MHz, CDCl$_3$) δ 11.75 (s, 1H), 8.31 (d, 1H), 8.25 (d, 1H), 8.14 (d, 1H), 7.87 (dd, 1H), 7.60 (s, 1H), 7.52 (m, 2H), 7.42 (s, 1H), 7.28 (m, 3H), 7.13 (m, 3H), 6.75 (m, 2H), 6.20 (d, 1H), 5.56 (s, 2H), 3.83 (s, 3H), 3.67 (s, 3H).

Step C: Preparation of N-(3-fluoro-4-(3-(1-methyl-1H-imidazol-5-yl)-1H-pyrazolo[3,4-b]pyridin-4-yloxy)phenyl)-2-(4-fluorophenyl)-3-oxo-2,3-dihydropyridazine-4-carboxamide: N-(4-(1-(4-Methoxybenzyl)-3-(1-methyl-1H-imidazol-5-yl)-1H-pyrazolo[3,4-b]pyridin-4-yloxy)-3-fluorophenyl)-2-(4-fluorophenyl)-3-oxo-2,3-dihydropyridazine-4-carboxamide (0.201 g, 0.3043 mmol) and CF$_3$COOH (2 mL) were charged in a 25 mL, single-neck, round-bottomed flask. The reaction mixture was stirred at 100° C. until the starting material had been consumed (7 days). Then the CF$_3$COOH was removed under reduced pressure. The residue was partitioned between DCM (50 mL) and saturated NaHCO$_3$ (50 mL). The phases were separated and the aqueous phase was extracted with DCM (3×50 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (133.5 mg, 81.18%). LRMS (APCI pos): >98% purity, 254 nm, m/e 541 (M+1). $^1$H NMR (400 MHz, DMSO-d$_6$) δ 11.74 (s, 1H), 9.31

(s, 1H), 8.46 (d, 1H), 8.39 (d, 1H), 8.26 (d, 1H), 8.10 (s, 1H), 8.07 (d, 1H), 7.68 (m, 2H), 7.62 (m, 2H), 7.42 (m, 2H), 6.46 (d, 1H), 4.07 (s, 3H).

Example 152

N-(3-fluoro-4-(3-(piperidin-4-ylmethyl)-1H-pyrazolo[3,4-b]pyridin-4-yloxy)phenyl)-4-(4-fluorophenyl)-3-oxo-3,4-dihydropyrazine-2-carboxamide

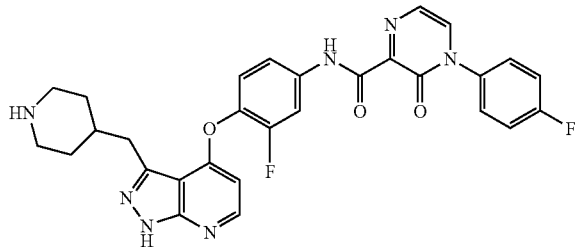

Step A: Preparation of tert-butyl 4-((4-(2-fluoro-4-(4-(4-fluorophenyl)-3-oxo-3,4-dihydropyrazine-2-carboxamido)phenoxy)-1-(4-methoxybenzyl)-1H-pyrazolo[3,4-b]pyridin-3-yl)methyl)piperidine-1-carboxylate: Prepared according to the procedure of Example 137, Step B, substituting 4-(4-fluorophenyl)-3-oxo-3,4-dihydropyrazine-2-carboxylic acid (40 mg, 0.17 mmol) for 2-(4-fluorophenyl)-3-oxo-2,3-dihydropyridazine-4-carboxylic acid. Title compound was purified by Si column chromatography (Biotage 25M) loading with DCM and eluting with 3% MeOH in DCM to afford desired product as yellow foam. Yield: 43 mg, 65%. $^1$H NMR (400 MHz, DMSO-d6) δ 11.82 (s, 1H), 8.28 (d, 1H), 7.99 (d, 1H), 7.94 (d, 1H), 7.51 (d, 2H), 7.45 (m, 3H), 7.32 (t, 3H), 7.21 (t, 1H), 6.82 (d, 2H), 6.21 (d, 1H), 5.59 (s, 2H), 3.76 (s, 3H), 3.02 (d, 2H), 2.66 (br m, 2H), 2.03 (br m, 1H), 1.64 (br m, 4H), 1.44 (s, 9H), 1.25 (br m, 3H). LRMS (APCI pos) m/e 778.0 (M+H).

Step B: Preparation of N-(3-fluoro-4-(1-(4-methoxybenzyl)-3-(piperidin-4-ylmethyl)-1H-pyrazolo[3,4-b]pyridin-4-yloxy)phenyl)-4-(4-fluorophenyl)-3-oxo-3,4-dihydropyrazine-2-carboxamide: Dissolved tert-butyl 4-((4-(2-fluoro-4-(4-(4-fluorophenyl)-3-oxo-3,4-dihydropyrazine-2-carboxamido)phenoxy)-1-(4-methoxybenzyl)-1H-pyrazolo[3,4-b]pyridin-3-yl)methyl)piperidine-1-carboxylate (43 mg, 0.055 mmol) in DCM (1 mL) and added excess TFA (d 1.48) (0.100 ml). The mixture was stirred at room temperature for 18 hours. The solvent was removed, and the crude was partitioned between DCM (15 mL) and aqueous 10% Na$_2$CO$_3$ (20 mL). The organic layer was washed with brine, dried over sodium sulfate and evaporated to afford title compound as free-base. Yield 41 mg, 89% purity by HPLC, 97%. LRMS (APCI pos) m/e 678.3 (M+H).

Step C: Preparation of N-(3-fluoro-4-(3-(piperidin-4-ylmethyl)-1H-pyrazolo[3,4-b]pyridin-4-yloxy)phenyl)-4-(4-fluorophenyl)-3-oxo-3,4-dihydropyrazine-2-carboxamide: Prepared according to the procedure of Example 53, Step B, substituting tert-butyl 4-((4-(2-fluoro-4-(4-(4-fluorophenyl)-3-oxo-3,4-dihydropyrazine-2-carboxamido)phenoxy)-1-(4-methoxybenzyl)-1H-pyrazolo[3,4-b]pyridin-3-yl)methyl)piperidine-1-carboxylate (10 mg, 0.015 mmol) for N-(3-fluoro-4-(1-(4-methoxybenzyl)-3-(3-(methylcarbamoyl)phenyl)-1H-pyrazolo[3,4-b]pyridin-4-yloxy)phenyl)-N-(4-fluorophenyl)cyclopropane-1,1-dicarboxamide. The solvent was removed, and the crude was partitioned between DCM (15 mL) and aqueous 10% Na$_2$CO$_3$ (20 mL). The organic layer was washed with brine, dried over sodium sulfate and evaporated to afford crude free-base. Di-HCl salt was prepared by dissolution in MeOH and added 2N HCl/ether. The solution was stirred for 10 minutes. The solvent was evaporated, and the residue was triturated with 20% MeOH/ether to afford title compound as yellow solid. Yield 4.2 mg, 90% purity by HPLC, 41%. LRMS (APCI pos) m/e 558.3 (M+H).

Example 153

N-(4-(3-((1-ethylpiperidin-4-yl)methyl)-1H-pyrazolo[3,4-b]pyridin-4-yloxy)-3-fluorophenyl)-4-(4-fluorophenyl)-3-oxo-3,4-dihydropyrazine-2-carboxamide

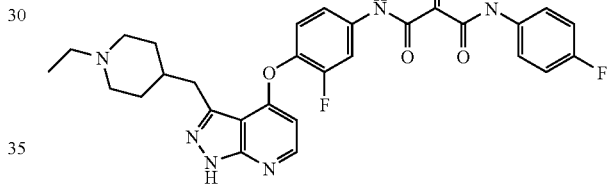

Step A: Preparation of N-(4-(1-(4-methoxybenzyl)-3-((1-ethylpiperidin-4-yl)methyl)-1H-pyrazolo[3,4-b]pyridin-4-yloxy)-3-fluorophenyl)-4-(4-fluorophenyl)-3-oxo-3,4-dihydropyrazine-2-carboxamide: N-(4-(1-(4-methoxybenzyl)-3-(piperidin-4-ylmethyl)-1H-pyrazolo[3,4-b]pyridin-4-yloxy)-3-fluorophenyl)-4-(4-fluorophenyl)-3-oxo-3,4-dihydropyrazine-2-carboxamide (17 mg, 0.025 mmol; prepared as in Example 152, Step B) was added to a small round bottom flask and dissolved in dry THF (1.5 mL). Acetaldehyde (5.56 mg, 0.126 mmol) and a drop of acetic acid (d 1.049) were added. The reaction mixture was stirred for 10 minutes under N$_2$(g) at room temperature. NaBH(OAc)$_3$ (53.5 mg, 0.252 mmol) was added and stirred at room temperature for 1 hour. The reaction mixture was partitioned between water and DCM and extracted with a second portion of DCM (10 mL). The combined organics were dried over sodium sulfate and evaporated to afford desired product, used as crude in next step. Yield 18.6 mg, 90% purity by HPLC, 94%. LRMS (APCI pos) m/e 706.3 (M+H).

Step B: Preparation of N-(4-(3-((1-ethylpiperidin-4-yl)methyl)-1H-pyrazolo[3,4-b]pyridin-4-yloxy)-3-fluorophenyl)-4-(4-fluorophenyl)-3-oxo-3,4-dihydropyrazine-2-carboxamide: N-(4-(1-(4-methoxybenzyl)-3-((1-ethylpiperidin-4-yl)methyl)-1H-pyrazolo[3,4-b]pyridin-4-yloxy)-3-fluorophenyl)-4-(4-fluorophenyl)-3-oxo-3,4-dihydropyrazine-2-carboxamide (18 mg, 0.025 mmol) was added to a small round bottom flask and dissolved in excess TFA (d 1.48) (0.2 ml, 2.550 mmol). The mixture was stirred at 70° C. overnight. The solvent was evaporated, and the crude was chromatographed on Si (preparative TLC) 0.5 mm thickness, eluting with 10% MeOH/DCM w/1% NH$_4$OH. Product isolated and determined to by mono-TFA salt by $^{19}$F-NMR. Yield 1.4 mg, 8%. $^1$H NMR (400 MHz, MeOD) δ 8.29 (d, 1H), 8.08 (d, 1H), 7.93 (d, 1H), 7.79 (d, 2H), 7.60 (m, 2H), 7.54 (br d, 1H), 7.41 (t, 1H), 7.35 (t, 2H), 6.33 (d, 1H), 3.10 (d, 2H), 2.75 (br s, 2H), 2.43 (br s, 2H), 2.11 (br m, 1H), 1.88 (d, 2H), 1.55 (m, 2H), 1.19 (t, 3H). LRMS (APCI pos) m/e 586.3 (M+H).

Example 154

N-(3-fluoro-4-((2-morpholinoethyl)(1H-pyrazolo[3,4-b]pyridin-4-yl)amino)phenyl)-2-(4-fluorophenyl)-3-oxo-2,3-dihydropyridazine-4-carboxamide

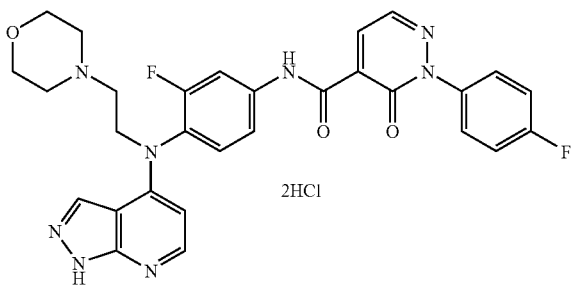

2HCl

Step A: Preparation of 1-(4-methoxybenzyl)-N-(2-morpholinoethyl)-1H-pyrazolo[3,4-b]pyridin-4-amine: 1-(4-methoxybenzyl)-4-chloro-1H-pyrazolo[3,4-b]pyridine (0.200 g, 0.731 mmol) was charged to a pressure tube in 5 mL of NMP. 2-morpholinoethanamine (0.144 ml, 1.10 mmol) was added and the reaction was heated to 150° C. for 72 hours. After cooling, the reaction mixture was diluted with 25 mL of EtOAc and washed with water (2×15 mL) and then dried with brine and Na$_2$SO$_4$. Purification via flash Si 10 g eluting with 1-5% MeOH/DCM with NH$_4$OH to afford 151 mg (55%) of product as a yellow oil. $^1$H NMR (400 MHz, CDCl$_3$) δ 8.20 (d, 1H), 7.92 (s, 1H), 7.30 (t, 2H), 6.83 (m, 2H), 6.14 (d, 1H), 5.56 (s, 2H), 5.41 (s, 1H), 3.75 (m, 7H), 3.44 (m, 2H), 2.73 (t, 2H), 2.51 (bs, 4H).

Step B: Preparation of 1-(4-methoxybenzyl)-N-(2-fluoro-4-nitrophenyl)-N-(2-morpholinoethyl)-1H-pyrazolo[3,4-b]pyridin-4-amine: 1-(4-Methoxybenzyl)-N-(2-morpholinoethyl)-1H-pyrazolo[3,4-b]pyridin-4-amine (0.025 g, 0.06804 mmol) was charged to a pressure tube in DMF (1 mL). NaH (0.004082 g, 0.1021 mmol) was added, and the reaction was allowed to stir at room temperature for 15 minutes. 1,2-difluoro-4-nitrobenzene (0.009389 ml, 0.08505 mmol) was added, and the reaction was stirred at room temperature for 3 hours. The reaction mixture was diluted with EtOAc (25 mL) and washed with water (15 mL). The organics were then dried with brine, dried over Na$_2$SO$_4$, filtered and concentrated. Purification via flash Si 5 g eluting with 1-5% MeOH/DCM to afford 28 mg (80%) of product as a yellow oil. $^1$H NMR (400 MHz, CDCl$_3$) δ 8.32 (d, 1H), 8.14 (m, 2H), 7.61 (t, 1H), 7.30 (m, 2H), 6.82 (d, 3H), 6.43 (d, 1H), 5.54 (s, 2H), 4.05 (t, 2H), 3.75 (s, 3H), 3.59 (t, 4H), 2.76 (t, 2H), 2.44 (m, 4H); $^{19}$F NMR (376 MHz, CDCl$_3$) δ−113.92 (s, 1F); LRMS (apci pos): 307.1 (M+H)$^+$.

Step C: Preparation of N1-(1-(4-methoxybenzyl)-1H-pyrazolo[3,4-b]pyridin-4-yl)-2-fluoro-N1-(2-morpholinoethyl)benzene-1,4-diamine: 1-(4-methoxybenzyl)-N-(2-fluoro-4-nitrophenyl)-N-(2-morpholinoethyl)-1H-pyrazolo[3,4-b]pyridin-4-amine (0.024 g, 0.0474 mmol) and SnCl2-dihydrate (0.0535 g, 0.237 mmol) were stirred in EtOH (2 mL) for 2 hours at reflux. The reaction was cooled to room temperature and then concentrated under reduced pressure and dried in vacuo. The residue was diluted with EtOAc and washed with saturated Na$_2$CO$_3$ (20 mL). The organics were dried over Na$_2$SO$_4$. The organics were filtered and concentrated to give 21 mg (92%) of product as a light yellow oil. $^1$H NMR (400 MHz, CDCl$_3$) δ 8.21 (d, 1H), 7.27 (m, 2H), 7.11 (m, 1H), 6.558 (bs, 1H), 6.49 (m, 2H), 6.29 (d, 1H), 5.48 (s, 2H), 4.12 (m, 4H), 3.73 (s, 3H), 3.69 (m, 4H), 2.73 (t, 2H), 2.48 (m, 4H); F NMR (400 MHz, CDCl$_3$) δ−120.43 (s, 1F); LRMS (apci pos): 477.3 (M+H)$^+$.

Step D: Preparation of N-(4-((1-(4-methoxybenzyl)-1H-pyrazolo[3,4-b]pyridin-4-yl)(2-morpholinoethyl)amino)-3-fluorophenyl)-2-(4-fluorophenyl)-3-oxo-2,3-dihydropyridazine-4-carboxamide: 2-(4-fluorophenyl)-3-oxo-2,3-dihydropyridazine-4-carboxylic acid (0.0310 g, 0.132 mmol) (prepared according to the procedure of Example 19, Step C) was taken up in DMF (1 mL). EDCI (0.0422 g, 0.220 mmol), HOBt (0.0298 g, 0.220 mmol), and DIEA (0.0384 ml, 0.220 mmol) were then added. After stirring under N$_2$ for 15 minutes, N1-(1-(4-methoxybenzyl)-1H-pyrazolo[3,4-b]pyridin-4-yl)-2-fluoro-N1-(2-morpholinoethyl)benzene-1,4-diamine (0.021 g, 0.0441 mmol) was added in DMF (1 mL). After stirring for 5.5 hours, DCM was removed. The product was taken up into EtOAc and washed with diluted NaHCO$_3$ and brine. The product was dried over Na$_2$SO$_4$, filtered and concentrated. Purification via Flash Si 5 g eluting with 1-5% MeOH/DCM with NH$_4$OH to obtain 15.7 mg (51%) of product as a yellow oil. $^1$H NMR (400 MHz, CDCl$_3$) δ 11.88 (s, 1H), 8.41 (d, 1H), 8.24 (m, 2H), 7.93 (dd, 1H), 7.63 (m, 2H), 7.43 (m, 1H), 7.35 (m, 1H), 7.27 (m, 4H), 6.80 (m, 2H), 6.61 (br s, 1H), 6.31 (d, 1H), 5.48 (s, 2H), 3.94 (t, 2H), 3.75 (s, 3H), 3.65 (t, 3H), 2.88 (s, 1H), 2.75 (t, 2H), 2.47 (t, 4H); $^{19}$F NMR (376 MHz, CDCl$_3$) δ−111.41 (s, 1F), −117.59 (s, 1F); LRMS (apci pos): 693.3 (M+H)$^+$.

Step E: Preparation of N-(3-fluoro-4-((2-morpholinoethyl)(1H-pyrazolo[3,4-b]pyridin-4-yl)amino)phenyl)-2-(4-fluorophenyl)-3-oxo-2,3-dihydropyridazine-4-carboxamide: N-(4-((1-(4-methoxybenzyl)-1H-pyrazolo[3,4-b]pyridin-4-yl)(2-morpholinoethyl)amino)-3-fluorophenyl)-2-(4-fluorophenyl)-3-oxo-2,3-dihydropyridazine-4-carboxamide (0.015 g, 0.02165 mmol) was dissolved in TFA (0.1668 ml, 2.165 mmol) and stirred at 60° C. for 18 hours. Excess TFA was evaporated, and the crude product was then resuspended in toluene and reconcentrated to remove trace TFA. The crude solid was then partitioned between EtOAc and NaHCO$_3$. The organic layer was separated and dried over sodium sulfate. After filtration to remove sodium sulfate and concentration, the residual crude solid was taken up in a small amount of DCM and treated with 2N HCl in ether. The suspension was evaporated to dryness to give 14 mg (95%) of product as a brown solid. LRMS (apci pos): 573.3 (M+H)$^+$.

Example 155

N-(3-fluoro-4-((2-morpholinoethyl)(1H-pyrazolo[3,4-b]pyridin-4-yl)amino)phenyl)-4-(4-fluorophenyl)-3-oxo-3,4-dihydropyrazine-2-carboxamide

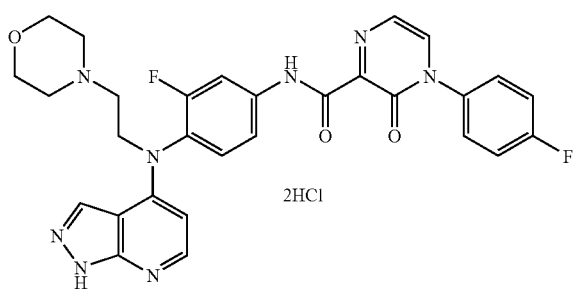

Step A: Preparation of N-(3-fluoro-4-((1-(4-methoxybenzyl)-1H-pyrazolo[3,4-b]pyridin-4-yl)(2-morpholinoethyl)amino)phenyl)-4-(4-fluorophenyl)-3-oxo-3,4-dihydropyrazine-2-carboxamide: Prepared according to the procedure of Example 154, Step D substituting 2-(4-fluorophenyl)-3-oxo-2,3-dihydropyrazine-4-carboxylic acid for 2-(4-fluorophenyl)-3-oxo-2,3-dihydropyridazine-4-carboxylic acid.

Step B: Preparation of N-(3-fluoro-4-((2-morpholinoethyl)(1H-pyrazolo[3,4-b]pyridin-4-yl)amino)phenyl)-4-(4-fluorophenyl)-3-oxo-3,4-dihydropyrazine-2-carboxamide: Prepared according to the procedure of Example 154, step E using N-(3-fluoro-4-((1-(4-methoxybenzyl)-1H-pyrazolo[3,4-b]pyridin-4-yl)(2-morpholinoethyl)amino)phenyl)-4-(4-fluorophenyl)-3-oxo-3,4-dihydropyrazine-2-carboxamide. LRMS (apci pos): 573.2 (M+H)+.

Example 156

N-(3-fluoro-4-(3-(4-isopropylpiperazine-1-carbonyl)-1H-pyrazolo[3,4-b]pyridin-4-yloxy)phenyl)-4-(4-fluorophenyl)-3-oxo-3,4-dihydropyrazine-2-carboxamide

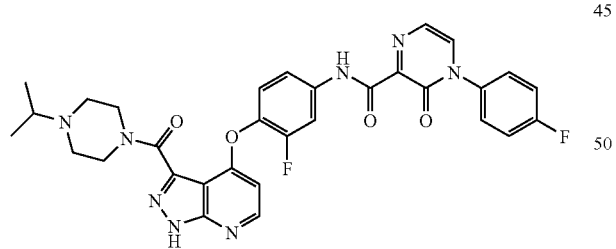

Step A: Preparation of N-(3-fluoro-4-(3-(4-isopropylpiperazine-1-carbonyl)-1H-pyrazolo[3,4-b]pyridin-4-yloxy)phenyl)-4-(4-fluorophenyl)-3-oxo-3,4-dihydropyrazine-2-carboxamide: Prepared according to the procedure of Example 158, Step B, substituting 4-(4-fluorophenyl)-3-oxo-3,4-dihydropyrazine-2-carboxylic acid (18.5 mg, 0.0791 mmol) for 2-(4-fluorophenyl)-3-oxo-2,3-dihydropyridazine-4-carboxylic acid. The crude product isolated was the double addition product with amide formation at both the aniline NH₂ and pyrazole NH. The crude was dissolved in MeOH (1 mL) and treated with triethylamine (5 eq.) at 50° C. to affect hydrolysis of pyrazole amide. Title compound was purified by preparative TLC (0.5 mm thickness) eluting with 90/10 DCM/MeOH to afford desired product as pale yellow solid. Yield: 3.4 mg, 20%. ¹H NMR (400 MHz, DMSO-d6) δ 14.04 (s, 1H), 11.32 (s, 1H), 8.39 (d, 2H), 8.00 (m, 1H), 7.99 (s, 1H), 7.96 (s, 1H), 7.65 (m, 2H), 7.56 (d, 1H), 7.45 (m, 3H), 6.42 (d, 1H), 3.64 (br s, 2H), 2.67 (m, 1H), 2.39 (br s, 2H), 2.33 (br s, 2H), 0.91 (d, 6H). LRMS (APCI pos) m/e 615.3 (M+H).

Example 157

N-(3-fluoro-4-(3-(8-methyl-8-azabicyclo[3.2.1]octan-3-ylamino)-1H-pyrazolo[3,4-b]pyridin-4-yloxy)phenyl)-4-(4-fluorophenyl)-3-oxo-3,4-dihydropyrazine-2-carboxamide

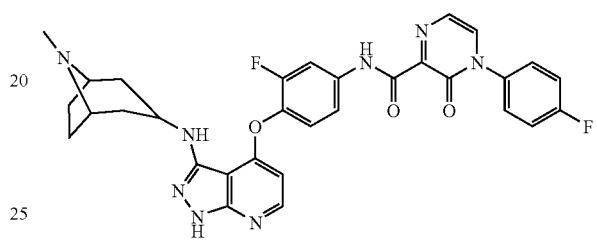

Prepared by a 2-step process from 4-(4-amino-2-fluorophenoxy)-1-(4-methoxybenzyl)-N-(8-methyl-8-azabicyclo[3.2.1]octan-3-yl)-1H-pyrazolo[3,4-b]pyridin-3-amine (prepared as described in Example 101, Step A except using 8-methyl-8-azabicyclo[3.2.1]octan-3-amine) and 4-(4-fluorophenyl)-3-oxo-3,4-dihydropyrazine-2-carboxylic acid (Example 125, Step E) according to the procedure of Example 101, Step B. The crude was rinsed with Et₂O to afford 7 mg (18%) of the desired product. The desired product was treated with 2N HCl (Et₂O solution) in a solution of MeOH and EtOAc to afford HCl salt compound. LRMS (ESIpos) m/e 599.2 (M+1). ¹H-NMR (400 MHz, CD₃OD) δ 8.36 (m, 1H), 8.14 (d, 1H), 7.94 (m, 1H), 7.80 (m, 1H), 7.60 (m, 4H), 7.35 (t, 2H), 6.54 (d, 1H), 4.07 (m, 1H), 3.93 (m, 2H), 2.81 (s, 3H), 2.35-2.58 (m, 8H); ¹⁹F NMR (376 MHz, CD₃OD) δ −113.5, −129.6.

Example 158

N-(3-fluoro-4-(3-(4-isopropylpiperazine-1-carbonyl)-1H-pyrazolo[3,4-b]pyridin-4-yloxy)phenyl)-2-(4-fluorophenyl)-3-oxo-2,3-dihydropyridazine-4-carboxamide

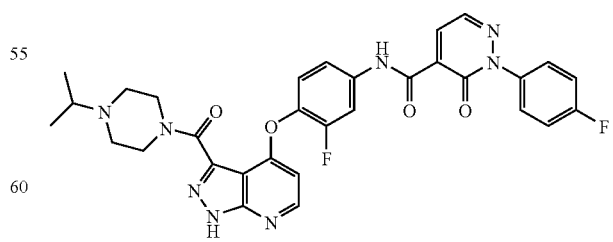

Step A: Preparation of (4-(4-amino-2-fluorophenoxy)-1H-pyrazolo[3,4-b]pyridin-3-yl)(4-isopropylpiperazin-1-yl)methanone: Prepared according to the procedure of Example 144, Step B, substituting 1-isopropylpiperazine (346 mg, 2.70 mmol) for 1-methylpiperazine. Purified by preparative TLC (0.5 mm thickness) eluting with 90/10/1 DCM/MeOH/NH₄OH to afford the desired product as pale yellow solid. Yield: 30 mg, 28%. LRMS (APCI pos) m/e 399.2 (M+H).

Step B: Preparation of N-(3-fluoro-4-(3-(4-isopropylpiperazine-1-carbonyl)-1H-pyrazolo[3,4-b]pyridin-4-yloxy)phenyl)-2-(4-fluorophenyl)-3-oxo-2,3-dihydropyridazine-4-carboxamide: Prepared according to the procedure of Example 82, Step B, substituting (4-(4-amino-2-fluorophenoxy)-1H-pyrazolo[3,4-b]pyridin-3-yl)(4-isopropylpiperazin-1-yl)methanone (30 mg, 0.075 mmol) for tert-butyl 4-(1-(4-methoxybenzyl)-4-(4-amino-2-fluorophenoxy)-1H-pyrazolo[3,4-b]pyridin-3-yl)piperazine-1-carboxylate. Purified by preparative TLC (0.5 mm thickness) eluting with 90/10/1 DCM/MeOH/NH₄OH to afford the desired product as pale yellow solid. Yield: 16 mg, 35%. $^1$H NMR (400 MHz, DMSO-d6) δ 11.69 (s, 1H), 8.39 (m, 2H), 8.27 (s, 1H), 8.03 (d, 1H), 7.68 (m, 2H), 7.57 (d, 1H), 7.41 (t, 3H), 6.43 (d, 1H), 3.62 (br s, 2H), 2.64 (m, 1H), 2.40 (br d, 4H), 0.90 (d, 6H). LRMS (APCI pos) m/e 615.3 (M+H).

Example 159

±N-(3-fluoro-4-(3-((3R*,4S*)-3-fluoropiperidin-4-ylamino)-1H-pyrazolo[3,4-b]pyridin-4-yloxy)phenyl)-4-(4-fluorophenyl)-3-oxo-3,4-dihydropyrazine-2-carboxamide dihydrochloride

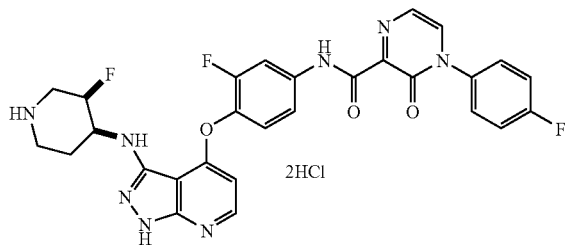

Step A: Preparation of ±(3R*,4S*)-tert-butyl 4-(1-(4-methoxybenzyl)-4-(2-fluoro-4-(1-(4-fluorophenyl)-2-oxo-1,2-dihydropyrazine-3-carboxamido)phenoxy)-1H-pyrazolo[3,4-b]pyridin-3-ylamino)-3-fluoropiperidine-1-carboxylate: Prepared from 4-(4-fluorophenyl)-3-oxo-3,4-dihydropyrazine-2-carboxylic acid (190 mg, 0.811 mmol, prepared according to the procedure for Example 125, Step E) and ±(3R*,4S*)-tert-butyl 4-(1-(4-methoxybenzyl)-4-(4-amino-2-fluorophenoxy)-1H-pyrazolo[3,4-b]pyridin-3-ylamino)-3-fluoropiperidine-1-carboxylate (157 mg, 0.270 mmol, obtained from Example 145, Step A) according to the procedure described for Example 145, Step B. Yield: 138 mg (51%).

Step B: Preparation of ±N-(3-fluoro-4-(3-((3R*,4S*)-3-fluoropiperidin-4-ylamino)-1H-pyrazolo[3,4-b]pyridin-4-yloxy)phenyl)-4-(4-fluorophenyl)-3-oxo-3,4-dihydropyrazine-2-carboxamide dihydrochloride: Prepared from ±(3R*,4S*)-tert-butyl 4-(1-(4-methoxybenzyl)-4-(2-fluoro-4-(1-(4-fluorophenyl)-2-oxo-1,2-dihydropyrazine-3-carboxamido)phenoxy)-1H-pyrazolo[3,4-b]pyridin-3-ylamino)-3-fluoropiperidine-1-carboxylate (138 mg, 0.173 mmol) and 2,2,2-trifluoroacetic acid (1.33 mL, 17.3 mmol) according to the procedure described for Example 145, Step C. The product was obtained as a pale yellow powder (30 mg, 25%). HPLC: 94% purity (254 nm); LRMS (ESI+): 577 m/z (M+1) detected; $^1$H NMR (400 MHz, CDCl₃, free base) δ 11.83 (s, 1H), 10.22 (br s, 1H), 8.22 (d, J=5 Hz, 1H), 8.01 (d, J=12 Hz, 1H), 7.94 (d, J=4 Hz, 1H), 7.52 (d, J=4 Hz, 1H), 7.46 (m, 4H), 7.32 (t, J=8 Hz, 2H), 7.27 (m, 3H), 6.10 (d, J=5 Hz, 1H), 4.95 (d, J=42 Hz, 1H), 4.88 (s, 1H), 4.06 (m, 1H), 3.39 (m, 1H), 3.17 (m, 1H), 2.92 (m, 1H), 2.77 (m, 1H), 2.03 (m, 1H), 1.76 (m, 1H).

Example 160

±N-(3-fluoro-4-(3-((3S*,4S*)-3-fluoropiperidin-4-ylamino)-1H-pyrazolo[3,4-b]pyridin-4-yloxy)phenyl)-4-(4-fluorophenyl)-3-oxo-3,4-dihydropyrazine-2-carboxamide dihydrochloride

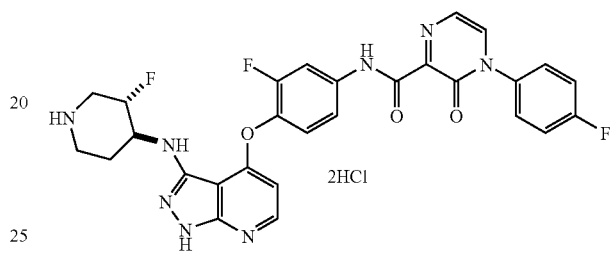

Step A: Preparation of ±(3S*,4S*)-tert-butyl 4-(1-(4-methoxybenzyl)-4-(2-fluoro-4-(1-(4-fluorophenyl)-2-oxo-1,2-dihydropyrazine-3-carboxamido)phenoxy)-1H-pyrazolo[3,4-b]pyridin-3-ylamino)-3-fluoropiperidine-1-carboxylate: Prepared from 4-(4-fluorophenyl)-3-oxo-3,4-dihydropyrazine-2-carboxylic acid (60 mg, 0.26 mmol, prepared according to the procedure for Example 125, Step E) and ±(3S*,4S*)-tert-butyl 4-(1-(4-methoxybenzyl)-4-(4-amino-2-fluorophenoxy)-1H-pyrazolo[3,4-b]pyridin-3-ylamino)-3-fluoropiperidine-1-carboxylate (50 mg, 0.086 mmol, obtained from Example 146, Step A) according to the procedure described for Example 145, Step B. Yield: 42 mg (58%).

Step B: Preparation of ±N-(3-fluoro-4-(3-((3S*,4S*)-3-fluoropiperidin-4-ylamino)-1H-pyrazolo[3,4-b]pyridin-4-yloxy)phenyl)-4-(4-fluorophenyl)-3-oxo-3,4-dihydropyrazine-2-carboxamide dihydrochloride: Prepared from ±(3S*,4S*)-tert-butyl 4-(1-(4-methoxybenzyl)-4-(2-fluoro-4-(1-(4-fluorophenyl)-2-oxo-1,2-dihydropyrazine-3-carboxamido)phenoxy)-1H-pyrazolo[3,4-b]pyridin-3-ylamino)-3-fluoropiperidine-1-carboxylate (42 mg, 0.053 mmol) and 2,2,2-trifluoroacetic acid (0.41 ml, 5.3 mmol) according to the procedure described for Example 145, Step C. The product was obtained as a pale yellow powder (19 mg, 55%). HPLC: 99% purity (254 nm); LRMS (ESI+): 577 m/z (M+1) detected; $^1$H NMR (400 MHz, CDCl₃, free base) δ 11.84 (s, 1H), 9.92 (br s, 1H), 8.21 (d, J=5 Hz, 1H), 8.02 (m, 1H), 7.94 (d, J=4 Hz, 1H), 7.52 (d, J=4 Hz, 1H), 7.46 (m, 3H), 7.32 (t, J=8 Hz, 2H), 7.26 (m, 1H), 6.11 (d, J=5 Hz, 1H), 4.82 (d, J=6 Hz, 1H), 4.58 (m, 1H), 4.01 (m, 1H), 3.39 (m, 1H), 3.02 (m, 1H), 2.82 (m, 2H), 2.46 (m, 1H), 1.60 (m, 1H).

Example A c-Met Enzyme Assay

The assay for the determination of cMet kinase activity is based on an enzyme linked immunosorbant assay (ELISA). A compound of Formula I, 50 pM cMet (His-tagged recombinant human Met (amino acids 974-end), expressed by baculovirus), and 5 μM ATP in assay buffer (25 mM MOPS, pH 7.4, 5 mM MgCl$_2$, 0.5 mM MnCl$_2$, 100 μM Sodium Orthovanadate, 0.01% Triton X-100, 1 mM DTT, final DMSO concentration 1% (v/v)) are incubated on a 0.25 mg/mL PGT coated plates for 20 minutes at room temperature. The reaction mixture is removed by washing and the phosphorylated polymer substrate is detected with 0.2 μg/mL phosphotyrosine specific monoclonal antibody (PY20) conjugated to horseradish peroxidase (HRP). After the addition of 1M phosphoric acid to stop the development, the chromogenic substrate (TMB) color is quantitated by spectrophotometry at 450 nm. Certain compounds of this invention had IC$_{50}$'s of less than 1 μM in this assay.

Example B

The cellular activity of the compounds of the present invention may be determined by the following procedure. MKN45 cells were plated in Costar 3904 96-well plates in growth media (RPMI, 10% FBS) at a density of 15000 cells/well and incubated at 37° C., 5% CO$_2$ overnight. The following day, one-tenth volume of a 10x concentration of compounds was added to the wells in a 11-point dilution series. The dilutions series was composed of an initial 1:3 dilution in DMSO, followed by a 1:20 dilution in HBSS, for a final DMSO concentration on cells of 0.5%. Control wells were treated with 0.5% DMSO. The typical range of dilution was 5 μM to 0.3 nM, which was expanded to 25 μM depending on the potency of the compound. Once compound was added to the cells, plates were incubated for one hour at 37° C., 5% CO$_2$. Plates were then washed in PBS, fixed in 4% formaldehyde and rehydrated with a 10% methanol solution. The plates were then blocked with Licor blocking buffer. The total phosphorylated cMet levels were measured by incubating with a rabbit polyclonal antibody against phosphorylated cMet followed by an anti-rabbit antibody conjugated to Alexa Fluor 680. Signal was normalized for differences in cell number by reference to the levels of the housekeeping protein GAPDH. Cells were incubated with a mouse monoclonal antibody against GAPDH followed by an anti-mouse antibody labeled with IRdye 800. Signal was measured on the Licor. The overall fluorescent signal from the Alexa Fluor 680 is normalized by dividing the value by the fluorescent value of the IRdye 800 signal. The fluorescent signal of the control wells was defined as 100% and the percent of inhibition of phosphorylated cMet was expressed as percent of control. IC$_{50}$ values were determined from the percent of control data using a standard 4-parameter logistical model.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound selected from Formulas Ia and Ib:

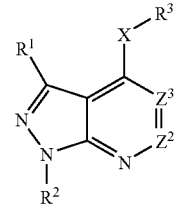

Ia

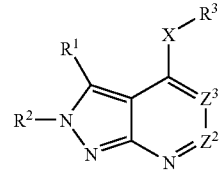

Ib and pharmaceutically acceptable salts thereof, wherein:

X is O, S or NR$^{10}$;

Z$^2$ and Z$^3$ are CR$^4$;

R$^1$ is C$_1$-C$_{12}$ alkyl, C$_2$-C$_8$ alkenyl, C$_2$-C$_8$ alkynyl, —C(=O)NR$^{10}$R$^{11}$, or —(CR$^{14}$R$^{15}$)$_t$NR$^{10}$R$^{11}$, or R$^1$ is C$_3$-C$_{12}$ carbocyclyl, C$_2$-C$_{20}$ heterocyclyl, C$_6$-C$_{20}$ aryl or C$_1$-C$_{20}$ heteroaryl, wherein said alkyl, alkenyl, alkynyl, carbocyclyl, heterocyclyl, aryl and heteroaryl are optionally substituted with one or more groups independently selected from F, Cl, Br, I, CN, CF$_3$, oxo, —OR$^{10}$, SR$^{10}$, —C(=Y)R$^{10}$, —C(=Y)OR$^{10}$, —C(=Y)NR$^{10}$R$^{11}$, —(CR$^{14}$R$^{15}$)$_n$—NR$^{10}$R$^{11}$, —NR$^{10}$C(=Y)R$^{13}$, —NR$^{10}$C(=Y)OR$^{11}$, —NR$^{12}$C(=Y)NR$^{10}$R$^{11}$, —NR$^{12}$SO$_2$R$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —S(O)R$^{10}$, —S(O)$_2$R$^{10}$, —S(O)$_2$NR$^{10}$R$^{11}$, —S(O)(OR$^{10}$), —S(O)$_2$ (OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ cycloalkyl, C$_2$-C$_{20}$ heterocyclyl, C$_6$-C$_{20}$ aryl, C$_1$-C$_{20}$ heteroaryl, —(CR$^{14}$R$^{15}$)—NR$^{12}$C (=O)(CR$^{14}$R$^{15}$)NR$^{10}$R$^{11}$, and (CR$^{14}$R$^{15}$)$_t$NR$^{10}$R$^{11}$, or R$^1$ is NR$^x$R$^y$;

R$^2$ is H, CF$_3$, CN, —C(=Y)R$^{10}$, —C(=Y)OR$^{10}$, —C(=Y)NR$^{10}$R$^{11}$, —C(=O)NR$^{12}$(CR$^{14}$R$^{15}$)$_t$ NR$^{10}$R$^{11}$, —SR$^{10}$, —S(O)R$^{10}$, —S(O)$_2$R$^{10}$, S(O)$_2$ NR$^{10}$R$^{11}$, —SC(=Y)R$^{10}$, —SC(=Y)OR$^{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, (CH$_2$)$_n$OR$^{10}$, (CH$_2$)$_n$NR$^{10}$R$^{11}$, heteroaryl and heterocyclyl;

R$^3$ is

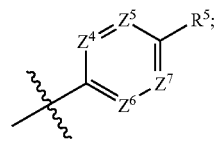

Z$^4$, Z$^5$, Z$^6$, and Z$^7$ are independently CR$^{4a}$ or N and 0, 1, or 2 of Z$^4$, Z$^5$, Z$^6$, and Z$^7$ is N, wherein when Z$^4$ and Z$^5$ or $Z^6$ and $Z^7$ are $CR^{4a}$, then $Z^4$ and $Z^5$ or $Z^6$ and $Z^7$ optionally form a partially unsaturated or fully unsaturated carbocyclic or heterocyclic ring;

each $R^{4a}$ is independently H, F, Cl, Br, $CF_3$, CN, —C(Y)$R^{10}$, —C(=Y)$OR^{10}$, —C(=Y)$NR^{10}R^{11}$, —$NR^{10}R^{11}$, $NR^{10}C(=Y)R^{11}$, $NR^{10}C(=Y)OR^{11}$, $NR^{12}C(=Y)NR^{10}R^{11}$, —$NR^{12}SO_2NR^{10}R^{11}$, —$OR^{10}$, —OC(=Y)$R^{10}$, —OC(=Y)$OR^{10}$, —OC(=Y)$NR^{10}R^{11}$, —C(=O)$NR^{12}(CR^{14}R^{15})_rNR^{10}R^{11}$, —OP(=Y)($OR^{10}$)($OR^{11}$), —OP($OR^{10}$)($OR^{11}$), —$SR^{10}$, —S(O)$R^{10}$, —$S(O)_2R^{10}$, —$S(O)_2NR^{10}R^{11}$, —SC(=Y)$R^{10}$, —$SC(=Y)_2OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^5$ is F, Cl, Br, I, CN, $CF_3$, $OR^{10}$, $SR^{10}$, —C(=Y)$R^{10}$, —C(=Y)$OR^{10}$, —C(=Y)$NR^{10}R^{11}$, —$NR^{10}R^{11}$, —$NR^{10}C(=Y)R^{13}$, —$NR^{10}C(=Y)OR^{11}$, —$NR^{12}C(=Y)NR^{10}R^{11}$, —$NR^{12}C(=O)C(=O)R^{10}R^{11}$, —$NR^{12}C(=O)C(=O)OR^a$, —$NR^{12}SO_2R^{10}$, —$NR^{12}C(=Y^1)(CR^{14}R^{15})_nC(=Y^2)NR^{10}R^{11}$, —$NR^{12}C(=Y^1)NR^{10}C(=Y^2)(CR^{14}R^{15})_nR^{11}$, —$NR^{12}C(=Y^1)(CR^{14}R^{15})_nC(=Y^2)(CR^{14}R^{15})_mR^{10}$, —OC(=Y)$R^{10}$, —OC(=Y)$OR^{10}$, —OC(=Y)$NR^{10}R^{11}$, —$OS(O)_2(OR^{10})$, —OP(=Y)($OR^{10}$)($OR^{11}$), —OP($OR^{10}$)($OR^{11}$), —S(O)$R^{10}$, —$S(O)_2R^{10}$, —$S(O)_2NR^{10}R^{11}$, —$S(O)_2(OR^{10})$, —$S(O)_2(OR^{10})$, —SC(=Y)$R^{10}$, —SC(=Y)$OR^{10}$, —SC(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from alkyl, $NR^{10}R^{11}$, and $(CR^{14}R^{15})_n$-aryl;

$R^4$ is H;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $(CR^{14}R^{15})_n$ $C_2$-$C_{20}$ heterocyclyl, $(CR^{14}R^{15})_nC_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, $SO_2R^c$, CN, $OR^a$, $NR^aR^b$, C(=O)$NR^aR^b$, $CR^aC(=O)R^b$, $C_1$-$C_{12}$ alkyl, $C_2$-$C_8$ alkenyl, $C_2$-$C_8$ alkynyl, $C_3$-$C_{12}$ carbocyclyl, $C_6$-$C_{20}$ aryl, and $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_nOR^a$, $NR^aR^b$, $CF_3$, F, Cl, Br, I, $SO_2R^a$, C(=O)$R^a$, $NR^{10}C(=Y)R^{11}$, C(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, or $R^{10}$ and $R^{12}$ together with the atoms to which they are attached form an oxo-substituted $C_3$-$C_{20}$ heterocyclic ring optionally fused to a benzene ring;

$R^{13}$ is H, $C_1$-$C_{12}$ alkyl, $C_2$-$C_8$ alkenyl, $C_2$-$C_8$ alkynyl, $(CR^{14}R^{15})_n$-cycloalkyl, $(CR^{14}R^{15})_n$-heterocyclyl, $(CR^{14}R^{15})_n$-aryl, $(CR^{14}R^{15})_n$-heteroaryl, $(CR^{14}R^{15})_n$ $(CR^{14}R^{15})_m$-aryl, $(CR^{14}R^{15})_n$—$OR^{10}$, $(CR^{14}R^{15})_n$—$NR^{10}R^{11}$, $(CR^{14}R^{15})_n$—$NR^{10}C(=O)R^{11}$, or $(CR^{14}R^{15})_n$—$NR^{10}(SO_2)$—$R^{11}$, wherein said alkyl, alkenyl, alkynyl, cycloalkyl, heterocyclyl, and heteroaryl portions are optionally substituted with one or more groups independently selected from F, Cl, Br, I, oxo, $SO_2R^c$, CN, $OR^a$, C(=O)$R^a$, C(=O)$OR^a$, $NR^aR^b$, $NR^aC(=O)R^b$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, and $C_1$-$C_{20}$ heteroaryl;

each $R^{14}$ and $R^{15}$ is independently H, $C_1$-$C_{12}$ alkyl, or $(CH_2)_t$-aryl, or $R^{14}$ and $R^{15}$ together with the atoms to which they are attached form a saturated or partially unsaturated $C_3$-$C_{12}$ carbocyclic ring, or $R^{10}$ and $R^{15}$ together with the atoms to which they are attached form an oxo-substituted saturated or partially unsaturated monocyclic or bicyclic $C_1$-$C_{20}$ heterocyclic ring optionally further substituted with one or more groups independently selected from F, Cl, Br, I, $OR^a$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, or $C_1$-$C_{20}$ heteroaryl, wherein said alkyl and aryl are optionally substituted with one or more groups independently selected from F, Cl, Br, and I, or $R^{14}$ is null and $R^{10}$ and $R^{15}$ together with the atoms to which they are attached form a $C_1$-$C_{20}$ heteroaryl ring having one or more heteroatoms;

$R^a$ and $R^b$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more alkyl groups;

$R^c$ is $C_1$-$C_{12}$ alkyl or $C_6$-$C_{20}$ aryl, wherein said alkyl and aryl are optionally substituted with one or more groups independently selected from F, Cl, Br, I, $OR^a$ and C(=O)$NR^aR^b$;

$R^x$ is H or $C_1$-$C_6$ alkyl;

$R^y$ is (i) $(C_1$-$C_6$ alkyl)$NR^jR^k$ wherein $R^j$ and $R^k$ are independently H or $C_1$-$C_6$ alkyl; (ii) $C_5$-$C_6$ cycloalkyl optionally substituted with OH or —OC(=O)$CF_3$; or (iii) a 5-6 membered heterocyclic ring having 1 to 2 ring heteroatoms independently selected from N and O and optionally substituted with a halogen group, $C_1$-$C_6$ alkyl, $(C_1$-$C_6$ alkyl)OH, $(C_1$-$C_6$ alkyl)O($C_1$-$C_6$ alkyl), or $C_1$-$C_6$ fluoroalkyl;

Y, $Y^1$ and $Y^2$ are independently O or S;

t is 1, 2, 3, 4, 5 or 6; and n and m are independently 0, 1, 2, 3, 4, 5 or 6.

2. The compound of claim 1, wherein:

X is O, S or $NR^{10}$;

$Z^2$ and $Z^3$ are independently selected from $CR^4$;

$R^1$ is $C_1$-$C_{12}$ alkyl, $C_2$-$C_8$ alkenyl, $C_2$-$C_8$ alkynyl, —C(O)$NR^{10}R^{11}$, or $—(CR^{14}R^{15})_rNR^{10}R^{11}$, or $R^1$ is $C_3$-$C_{12}$ carbocyclyl, $C_2$-$C_{20}$ heterocyclyl, $C_6$-$C_{20}$ aryl or $C_1$-$C_{20}$ heteroaryl, wherein said alkyl, alkenyl, alkynyl, carbocyclyl, heterocyclyl, aryl and heteroaryl are optionally substituted with one or more groups independently selected from F, Cl, Br, I, CN, $CF_3$, oxo, —$OR^{10}$, $SR^{10}$, —C(=Y)$R^{10}$, —C(=Y)$OR^{10}$, —C(=Y)$NR^{10}R^{11}$, $—(CR^{14}R^{15})_n—NR^{10}R^{11}$, $NR^{10}C(=Y)R^{13}$, $NR^{10}C(=Y)OR^{11}$, —$NR^{12}C(=Y)NR^{10}R^{11}$, —$NR^{12}SO_2R^{10}$, —OC(=Y)$R^{10}$, —OC(=Y)$OR^{10}$, —OC(=Y)$NR^{10}R^{11}$, —$OS(O)_2(OR^{10})$, —OP(=Y)($OR^{10}$)($OR^{11}$), —OP($OR^{10}$)($OR^{11}$), —S(O)$R^{10}$, —$S(O)_2R^{10}$, —$S(O)_2NR^{10}R^{11}$, —$S(O)(OR^{10})$, —$S(O)_2(OR^{10})$, —SC(=Y)$R^{10}$, —SC(=Y)$OR^{10}$, —SC(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, $C_1$-$C_{20}$ heteroaryl, $—(CR^{14}R^{15})—NR^{12}C(=O)(CR^{14}R^{15})NR^{10}R^{11}$, and $(CR^4R^5)_tNR^{10}R^{11}$, $R^2$ is H, $CF_3$, CN, —C(=Y)$R^{10}$, —C(=Y)O$R^{10}$, —C(=Y)N$R^{10}R^{11}$, —C(=O)N$R^{12}(CR^{14}R^{15})_t$ N$R^{10}R^{11}$, —S$R^{10}$, —S(O)$R^{10}$, —S(O)$_2R^{10}$, S(O)$_2$N$R^{10}R^{11}$, —SC(=Y)$R^{10}$, —SC(=Y)O$R^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, $(CH_2)_n$O$R^{10}$, $(CH_2)_n$N$R^{10}R^{11}$, heteroaryl and heterocyclyl;

$R^3$ is

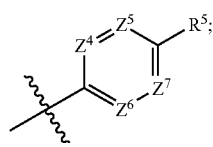

$Z^4$, $Z^5$, $Z^6$, and $Z^7$ are independently $CR^{4a}$ or N and 0, 1, or 2 of $Z^4$, $Z^5$, $Z^6$, and $Z^7$ is N, wherein when $Z^4$ and $Z^5$ or $Z^6$ and $Z^7$ are $CR^{4a}$, then $Z^4$ and $Z^5$ or $Z^6$ and $Z^7$ optionally form a partially unsaturated or fully unsaturated carbocyclic or heterocyclic ring;

each $R^{4a}$ is independently H, F, Cl, Br, $CF_3$, CN, —C(=Y)$R^{10}$, —C(=Y)O$R^{10}$, —C(=Y)N$R^{10}R^{11}$, —N$R^{10}R^{11}$, N$R^{10}$C(=Y)$R^{11}$, N$R^{10}$C(=Y)O$R^{11}$, N$R^{12}$C(=Y)N$R^{10}R^{11}$, —N$R^{12}$SO$_2$N$R^{10}R^{11}$, —O$R^{10}$, —OC(=Y)$R^{10}$, —OC(=Y)O$R^{10}$, —OC(=Y)N$R^{10}R^{11}$, —C(=O)N$R^{12}(CR^{14}R^{15})_t$N$R^{10}R^{11}$, —OP(=Y)(O$R^{10}$)(O$R^{11}$), —OP(O$R^{10}$)(O$R^{11}$), —S$R^{10}$, —S(O)$R^{10}$, —S(O)$_2R^{10}$, —S(O)$_2$N$R^{10}R^{11}$, —SC(=Y)$R^{10}$, —SC(=Y)O$R^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^5$ is F, Cl, Br, I, CN, $CF_3$, O$R^{10}$, S$R^{10}$, —C(=Y)$R^{10}$, —C(=Y)O$R^{10}$, —C(=Y)N$R^{10}R^{11}$, —N$R^{10}R^{11}$, —N$R^{10}$C(=Y)$R^{13}$, —N$R^{10}$C(=Y)O$R^{11}$, —N$R^{12}$C(=Y)N$R^{10}R^{11}$, —N$R^{12}$C(=O)C(O)$R^{10}R^{11}$, —N$R^{12}$C(=O)C(=O)O$R^a$, —N$R^{12}$SO$_2R^{10}$, —N$R^{12}$C(=$Y^1$)$(CR^{14}R^{15})_n$C(=$Y^2$)N$R^{10}R^{11}$, —N$R^{12}$C(=$Y^1$)N$R^{10}$C(=$Y^2$)$(CR^{14}R^{15})_n R^{11}$, —N$R^{12}$C(=$Y^1$)$(CR^{14}R^{15})_n$C(=$Y^2$)$(CR^{14}R^{15})_m R^{10}$, —OC(=Y)$R^{10}$, —OC(=Y)O$R^{10}$, —OC(=Y)N$R^{10}R^{11}$, —OS(O)$_2$(O$R^{10}$), —OP(=Y)(O$R^{10}$)(O$R^{11}$), —OP(O$R^{10}$)(O$R^{11}$), —S(O)$R^{10}$, —S(O)$_2R^{10}$, —S(O)$_2$N$R^{10}R^{11}$, —S(O)(O$R^{10}$), —S(O)$_2$ (O$R^{10}$), —SC(=Y)$R^{10}$, —SC(=Y)O$R^{10}$, —SC(=Y)N$R^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from alkyl, N$R^{10}R^{11}$, and $(CR^{14}R^{15})_n$-aryl;

$R^4$ is H;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, SO$_2R^c$, CN, O$R^a$, N$R^aR^b$, C(=O)N$R^aR^b$, $CR^a$C(=O)$R^b$, $C_1$-$C_{12}$ alkyl, $C_2$-$C_8$ alkenyl, $C_2$-$C_8$ alkynyl, $C_3$-$C_{12}$ carbocyclyl, $C_6$-$C_{20}$ aryl, and $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_n$O$R^a$, N$R^aR^b$, $CF_3$, F, Cl, Br, I, SO$_2R^a$, C(=O)$R^a$, N$R^{10}$C(=Y)$R^{11}$, C(=Y)N$R^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, or $R^{10}$ and $R^{12}$ together with the atoms to which they are attached form an oxo-substituted $C_3$-$C_{20}$ heterocyclic ring optionally fused to a benzene ring;

$R^{13}$ is H, $C_1$-$C_{12}$ alkyl, $C_2$-$C_8$ alkenyl, $C_2$-$C_8$ alkynyl, $(CR^{14}R^{15})_n$-cycloalkyl, $(CR^{14}R^{15})_n$-heterocyclyl, $(CR^{14}R^{15})_n$-aryl, $(CR^{14}R^{15})_n$-heteroaryl, $(CR^{14}R^{15})_n$—O—$(CR^{14}R^{15})_m$-aryl, $(CR^{14}R^{15})_n$—O$R^{10}$, $(CR^{14}R^{15})_n$—N$R^{10}R^{11}$, $(CR^{14}R^{15})_n$—N$R^{10}$C(=O)$R^{11}$, or $(CR^{14}R^{15})_n$—N$R^{10}$(SO$_2$Me)—$R^{11}$, wherein said alkyl, alkenyl, alkynyl, cycloalkyl, heterocycloalkyl, and heteroaryl portions are optionally substituted with one or more groups independently selected from F, Cl, Br, I, oxo, SO$_2R^c$, CN, O$R^a$, C(=O)$R^a$, C(=O)O$R^a$, N$R^aR^b$, N$R^a$C(=O)$R^b$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, and $C_1$-$C_{20}$ heteroaryl;

each $R^{14}$ and $R^{15}$ is independently H, $C_1$-$C_{12}$ alkyl, or $(CH_2)_t$-aryl, or $R^{14}$ and $R^{15}$ together with the atoms to which they are attached form a saturated or partially unsaturated $C_3$-$C_{12}$ carbocyclic ring, or $R^{10}$ and $R^{15}$ together with the atoms to which they are attached form an oxo-substituted saturated or partially unsaturated $C_1$-$C_{20}$ heterocyclic ring optionally further substituted with one or more groups independently selected from F, Cl, Br, I, O$R^a$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, or $C_1$-$C_{20}$ heteroaryl, wherein said alkyl and aryl are optionally substituted with one or more groups independently selected from F, Cl, Br, and I, or $R^{14}$ is null and $R^{10}$ and $R^{15}$ together with the atoms to which they are attached form a $C_1$-$C_{20}$ heteroaryl ring having one or more heteroatoms;

$R^a$ and $R^b$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from $C_1$-$C_6$ alkyl and halogen;

$R^c$ is $C_1$-$C_{12}$ alkyl or $C_6$-$C_{20}$ aryl, wherein said alkyl and aryl are optionally substituted with one or more groups independently selected from F, Cl, Br, I, O$R^a$ and C(=O)N$R^aR^b$;

Y, $Y^1$ and $Y^2$ are independently O or S;

t is 1, 2, 3, 4, 5 or 6; and n and m are independently 0, 1, 2, 3, 4, 5 or 6.

3. The compound of claim 1, wherein Formulas Ia and Ib are:

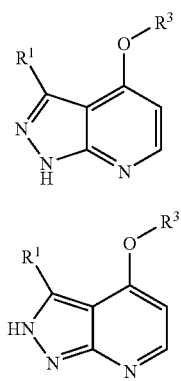

wherein $R^1$ is $C_1$-$C_{12}$ alkyl, $C_2$-$C_8$ alkenyl, $C_2$-$C_8$ alkynyl, —C(O)NR$^{10}$R$^{11}$, or —(CR$^{14}$R$^{15}$)$_t$NR$^{10}$R$^{11}$, or $R^1$ is $C_3$-$C_{12}$ carbocyclyl, $C_2$-$C_{20}$ heterocyclyl, $C_6$-$C_{20}$ aryl or $C_1$-$C_{20}$ heteroaryl, wherein said alkyl, alkenyl, alkynyl, carbocyclyl, heterocyclyl, aryl and heteroaryl are optionally substituted with one or more groups independently selected from F, Cl, Br, I, CN, CF$_3$, oxo, —OR$^{10}$, SR$^{10}$, —C(=Y)R$^{10}$, —C(=Y)OR$^{10}$, —C(=Y)NR$^{10}$R$^{11}$, —(CR$^{14}$R$^{15}$)$_n$—NR$^{10}$R$^{11}$, —NR$^{10}$C(=Y)R$^{13}$, —NR$^{10}$C(=Y)OR$^{11}$, —NR$^{12}$C(=Y)NR$^{10}$R$^{11}$, —NR$^{12}$SO$_2$R$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —S(O)R$^{10}$, —S(O)$_2$R$^{10}$, —S(O)$_2$NR$^{10}$R$^{11}$, —S(O)(OR$^{10}$), —S(O)$_2$ (OR$^{10}$), —SC(=Y)R$^{10}$, —SC(=Y)OR$^{10}$, —SC(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, $C_1$-$C_{20}$ heteroaryl, —(CR$^{14}$R$^{15}$)—NR$^{12}$C(=O)(CR$^{14}$R$^{15}$)NR$^{10}$R$^{11}$, and (CR$^{14}$R$^{15}$)$_t$NR$^{10}$R$^{11}$, or $R^1$ is NR$^x$R$^y$; and $R^3$ is

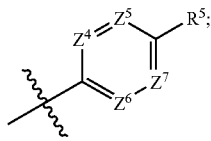

$Z^4$, $Z^5$, $Z^6$, and $Z^7$ are independently CR$^{4a}$ or N and 0, 1, or 2 of $Z^4$, $Z^5$, $Z^6$, and $Z^7$ is N, wherein when $Z^4$ and $Z^5$ or $Z^6$ and $Z^7$ are CR$^{4a}$, then $Z^4$ and $Z^5$ or $Z^6$ and $Z^7$ optionally form a partially unsaturated or fully unsaturated carbocyclic or heterocyclic ring;

each $R^{4a}$ is independently H, F, Cl, Br, CF$_3$, CN, —C(=Y)R$^{10}$, —C(=Y)OR$^{10}$, —C(=Y)NR$^{10}$R$^{11}$, —NR$^{10}$R$^{11}$, NR$^{10}$C(=Y)R$^{11}$, NR$^{10}$C(=Y)OR$^{11}$, NR$^{12}$C(=Y)NR$^{10}$R$^{11}$, —NR$^{12}$SO$_2$NR$^{10}$R$^{11}$, —OR$^{10}$, —OC(=Y)R$^{10}$, —OC(=Y)OR$^{10}$, —OC(=Y)NR$^{10}$R$^{11}$, —C(=O)NR$^{12}$(CR$^{14}$R$^{15}$)$_t$NR$^{10}$R$^{11}$, —OP(=Y)(OR$^{10}$)(OR$^{11}$), —OP(OR$^{10}$)(OR$^{11}$), —SR$^{10}$, —S(O)R$^{10}$, —S(O)$_2$R$^{10}$, —S(O)$_2$NR$^{10}$R$^{11}$, —SC(=Y)R$^{10}$, —SC(=Y)OR$^{10}$, $C_1$-$C_{12}$ alkyl, $C_2$-$C_8$ alkenyl, $C_2$-$C_9$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^5$ is F, Cl, Br, I, CN, CF$_3$, OR$^{10}$, SR$^{10}$, —C(=Y)R$^{10}$, —C(=Y)OR$^{10}$, —C(=Y)NR$^{10}$R$^{11}$, —NR$^{10}$R$^{11}$, —NR$^{10}$C(=Y)R$^{13}$, —NR$^{10}$C(=Y)OR$^{11}$, NR$^{12}$C(=Y)NR$^{10}$R$^{11}$, NR$^{12}$C(=O)C(=O)R$^{10}$R$^{11}$, —NR$^{12}$C(=O)C(=O)OR$^a$, —NR$^{12}$SO$_2$R$^{10}$, —NR$^{12}$C(=Y$^1$)(CR$^{14}$R$^{15}$)$_n$C(=Y$^2$)NR$^{10}$R$^{11}$, —NR$^{12}$C(=Y$^1$)NR$^{10}$C(=Y$^2$)(CR$^{14}$R$^{15}$)$_n$R$^{11}$, —NR$^{12}$C(=Y$^1$)(CR$^{14}$R$^{15}$)$_n$C(=Y$^2$)(CR$^{14}$R$^{15}$)$_m$R$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —S(O)R$^{10}$, —S(O)$_2$R$^{10}$, —S(O)$_2$NR$^{10}$R$^{11}$, —S(O)(OR$^{10}$), —S(O)$_2$ (OR$^{10}$), —SC(=Y)R$^{10}$, —SC(=Y)OR$^{10}$, —SC(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from alkyl, NR$^{10}$R$^{11}$, and (CR$^{14}$R$^{15}$)$_n$-aryl.

4. The compound of claim 1, wherein $R^2$ is $C_1$-$C_6$ alkyl or H.

5. The compound of claim 1, wherein X is O.

6. The compound of claim 1, wherein X is NR$^{10}$.

7. The compound of claim 6, wherein $R^1$ is $C_1$-$C_4$ alkyl, CF$_3$, CHF$_2$ or CH$_2$F.

8. The compound of claim 5, wherein $R^1$ is alkynyl optionally substituted by (CR$^{14}$R$^{15}$)—NR$^{12}$C(=O)(CR$^{14}$R$^{15}$)NR$^{10}$R$^{11}$ or (CR$^4$R$^5$)$_n$NR$^{10}$R$^{11}$.

9. The compound of claim 8 wherein $R^1$ is selected from the structures:

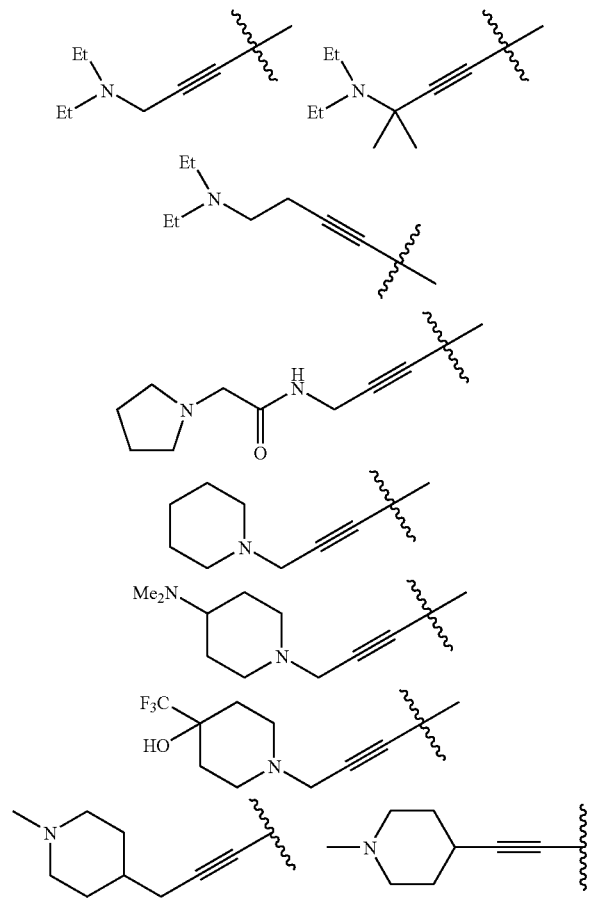

-continued

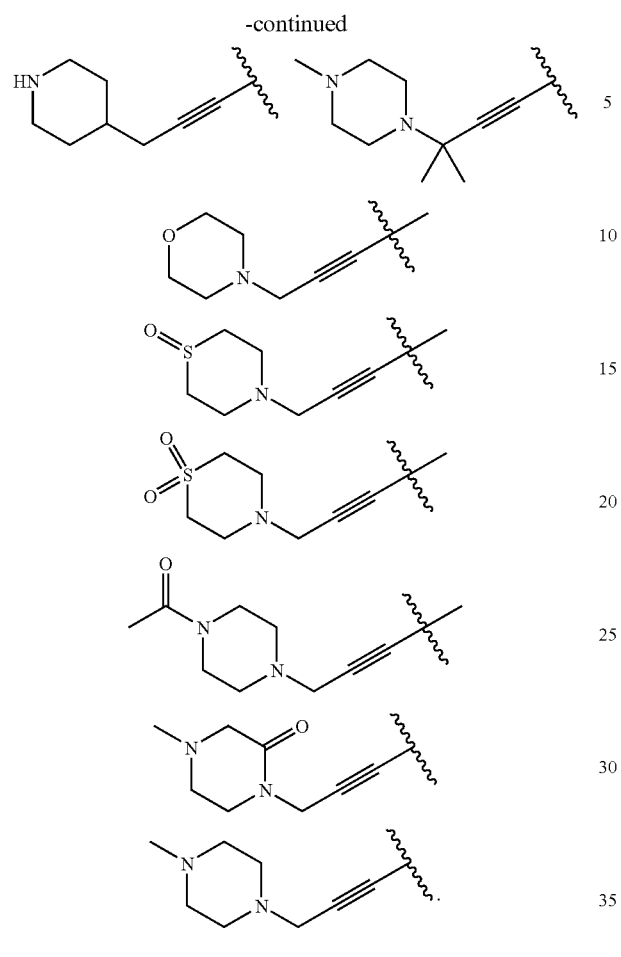

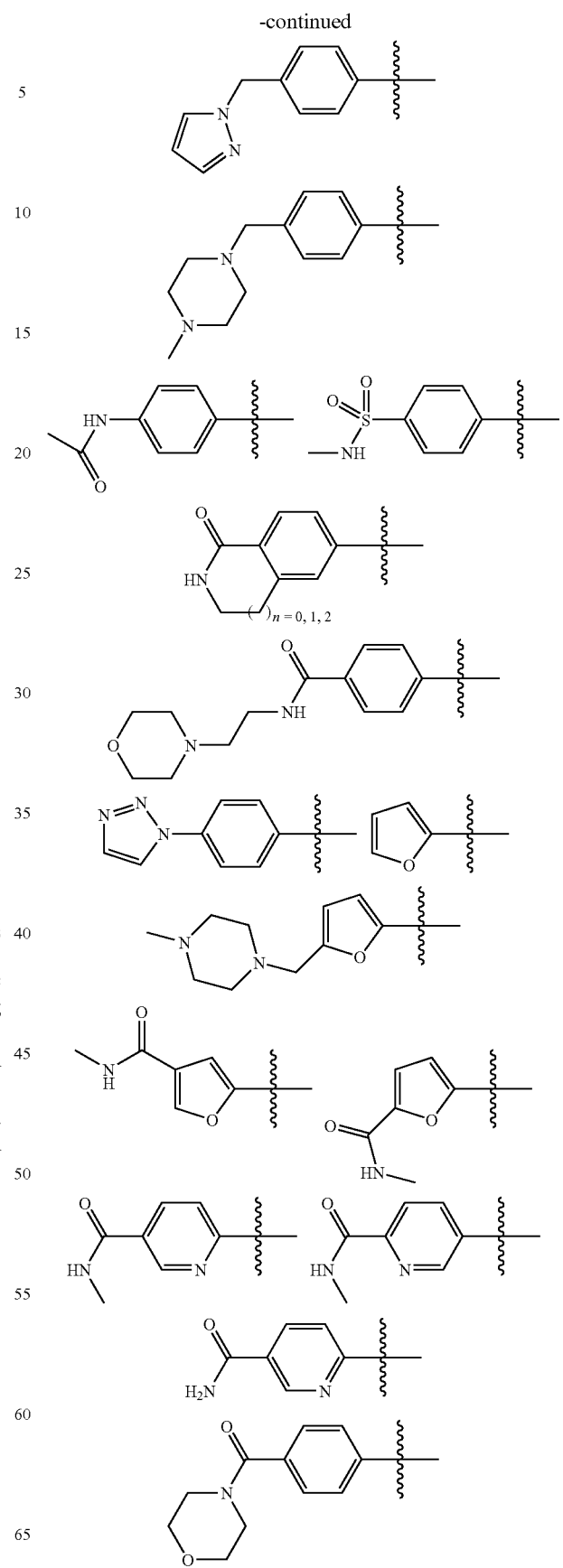

10. The compound of claim 5 wherein $R^1$ is
   (i) phenyl optionally substituted with F, Cl, Br, I, $C_1$-$C_6$ alkyl, C(=O)$C_1$-$C_6$ alkyl, C(=O)($C_3$-$C_6$ cycloalkyl), C(=O)O($C_1$-$C_6$ alkyl), C(=O)NH(CH$_2$)$_2$-hetCyc wherein hetCyc is a 6 membered ring having 1 to 2 ring heteroatoms independently selected from N and O, SO$_2$NH($C_1$-$C_6$ alkyl), C(=O)NR$^h$R$^i$, or NR$^h$R$^i$ wherein R$^h$ and R$^i$ are independently H or $C_1$-$C_6$ alkyl, or
   (ii) a 5-6 membered heteroaryl having a ring heteroatom selected from N and O and optionally substituted with C(=O)NH($C_1$-$C_6$ alkyl).

11. The compound of claim 10 wherein $R^1$ is selected from:

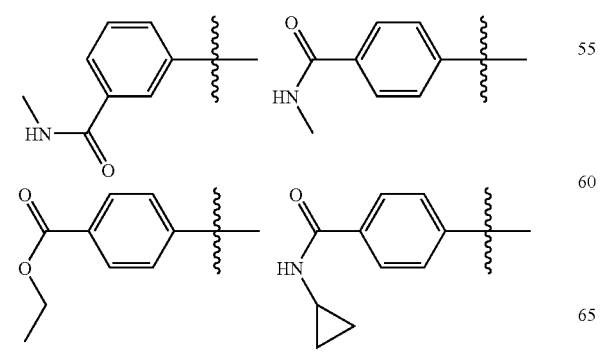

-continued

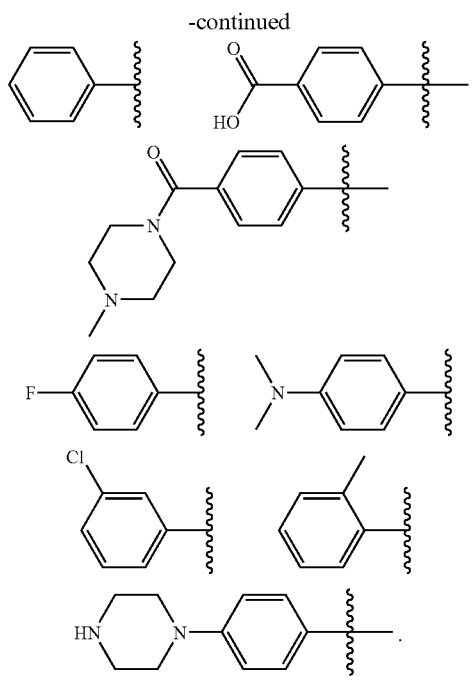

12. The compound of claim 5, wherein $R^1$ is a 5 membered heteroaryl having at least one N heteroatom and optionally substituted with $C_1$-$C_6$ alkyl.

13. The compound of claim 12, wherein $R^1$ is selected from the structures:

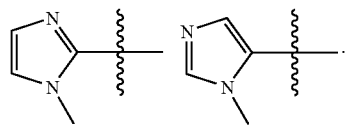

14. The compound of claim 5, wherein $R^1$ is —C(O)NR$^{10}$R$^{11}$ or —(CR$^{14}$R$^{15}$)$_t$NR$^{10}$R$^{11}$.

15. The compound of claim 14, wherein $R^1$ is selected from the structures

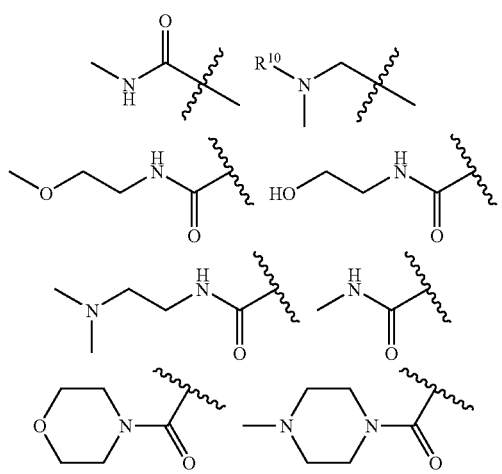

-continued

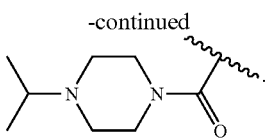

16. The compound of claim 5, wherein $R^1$ is alkyl optionally substituted with one or more groups independently selected from OR$^{10}$, NR$^{10}$R$^{11}$, $C_2$-$C_{20}$ heterocyclyl and $C_1$-$C_{20}$ heteroaryl.

17. The compound of claim 16, wherein $R^1$ is methyl, $CH_2OH$, $CH_2CH_2OH$, $CH_2CH_2CH_2OH$, $CH(OH)CH_2OH$,

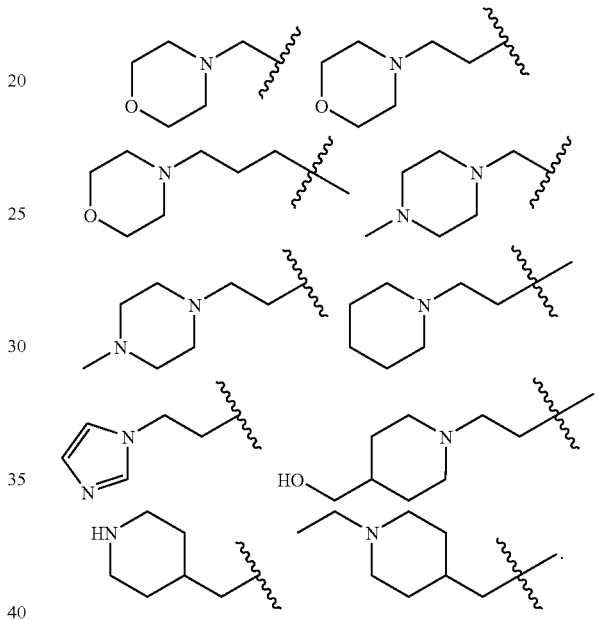

18. The compound of claim 5, wherein $R^1$ is a 5-6 membered heteroaryl ring having 1 to 2 ring heteroatoms independently selected from N and O and optionally substituted with one or more groups independently selected from Br, hetCyc and $CH_2$-hetCyc, wherein hetCyc is a 6 membered heterocyclic ring having a ring nitrogen atom and optionally having a second ring heteroatom selected from N and O, wherein hetCyc is optionally substituted with $C_1$-$C_6$ alkyl.

19. The compound of claim 18, wherein $R^1$ is selected from the structures:

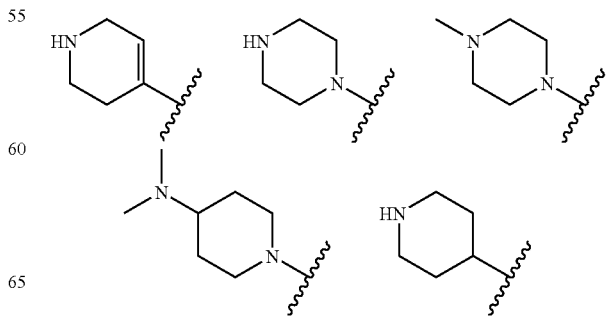

-continued

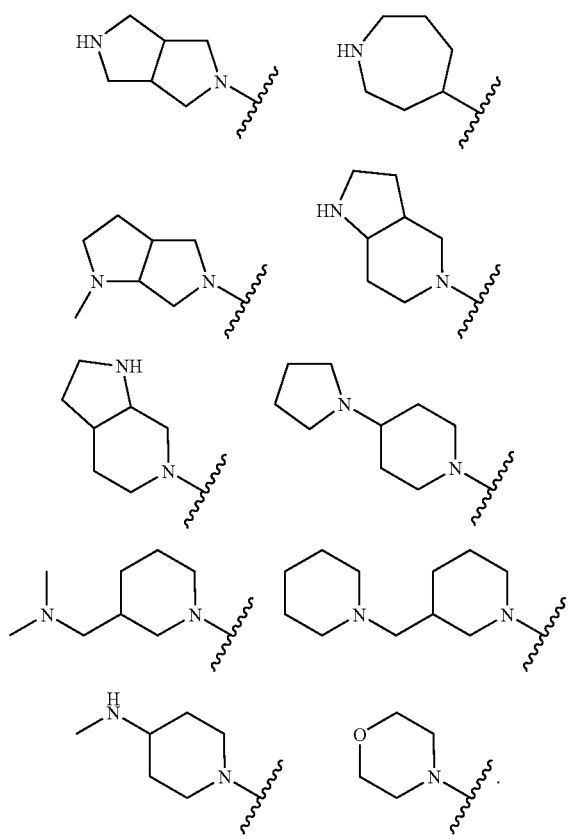

20. The compound of claim 5, wherein $R^1$ is a saturated or partially unsaturated 5-10 membered monocyclic or bicyclic heterocyclic ring, wherein said ring has one or two ring atoms independently selected from N and O and is optionally substituted with $C_1$-$C_6$ alkyl, $NR^{10}R^{11}$ or $CH_2NR^{10}R^{11}$ wherein $R^{10}$ and $R^{11}$ are independently H, $C_1$-$C_6$ alkyl, hetCyc or $CH_2$hetCyc, wherein hetCyc is a 5-6 membered ring having one or two ring nitrogen atoms.

21. The compound of claim 20, wherein $R^1$ is:

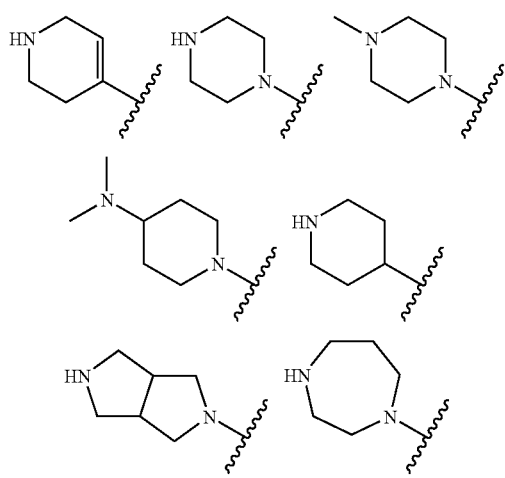

-continued

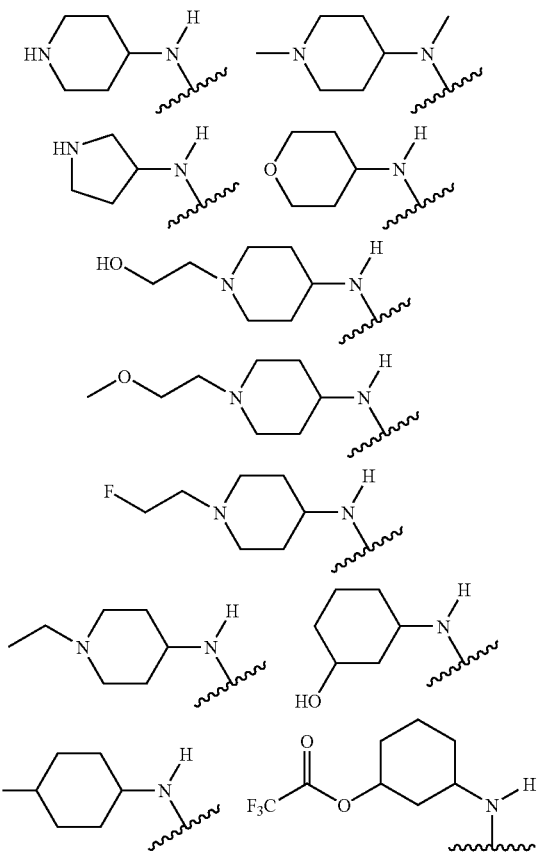

22. The compound of claim 5, wherein $R^1$ is $NR^xR^y$.

23. The compound of claim 22, wherein $R^1$ is

-continued

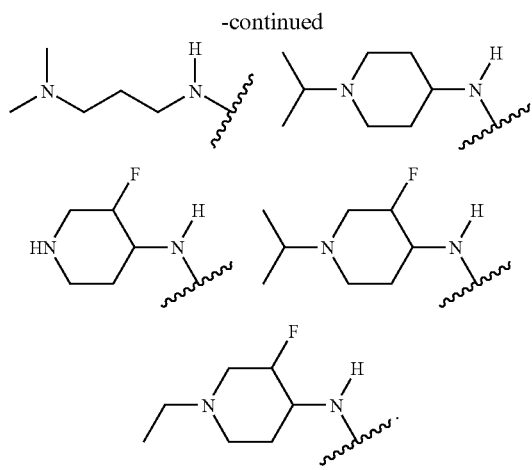

24. The compound of claim 5, wherein $R^1$ is —$(CR^{14}R^{15})_t$ $NR^{10}R^{11}$.

25. The compound of claim 5, wherein $R^1$ is the structure:

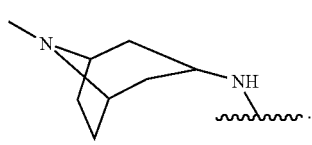

26. The compound of claim 1, wherein $R^3$ is selected from the structures:

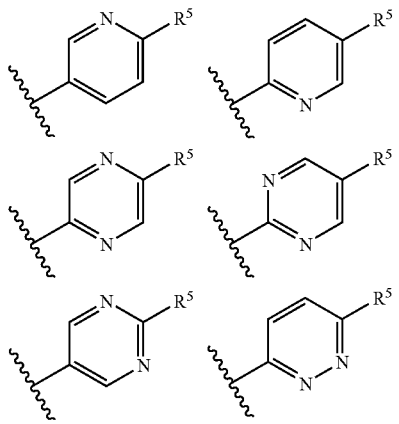

and substituted forms thereof.

27. The compound of claim 26, wherein $R^3$ is selected from the structures

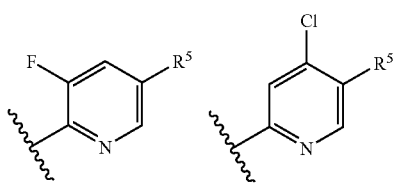

-continued

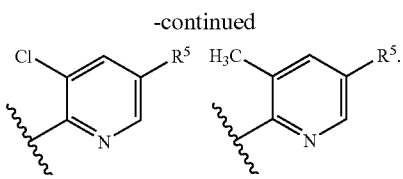

28. The compound of claim 1, wherein $R^3$ is

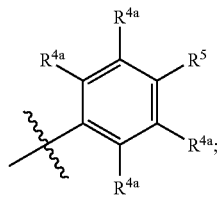

and each $R^{4a}$ is independently H, F, Cl, $C_1$-$C_6$ alkyl, O—($C_1$-$C_6$ alkyl), or CN.

29. The compound of claim 28, wherein $R^3$ is selected from the structures:

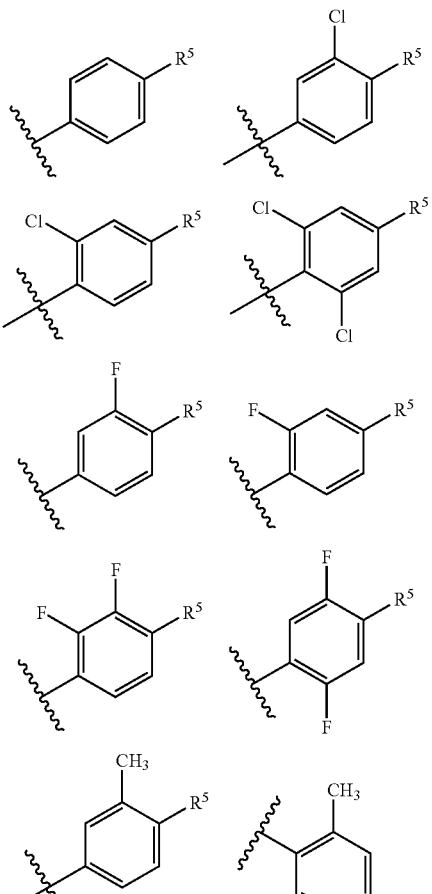

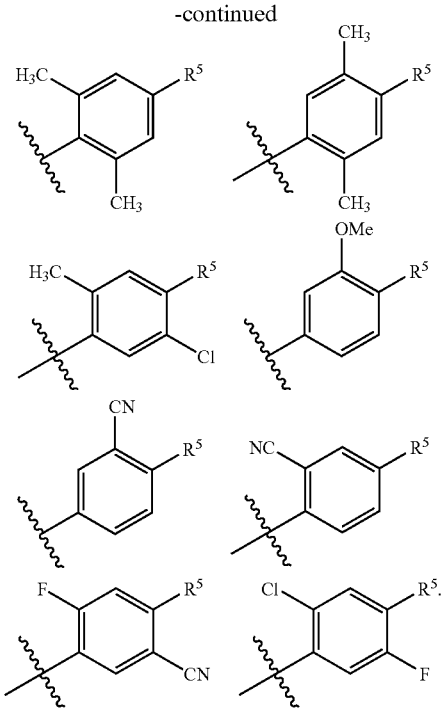

30. The compound of claim 1, wherein $R^5$ is

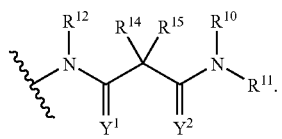

31. The compound of claim 30, wherein $R^{11}$ is an $C_6$-$C_{20}$aryl group optionally substituted with F.
32. The compound of claim 30, wherein $R^{14}$ and $R^{15}$ together with the atom to which they are attached form a $C_3$-$C_{12}$carbocyclic ring.
33. The compound of claim 30, wherein $R^{15}$ and $R^{10}$ together with the atoms to which they are attached form an oxo-substituted 5, 6 or 7 membered monocyclic or bicyclic heterocycle.
34. The compound of claim 30, wherein $R^5$ is

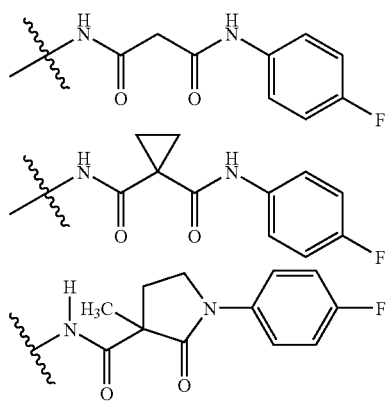

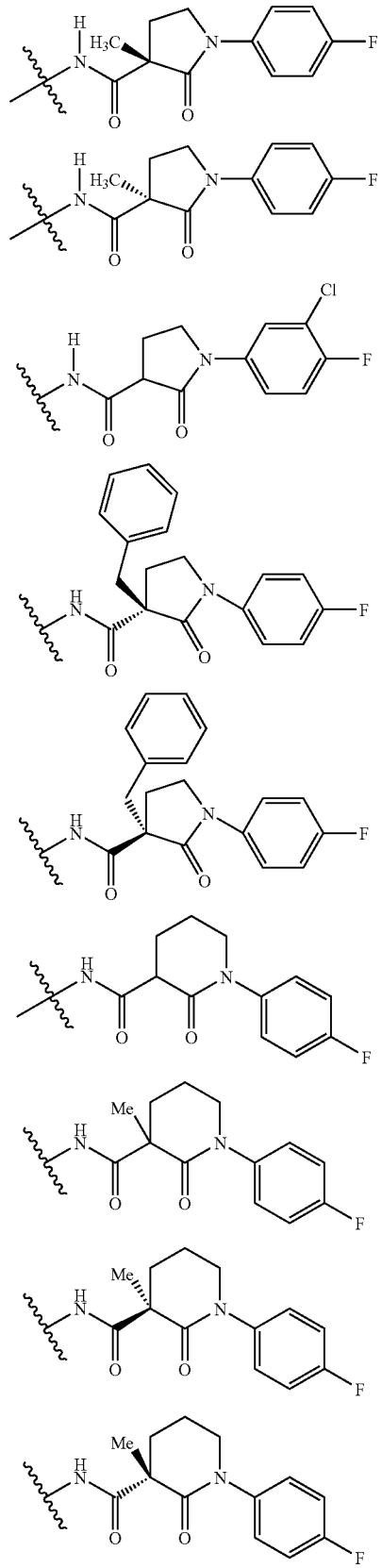

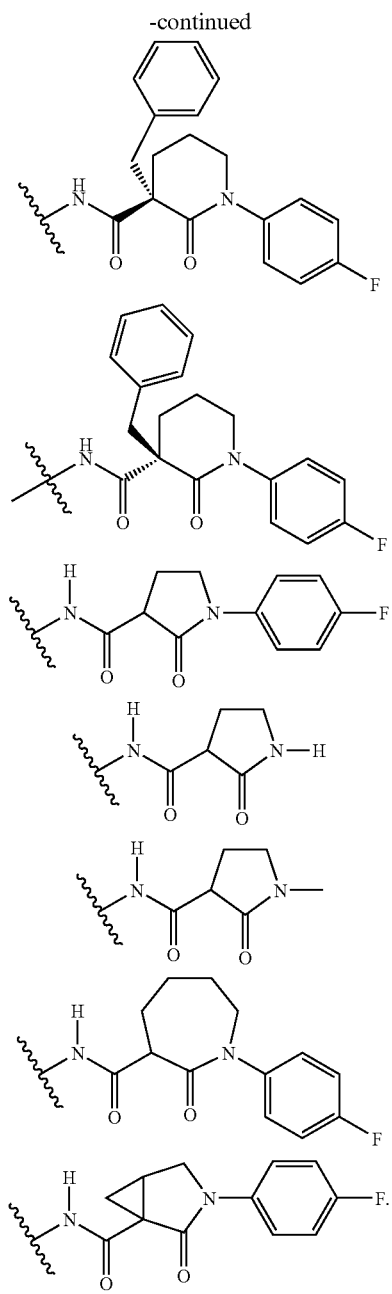
35. The compound of claim 30, wherein $R^{14}$ is null and $R^{10}$ and $R^{15}$ together with the atoms to which they are attached form an oxo-substituted 6 membered heteroaryl ring having one or two ring nitrogen atoms.
36. The compound of claim 35, wherein $R^5$ is selected from the structures:
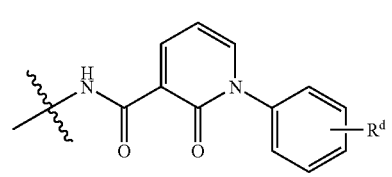
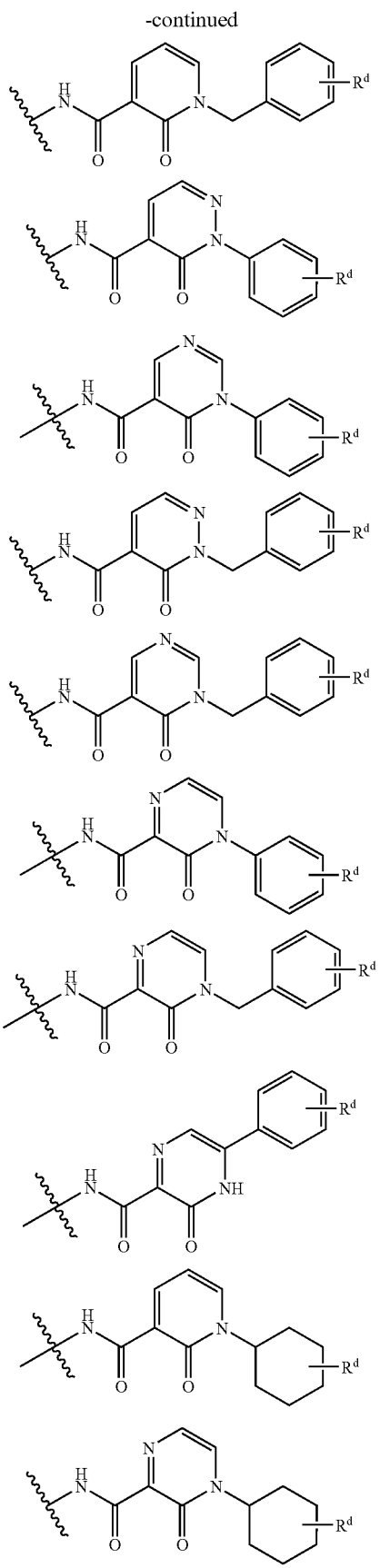

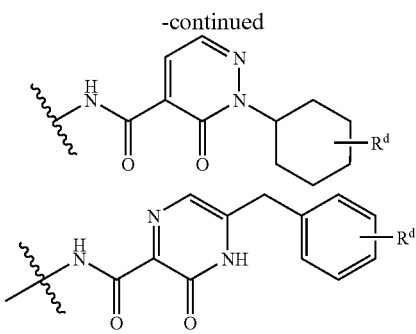

wherein R$^d$ is F, Cl, Br, I, SO$_2$R$^c$, CN, OR$^a$, NR$^a$R$^b$, C(=O)NR$^a$R$^b$, CR$^a$C(=O)R$^b$, C$_1$-C$_{12}$ alkyl, C$_2$-C$_8$ alkenyl, C$_2$-C$_8$ alkynyl, C$_6$-C$_{20}$ aryl, or C$_1$-C$_{20}$ heteroaryl.

37. The compound of claim 1, wherein R$^5$ has the structure:

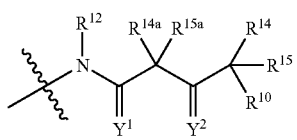

wherein R$^{14a}$ and R$^{15a}$ together with the atoms to which they are attached form a cyclopropylidine group.

38. The compound of claim 37, wherein R$^{10}$ is phenyl or CH$_2$-phenyl optionally substituted with F, Cl, Br or I.

39. The compound of claim 38, wherein R$^5$ is selected from the structures:

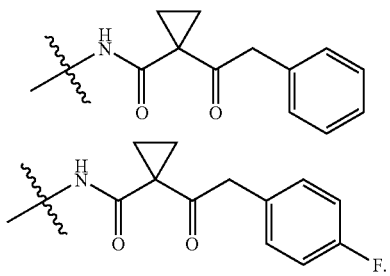

40. The compound of claim 1, wherein R$^5$ has the structure:

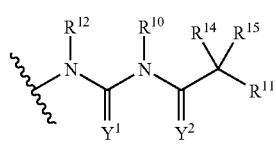

wherein R$^{11}$ is phenyl optionally substituted with halogen.

41. The compound of claim 40, wherein R$^5$ is selected from the structures

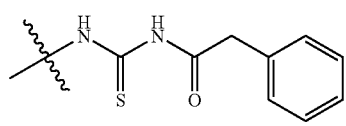

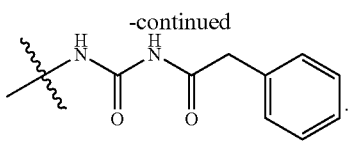

42. The compound of claim 1, wherein R$^5$ has the structure:

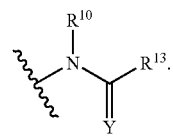

wherein R$^{13}$ is:
(i) C$_1$-C$_6$ alkyl;
(ii) (CR$^{14}$R$^{15}$)—O—(CH$_2$)$_m$-phenyl, wherein R$^{14}$ and R$^{15}$ are independently H or methyl, and m is 0 or 1;
(iii) OR$^a$, wherein R$^1$ is C$_1$-C$_6$ alkyl or phenyl;
(iv) (C$_1$-C$_3$ alkyl)-phenyl;
(v) (C$_1$-C$_2$ alkyl)-hetAr wherein hetAr is a 6 membered heteroaryl ring having one or two ring nitrogen atoms,
(vi) a 5-6 membered heteroaryl ring having 1 to 2 ring atoms independently selected from N, O and S and optionally substituted with one or two groups independently selected from NH-phenyl, morpholinyl, phenyl, and C$_1$-C$_6$ alkyl;
(vii) phenyl;
(viii) CH$_2$—N(C$_1$-C$_4$ alkyl)SO$_2$R$^a$ or CH$_2$—N(CH$_2$Ph)SO$_2$R$^a$, wherein R$^a$ is C$_1$-C$_6$ alkyl, phenyl or a 5 membered heteroaryl ring having one or two ring heteroatoms independently selected from N and O and optionally substituted with C$_1$-C$_6$ alkyl;
(ix) (CH$_2$)$_n$-hetCyc wherein n is 0 or 1 and hetCyc is a saturated or partially saturated 6 membered heterocyclic ring having a ring nitrogen atom and optionally substituted with oxo, C(=O)(C$_1$-C$_6$ alkyl), SO$_2$—(C$_1$-C$_6$ alkyl), SO$_2$-phenyl or C(=O)O(C$_1$-C$_6$ alkyl);
(x) C$_1$-C$_6$ alkyl optionally substituted with (C$_3$-C$_6$)cycloalkyl or O—(C$_1$-C$_6$ alkyl);
(xi) CH$_2$N(C$_1$-C$_6$ alkyl)C(=O)phenyl; or
(xii) (CR$^{14}$R$^{15}$)heteroaryl.

43. The compound of claim 42, wherein R$^5$ is selected from the structures:

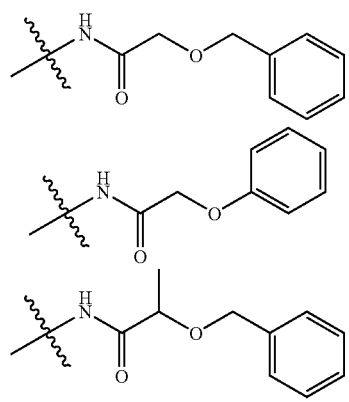

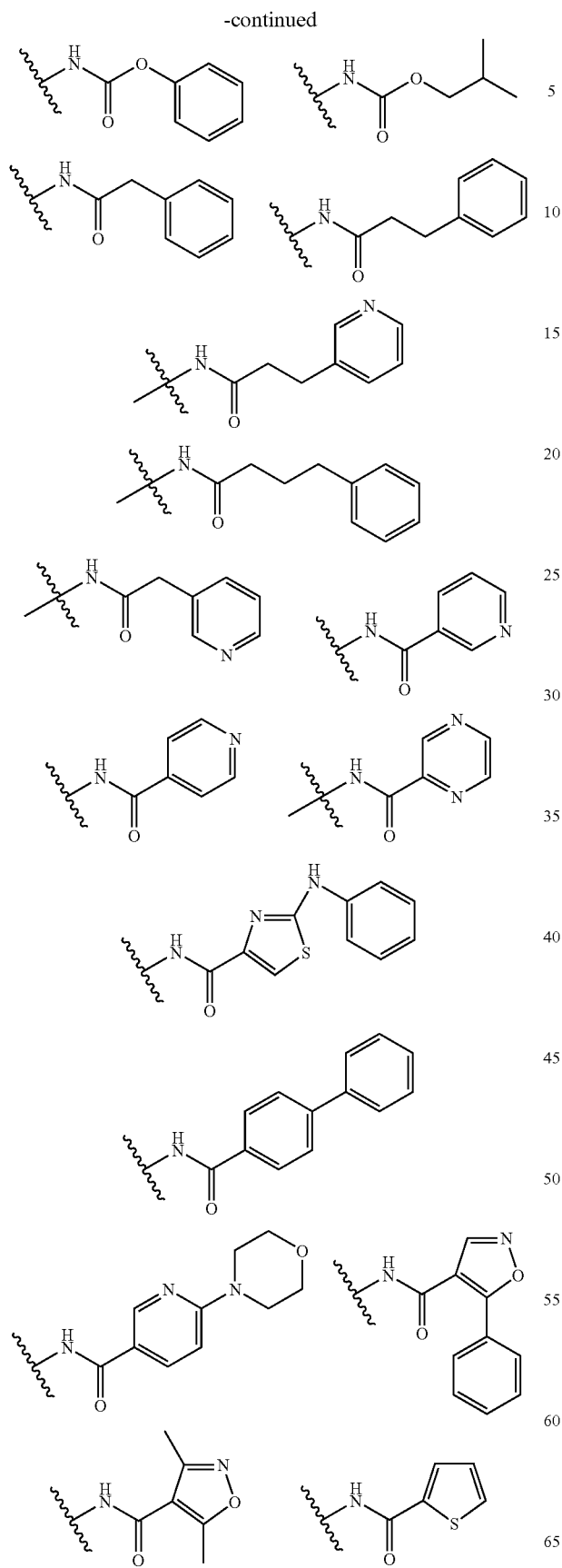
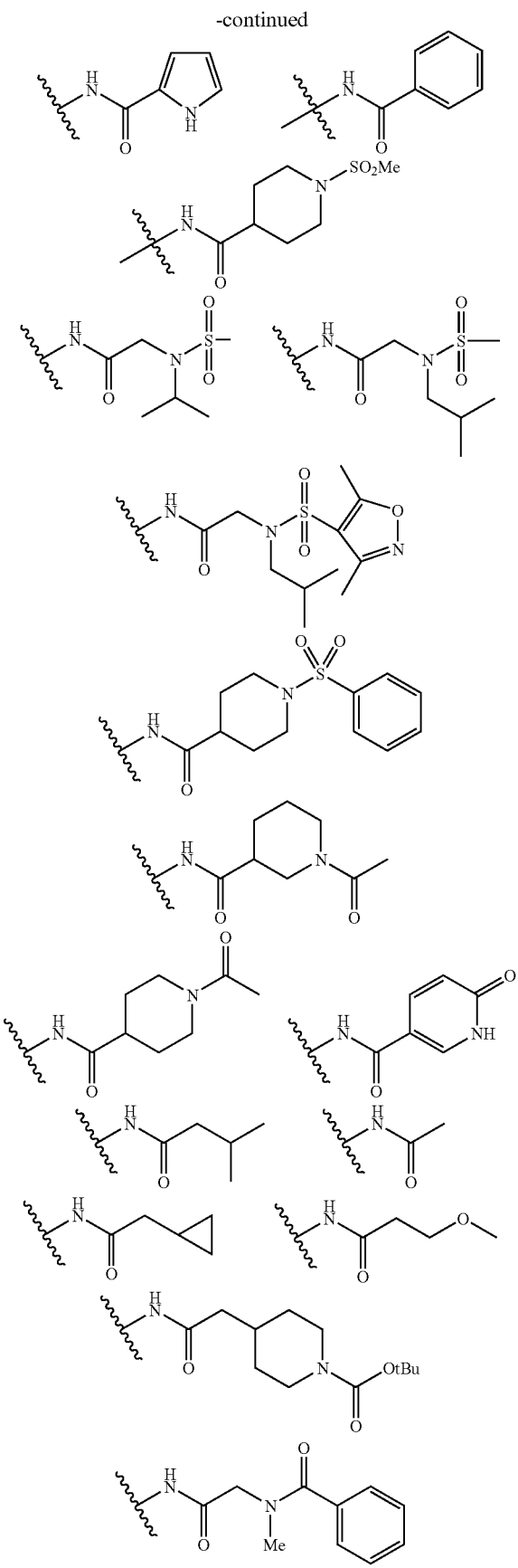

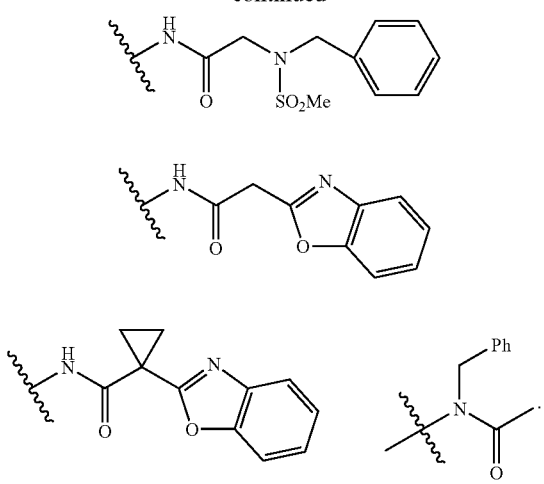

44. The compound of claim 1, wherein $R^5$ is

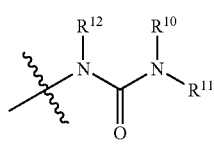

wherein $R^{11}$ is aryl or heteroaryl optionally substituted with $C_1$-$C_6$ alkyl.

45. The compound of claim 44, wherein $R^5$ is selected from the structures:

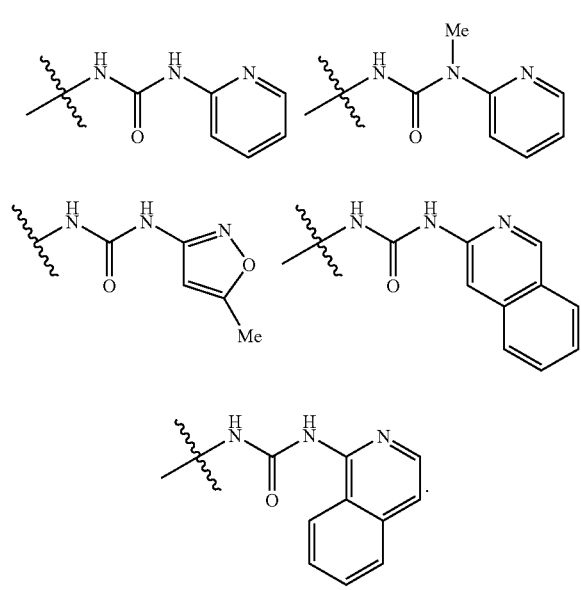

46. The compound of claim 44, wherein $R^{10}$ and $R^{12}$ together with the atoms to which they are attached form an oxo-substituted 6 membered heterocyclic ring, wherein said heterocyclic ring is optionally fused to a benzene ring.

47. The compound of claim 46, wherein $R^5$ is selected from the structures:

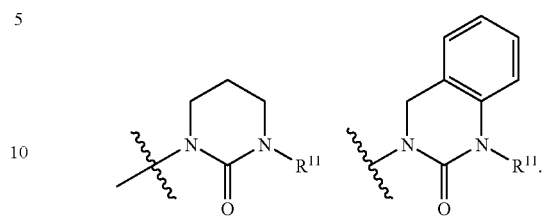

48. The compound of claim 1, wherein $R^5$ is $NR^{12}SO_2R^{10}$, wherein $R^{10}$ is phenyl optionally substituted with F, Cl, Br, I, O—($C_1$-$C_6$ alkyl), or C(=O)NH($C_1$-$C_6$ alkyl).

49. The compound of claim 48, wherein $R^5$ is selected from the structures:

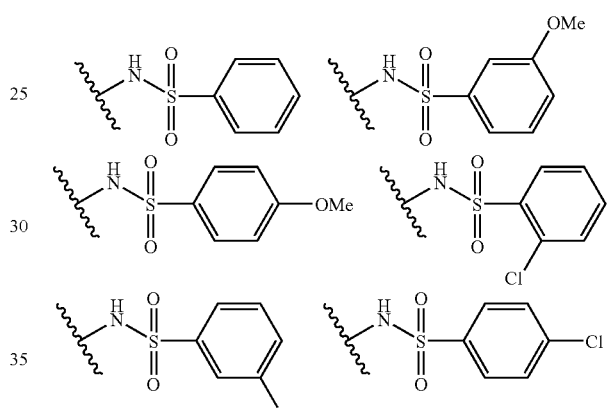

50. The compound of claim 1, wherein $R^5$ is $NR^{12}C(=O)C(=O)NR^{10}R^{11}$.

51. The compound of claim 50, wherein $R^5$ is

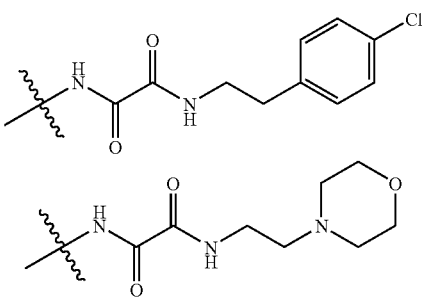

-continued

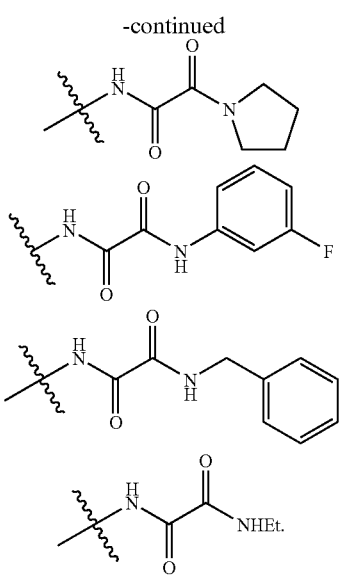

52. The compound of claim 1, wherein $R^5$ is $NR^{12}C(=O)C(=O)OR^a$.

53. The compound of claim 52, wherein $R^5$ is

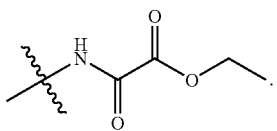

54. The compound of claim 1, wherein $R^5$ is selected from the structures:

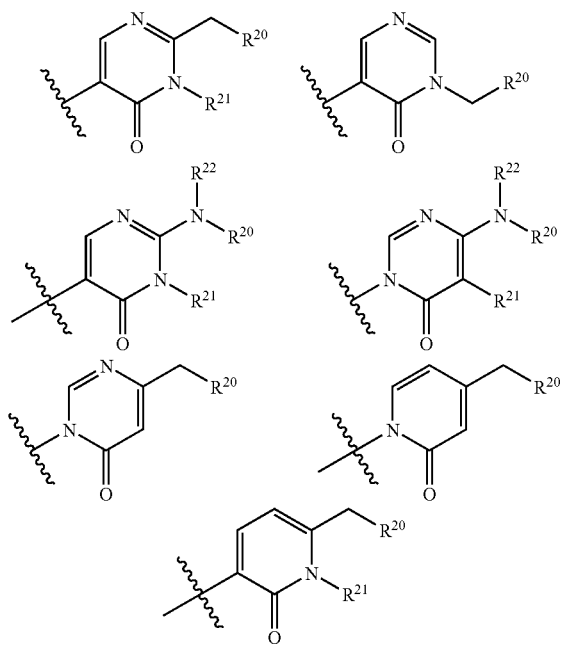

wherein $R^{20}$ is alkyl, or aryl, and $R^{21}$ and $R^{22}$ are independently selected from H or alkyl.

55. The compound of claim 1, wherein $R^5$ is $NR^{10}R^{11}$, wherein $R^{10}$ is H and $R^{11}$ is hetAr, wherein hetAr is a substituted or unsubstituted 5-6 membered heteroaryl group having at least one ring nitrogen atom and optionally having a second ring heteroatom selected from N and O, and hetAr is optionally substituted with one or two groups independently selected from $C_1$-$C_6$ alkyl and $C(=O)NR^aR^b$.

56. A pharmaceutical composition comprising a compound according to claim 1 and a pharmaceutically acceptable carrier.

57. The composition according to claim 56, further comprising an additional therapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

58. A compound of claim 1, selected from:
N-(3-fluoro-4-(3-methyl-1H-pyrazolo[3,4-b]pyridin-4-yloxy)phenylcarbamothioyl)-2-phenylacetamide;
N-(3-fluoro-4-(3-methyl-1H-pyrazolo[3,4-b]pyridin-4-yloxy)phenyl)-N-(4-fluorophenyl)cyclopropane-1,1-dicarboxamide;
N-(3-fluoro-4-(3-(3-(4-methylpiperazin-1-yl)prop-1-ynyl)-1H-pyrazolo[3,4-b]pyridin-4-yloxy)phenyl)-N-(4-fluorophenyl)cyclopropane-1,1-dicarboxamide;
N-(3-fluoro-4-(3-(2-hydroxyethyl)-1H-pyrazolo[3,4-b]pyridin-4-yloxy)phenyl)-N-(4-fluorophenyl)cyclopropane-1,1-dicarboxamide;
N-(3-fluoro-4-(3-(2-(4-methylpiperazin-1-yl)ethyl)-1H-pyrazolo[3,4-b]pyridin-4-yloxy)phenyl)-N-(4-fluorophenyl)cyclopropane-1,1-dicarboxamide;
N-(3-fluoro-4-(3-(2-morpholinoethyl)-1H-pyrazolo[3,4-b]pyridin-4-yloxy)phenyl)-N-(4-fluorophenyl)cyclopropane-1,1-dicarboxamide;
N-(3-fluoro-4-(3-(2-(piperidin-1-yl)ethyl)-1H-pyrazolo[3,4-b]pyridin-4-yloxy)phenyl)-N-(4-fluorophenyl)cyclopropane-1,1-dicarboxamide
N-(3-fluoro-4-(3-(2-(4-(hydroxymethyl)piperidin-1-yl)ethyl)-1H-pyrazolo[3,4-b]pyridin-4-yloxy)phenyl)-N-(4-fluorophenyl)cyclopropane-1,1-dicarboxamide;
N-(4-fluorophenyl)-N-(4-(3-methyl-1H-pyrazolo[3,4-b]pyridin-4-yloxy)phenyl)cyclopropane-1,1-dicarboxamide;
N-(2-chloro-5-methyl-4-(3-methyl-1H-pyrazolo[3,4-b]pyridin-4-yloxy)phenyl)-N-(4-fluorophenyl)cyclopropane-1,1-dicarboxamide;
N-(3-cyano-4-(3-methyl-1H-pyrazolo[3,4-b]pyridin-4-yloxy)phenyl)-N-(4-fluorophenyl)cyclopropane-1,1-dicarboxamide
N-(3,4-dichloro-4-(3-methyl-1H-pyrazolo[3,4-b]pyridin-4-yloxy)phenyl)-N-(4-fluorophenyl)cyclopropane-1,1-dicarboxamide;
N-(4-fluorophenyl)-N-(3-methyl-4-(3-methyl-1H-pyrazolo[3,4-b]pyridin-4-yloxy)phenyl)cyclopropane-1,1-dicarboxamide;
N-(4-fluorophenyl)-N-(6-(3-methyl-1H-pyrazolo[3,4-b]pyridin-4-yloxy)pyridin-3-yl)cyclopropane-1,1-dicarboxamide;
2-(4-fluorophenyl)-N-(6-(3-methyl-1H-pyrazolo[3,4-b]pyridin-4-yloxy)pyridin-3-yl)-3-oxo-2,3-dihydropyridazine-4-carboxamide;
1-(3-Fluoro-4-(3-methyl-1H-pyrazolo[3,4-b]pyridin-4-yloxy)phenyl)-3-(pyridin-2-yl)urea;

N-(3-fluoro-4-(3-methyl-1H-pyrazolo[3,4-b]pyridin-4-yloxy)phenyl)-1-(4-fluorophenyl)-2-oxo-1,2-dihydropyridine-3-carboxamide;

N-(3-fluoro-4-(3-methyl-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(3-methyl-1H-pyrazolo[3,4-b]pyridin-4-yloxy)phenyl)-2-methyl-3-oxo-2,3-dihydropyridazine-4-carboxamide;

N-(3-fluoro-4-(3-methyl-1H-pyrazolo[3,4-b]pyridin-4-yloxy)phenyl)-1-(4-fluorophenyl)-2-oxopyrrolidine-3-carboxamide;

N-(4-(3-(1,2-dihydroxyethyl)-1H-pyrazolo[3,4-b]pyridin-4-yloxy)-3-fluorophenyl)-N-(4-fluorophenyl)cyclopropane-1,1-dicarboxamide;

N-(3-fluoro-4-(3-(3-morpholinopropyl)-1H-pyrazolo[3,4-b]pyridin-4-yloxy)phenyl)-N-(4-fluorophenyl)cyclopropane-1,1-dicarboxamide;

N-(3-fluoro-4-(3-(morpholinomethyl)-1H-pyrazolo[3,4-b]pyridin-4-yloxy)phenyl)-N-(4-fluorophenyl)cyclopropane-1,1-dicarboxamide;

N-(3-fluoro-4-(3-(5-((4-methylpiperazin-1-yl)methyl)furan-2-yl)-1H-pyrazolo[3,4-b]pyridin-4-yloxy)phenyl)-N-(4-fluorophenyl)cyclopropane-1,1-dicarboxamide;

N-(3-fluoro-4-(3-(5-(morpholinomethyl)furan-2-yl)-1H-pyrazolo[3,4-b]pyridin-4-yloxy)phenyl)-N-(4-fluorophenyl)cyclopropane-1,1-dicarboxamide;

N-(3-fluoro-4-(3-(3-hydroxypropyl)-1H-pyrazolo[3,4-b]pyridin-4-yloxy)phenyl)-N-(4-fluorophenyl)cyclopropane-1,1-dicarboxamide;

N-(3-fluoro-4-(3-(hydroxymethyl)-1H-pyrazolo[3,4-b]pyridin-4-yloxy)phenyl)-N-(4-fluorophenyl)cyclopropane-1,1-dicarboxamide;

N-(3-fluoro-4-(3-((4-methylpiperazin-1-yl)methyl)-1H-pyrazolo[3,4-b]pyridin-4-yloxy)phenyl)-N-(4-fluorophenyl)cyclopropane-1,1-dicarboxamide;

N-(4-(3-(2-(1H-imidazol-1-yl)ethyl)-1H-pyrazolo[3,4-b]pyridin-4-yloxy)-3-fluorophenyl)-N-(4-fluorophenyl)cyclopropane-1,1-dicarboxamide;

N-(4-fluorophenyl)-N-(5-methyl-6-(3-methyl-1H-pyrazolo[3,4-b]pyridin-4-yloxy)pyridin-3-yl)cyclopropane-1,1-dicarboxamide;

N-(4-fluorophenyl)-N-(5-(3-methyl-1H-pyrazolo[3,4-b]pyridin-4-yloxy)pyridin-2-yl)cyclopropane-1,1-dicarboxamide;

N-(4-fluorophenyl)-N-(2-(3-methyl-1H-pyrazolo[3,4-b]pyridin-4-yloxy)pyrimidin-5-yl)cyclopropane-1,1-dicarboxamide;

N-(5-chloro-6-(3-methyl-1H-pyrazolo[3,4-b]pyridin-4-yloxy)pyridin-3-yl)-N-(4-fluorophenyl)cyclopropane-1,1-dicarboxamide;

N-(2-chloro-4-(3-methyl-1H-pyrazolo[3,4-b]pyridin-4-yloxy)phenyl)-N-(4-fluorophenyl)cyclopropane-1,1-dicarboxamide;

N-(4-fluorophenyl)-N-(5-(3-methyl-1H-pyrazolo[3,4-b]pyridin-4-yloxy)pyrimidin-2-yl)cyclopropane-1,1-dicarboxamide;

N-(4-(5-chloro-3-methyl-1H-pyrazolo[3,4-b]pyridin-4-yloxy)-3-fluorophenyl)-N-(4-fluorophenyl)cyclopropane-1,1-dicarboxamide;

N-(3-fluoro-4-(5-fluoro-3-methyl-1H-pyrazolo[3,4-b]pyridin-4-yloxy)phenyl)-N-(4-fluorophenyl)cyclopropane-1,1-dicarboxamide;

N-(4-(5-carbamoyl-3-methyl-1H-pyrazolo[3,4-b]pyridin-4-yloxy)-3-fluorophenyl)-N-(4-fluorophenyl)cyclopropane-1,1-dicarboxamide;

3-(4-chlorobenzyl)-5-(3-fluoro-4-(3-methyl-1H-pyrazolo[3,4-b]pyridin-4-yloxy)phenyl)pyrimidin-4(3H)-one;

3-(3-fluoro-4-(3-methyl-1H-pyrazolo[3,4-b]pyridin-4-yloxy)phenyl)-3,4-dihydroquinazolin-2(1H)-one;

5-(3-fluoro-4-(3-methyl-1H-pyrazolo[3,4-b]pyridin-4-yloxy)phenyl)-3-methyl-2-(phenylamino)pyrimidin-4(3H)-one;

2-(cyclopropylmethylamino)-5-(3-fluoro-4-(3-methyl-1H-pyrazolo[3,4-b]pyridin-4-yloxy)phenyl)-3-methylpyrimidin-4(3H)-one;

4-benzyl-N-(3-fluoro-4-(3-methyl-1H-pyrazolo[3,4-b]pyridin-4-yloxy)phenyl)-3-oxo-3,4-dihydropyrazine-2-carboxamide;

N-(3-fluoro-4-(3-methyl-1H-pyrazolo[3,4-b]pyridin-4-yloxy)phenyl)-2-oxopyrrolidine-3-carboxamide;

N-(3-fluoro-4-(3-methyl-1H-pyrazolo[3,4-b]pyridin-4-yloxy)phenyl)-1-methyl-2-oxopyrrolidine-3-carboxamide;

N-(3-fluoro-4-(3-methyl-1H-pyrazolo[3,4-b]pyridin-4-yloxy)phenyl)-1-methyl-2-oxo-1,2-dihydropyridine-3-carboxamide;

5-(3-fluoro-4-(3-methyl-1H-pyrazolo[3,4-b]pyridin-4-yloxy)phenyl)-2-(4-fluorophenylamino)-3-methylpyrimidin-4(3H)-one;

N-(3-fluoro-4-(3-(2-hydroxyethyl)-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(3-(3-(methylcarbamoyl)phenyl)-1H-pyrazolo[3,4-b]pyridin-4-yloxy)phenyl)-N-(4-fluorophenyl)cyclopropane-1,1-dicarboxamide;

N-(4-(3-(4-carbamoylphenyl)-1H-pyrazolo[3,4-b]pyridin-4-yloxy)-3-fluorophenyl)-N-(4-fluorophenyl)cyclopropane-1,1-dicarboxamide;

N-(3-fluoro-4-(3-(4-(morpholine-4-carbonyl)phenyl)-1H-pyrazolo[3,4-b]pyridin-4-yloxy)phenyl)-N-(4-fluorophenyl)cyclopropane-1,1-dicarboxamide;

N-(3-fluoro-4-(3-(4-(methoxy(methyl)carbamoyl)phenyl)-1H-pyrazolo[3,4-b]pyridin-4-yloxy)phenyl)-N-(4-fluorophenyl)cyclopropane-1,1-dicarboxamide;

N-(4-(3-(4-((1H-pyrazol-1-yl)methyl)phenyl)-1H-pyrazolo[3,4-b]pyridin-4-yloxy)-3-fluorophenyl)-N-(4-fluorophenyl)cyclopropane-1,1-dicarboxamide;

N-(4-fluorophenyl)-N-(6-(3-methyl-1H-pyrazolo[3,4-b]pyridin-4-yloxy)benzo[d]thiazol-2-yl)cyclopropane-1,1-dicarboxamide;

N-(2,5-dimethyl-4-(3-methyl-1H-pyrazolo[3,4-b]pyridin-4-yloxy)phenyl)-N-(4-fluorophenyl)cyclopropane-1,1-dicarboxamide;

N-(4-fluorophenyl)-N-(2-methyl-4-(3-methyl-1H-pyrazolo[3,4-b]pyridin-4-yloxy)phenyl)cyclopropane-1,1-dicarboxamide;

N-(4-(3-(4-(cyclopropylcarbamoyl)phenyl)-1H-pyrazolo[3,4-b]pyridin-4-yloxy)-3-fluorophenyl)-N-(4-fluorophenyl)cyclopropane-1,1-dicarboxamide;

N-(2-fluoro-4-(3-methyl-1H-pyrazolo[3,4-b]pyridin-4-yloxy)phenyl)-N-(4-fluorophenyl)cyclopropane-1,1-dicarboxamide N-(3-fluoro-4-(3-(4-(morpholine-4-carbonyl)phenyl)-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(3-phenyl-1H-pyrazolo[3,4-b]pyridin-4-yloxy)phenyl)-N-(4-fluorophenyl)cyclopropane-1,1-dicarboxamide 4-(4-(2-fluoro-4-(1-(4-fluorophenylcarbamoyl)cyclopropanecarboxamido)phenoxy)-1H-pyrazolo[3,4-b]pyridin-3-yl)benzoic acid;

N-(3-fluoro-4-(3-(5-((4-methylpiperazin-1-yl)methyl)furan-3-yl)-1H-pyrazolo[3,4-b]pyridin-4-yloxy)phenyl)-N-(4-fluorophenyl)cyclopropane-1,1-dicarboxamide;

N-(4-(3-(3-bromo-5-((4-methylpiperazin-1-yl)methyl)furan-2-yl)-1H-pyrazolo[3,4-b]pyridin-4-yloxy)-3-fluorophenyl)-N-(4-fluorophenyl)cyclopropane-1,1-dicarboxamide;

N-(3-fluoro-4-(3-(4-(4-methylpiperazine-1-carbonyl)phenyl)-1H-pyrazolo[3,4-b]pyridin-4-yloxy)phenyl)-N-(4-fluorophenyl)cyclopropane-1,1-dicarboxamide;

N-(3-fluoro-4-(3-(4-(2-methoxyethylcarbamoyl)phenyl)-1H-pyrazolo[3,4-b]pyridin-4-yloxy)phenyl)-N-(4-fluorophenyl)cyclopropane-1,1-dicarboxamide;

N-(3-fluoro-4-(3-(4-(2-hydroxyethylcarbamoyl)phenyl)-1H-pyrazolo[3,4-b]pyridin-4-yloxy)phenyl)-N-(4-fluorophenyl)cyclopropane-1,1-dicarboxamide;

N-(4-(3-(4-(2-(dimethylamino)ethylcarbamoyl)phenyl)-1H-pyrazolo[3,4-b]pyridin-4-yloxy)-3-fluorophenyl)-N-(4-fluorophenyl)cyclopropane-1,1-dicarboxamide;

N-(3-fluoro-4-(3-(4-(methylcarbamoyl)phenyl)-1H-pyrazolo[3,4-b]pyridin-4-yloxy)phenyl)-1-methyl-2-oxopyrrolidine-3-carboxamide;

N-(3-fluoro-4-(3-(4-fluorophenyl)-1H-pyrazolo[3,4-b]pyridin-4-yloxy)phenyl)-2-(4-fluorophenyl)-3-oxo-2,3-dihydropyridazine-4-carboxamide;

N-(2-chloro-5-methyl-4-(3-(4-(morpholine-4-carbonyl)phenyl)-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(3-(pyridin-3-yl)-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(1-methyl-3-phenyl-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(3-(4-fluorophenyl)-1-methyl-1H-pyrazolo[3,4-b]pyridin-4-yloxy)phenyl)-2-(4-fluorophenyl)-3-oxo-2,3-dihydropyridazine-4-carboxamide;

N-(3-Fluoro-4-(3-(1,2,3,6-tetrahydropyridin-4-yl)-1H-pyrazolo[3,4-b]pyridin-4-yloxy)phenyl)-2-(4-fluorophenyl)-3-oxo-2,3-dihydropyridazine-4-carboxamide;

N-(4-(3-(4-(dimethylamino)phenyl)-1H-pyrazolo[3,4-b]pyridin-4-yloxy)-3-fluorophenyl)-2-(4-fluorophenyl)-3-oxo-2,3-dihydropyridazine-4-carboxamide;

N-(4-(3-(3-chlorophenyl)-1H-pyrazolo[3,4-b]pyridin-4-yloxy)-3-fluorophenyl)-2-(4-fluorophenyl)-3-oxo-2,3-dihydropyridazine-4-carboxamide;

N-(4-(3-(1H-Pyrazol-4-yl)-1H-pyrazolo[3,4-b]pyridin-4-yloxy)-3-fluorophenyl)-2-(4-fluorophenyl)-3-oxo-2,3-dihydropyridazine-4-carboxamide;

N-(3-Fluoro-4-(3-(piperazin-1-yl)-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(3-(1-methyl-1H-pyrazol-4-yl)-1H-pyrazolo[3,4-b]pyridin-4-yloxy)phenyl)-2-(4-fluorophenyl)-3-oxo-2,3-dihydropyridazine-4-carboxamide;

5-(3-fluoro-4-(3-(4-(morpholine-4-carbonyl)phenyl)-1H-pyrazolo[3,4-b]pyridin-4-yloxy)phenyl)-3-methyl-2-(phenylamino)pyrimidin-4(3H)-one;

N-(3-fluoro-4-(3-o-tolyl-1H-pyrazolo[3,4-b]pyridin-4-yloxy)phenyl)-2-(4-fluorophenyl)-3-oxo-2,3-dihydropyridazine-4-carboxamide;

N-(3-Fluoro-4-(3-(4-methylpiperazin-1-yl)-1H-pyrazolo[3,4-b]pyridin-4-yloxy)phenyl)-2-(4-fluorophenyl)-3-oxo-2,3-dihydropyridazine-4-carboxamide;

4-benzyl-N-(3-fluoro-4-(3-(4-(morpholine-4-carbonyl)phenyl)-1H-pyrazolo[3,4-b]pyridin-4-yloxy)phenyl)-3-oxo-3,4-dihydropyrazine-2-carboxamide;

N-(3-fluoro-4-(3-(4-(morpholine-4-carbonyl)phenyl)-1H-pyrazolo[3,4-b]pyridin-4-yloxy)phenyl)-4-methyl-3-oxo-3,4-dihydropyrazine-2-carboxamide;

N-(3-fluoro-4-(3-(4-(piperazin-1-yl)phenyl)-1H-pyrazolo[3,4-b]pyridin-4-yloxy)phenyl)-2-(4-fluorophenyl)-3-oxo-2,3-dihydropyridazine-4-carboxamide;

5-(3-fluoro-4-(3-(4-fluorophenyl)-1H-pyrazolo[3,4-b]pyridin-4-yloxy)phenyl)-3-methyl-2-(phenylamino)pyrimidin-4(3H)-one;

2-(cyclohexylmethyl)-5-(3-fluoro-4-(3-(4-(morpholine-4-carbonyl)phenyl)-1H-pyrazolo[3,4-b]pyridin-4-yloxy)phenyl)-3-methylpyrimidin-4(3H)-one;

2-(4-fluorophenyl)-N-(2-(3-methyl-1H-pyrazolo[3,4-b]pyridin-4-yloxy)pyrimidin-5-yl)-3-oxo-2,3-dihydropyridazine-4-carboxamide;

N-(4-(3-(4-(Dimethylamino)piperidin-1-yl)-1H-pyrazolo[3,4-b]pyridin-4-yloxy)-3-fluorophenyl)-2-(4-fluorophenyl)-3-oxo-2,3-dihydropyridazine-4-carboxamide;

N-(3-fluoro-4-(3-(piperidin-4-yl)-1H-pyrazolo[3,4-b]pyridin-4-yloxy)phenyl)-2-(4-fluorophenyl)-3-oxo-2,3-dihydropyridazine-4-carboxamide;

N-benzyl-N-(3-fluoro-4-(3-methyl-1H-pyrazolo[3,4-b]pyridin-4-yloxy)phenyl)acetamide;

N-(2,5-difluoro-4-(3-methyl-1H-pyrazolo[3,4-b]pyridin-4-yloxy)phenyl)-2-(4-fluorophenyl)-3-oxo-2,3-dihydropyridazine-4-carboxamide;

N-(2,3-difluoro-4-(3-methyl-1H-pyrazolo[3,4-b]pyridin-4-yloxy)phenyl)-2-(4-fluorophenyl)-3-oxo-2,3-dihydropyridazine-4-carboxamide;

N-(4-(3-(4-(dimethylamino)piperidin-1-yl)-1H-pyrazolo[3,4-b]pyridin-4-yloxy)-3-fluorophenyl)-3-(4-fluorophenyl)-2-oxo-3-azabicyclo[3.1.0]hexane-1-carboxamide;

N-(3-fluoro-4-(3-(piperazin-1-yl)-1H-pyrazolo[3,4-b]pyridin-4-yloxy)phenyl)-3-(4-fluorophenyl)-2-oxo-3-azabicyclo[3.1.0]hexane-1-carboxamide;

N-(2-chloro-5-fluoro-4-(3-methyl-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(3-(1-methylpiperidin-4-ylamino)-1H-pyrazolo[3,4-b]pyridin-4-yloxy)phenyl)-2-(4-fluorophenyl)-3-oxo-2,3-dihydropyridazine-4-carboxamide;

2-(benzo[d]oxazol-2-yl)-N-(4-(3-(4-(dimethylamino)piperidin-1-yl)-1H-pyrazolo[3,4-b]pyridin-4-yloxy)-3-fluorophenyl)acetamide;

S)—N-(4-(3-(3-(dimethylamino)pyrrolidin-1-yl)-1H-pyrazolo[3,4-b]pyridin-4-yloxy)-3-fluorophenyl)-2-(4-fluorophenyl)-3-oxo-2,3-dihydropyridazine-4-carboxamide;

(R)—N-(4-(3-(3-(dimethylamino)pyrrolidin-1-yl)-1H-pyrazolo[3,4-b]pyridin-4-yloxy)-3-fluorophenyl)-2-(4-fluorophenyl)-3-oxo-2,3-dihydropyridazine-4-carboxamide;

N-(3-Fluoro-4-(3-(1-methylpiperidin-4-yl)-1H-pyrazolo[3,4-b]pyridin-4-yloxy)phenyl)-2-(4-fluorophenyl)-3-oxo-2,3-dihydropyridazine-4-carboxamide;

N-(3-Fluoro-4-(3-(hexahydropyrrolo[3,4-c]pyrrol-2(1H)-yl)-1H-pyrazolo[3,4-b]pyridin-4-yloxy)phenyl)-2-(4-fluorophenyl)-3-oxo-2,3-dihydropyridazine-4-carboxamide;

N-(4-(3-(1,4-Diazepan-1-yl)-1H-pyrazolo[3,4-b]pyridin-4-yloxy)-3-fluorophenyl)-2-(4-fluorophenyl)-3-oxo-2,3-dihydropyridazine-4-carboxamide;
N-(4-(3-(3-(dimethylamino)propylamino)-1H-pyrazolo[3,4-b]pyridin-4-yloxy)-3-fluorophenyl)-2-(4-fluorophenyl)-3-oxo-2,3-dihydropyridazine-4-carboxamide;
N-(3-fluoro-4-(3-(1-methylhexahydropyrrolo[3,4-b]pyrrol-5(1H)-yl)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(piperidin-4-ylamino)-1H-pyrazolo[3,4-b]pyridin-4-yloxy)phenyl)-2-(4-fluorophenyl)-3-oxo-2,3-dihydropyridazine-4-carboxamide;
±N-(3-fluoro-4-(3-((3R*,7S*)-hexahydro-1H-pyrrolo[3,2-c]pyridin-5(6H)-yl)-1H-pyrazolo[3,4-b]pyridin-4-yloxy)phenyl)-2-(4-fluorophenyl)-3-oxo-2,3-dihydropyridazine-4-carboxamide;
±N-(3-fluoro-4-(3-((3S*,7S*)-octahydropyrrolo[2,3-c]pyridin-6-yl)-1H-pyrazolo[3,4-b]pyridin-4-yloxy)phenyl)-2-(4-fluorophenyl)-3-oxo-2,3-dihydropyridazine-4-carboxamide;
1-(benzo[d]oxazol-2-yl)-N-(4-(3-(4-(dimethylamino)piperidin-1-yl)-1H-pyrazolo[3,4-b]pyridin-4-yloxy)-3-fluorophenyl)cyclopropanecarboxamide;
N-(3-fluoro-4-(3-(4-(pyrrolidin-1-yl)piperidin-1-yl)-1H-pyrazolo[3,4-b]pyridin-4-yloxy)phenyl)-2-(4-fluorophenyl)-3-oxo-2,3-dihydropyridazine-4-carboxamide;
N-(4-(3-(2-((dimethylamino)methyl)piperidin-1-yl)-1H-pyrazolo[3,4-b]pyridin-4-yloxy)-3-fluorophenyl)-2-(4-fluorophenyl)-3-oxo-2,3-dihydropyridazine-4-carboxamide;
N-(5-chloro-2-fluoro-4-(3-methyl-1H-pyrazolo[3,4-b]pyridin-4-yloxy)phenyl)-2-(4-fluorophenyl)-3-oxo-2,3-dihydropyridazine-4-carboxamide;
(R)—N-(3-fluoro-4-(3-(2-(pyrrolidin-1-ylmethyl)pyrrolidin-1-yl)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(1-methylpiperidin-4-ylamino)-1H-pyrazolo[3,4-b]pyridin-4-yloxy)phenyl)-1-(4-fluorophenyl)-2-oxo-1,2-dihydropyridine-3-carboxamide;
N-(3-fluoro-4-(3-(methyl(1-methylpiperidin-4-yl)amino)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(4-(methylamino)piperidin-1-yl)-1H-pyrazolo[3,4-b]pyridin-4-yloxy)pheriyl)-2-(4-fluorophenyl)-3-oxo-2,3-dihydropyridazine-4-carboxamide;
N-(3-Fluoro-4-(3-(pyrrolidin-3-ylamino)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(tetrahydro-2H-pyran-4-ylamino)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(1-methylpiperidin-4-ylamino)-1H-pyrazolo[3,4-b]pyridin-4-yloxy)phenyl)biphenyl-3-carboxamide;
N-(3-fluoro-4-(3-morpholino-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(1-methylpiperidin-4-ylamino)-1H-pyrazolo[3,4-b]pyridin-4-yloxy)phenyl)-4-(4-fluorophenyl)-3-oxo-3,4-dihydropyrazine-2-carboxamide;
N-(3-fluoro-4-(3-(1-(2-hydroxyethyl)piperidin-4-ylamino)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(1-methylpiperidin-4-ylamino)-1H-pyrazolo[3,4-b]pyridin-4-yloxy)phenyl)-1-(4-fluorophenyl)-2-oxoazepane-3-carboxamide;
N-(2-chloro-5-fluoro-4-(3-(1-methylpiperidin-4-ylamino)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(1-(piperidin-4-yl)-1H-pyrazol-4-yl)-1H-pyrazolo[3,4-b]pyridin-4-yloxy)phenyl)-2-(4-fluorophenyl)-3-oxo-2,3-dihydropyridazine-4-carboxamide;
2-(3-fluoro-4-(3-(1-methylpiperidin-4-ylamino)-1H-pyrazolo[3,4-b]pyridin-4-yloxy)phenylamino)-N-(4-fluorophenyl)nicotinamide;
3-(4-(2-fluoro-4-(2-(4-fluorophenyl)-3-oxo-2,3-dihydropyridazine-4-carboxamido)phenoxy)-1H-pyrazolo[3,4-b]pyridin-3-ylamino)cyclohexyl 2,2,2-trifluoroacetate;
N-(3-fluoro-4-(3-(3-hydroxycyclohexylamino)-1H-pyrazolo[3,4-b]pyridin-4-yloxy)phenyl)-2-(4-fluorophenyl)-3-oxo-2,3-dihydropyridazine-4-carboxamide;
Methyl 4-(2-fluoro-4-(2-(4-fluorophenyl)-3-oxo-2,3-dihydropyridazine-4-carboxamido)phenoxy)-1H-pyrazolo[3,4-b]pyridine-3-carboxylate;
N-(3-fluoro-4-(3-(4-methylpiperazin-1-yl)-1H-pyrazolo[3,4-b]pyridin-4-yloxy)phenyl)-3-oxo-2-(pyridin-2-yl)-2,3-dihydropyridazine-4-carboxamide;
N-(3-fluoro-4-(3-((1,4-trans)-4-hydroxycyclohexylamino)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-((1,4-trans)-4-hydroxycyclohexylamino)-1H-pyrazolo[3,4-b]pyridin-4-yloxy)phenyl)-4-(4-fluorophenyl)-3-oxo-3,4-dihydropyrazine-2-carboxamide;
N-(3-fluoro-4-(3-(piperidin-4-ylmethyl)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(1-(2-methoxyethyl)piperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride;
N-(3-fluoro-4-(3-(1-(2-fluoroethyl)piperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride;
N-(3-fluoro-4-(3-(4-(2-methoxyethyl)piperazin-1-yl)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(1-methylpiperidin-4-ylamino)-1H-pyrazolo[3,4-b]pyridin-4-yloxy)phenyl)-3-oxo-2-(pyridin-2-yl)-2,3-dihydropyridazine-4-carboxamide;
N-(4-(3-(1-ethylpiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide;
N-(3-fluoro-4-(3-(1-isopropylpiperidin-4-ylamino)-1H-pyrazolo[3,4-b]pyridin-4-yloxy)phenyl)-2-(4-fluorophenyl)-3-oxo-2,3-dihydropyridazine-4-carboxamide;
N-(3-fluoro-4-(3-(4-methylpiperazine-1-carbonyl)-1H-pyrazolo[3,4-b]pyridin-4-yloxy)phenyl)-2-(4-fluorophenyl)-3-oxo-2,3-dihydropyridazine-4-carboxamide;

±N-(3-fluoro-4-(3-((3R*,4S*)-3-fluoropiperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride;

±N-(3-fluoro-4-(3-((3S*,4S*)-3-fluoropiperidin-4-ylamino)-1H-pyrazolo[3,4-b]pyridin-4-yloxy)phenyl)-2-(4-fluorophenyl)-3-oxo-2,3-dihydropyridazine-4-carboxamide dihydrochloride;

N-(3-fluoro-4-(3-(1-methyl-1H-imidazol-2-yl)-1H-pyrazolo[3,4-b]pyridin-4-yloxy)phenyl)-2-(4-fluorophenyl)-3-oxo-2,3-dihydropyridazine-4-carboxamide;

±N-(4-(3-((3R*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide dihydrochloride;

±N-(4-(3-((3S*,4S*)-1-ethyl-3-fluoropiperidin-4-ylamino)-1H-pyrazolo[3,4-b]pyridin-4-yloxy)-3-fluorophenyl)-2-(4-fluorophenyl)-3-oxo-2,3-dihydropyridazine-4-carboxamide dihydrochloride;

N-(3-fluoro-4-(3-(1-isopropylpiperidin-4-ylamino)-1H-pyrazolo[3,4-b]pyridin-4-yloxy)phenyl)-4-(4-fluorophenyl)-3-oxo-3,4-dihydropyrazine-2-carboxamide;

N-(3-fluoro-4-(3-(1-methyl-1H-imidazol-5-yl)-1H-pyrazolo[3,4-b]pyridin-4-yloxy)phenyl)-2-(4-fluorophenyl)-3-oxo-2,3-dihydropyridazine-4-carboxamide;

N-(3-fluoro-4-(3-(piperidin-4-ylmethyl)-1H-pyrazolo[3,4-b]pyridin-4-yloxy)phenyl)-4-(4-fluorophenyl)-3-oxo-3,4-dihydropyrazine-2-carboxamide;

N-(4-(3-((1-ethylpiperidin-4-yl)methyl)-1H-pyrazolo[3,4-b]pyridin-4-yloxy)-3-fluorophenyl)-4-(4-fluorophenyl)-3-oxo-3,4-dihydropyrazine-2-carboxamide;

N-(3-fluoro-4-(3-(4-isopropylpiperazine-1-carbonyl)-1H-pyrazolo[3,4-b]pyridin-4-yloxy)phenyl)-4-(4-fluorophenyl)-3-oxo-3,4-dihydropyrazine-2-carboxamide;

N-(3-fluoro-4-(3-(8-methyl-8-azabicyclo[3.2.1]octan-3-ylamino)-1H-pyrazolo[3,4-b]pyridin-4-yloxy)phenyl)-4-(4-fluorophenyl)-3-oxo-3,4-dihydropyrazine-2-carboxamide;

N-(3-fluoro-4-(3-(4-isopropylpiperazine-1-carbonyl)-1H-pyrazolo[3,4-b]pyridin-4-yloxy)phenyl)-2-(4-fluorophenyl)-3-oxo-2,3-dihydropyridazine-4-carboxamide;

±N-(3-fluoropiperidin-4-(3-((3S*,4S*)-3-fluoropiperidin-4-ylamino)-1H-pyrazolo[3,4-b]pyridin-4-yloxy)phenyl)-4-(4-fluorophenyl)-3-oxo-3,4-dihydropyrazine-2-carboxamide dihydrochloride; and ±N-(3-fluoro-4-(3-((3S*,4S*)-3-fluoropiperidin-4-ylamino)-1H-pyrazolo[3,4-b]pyridin-4-yloxy)phenyl)-4-(4-fluorophenyl)-3-oxo-3,4-dihydropyrazine-2-carboxamide dihydrochloride.

\* \* \* \* \*